US012780800B1

(12) United States Patent
Zhang et al.

(10) Patent No.: US 12,780,800 B1

(45) Date of Patent: Nov. 3, 2026

(54) TRIAZOLE-PYRIDINYL SUBSTITUTED AZACYCLOHEXYL ACETIC ACID COMPOUNDS AS LPA RECEPTOR ANTAGONISTS

(71) Applicant: Viva Star Biosciences Limited, Causeway Bay (CN)

(72) Inventors: Hongjian Zhang, Plainsboro, NJ (US); Ping Chen, Shanghai (CN); Zhenwei Cai, Shanghai (CN); Fei Jiang, Shanghai (CN); Peihua Sun, Shanghai (CN)

(73) Assignee: VIVA STAR BIOSCIENCES LIMITED, Causeway Bay (HK)

( * ) Notice: Subject to any disclaimer, the term of this patent is extended or adjusted under 35 U.S.C. 154(b) by 772 days.

(21) Appl. No.: 18/020,911

(22) PCT Filed: Oct. 9, 2021

(86) PCT No.: PCT/IB2021/059266

§ 371 (c)(1),
(2) Date: Feb. 10, 2023

(87) PCT Pub. No.: WO2022/034568

PCT Pub. Date: Feb. 17, 2022

(51) Int. Cl.
*C07D 401/14* (2006.01)
*C07D 413/14* (2006.01)

(52) U.S. Cl.
CPC ......... *C07D 401/14* (2013.01); *C07D 413/14* (2013.01)

(58) Field of Classification Search
CPC ............................ C07D 401/14; C07D 413/14
See application file for complete search history.

(56) References Cited

U.S. PATENT DOCUMENTS

2014/0200215 A1 7/2014 Buckman et al.

FOREIGN PATENT DOCUMENTS

| | | | | |
|---|---|---|---|---|
| CN | 102459627 | A | 5/2012 | |
| JP | 2012-512178 | A | 5/2012 | |
| JP | 2016-515536 | A | 5/2016 | |
| WO | WO-02/062389 | A1 | 8/2002 | |
| WO | WO-2010/077883 | A2 | 7/2010 | |
| WO | WO-2012/100436 | A1 | 8/2012 | |
| WO | WO-2012/138648 | | 10/2012 | |
| WO | WO-2014/145873 | | 9/2014 | |
| WO | WO-2014145873 | A2 * | 9/2014 | .............. A61P 35/04 |
| WO | WO-2019/126087 | | 6/2019 | |
| WO | WO-2019/126093 | A1 | 6/2019 | |
| WO | WO-2019/126094 | A1 | 6/2019 | |
| WO | WO-2019/126098 | | 6/2019 | |
| WO | WO-2020/060915 | A1 | 3/2020 | |

OTHER PUBLICATIONS

International Search Report and Written Opinion issued for PCT/IB2021/059266 dated Jan. 19, 2022 (8 pages).
Berge et al., “Pharmaceutical salts”, J. Pharmaceutical Sciences, vol. 66, No. 1, 1977 (19 pages).
Budd and Qian., “Development of lysophosphatidic acid pathway modulators as therapies for fibrosis”, Future Med Chem. Oct. 2013;5(16):1935-52.
Bundgard, H., “Design of Prodrugs”, Elsevier, 1985 (9 pages).
Burger’s Medicinal Chemistry and Drug Discovery, 172-178, 949-982 (Manfred E. Wolff ed., 5th ed., 1995).
Chinese Office Action issued for CN App No. 202180067597.X dated Mar. 12, 2024 (12 pages).
Higuchi, T., et al., “Pro-drugs as Novel Delivery Systems,” A.C.S. Symposium Series, vol. 14, 1975 (4 pages).
Kihara et al., “Lysophospholipid receptors in drug discovery”, Experimental Cell Res, 333: 171-177, 2015.
Lopane et al., “Implications of the lysophosphatidic acid signaling axis in liver cancer.”, Biochimica et Biophysica Acta (BBA)-Reviews on Cancer, 1868 (2017), pp. 277-282.
Nakagawa et al., “Molecular Liver Cancer Prevention in Cirrhosis by Organ Transcriptome Analysis and Lysophosphatidic Acid Pathway Inhibition”, Cancer Cell. 30:879-890, 2016.
Rancoule et al., “Lysophosphatidic acid-1-receptor targeting agents for fibrosis” Expert Opin. Investig. Drugs (2011), 20(5): 657-667.
Swaney et al., “A novel, orally active LPA1 receptor antagonist inhibits lung fibrosis in the mouse bleomycin model”, Br. J. Pharmacol. 160:1699-1713, 2010.
Tager et al., “The lysophosphatidic acid receptor LPA1 links pulmonary fibrosis to lung injury by mediating fibroblast recruitment and vascular leak”, Nat. Med. 14:45-54, 2008.
Ueda., “Lysophosphatidic acid signaling is the definitive mechanism underlying neuropathic pain”, Pain, vol. 158, No. 4, 2017, pp. S55-S65.
Valdes-Rives and Gonzalez-Arenas., “Autotaxin-Lysophosphatidic Acid: From Inflammation to Cancer Development”, Mediators Inflamm 2017:9173090, 2017.
Weiskirchen et al., “Organ and tissue fibrosis: Molecular signals, cellular mechanisms and translational implications”, Molecular Aspects of Medicine, vol. 65, 2019 (14 pages).
Wilen et al., “Strategies in Optical Resolutions”, Tetrahedron, vol. 33, 1977 (12 pages).
Wilen, S. “Tables of Resolving Agents and Optical Resolutions” Univ. of Notre Dame Press, 1972 (11 pages).
Wynn T.A., “Fibrotic Disease and the TH1/TH2 Paradigm”, Nat. Rev. Immunol. 4:583-594, 2004.
Yang and Chen., “Production of extracellular lysophosphatidic acid in the regulation of adipocyte functions and liver fibrosis”, World J Gastroenterol 24:4132-4151, 2018.
Allanore Y, et.al., 2017 (Lysophosphatidic Acid Receptor 1 Antagonist SAR100842 for Patients with Diffuse Cutaneous Systemic Sclerosis: A Double-Blind, Randomized, Eight-Week Placebo-Controlled Study Followed by a Sixteen-Week Open-Label Extension Study. Arthritis Rheumatol. Oct. 2018;70(10):1634-1643. Epub Nov. 6, 2017.

(Continued)

*Primary Examiner* — Jeffrey S Lundgren
*Assistant Examiner* — Eric Tran
(74) *Attorney, Agent, or Firm* — Foley & Lardner LLP

(57) ABSTRACT

This application relates to novel substituted azacyclohexyl acetic acid compounds, their manufacture, pharmaceutical compositions comprising them, and their use as medicaments for treating a disease associated with dysregulation of lysophosphatidic acid receptors (LPA).

82 Claims, No Drawings

(56) References Cited

OTHER PUBLICATIONS

Lee et al.Lysophosphatidic Acid Signaling in Diabetic Nephropathy; Int. J. Mol. Sci. 2019, 20, 2850; doi:10.3390/ijms20112850.
Search Report received in BR112023002570-2 dated Jun. 9, 2026.

* cited by examiner

TRIAZOLE-PYRIDINYL SUBSTITUTED AZACYCLOHEXYL ACETIC ACID COMPOUNDS AS LPA RECEPTOR ANTAGONISTS

FIELD

This application relates to novel substituted azacyclohexyl acetic acid compounds and analogues, their manufacture, pharmaceutical compositions comprising them, and their use as medicaments for treating a disease associated with dysregulation of lysophosphatidic acid receptors (LPAR).

BACKGROUND

Lysophosphatidic acid (LPA) is a small glycerolphospholipid (1- or 2-acyl-sn-glycerol 3-phosphate) with a molecular weight of 430-480 Dalton, consisting of a glycerol backbone which is esterified with a phosphate group and a fatty acid with variable chain length and degree of saturation (Yang and Chen, World J Gastroenterol 24:4132-4151, 2018). LPA can be formed from precursor molecules in plasma, serum or tissues (membrane phospholipids) via several pathways: (1) hydrolysis of the choline group off lysophosphatidylcholine by lysophospholipase D (lysoPLD or autotaxin); (2) hydrolysis of a fatty acyl chain from phosphatidic acid to produce 2-acyl or 1-acyl LPA by phospholipase A1 or A2; and (3) de novo synthesis from glycerol-3-phosphate by acyltransferases (Kihara et al., Experimental Cell Res 333:171-177, 2015). In tissues or cells, LPA represents a mixture of 1- or 2-acyl-sn-glycerol 3-phosphates.

Lysophosphatidic acid (LPA) acts as a signaling molecule and exerts its effects by binding to G protein-coupled receptors, termed LPA receptors (LPAR). To date, there are six identified LPA receptors (LPAR1-6), which are expressed in various tissues and/or cells. LPA, through binding to its receptors, plays important roles in pathophysiological processes, such as autoimmune diseases, fibrotic diseases, cancer, inflammation, neuropathic pain, etc. (Budd and Qian, Future Med Chem 5:1935-52, 2013; Valdes-Rives and González-Arenas, Mediators Inflamm 2017:9173090, 2017; Lopane et al., Biochim Biophys Acta Rev Cancer 1868:277-282, 2017; Ueda H. Pain 158 Suppl 1:S55-S65, 2017).

Fibrosis is a reparative (or "healing") process characterized by the excessive accumulation of extracellular matrix (ECM). When tissue injury (caused by infections, autoimmune reactions, mechanical injuries, etc.) is chronic, a sustained production of pro-fibrotic mediators leads to an uncontrolled healing process, and the replacement of injured cells occurs with connective tissues associated with over production of ECM (Weiskirchen et al., Molecular Aspects Med. 65:2-15, 2019). Because it alters organs' architecture and function, fibrosis is tightly associated with and often responsible for morbidity and mortality. It is estimated that 45% of all deaths in the developed world are attributed to some type of chronic fibrosis, such as idiopathic pulmonary fibrosis, systemic sclerosis, liver cirrhosis, chronic cardiovascular diseases, progressive kidney diseases (kidney fibrosis) or diabetes (Wynn T. A. Nat. Rev. Immunol. 4:583-594, 2004).

The profibrotic action of LPA via binding to its receptor LPAR1 has been established in lung, liver and other organs or tissues with two main characteristics: 1) the existence of a positive correlation between the apparition of fibrosis markers and the increased production of LPA associated with an increased expression of the LPAR1; 2) the attenuation of fibrosis in LPAR1−/− mice or by treatment with LPAR antagonists (Rancoule et al., Expert Opin. Investig. Drugs 20:657-667, 2011). For example, in the bleomycin model of pulmonary fibrosis, LPA levels increased significantly in the bronchoaveolar lavage fluid following lung injury, and mice lacking the LPAR1 gene (LPAR1−/− mice) were remarkably protected from fibrosis and mortality (Tager et al., Nat. Med. 14:45-54, 2008). Treatment with small molecule LPAR1 antagonists could reduce the lung fibrosis in the bleomycin mouse model (Swanet et al., Br. J. Pharmacol. 160:1699-1713, 2010). More recently, in a chemical-induced cirrhosis and HCC rat model, the expression of Lapr1 was markedly increased in hepatic stellate cells, while lysoPLD (autotaxin) was higher in hepatocytes (Nakagawa et al., Cancer Cell. 30:879-890, 2016). Transcriptome analysis of human and rat liver tissues indicated that the LPA pathway via the activation of LPAR1 was a functional driver of cirrhosis and HCC. Consequently, inhibition of LPAR1 and lysoPLD by chemical inhibitors attenuated fibrosis progression and reduced HCC nodules in the cirrhosis-driven HCC rat model (Id.).

SUMMARY

In one aspect, the present invention relates to a compound of formula (I)

(I)

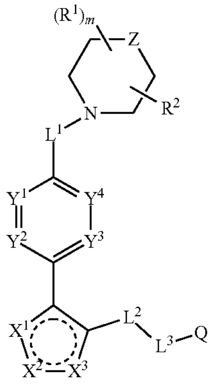

or a pharmaceutically acceptable salt, tautomer or stereoisomer thereof, wherein:

$L^1$ is a covalent bond or $CH_2$ optionally substituted with 1 or 2 methyl groups;

$L^2$ is a covalent bond or $(CR^7R^7)_p$;

$L^3$ is a covalent bond, O or $NR^7$, provided that at least one of $L^2$ and $L^3$ is not a covalent bond;

Q is $C({=}O)NR^9R^{10}$, $C({=}O)OR^{10}$, or a ring selected from a 5- or 6-membered heteroaryl group or a 5- or 6-membered heterocyclyl group, wherein the ring comprises at least one carbon atom, at least one nitrogen atom, and optionally 1-4 additional heteroatoms selected from nitrogen, oxygen and sulfur wherein oxygen may be a ring member and/or an oxo group attached to a ring member, and wherein the ring is substituted with $(R^3)_n$ and one $R^4$;

$X^1$ is N, O or $CR^{6a}$;

$X^2$ is N or $NR^6$;

$X^3$ is N, $NR^6$ or $CR^6$, wherein the dashed circle denotes bonds forming a five-membered aromatic ring;

$Y^1$, $Y^2$, $Y^3$ and $Y^4$ are each independently N or $CR^5$, provided that at least one but no more than two of $Y^1$, $Y^2$, $Y^3$ and $Y^4$ are N;

Z is $CH_2$ or O;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocyclyl, or two $R^1$ groups, together with the carbon atom to which they are attached, form C═O;

$R^2$ is $(CR^7R^7)_q$—$R^8$;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

each occurrence of $R^{6a}$ and $R^6$ is independently hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring;

$R^8$ is C(═O)$OR^7$, C(═O)$NR^aR^b$, CN, C(═O)NHC(═O)$R^7$, C(═O)NHS(═O)$_2R^7$, C(═O)NHS(═O)$R^7$, S(═O)$_2R^7$, P(═O)(OH)$_2$, or

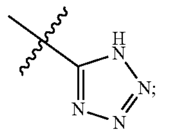 [SMILES: *c1nnn[nH]1]

each occurrence of $R^9$ and $R^{10}$ is independently hydrogen, $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or two $R^{12}$ groups, together with the carbon atom to which they are attached, form a 3-6-membered cycloalkyl ring; each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

m is 1, or 2;

n is 0, 1, or 2;

p at each occurrence is independently 1, 2, 3 or 4; and q at each occurrence is independently 0, 1, 2, 3 or 4.

The invention also relates to a pharmaceutical composition comprising a compound of formula (I), its manufacture and use as medicaments for treating a disease associated with dysregulation of lysophosphatidic acid receptor 1 (LPAi). Accordingly, the compounds of formula (I) are useful for treatment of pathological fibrosis (e.g., pulmonary, liver, renal, cardiac, dernal, ocular, or pancreatic fibrosis), idiopathic pulmonary fibrosis (IPF), non-alcoholic steatohepatitis (NASH), non-alcoholic fatty liver disease (NAFLD), chronic kidney disease, diabetic kidney disease, or systemic sclerosis.

DETAILED DESCRIPTION

In one aspect, the present technology provides compounds, and their pharmaceutically acceptable forms, including, but not limited to, salts, hydrates, solvates, isomers, sterioisomers, enantiomers, prodrugs, and isotopically labeled derivatives thereof.

In another aspect, the present technology provides methods of treating and/or managing various diseases and disorders, which comprises administering to a patient a therapeutically effective amount of a compound provided herein, or a pharmaceutically acceptable form (e.g., salts, hydrates, solvates, isomers, sterioisomers, enantiomers, prodrugs, and isotopically labeled derivatives) thereof. Non-limiting examples of diseases and disorders are described herein.

In another aspect, the present technology provides methods of preventing various diseases and disorders, which comprises administering to a patient in need of such prevention a prophylactically effective amount of a compound provided herein, or a pharmaceutically acceptable form (e.g., salts, hydrates, solvates, isomers, sterioisomers, prodrugs, and isotopically labeled derivatives) thereof. Non-limiting examples of diseases and disorders are described herein.

In another aspect, the present technology, a compound provided herein, or a pharmaceutically acceptable form (e.g., salts, hydrates, solvates, isomers, sterioisomers, prodrugs, and isotopically labeled derivatives) thereof, can be administered in combination with another drug ("second active agent") or treatment. Second active agents include small molecules and large molecules (e.g., proteins and antibodies).

Also provided herein are pharmaceutical compositions (e.g., single unit dosage forms) that can be used in the methods provided herein. In one embodiment, pharmaceutical compositions comprise a compound provided herein, or a pharmaceutically acceptable form (e.g., salts, hydrates, solvates, isomers, sterioisomers, prodrugs, and isotopically labeled derivatives) thereof, and optionally one or more second active agents.

While specific embodiments have been discussed, the specification is illustrative only and not restrictive. Many variations of this disclosure will become apparent to those skilled in the art upon review of this specification.

Unless defined otherwise, all technical and scientific terms used herein have the same meaning as is commonly understood by one of ordinary skill in the art to which this specification pertains.

Definitions

As used in the specification and claims, the singular form "a", "an" and "the" includes plural references unless the context clearly dictates otherwise.

As used herein, "agent," "additional agent," "therapeutic agent," or "second active agent" refers to a biological, pharmaceutical, or chemical compound or another moiety. Non-limiting examples include simple or complex organic or inorganic molecules, a peptide, a protein, an oligonucleotide, an antibody, an antibody derivative, an antibody fragment, a vitamin, a vitamin derivative, a carbohydrate, a toxin, or a chemotherapeutic compound, and metabolites thereof. Various compounds can be synthesized, for example, small molecules and oligomers (e.g., oligopeptides and oligonucleotides), and synthetic organic compounds based on various core structures. In addition, various natural sources can provide active compounds, such as plant or animal extracts, and the like. A skilled artisan can readily recognize that there is no limit as to the structural nature of the agents of this disclosure.

"Administration" of a disclosed compound encompasses the delivery to a subject of a compound as described herein, or a prodrug or other pharmaceutically acceptable derivative thereof, using any suitable formulation or route of administration, as discussed herein.

The term "co-administration," "administered in combination with," and their grammatical equivalents, as used herein, encompasses administration of two or more agents to the subject so that both agents and/or their metabolites are present in the subject at the same time. Co-administration includes simultaneous administration in separate compositions, administration at separate times in separate compositions, or administration in a composition in which both agents are present.

The term "effective amount" or "therapeutically effective amount" refers to that amount of a compound or pharmaceutical composition described herein that is sufficient to affect the intended application including, but not limited to, disease treatment, as illustrated below. In some embodiments, the amount is that effective for detectable inhibition of LPA1, which, for example, can be determined in an LPA1 functional antagonist assay. The therapeutically effective amount can vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a response in target cells, e.g., reduction of cell migration. The specific dose will vary depending on, for example, the compounds chosen, the species of subject and their age/existing health conditions or risk for health conditions, the dosing regimen to be followed, the severity of the disease, whether it is administered in combination with other agents, timing of administration, the tissue to which it is administered, and the physical delivery system in which it is carried.

All methods described herein can be performed in any suitable order unless otherwise indicated herein or otherwise clearly contradicted by context.

As used herein, the terms "treatment", "treating", "palliating" "managing" and "ameliorating" are used interchangeably herein. These terms refer to an approach for obtaining beneficial or desired results including, but not limited to, therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient can still be afflicted with the underlying disorder. For prophylactic benefit, the pharmaceutical compounds and/or compositions can be administered to a patient at risk of developing a disease, or to a patient reporting one or more of the physiological symptoms of a disease, even though a diagnosis of this disease may not have been made.

The terms "preventing" and "prophylaxis" as used herein refer to administering a pharmaceutical compound or medicament or a composition including the pharmaceutical compound or medicament to a subject before a disease, disorder, or condition fully manifests itself, to forestall the appearance and/or reduce the severity of one or more symptoms of the disease, disorder or condition. The person of ordinary skill in the art recognizes that the term "prevent" is not an absolute term. In the medical art it is understood to refer to the prophylactic administration of a drug to substantially diminish the likelihood or seriousness of a disease, disorder or condition, or a symptom thereof, and this is the sense that such terms are used in this disclosure.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The "subjects" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including rodents (e.g., mice, rats), cattle, pigs, horses, sheep, goats, cats, and/or dogs; and/or birds, including birds such as chickens, ducks, geese, quail, and/or turkeys.

The term "in vivo" refers to an event that takes place in a subject's body. In vivo also includes events occurring in rodents, such as rats, mice, guinea pigs, and the like.

The term "in vitro" refers to an event that takes places outside of a subject's body. For example, an in vitro assay encompasses any assay conducted outside of a subject. In vitro assays encompass cell-based assays in which cells, alive or dead, are employed. In vitro assays also encompass cell-free assays in which no intact cells are employed.

As used herein, the term "pharmaceutically acceptable salt" refers to those salts which are, within the scope of sound medical judgment, suitable for use in contact with the tissues of subjects without undue toxicity, irritation, allergic response and the like, and are commensurate with a reasonable benefit/risk ratio. Pharmaceutically acceptable salts are well known in the art. For example, Berge et al. (incorporated by reference herein) describes pharmaceutically acceptable salts in detail in *J. Pharmaceutical Sciences* (1977) 66:1-19. Pharmaceutically acceptable salts of the compounds provided herein include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, besylate, benzoate, bisulfate, borate, butyrate, camphorate, camphor sulfonate, citrate, cyclopentane propionate, digluconate, dodecyl sulfate, ethane sulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. In some embodiments, organic acids from which salts can be derived include, for example, acetic acid, propionic acid, glycolic acid, pyruvic acid, oxalic acid, lactic acid, trifluoracetic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

The salts can be prepared in situ during the isolation and purification of the disclosed compounds, or separately, such as by reacting the free base or free acid of a parent compound with a suitable base or acid, respectively. Pharmaceutically acceptable salts derived from appropriate bases include alkali metal, alkaline earth metal, ammonium and $N^{+}(C_{1-4}alkyl)^{4}$ salts. Representative alkali or alkaline earth metal salts include sodium, lithium, potassium, calcium, magnesium, iron, zinc, copper, manganese, aluminum, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Organic bases from which salts can be derived include, for example, primary, secondary, and tertiary amines, substituted amines, including naturally occurring substituted amines, cyclic amines, basic ion exchange resins, and the like, such as isopropylamine, trimethylamine, diethylamine, triethylamine, tripropylamine, and ethanolamine. In some embodiments, the pharmaceutically acceptable base addition salt can be chosen from ammonium, potassium, sodium, calcium, and magnesium salts.

As used herein, the term "solvate" refers to compounds that further include a stoichiometric or non-stoichiometric amount of solvent bound by non-covalent intermolecular forces. The solvate can be of a disclosed compound or a pharmaceutically acceptable salt thereof. Where the solvent is water, the solvate is a "hydrate". Pharmaceutically acceptable solvates and hydrates are complexes that, for example, can include 1 to about 100, or 1 to about 10, or 1 to about 2, about 3 or about 4, solvent or water molecules. It will be understood that the term "compound" as used herein encompasses the compound and solvates of the compound, as well as mixtures thereof.

In some embodiments, the pharmaceutically acceptable form is a prodrug. As used herein, the term "prodrug" refers to compounds that are transformed in vivo to yield a disclosed compound or a pharmaceutically acceptable form of the compound. A prodrug can be inactive when administered to a subject, but is converted in vivo to an active compound, for example, by hydrolysis (e.g., hydrolysis in blood). In certain cases, a prodrug has improved physical and/or delivery properties over the parent compound. Prodrugs can increase the bioavailability of the compound when administered to a subject (e.g., by permitting enhanced absorption into the blood following oral administration) or which enhance delivery to a biological compartment of interest (e.g., the brain or lymphatic system) relative to the parent compound. Exemplary prodrugs include derivatives of a disclosed compound with enhanced aqueous solubility or active transport through the gut membrane, relative to the parent compound.

The prodrug compound often offers advantages of solubility, tissue compatibility or delayed release in a mammalian organism (see, e.g., Bundgard, H., *Design of Prodrugs* (1985), pp. 7-9, 21-24 (Elsevier, Amsterdam). A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein. Exemplary advantages of a prodrug can include, but are not limited to, its physical properties, such as enhanced water solubility for parenteral administration at physiological pH compared to the parent compound, or it can enhance absorption from the digestive tract, or it can enhance drug stability for long-term storage.

The term "prodrug" is also meant to include any covalently bonded carriers, which release the active compound in vivo when such prodrug is administered to a subject. Prodrugs of an active compound, as described herein, can be prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a subject, cleaves to form a free hydroxy, free amino or free mercapto group, respectively. Examples of prodrugs include, but are not limited to, acetate, formate and benzoate derivatives of an alcohol or acetamide, formamide and benzamide derivatives of an amine functional group in the active compound and the like. Other examples of prodrugs include compounds that comprise —NO, $—NO_2$, —ONO, or $—ONO_2$moieties. Prodrugs can typically be prepared using well known methods, such as those described in *Burger's Medicinal Chemistry and Drug Discovery,* 172-178, 949-982 (Manfred E. Wolff ed., 5th ed., 1995), and *Design of Prodrugs* (H. Bundgaard ed., Elselvier, New York, 1985).

For example, if a disclosed compound or a pharmaceutically acceptable form of the compound contains a carboxylic acid functional group, a prodrug can comprise a pharmaceutically acceptable ester formed by the replacement of the hydrogen atom of the acid group with a group such as $(C_{1-8})$alkyl, $(C_{1-12})$alkanoyloxymethyl, 1-(alkanoyloxy) ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 10 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N —$(C_{1-2})$alkylamino$(C_{2-3})$alkyl (such as [3-dimethylaminoethyl), carbamoyl-$(C_{1-2})$alkyl, N,N-di$(C_{1-2})$alkylcarbamoyl-$(C_{1-2})$alkyl and piperidino-, pyrrolidino- or morpholino $(C_{2-3})$alkyl.

Similarly, if a disclosed compound contains an alcohol functional group, a prodrug can be formed by the replacement of the hydrogen atom of the alcohol group with a group such as $(C_{1-6})$alkanoyloxymethyl, 1-($(C_{1-6})$alkanoyloxy) ethyl,1-methyl-1-($(C_{1-6})$alkanoyloxy)ethyl, $(C_{1-6})$alkoxycarbonyloxymethyl, N—$(C_{1-6})$alkoxycarbonylaminomethyl, succinoyl, $(C_{1-6})$alkanoyl, α-amino$(C_{1-4})$alkanoyl, arylacyl, and α-aminoacyl, or α-aminoacyl-α-aminoacyl, where each α-aminoacyl group is independently selected from the naturally occurring L-amino acids, —$P(O)(OH)_2$, —$P(O)(O(C_{1-6})alkyl)_2$ or glycosyl (the radical resulting from the removal of a hydroxyl group of the hemiacetal form of a carbohydrate).

If a disclosed compound incorporates an amine functional group, a prodrug can be formed by the replacement of a hydrogen atom in the amine group with a group such as R-carbonyl, RO-carbonyl, NRR'-carbonyl where R and R' are each independently selected from $(C_{1-10})$alkyl, $(C_{3-7})$ cycloalkyl, benzyl, a natural α-aminoacyl or natural α-aminoacyl-natural-α-aminoacyl, —C(OH)C(O)O$Y^1$ wherein $Y^1$ is H, $(C_{1-6})$alkyl or benzyl; —C(O$Y^2$)$Y^3$ wherein $Y^2$ is $(C_{1-4})$alkyl and $Y^3$ is $(C_{1-6})$alkyl, carboxy$(C_{1-6})$alkyl, amino $(C_{1-4})$alkyl or mono-N- or di-N,N—$(C_{1-6})$alkylaminoalkyl; and —C($Y^4$)$Y^5$ wherein $Y^4$ is H or methyl and $Y^5$ is mono-N- or di-N—$(C_{1-6})$alkylamino, morpholino, piperidin-1-yl or pyrrolidin-1-yl.

In some embodiments, the disclosed compounds may encompass an isomer. "Isomers" are different compounds that have the same molecular formula. "Stereoisomers" are isomers that differ only in the way the atoms are arranged in space. As used herein, the term "isomer" includes any and all geometric isomers and stereoisomers. For example, "isomers" include geometric double bond cis- and trans-isomers, also termed E- and Z-isomers; R- and S-enantiomers; diastereomers, (d)-isomers and (l)-isomers, racemic mixtures thereof; and other mixtures thereof, as falling within the scope of this disclosure.

Geometric isomers can be represented by the symbol ⎓ which denotes a bond that can be a single, double or triple bond as described herein. Provided herein are various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or"trans," where "cis" represents substituents on the same side of the double bond and "trans" represents substituents on opposite sides of the double bond. The arrangement of substituents around a carbocyclic ring can also be designated as "cis" or "trans." The term "cis" represents substituents on the same side of the plane of the ring, and the term "trans" represents substituents on opposite sides of the plane of the ring. Mixtures of compounds wherein the substituents are disposed on both the same and opposite sides of plane of the ring are designated "cis/trans."

"Enantiomers" are a pair of stereoisomers that are non-superimposable mirror images of each other. "Diastereoisomers" are stereoisomers that have at least two asymmetric atoms, but which are not mirror-images of each other. The absolute stereochemistry is specified according to the Cahn-Ingold-Prelog R-S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

A mixture of a pair of enantiomers in any proportion can be known as a "racemic" mixture. The term "(±)" is used to designate a racemic mixture where appropriate. In some embodiments, a compound of the present technology is a racemic mixture of (S)- and (R)-isomers. In some embodiments, the racemic mixture has equal amounts of two enantiomers.

In some embodiments, an enantiomer is provided partly or substantially free of the corresponding enantiomer, and may be referred to as "optically enriched," "enantiomerically enriched," "enantiomerically pure," and "non-racemic," as used interchangeably herein. The "enantiomeric excess" or "% enantiomeric excess" of such a composition can be calculated using the equation shown below. In the example shown below, a composition contains 90% of one enantiomer, e.g., the S enantiomer, and 10% of the other enantiomer, e.g., the R enantiomer.

$$ee=(90-10)/100=80\%.$$

Thus, a composition containing 90% of one enantiomer and 10% of the other enantiomer is said to have an enantiomeric excess of 80%. In some embodiments, compositions described herein contain an enantiomeric excess of at least about 50%, at least about 60%, at least about 70%, at least about 80%, at least about 90%, at least about 95%, at least about 98%, at least about 99%, or at least about 99.5% of the S enantiomer, or a range between and including any two of the foregoing values (e.g., 50-99.5% ee). In other words, the compositions contain an enantiomeric excess of the S enantiomer over the R enantiomer. In other embodiments, some compositions described herein contain an enantiomeric excess of at least about 50%, at least about 60%, at least about 70%, at least about 80%, at least about 90%, at least about 95%, at least about 98%, at least about 99%, or at least about 99.5% of the R enantiomer or a range between any two of the foregoing values (e.g., 50-99.5% ee). In other words, the compositions contain an enantiomeric excess of the R enantiomer over the S enantiomer. Where the enrichment of one enantiomer is much greater than about 80% by weight, the compositions are referred to as "substantially enantiomerically enriched," "substantially enantiomerically pure" or a "substantially non-racemic" preparation.

Enantiomers can be isolated from racemic mixtures by any method known to those skilled in the art, including chiral high-pressure liquid chromatography (HPLC), the formation and crystallization of chiral salts, or prepared by asymmetric syntheses. See, for example, *Enantiomers, Racemates and Resolutions* (Jacques, Ed., Wiley Interscience, New York, 1981); Wilen et al., *Tetrahedron* 33:2725 (1977); *Stereochemistry of Carbon Compounds* (E. L. Eliel, Ed., McGraw-Hill, NY, 1962); and *Tables of Resolving Agents and Optical Resolutions* p. 268 (E. L. ElM, Ed., Univ. of Notre Dame Press, Notre Dame, Ind. 1972).

Optical isomers can be obtained by resolution of the racemic mixtures according to conventional processes, e.g., by formation of diastereoisomeric salts, by treatment with an optically active acid or base. Examples of appropriate acids include, but are not limited to, tartaric, diacetyltartaric, dibenzoyltartaric, ditoluoyltartaric, and camphorsulfonic acid. The separation of the mixture of diastereoisomers by crystallization followed by liberation of the optically active bases from these salts affords separation of the isomers. Another method involves synthesis of covalent diastereoisomeric molecules by reacting disclosed compounds with an optically pure acid in an activated form or an optically pure isocyanate. The synthesized diastereoisomers can be separated by conventional means such as chromatography, distillation, crystallization or sublimation, and then hydrolyzed to deliver the enantiomerically enriched compound. Optically active compounds can also be obtained by using active starting materials. In some embodiments, these isomers can be in the form of a free acid, a free base, an ester or a salt.

In any embodiments, the pharmaceutically acceptable form is a tautomer. As used herein, the term "tautomer" is a type of isomer that includes two or more interconvertible compounds resulting from at least one formal migration of a hydrogen atom and at least one change in valency (e.g., a single bond to a double bond, a triple bond to a single bond, or vice versa). "Tautomerization" includes prototropic or proton-shift tautomerization, which is considered a subset of acid-base chemistry. "Prototropic tautomerization" or "proton-shift tautomerization" involves the migration of a proton accompanied by changes in bond order. The exact ratio of the tautomers depends on several factors, including temperature, solvent, and pH. Where tautomerization is possible (e.g., in solution), a chemical equilibrium of tautomers can be reached. Tautomerizations (i.e., the reaction providing a tautomeric pair) can be catalyzed by acid or base, or can occur without the action or presence of an external agent. Exemplary tautomerizations include, but are not limited to, keto-to-enol; amide-to-imide; lactam-to-lactim; enamine-to-imine; and enamine-to-(a different) enamine tautomerizations. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

The disclosure also embraces pharmaceutically acceptable forms that are "isotopically labeled derivatives" which are compounds that are identical to those recited herein, except that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Certain isotopically-labeled disclosed compounds (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes can allow for ease of preparation and detectability. Further, substitution with heavier isotopes such as deuterium (i.e., $^{2}H$) can afford certain therapeutic advantages resulting from greater metabolic stability (e.g., increased in vivo half-life or reduced dosage requirements). Isotopically labeled disclosed compounds can generally be prepared by substituting an isotopically labeled reagent for a non-isotopically labeled reagent. In some embodiments, provided herein are compounds that can also contain unnatural proportions of atomic isotopes at one or more of atoms that constitute such compounds. All isotopic variations of the compounds as disclosed herein, whether radioactive or not, are encompassed within the scope of the present disclosure. In some embodiments, radiolabeled compounds are useful for studying metabolism and/or tissue distribution of the compounds or to alter the rate or path of metabolism or other aspects of biological functioning.

"Pharmaceutically acceptable carrier" or "pharmaceutically acceptable excipient" includes any and all solvents, dispersion media, coatings, antibacterial and antifungal agents, isotonic and absorption delaying agents and the like. The pharmaceutically acceptable carrier or excipient does not destroy the pharmacological activity of the disclosed compound and is nontoxic when administered in doses sufficient to deliver a therapeutic amount of the compound. The use of such media and agents for pharmaceutically active substances is well known in the art. Except insofar as any conventional media or agent is incompatible with the active ingredient, its use in the therapeutic compositions as disclosed herein is contemplated. Non-limiting examples of pharmaceutically acceptable carriers and excipients include sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols, such as polyethylene glycol and propylene glycol; esters such as ethyl oleate and ethyl laurate; agar; buffering agents such as magnesium hydroxide and aluminum hydroxide; alginic acid; isotonic saline; Ringer's solution; ethyl alcohol; phosphate buffer solutions; non-toxic compatible lubricants such as sodium lauryl sulfate and magnesium stearate; coloring agents; releasing agents; coating agents; sweetening, flavoring and perfuming agents; preservatives; antioxidants; ion exchangers; alumina; aluminum stearate; lecithin; self emulsifying drug delivery systems (SEDDS) such as d-atocopherol polyethyleneglycol 1000 succinate; surfactants used in pharmaceutical dosage forms such as Tweens or other similar polymeric delivery matrices; serum proteins such as human serum albumin; glycine; sorbic acid; potassium sorbate; partial glyceride mixtures of saturated vegetable fatty acids;

water, salts or electrolytes such as protamine sulfate, disodium hydrogen phosphate, potassium hydrogen phosphate, sodium chloride, and zinc salts; colloidal silica; magnesium trisilicate; polyvinyl pyrrolidone; cellulose-based substances; polyacrylates; waxes; and polyethylene-polyoxypropylene-block polymers. Cyclodextrins such as α-, β-, and γ-cyclodextrin, or chemically modified derivatives such as hydroxyalkylcyclodextrins, including 2- and 3-hydroxypropyl-cyclodextrins, or other solubilized derivatives can also be used to enhance delivery of compounds described herein.

Definitions of specific functional groups and chemical terms are described in more detail below. The chemical elements are identified in accordance with the Periodic Table of the Elements, CAS version, Handbook of Chemistry and Physics, 75th ed., inside cover, and specific functional groups are generally defined as described therein. Additionally, general principles of organic chemistry, as well as specific functional moieties and reactivity, are described in *Organic Chemistry*, Thomas Sorrell, University Science Books, Sansalito, 1999; Smith and March *March's Advanced Organic Chemistry,* 5th ed., John Wiley & Sons, Inc., New York, 2001; Larock, *Comprehensive Organic Transformations*, VCH Publishers, Inc., New York, 1989; and Carruthers, *Some Modern Methods of Organic Synthesis,* 3rd ed., Cambridge University Press, Cambridge, 1987.

Recitation of ranges of values herein are merely intended to serve as a shorthand method of referring individually to each separate value and sub-range falling within the range, unless otherwise indicated herein, and each separate value and sub-range is incorporated into the specification as if it were individually recited herein. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a straight or branched hydrocarbon chain radical consisting solely of carbon and hydrogen atoms, containing no unsaturation, having from one to ten carbon atoms (e.g., $C_{1-10}$ alkyl). Whenever it appears herein, a numerical range such as "1 to 10" refers to each integer in the given range; e.g., "1 to 10 carbon atoms" means that the alkyl group can consist of 1, 2, 3, 4 5, 6, 7, 8, 9, or 10 carbon atoms, although the present definition also covers the occurrence of the term "alkyl" where no numerical range is designated. In some embodiments, alkyl groups have 1 to 10, 1 to 8, 1 to 6, or 1 to 3 carbon atoms. Representative saturated straight chain alkyls include, but are not limited to, methyl, ethyl, n-propyl, n-butyl, n-pentyl, and n-hexyl groups; while saturated branched alkyls include, but are not limited to, isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, and the like. The alkyl is attached to the parent molecule by a single bond. Unless stated otherwise in the specification, an alkyl group may be optionally substituted by one or more of substituents disclosed herein. In a non-limiting embodiment, a substituted alkyl can be selected from fluoromethyl, difluoromethyl, trifluoromethyl, 2-fluoroethyl, 3-fluoropropyl, hydroxymethyl, 2-hydroxyethyl, 3-hydroxypropyl, benzyl, and phenethyl.

"Alkenyl" refers to a straight or branched hydrocarbon chain radical group consisting solely of carbon and hydrogen atoms, containing at least one double bond, and having from two to ten carbon atoms (i.e., $C_{2-10}$ alkenyl). Whenever it appears herein, a numerical range such as "2 to 10" refers to each integer in the given range; e.g., "2 to 10 carbon atoms" means that the alkenyl group can consist of 2 carbon atoms, 3 carbon atoms, etc., up to and including 10 carbon atoms. In any embodiments, an alkenyl comprises two to eight carbon atoms. In other embodiments, an alkenyl comprises two to six carbon atoms (e.g., $C_{2-6}$ alkenyl). The alkenyl is attached to the parent molecular structure by a single bond, for example, ethenyl (i.e., vinyl), prop-1-enyl (i.e., allyl), but-1-enyl, pent-1-enyl, penta-1,4-dienyl, and the like. The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), 2-methylprop-2-enyl ($C_4$), butadienyl ($C_4$) and the like. Examples of $C_{2-6}$ alkenyl groups include the aforementioned $C_{2-4}$ alkenyl groups as well as pentenyl ($C_5$), pentadienyl ($C_5$), hexenyl ($C_6$), 2,3-dimethyl-2-butenyl ($C_6$) and the like. Additional examples of alkenyl include heptenyl ($C_7$), octenyl ($C_8$), octatrienyl ($C_8$) and the like. Unless stated otherwise in the specification, an alkenyl group may be optionally substituted by one or more of substituents disclosed herein.

"Alkynyl" refers to a straight or branched hydrocarbon chain radical group consisting solely of carbon and hydrogen atoms, containing at least one triple bond, having from two to ten carbon atoms (i.e., $C_{2-10}$ alkynyl). Whenever it appears herein, a numerical range such as "2 to 10" refers to each integer in the given range; e.g., "2 to 10 carbon atoms" means that the alkynyl group can consist of 2 carbon atoms, 3 carbon atoms, etc., up to and including 10 carbon atoms. In any embodiments, an alkynyl comprises two to eight carbon atoms. In other embodiments, an alkynyl has two to six carbon atoms (e.g., $C_{2-6}$ alkynyl). The alkynyl is attached to the parent molecular structure by a single bond, for example, ethynyl, propynyl, butynyl, pentynyl, 3-methyl-4-pentenyl, hexynyl, and the like. Unless stated otherwise in the specification, an alkynyl group may be optionally substituted by one or more of substituents disclosed herein.

"Alkoxy" refers to the group —O-alkyl, including from 1 to 10 carbon atoms of a straight, branched, saturated cyclic configuration and combinations thereof, attached to the parent molecular structure through an oxygen. Examples include methoxy, ethoxy, propoxy, isopropoxy, butoxy, t-butoxy, pentoxy, cyclopropyloxy, cyclohexyloxy and the like. "Lower alkoxy" refers to alkoxy groups containing one to six carbons. In some embodiments, $C_{1-4}$alkoxy is an alkoxy group which encompasses both straight and branched chain alkyls of from 1 to 4 carbon atoms. Unless stated otherwise in the specification, an alkoxy group may be optionally substituted by one or more of substituents disclosed herein. The terms "alkenoxy" and "alkynoxy" mirror the above description of "alkoxy" wherein the prefix "alk" is replaced with "alken" or "alkyn" respectively, and the parent "alkenyl" or "alkynyl" terms are as described herein.

"Aromatic" or "aryl" refers to a radical with 6 to 14 ring atoms (e.g., $C_{6-14}$ aromatic or $C_{6-14}$ aryl) which has at least one ring having a conjugated pi electron system which is carbocyclic (e.g., phenyl, fluorenyl, and naphthyl). In some embodiments, the aryl is a $C_{6-10}$ aryl group. For example, bivalent radicals formed from substituted benzene derivatives and having the free valences at ring atoms are named as substituted phenylene radicals. In other embodiments, bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 14 aryl"

refers to each integer in the given range; e.g., "6 to 14 ring atoms" means that the aryl group can consist of 6 ring atoms, 7 ring atoms, etc., up to and including 14 ring atoms. The term includes monocyclic or fused-ring polycyclic (i.e., rings which share adjacent pairs of ring atoms) groups. Polycyclic aryl groups include bicycles, tricycles, tetracycles, and the like. In a multi-ring group, only one ring is required to be aromatic, so groups such as indanyl are encompassed by the aryl definition. Non-limiting examples of aryl groups include phenyl, phenalenyl, naphthalenyl, tetrahydronaphthyl, phenanthrenyl, anthracenyl, fluorenyl, indolyl, indanyl, and the like. Unless stated otherwise in the specification, an aryl group may be optionally substituted by one or more of substituents disclosed herein.

"Cycloalkyl" and "carbocyclyl" each refer to a monocyclic or polycyclic radical that contains only carbon and hydrogen, and can be saturated or partially unsaturated. Partially unsaturated cycloalkyl groups can be termed "cycloalkenyl" if the carbocycle contains at least one double bond, or "cycloalkynyl" if the carbocycle contains at least one triple bond. Cycloalkyl groups include groups having from 3 to 13 ring atoms (i.e., $C_{3-13}$ cycloalkyl). Whenever it appears herein, a numerical range such as "3 to 10" refers to each integer in the given range; e.g., "3 to 13 carbon atoms" means that the cycloalkyl group can consist of 3 carbon atoms, 4 carbon atoms, 5 carbon atoms, etc., up to and including 13 carbon atoms. The term "cycloalkyl" also includes bridged and spiro-fused cyclic structures containing no heteroatoms. The term also includes monocyclic or fused-ring polycyclic (i.e., rings which share adjacent pairs of ring atoms) groups. Polycyclic aryl groups include bicycles, tricycles, tetracycles, and the like. In some embodiments, "cycloalkyl" can be a $C_{3-8}$ cycloalkyl radical. In some embodiments, "cycloalkyl" can be a $C_{3-5}$ cycloalkyl radical. Illustrative examples of cycloalkyl groups include, but are not limited to the following moieties: $C_{3-6}$ carbocyclyl groups include, without limitation, cyclopropyl ($C_3$), cyclobutyl ($C_4$), cyclopentyl ($C_5$), cyclopentenyl ($C_5$), cyclohexyl ($C_6$), cyclohexenyl ($C_6$), cyclohexadienyl ($C_6$) and the like. Examples of $C_{3-7}$ carbocyclyl groups include norbornyl ($C_7$). Examples of $C_{3-8}$ carbocyclyl groups include the aforementioned $C_{3-7}$ carbocyclyl groups as well as cycloheptyl($C_7$), cycloheptadienyl ($C_7$), cycloheptatrienyl ($C_7$), cyclooctyl ($C_8$), bicyclo[2.2.1]heptanyl, bicyclo[2.2.2]octanyl, and the like. Examples of $C_{3-13}$ carbocyclyl groups include the aforementioned $C_{3-8}$ carbocyclyl groups as well as octahydro-1H indenyl, decahydronaphthalenyl, spiro[4.5]decanyl and the like. Unless stated otherwise in the specification, a cycloalkyl group may be optionally substituted by one or more of substituents disclosed herein. The terms "cycloalkenyl" and "cycloalkynyl" mirror the above description of "cycloalkyl" wherein the prefix "alk" is replaced with "alken" or "alkyn" respectively, and the parent "alkenyl" or "alkynyl" terms are as described herein. For example, a cycloalkenyl group can have 3 to 13 ring atoms, such as 5 to 8 ring atoms. In some embodiments, a cycloalkynyl group can have 5 to 13 ring atoms.

"Halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof, preferably substituted with one, two, or three halo groups. For example, the terms "fluoroalkyl" and "fluoroalkoxy" include haloalkyl and haloalkoxy groups, respectively, in which the halo is fluorine, such as, but not limited to, trifluoromethyl, difluoromethyl, 2,2,2-trifluoroethyl, 1-fluoromethyl-2-fluoroethyl, $—O—CHF_2$, and the like. Each of the alkyl, alkenyl, alkynyl and alkoxy groups are as defined herein and can be optionally further substituted as defined herein.

"Heteroaryl" or, alternatively, "heteroaromatic" refers to a refers to a radical of a 5-18 membered monocyclic or polycyclic (e.g., bicyclic, tricyclic, tetracyclic and the like) aromatic ring system (e.g., having 6, 10 or 14 $\pi$ electrons shared in a cyclic array) having ring carbon atoms and 1-6 ring heteroatoms provided in the aromatic ring system, wherein each heteroatom is independently selected from nitrogen, oxygen, phosphorous and sulfur ("5-18 membered heteroaryl"). Heteroaryl polycyclic ring systems can include one or more heteroatoms in one or both rings. Whenever it appears herein, a numerical range such as "5 to 18" refers to each integer in the given range; e.g., "5 to 18 ring atoms" means that the heteroaryl group can consist of 5 ring atoms, 6 ring atoms, etc., up to and including 18 ring atoms. In some instances, a heteroaryl can have 5 to 14 ring atoms. In some embodiments, the heteroaryl has, for example, bivalent radicals derived from univalent heteroaryl radicals whose names end in "-yl" by removal of one hydrogen atom from the atom with the free valence are named by adding "-ene" to the name of the corresponding univalent radical, e.g., a pyridyl group with two points of attachment is a pyridylene.

For example, an N-containing "heteroaromatic" or "heteroaryl" moiety refers to an aromatic group in which at least one of the skeletal atoms of the ring is a nitrogen atom. One or more heteroatom(s) in the heteroaryl radical can be optionally oxidized. One or more nitrogen atoms, if present, can also be optionally quaternized. Heteroaryl also includes ring systems substituted with one or more nitrogen oxide (—O—) substituents, such as pyridinyl N-oxides. The heteroaryl is attached to the parent molecular structure through any atom of the ring(s).

"Heteroaryl" also includes ring systems wherein the heteroaryl ring, as defined above, is fused with one or more aryl groups wherein the point of attachment to the parent molecular structure is either on the aryl or on the heteroaryl ring, or wherein the heteroaryl ring, as defined above, is fused with one or more cycloalkyl or heterocyclyl groups wherein the point of attachment to the parent molecular structure is on the heteroaryl ring. For polycyclic heteroaryl groups wherein one ring does not contain a heteroatom (e.g., indolyl, quinolinyl, carbazolyl and the like), the point of attachment to the parent molecular structure can be on either ring, i.e., either the ring bearing a heteroatom (e.g., 2-indolyl) or the ring that does not contain a heteroatom (e.g., 5-indolyl). In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, phosphorous, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, phosphorous, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, phosphorous, and sulfur ("5-6 membered heteroaryl"). In some embodiments, the 5-6 membered heteroaryl has 1-3 ring heteroatoms selected from nitrogen, oxygen, phosphorous, and sulfur. In some embodiments, the 5-6 membered heteroaryl has 1-2 ring heteroatoms selected from nitrogen, oxygen, phosphorous, and sulfur. In some embodiments, the 5-6 membered heteroaryl has 1 ring heteroatom selected from nitrogen, oxygen, phosphorous, and sulfur.

Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzopyranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimdinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thiapyranyl, triazolyl, tetrazolyl, triazinyl, thieno[2,3-d]pyrimidinyl, thieno[3,2-d]pyrimidinyl, thieno[2,3-c]pridinyl, and thiophenyl (i.e., thienyl). Unless stated otherwise in the specification, a heteroaryl group may be optionally substituted by one or more of substituents disclosed herein.

"Heterocyclyl", "heterocycloalkyl" or "heterocarbocyclyl" each refer to any 3 to 18-membered non-aromatic radical monocyclic or polycyclic moiety comprising at least one carbon atom and at least one heteroatom selected from nitrogen, oxygen, phosphorous and sulfur. A heterocyclyl group can be a monocyclic, bicyclic, tricyclic or tetracyclic ring system, wherein the polycyclic ring systems can be a fused, bridged or spiro ring system. Heterocyclyl polycyclic ring systems can include one or more heteroatoms in one or both rings. A heterocyclyl group can be saturated or partially unsaturated. Partially unsaturated heterocycloalkyl groups can be termed "heterocycloalkenyl" if the heterocyclyl contains at least one double bond, or "heterocycloalkynyl" if the heterocyclyl contains at least one triple bond. Whenever it appears herein, a numerical range such as "5 to 18" refers to each integer in the given range; e.g., "5 to 18 ring atoms" means that the heterocyclyl group can consist of 5 ring atoms, 6 ring atoms, etc., up to and including 18 ring atoms. For example, bivalent radicals derived from univalent heterocyclyl radicals whose names end in "-yl" by removal of one hydrogen atom from the atom with the free valence are named by adding "-ene" to the name of the corresponding univalent radical, e.g., a piperidine group with two points of attachment is a piperidylene.

An N-containing heterocyclyl moiety refers to a non-aromatic group in which at least one of the ring atoms is a nitrogen atom. The heteroatom(s) in the heterocyclyl radical can be optionally oxidized. One or more nitrogen atoms, if present, can be optionally quaternized. Heterocyclyl also includes ring systems substituted with one or more nitrogen oxide (—O—) substituents, such as piperidinyl N-oxides. The heterocyclyl is attached to the parent molecular structure through any atom of any of the ring(s).

"Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment to the parent molecular structure is on the heterocyclyl ring. In some embodiments, a heterocyclyl group is a 5-14 membered non-aromatic ring system having ring carbon atoms and 1-4 ring heteroatoms, wherein each heteroatom is independently selected from nitrogen, oxygen, phosphorous and sulfur ("5-14 membered heterocyclyl"). In some embodiments, a heterocyclyl group is a 3-10 membered non-aromatic ring system having ring carbon atoms and 1-4 ring heteroatoms, wherein each heteroatom is independently selected from nitrogen, oxygen, phosphorous and sulfur ("3-10 membered heterocyclyl"). In some embodiments, a heterocyclyl group is a 5-8 membered non-aromatic ring system having ring carbon atoms and 1-4 ring heteroatoms, wherein each heteroatom is independently selected from nitrogen, oxygen, phosphorous and sulfur ("5-8 membered heterocyclyl"). In some embodiments, a heterocyclyl group is a 5-6 membered non-aromatic ring system having ring carbon atoms and 1-4 ring heteroatoms, wherein each heteroatom is independently selected from nitrogen, oxygen, phosphorous and sulfur ("5-6 membered heterocyclyl"). In some embodiments, the 5-6 membered heterocyclyl has 1-3 ring heteroatoms selected from nitrogen, oxygen phosphorous and sulfur. In some embodiments, the 5-6 membered heterocyclyl has 1-2 ring heteroatoms selected from nitrogen, oxygen, phosphorous and sulfur. In some embodiments, the 5-6 membered heterocyclyl has 1 ring heteroatom selected from nitrogen, oxygen, phosphorous and sulfur.

"Heterocyclyl" may include one or more ketone group (—C(═O)—) as part of the ring. Examples of a ketone-containing heterocycle include, without limitation, pyridin-2(1H)-one, pyrazin-2(1H)-one, pyrimidin-2(1H)-one, pyrimidin-4(3H)-one, pyridazin-3(2H)-one, pyridin-4(1H)-one, imidazolidin-2-one, 1,3-dihydro-2H-imidazol-2-one, 2,4-dihydro-3H-1,2,4-triazol-3-one, oxazol-2(3H)-one, and oxazolidin-2-one. A ketone-containing heterocyclyl is obtainable by removing a hydrogen atom from its corresponding ketone-containing heterocycle at any available N—H or C—H position.

Exemplary 3-membered heterocyclyls containing 1 heteroatom include, without limitation, azirdinyl, oxiranyl, and thiorenyl. Exemplary 4-membered heterocyclyls containing 1 heteroatom include, without limitation, azetidinyl, oxetanyl and thietanyl. Exemplary 5-membered heterocyclyls containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyls containing 2 heteroatoms include, without limitation, dioxolanyl, oxathiolanyl, thiazolidinyl, and dithiolanyl. Exemplary 5-membered heterocyclyls containing 3 heteroatoms include, without limitation, triazolinyl, diazolonyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6 membered heterocyclyl groups containing 2 heteroatoms include, without limitation, piperazinyl, morpholinyl, thiomorpholinyl, dithianyl, dioxanyl, and triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, benzoxanyl, benzopyrrolidinyl, benzopiperidinyl, benzoxolanyl, benzothiolanyl, benzothianyl, tetrahydroindolyl, tetrahydroquinolinyl, tetrahydroisoquinolinyl, decahydroquinolinyl, decahydroisoquinolinyl, 3-1H-benzimidazol-2-one, (1-substituted)-2-oxo-benzimidazol-3-yl, octahydrochromenyl, octahydroisochromenyl, decahydronaphthyridinyl, decahydro-1,8-naphthyridinyl, octahydropyrrolo[3,2-b]pyrrole, phenanthridinyl, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, hydrofuro[2,3-c]pyridinyl, 4,5,6,7 tetrahydro-1H-pyrrolo[2,3-b]pyridinyl, 4,5,6,7-tetrahydrofuro [3,2-c]pyridinyl, 4,5,6,7-tetrahydrothieno[3,2-b]pyridinyl, 1,2,3,4-tetrahydro-1,6-naphthyridinyl, and the like.

Unless stated otherwise in the specification, a heterocyclyl group may be optionally substituted by one or more of substituents disclosed herein.

Where substituent groups are specified by their conventional chemical Formulae, written from left to right, they equally encompass the chemically identical substituents that would result from writing the structure from right to left, e.g., $—CH_2O—$ is equivalent to $—OCH_2—$.

A "leaving group or atom" is any group or atom that will, under the reaction conditions, cleave from the starting material, thus promoting reaction at a specified site. Suitable non-limiting examples of such groups unless otherwise specified include halogen atoms, mesyloxy, p-nitrobenzensulphonyloxy, trifluoromethyloxy, and tosyloxy groups.

"Protecting group" has the meaning conventionally associated with it in organic synthesis, i.e., a group that selectively blocks one or more reactive sites in a multifunctional compound such that a chemical reaction can be carried out selectively on another unprotected reactive site and such that the group can readily be removed after the selective reaction is complete. Non-limiting embodiments of functional groups that can be masked with a protecting group include an amine, hydroxy, thiol, carboxylic acid, and aldehyde. For example, a hydroxy protected form is where at least one of the hydroxy groups present in a compound is protected with a hydroxy protecting group. A variety of protecting groups are disclosed, for example, Greene's Protective Groups in Organic Synthesis, Fifth Edition, Wiley (2014), incorporated herein by reference in its entirety. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); Greene's Protective Groups in Organic Synthesis, Fifth Edition, Wiley (2014); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995). These references are incorporated herein by reference in their entirety.

The terms "substituted" or "substitution" mean that at least one hydrogen present on a group atom (e.g., a carbon or nitrogen atom) is replaced with a permissible substituent, e.g., a substituent which upon substitution for the hydrogen results in a stable compound, e.g., a compound which does not spontaneously undergo transformation such as by rearrangement, cyclization, elimination, or other reaction. Unless otherwise indicated, a "substituted" group can have a substituent at one or more substitutable positions of the group, and when more than one position in any given structure is substituted, the substituent is either the same or different at each position. Substituents include one or more group(s) individually and independently selected from acyl, alkyl, alkenyl, alkynyl, alkoxy, alkylaryl, cycloalkyl, aralkyl, aryl, aryloxy, amino, amido, amidino, imino, azide, carbonate, carbamate, carbonyl, heteroalkyl, heteroaryl, heteroarylalkyl, heterocycloalkyl, hydroxy, cyano, halo (i.e., F, Cl, Br, I), haloalkoxy, haloalkyl, ester, ether, mercapto, thio, alkylthio, arylthio, thiocarbonyl, nitro, oxo, phosphate, phosphonate, phosphinate, silyl, sulfinyl, sulfonyl, sulfonamidyl, sulfoxyl, sulfonate, urea, $—Si(R^a)_3$, $—OR^a$, $—SR^a$, $—OC(O)—R^a$, $—N(R^a)_2$, $—C(O)R^a$, $—C(O)OR^a$, $—OC(O)N(R^a)_2$, $—C(O)N(R^a)_2$, $—N(R^a)C(O)OR^a$, $—N(R^a)C(O)R^a$, $—N(R^a)C(O)N(R^a)_2$, $—N(R^a)C(NR^a)N(R^a)_2$, $—N(R^a)S(O)_tN(R^a)_2$ (where t is 1 or 2), $—P(=O)(R^a)(R^a)$, or $—O—P(=O)(OR^a)_2$ where each $R^a$ is independently hydrogen, alkyl, haloalkyl, carbocyclyl, carbocyclylalkyl, aryl, aralkyl, heterocycloalkyl, heterocycloalkylalkyl, heteroaryl or heteroarylalkyl, and each of these moieties (other than hydrogen) can be optionally substituted with one or more substituents (up to six, valence permitting) selected from OH, $NH_2$, oxo, halo, nitro, COOH, $C(O)NH_2$ or cyano. For example, a cycloalkyl substituent can have a halide substituted at one or more ring carbons, and the like. The protecting groups that can form the protective derivatives of the above substituents are known to those of skill in the art and can be found in references such as Greene and Wuts, above.

Suitable substituents include, but are not limited to, haloalkyl and trihaloalkyl, alkoxyalkyl, halophenyl, -M-heteroaryl, -M-heterocycle, -M-aryl, $-M-OR^a$, $-M-SR^a$, $-M-N(R^a)_2$, $-M-OC(O)N(R^a)_2$, $-M-C(=NR^a)N(R^a)_2$, $-M-C(=NR^a)OR^a$, $-M-P(O)(R^a)_2$, $Si(R^a)_3$, $-M-NR^aC(O)R^a$, $-M-O\ RNR^aC(O)OR^a$, $-M-C(O)R^a$, $-M-C(=S)R^a$, $-M-C(=S)NR^aR^a$, $-M-C(O)N(R^a)_2$, $-M-C(O)NR^a-M-N(R^a)_2$, $-M-NR^aC(NR^a)N(R^a)_2$, $-M-NR^aC(S)N(R^a)_2$, $-M-S(O)_2R^a$, $-M\ C(O)R^a$, $-M-OC(O)R^a$, $-MC(O)SR^a$, $-M-S(O)_2N(R^a)_2$, $—C(O)-M-C(O)R^a$, $-MCO_2R^a$, $-MC(=O)N(R^a)_2$, $-M-C(=NH)N(R^a)_2$, and $-M-OC(=NH)N(R^a)_2$ (wherein M is a $C_{1-6}$ alkyl group).

When a ring system (e.g., cycloalkyl, heterocyclyl, aryl, or heteroaryl) is substituted with several substituents varying within an expressly defined range, it is understood that the total number of substituents does not exceed the normal available valencies under the existing conditions. Thus, for example, a phenyl ring substituted with "p" substituents (where "p" ranges from 0 to 5) can have 0 to 5 substituents, whereas it is understood that a pyridinyl ring substituted with "p" substituents has several substituents ranging from 0 to 4. The maximum number of substituents that a group in the disclosed compounds can have can be easily determined. The substituted group encompasses only those combinations of substituents and variables that result in a stable or chemically feasible compound. A stable compound or chemically feasible compound is one that, among other factors, has stability sufficient to permit its preparation and detection. In some embodiments, disclosed compounds are sufficiently stable that they are not substantially altered when kept at a temperature of 40° C. or less, in the absence of moisture (e.g., less than about 10%, less than about 5%, less than about 2%, less than about 1%, or less than about 0.5%) or other chemically reactive conditions, for e.g., at least about 3 days, at least about a week, at least about 2 weeks, at least about 4 weeks, or at least about 6 weeks.

The terms "combine, combining, to combine, combination" refer to the action of adding at least one chemical substance to another chemical substance(s) either sequentially or simultaneously. In some embodiments, bringing these chemical substances together can result in transformation of the initial chemical substances into one or more different chemical substances. This transformation can occur through one or more chemical reactions, e.g., where covalent bonds are formed, broken, rearranged and the like. A non-limiting example can include hydrolysis of an ester into an alcohol and carboxylic acid which can result from the combination of the ester with a suitable base. In another non-limiting example, an aryl fluoride can be combined with an amine to provide an aryl amine through a substitution process. These terms also include changes in association of charged chemical substances and creation of charged chemical substances, such as, but not limited to, N-oxide formation, acid addition salt formation, basic addition salt formation, and the like. These terms include the creation and/or transformation of radical chemical substances and isotopically labeled chemical substances.

The terms "convert, converting, to convert, conversion" refer to a subset of "combination" and its grammatical equivalents, where the action of one or more reagents transforms one or more functional groups on a chemical substance to another functional group(s). For example, a conversion includes, but is not limited to, transforming a nitro functional group on a chemical substance to an amine with a reducing agent. Conversions also include changes in charged chemical substances, radical chemical substances and isotopically labeled chemical substances. However, the term "convert" does not include alteration of conserved bonds in disclosed genuses and compounds.

Compounds

In one aspect, the present invention relates to a compound of Formula (I):

(I)

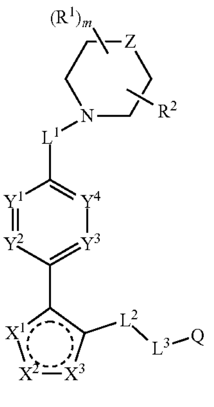

or a pharmaceutically acceptable salt, tautomer or stereoisomer thereof, wherein:

Z is $CH_2$ or O;

$Y^1$, $Y^2$, $Y^3$ and $Y^4$ are each independently N or $CR^5$, provided that at least one but no more than two of $Y^1$, $Y^2$, $Y^3$ and $Y^4$ are N;

$X^1$ is N, O or $CR^{6a}$;

$X^2$ is N or $NR^6$;

$X^3$ is N, $NR^6$ or $CR^6$, wherein the dashed circle denotes bonds forming a five-membered aromatic ring;

$L^1$ is a covalent bond or $CH_2$ optionally substituted with 1 or 2 methyl groups;

$L^2$ is a covalent bond or $(CR^7R^7)_p$;

$L^3$ is a covalent bond, O or $NR^7$, provided that at least one of $L^2$ and $L^3$ is not a covalent bond;

Q is $C(=O)NR^9R^{10}$, $C(=O)OR^{10}$, or a ring selected from a 5- or 6-membered heteroaryl group or a 5- or 6-membered heterocyclyl group, wherein the ring comprises at least one carbon atom, at least one nitrogen atom, and optionally 1-4 additional heteroatoms selected from the group consisting of nitrogen, oxygen and sulfur, wherein oxygen may be a ring member and/or an oxo group attached to a ring member, and wherein the ring is substituted with $(R^3)_n$ and one $R^4$;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C=O;

$R^2$ is $(CR^7R^7)_q$—$R^8$;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

each occurrence of $R^{6a}$ and $R^6$ is independently hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring; $R^8$ is $C(=O)OR^7$, $C(=O)NR^aR^b$, CN, $C(=O)NHC=OR^7$, $C(=O)NHS(=O)_2R^7$, $C(=O)NHS(=O)R^7$, $S(=O)_2R^7$, $P(=O)(OH)_2$, or

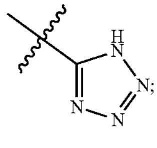 [SMILES: *c1nnn[nH]1]

;

each occurrence of $R^9$ and $R^{10}$ is independently hydrogen, $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or two $R^{12}$ groups, together with the carbon atom to which they are attached, form a 3-6-membered cycloalkyl ring; each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

m is 1, or 2;

n is 0, 1, or 2;

p at each occurrence is independently 1, 2, 3 or 4; and q at each occurrence is independently 0, 1, 2, 3 or 4.

In some embodiments, the compound of Formula (I) includes a compound of Formula (II):

(II)

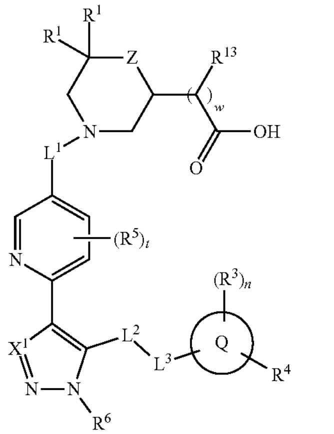

or a pharmaceutically acceptable salt, tautomer or stereoisomer thereof, wherein:

$L^1$ is a covalent bond or $CH_2$ optionally substituted with 1 or 2 methyl groups;

$L^2$ is a covalent bond or $(CR^7R^7)_p$;

$L^3$ is a covalent bond, O or $NR^7$, provided that at least one of $L^2$ and $L^3$ is not a covalent bond;

Q is a ring selected from the group consisting of 5-membered heteroaryl, 5-membered heterocyclyl, 6-membered heteroaryl, and 6-membered heterocyclyl, wherein the ring comprises at least one carbon atom, at least one nitrogen atom and optionally 1-4 additional heteroatoms selected from the group consisting of nitrogen, oxygen and sulfur, wherein oxygen may be a ring member and/or an oxo (═O) attached to a ring member, and wherein the ring is substituted with $(R^3)_n$ and one $R^4$;

$X^1$ is N, or $CR^{6a}$;

Z is $CH_2$ or O;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C═O;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$ alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$ cycloalkyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$; $R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or $R^7$ and $R^7$, together with the carbon atom to which they are attached, form a 3-5-membered cycloalkyl ring;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{13}$ at each occurrence is independently hydrogen, $C_{1-4}$alkyl, or $C_{3-5}$cycloalkyl; each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

n is 0, 1 or 2;

p at each occurrence is independently 1, 2, 3 or 4;

t is 0, 1, 2 or 3; and w is 0 or 1, provided that when $L^1$ is a covalent bond, w is 1, and further provided that when $L^1$ is $CH_2$ optionally substituted with 1 or 2 methyl groups, w is 0.

In some embodiments, the compound of Formula I includes a compound of Formula (IIa) or (IIaa):

(IIa)

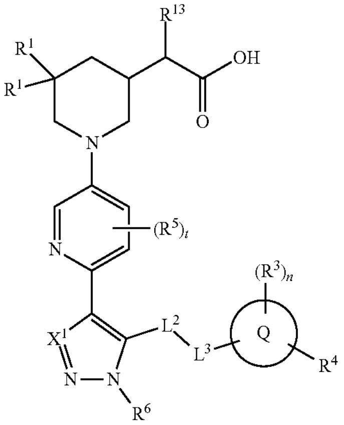

or (IIaa)

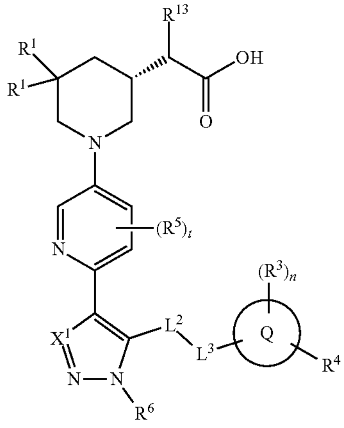

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

Q is a ring selected from the group consisting of 5-membered heteroaryl, 5-membered heterocyclyl, 6-membered heteroaryl, and 6-membered heterocyclyl, wherein the ring comprises at least one carbon atom, at least one nitrogen atom and optionally 1-4 additional heteroatoms selected from the group consisting of nitrogen, oxygen and sulfur, wherein oxygen may be a ring member and/or an oxo attached to a ring member, and wherein the ring is substituted with $(R^3)_n$ and one $R^4$;

$X^1$ is N, or $CR^{6a}$;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocyclyl, or two $R^1$ groups, together with the carbon atom to which they are attached, form C═O;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$ alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, O$(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, O$(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or $R^7$ and $R^7$, together with the carbon atom to which they are attached, form a 3-5-membered cycloalkyl ring;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, O$(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, O$(CH_2)_p$—$C_{3-7}$cycloalkyl, in which each phenyl is independently optionally substituted with 1-3 of halogen, $C_{1-6}$alkyl, or $C_{1-6}$alkoxy;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

n is 0, 1 or 2;

p at each occurrence is independently 1, 2, 3 or 4; and t is 0, 1, 2 or 3.

In some embodiments, the compound of Formula I includes a compound of Formula (IIb) or (IIbb):

(IIb)

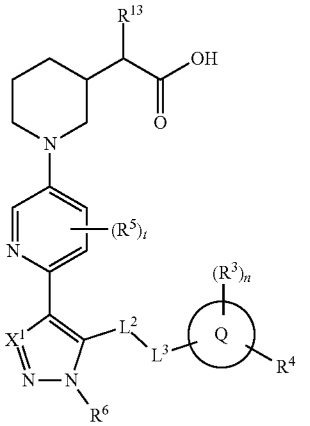

or

-continued (IIbb)

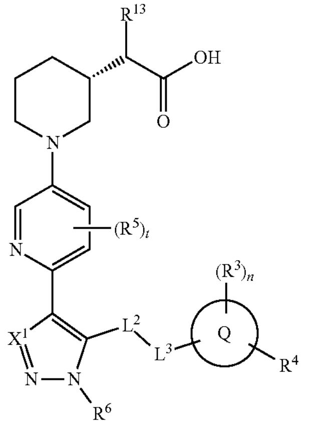

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

Q is a ring selected from the group consisting of 5-membered heteroaryl, 5-membered heterocyclyl, 6-membered heteroaryl, and 6-membered heterocyclyl, wherein the ring comprises at least one carbon atom, at least one nitrogen atom and optionally 1-4 additional heteroatoms selected from the group consisting of nitrogen, oxygen and sulfur, and wherein the ring is substituted with $(R^3)_n$ and one $R^4$;

$X^1$ is N, or $CR^{6a}$;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$ alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or $R^7$ and $R^7$, together with the carbon atom to which they are attached, form a 3-5-membered cycloalkyl ring;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

n is 0, 1 or 2;

p at each occurrence is independently 1, 2, 3 or 4; and t is 0, 1, 2 or 3.

In some embodiments, the compound of Formula I includes a compound of Formula (IIc) or (IIcc):

(IIc)

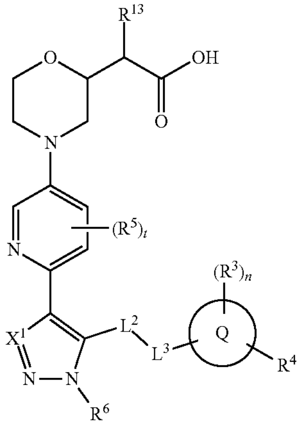

or (IIcc)

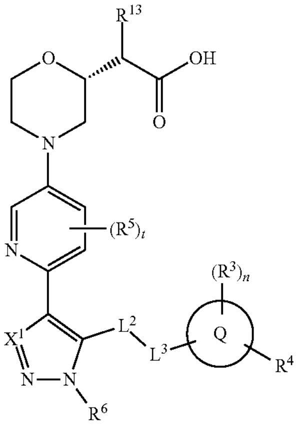

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

Q is a ring selected from the group consisting of 5-membered heteroaryl, 5-membered heterocyclyl, 6-membered heteroaryl, and 6-membered heterocyclyl, wherein the ring contains at least one carbon atom, at least one nitrogen atom, and optionally contains 1-4 additional heteroatoms selected from the group consisting of nitrogen, oxygen and sulfur, and wherein the ring is substituted with $(R^3)_n$ and one $R^4$;

$X^1$ is N, or $CR^{6a}$;

$R^3$ at each occurrence is independently hydrogen, halogen, CN, $C_{1-6}$alkyl, or $C_{3-7}$cycloalkyl;

$R^4$ is hydrogen, halogen, $C_{1-6}$alkyl, halo$C_{1-6}$alkyl, $C_{2-6}$alkenyl, $C_{2-6}$alkynyl, $C_{1-6}$alkoxy, $(CH_2)_p$ —$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl, $O(CH_2)_p$—$C_{3-7}$cycloalkyl, $(CH_2)_q$-5-6-membered heteroaryl ring substituted with 1-4 $R^{11}$, or $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or $R^7$ and $R^7$, together with the carbon atom to which they are attached, form a 3-5-membered cycloalkyl ring;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

n is 0, 1 or 2;

p at each occurrence is independently 1, 2, 3 or 4; and t is 0, 1, 2 or 3.

In some embodiments, the compound of Formula I includes a compound of Formula (IId) or (IIdd):

(IId)

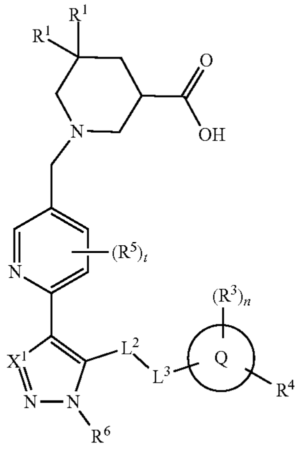

or

-continued (IIdd)

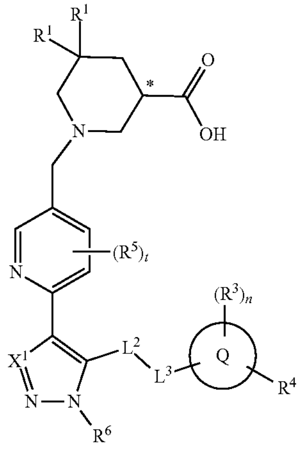

or a pharmaceutically acceptable salt, tautomer or stereoisomer thereof, wherein:

* in Formula (IIdd) represents a chiral center with R or S configuration;

$L^2$ is a covalent bond or $(CR^7R^7)_p$;

$L^3$ is a covalent bond, O or $NR^7$, provided that at least one of $L^2$ and $L^3$ is not a covalent bond;

Q is a ring selected from the group consisting of 5-membered heteroaryl, 5-membered heterocyclyl, 6-membered heteroaryl, and 6-membered heterocyclyl, wherein the ring comprises at least one carbon atom, at least one nitrogen atom, and optionally 1-4 additional heteroatoms selected from the group consisting of nitrogen, oxygen and sulfur, wherein oxygen may be a ring member and/or an oxo (=O) attached to a ring member, and wherein the ring is substituted with $(R^3)_n$ and one $R^4$;

$X^1$ is N, or $CR^{6a}$;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C=O;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$ alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$ cycloalkyl, $C_{2-6}$alkenyl-$C_{3-7}$cycloalkyl, $C_{2-6}$alkynyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

n is 0, 1 or 2;

p at each occurrence is independently 1, 2, 3 or 4; and t is 0, 1, 2 or 3.

In some embodiments, the compound of Formula I includes a compound of Formula (III):

(III)

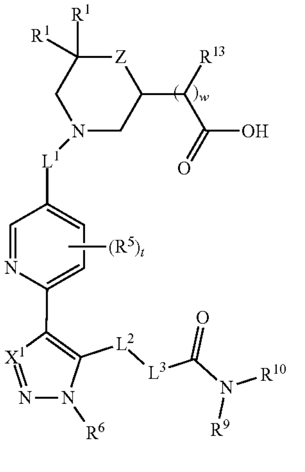

or a pharmaceutically acceptable salt, tautomer or stereoisomer thereof, wherein:

$X^1$ is N, or $CR^{6a}$;

Z is $CH_2$ or O;

$L^1$ is a covalent bond or $CH_2$ optionally substituted with 1 or 2 methyl groups;

$L^2$ is a covalent bond or $(CR^7R^7)_p$;

$L^3$ is a covalent bond, O or $NR^7$, provided that at least one of $L^2$ and $L^3$ is not a covalent bond;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C═O;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring;

each occurrence of $R^9$ and $R^{10}$ is independently hydrogen, $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or two $R^{12}$ groups, together with the carbon atom to which they are attached, form a 3-6-membered cycloalkyl ring;

$R^{13}$ at each occurrence is independently $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

p at each occurrence is independently 1, 2, 3 or 4;

q at each occurrence is independently 0, 1, 2, 3 or 4;

t is 0, 1, 2 or 3; and w is 0 or 1, provided that when $L^1$ is a covalent bond, w is 1, and further provided that when $L^1$ is $CH_2$ optionally substituted with 1-2 methyl, w is 0.

In some embodiments, the compound of Formula I includes a compound of Formula (IIIa) or (IIIaa):

(IIIa)

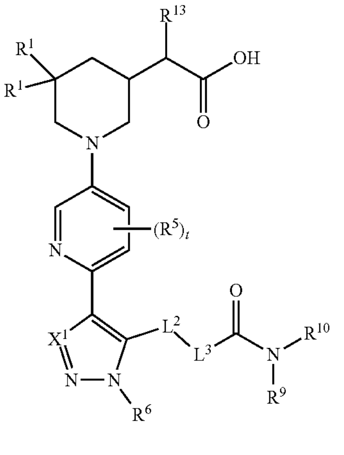

or

-continued (IIIaa)

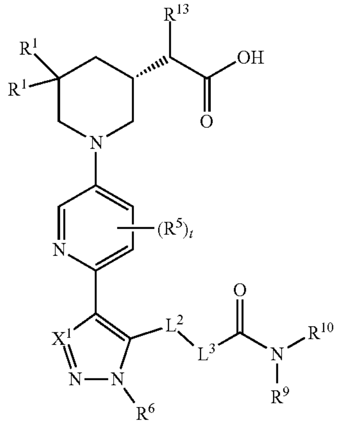

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

$X^1$ is N, or $CR^{6a}$;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C═O;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring;

each occurrence of $R^9$ and $R^{10}$ is independently hydrogen, $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or $R^{12}$ and $R^{12}$, together with the carbon atom to which they are attached, form a 3-6-membered cycloalkyl ring;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

t is 0, 1, 2 or 3;

p at each occurrence is independently 1, 2, 3 or 4; and q at each occurrence is independently 0, 1, 2, 3 or 4.

In some embodiments, the compound of Formula I includes a compound of Formula (IIIb) or (IIbb):

(IIIb)

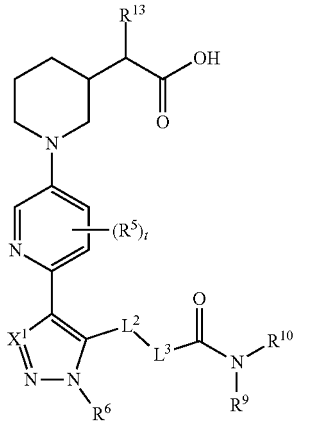

or (IIIbb)

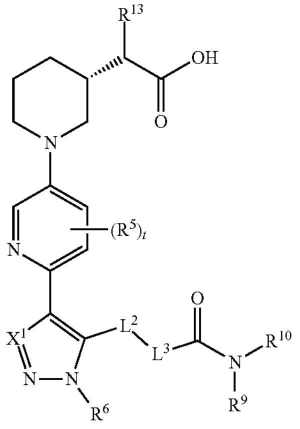

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

$X^1$ is N, or $CR^{6a}$;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

each occurrence of $R^7$ is independently hydrogen, $C_{1-4}$alkyl, $C_{3-5}$cycloalkyl, or $R^7$ and $R^7$, together with the carbon atom to which they are attached, form a 3-5-membered cycloalkyl ring;

each occurrence of $R^9$ and $R^{10}$ is independently hydrogen, $C_{1-6}$alkyl substituted with 1-4 $R^{11}$, $(CR^{12}R^{12})_q$—$C_{2-6}$ alkenyl substituted with 1-4 $R^{11}$, $(CR^{12}R^{12})_q$—$C_{2-6}$ alkynyl substituted with 1-4 $R^{11}$, $(CR^{12}R^{12})_q$—$C_{3-7}$ cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

each occurrence of $R^{11}$ is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

each occurrence of $R^{12}$ is independently hydrogen, $C_{1-4}$alkyl, $C_{3-7}$cycloalkyl, or $R^{12}$ and $R^{12}$, together with the carbon atom to which they are attached, form a 3-6-membered cycloalkyl ring;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

t is 0, 1, 2 or 3;

p at each occurrence is independently 1, 2, 3 or 4; and q at each occurrence is independently 0, 1, 2, 3 or 4.

In some embodiments, the compound of Formula I includes a compound of Formula (IIIc) or (IIIcc):

(IIIc)

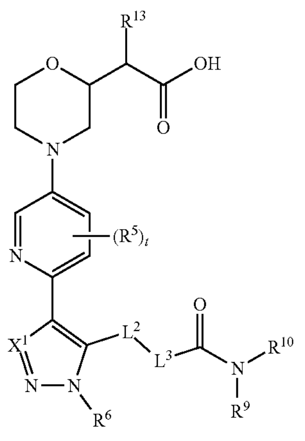

or

-continued (IIIcc)

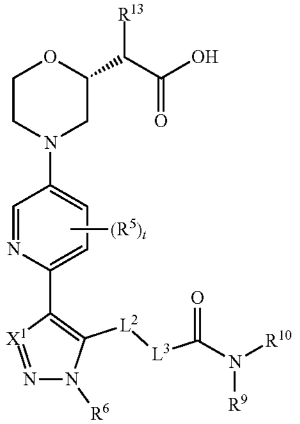

or a pharmaceutically acceptable salt, tautomer or stereoisomer thereof, wherein:

$L^2$ is a covalent bond or $(CR^7R^7)_p$;

$L^3$ is a covalent bond, O or $NR^7$, provided that at least one of $L^2$ and $L^3$ is not a covalent bond;

$X^1$ is N, or $CR^{6a}$;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

$R^7$ at each occurrence is independently hydrogen, $C_{1-4}$alkyl, $C_{3-5}$cycloalkyl, or $R^7$ and $R^7$, together with the carbon atom to which they are attached, form a 3-5-membered cycloalkyl ring;

each occurrence of $R^9$ and $R^{10}$ is independently hydrogen, $C_{1-6}$alkyl substituted with 1-4 $R^{11}$, $(CR^{12}R^{12})_q$—$C_{2-6}$ alkenyl substituted with 1-4 $R^{11}$, $(CR^{12}R^{12})_q$—$C_{2-6}$ alkynyl substituted with 1-4 $R^{11}$, $(CR^{12}R^{12})_q$—$C_{3-7}$ cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or $R^{12}$ and $R^{12}$, together with the carbon atom to which they are attached, form a 3-6-membered cycloalkyl ring;

$R^{13}$ at each occurrence is independently hydrogen, $C_{1-4}$alkyl, or $C_{3-5}$cycloalkyl;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

t is 0, 1, 2 or 3;

p at each occurrence is independently 1, 2, 3 or 4; and q at each occurrence is independently 0, 1, 2, 3 or 4.

In some embodiments, the compound of Formula I includes a compound of Formula (IIId) or (IIIdd):

(IIId)

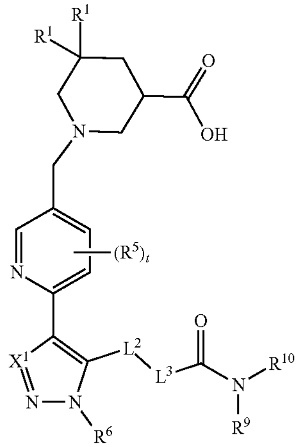

or (IIIdd)

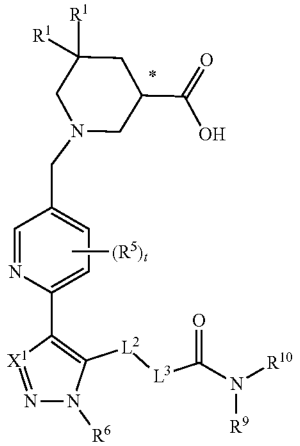

or a pharmaceutically acceptable salt, tautomer or stereoisomer thereof, wherein:

* in Formula (IIIdd) represents a chiral center with R or S configuration;

$L^2$ is a covalent bond or $(CR^7R^7)_p$;

$L^3$ is a covalent bond, O or $NR^7$, provided that at least one of $L^2$ and $L^3$ is not a covalent bond;

$X^1$ is N, or $CR^{6a}$;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C═O;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

$R^{6a}$ is hydrogen, or methyl;

$R^6$ is hydrogen, halogen, CN, methyl, ethyl, propyl, or cyclopropyl;

each occurrence of $R^7$ is independently hydrogen, $C_{1-4}$alkyl, $C_{3-5}$cycloalkyl, or $R^7$ and $R^7$, together with the carbon atom to which they are attached, form a 3-5-membered cycloalkyl ring;

each occurrence of $R^9$ and $R^{10}$ is independently hydrogen, $C_{1-6}$alkyl substituted with 1-4 $R^{11}$, $(CR^{12}R^{12})_q$—$C_{2-6}$ alkenyl substituted with 1-4 $R^{11}$, $(CR^{12}R^{12})_q$—$C_{2-6}$ alkynyl substituted with 1-4 $R^{11}$, $(CR^{12}R^{12})_q$—$C_{3-7}$ cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

each occurrence of $R^{11}$ is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

each occurrence of $R^{12}$ is independently hydrogen, $C_{1-4}$alkyl, $C_{3-7}$cycloalkyl, or $R^{12}$ and $R^{12}$, together with the carbon atom to which they are attached, form a 3-6-membered cycloalkyl ring;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

t is 0, 1, 2 or 3;

p at each occurrence is independently 1, 2, 3 or 4; and q at each occurrence is independently 0, 1, 2, 3 or 4.

In any embodiments, Z is $CH_2$. In certain other embodiments, Z is O.

In any embodiments, $L^1$ is a covalent bond. In certain other embodiments, $L^1$ is $CH_2$ optionally substituted with 1-2 methyl. In yet other embodiments, $L^1$ is $CH_2$.

In any embodiments, $L^1$ is a covalent bond, and w is 1. In certain other embodiments, $L^1$ is $CH_2$ optionally substituted with 1-2 methyl, and w is 0.

In any embodiments, each occurrence of $R^1$ is independently hydrogen. In certain other embodiments, each occurrence of $R^1$ is independently halogen. In yet other embodiments, m is 2, one $R^1$ is hydrogen, and the other $R^1$ is halogen. In yet other embodiments, m is 2, one $R^1$ is hydrogen, and the other $R^1$ is F. In yet other embodiments, each occurrence of $R^1$ is independently F.

In any embodiments, $Y^2$ is N, and each of $Y^1$, $Y^3$ and $Y^4$ is independently $CR^5$. In certain other embodiments, $Y^1$ is $CR^5$, $Y^2$ is N, and each of $Y^3$ and $Y^4$ is independently CH. In yet other embodiments, $Y^1$ is $CR^5$, $Y^2$ is N, $Y^3$ is N, and $Y^4$ CH.

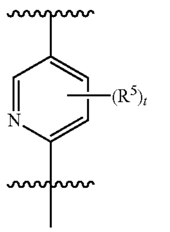

In any embodiments, the moiety in Formulae (II), (IIa), (IIaa), (IIb), (IIbb), (IIc), (IIcc), (IId), (IIdd), and (III), (IIIa), (IIIaa), (IIIb), (IIIbb), (IIIc), (IIIcc), (IIId), and (IIIdd), is

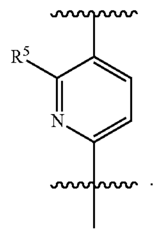

In any embodiments, $R^5$ is methyl or ethyl. In certain other embodiments, $R^5$ is $CHF_2$ or $CF_3$. In yet other embodiments, $R^5$ is hydrogen, or CN.

In any embodiments, t is 0. In certain other embodiments, t is 1. In yet other embodiments, t is 2. In yet other embodiments, t is 3.

In any embodiments, $X^1$ is N, $X^2$ is N, and $X^3$ is $NR^6$. In certain other embodiments, $X^1$ is CH, $X^2$ is N, and $X^3$ is $NR^6$. In yet other embodiments, $X^1$ is 0, $X^2$ is N, and $X^3$ is $CR^6$.

In any embodiments, $R^6$ is hydrogen. In certain other embodiments, $R^6$ is methyl. In yet other embodiments, $R^6$ is ethyl. In yet other embodiments, $R^6$ is cyclopropyl.

In any embodiments, $R^{6a}$ is hydrogen. In certain other embodiments, $R^{6a}$ is methyl. In yet other embodiments, $R^{6a}$ is ethyl. In yet other embodiments, $R^{6a}$ is cyclopropyl.

In any embodiments, $L^2$ is a covalent bond. In certain other embodiments, $L^2$ is $(CR^7R^7)_p$. In yet other embodiments, $L^2$ is $CH_2$.

In any embodiments, $L^3$ is a covalent bond. In certain other embodiments, $L^3$ is O. In yet other embodiments, $L^3$ is $NR^7$.

In any embodiments, each occurrence of $R^7$ is independently hydrogen. In certain other embodiments, each occurrence of $R^7$ is independently $C_{1-4}$alkyl. In yet other embodiments, each occurrence of $R^7$ is independently $C_{3-5}$cycloalkyl. In yet other embodiments, each occurrence of $R^7$ is independently hydrogen or methyl.

In any embodiments, q is 0. In certain other embodiments, q is 1. In yet other embodiments, q is 2.

In any embodiments, $R^8$ is COOH.

In any embodiments, $R^9$ is $C_{1-4}$alkyl. In certain other embodiments, $R^9$ is methyl. In yet other embodiments, $R^9$ is ethyl.

In any embodiments, $R^{10}$ is $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$. In certain other embodiments, $R^{10}$ is $C_{1-6}$alkyl. $R^{10}$ is $(CH_2)_p$—$C_{3-7}$cycloalkyl. In yet other embodiments, $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur.

In any embodiments, Q is $C(=O)NR^9R^{10}$. In certain other embodiments, Q is a ring (also referred to herein the "Q ring") selected from the group consisting of 5-membered heteroaryl, 5-membered heterocyclyl, 6-membered heteroaryl, and 6-membered heterocyclyl, wherein the ring comprises at least on carbon atom, at least one nitrogen atom and optionally 1-3 heteroatoms selected from nitrogen, oxygen and sulfur wherein oxygen may be a ring member and/or an oxo attached to a ring member, and wherein the ring is substituted with $(R^3)_n$ and $R^4$.

In any embodiments, Q is

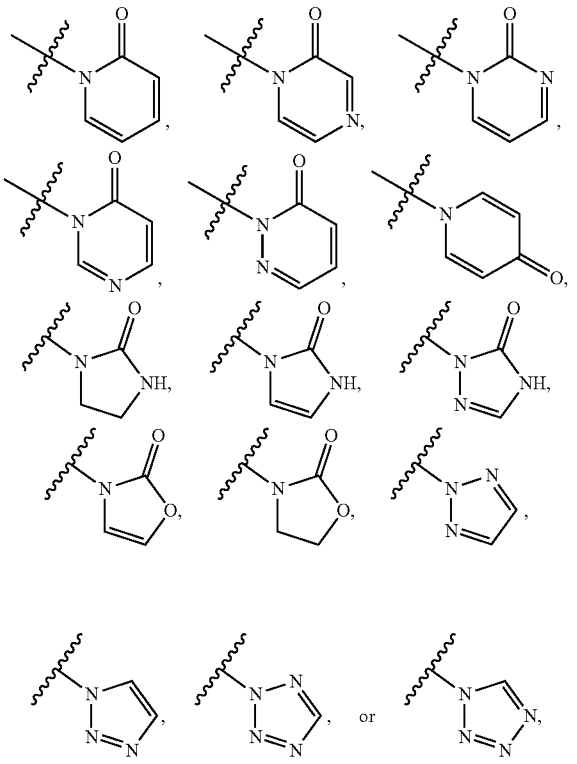

and each of which is substituted with $(R^3)_n$ and one $R^4$ at any available carbon or nitrogen position.

In any embodiments, Q is

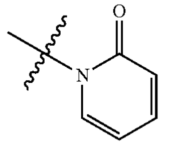 [SMILES: *n1ccccc1=O]

substituted with $(R^3)_n$ and one $R^4$ at any available carbon position.

In any embodiments, Q is

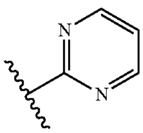, 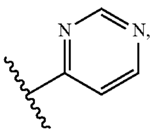 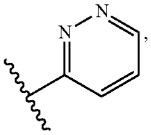,

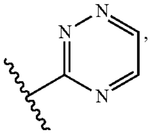, 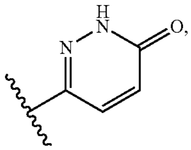 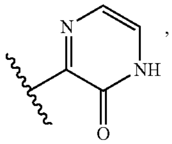,

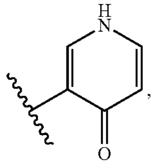, 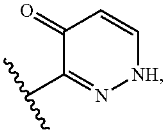 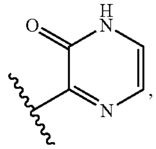,

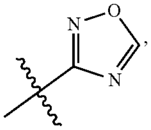, 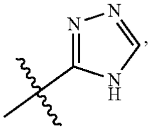, 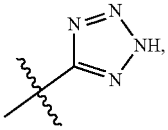

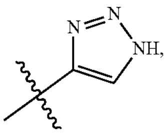 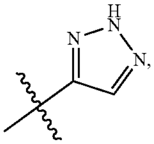 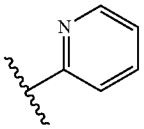, or

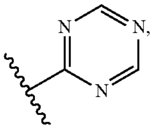

and each of which is substituted with $(R^3)_n$ and one $R^4$ at any available carbon or nitrogen position.

In any embodiments, each occurrence of $R^3$ is independently hydrogen, halogen, or $C_{1-4}$alkyl. In certain other embodiments, each occurrence of $R^3$ is independently $C_{1-4}$alkyl. In yet other embodiments, each occurrence of $R^3$ is independently methyl.

In any embodiments, n is 0. In certain other embodiments, n is 1. In yet other embodiments, n is 2.

In any embodiments, $R^4$ is independently hydrogen, $C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$ cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy. In certain other embodiments, $R^4$ is independently $(CH_2)_q$-5-6-membered heteroaryl ring substituted with 1-4 $R^{11}$, or $(CH_2)_q$-5-7-membered heterocyclyl ring substituted with 1-4 $R^{11}$. In yet other embodiments, $R^4$ is independently $C_{1-6}$alkyl, $C_{2-6}$alkynyl, $C_{1-6}$alkoxy, $(CH_2)_p$—$C_{1-6}$alkoxy, $C_{3-7}$cycloalkyl, $(CH_2)_p$—$C_{3-7}$cycloalkyl, or $C_{2-6}$alkenyl-$C_{3-7}$ cycloalkyl.

In any embodiments, each occurrence of $R^{11}$ is independently hydrogen. In certain other embodiments, each occurrence of $R^{11}$ is independently $C_{1-6}$alkyl. In yet other embodiments, each occurrence of $R^{11}$ is independently $C_{1-6}$alkoxy. In yet other embodiments, each occurrence of $R^{11}$ is independently $(CH_2)_p$—$C_{1-6}$alkox. In yet other embodiments, each occurrence of $R^{11}$ is independently phenyl. In yet other embodiments, each occurrence of $R^{11}$ is independently $(CH_2)_p$-phenyl. In yet other embodiments, each occurrence of $R^{11}$ is independently $C_{3-7}$cycloalkyl. In yet other embodiments, each occurrence of $R^{11}$ is independently $(CH_2)_p$—$C_{3-7}$cycloalkyl. In yet other embodiments, each occurrence of $R^{11}$ is independently $C_{2-6}$alkynyl-$C_{3-7}$cycloalkyl. In yet other embodiments, each occurrence of $R^{11}$ is independently $O(CH_2)_p$—$C_{3-7}$cycloalkyl. In any embodiments, each phenyl is independently optionally substituted with 1-3 of halogen, $C_{1-6}$alkyl, or $C_{1-6}$alkoxy.

In any embodiments, each occurrence of $R^{12}$ is independently hydrogen. In certain other embodiments, each occurrence of $R^{12}$ is independently $C_{1-4}$alkyl. In yet other embodiments, each occurrence of $R^{12}$ is independently $C_{3-7}$cycloalkyl. In yet other embodiments, $R^{12}$ and $R^{12}$, together with the carbon atom to which they are attached, form a 3-6-membered cycloalkyl ring.

In any embodiments, each occurrence of $R^a$ and $R^b$ is independently hydrogen. In certain other embodiments, each occurrence of $R^a$ and $R^b$ is independently $C_{1-6}$alkyl. In yet other embodiments, each occurrence of $R^{12}$ is independently $C_{3-7}$cycloalkyl. In yet other embodiments, $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl.

In any embodiments, the

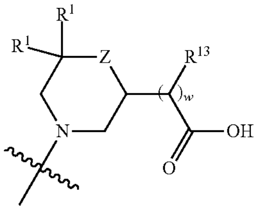

moiety in Formula (II) and (III) is

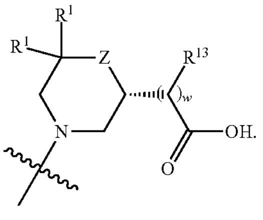

In certain other embodiments, the
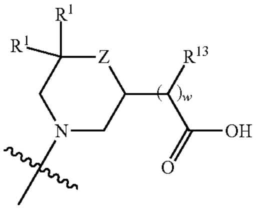
moiety in Formula (II) and (III) is
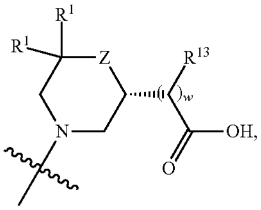
and w is 1.
In any embodiments, $R^{13}$ is hydrogen. In certain other embodiments, $R^{13}$ is methyl. In yet other embodiments, $R^{13}$ is cyclopropyl.
In any embodiments, the compound is selected from:
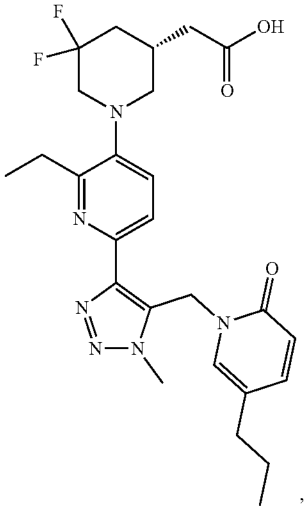
,
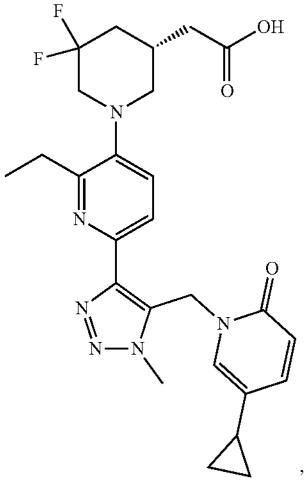
,
-continued
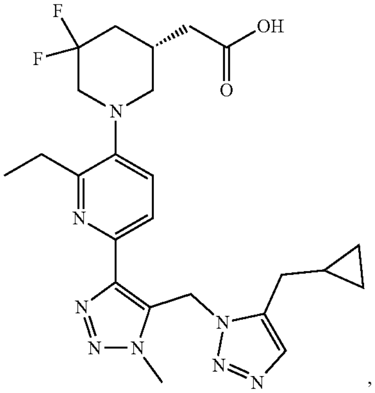
,
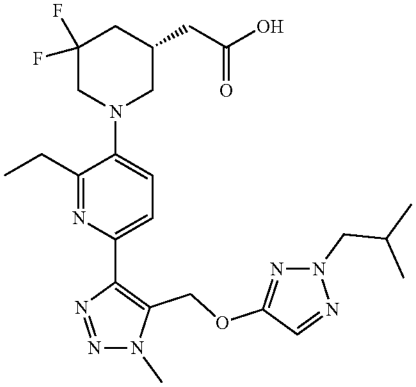
and
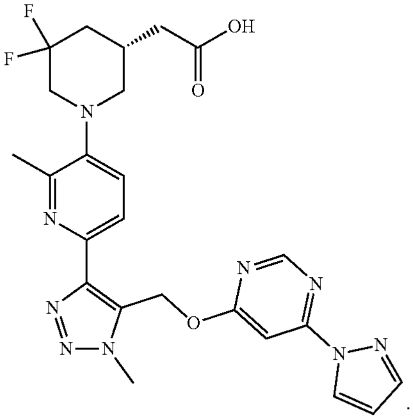
.
In any embodiments, the compound is selected from:
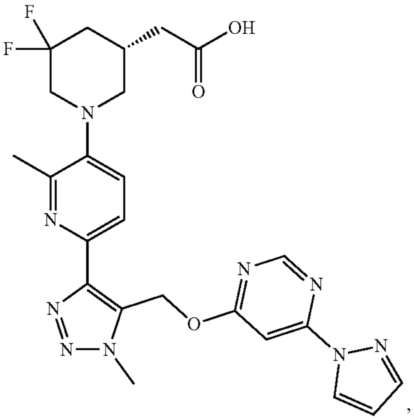
, -continued
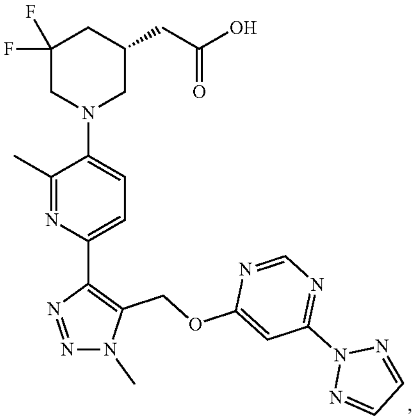,
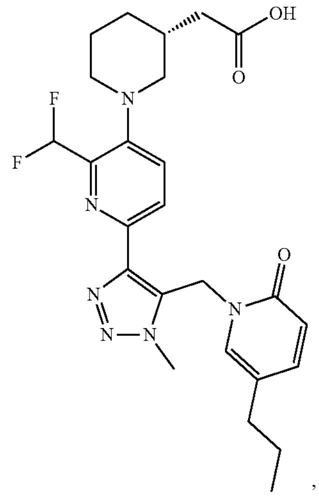,
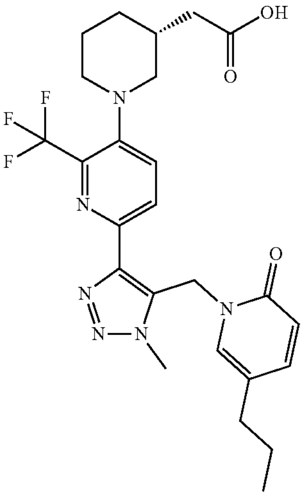 and
-continued
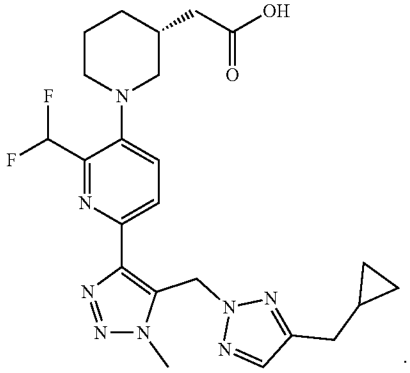.
In any embodiments, the compound is selected from:
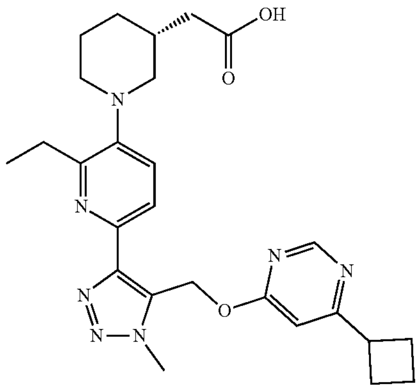,
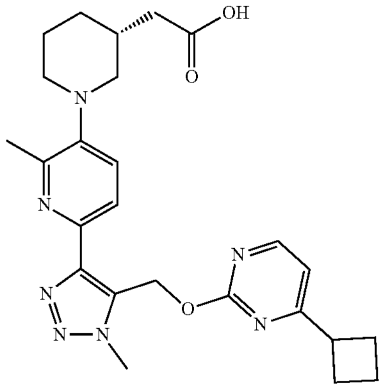,
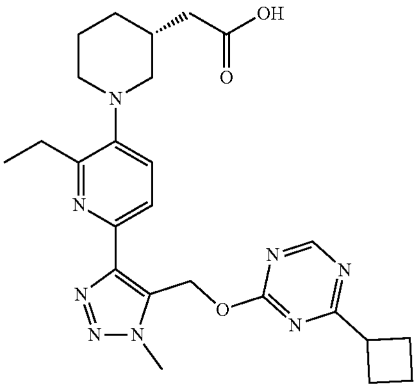, -continued

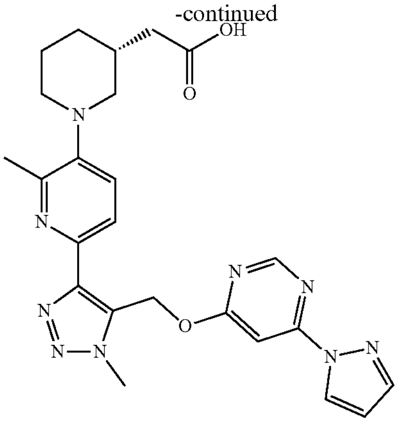

and

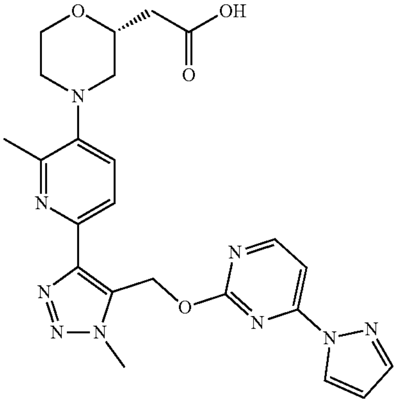

.

In any embodiments, the compound is selected from:

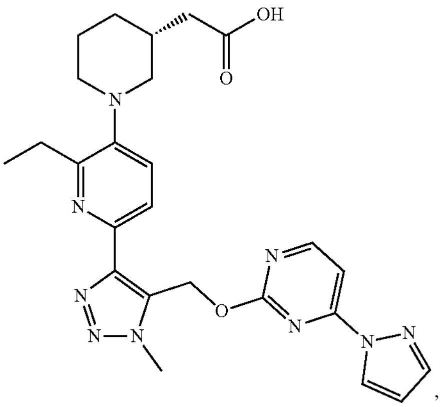

,

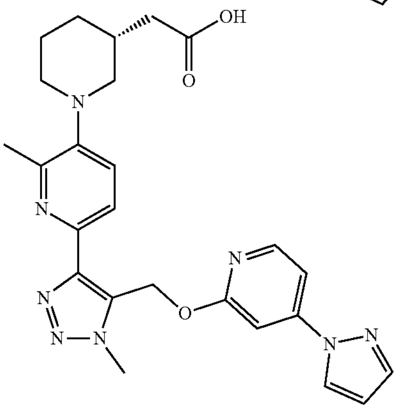

,

-continued

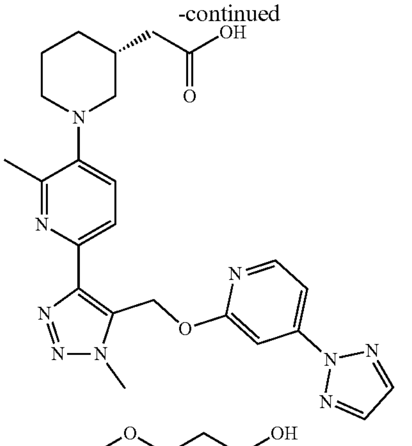

and

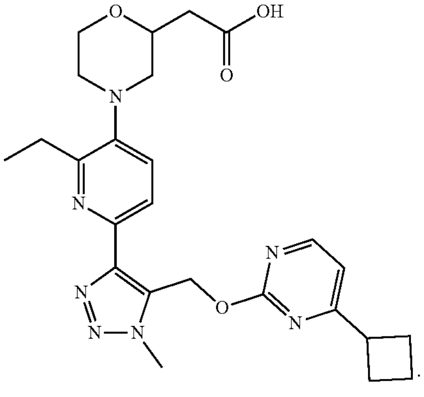

.

In another aspect, the present invention relates to a pharmaceutical composition comprising a compound disclosed herein, and a pharmaceutically acceptable carrier.

In yet another aspect, the present invention relates to a method for treating a disease associated with dysregulation of lysophosphatidic acid receptor 1 (LPAi) in a subject in need thereof, comprising administering an effective amount of a compound disclosed herein to the subject. In some embodiments, the disease is pathological fibrosis (e.g., pulmonary, liver, renal, cardiac, dernal, ocular, or pancreatic fibrosis), idiopathic pulmonary fibrosis (IPF), non-alcoholic steatohepatitis (NASH), non-alcoholic fatty liver disease (NAFLD), chronic kidney disease, diabetic kidney disease, or systemic sclerosis.

In yet another aspect, the present invention relates to a process of making a compound of Formulae (I), (II), (IIa), (IIaa), (IIb), (IIbb), (IIc), (IIcc), (IId), (IIdd), (III), (IIIa), (IIIaa), (IIIb), (IIIbb), (IIIc), (IIIcc), (IIId), and (IIIdd), including each exemplified compound and intermediates described herein.

In any embodiments, the present invention relates to an intermediate selected from:

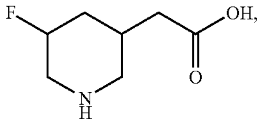

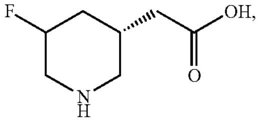

and

-continued

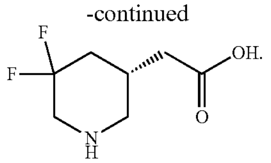

General Synthetic Methods

The compounds of the present invention can be synthesized using the methods described herein, together with synthetic methods known in the art of synthetic organic chemistry, or by variations thereon as appreciated by those skilled in the art. Proffered methods include, but are not limited to, those exemplary schemes and working examples described below. All substituents are as defined hereinabove unless otherwise indicated. The reactions are performed in a solvent or solvent mixture appropriate to the reagents and materials employed and suitable for the transformations proposed. This will sometimes require a judgment to modify the order of synthetic steps or to select on particular process scheme over another in order to obtain a desired compound of the invention.

It will be recognized that another major consideration in the planning of any synthetic route in this field is the judicious choice of the protecting group used for protection of the reactive functional groups present in the compounds described in this invention. An authoritative account describing the many alternatives to the trained practitioner is by Greene et al., Greene's Protective Groups in Organic Synthesis, Fifth Edition, Wiley (2014). It will also be recognized that the compound names referred to in the decryptions of Schemes 1-12 are for convenience only, and do not necessarily reflect the actual chemical names of those compounds.

Scheme 1

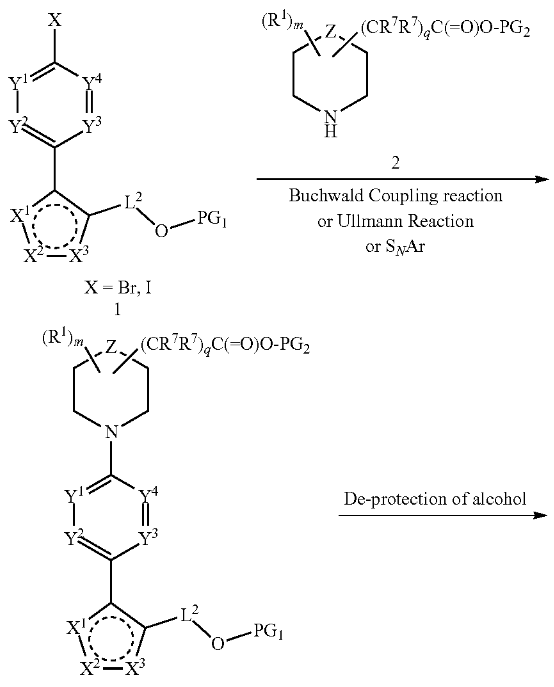

1
2
3

-continued

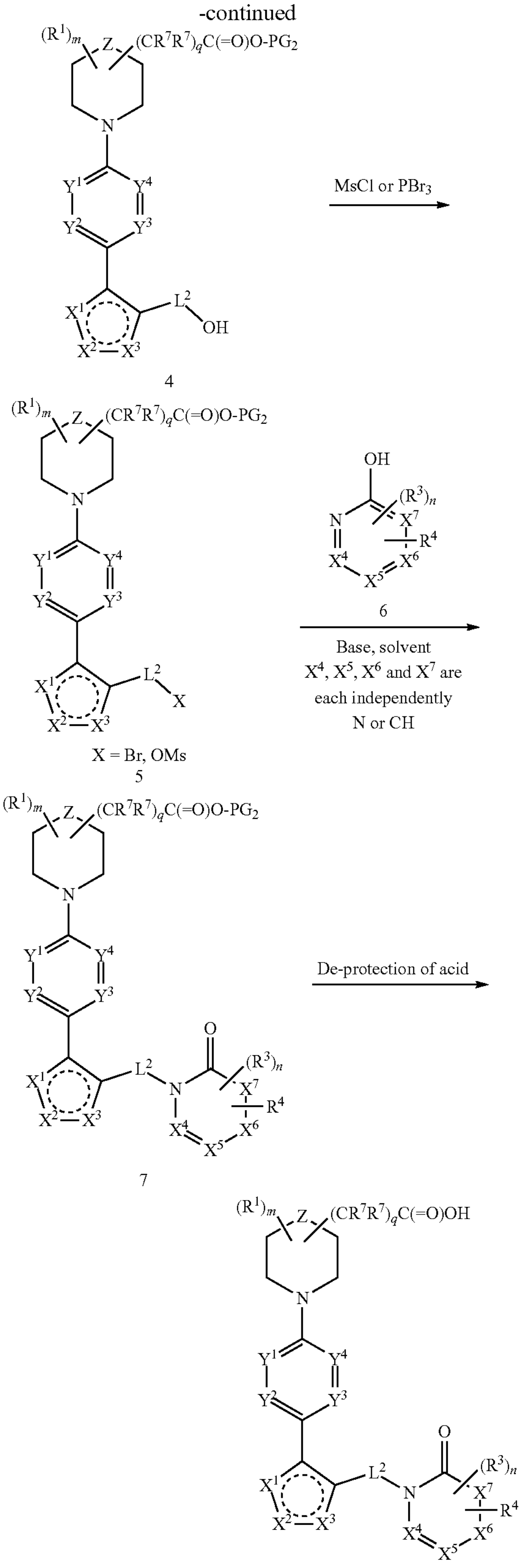

4
6
5
7
8

Scheme 1 describes the synthesis of carbonyl azine azole N-heteroaryl-azacyclohexyl acetic acids 8. $PG_1$ and $PG_2$ each represents a protecting group, and $L^2$ is $(CR^7R^7)_p$ (e.g., $CH_2$). The halo azine derivative 1 is reacted with piperidine acetic ester 2 under Buckwald conditions with appropriate catalyst (e.g. $Pd(OAc)_2$/BINAP) or nucleophilic aromatic substitution reaction or Ullmann reaction to give the corresponding carbonyl azine N-heteroaryl-piperidine acetic carboxylate 3. Deprotection of the protected hydroxylmethyl azole 3 provides the hydroxylmethyl azole 4, which is then reacted with MsCl (or $PBr_3$) to give the mesylate (or Br) 5. Treatment of the mesylate (or Br) 5 with 2-hydroxy azine 6 in the presence of an appropriate base (e.g. $K_2CO_3$, nucleophilic substitution reactions) gives the corresponding carbonyl azine N-heteroaryl-piperidine acetic carboxylate 7, which then undergoes ester deprotection to give the desired carbonyl azine $L^2$-azole N-heteroaryl-azacyclohexyl acetic acids 8.

-continued

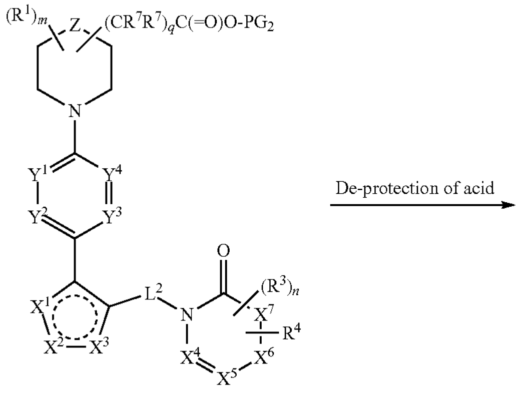

7

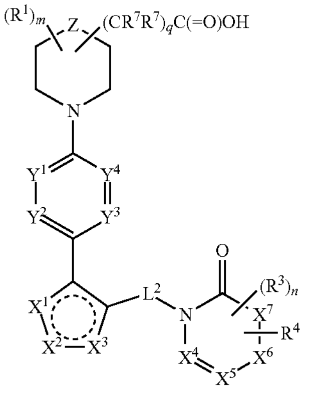

8

Scheme 2

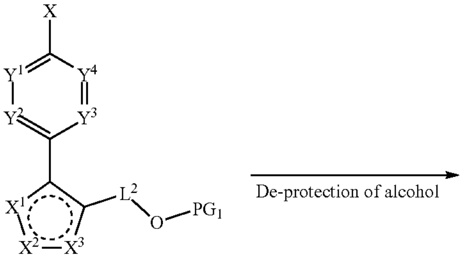

X = Br, I
1

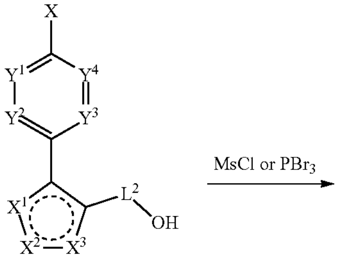

9

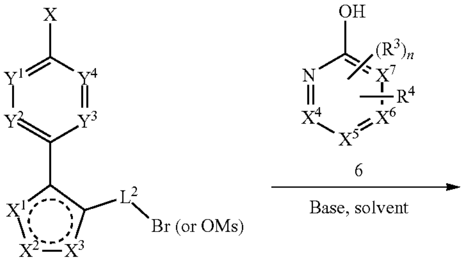

10

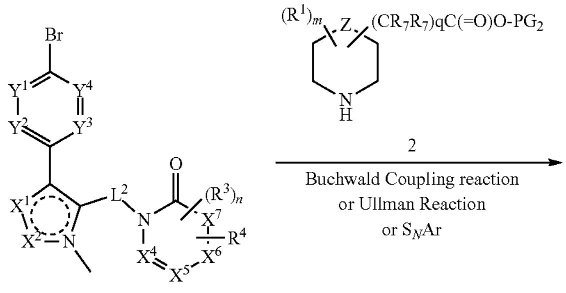

11

Scheme 2 describes an alternative synthetic route to the carbonyl azine N-heteroaryl-azacyclohexyl acetic acids 8. $PG_1$ and $PG_2$ each represents a protecting group, and $L^2$ is $(CR^7R^7)_p$ (e.g., $CH_2$). Deprotection of the protected hydroxylmethyl azole derivative 1 gives hydroxylmethyl azole 9, which is then reacted with MsCl (or $PBr_3$) to give the mesylate (or Br) 10. Treatment of mesylate (or Br) 10 with 2-hydroxy azine in the presence of an appropriate base (e.g. $K_2CO_3$, nucleophilic substitution reactions) gives the corresponding N-substituted carbonyl azine 11. The halo azine derivative 11 is reacted with piperidine acetic carboxylate under Buckwald conditions with appropriately catalyst (e.g. $Pd(OAc)_2$/BINAP) or nucleophilic aromatic substitution reaction or Ullmann reaction to give the corresponding piperidine acetic carboxylate 7, which then undergoes ester deprotection to give the desired carbonyl azine $L^2$-azole N-heteroaryl-azacyclohexyl acetic acids 8.

Scheme 3

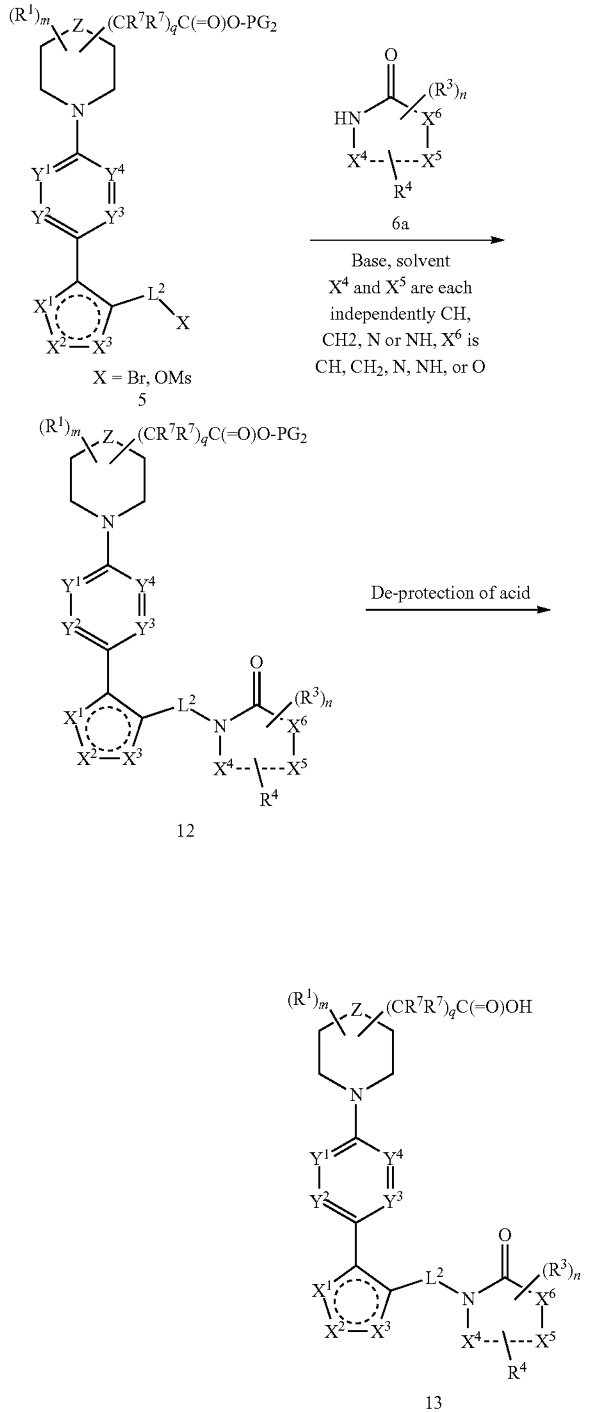

Scheme 4

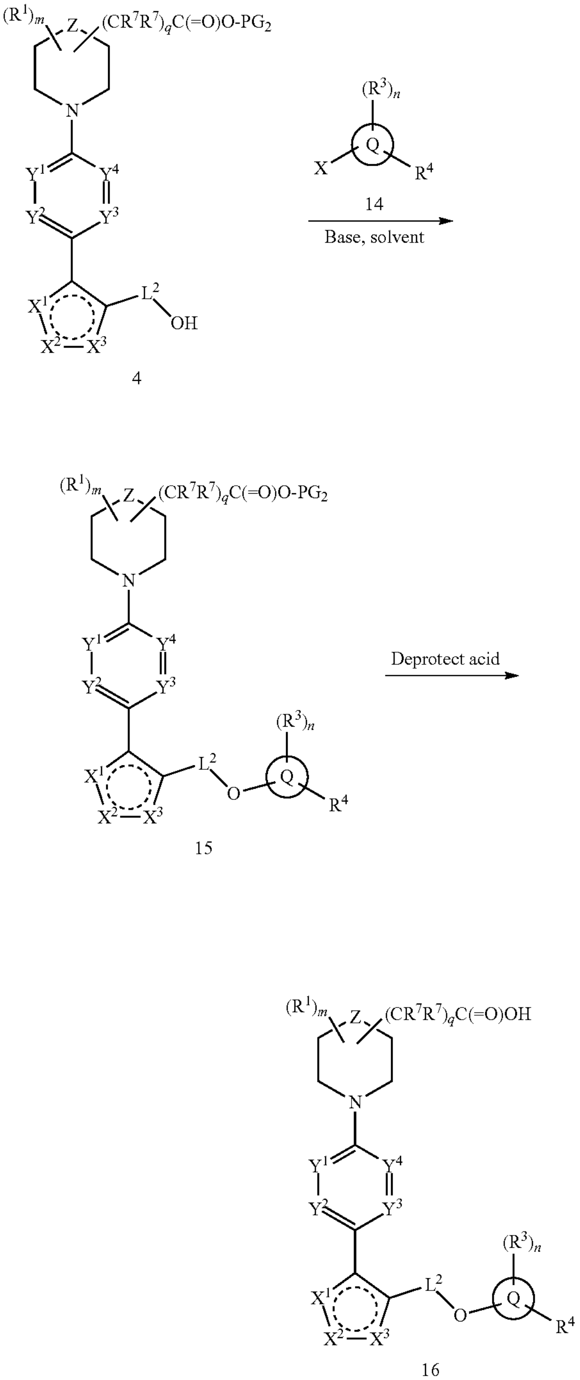

Scheme 3 describes the synthesis of N-substituted aza-heterocyclopentyl ketone N-heteroaryl-azacyclohexyl acetic acids 13. Treatment of the mesylate (or Br) 5 with aza-heterocyclopentyl ketone 6a in the presence of an appropriate base (e.g. t-BuOK, nucleophilic substitution reactions) gives the corresponding N-substituted aza-cyclopentyl ketone 12, which then undergoes ester deprotection to give the desired N-substituted aza-cyclopentyl ketone-N-heteroaryl-azacyclohexyl acetic acids 13.

Scheme 4 describes the synthesis of oxy-Q ring N-heteroaryl-azacyclohexyl acetic acid wherein Q represents a 5-membered heteroaryl or heterocyclyl or 6-membered heteroaryl or heterocyclyl. Base-mediated $S_NAr$ reaction of hydroxyl methyl azole 4 with an appropriate halo- or methylsulfonyl-substituted Q ring 14 (X is halo or methylsulfonyl) provides the oxy-Q ring N-heteroaryl piperidine acetic ester 15, which then undergoes ester deprotection to give the desired oxy-Q ring N-heteroaryl-azacyclohexyl acetic acids 16.

Scheme 5

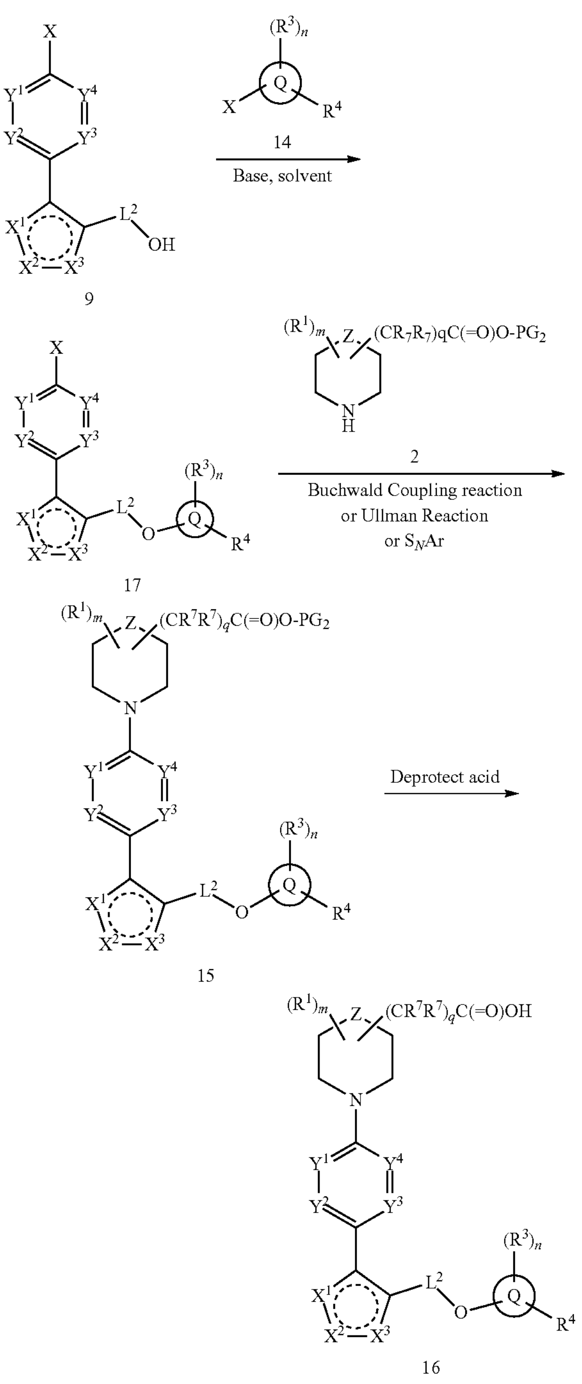

Scheme 5 describes an alternative synthesis of oxy-Q ring N-heteroaryl-azacyclohexyl acetic acid 16, wherein Q represents a 5-membered heteroaryl or heterocyclyl or 6-membered heteroaryl or heterocyclyl. Base-mediated $S_NAr$ reaction of hydroxylmethyl azole 9 with an appropriate halo- or methylsulfonyl-substituted Q ring 14 (X is halo or methylsulfonyl) provides the oxy-Q ring 17, which is reacted with piperidine ethyl ester derivative under Buckwald conditions with appropriately catalyst (e.g. $Pd(OAc)_2$/BINAP) or nucleophilic aromatic substitution reaction or Ullmann reaction to give the corresponding oxy-Q ring N-heteroaryl piperidine acetic ester 15, which then undergoes ester deprotection to give the desired oxy-Q ring N-heteroaryl-azacyclohexyl acetic acids 16.

Scheme 6

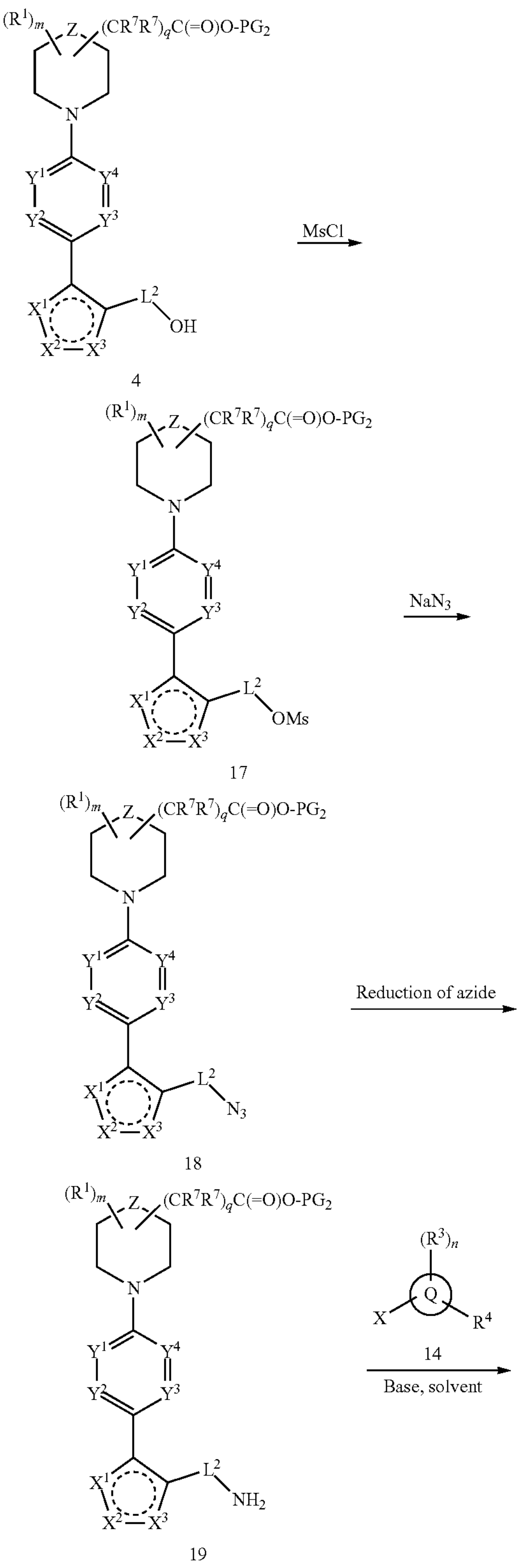

-continued

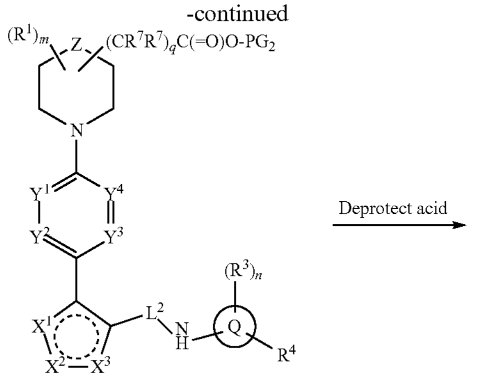

20

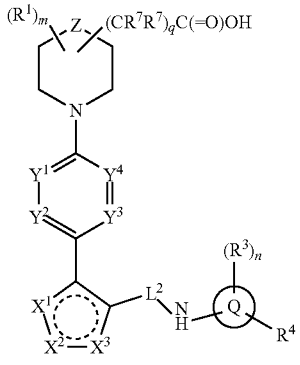

21

Scheme 6 describes the synthesis of amino-Q ring N-heteroaryl-azacyclohexyl acetic acids 21. The hydroxylmethyl azole 4 is reacted with MsCl with appropriately base (e.g. TEA) to give the corresponding mesylate 17. Displacement of the mesylate 17 with $NaN_3$ (or other azide reagent) gives azide 18, which then undergoes reduction (e.g. Staudinger reduction with $PPh_3$/water) to give the amine 19. Amine 19 is then reacted with halo- or methylsulfonyl-substituted Q ring 14 (X is halo or methylsulfonyl) in the presence of an appropriate base or via Pd catalyzed amination to give amino-azine piperidine acetic ester 20, which then undergoes ester deprotection to give the desired amino-Q ring N-heteroaryl-azacyclohexyl acetic acids 21.

-continued

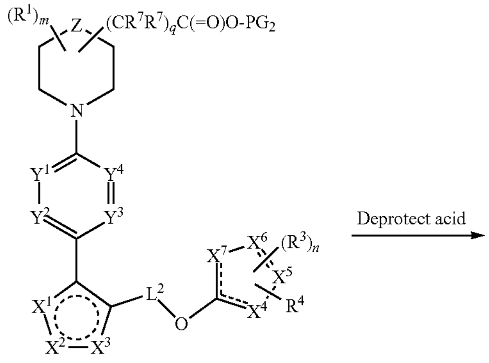

23

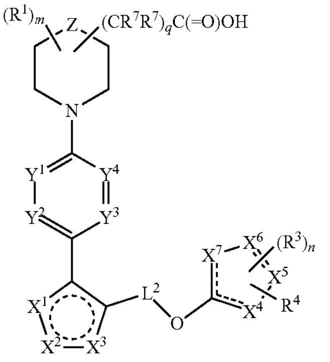

24

Scheme 7 describes the synthesis of oxy-azole N-heteroaryl-azacyclohexyl acetic acids 24. The hydroxylmethyl azole 4 is reacted with an appropriate haloazole or methylsulfonyl azole 22 (which is a 5-membered heteroaryl ring that contains at least one nitrogen and may contain additional 1-3 heteroatoms selected from N, O and S) in the presence of an appropriate base (nucleophilic aromatic substitution reaction) to give oxy-azole N-heteroaryl piperidine acetic ester 23, which then undergoes ester deprotection to give the desired oxy-azole N-heteroaryl-azacyclohexyl acetic acids 24.

Scheme 7

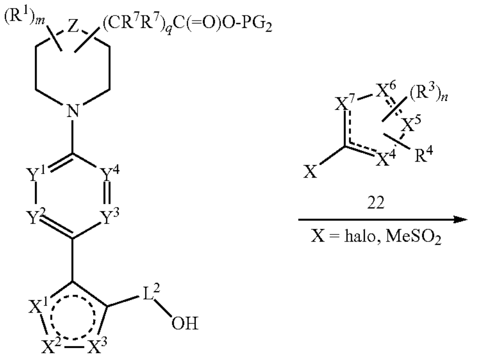

22

4

Scheme 8

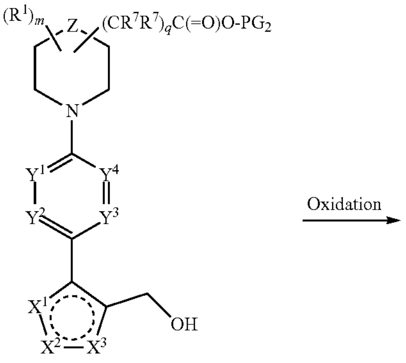

4a

-continued

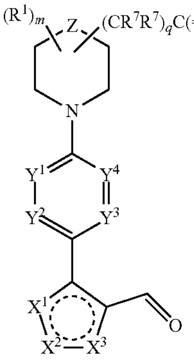

25

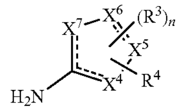

26

Reductive Amination

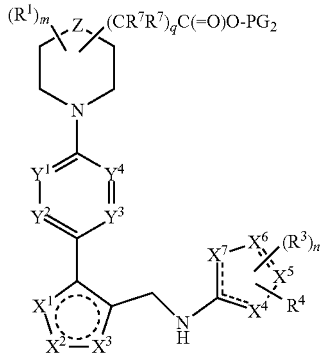

27

Deprotect acid

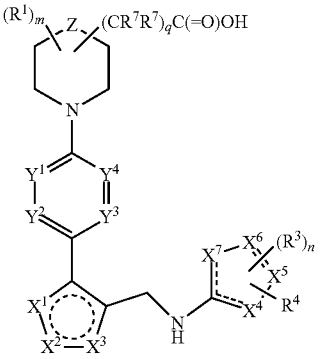

28

Scheme 8 describes the synthesis of amino-azole N-heteroaryl-azacyclohexyl acetic acids 28. The hydroxylmethyl azole 4a is oxidized to the corresponding aldehyde 25 (e.g. with Dess-Martin periodinane or Swern Oxidation). The aldehyde 25 can then undergo reductive amination with an appropriate amino-azole 26 (which is a 5-membered heteroaryl ring that contains at least one nitrogen and may contain additional 1-3 heteroatoms selected from N, O and S) to give amino-azole N-heteroaryl piperidine acetic ester 27. Subsequent deprotection of ester 27 provides the amino-azole N-heteroaryl-azacyclohexyl acetic acids 28.

Scheme 9

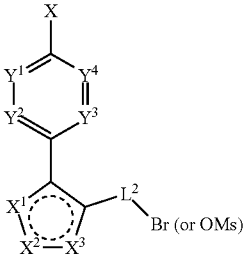

10

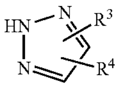

29

Base, solvent

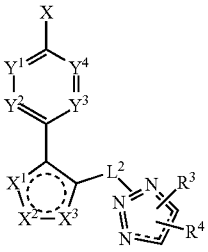

30

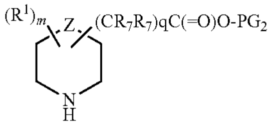

2

Buchwald Coupling reaction
or Ullman Reaction
or $S_NAr$

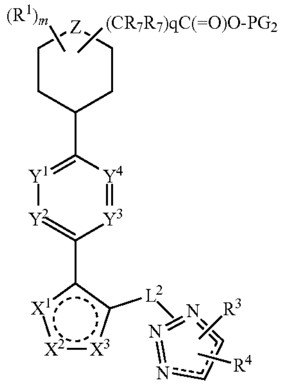

31

Deprotect acid

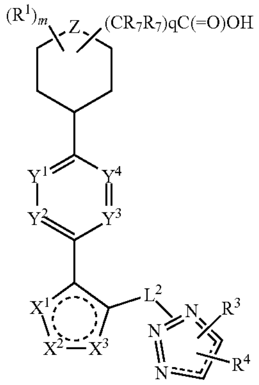

32

Scheme 9 describes the synthesis of alkylated-triazole N-heteroaryl-azacyclohexyl acetic acids 32. Treatment of the mesylate or Br-substituted compound 10 with triazole 29 in the presence of appropriate base gives the alkylated triazole 30. The halo-azine 30 is then reacted with piperidine acetic ester 2 under Buckwald conditions with appropriately catalyst (e.g. $Pd(OAc)_2$/BINAP) to give the corresponding alkylated-triazole N-heteroaryl piperidine acetic ester 31, which then undergoes ester deprotection to give the desired alkylated-triazole N-heteroaryl-azacyclohexyl acetic acids 32.

Scheme 10
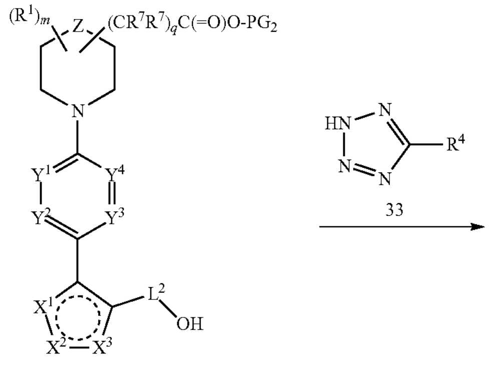
4 33
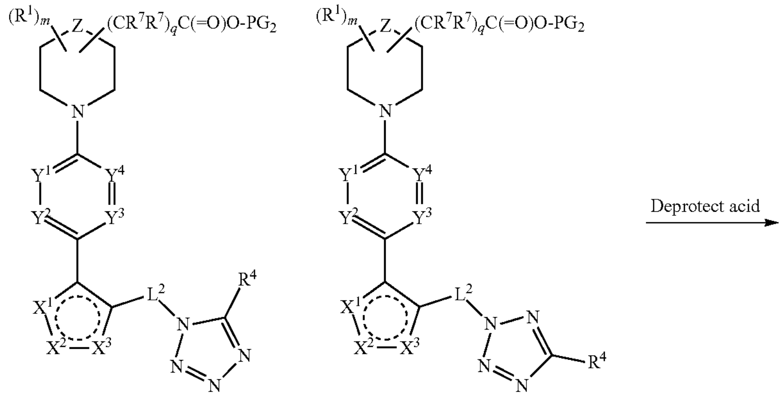
34 35
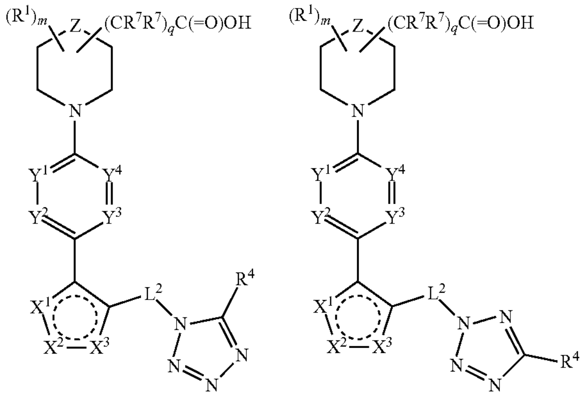
36 37

Scheme 10 describes the synthesis of alkylated-tetrazole N-heteroaryl-azacyclohexyl acetic acids 36 and 37. The hydroxylmethyl azole 4 is reacted with tetrazole 33 under Mitsunobu conditions to provide the regioisomeric tetrazoles 34 and 35. Deprotection piperidine acetic ester 34 and 35 provides the regioisomeric alkylated-tetrazole N-heteroaryl-azacyclohexyl acetic acids 36 and 37.

Scheme 11

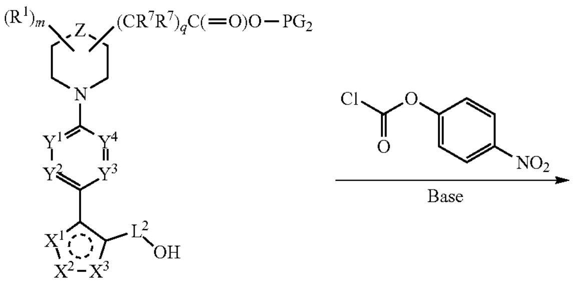

4

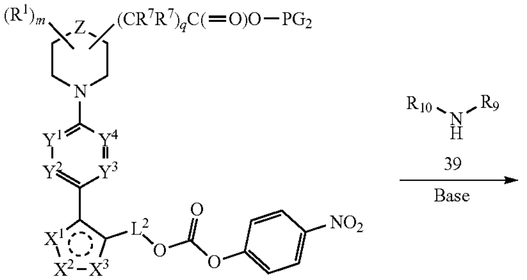

38

-continued

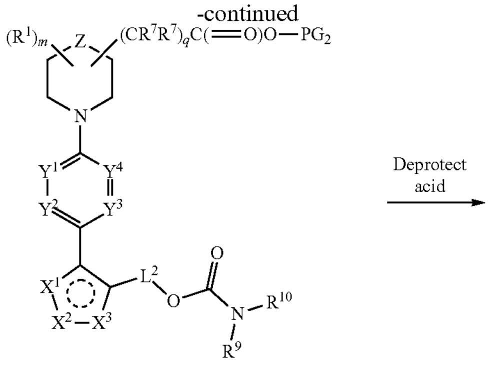

40

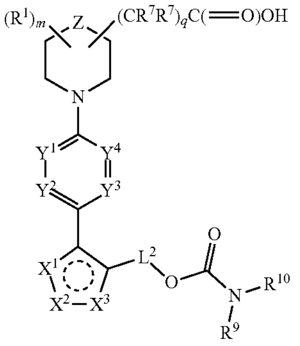

41

Scheme 11 describes the synthesis of carbamoyloxymethyl azole N-heteroaryl-azacyclohexyl acetic acids 41. The hydroxylmethyl azole 4 is reacted with 4-nitrophenyl chloroformate in the presence of an appropriate base to give the corresponding 4-nitrophenyl carbonate 38, which is then reacted with an amine 39 in the presence of an appropriate base to give the carbamate 40. Subsequent deprotection of ester 40 provides the carbamoyloxymethyl azole N-heteroaryl-azacyclohexyl acetic acids 41.

Scheme 12

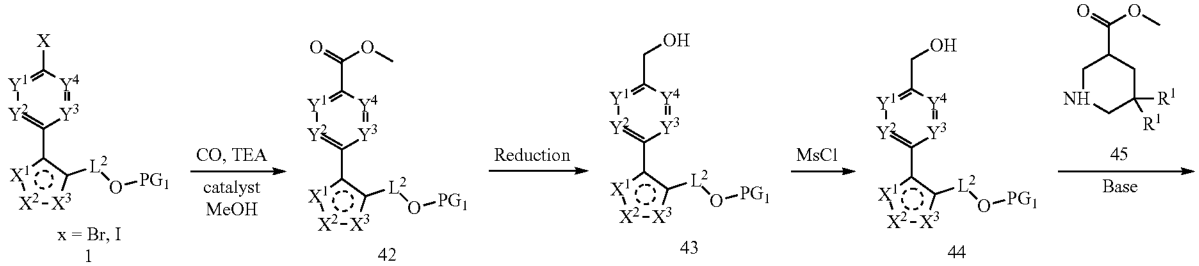

x = Br, I
1

42

43

44

-continued

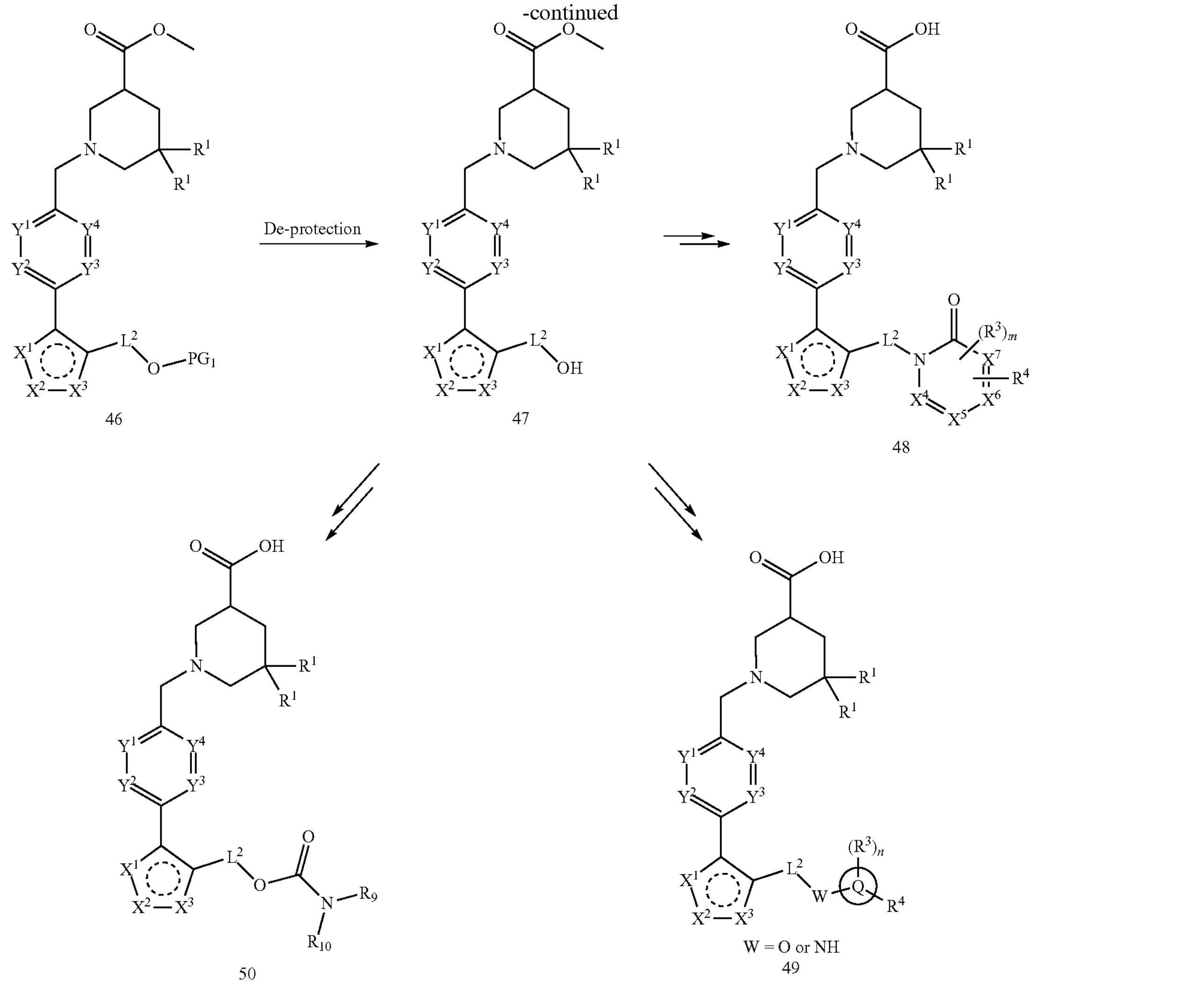

46 47 48 50 W = O or NH 49

Scheme 12 describes the synthesis of 1-aminomethyl-piperidine-3-carboxylic acids 48, 49 and 50. Carbonyl insertion of azine halide 1 in the presence of CO gas and appropriate catalyst in methanol gives azine carboxylate 42, which is then reduced with appropriate reductant to give azine methyl alcohol 43. Treatment of azine methyl alcohol 43 with MsCl in the presence of appropriate base gives the corresponding mesylate 44. Alkylation piperidine carboxylate 45 with mesylate 44 in the presence appropriate base affords azine methyl-piperidine-3-carboxylate 46. Deprotection of azine methyl-piperidine-3-carboxylate 46 gives hydroxylmethyl azole 47, which is then converted to corresponding acids 48, 49 and 50 using similar methods as described herein over several steps.

Pharmaceutical Compositions and Methods

The compounds utilized in the methods described herein may be formulated together with a pharmaceutically acceptable carrier or adjuvant into pharmaceutically acceptable compositions prior to be administered to a subject. In another embodiment, such pharmaceutically acceptable compositions further comprise additional therapeutic agents in amounts effective for achieving a modulation of disease or disease symptoms, including those described herein.

The term "pharmaceutically acceptable carrier or adjuvant" refers to a carrier or adjuvant that may be administered to a subject, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

The compounds described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.5 to about 100 mg/kg of body weight, alternatively dosages between 1 mg and 1000 mg/dose, every 4 to 120 hours, or according to the requirements of the drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any subject will depend upon a variety of factors, including the activity of the specific compound employed, the age, body weight, general health status, sex, diet, time of administration, rate of excretion, drug combination, the severity and course of the disease, condition or symptoms, the subject's disposition to the disease, condition or symptoms, and the judgment of the treating physician.

Upon improvement of a subject's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Subjects may, however, require intermittent treatment on a long-term basis upon any recurrence of disease symptoms.

The pharmaceutical compositions described above comprising a compound of Formula (I) may further comprise another therapeutic agent useful for treating a disease associated with dysregulation of lysophosphatidic acid receptor 1 (LPAi). In particular, such combination may be useful for treating pathological fibrosis (e.g., pulmonary, liver, renal, cardiac, dernal, ocular, or pancreatic fibrosis), idiopathic pulmonary fibrosis (IPF), non-alcoholic steatohepatitis (NASH), non-alcoholic fatty liver disease (NAFLD), chronic kidney disease, diabetic kidney disease, or systemic sclerosis.

All publications, patents, and patent applications mentioned in this specification are herein incorporated by reference to the same extent as if each individual publication, patent, or patent application was specifically and individually indicated to be incorporated by reference. In case of conflict, the present application, including any definitions herein, will control.

The examples herein are provided to illustrate advantages of the present technology and to further assist a person of ordinary skill in the art with preparing or using the compounds of the present technology or salts, pharmaceutical compositions, derivatives, solvates, metabolites, prodrugs, racemic mixtures or tautomeric forms thereof. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

Abbreviations used herein are as follows:

| Abbrv. | Full Name | Abbrv. | Full Name |
|---|---|---|---|
| anhy. | anhydrous | aq. | aqueous |
| min | minute(s) | satd. | saturated |
| mL | milliliter | hrs | hours |
| mmol | millimole(s) | mol | mole(s) |
| MS | mass spectrometry | NMR | nuclear magnetic resonance |
| TLC | thin layer chromatography | HPLC | high-performance liquid chromatography |
| LCMS | Liquid chromatography-mass spectrometry | PPTS | Pyridinium p-Toluenesulfonate |
| DCE | 1,2-dichloroethane | $CHCl_3$ | chloroform |
| DCM | dichloromethane | DMF | dimethylformamide |
| $Et_2O$ | diethyl ether | EtOH | ethyl alcohol |
| EtOAc | ethyl acetate | MeOH | methyl alcohol |
| MeCN | acetonitrile | PE | petroleum ether |
| THF | tetrahydrofuran | DMSO | dimethyl sulfoxide |
| AcOH | acetic acid | HCl | hydrochloric acid |
| $H_2SO_4$ | sulfuric acid | $NH_4Cl$ | ammonium chloride |
| KOH | potassium hydroxide | NaOH | sodium hydroxide |
| $K_2CO_3$ | potassium carbonate | $Na_2CO_3$ | sodium carbonate |
| TFA | trifluoroacetic acid | $Na_2SO_4$ | sodium sulfate |
| $NaBH_4$ | sodium borohydride | $NaHCO_3$ | sodium bicarbonate |
| LiHMDS | lithium hexamethyldisilylamide | $NaBH_4$ | sodium borohydride |
| $Et_3N$ or TEA | Triethylamine | Py or Pyr | pyridine |
| TBAF | Tetrabutylammonium fluoride | MsCl | Methanesulfonyl chloride |
| BnBr | Benzyl bromide | DHP | 3,4-Dihydro-2H-pyran |
| Cbz | carbobenzyloxy | m-CPBA | 3-Chloroperoxybenzoic acid |
| Dess-Martin | 1,1,1-Triacetoxy-1,1-Dihydro-1,2-Benziodoxol-3(1H)-On | DIAD | Diisopropyl azodicarboxylate |
| DMAP | 4-(dimethylamino)pyridine | DIPEA | N,N-diisopropylethylamine |
| TMSCHN2 | (Trimethylsilyl)diazomethane | TMSCH2N3 | Trimethylsilylmethyl azide |
| Ruphos | 2-Dicyclohexylphosphino-2',6'-diisopropoxybiphenyl | | |
| RuPhosPd G3 | Methanesulfonato(2-dicyclohexylphosphino-2',6'-di-i-propoxy-1,1'-biphenyl)(2'-amino-1,1'-biphenyl-2-yl)palladium(II) | | |

General Conditions and Procedures

In the following examples, the chemical reagents were purchased from commercial sources (such as Alfa, Acros, Sigma Aldrich, TCI and Shanghai Chemical Reagent Company), and used without further purification. THE was continuously refluxed and freshly distilled from sodium and benzophenone under nitrogen, dichloromethane was continuously refluxed and freshly distilled from $CaH_2$ under nitrogen.

Flash chromatography was performed on an Ez Purifier III via column with silica gel particles of 200-300 mesh. Analytical and preparative thin layer chromatography plates (TLC) were HSGF 254 (0.15-0.2 mm thickness, Shanghai Anbang Company, China). Nuclear magnetic resonance (NMR) spectra were recorded using Brucker AMX-300 or AMX-400 NMR (Brucker, Switzerland) at around 20-30° C. unless otherwise specified. The following abbreviations are used: s, singlet; d, doublet; t, triplet; q, quartet; m, multiplet; dd, doublet of doublets; ddd, doublet of doublet of doublet; dt, doublet of triplets; bs, broad signal. Chemical shifts were reported in parts per million (ppm, S) downfield from tetramethylsilane. Mass spectra were run with electrospray ionization (ESI) from a Waters LCT TOF Mass Spectrometer (Waters, USA). Compound purification was carried out as needed using a variety of traditional methods including, but not limited to, preparative chromatography under acidic, neutral, or basic conditions using either normal phase or reverse phase HPLC or flash columns or Prep-TLC plates.

Preparative HPLC: unless otherwise described, the compounds were purified using a WATERS Fractionlynx system equipped with a YMC Pack Pro ds Column (5 m, 120A, 50×20 mm) and the following solvent system: $H_2O$, AcCN, and 2% TFA in $H_2O$. Specific elution gradients were based on the retention times obtained with an analytical LC-MS, however, in general all elution gradients of $H_2O$ and MeCN were run over a 7 minute run time with a flow rate of 35 mL/min. An autoblend method was used to ensure a concentration of 0.1% TFA throughout each run. Specific elution gradients were based on the retention times obtained with an analytical LC-MS, however, in general, all elution gradients of $H_2O$ and MeCN were run over at 8 minute run time with a flow rate of 50 mL/min.

Analytical LC-MS: analytical LC-MS was performed on a WATERS Acquity UPLC-MS instrument equipped with a ACQUITY UPLC BEH Cig Column (2.1×50 mm, 1.7μιη), a column temperature of 45° C. and using the following solvent system: Solvent A: 0.1% HCOOH in $H_2O$; and Solvent B: 0.1% HCOOH in AcCN. All compounds were run using the same elution gradient, i.e., 5% to 95% Solvent B over a 1.5 min run time with a flow rate of 0.6 mL/min.

Preparative Chiral SFC Separation: stereoisomer mixtures were separated using a Berger Minigram SFC instrument on one of the following columns: ChiralPak AS-H (10×250 mm), ChiralPak IA (10×250 mm), ChiralPak AD-H (21×250 mm), Phenomenex Lux-2 (21.2×250 mm), or ChiralPak IC (10×250 mm); eluting with either 0.1% diethylamine in MeOH/$C_{02}$, or 0.1% diethylamine in EtOH/$CO_2$ or 0.1% diethylamine in isopropanol/$CO_2$ with a flow rate of 2.5 mL/min and a column temperature of 35° C.

Analytical Chiral SFC Separation: stereoisomer mixtures or single enantiomers were analyzed using a JASCO analytical SFC instrument on one of the following columns: ChiralPak AS-H (4.6×250 mm), ChiralPak IA (4.6×250 mm), ChiralPak AD-H (4.6×250 mm), Phenomenex Lux-2 (4.6×250 mm), or ChiralPak IC (4.6×250 mm); eluting with either 0.1% diethylamine in MeOH/$CO_2$, or 0.1% diethylamine in EtOH/$CO_2$ or 0.1% diethylamine in isopropanol/$CO_2$, with a flow rate of 6.0 imL/min and a column temperature of 35° C.

Intermediate 1: 3-bromo-2-ethyl-6-(1-methyl-5-(((tetrahydro-2H-pyran-2-yl)oxy)methyl)-1H-1,2,3-triazol-4-yl)pyridine

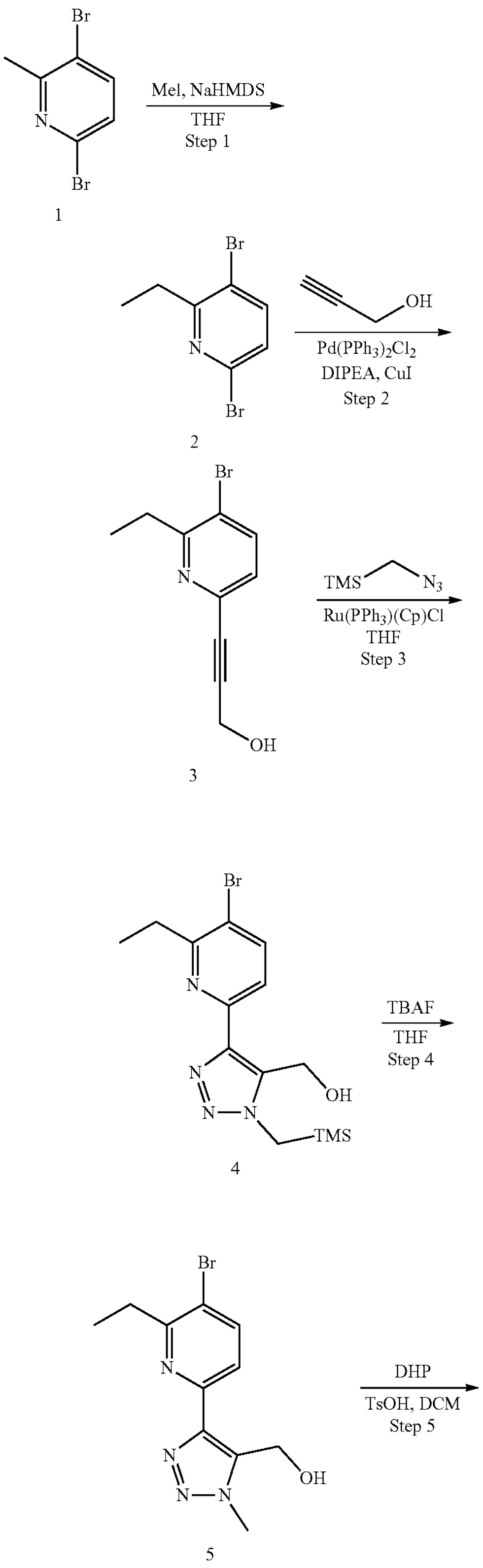

-continued

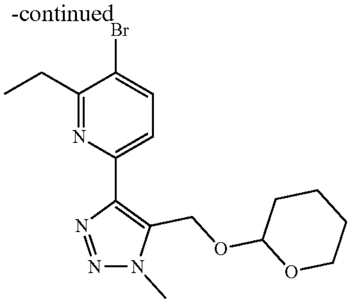

intermediate 1

Step 1: 3,6-dibromo-2-ethylpyridine

To a solution of 3,6-dibromo-2-methylpyridine (75 g, 0.299 mol) in THE (1 L) was added NaHMDS (180 mL, 0.36 mol, 2M in THF) drop-wisely at −50° C. and the mixture was stirred at this temperature for 30 mins. MeI (46.5 mL, 0.75 mol) was added to the above mixture and the resulting mixture was stirred at −50° C. to room temperature for 16 hrs. The reaction mixture was quenched with saturated aq·$NH_4Cl$ solution (500 mL) at 0° C., and extracted with EtOAc (2×500 mL). The combined organic layers were washed with brine, dried over $Na_2SO_4$, filtered and concentrated under reduced pressure to dryness. The residue was purified by silica column chromatography (PE:DCM=300:1 to 200:1) to give the title compound (47 g, 59.1% yield) as yellow oil. $^1H$ NMR (400 MHz, $CD_3OD$) δ 7.61-7.59 (d, J=8 Hz, 1H), 7.61-7.59 (d, J=8.4 Hz, 1H), 2.94-2.88 (q, 2H), 1.38-1.27 (t, 3H).

Step 2: 3-(5-bromo-6-ethylpyridin-2-yl)prop-2-yn-1-ol

To a solution of 3,6-dibromo-2-ethylpyridine (47 g, 0.177 mol) in THE (0.65 L) was added prop-2-yn-1-ol (11.9 g, 0.212 mol), CuI (3.4 g, 17.7 mmol), DIPEA (35.1 mL, 0.212 mol) and $Pd(PPh_3)_2Cl_2$ (12.4 g, 17.7 mmol) and the mixture was degassed under $N_2$ atmosphere for three times and stirred under $N_2$ atmosphere at r.t. for 16 hrs. The mixture was diluted with EtOAc (500 m L) and filtered. The filtrate was washed with water and brine, dried over $Na_2SO_4$, filtered and concentrated to dryness. The residue was purified by silica column chromatography (DCM:EtOAc=10:1 to 4:1) to give the title compound (40 g, 94.1% yield) as brown solid. LC/MS (ESI) m/z: 240/242 $(M+H)^+$.

Step 3: (4-(5-bromo-6-ethylpyridin-2-yl)-1-((trimethylsilyl)methyl)-1H-1,2,3-triazol-5-yl)methanol To a solution of intermediate 3-(5-bromo-6-ethylpyridin-2-yl)prop-2-yn-1-ol (20 g, 0.083 mol) in THE (400 mL) was added Chlorocyclopentadienylbis(triphenylphosphine)ruthenium(II) (3.5 g, 4.16 mmol) and TMS-methyl azide (14 g, 0.108 mol) at 0° C. under $N_2$ atmosphere. The mixture was degassed under $N_2$ atmosphere for three times and stirred at room temperature for 16 hrs. The mixture was diluted with EtOAc (500 mL) and filtered. The filtrate was concentrated to dryness to give crude product, which was triturated with PE/EtOAc (1000 mL, 10/1 v/v) to give the title compound (28 g, 91.3% yield) as white solid. $^1H$ NMR (400 MHz, $CDCl_3$) δ 8.03-8.01 (d, J=8.4 Hz, 1H), 7.95-7.93

(d, J=8.4 Hz, 1H), 6.77-6.74 (t, J=6.8 Hz, 1H), 4.79-4.78 (d, J=6.8 Hz, 1H), 3.80 (s, 3H), 3.03-3.01 (q, 1H), 1.34-1.30 (t, J=7.6 Hz, 3H), 0.20 (s, 9H).

Step 4: (4-(5-bromo-6-ethylpyridin-2-yl)-1-methyl-1H-1,2,3-triazol-5-yl)methanol To a solution of (4-(5-bromo-6-ethylpyridin-2-yl)-1-((trimethylsilyl)methyl)-1H-1,2,3-triazol-5-yl)methanol (25 g, 67.7 mmol) in THE (300 mL) was added TBAF·$3H_2O$ (25.6 g, 81.2 mmol) and the mixture was stirred at room temperature overnight. The mixture was diluted with EtOAc (500 mL), washed with saturated aq·$NH_4Cl$ solution (3×50 mL) and brine, dried over $Na_2SO_4$, filtered and concentrated to dryness. The residue was purified by silica column chromatography (DCM:EtOAc=8:1 to 4:1) to give the title compound (19 g, 94.4% yield) as gray solid. LC/MS (ESI) m/z: 297/299 $(M+H)^+$.

Step 5: 3-bromo-2-ethyl-6-(1-methyl-5-(((tetrahydro-2H-pyran-2-yl)oxy)methyl)-1H-1,2,3-triazol-4-yl)pyridine To the mixture of (4-(5-bromo-6-ethylpyridin-2-yl)-1-methyl-1H-1,2,3-triazol-5-yl)methanol (25 g, 0.084 mol) and TosOH (2.2 g, 12.6 mmol) in DCM (300 mL) was added DHP (10.6 g, 0.126 mol) at 0° C. and the mixture was stirred at room temperature for 16 hrs. The mixture was washed with water and brine, dried over $Na_2SO_4$, filtered and concentrated to dryness. The residue was purified by silica column chromatography (DCM:EtOAc=8:1) to give the title compound (30 g, 93.6% yield) as yellow solid. LC/MS (ESI) m/z: 381/383 (M+H)+. $^1H$ NMR (400 MHz, $CDCl_3$) δ 7.91 (d, J=8.3 Hz, 1H), 7.86 (d, J=8.3 Hz, 1H), 5.36 (dd, J=36.5, 12.8 Hz, 2H), 4.75-4.67 (m, 1H), 4.16 (s, 3H), 3.88-3.80 (m, 1H), 3.55-3.46 (m, 1H), 3.00 (q, J=7.5 Hz, 2H), 1.84-1.67 (m, 2H), 1.65-1.58 (m, 2H), 1.54-1.45 (m, 2H), 1.34 (t, J=7.5 Hz, 3H).

Intermediate 2: 3-bromo-2-methyl-6-(1-methyl-5-(((tetrahydro-2H-pyran-2-yl)oxy)methyl)-1H-1,2,3-triazol-4-yl)pyridine intermediate 2

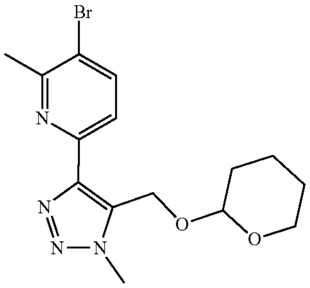

Intermediate 2 was synthesized according the same sequence as was used for the synthesis of intermediate 1. LC/MS (ESI) m/z: 367/369 $(M+H)^+$. $^1H$ NMR (400 MHz, $CDCl_3$) δ 7.73 (d, J=8.3 Hz, 1H), 7.69 (d, J=8.3 Hz, 1H), 5.15 (q, J=12.7 Hz, 2H), 4.61-4.54 (m, 1H), 3.99 (s, 3H), 3.74-3.64 (m, 1H), 3.38-3.30 (m, 1H), 2.51 (s, 3H), 1.66-1.50 (m, 2H), 1.46-1.40 (m, 2H), 1.39-1.32 (m, 2H).

Intermediate 3: (4-(6-ethyl-5-iodopyridin-2-yl)-1-methyl-11H-1,2,3-triazol-5-yl)methanol

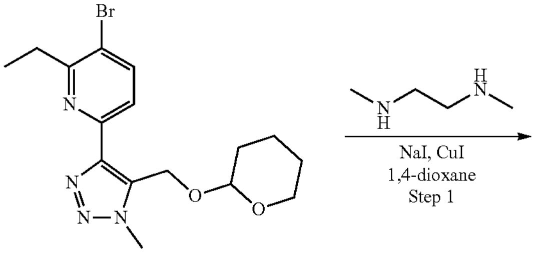

1

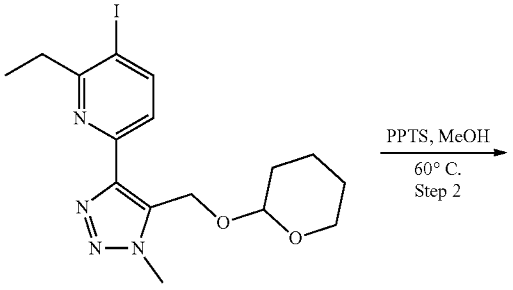

2

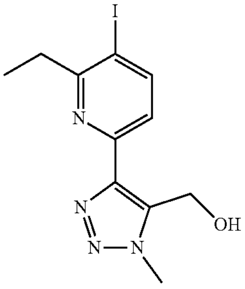

Intermediate 3

Step 1: 2-ethyl-3-iodo-6-(1-methyl-5-(((tetrahydro-2H-pyran-2-yl)oxy)methyl)-1H-1,2,3-triazol-4-yl) pyridine To a mixture of 3-bromo-2-ethyl-6-{1-methyl-5-[(oxan-2-yloxy)methyl]-1H-1,2,3-triazol-4-yl}pyridine (7.2 g, 18.9 mmol) and NaI (14.2 g, 94.4 mmol) in 1,4-dioxane (80 mL) was added $N_1$,$N_2$-diMethylethane-1,2-diaMine (1.55 g, 11.3 mmol) and CuI (1.80 g, 9.44 mmol) and the mixture was degassed under $N_2$ atmosphere for three times and stirred at 110° C. for 20 hrs. The mixture was filtered and the filter cake was washed with EtOAc (2×50 mL). The combined filtrate was washed with water and brine, dried over $Na_2SO_4$, filtered and concentrated to dryness to give crude product, which was purified by silica gel chromatography (PE:EtOAc=4:1 to 1:1) to give the title compound (6.1 g, 74.2%) as light yellow solid. LC/MS (ESI) (m/z): 429 $(M+H)^+$. $^1H$ NMR (400 MHz, $CDCl_3$) δ 8.11-8.09 (d, J=8.4 Hz, 1H), 7.75-7.73 (d, J=8.3 Hz, 1H), 5.42-5.29 (q, J=12.7 Hz, 2H), 4.72-4.70 (m, 1H), 4.16 (s, 3H), 3.84-3.82 (m, 1H), 3.56-3.49 (m, 1H), 3.02-2.97 (q, J=7.22H), 1.63-1.59 (m, 2H), 1.56-1.53 (m, 4H), 1.34-1.30 (t, J=7.6 Hz, 3H).

Step 2: (4-(6-ethyl-5-iodopyridin-2-yl)-1-methyl-1H-1,2,3-triazol-5-yl) methanol (6)

To a solution of 2-ethyl-3-iodo-6-(1-methyl-5-(((tetra-hydro-2H-pyran-2-yl)oxy)methyl)-1H-1,2,3-triazol-4-yl) pyridine (1.0 g, 2.34 mmol) in MeOH (10 mL) was added PPTS (0.59 g, 2.34 mmol) and the mixture was stirred at 60° C. for 16 hrs. The mixture was diluted with EtOAc, washed with saturated aq·$NaHCO_3$ solution and brine, dried over anhydrous $Na_2SO_4$, filtered and concentrated to dryness. The residue was purified by flash chromatography (eluted with PE:EtOAc=20:1 to 2:1) to give the title compound (698 mg, 86.9% yield) as white solid. LC/MS (ESI) m/z: 345 $(M+H)^+$.

Intermediate 4: 5-bromo-4-ethyl-2-(1-methyl-5-(((tetrahydro-2H-pyran-2-yl)oxy)methyl)-1H-pyrazol-4-yl)pyrimidine

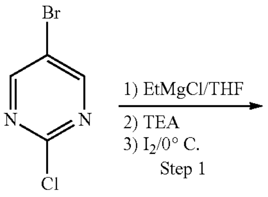

1

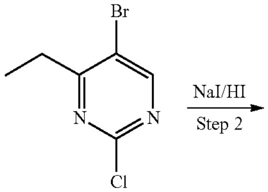

2

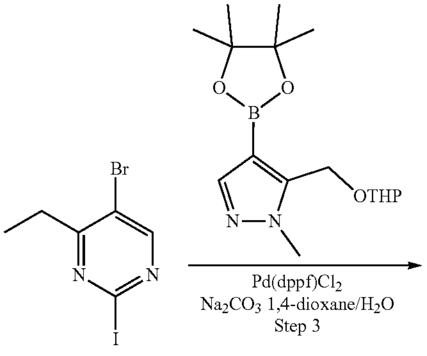

3

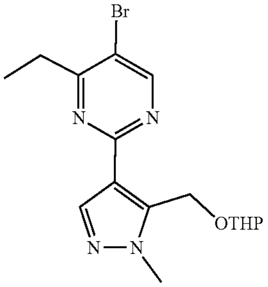

intermediate 4

Step 1: 5-bromo-2-chloro-4-ethylpyrimidine

To a solution of 5-bromo-2-chloropyrimidine (60 g, 0.31 mol) in THF (600 mL) was added EtMgCl (186 mL, 0.37 mol, 2M in THF) drop-wisely at 10° C. under $N_2$ atmosphere and the resulting mixture was stirred at this temperature for 1 hr. TEA (43 mL, 0.31 mol) was added to the mixture drop-wisely at 0° C. under $N_2$ atmosphere. After stirring at 0° C. for 20 min, a solution of iodine (79.0 g, 0.31 mol) in THF (120 mL) was added and the resulting mixture was stirred at r.t. for 16 hrs. The reaction was quenched with water and extracted with EtOAc (2×300 mL). The combined organic layers were washed with saturated aq·$Na_2SO_3$ solution and brine, dried over $Na_2SO_4$, filtered and concentrated to dryness. The residue was purified by silica gel column chromatography (EtOAc:PE=0 to 200:1) to give the title compound (35.3 g, 51.4% yield) as light yellow solid. $^1$H NMR (400 MHz, DMSO-$d_6$) δ 8.87 (s, 1H), 2.89-2.83 (q, J=7.5 Hz, 2H), 1.22-1.18 (t, J=7.5 Hz, 3H).

Step 2: 5-bromo-4-ethyl-2-iodopyrimidine

To a solution of 5-bromo-2-chloro-4-ethylpyrimidine (20 g, 0.09 mol) in DCM (50 mL) was added aq·HI (200 mL, 57% wt) drop-wisely followed by NaI (30 g, 0.2 mol) at 0° C. and the mixture was stirred at 5° C. for 16 hrs. The reaction mixture was quenched with saturated aq·$Na_2S_2O_3$ solution (100 mL) and extracted with DCM (2×200 mL). The combined organic layers were concentrated under reduced pressure to give a colorless residue. The resulting residue was purified by silica gel column chromatography (PE:EtOAc=4:1) to give the title compound (25.3 g, 89.8% yield) as light yellow solid. $^1$H NMR (400 MHz, DMSO-$d_6$) δ 8.64 (s, 1H), 2.82-2.75 (q, J=7.5 Hz, 2H), 1.19-1.16 (t, J=7.5 Hz, 3H).

Step 3: 5-bromo-4-ethyl-2-(1-methyl-5-(((tetrahydro-2H-pyran-2-yl)oxy)methyl)-1H -pyrazol-4-yl) pyrimidine To a solution of 5-bromo-4-ethyl-2-iodopyrimidine (17.5 g, 55.9 mmol) and 1-methyl-5-(((tetrahydro-2H-pyran-2-yl) oxy)methyl)-4-(4,4,5,5-tetramethyl-1,3,2-dioxaborolan-2-yl)-1H-pyrazole (15.8 g, 46.6 mmol, prepared as WO2014081619) in 1,4-dioxane (300 mL) and water (60 mL) were added $Na_2CO_3$ (9.9 g, 93.2 mmol), Pd(dppf)$Cl_2$ (1.7 g, 2.3 mmol) in one portion under $N_2$ atmosphere, the mixture was degassed under $N_2$ for three times and stirred under $N_2$ atmosphere at 75° C. for 16 hrs. The mixture was poured into ice-water and extracted with DCM (2×200 mL). The combined organic layers were washed with brine, dried over $Na_2SO_4$, filtered and concentrated under reduced pressure to dryness. The resulting residue was purified by silica gel chromatography (PE:EtOAc=10:1) to give the title compound (12.7 g, 59.6% yield) as yellow solid. LC/MS (ESI) m/z: 381/383 $(M+H)^+$. $^1$H NMR (400 MHz, DMSO-$d_6$) δ 8.80 (s, 1H), 8.01 (s, 1H), 5.32-5.29 (d, J=12 Hz, 1H), 5.14-5.11 (d, J=12 Hz, 1H), 4.73-4.69 (m, 1H), 3.90 (s, 3H), 3.79-3.72 (m, 1H), 3.45-3.41 (m, 1H), 2.88-2.83 (q, J=7.4 Hz, 2H), 1.68-1.55 (m, 2H), 1.55-1.42 (m, 4H), 1.28-1.24 (t, J=7.5 Hz, 3H).

Intermediate 5: methyl (S)-2-(5,5-difluoropiperidin-3-yl)acetate (intermediate 5A)

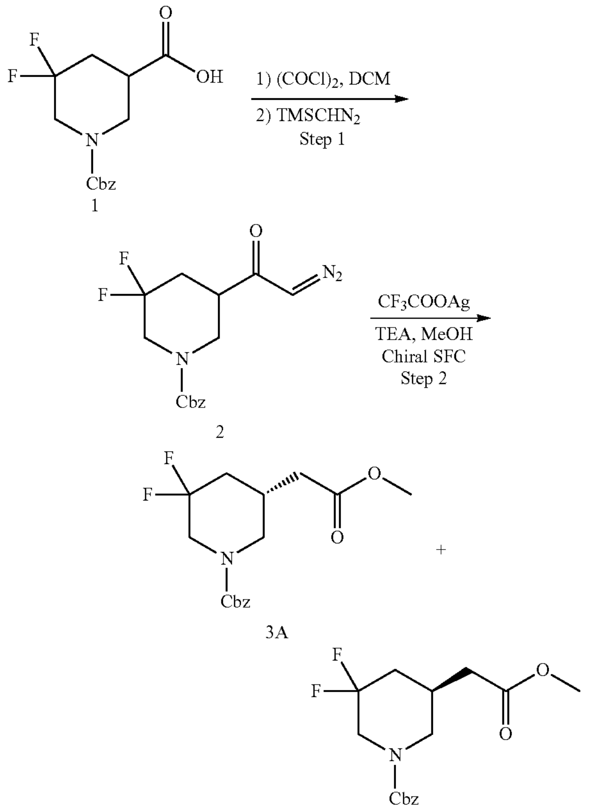

1 2 3A + 3B

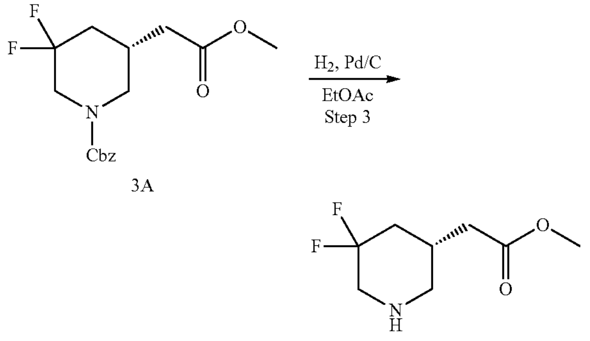

3A intermediate 5

Step 1: benzyl 5-(2-diazoacetyl)-3,3-difluoropiperidine-1-carboxylate

To a solution of 1-((benzyloxy)carbonyl)-5,5-difluoropiperidine-3-carboxylic acid (51 g, 0.17 mol) in DCM (500 mL) was added DMF (2 mL) followed by drop-wise addition of $(COCl)_2$ (43 g, 0.34 mol) at 0° C. and the mixture was stirred at 0° C. to r.t. for 2 hrs. The reaction was concentrated to dryness and the residue was co-evaporated with toluene for three times. The residue was dissolved in THE (500 mL) and $TMSCHN_2$ solution (250 mL, 0.5 mol, 2M in hexane) was added drop-wisely at 0° C. The resulting mixture was stirred at r.t. for 16 hrs. The reaction was quenched with AcOH (60 mL) at 0° C. and the mixture was concentrated to dryness to give the title compound (55 g, 100% yield) as yellow oil, which was directly used to the next reaction without purification. LC/MS (ESI) m/z: 324 $(M+H)^+$.

Step 2: benzyl (S)-3,3-difluoro-5-(2-methoxy-2-oxoethyl)piperidine-1-carboxylate (3A) and benzyl (R)-3,3-difluoro-5-(2-methoxy-2-oxoethyl)piperidine-1-carboxylate (3B)

To a solution of benzyl 5-(2-diazoacetyl)-3,3-difluoropiperidine-1-carboxylate (55 g, 0.17 mol) in MeOH (500 mL) was added $CF_3COOAg$ (7.4 g, 0.03 mol) and TEA (67.6 g, 0.67 mol) and the mixture was stirred at 20° C. for 2 hrs. The reaction mixture was concentrated to dryness and the residue was purified by silica gel chromatography (PE:EtOAc=3:1) to give the title compound (37 g, 62.9% yield) as light yellow oil. LC/MS (ESI) m/z: 328 $(M+H)^+$. The two enantiomers were separated by chiral SFC to give benzyl (S)-3,3-difluoro-5-(2-methoxy-2-oxoethyl)piperidine-1-carboxylate (peak 2, retention time: 4.414 min) (13.8 g, 24.8% yield) and benzyl (R)-3,3-difluoro-5-(2-methoxy-2-oxoethyl)piperidine-1-carboxylate (peak 1, retention time: 4.109 min) (16.1 g, 28.9% yield) as light yellow oil. $^1H$ NMR (400 MHz, $CDCl_3$) δ 7.41-7.28 (m, 5H), 5.15 (s, 2H), 4.25-3.94 (m, 2H), 3.66 (d, J=25.3 Hz, 3H), 3.30-3.12 (m, 1H), 2.91-2.67 (m, 1H), 2.42-2.23 (m, 4H), 1.75-1.60 (m, 1H). SFC condition: Column: ChiralPak IC-H, 250×4.6 mm I.D., 5 μm; Mobile phase: A for $C_{02}$ and B for Methanol (0.05% $NH_4OH$); Gradient: B 5%-40%; Flow rate: 50 mL/min;

Step 3: Methyl (S)-2-(5,5-difluoropiperidin-3-yl)acetate

To a solution of benzyl (S)-3,3-difluoro-5-(2-methoxy-2-oxoethyl)piperidine-1-carboxylate (4.2 g, 12.83 mmol) in EtOAc (40 mL) was added Pd/C (300 mg, 10% wt) at 0° C. The mixture was degassed under $N_2$ atmosphere for three times and stirred under a $H_2$ balloon at room temperature for 2 hrs. The mixture was filtered and the filtrate was concentrated to dryness to give the title compound (2.37 g, 95.6%) as off-white solid. LC/MS (ESI) (m/z): 194 $(M+H)^+$. H NMR (400 MHz, $CDCl_3$) δ 3.69 (s, 3H), 3.18-3.06 (m, 2H), 2.85-2.65 (m, 1H), 2.36-2.20 (m, 5H), 1.62-1.48 (m, 1H).

Intermediate 6: Methyl (R)-2-(5,5-difluoropiperidin-3-yl)acetate intermediate 6

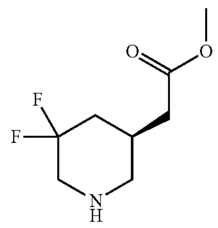

The title compound was prepared from benzyl (R)-3,3-difluoro-5-(2-methoxy-2-oxoethyl)piperidine-1-carboxylate using the same procedure as methyl (S)-2-(5,5-difluoropiperidin-3-yl)acetate. LC/MS (ESI) (m/z): 194 $(M+H)^+$.

Intermediate 7: methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate

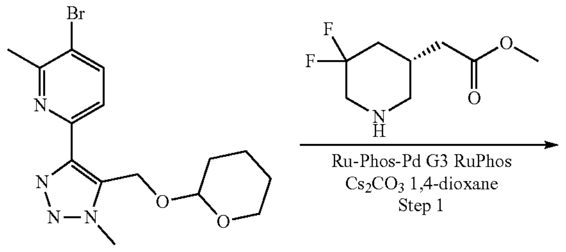

1

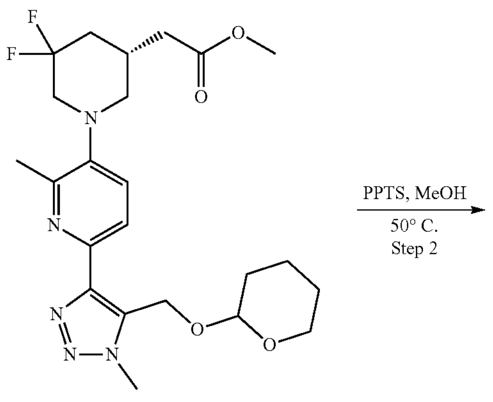

2

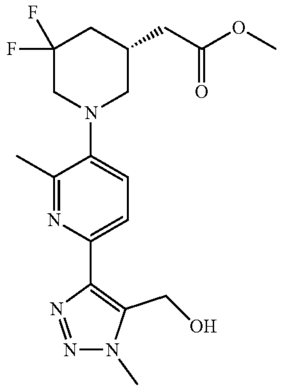

intermediate 7

Step 1: 2-((3S)-5,5-difluoro-1-(2-methyl-6-(1-methyl-5-(((tetrahydro-2H-pyran-2-yl)oxy)methyl)-1H-1,2,3-triazol-4-yl)pyridin-3-yl)piperidin-3-yl) acetic acid To a mixture of 3-bromo-2-methyl-6-(1-methyl-5-(((tetrahydro-2H-pyran-2-yl)oxy)methyl)-1H-1,2,3-triazol-4-yl) pyridine (1.5 g, 4.1 mmol) and methyl (S)-2-(5,5-difluoropiperidin-3-yl)acetate (790 mg, 4.1 mmol) in dry 1,4-dioxane (30 mL) was added $Cs_2CO_3$ (2.66 g, 8.2 mmol), RuPhos (381 mg, 0.82 mmol) and RuPhos-Pd-G3 (342 mg, 0.41 mmol) under $N_2$ atmosphere. The mixture was degassed under $N_2$ atmosphere for three times and stirred under $N_2$ atmosphere at 100° C. for 16 hrs. The mixture was filtered and the filtrate was concentrated to dryness. The residue was purified by flash chromatography (0~50% EtOAc in PE) to give the title compound (1.6 g, 81.7% yield) as light yellow solid. LC/MS (ESI) m/z: 480 $(M+H)^+$. $^1H$ NMR (400 MHz, $CDCl_3$) δ 7.97 (d, J=8.3 Hz, 1H), 7.33 (d, J=8.3 Hz, 1H), 5.38-5.26 (m, 2H), 4.77 (t, J=3.2 Hz, 1H), 4.15 (s, 3H), 3.92-3.85 (m, 1H), 3.70 (s, 3H), 3.57-3.50 (m, 1H), 3.32-3.22 (m, 2H), 3.03-2.93 (m, 1H), 2.63-2.53 (m, 2H), 2.57 (s, 3H), 2.44-2.41 (m, 2H), 2.35-2.25 (m, 1H), 1.84-1.77 (m, 1H), 1.75-1.67 (m, 2H), 1.62-1.55 (m, 2H), 1.54-1.45 (m, 2H).

Step 2: methyl (S)-2-(5,5-difluoro-1-(6-(5-(hydroxymethyl)-1-methyl-11H-1,2,3-triazol-4-yl)-2-methylpyridin-3-yl)piperidin-3-yl)acetate To a solution of methyl 2-((3S)-5,5-difluoro-1-(2-methyl-6-(1-methyl-5-(((tetrahydro-2H-pyran-2-yl)oxy)methyl)-1H-1,2,3-triazol-4-yl)pyridin-3-yl)piperidin-3-yl)acetate (1.6 g, 3.3 mmol) in MeOH (20 mL) was added PPTS (1.6 g, 6.6 mmol) and the mixture was stirred at 50° C. for 16 hrs. The mixture was concentrated to dryness and the residue was dissolved in EtOAc (20 mL). The mixture was washed with water and brine, dried over anhydrous $Na_2SO_4$, filtered and concentrated to dryness. The residue was purified by flash chromatography (0~60% EtOAc in PE) to give the title compound (1.2 g, 90.0% yield) as light yellow solid. LC/MS (ESI) m/z: 396 $(M+H)^+$. $^1H$ NMR (400 MHz, $CDCl_3$) δ 8.11 (d, J=8.4 Hz, 1H), 7.44 (d, J=8.4 Hz, 1H), 4.82 (s, 2H), 4.08 (s, 3H), 3.70 (s, 3H), 3.36-3.21 (m, 2H), 3.06-2.96 (m, 1H), 2.65-2.56 (m, 2H), 2.61 (s, 3H), 2.46-2.40 (m, 2H), 2.37-2.28 (m, 1H), 1.78-1.70 (m, 1H).

Intermediate 8: methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate intermedaite 8

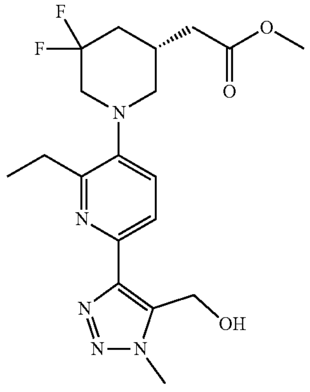

Intermediate 8 was synthesized according the same sequence as was used for the synthesis of intermediate 7. LC/MS (ESI) m/z: 410 $(M+H)^+$. $^1H$ NMR (400 MHz, $CDCl_3$) δ 8.12 (d, J=8.4 Hz, 1H), 7.48 (d, J=8.4 Hz, 1H), 4.84 (s, 2H), 4.08 (s, 3H), 3.70 (s, 3H), 3.30-3.17 (m, 2H), 3.07-2.99 (m, 1H), 2.99-2.93 (m, 2H), 2.63-2.58 (m, 2H), 2.48-2.38 (m, 2H), 2.36-2.28 (m, 1H), 1.74-1.63 (m, 1H), 1.34 (t, J=7.5 Hz, 3H).

Intermediate 9: methyl (S)-2-(1-(4-ethyl-2-(5-(hydroxymethyl)-1-methyl-1H-pyrazol-4-yl)pyrimidin-5-yl)-5,5-difluoropiperidin-3-yl)acetate

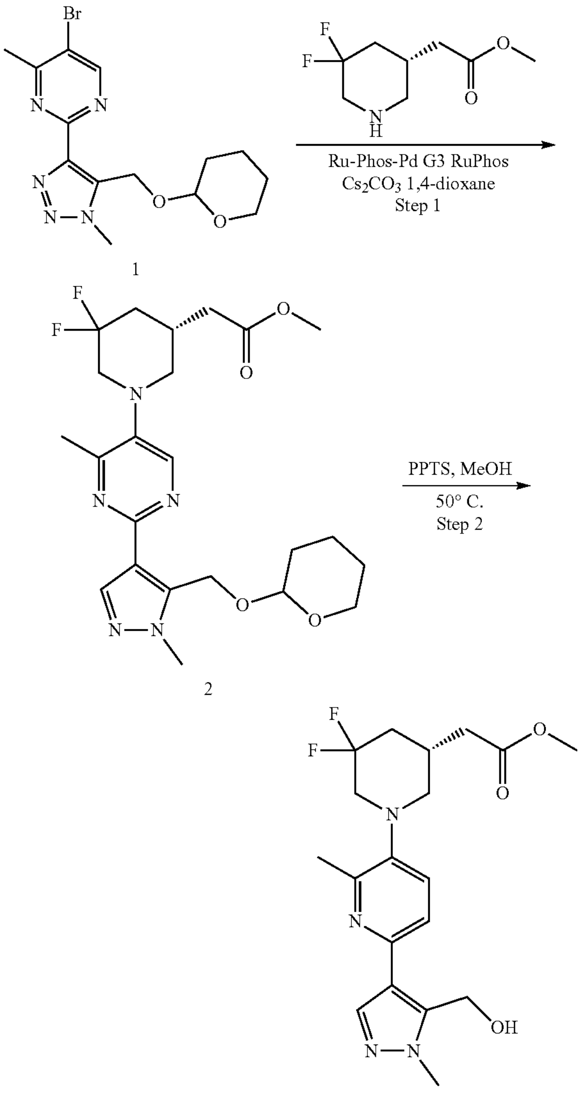

1

2 intermediate 9

Step 1: methyl 2-((3S)-5,5-difluoro-1-(4-methyl-2-(1-methyl-5-(((tetrahydro-2H-pyran-2-yl)oxy)methyl)-1H-pyrazol-4-yl)pyrimidin-5-yl)piperidin-3-yl)acetate To a solution of 5-bromo-4-ethyl-2-(1-methyl-5-(((tetrahydro-2H-pyran-2-yl)oxy)methyl)-1H-pyrazol-4-yl)pyrimidine (420 mg, 1.1 mmol) in toluene (5 mL) were added methyl (S)-2-(5,5-difluoropiperidin-3-yl)acetate (212 mg, 1.1 mmol), followed by the addition of $Cs_2CO_3$ (710 mg, 2.2 mmol), BINAP (135 mg, 0.20 mmol) and $Pd(OAc)_2$ (49 mg, 0.22 mmol) under $N_2$ atmosphere. The reaction was stirred under $N_2$ atmosphere at 100° C. for 16 hrs. The mixture was diluted with EtOAc (10 mL), washed with water and brine, dried over $Na_2SO_4$, filtered and concentrated to dryness. The residue was purified by flash chromatography (0~50%

EtOAc in PE) to give the title compound (160 mg, 28.7% yield) as a yellow oil. LC-MS (ESI) m/z 494 $(M+H)^+$.

Step 2: methyl (S)-2-(1-(4-ethyl-2-(5-(hydroxymethyl)-1-methyl-1H-pyrazol-4-yl)pyrimidin-5-yl)-5,5-difluoropiperidin-3-yl)acetate Intermediate 9 was synthesized according the same sequence as was used for the synthesis of intermediate 5. LC/MS (ESI) m/z: 410 $(M+H)^+$.

Intermediate 10: ethyl (R)-2-(1-(6-(5-(hydroxymethyl)-1-methyl-1H-1,2,3-triazol-4-yl)-2-methylpyridin-3-yl)piperidin-3-yl)acetate intermediaite 10

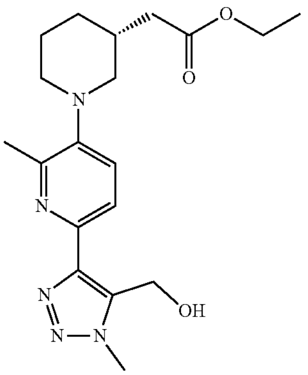

Intermediate 10 was synthesized from commercial available ethyl (R)-2-(piperidin-3-yl)acetate according the same sequence that was used for the synthesis of intermediate 7. LC/MS (ESI) m/z: 374 $(M+H)^+$. $^1H$ NMR (400 MHz, $CDCl_3$) δ 8.07 (d, J=8.4 Hz, 1H), 7.43 (d, J=8.4 Hz, 1H), 4.81 (s, 2H), 4.14 (q, J=7.1 Hz, 2H), 4.07 (s, 3H), 3.21-3.14 (m, 1H), 3.09-3.02 (m, 1H), 2.72-2.67 (m, 1H), 2.57 (s, 3H), 2.48-2.39 (m, 1H), 2.35-2.26 (m, 3H), 1.93-1.86 (m, 1H), 1.84-1.68 (m, 2H), 1.26 (t, J=7.1 Hz, 3H), 1.23-1.15 (m, 1H).

Intermediate 11: ethyl (R)-2-(1-(2-ethyl-6-(5-(hydroxymethyl)-1-methyl-11H-1,2,3-triazol-4-yl)pyridin-3-yl)piperidin-3-yl)acetate intermediaite 11

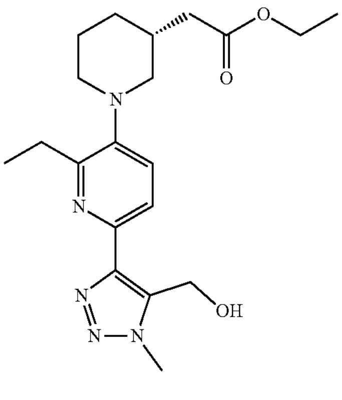

Intermediate 11 was synthesized from commercial available ethyl (R)-2-(piperidin-3-yl)acetate according the same sequence that was used for the synthesis of intermediate 7. LC/MS (ESI) m/z: 388 $(M+H)^+$. $^1H$ NMR (400 MHz, $CDCl_3$) δ 8.09 (d, J=8.4 Hz, 1H), 7.47 (d, J=8.4 Hz, 1H), 4.83 (s, 2H), 4.14 (q, J=7.5 Hz, 2H), 4.08 (d, J=6.8 Hz, 3H), 3.12 (d, J=10.8 Hz, 1H), 3.05-2.98 (m, 1H), 2.92 (q, J=7.5 Hz, 2H), 2.73-2.67 (m, 1H), 2.50-2.40 (m, 1H), 2.35-2.25 (m, 3H), 1.95-1.85 (m, 1H), 1.84-1.80 (m, 1H), 1.79-1.71 (m, 1H), 1.33 (t, J=7.5 Hz, 3H), 1.26 (t, J=7.5, 0.7 Hz, 3H), 1.23-1.13 (m, 1H).

Intermediate 12: Methyl 5,5-difluoro-1-((6-(5-(hydroxymethyl)-1-methyl-1H-1,2,3-triazol-4-yl)-2-methylpyridin-3-yl)methyl)piperidine-3-carboxylate

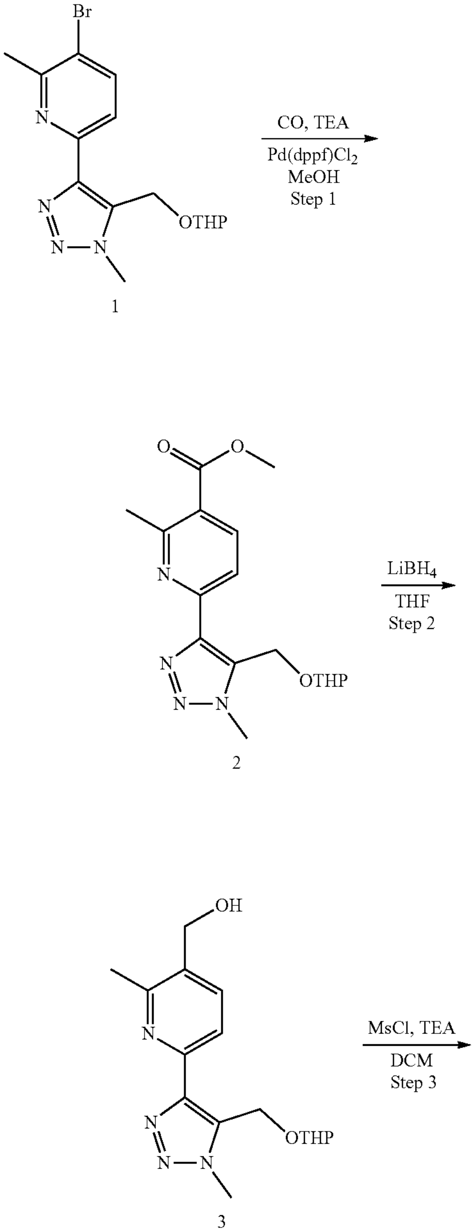

1

2

3

-continued

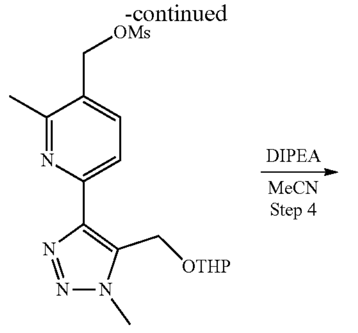

4

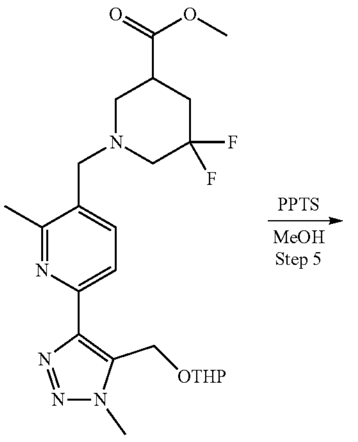

5

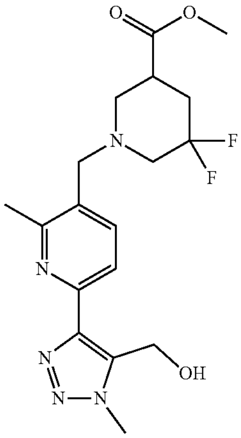

Intermediate 12

Step 1: Methyl 2-methyl-6-(1-methyl-5-(((tetrahydro-2H-pyran-2-yl)oxy)methyl)-1H-1,2,3-triazol-4-yl)nicotinate To a solution of 3-bromo-2-methyl-6-{1-methyl-5-[(oxan-2-yloxy)methyl]-1H-1,2,3-triazol-4-yl}pyridine (5.0 g, 13.6 mmol) in MeOH (50 mL) was added TEA (9.5 mL, 68.1 mmol) followed by Pd(dppf)$Cl_2$ (1.0 g, 1.4 mmol). The mixture was degassed under $N_2$ atmosphere for three times and stirred under 60 psi of CO gas at 70° C. for 16 hrs. The mixture was filtered through Celite pad and the filtrate was concentrated to dryness. The residue was purified by flash chromatography (0~50% EtOAc in PE) to give the title compound (3.8 g, 80.6% yield) as yellow solid. LC-MS (ESI) m/z 347 $(M+H)^+$. $^1$H NMR (400 MHz, $CDCl_3$) δ 8.28 (d, J=8.2 Hz, 1H), 8.10 (d, J=8.2 Hz, 1H), 5.39 (dd, J=29.2, 12.7 Hz, 2H), 4.77-4.75 (m, 1H), 4.17 (s, 3H), 3.93 (s, 3H), 3.90-3.83 (m, 1H), 3.55-3.50 (m, 1H), 2.86 (s, 3H), 1.84-1.66 (m, 2H), 1.65-1.57 (m, 2H), 1.55-1.48 (m, 2H).

Step 2: (2-methyl-6-(1-methyl-5-(((tetrahydro-2H-pyran-2-yl)oxy)methyl)-1H-1,2,3-triazol-4-yl)pyridin-3-yl)methanol To a solution of Methyl 2-methyl-6-(1-methyl-5-(((tetrahydro-2H-pyran-2-yl)oxy)methyl)-1H-1,2,3-triazol-4-yl) nicotinate (1.50 g, 4.33 mmol) in THE (20 mL) was added $LiBH_4$ (5.20 mL, 10.40 mmol, 2M in THF) drop-wisely at 0° C. After addition, the mixture was stirred at 55° C. for 3 hrs. The mixture was poured into saturated aq·$NH_4Cl$ solution and extracted with EtOAc (2×20 mL). The combined organic layers were washed with brine, dried over anhydrous $Na_2SO_4$, filtered and concentrated under reduced pressure to dryness. The residue was purified by flash chromatography (0~50% EtOAc in PE) to give the title compound (1.3 g, 94.3% yield) as light yellow solid. LC/MS (ESI) (m/z): 319 $(M+H)^+$. $^1$H NMR (400 MHz, $CDCl_3$) δ 8.00 (d, J=7.9 Hz, 1H), 7.74 (d, J=8.0 Hz, 1H), 5.34 (dd, J=33.4, 12.6 Hz, 2H), 4.80-4.75 (m, 1H), 4.74 (s, 2H), 4.16 (s, 3H), 3.92-3.84 (m, 1H), 3.55-3.48 (m, 1H), 2.57 (s, 3H), 1.82-1.71 (m, 2H), 1.58-1.48 (m, 4H).

Step 3: 3-(chloromethyl)-2-methyl-6-(1-methyl-5-(((tetrahydro-2H-pyran-2-yl)oxy)methyl)-1H-1,2,3-triazol-4-yl)pyridine To a solution of (2-methyl-6-(1-methyl-5-(((tetrahydro-2H-pyran-2-yl)oxy)methyl)-1H-1,2,3-triazol-4-yl)pyridin-3-yl)methanol (1.3 g, 4.1 mmol) in DCM (30 mL) were added TEA (1.7 mL, 12.25 mmol) followed by drop-wise addition of MsCl (0.70 g, 6.1 mmol) at 0° C. The reaction was stirred at r.t. for 2 hrs. The mixture was washed with saturated aq·$NaHCO_3$ solution and brine, dried over anhydrous $Na_2SO_4$, filtered and concentrated under reduced pressure to dryness. The residue was purified by flash chromatography (0~50% EtOAc in PE) to give the title compound (1.7 g, 87.3% yield) as yellow solid. LC/MS (ESI) (m/z): 367 $(M+H)^+$. $^1$HNMR (400 MHz, $CDCl_3$) δ 8.03 (d, J=8.0 Hz, 1H), 7.68 (d, J=8.0 Hz, 1H), 5.35 (dd, J=33.2, 12.7 Hz, 2H), 4.80-4.73 (m, 1H), 4.62 (s, 2H), 4.16 (s, 3H), 3.93-3.82 (m, 1H), 3.56-3.42 (m, 1H), 2.66 (s, 3H), 1.81-1.67 (m, 2H), 1.61-1.49 (m, 4H).

Step 4: Methyl 5,5-difluoro-1-((2-methyl-6-(1-methyl-5-(((tetrahydro-2H-pyran-2-yl)oxy)methyl)-1H-1,2,3-triazol-4-yl)pyridin-3-yl)methyl)piperidine-3-carboxylate To the solution of 3-(chloromethyl)-2-methyl-6-(1-methyl-5-(((tetrahydro-2H-pyran-2-yl)oxy)methyl)-1H-1,2,3-triazol-4-yl)pyridine (935 mg, 2.78 mmol) in $CH_3CN$ (20 mL) was added methyl 5,5-difluoropiperidine-3-carboxylate (994 mg, 3.6 mmol) followed by DIPEA (1.2 mL, 7.1 mmol) and the reaction was stirred at 80° C. for 3.5 hrs. The mixture was diluted with EtOAc (10 mL) and was washed with brine, dried over anhydrous $Na_2SO_4$, filtered and concentrated under reduced pressure to dryness. The residue was purified by flash chromatography (0~50% EtOAc in PE) to give the title compound (800 mg, 60.1% yield) as yellow oil. LC/MS (ESI) (m/z): 480 $(M+H)^+$. $^1$H NMR (400 MHz, $CDCl_3$) δ 7.98 (d, J=7.9 Hz, 1H), 7.62 (d, J=7.9 Hz, 1H), 5.43-5.30 (m, 2H), 4.78-4.76 (m, 1H), 4.15 (s, 3H), 3.93-

3.85 (m, 1H), 3.68 (s, 3H), 3.65-3.57 (m, 2H), 3.56-3.49 (m, 1H), 3.12-3.01 (m, 2H), 2.92-2.85 (m, 1H), 2.81-2.75 (m, 1H), 2.58 (s, 3H), 2.42-2.35 (m, 1H), 2.32-2.22 (m, 1H), 1.93-1.86 (m, 1H), 1.82-1.66 (m, 2H), 1.62-1.48 (m, 4H).

Step 5: Methyl 5,5-difluoro-1-((6-(5-(hydroxymethyl)-1-methyl-11H-1,2,3-triazol-4-yl)-2-methylpyridin-3-yl)methyl)piperidine-3-carboxylate To the solution of Methyl 5,5-difluoro-1-((2-methyl-6-(1-methyl-5-(((tetrahydro-2H-pyran-2-yl)oxy)methyl)-1H-1,2,3-triazol-4-yl)pyridin-3-yl)methyl)piperidine-3-carboxylate (800 mg, 1.67 mmol) in MeOH (15 mL) was added PPTS (0.84 g, 3.34 mmol) and the reaction was stirred at 50° C. for 16 hrs. The mixture was concentrated to dryness and the residue was diluted with EtOAc (10 mL). The mixture was washed with saturated aq·$NaHCO_3$ solution and brine, dried over $Na_2SO_4$, filtered and concentrated to dryness. The residue was purified by flash chromatography (0~60% EtOAc in PE) to give the title compound (620 mg, 94.0% yield) as yellow oil. LC/MS (ESI) (m/z): 396 $(M+H)^+$. $^1H$ NMR (400 MHz, $CDCl_3$) δ 8.14 (d, J=8.0 Hz, 1H), 7.73 (d, J=8.0 Hz, 1H), 4.85 (s, 2H), 4.09 (s, 3H), 3.69 (s, 3H), 3.62 (d, J=3.2 Hz, 2H), 3.12-2.97 (m, 2H), 2.95-2.83 (m, 1H), 2.62 (s, 3H), 2.48-2.38 (m, 2H), 2.34-2.28 (m, 1H), 2.03-1.86 (m, 1H).

Intermediate 13: methyl 1-((2-ethyl-6-(5-(hydroxymethyl)-1-methyl-11H-1,2,3-triazol-4-yl)pyridin-3-yl)methyl)-5,5-difluoropiperidine-3-carboxylate intermediate 13

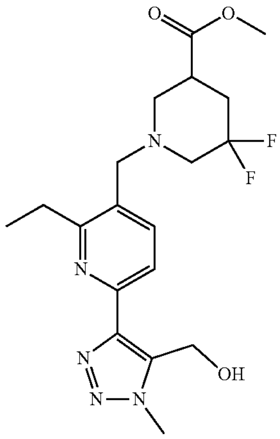

The title compound was prepared from 3-bromo-2-ethyl-6-(1-methyl-5-(((tetrahydro-2H-pyran-2-yl)oxy)methyl)-1H-1,2,3-triazol-4-yl)pyridine using the same sequence as the synthesis of intermediate 12. LC/MS (ESI) (m/z): 410 $(M+H)^+$. $^1H$ NMR (400 MHz, $CDCl_3$) δ 8.13 (d, J=8.0 Hz, 1H), 7.75 (d, J=8.0 Hz, 1H), 4.85 (s, 2H), 4.10 (s, 3H), 3.69 (s, 3H), 3.64 (s, 2H), 3.12-3.00 (m, 2H), 2.94-2.88 (m, 2H), 2.44-2.37 (m, 2H), 2.33-2.27 m, 1H), 2.07-1.86 (m, 2H), 1.31 (t, J=7.6 Hz, 3H).

Intermediate 14: 4-(cyclopropylmethyl)-3-methylpyridin-2(1H)-one

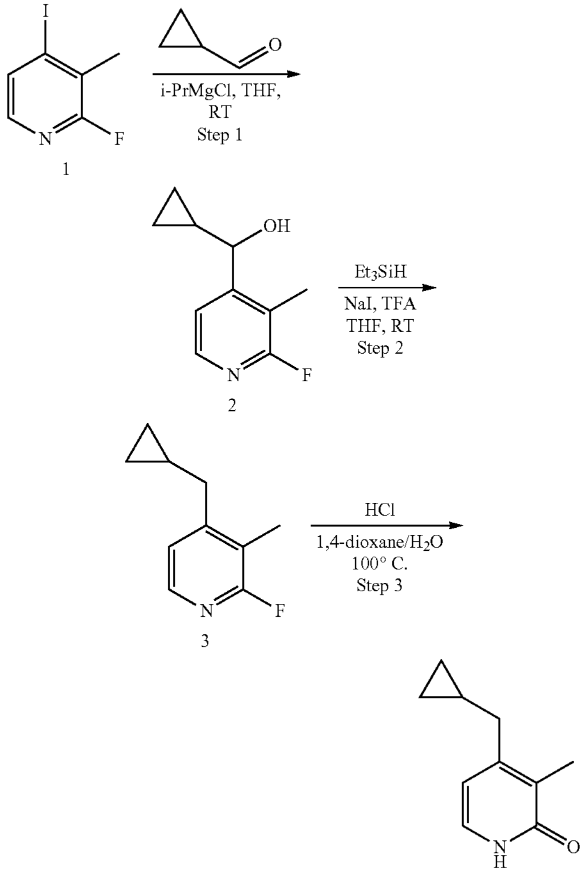

Intermediate 14

Step 1: cyclopropyl(2-fluoro-3-methylpyridin-4-yl)methanol

To a solution of 2-fluoro-4-iodo-3-methylpyridine (4 g, 16.9 mmol) in THF (40 mL) was added i-Pr—MgCl (16.9 mmol, 8.4 mL, 2 M in THF) drop-wisely at 0° C. under $N_2$ and the mixture was stirred at r.t. for 1 hr. Cyclopropanecarbaldehyde (1.18 g, 16.9 mmol) was added and the mixture was stirred at r.t. for 2 hrs. The mixture was quenched with ice-water (20 mL) and extracted with EtOAc (2×30 mL). The combined organic layers were washed with brine, dried over anhydrous $Na_2SO_4$, filtered and concentrated to dryness. The residue was purified by flash chromatography (eluted with PE:EtOAc=100:1 to 10:1) to give the title compound (2.37 g, 77.6% yield) as colorless oil. LC/MS (ESI) m/z: 182 $(M+H)^+$.

Step 2: 4-(cyclopropylmethyl)-2-fluoro-3-methylpyridine

To a solution of cyclopropyl(2-fluoro-3-methylpyridin-4-yl)methanol (810 mg, 4.47 mmol) in $CH_3CN$ (8 mL) were added NaI (2.68 g, 17.9 mmol) and TFA (2.61 g, 22.4 mmol) followed by drop-wise addition of $Et_3SiH$ (2.60 g, 22.4 mmol) at 0° C. under $N_2$ atmosphere and the mixture was stirred at r.t. for 16 hrs. The mixture was quenched with saturated aq·$NaHCO_3$ solution and extracted with EtOAc (2×15 mL). The combined organic layers were washed with brine, dried over anhydrous $Na_2SO_4$, filtered and concentrated to dryness. The residue was purified by flash chromatography (eluted with PE:EtOAc=100:1 to 10:1) to give the title compound (420 mg, 56.9% yield) as colorless oil. LC/MS (ESI) m/z: 166 $(M+H)^+$.

Step 3: 4-(cyclopropylmethyl)-3-methylpyridin-2(1H)-one

To a solution of 4-(cyclopropylmethyl)-2-fluoro-3-methylpyridine (420 mg, 2.54 mmol) in 1,4-dioxane (4.2 mL) and water (4.2 mL) was added aq·HCl (0.84 mL, 36% wt) and the mixture was stirred at 100° C. for 16 hrs. The mixture was diluted with water and extracted with DCM (2×10 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound (322 mg, 77.6% yield) as light yellow solid. $^1H$ NMR (400 MHz, DMSO-$d_6$) δ 11.13 (s, 1H), 6.95 (d, J=6.8 Hz, 1H), 5.97 (d, J=6.8 Hz, 1H), 2.19 (d, J=6.8 Hz, 2H), 1.75 (s, 3H), 0.78-0.67 (m, 1H), 0.32-0.23 (m, 2H), 0.02-0.04 (m, 2H). LC/MS (ESI) m/z: 164 $(M+H)^+$.

Intermediate 15: 4-(cyclopropylmethyl-3-methylpyridin-2(1H)-one

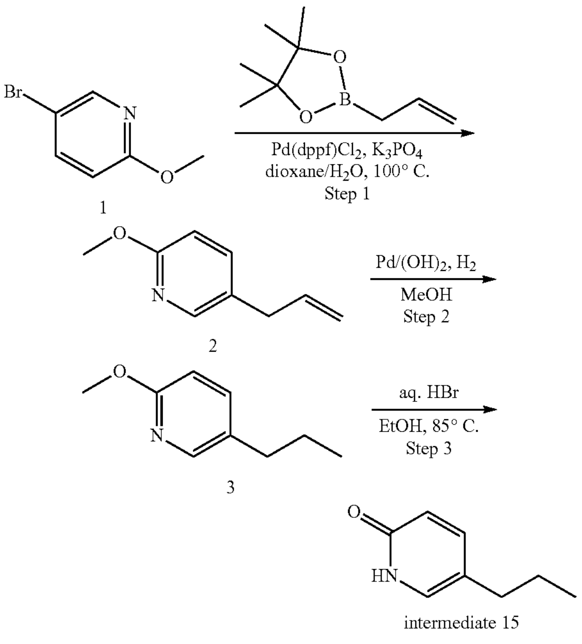

1
2
3
intermediate 15

Step 1: 5-allyl-2-methoxypyridine

To a solution of 5-bromo-2-methoxypyridine (4.2 g, 22.3 mmol) and 2-allyl-4,4,5,5-tetramethyl-1,3,2-dioxaborolane (5.63 g, 33.5 mmol) in 1,4-dioxane (42 mL) and water (8.4 mL) were added $K_3PO_4$ (14.23 g, 67.0 mmol), Pd(dppf)$Cl_2$ (1.63 g, 2.23 mmol) under $N_2$ atmosphere and the mixture was degassed under $N_2$ atmosphere for three times and stirred under $N_2$ atmosphere at 100° C. for 2 hrs. The mixture was diluted EtOAc (50 mL), washed with water and brine, dried over anhydrous $Na_2SO_4$, filtered and concentrated to dryness. The residue was purified by flash chromatography (eluted with PE:EtOAc=50:1 to 10:1) to give the title compound (3 g, 90% yield) as light yellow oil. LC/MS (ESI) m/z: 150 $(M+H)^+$.

Step 2: 2-methoxy-5-propylpyridine

To a solution of 5-allyl-2-methoxypyridine (3 g, 20.1 mmol) in MeOH (30 mL) was added $Pd(OH)_2/C$ (0.28 g, 10% wt) under $N_2$ atmosphere. After addition, the mixture was degassed under $N_2$ atmosphere for three times and stirred under a $H_2$ balloon at 25° C. for 16 hrs. The mixture was filtered and the filtrate was concentrated to dryness to give the title compound (2.74 g, 90.1% yield) as colorless oil, which was used in next step directly. LC/MS (ESI) m/z: 152 $(M+H)^+$.

Step 3: 5-propylpyridin-2(1H)-one (4)

To a solution of 2-methoxy-5-propylpyridine (2.74 g, 18.12 mmol) in EtOH (27 mL) was added aq·HBr (27 mL, 40% wt) and the mixture was stirred at 85° C. for 16 hrs. The mixture was quenched with saturated aq·$NaHCO_3$ solution and extracted with DCM (2×20 mL). The combined organic layers were washed with brine, dried over anhydrous $Na_2SO_4$, filtered and concentrated to dryness. The residue was purified by flash chromatography (eluted with PE:EtOAc=10:1 to 1:1) to give the title compound (723 mg, 29.1% yield) as white solid. $^1H$ NMR (400 MHz, $CDCl_3$) δ 13.21 (s, 1H), 7.35 (dd, J=9.2, 2.5 Hz, 1H), 7.14 (d, J=2.2 Hz, 1H), 6.55 (d, J=9.2 Hz, 1H), 2.35 (t, J=7.6 Hz, 1H), 1.60-1.48 (m, 1H), 0.92 (t, J=7.2 Hz, 2H). LC/MS (ESI) m/z: 138 $(M+H)^+$.

Intermediate 16: 5-(cyclopropylmethyl)pyridin-2(1H)-one

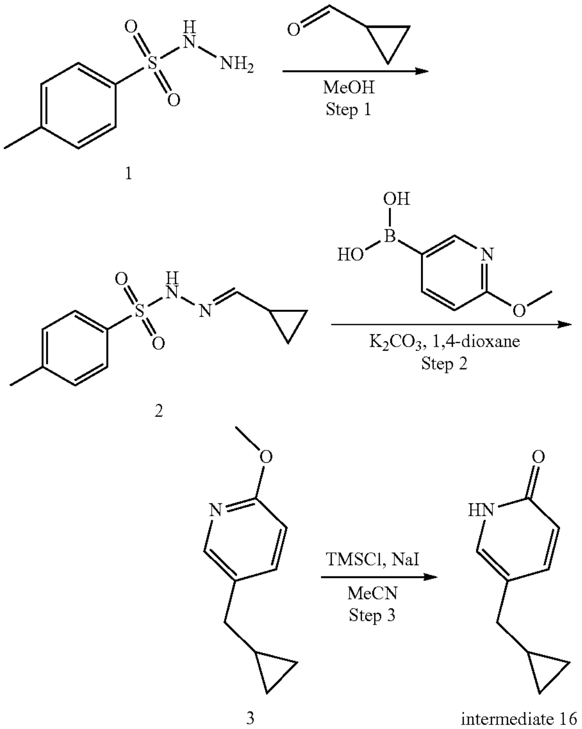

1
2
3
intermediate 16

Step 1: N'-[(1E)-cyclopropylmethylidene]-4-methylbenzene-1-sulfonohydrazide

To a solution of 4-methylbenzene-1-sulfonohydrazide (1 g, 5.4 mmol) in MeOH (10 mL) was added cyclopropanecarbaldehyde (0.40 mL, 5.4 mmol) drop-wisely at 0° C. and the mixture was stirred at 70° C. for 10 mins. The mixture was concentrated to dryness and the residue was purified by flash chromatography (0~40% EtOAc in PE) to give the title compound (1.1 g, 86.0% yield) as white solid. LC-MS (ESI) m/z 239 $(M+H)^+$.

Step 2: 5-(cyclopropylmethyl)-2-methoxypyridine

To mixture of N'-[(1E)-cyclopropylmethylidene]-4-methylbenzene-1-sulfonohydrazide (1 g, 4.2 mmol) and (6-methoxypyridin-3-yl)boronic acid (0.64 g, 4.2 mmol) in 1,4-dioxane (10 mL) was added $K_2CO_3$ (580 mg, 4.2 mmol) and the mixture was stirred at 110° C. for 16 hrs. The mixture was diluted with EtOAc (15 mL), washed with brine, dried over $Na_2SO_4$, filtered and concentrated to dryness. The residue was purified by flash chromatography (0~5% EtOAc in PE) to give 5-(cyclopropylmethyl)-2-methoxypyridine (210 mg, 30.7% yield) as colorless oil. LC-MS (ESI) m/z 164 $(M+H)^+$. $^1H$ NMR (400 MHz, $CDCl_3$) δ 8.03 (d, J=1.9 Hz, 1H), 7.48 (dd, J=8.4, 1.9 Hz, 1H), 6.68 (d, J=8.4 Hz, 1H), 3.92 (s, 3H), 2.46 (d, J=6.9 Hz, 2H), 1.01-0.84 (m, 1H), 0.57-0.46 (m, 2H), 0.20-0.17 (m, 2H).

Step 3: 5-(cyclopropylmethyl)pyridin-2(1H)-one

To a mixture of 5-(cyclopropylmethyl)-2-methoxypyridine (200 mg, 1.2 mmol) in MeCN (5 mL) was added NaI (367 mg, 2.5 mmol) and TMSCl (0.31 mL, 2.5 mmol) and the reaction mixture was stirred at 70° C. for 16 hrs. The mixture was diluted with EtOAc (5 mL), washed with water and brine, dried over $Na_2SO_4$, filtered and was concentrated to dryness. The residue was purified by flash chromatography (0~50% EtOAc in PE) to give 5-(cyclopropylmethyl)pyridin-2(1H)-one (50 mg, 27.4% yield) as colorless oil. LC-MS (ESI) m/z 150 $(M+H)^+$.

Intermediate 17: 5-(cyclobutylmethyl)pyridin-2(1H)-one intermediate 17

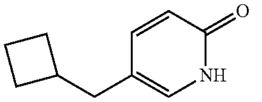

The title compound was prepared from cyclobutanecarbaldehyde using the same sequence as the synthesis of intermediate 16. LC-MS (ESI) m/z 164 $(M+H)^+$.

Intermediate 18: 5-(cyclobutylmethyl)pyridin-2(1H)-one intermediate 18

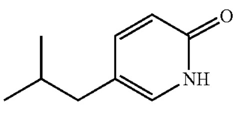

The title compound was prepared from isobutyraldehyde using the same sequence as the synthesis of intermediate 16. LC-MS (ESI) m/z 152 $(M+H)^+$.

Intermediate 19: 5-isopropylpyridin-2(1H)-one

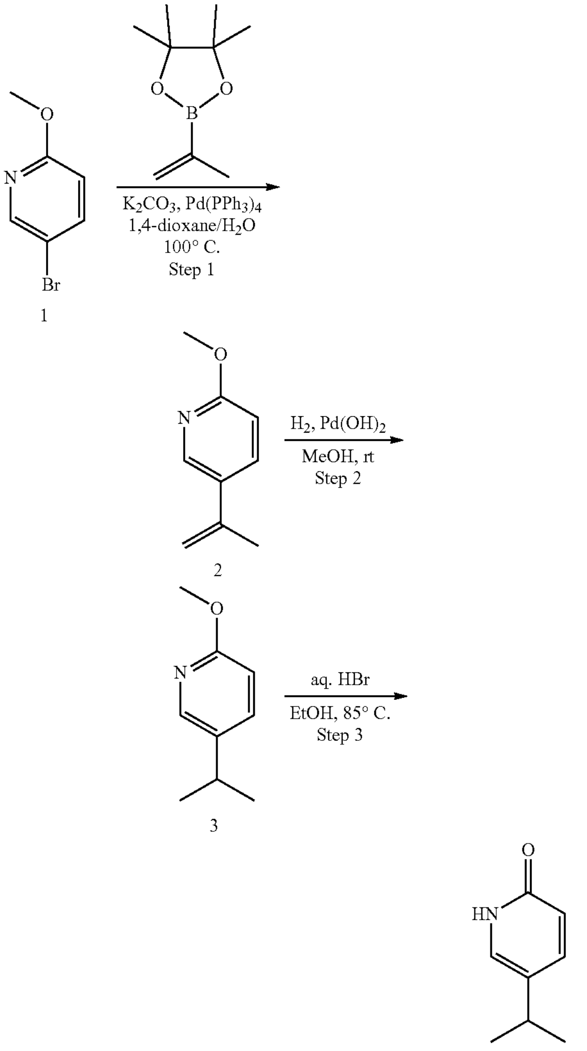

1

2

3

Intermediate 19

Step 1: 2-methoxy-5-(prop-1-en-2-yl)pyridine

To a solution of 5-bromo-2-methoxypyridine (1.0 g, 5.32 mmol) and 4,4,5,5-tetramethyl-2-(prop-1-en-2-yl)-1,3,2-dioxaborolane (1.34 g, 7.98 mmol) in 1,4-dioxane (10 ml) and water (2 mL) were added $K_2CO_3$ (1.47 g, 10.64 mmol), $Pd(PPh_3)_4$ (0.61 g, 0.53 mmol) under $N_2$ atmosphere, after addition, the mixture was degassed under $N_2$ atmosphere for three times and stirred at 100° C. for 16 hrs. The mixture was diluted with water and extracted with EtOAc (2×15 mL). The combined organic layers were washed with brine, dried over anhydrous $Na_2SO_4$, filtered and concentrated to dryness. The residue was purified by flash chromatography (eluted with PE:EtOAc=200:1 to 20:1) to give the title compound (600 mg, 75.6% yield) as colorless oil. LC/MS (ESI) m/z: 150 $(M+H)^+$. $^1H$ NMR (400 MHz, $CDCl_3$) δ 8.25

(d, J=2.4 Hz, 1H), 7.69 (dd, J=8.6, 2.6 Hz, 1H), 6.71 (dd, J=8.6, 0.6 Hz, 1H), 5.29 (s, 1H), 5.05-5.01 (m, 1H), 3.94 (s, 1H), 2.13 (d, J=0.5 Hz, 1H).

Step 2: 5-isopropyl-2-methoxypyridine

To a solution of 2-methoxy-5-(prop-1-en-2-yl)pyridine (600 mg, 4.02 mmol) in MeOH (6 mL) was added $Pd(OH)_2$ (50 mg, 10% wt) under $N_2$ atmosphere, after addition, the mixture was degassed under $N_2$ atmosphere for three times and stirred under a $H_2$ balloon at 25° C. for 16 hrs. The mixture was filtered and the filtrate was concentrated to dryness to give the title compound (290 mg, 47.7% yield) as colorless oil, which was used in next step directly. $^1H$ NMR (400 MHz, $CD_3OD$) δ 7.95 (d, J=2.4 Hz, 1H), 7.59 (dd, J=8.6, 2.5 Hz, 1H), 6.74 (d, J=8.6 Hz, 1H), 3.87 (s, 3H), 2.93-2.85 (m, 1H), 1.24 (d, J=6.9 Hz, 6H). LC/MS (ESI) m/z: 152 $(M+H)^+$.

Step 3: 5-isopropylpyridin-2(1H)-one

To a solution of 5-isopropyl-2-methoxypyridine (150 mg, 0.99 mmol) in EtOH (1.5 mL) was added aq·HBr (1.5 mL, 40% wt) under $N_2$ atmosphere and the mixture was stirred at 85° C. for 16 hrs. The mixture was quenched with saturated aq·$NaHCO_3$ solution and extracted with DCM (3×5 mL). The combined organic layers were washed with brine, dried over anhydrous $Na_2SO_4$, filtered and concentrated to dryness to give the title compound (115 mg, 84.5% yield) as white solid. LC/MS (ESI) m/z: 138 $(M+H)^+$.

Intermediate 20: 5-cyclobutylpyridin-2(1H)-one

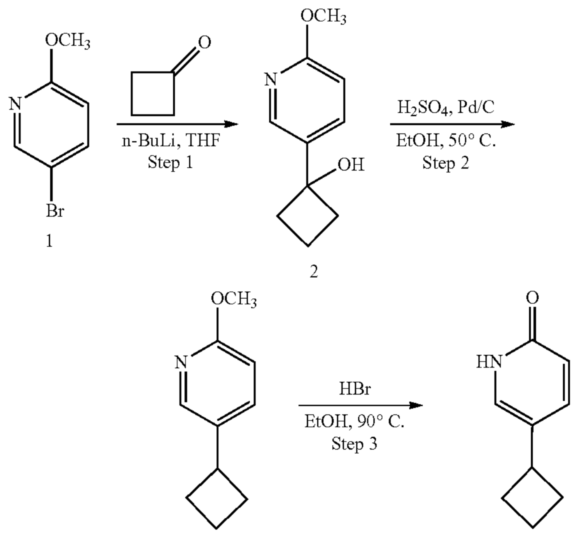

1 2 3 intermediate 20

Step 1: 1-(6-methoxypyridin-3-yl)cyclobutan-1-ol

To a stirred solution of 5-bromo-2-methoxypyridine (1.38 mL, 10.6 mmol) in dry THE (25 mL) was added n-BuLi (5.5 mL, 13.8 mmol) drop-wisely at −78° C. After stirring at this temperature for 30 mins, cyclobutanone (1.2 mL, 15.9 mmol) was added and the resulting mixture was stirred at −78° C. for 30 mins and r.t. for 30 mins. The mixture was quenched with ice-water and extracted with EtOAc (2×10 mL). The combined organic layers were washed with brine, dried over anhydrous $Na_2SO_4$, filtered and concentrated to dryness, the residue was purified by flash chromatography (PE:EtOAc=10:1) to give the title compound (1.5 g, 78.6% yield). LC/MS (ESI) m/z: 180 $(M+H)^+$. $^1H$ NMR (400 MHz, $CDCl_3$) δ 8.29 (d, J=2.2 Hz, 1H), 7.72 (dd, J=8.6, 2.6 Hz, 1H), 6.76 (dd, J=8.6, 0.6 Hz, 1H), 3.94 (s, 3H), 2.62-2.46 (m, 2H), 2.41-2.32 (m, 2H), 2.08-1.94 (m, 2H), 1.69-1.59 (m, 2H).

Step 2: 5-cyclobutyl-2-methoxypyridine

To a solution of 1-(6-methoxypyridin-3-yl)cyclobutan-1-ol (1 g, 5.5 mmol) in MeOH (3 mL) was added conc·$H_2SO_4$ (1 mL) followed by Pd/C (80 mg, 10% wt) at 0° C., the mixture was degassed under $N_2$ atmosphere for three times and stirred under a $H_2$ balloon at r.t. for 1 hr. The mixture was filtered and the filtrate was concentrated to dryness. The residue was purified by flash chromatography (PE: EtOAc=10:1 to 5:1) to give the title compound (300 mg, 32.9% yield) as light yellow oil. LC/MS (ESI) (m/z): 164 $(M+H)^+$. $^1H$ NMR (400 MHz, $CDCl_3$) δ 7.98 (t, J=4.4 Hz, 1H), 7.47 (dd, J=8.5, 2.5 Hz, 1H), 6.69 (d, J=8.5 Hz, 1H), 3.91 (s, 3H), 3.46 (dd, J=17.4, 8.7 Hz, 1H), 2.40-2.28 (m, 2H), 2.16-2.02 (m, 3H), 1.91-1.82 (m, 1H).

Step 3: 5-cyclobutylpyridin-2-ol

To a solution of 5-cyclobutyl-2-methoxypyridine (100 mg, 0.6 mmol) in EtOH (5 mL) was added aq·HBr (2 mL, 48% wt) and the mixture stirred at 70° C. under $N_2$ atmosphere for 16 hrs. The mixture was poured into ice-cooled saturated aq·$NaHCO_3$ solution and extracted with DCM (2×5 mL). The combined organic layers were washed with brine, dried over anhydrous $Na_2SO_4$, filtered and concentrated under reduced pressure to dryness to give the title compound (70 mg, 76.5% yield). LC/MS (ESI) (m/z): 150 $(M+H)^+$. $^1H$ NMR (400 MHz, $CDCl_3$) δ 12.76 (s, 1H), 7.42 (dd, J=9.3, 2.4 Hz, 1H), 7.14 (d, J=1.8 Hz, 1H), 6.56 (d, J=9.3 Hz, 1H), 3.34-3.23 (dt, J=17.2, 8.7 Hz, 1H), 2.27-2.23 (m, 2H), 2.06-1.92 (m, 3H), 1.89-1.76 (m, 1H).

Intermediate 21: 5-cyclopropyl-4-methylpyridin-2(1H)-one

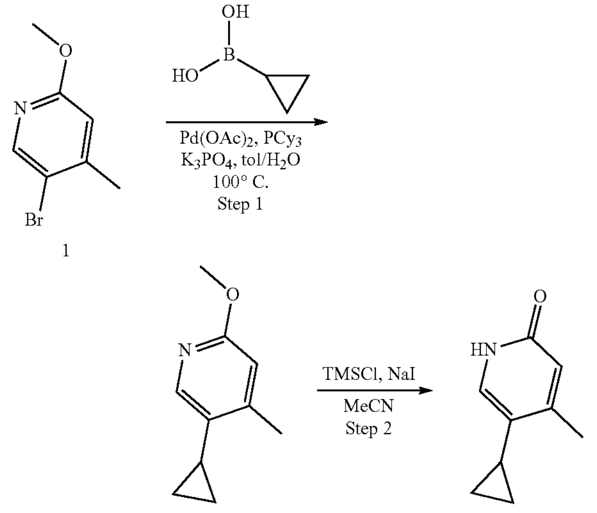

1 2 Intermediate 21

Step 1: 5-cyclopropyl-2-methoxy-4-methylpyridine

To a solution of 5-bromo-2-methoxy-4-methylpyridine (2 g, 9.90 mmol) and cyclopropylboronic acid (1.11 g, 12.87 mmol) in toluene (30 mL) and water (3 mL) were added $K_3PO_4$ (6.30 g, 29.67 mmol), tricyclohexyl phosphine (0.28 g, 0.99 mmol), $Pd(OAc)_2$ (0.11 g, 0.50 mmol) under $N_2$ atmosphere, after addition, the mixture was degassed under $N_2$ atmosphere for three times and stirred at 100° C. for 16 hrs. The mixture was diluted with water (20 mL) and extracted with EtOAc (2×10 mL). The combined organic layers were washed with brine, dried over anhydrous $Na_2SO_4$, filtered and concentrated to dryness. The residue was purified by flash chromatography (eluted with PE:EtOAc=200:1 to 10:1) to give the title compound (1.42 g, 88.1% yield) as yellow oil. LC/MS (ESI) m/z: 164 $(M+H)^+$.

Step 2: 5-cyclopropyl-4-methylpyridin-2(1H)-one (3)

To a solution of 5-cyclopropyl-2-methoxy-4-methylpyridine (1 g, 6.12 mmol) in $CH_3CN$ (10 mL) were added NaI (1.84 g, 12.25 mmol), TMSCl (1.33 g, 12.25 mmol). The mixture was stirred at 70° C. overnight. The mixture was quenched with saturated aq·$NaHCO_3$ solution and extracted with EtOAc (2×10 mL). The combined organic layers were washed with brine, dried over anhydrous $Na_2SO_4$, filtered and concentrated to dryness. The residue was purified by flash chromatography (eluted with PE:EtOAc=20:1 to 1:1) to give the title compound (525 mg, 57.4% yield) as brown solid. $^1$H-NMR (400 MHz, DMSO-$d_6$) δ 10.96 (s, 1H), 6.67 (s, 1H), 5.91 (s, 1H), 1.97 (d, J=0.6 Hz, 1H), 1.38-1.27 (m, 1H), 0.56-0.46 (m, 1H), 0.24-0.16 (m, 1H). LC/MS (ESI) m/z: 150 $(M+H)^+$.

Intermediate 22: 4-cyclopropyl-5-methylpyridin-2(1H)-one

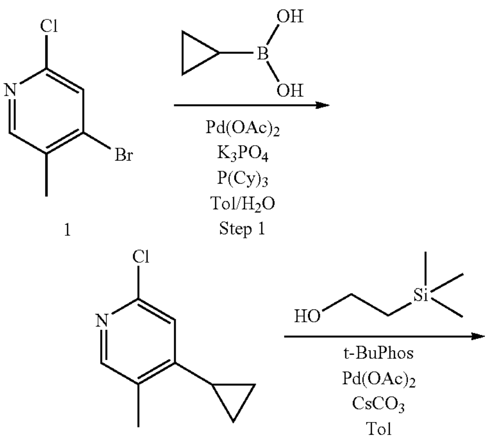

1

2

-continued

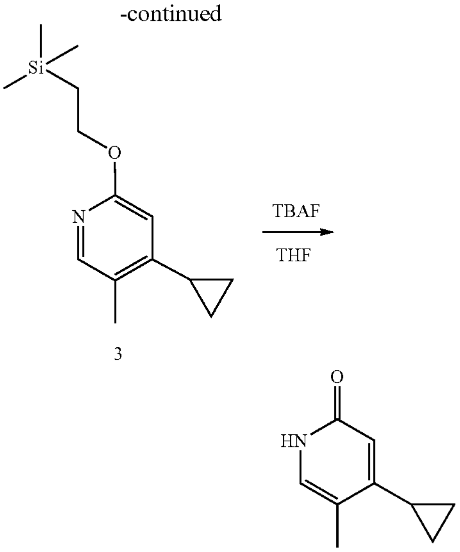

3

Intermediate 22

Step 1: 2-chloro-4-cyclopropyl-5-methylpyridine

To a mixture of 4-bromo-2-chloro-5-methylpyridine (700 mg, 3.39 mmol), $K_3PO_4$ (2.15 g, 10.17 mmol) and cyclopropylboronic acid (349 mg, 4.07 mmol) in 1,4-dioxane (25 mL) was added $Pd(OAc)_2$ (38 mg, 0.17 mmol) and Tricyclohexyl phosphine (95 mg, 0.34 mmol) under $N_2$ atmosphere and the mixture was stirred at 110° C. for 16 hrs. The mixture was diluted with EtOAc (10 mL) and filtered. The filtrate was concentrated to dryness and the residue was purified by flash chromatography (silica gel, 0-100% EtOAc in PE) to the title compound (420 mg, 73.9% yield) as colorless oil. LC/MS (ESI) m/z: 168$(M+H)^+$.

Step 2: 4-cyclopropyl-5-methyl-2-[2-(trimethylsilyl)ethoxy]pyridine

To a solution of 2-chloro-4-cyclopropyl-5-methylpyridine (250 mg, 1.49 mmol) in toluene (5 mL) was added 2-(trimethylsilyl)ethan-1-ol (2.1 mL, 14.91 mmol), $Cs_2CO_3$ (1.46 g, 4.47 mmol), $Pd(OAc)_2$ (33 mg, 0.15 mmol), t-BuPhos (89 mg, 0.15 mmol), the mixture was degassed under $N_2$ for three times and stirred at 110° C. for 16 hrs. The reaction mixture was concentrated to dryness and the residue was purified by flash chromatography (silica gel, 0-30% EtOAc in PE) to give the title compound (201 mg, 54.0% yield) as light yellow oil. LC/MS (ESI) m/z: 250$(M+H)^+$.

Step 3: 4-cyclopropyl-5-methylpyridin-2-ol

To a solution of 4-cyclopropyl-5-methyl-2-[2-(trimethylsilyl)ethoxy]pyridine (200 mg, 0.80 mmol) in THF (3 mL) was added TBAF (418 mg, 1.60 mmol) and the mixture was stirred at 25° C. for 3 hrs. The reaction mixture was diluted with EtOAc (10 mL) and washed with saturated water and brine, dried over anhydrous $Na_2SO_4$, filtered and concentrated to dryness. The residue was purified by flash chromatography (silica gel, 0-20% MeOH in DCM) to give the title compound (56 mg, 46.8% yield) as white solid. LC/MS (ESI) m/z: 150 $(M+H)^+$. $^1$H NMR (400 MHz, DMSO-$d_6$) δ

11.12 (s, 1H), 7.08 (s, 1H), 5.83 (s, 1H), 2.08 (d, J=0.8 Hz, 3H), 1.80-1.72 (m, 1H), 0.97-0.91 (m, 2H), 0.68-0.62 (m, 2H).

Intermediate 23: 5-(cyclopropylethynyl)pyridin-2(1H)-one

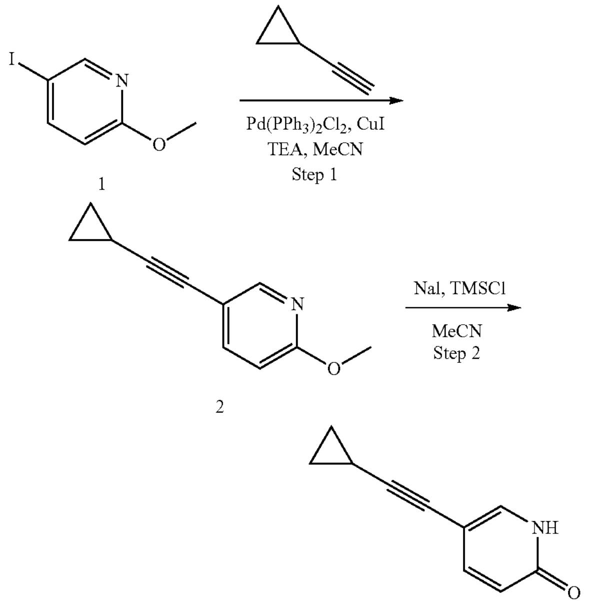

Intermediate 23

Step 1: 5-(2-cyclopropylethynyl)-2-methoxypyridine

To a solution of 5-iodo-2-methoxypyridine (1 g, 4.26 mmol) in $CH_3CN$ (20 mL) was added TEA (1.8 mL, 12.77 mmol) followed by the addition of Bis(triphenylphosphine) palladium(II) chloride (0.17 g, 0.21 mmol), CuI (0.16 g, 0.85 mmol) and ethynylcyclopropane (0.43 mL, 5.11 mmol) under $N_2$ with stirring. And the mixture was stirred at r.t. for 16 hrs. The reaction mixture was filtered through a Celite pad, and the filtrate was concentrated to dryness. The residue was purified by flash chromatography (silica gel, 0~30% EtOAc in PE) to give the title compound (700 mg, 95.0% yield) as white solid. LC/MS (ESI) m/z: 174 $(M+H)^+$.

Step 2: 5-(2-cyclopropylethynyl)-1,2-dihydropyridin-2-one

To solution of 5-(2-cyclopropylethynyl)-2-methoxypyridine (500 mg, 2.89 mmol) in $CH_3CN$ (10 mL) was added NaI (865 mg, 5.78 mmol) and TMSCl (0.74 mL, 5.773 mmol) and the reaction was stirred at 70° C. for 16 hrs. The mixture was diluted with EtOAc (10 mL), washed with water and brine, dried over anhydrous $Na_2SO_4$, filtered and concentrated to dryness. The residue was purified by flash chromatography (0~5% MeOH in DCM) to give 5-(2-cyclopropylethynyl)-1,2-dihydropyridin-2-one (300 mg, 65.3% yield) as yellow solid. LC/MS (ESI) m/z: 160 $(M+H)^+$.

Intermediate 24: 4-(cyclopropylethynyl)pyridin-2(1H)-one intermediate 24

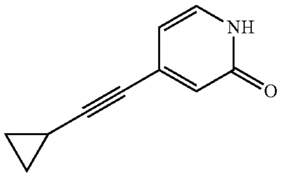

Intermediate 24 was prepared from 4-iodo-2-methoxypyridine using the same sequence that was used to synthesize intermediate 23. LC/MS (ESI) m/z: 160 $(M+H)^+$.

Intermediate 25: 5-cyclopropoxypyridin-2(1H)-one

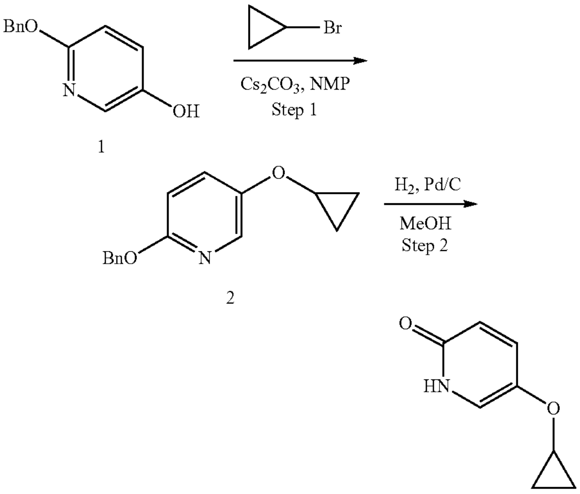

Intermediate 25

Step 1: 2-(benzyloxy)-5-cyclopropoxypyridine

To a mixture of 6-(benzyloxy)pyridin-3-ol (300 mg, 1.5 mmol) and bromocyclopropane (1.2 mL, 14.9 mmol) in NMP (5 mL) was added $CS_2CO_3$ (1.4 g, 4.4 mmol) and the resulting solution was stirred in an autoclave at 150° C. for 8 hrs. The mixture was cooled to r.t. and diluted with EtOAc (10 mL), washed with water and brine, dried over $Na_2SO_4$, filtered and concentrated to dryness. The residue was purified by flash chromatography (0~50% of EtOAc in PE) to give the title compound (180 mg, 50% yield) as light yellow oil. LC/MS (ESI) m/z 242 [M+1]*.

Step 2: 5-cyclopropoxypyridin-2(1H)-one

To a solution of 2-(benzyloxy)-5-cyclopropoxypyridine (180 mg, 0.7 mmol) in MeOH (3 mL) was added Pd/C (20 mg, 10% wt) at 0° C. and the mixture was degassed under $N_2$ atmosphere for three times and stirred under a $H_2$ balloon at room temperature for 1 hr. The mixture was filtered and the filtrate was concentrated to dryness. The residue was purified by prep·TLC (PE:EtOAc=2:1) to give the title compound (40 mg, 35.4% yield) as white foam-like solid. LC/MS (ESI) (m/z): 152 $(M+H)^+$.

Intermediate 26: 5-propoxypyridin-2(1H)-one

Intermediate 26

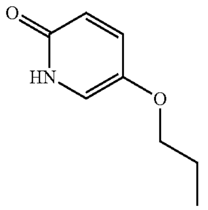

Intermediate 26 was synthesized according the same sequence as was used for the synthesis of intermediate 25. LC/MS (ESI) (m/z): 154 $(M+H)^+$.

Intermediate 27: 5-propoxypyridin-2(1H)-one

Intermediate 27

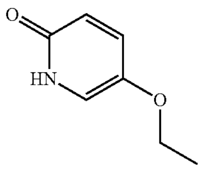

Intermediate 27 was synthesized according the same sequence as was used for the synthesis of intermediate 25. LC/MS (ESI) (m/z): 140 $(M+H)^+$.

Intermediate 28: 5-(azetidin-1-yl)pyridin-2(1H)-one

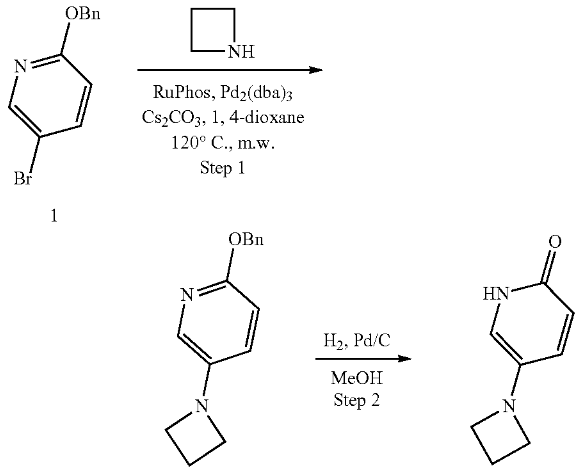

1

2

Intermediate 28

Step 1: 5-(azetidin-1-yl)-2-(benzyloxy)pyridine

To solution of 2-(benzyloxy)-5-bromopyridine (850 mg, 3.2 mmol) in 1,4-dioxane (5 mL) was added azetidine (0.65 mL, 9.6 mmol) followed by $CS_2CO_3$ (2.1 g, 6.4 mmol), RuPhos (300 mg, 0.64 mmol) and $Pd_2(dba)_3$ (260 mg, 0.3 mmol), the mixture was degassed under $N_2$ atmosphere for three times and stirred in CEM reactor at 100° C. for 2 hrs. The mixture was diluted with EtOAc (10 mL), washed with water and brine, dried over anhydrous $Na_2SO_4$, filtered and concentrated to dryness. The residue was purified by flash chromatography (0~50% EtOAc in PE) to give the title compound (650 mg, 84.3% yield) as yellow oil. LC-MS (ESI) m/z 241 $(M+H)^+$.

Step 2: 5-(azetidin-1-yl)pyridin-2-ol

To solution of 5-(azetidin-1-yl)-2-(benzyloxy)pyridine (400 mg, 1.7 mmol) in MeOH (10 mL) was added Pd/C (50 mg, 10% wt). The mixture was degassed under $N_2$ atmosphere and stirred under a $H_2$ balloon at r.t. for 3 hrs. The mixture was filtered and the filtrate was concentrated to dryness to give the title compound (230 mg, 90% yield) as yellow solid. LC-MS (ESI) m/z 151 $(M+H)^+$.

Intermediate 29: 5-propylpyrazin-2-ol

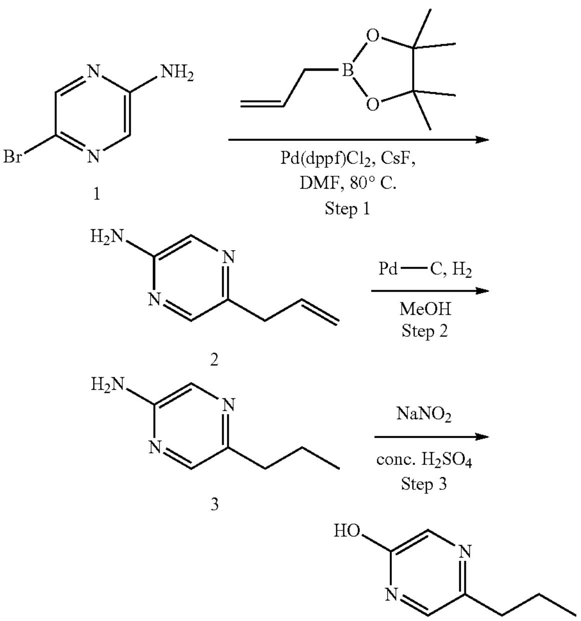

1

2

3

Intermediate 29

Step 1: 5-allylpyrazin-2-amine

To a mixture of 5-bromopyrazin-2-amine (500 mg, 2.87 mmol) and 4,4,5,5-tetramethyl-2-(prop-2-en-1-yl)-1,3,2-dioxaborolane (0.81 mL, 4.31 mmol) in DMF (10 mL) was added CsF (1.3 g, 8.6 mmol) and $Pd(dppf)Cl_2$ (430 mg, 0.57 mmol). The mixture was degassed under $N_2$ atmosphere for three times and stirred under $N_2$ atmosphere at 100° C. for 9 hrs. The mixture was diluted with EtOAc (10 mL) and washed with water and brine, dried and concentrated to dryness. The residue was purified by flash chromatography (PE:EtOAc=4:1) to give the title compound (250 mg, 64.1% yield) as yellow oil. LC/MS (ESI) (m/z): 135 $(M+H)^+$.

Step 2: 5-propylpyrazin-2-amine

To a solution of 5-allylpyrazin-2-amine (240 mg, 1.78 mmol) in MeOH (10 mL) was added Pd/C (20 mg, 10% wt). The mixture was degassed under $H_2$ atmosphere for three times and stirred under a $H_2$ balloon at room temperature for 16 hrs. The mixture was filtered and the filtrate was concentrated to dryness to give the title compound (200 mg, 82.1% yield) as yellow oil. LC/MS (ESI) (m/z): 138 $(M+H)^+$.

Step 3: 5-propylpyrazin-2-ol

To a solution of $NaNO_2$ (3 g, 43.74 mmol) in con·$H_2SO_4$ (10 mL) was added propylpyrazin-2-amine (1 g, 7.3 mmol) in portions at 0° C. and the mixture was stirred at 100° C. for 2 hrs. The mixture was diluted with ice water, neutralized with 1M aq·NaOH solution to pH=5 and extracted with DCM (2×10 mL). The combined organic layers were washed with brine, dried over anhydrous $Na_2SO_4$, filtered and concentrated under reduced pressure to dryness. The residue was purified by chromatography on silica gel (eluted with DCM:MeOH=15:1) to give the title compound (320 mg, 31.8% yield). LC/MS (ESI) (m/z): 139 $[M+H]^+$.

Intermediate 30: 5-propylpyrimidin-2(1H)-one

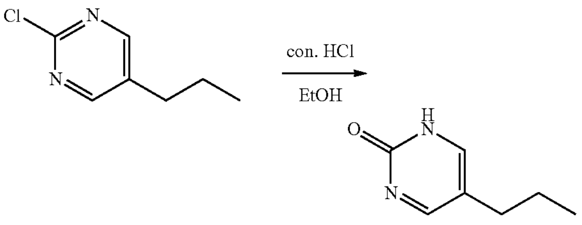

Intermediate 30

To a solution of 2-chloro-5-propylpyrimidine (500 mg, 3.19 mmol) in EtOH (5 mL) was added con·HCl (5 mL) at 0° C. and the mixture was stirred under $N_2$ atmosphere at 100° C. for 16 hrs. The mixture was diluted with ice water (10 mL), neutralized with saturated aq·$NaHCO_3$ solution to pH=7 and extracted with DCM (2×10 mL). The combined organic layers were washed with brine, dried over anhydrous $Na_2SO_4$, filtered and concentrated under reduced pressure to dryness. The residue was purified by chromatography on silica gel (eluted with DCM:MeOH=15:1) to give the title compound (200 mg, 45.3% yield) as yellow oil. LC/MS (ESI) m/z: 139 $(M+H)^+$.

Intermediate 31: 6-propylpyrimidin-4(3H)-one

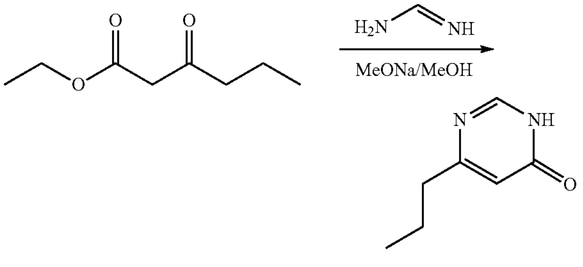

Intermediate 31

To a mixture of ethyl 3-oxohexanoate (1.6 mL, 10 mmol) and formamidine acetate (1 g, 10 mmol) in MeOH (10 mL) was added MeONa (7.5 mL, 1.5 M in MeOH) drop-wisely at 0° C. and the mixture was stirred at 60° C. overnight. The reaction mixture was diluted with DCM (20 mL), washed with water, dried over anhydrous $Na_2SO_4$, filtered and concentrated to dryness. The residue was purified by flash chromatography (0~100% of EtOAc in PE) to give the title compound (410 mg, 29.0% yield) as white solid. LC/MS (ESI) m/z: 139 $(M+H)^+$.

Intermediate 32:4propylpyridazin-3(2H)-one

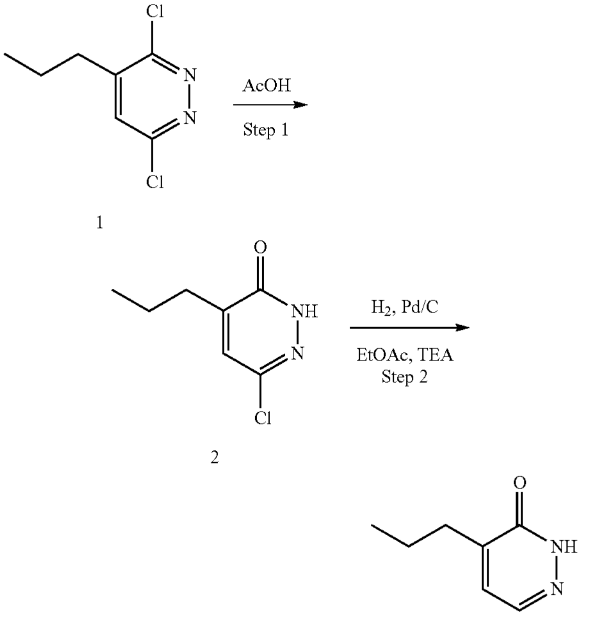

Intermediate 32

Step 1: 6-chloro-4-propylpyridazin-3(2H)-one

A solution of 3,6-dichloro-4-propylpyridazine (1.00 g, 5.23 mmol) in AcOH (10 mL) was stirred at 120° C. under $N_2$ atmosphere for 5 hrs. The mixture was concentrated to dryness and the residue was neutralized with saturated aq·$NaHCO_3$ solution. The mixture was extracted with EtOAc (2×20 mL) and the combined organic layers were washed with brie, dried over $Na_2SO_4$, filtered and concentrated to dryness. The residue was purified by silica gel chromatography (PE:EtOAc=8:1 to 5:1) to give the title compound (550 mg, 60.9% yield) as yellow oil. LC/MS (ESI) m/z: 173 $(M+H)^+$.

Step 2: 4-propylpyridazin-3(2H)-one

To a solution of 6-chloro-4-propylpyridazin-3(2H)-one (500 mg, 2.90 mmol) in EtOAc (5 mL) was added TEA (0.05 mL, 0.360 mmol) and Pd/C (60 mg, 10% wt) and the mixture was degassed under $N_2$ atmosphere for three times and stirred under a $H_2$ balloon at 0° C. for 3 hrs. The reaction was filtered and the filtrate was concentrated to dryness. The residue was purified by column chromatography (PE:EtOAc=5:1 to 1:1) to give the title compound (75 mg, 18.7% yield) as off-white solid. LC/MS (ESI) m/z: 139 $(M+H)^+$.

Intermediate 33: 6-propylpyridazin-3-ol

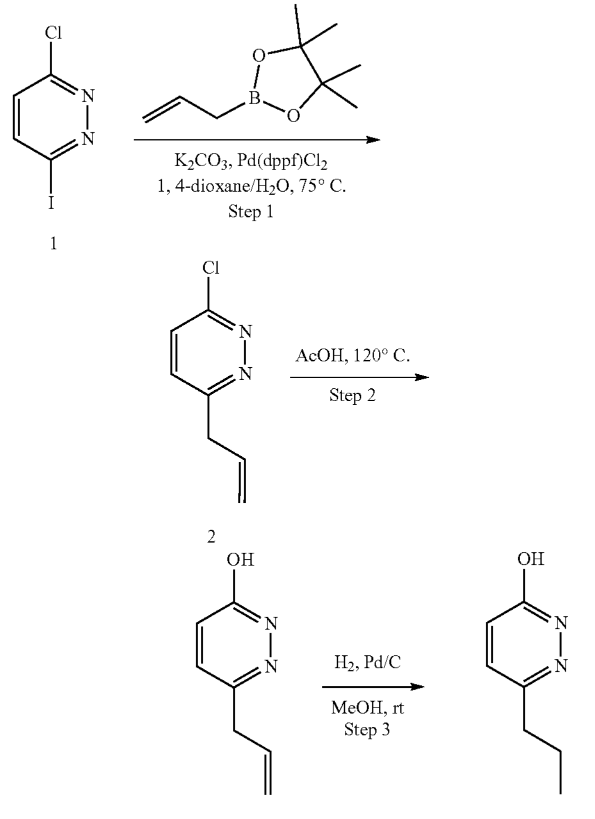

1 2 3 Intermediate 33

Step 1: 3-allyl-6-chloropyridazine

To a mixture of 2-allyl-4,4,5,5-tetramethyl-1,3,2-dioxaborolane (705 mg, 4.2 mmol) and 3-chloro-6-iodopyridazine (1 g, 4.2 mmol) in 1,4-dioxane (10 mL) and water (2 mL) were added $K_2CO_3$ (1.74 g, 12.582 mmol) and Pd(dppf)$Cl_2$ (153.44 mg, 0.210 mmol) under $N_2$ atmosphere. Then the mixture reaction was stirred at 75° C. for 16 hrs. The mixture was diluted with water and extracted with EtOAc (2×10 mL). The combined organic layers were washed with brine, dried over anhydrous $Na_2SO_4$, and concentrated under reduced pressure to dryness. The residue was purified by chromatography on silica gel (PE:EtOAc=5:1) to give the title compound (130 mg, 20.3% yield) as yellow oil. LC/MS (ESI) (m/z): 155 $(M+H)^+$.

Step 2: 6-allylpyridazin-3-ol

A solution of 3-allyl-6-chloropyridazin (130 mg, 0.85 mmol) in AcOH (6 mL) was stirred at 120° C. for 2 hrs. The mixture reaction was concentrated to dryness and the residue was purified by chromatography on silica gel (PE:EtOAc=3:1) to give the title compound (70 mg, 61.3% yield) as yellow solid. LC/MS (ESI) (m/z): 137 $(M+H)^+$.

Step 3: 6-propylpyridazin-3-ol

To a solution of 6-allylpyridazin-3-ol (70 mg, 0.459 mmol) in MeOH (3 mL) was added Pd/C (20 mg, 10% wt) at 0° C., the mixture was degassed under $N_2$ atmosphere for three times and stirred under a $H_2$ balloon at room temperature for 2 hrs. The mixture was filtered and the filtrate was concentrated to dryness to give the title compound (32 mg, 51.2% yield) as yellow solid. LC/MS (ESI) (m/z): 139 $(M+H)^+$.

Intermediate 34: 6-(cyclopropylmethyl)pyridazin-3-ol

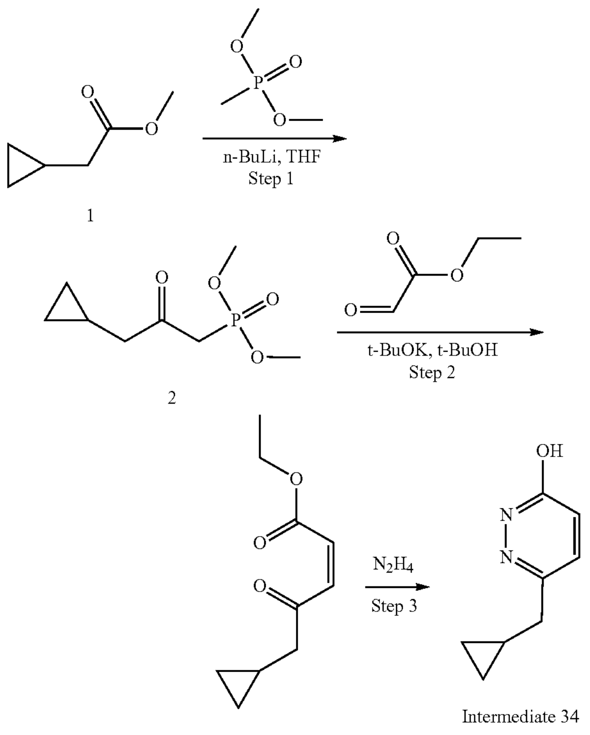

1 2 3 Intermediate 34

Step 1: dimethyl (3-cyclopropyl-2-oxopropyl)phosphonate

To a solution of dimethyl methylphosphonate (652 mg, 5.25 mmol) in THE (5 mL) was added n-BuLi (2.62 mL, 5.25 mmol, 2M in THF) drop-wisely at −70° C. and the mixture was stirred at this temperature for 15 mins. A solution of methyl 2-cyclopropylacetate (300 mg, 2.62 mmol) in THF (3 mL) was added to the above mixture at −70° C. and the resulting mixture was stirred at −70° C. for 1 hr. The reaction mixture was quenched with saturated aq·$NH_4Cl$ solution at 0° C. and extracted with EtOAc (2×10 mL). The combined organic layers were washed with brine, dried over anhydrous $Na_2SO_4$, filtered and concentrated to dryness to give the title compound (460 mg, 84.9% yield) as yellow solid. LC/MS (ESI) m/z: 207 $(M+H)^+$.

Step 2: ethyl (2Z)-5-cyclopropyl-4-oxopent-2-enoate

To a solution of dimethyl (3-cyclopropyl-2-oxopropyl) phosphonate (460 mg, 2.23 mmol) in t-BuOH (5 mL) was added t-BuOK (250 mg, 2.23 mmol), ethyl 2-oxoacetate (0.22 mL, 2.23 mmol), and then the mixture was stirred at 25° C. for 16 hrs. The reaction mixture was diluted with EtOAc (10 mL) and washed with saturated aq·$NH_4Cl$ solution and brine, dried over anhydrous $Na_2SO_4$, filtered and concentrated to dryness. The residue was purified by flash chromatography (silica gel, 0-5% EtOAc in PE) to give the title compound (81 mg, 19.9% yield) as yellow oil. LC/MS (ESI) m/z: 183 $(M+H)^+$. $^1H$ NMR (400 MHz, $CDCl_3$) δ 6.55 (d, J=12.1 Hz, 1H), 6.02 (d, J=12.1 Hz, 1H), 4.21 (q, J=7.2 Hz, 2H), 2.52 (d, J=7.0 Hz, 2H), 1.29 (dd, J=9.4, 4.8 Hz, 3H), 1.01 (dd, J=13.9, 6.1 Hz, 1H), 0.59 (q, J=5.3 Hz, 2H), 0.17 (q, J=5.0 Hz, 2H).

Step 3: 6-(cyclopropylmethyl)pyridazin-3-ol

To a solution of methyl (2Z)-5-cyclopropyl-4-oxopent-2-enoate (80 mg, 0.47 mmol) in EtOH (6 mL) and $H_2O$ (2 mL) was added hydrazine hydrate (0.1 mL), AcOH (2 mL), and the mixture was stirred at 100° C. for 16 hrs. The reaction mixture was diluted with EtOAc (5 mL) and washed with saturated aq·$NH_4Cl$ solution and brine, dried over anhydrous $Na_2SO_4$, filtered and concentrated to dryness. The residue was purified by flash chromatography (silica gel, 0-10% MeOH in DCM) to give the title compound (32 mg, 44.8% yield) as white solid. LC/MS (ESI) m/z: 151 $(M+H)^+$. $^1H$ NMR (400 MHz, DMSO-$d_6$) δ 12.55 (s, 1H), 7.22 (d, J=9.7 Hz, 1H), 6.63 (d, J=9.7 Hz, 1H), 2.22 (d, J=7.0 Hz, 2H), 0.80-0.70 (m, 1H), 0.27 (dt, J=7.7, 4.9 Hz, 2H), −0.01 (q, J=4.9 Hz, 2H).

Intermediate 35: 5-(1H-pyrazol-1-yl)pyridin-2(1H)-one

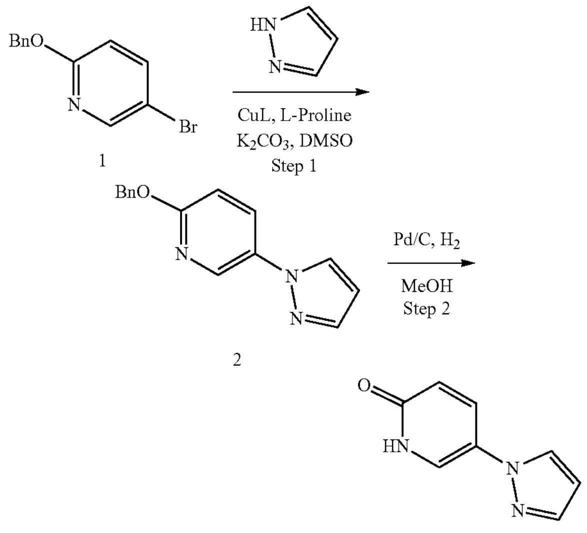

1

2

Intermediate 35

Step 1: 2-(benzyloxy)-5-(1H-pyrazol-1-yl)pyridine

To a mixture of 2-(benzyloxy)-5-bromopyridine (1 g, 3.79 mmol) and 1H-pyrazole (392 mg, 5.68 mmol) in DMSO (10 mL) were added CuI (145 mg, 0.76 mmol), L-Proline (87 mg, 0.757 mmol) and $K_2CO_3$ (1047 mg, 7.57 mmol) under $N_2$ atmosphere and the mixture was stirred under $N_2$ atmosphere at 120° C. for 16 hrs. The mixture was diluted with water and extracted with EtOAc (2×10 mL). The combined organic layers were washed with brine, dried over anhydrous $Na_2SO_4$, filtered and concentrated under reduced pressure to dryness. The residue was purified by chromatography on silica gel (PE:EtOAc=5:1) to give the title compound (350 mg, 36.8% yield) as white solid. LC/MS (ESI) (m/z): 252 $(M+H)^+$.

Step 2: 5-(1H-pyrazol-1-yl)pyridin-2-ol

To a solution of 2-(benzyloxy)-5-(1H-pyrazol-1-yl)pyridine (450 mg, 1.791 mmol) in MeOH (10 mL) was added Pd/C (45 mg, 10% wt) and the mixture was degassed under $N_2$ atmosphere for three times and stirred under $H_2$ balloon at r.t. for 3 hrs. The mixture was filtered and the filtrate was concentrated to dryness to give the title compound (290 mg, 100.5% yield) as a colorless oil. LC/MS (ESI) m/z: 162 $(M+H)^+$.

Intermediate 36: (R)-5-(cyclopropylmethyl)-1-methylimidazolidin-2-one

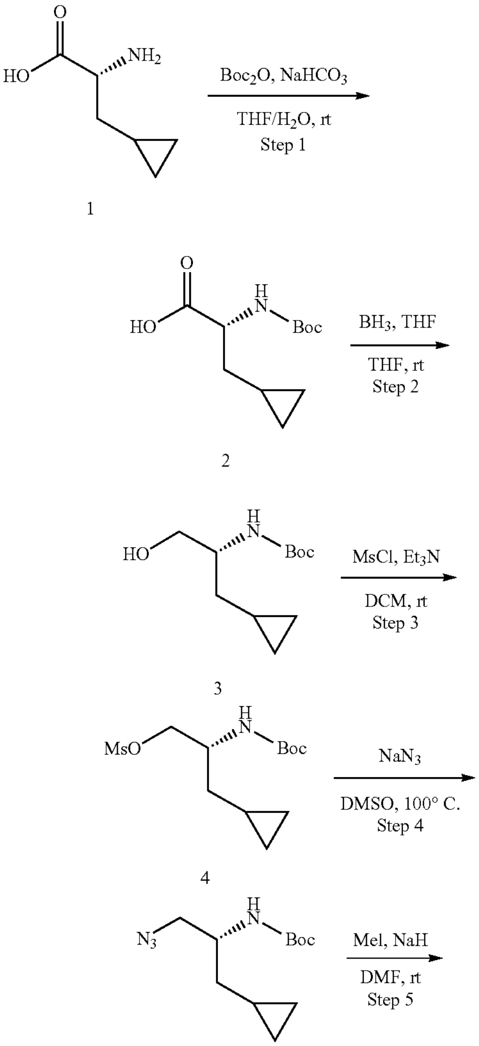

1

2

3

4

5

-continued

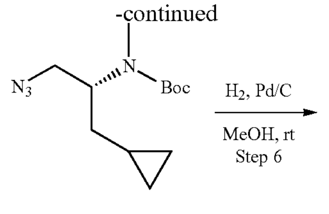

6

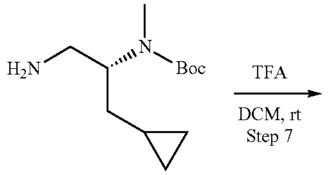

7

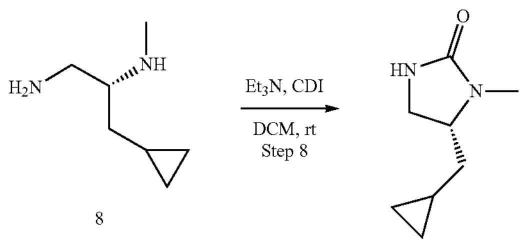

8 intermediate 36

Step 1: (R)-2-((tert-butoxycarbonyl)amino)-3-cyclopropylpropanoic acid

To a solution of (2R)-2-amino-3-cyclopropylpropanoic acid (6 g, 46.4 mmol) in THF (60 mL) and water (60 mL) were added $NaHCO_3$ (11.1 g, 139.2 mmol) and di-tert-butyl decarbonate (12.9 mL, 60.4 mmol) at 0° C. and the mixture was stirred at room temperature for 16 hrs. The reaction mixture was diluted with water and extracted with EtOAc (3×20 mL). The combined organic layers were washed with brine, dried over anhydrous $Na_2SO_4$, filtered and concentrated under reduced pressure to dryness. The residue was purified by chromatography on silica gel (DCM:MeOH=10:1) to give the title compound (10 g, 93.9% yield) as yellow oil. $^1$H NMR (400 MHz, $CDCl_3$) δ 6.04 (s, 1H), 5.30 (d, J=7.7 Hz, 1H), 4.35 (d, J=6.0 Hz, 1H), 1.68-1.65 (m, 2H), 1.43-1.42 (m, 9H), 0.73-0.74 (m, 1H), 0.47-0.46 (m, 2H), 0.10-0.12 (m, 2H). LC/MS (ESI) (m/z): 174 $(M+H-56)^+$.

Step 2: (R)-tert-butyl (1-cyclopropyl-3-hydroxypropan-2-yl)carbamate

To a solution of (R)-2-((tert-butoxycarbonyl)amino)-3-cyclopropylpropanoic acid (6 g, 17.4 mmol) in THF (50 mL) was added $BH_3$-THF complex (52.3 mL, 52.3 mmol, 1M in THF) drop-wisely at 0° C. and the mixture was stirred at room temperature for 16 hrs. The reaction was quenched with MeOH at 0° C. and concentrated to dryness. The residue was purified by chromatography on silica gel (DCM:MeOH=10:1) to give the title compound (2 g, 35.5% yield) as yellow oil. LC/MS (ESI) (m/z): 160 $(M+H-56)^+$.

Step 3: (R)-2-((tert-butoxycarbonyl)amino)-3-cyclopropylpropyl methanesulfonate

To a solution of (R)-tert-butyl (1-cyclopropyl-3-hydroxypropan-2-yl)carbamate (2.0 g, 9.3 mmol) in DCM (30 mL) were added TEA (3.9 mL, 27.9 mmol) followed by dropwise addition of MsCl (1.44 mL, 18.6 mmol) at 0° C. and the mixture was stirred at room temperature for 16 hrs. The mixture was diluted with water (10 mL) and extracted with DCM (2×15 mL). The combined organic layers were washed with brine, dried over anhydrous $Na_2SO_4$, filtered and concentrated under reduced pressure to dryness. The residue was purified by chromatography on silica gel (PE:EtOAc=5:1) to give the title compound (2.0 g, 73.4% yield) as yellow oil. LC/MS (ESI) (m/z): 238 $(M+H-56)^+$.

Step 4: (R)-tert-butyl (1-azido-3-cyclopropylpropan-2-yl)carbamate

To a solution of (R)-2-((tert-butoxycarbonyl)amino)-3-cyclopropylpropyl methanesulfonate (1.5 g, 5.1 mmol) in DMSO (20 mL) was added $NaN_3$ (1.0 g, 15.3 mmol) and the mixture was stirred at 100° C. for 16 hrs. The reaction mixture was diluted with water (10 mL) and extracted with EtOAc (2×15 mL). The combined organic layers were washed with brine, dried over anhydrous $Na_2SO_4$, filtered and concentrated under reduced pressure to dryness. The residue was purified by chromatography on silica gel (PE:EtOAc=5:1) to give the title compound (525 mg, 42.7% yield) as yellow oil. $^1$H NMR (400 MHz, $CDCl_3$) δ 4.64 (d, J=5.2 Hz, 1H), 3.82 (s, 1H), 3.54-3.45 (m, 2H), 1.63 (s, 1H), 1.45 (s, 10H), 0.71-0.64 (m, 1H), 0.52-0.47 (m, 2H), 0.11-0.08 (m, 2H).

Step 5: (R)-tert-butyl (1-azido-3-cyclopropylpropan-2-yl)(methyl)carbamate

To a solution of (R)-tert-butyl (1-azido-3-cyclopropylpropan-2-yl)carbamate (525 mg, 2.19 mmol) in DMF (10 mL) was added NaH (114 mg, 2.84 mmol, 60% dispersion in mineral oil) in portions at 0° C. and the mixture was stirred at 0° C. for 1 hr. Then MeI (0.33 mL, 4.37 mmol) was added and the mixture was stirred at room temperature for 16 hrs. The reaction mixture was quenched with water (10 mL) and extracted with EtOAc (2×10 mL). The combined organic layers were washed with brine, dried over anhydrous $Na_2SO_4$, filtered and concentrated under reduced pressure to dryness. The residue was purified by chromatography on silica gel (PE:EtOAc=5:1) to give the title compound (480 mg, yield 86.4%) as white solid. $^1$H NMR (400 MHz, $CDCl_3$) δ 4.21 (s, 1H), 3.52-3.22 (m, 2H), 2.78 (s, 3H), 1.62-1.54 (m, 1H), 1.48 (s, 9H), 1.33-1.26 (m, 1H), 0.68-0.58 (m, 1H), 0.48-0.46 (m, 2H), 0.1-0.03 (m, 2H). LC/MS (ESI) (m/z): 199 $(M+H-56)^+$.

Step 6: (R)-tert-butyl (1-amino-3-cyclopropylpropan-2-yl)(methyl)carbamate

To a solution of (R)-tert-butyl (1-azido-3-cyclopropylpropan-2-yl)(methyl)carbamate (480 mg, 1.89 mmol) in MeOH (6 mL) was added Pd/C (80 mg, 10% wt) at 0° C. and the mixture was degassed under $N_2$ atmosphere for three times and stirred under a $H_2$ balloon at room temperature for 2 hrs. The mixture was filtered and the filtrate was concentrated to dryness to give the title compound (230 mg, 53.4% yield) as yellow solid. LC/MS (ESI) (m/z): 229 $(M+H)^+$.

Step 7: (R)-3-cyclopropyl-$N_2$-methylpropane-1,2-diamine

To a solution of (R)-tert-butyl (1-amino-3-cyclopropylpropan-2-yl)(methyl)carbamate (230 mg, 1.0 mmol) in DCM (4 mL) was added TFA (4 mL) at 0° C. and the reaction mixture was stirred at room temperature for 2 hrs. The reaction mixture was concentrated under reduced pressure to dryness to give the title compound (120 mg, 92.9% yield) as yellow oil. LC/MS (ESI) (m/z): 129 $(M+H)^+$.

Step 8: (S)-5-(cyclopropylmethyl)-1-methylimidazolidin-2-one

To a solution of (R)-3-cyclopropyl-$N_2$-methylpropane-1,2-diamine (120 mg, 0.94 mmol) in DCM (5 mL) were added TEA (0.39 mL, 2.8 mmol) and CDI (152 mg, 0.94 mmol) and the mixture was stirred at room temperature for 16 hrs. The reaction mixture was diluted with water (5 mL) and extracted with DCM (2×5 mL). The combined organic layers were washed with brine, dried over anhydrous $Na_2SO_4$, filtered and concentrated under reduced pressure to dryness. The residue was purified by chromatography on silica gel (PE:EtOAc=1:2) to give the title compound (120 mg, 82.7% yield) as white solid. LC/MS (ESI) (m/z): 155 $(M+H)^+$. $^1$H-NMR (400 MHz, $CDCl_3$) δ 4.57 (s, 1H), 3.64-3.53 (m, 2H), 3.22-3.18 (m, 1H), 2.75 (s, 3H), 1.65-1.50 (m, 2H), 0.69-0.59 (m, 1H), 0.52-0.50 (m, 2H), 0.12-0.07 (m, 2H).

Intermediate 37: (S)-5-(cyclopropylmethyl)-1-methylimidazolidin-2-one

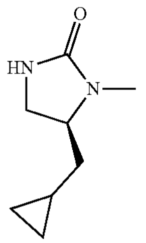

intermediate 37

Intermediate 37 was prepared from (S)-2-amino-3-cyclopropylpropanoic acid using the same synthetic sequence that was used to synthesize intermediate 36. LC/MS (ESI) (m/z): 155 $(M+H)^+$.

Intermediate 38: 1-(cyclopropylmethyl)-1,3-dihydro-2H-imidazol-2-one

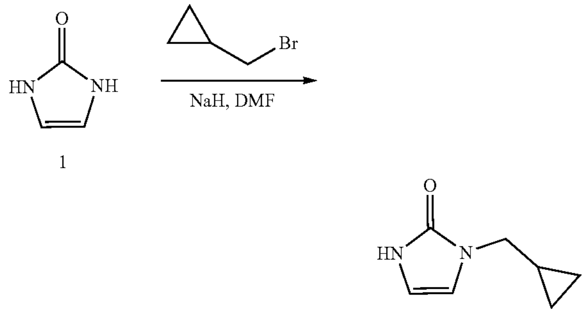

1 intermediate 38

To a solution of 1-methyl-2,3-dihydro-1H-imidazol-2-one (1 g, 10.2 mmol) in DMF (10 mL) was added NaH (410 mg, 10.2 mmol, 60% dispersion in mineral oil) in portions at 0° C. and the mixture was stirred at this temperature for 30 min. (Bromomethyl)cyclopropane (1.2 mL, 12.2 mmol) was added to the mixture and the resulting mixture was stirred at r.t. for 16 hrs. The mixture was diluted with EtOAc (20 mL), washed with saturated aq·$NH_4Cl$ solution and brine, dried over anhydrous $Na_2SO_4$, filtered and concentrated to dryness. The residue was purified by chromatography on silica gel (PE:EtOAc=6:1) to give the title compound (450 mg, 31.9% yield) as colorless oil. LC/MS (ESI) (m/z): 139 $(M+H)^+$. $^1$H NMR (400 MHz, $CDCl_3$) δ 10.34 (s, 1H), 6.35-6.22 (m, 2H), 3.52-3.45 (m, 2H), 1.11 (s, 1H), 0.62-0.53 (m, 2H), 0.33 (t, J=5.3 Hz, 2H).

Intermediate 39: 1-isobutyl-1,3-dihydro-2H-imidazol-2-one intermediate 39

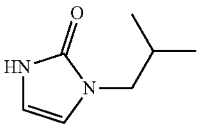

Intermediate 39 was prepared from 1-methyl-2,3-dihydro-1H-imidazol-2-one and 1-bromo-2-methylpropane according to the synthesis of intermediate 38. LC/MS (ESI) (m/z): 141 $(M+H)^+$.

Intermediate 40: 1-(sec-butyl)-1,3-dihydro-2H-imidazol-2-one intermediate 40

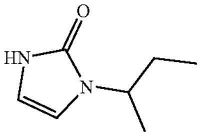

Intermediate 40 was prepared from 1-methyl-2,3-dihydro-1H-imidazol-2-one and 2-bromobutane according to the synthesis of intermediate 38. LC/MS (ESI) (m/z): 141 $(M+H)^+$.

Intermediate 41: 4-chloro-6-(1H-pyrazol-1-yl)pyrimidine

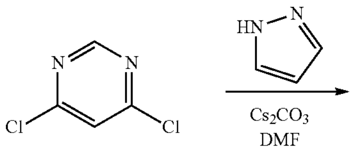

1

-continued

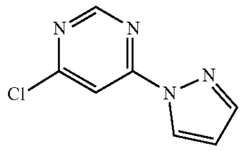

intermediate 41

To the mixture of 4,6-dichloropyrimidine (1 g, 6.71 mmol) and 1H-pyrazole (457 mg, 6.71 mmol) in DMF (20 mL) was added $Cs_2CO_3$ (4.37 g, 13.4 mmol) and the mixture was stirred at r.t. for 18 hrs. The mixture was diluted with EtOAc (40 mL) and the mixture was washed with water and brine, dried over $Na_2SO_4$, filtered and concentrated to dryness. The residue was triturated with EtOAc (10 mL) and filtered. The filter cake was dried under vacuum to give the title compound (660 mg, 54.4% yield) as white solid. LC/MS (ESI) m/z: 181 $(M+H)^+$. $^1H$ NMR (400 MHz, $CDCl_3$) δ 8.79-8.79 (d, J=0.8 Hz, 1H), 8.55-8.57 (dd, J=2.7, 0.5 Hz, 1H), 7.97-7.98 (d, J=1.0 Hz, 1H), 7.81 (d, J=1.0 Hz, 1H), 6.53-6.54 (dd, J=2.7, 1.6 Hz, 1H).

Intermediate 42: 2-chloro-4-cyclobutylpyrimidine

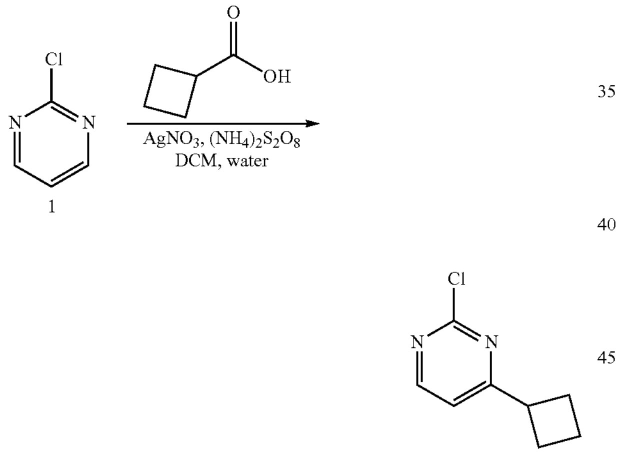

1 intermediate 42

To a mixture of 2-chloropyrimidine (3 g, 26.2 mmol) and cyclobutanecarboxylic acid (2.3 mL, 23.6 mmol) in DCM (15 mL) and water (15 mL) was added $AgNO_3$ (890 mg, 5.2 mmol), followed by in portions addition of $(NH_4)_2S208$ (6.0 g, 26.2 mmol) at room temperature and the mixture was stirred at 25° C. for 16 hrs. The mixture was diluted with DCM (50 mL), washed with water and brine, dried over anhydrous $Na_2SO_4$, filtered and concentrated to dryness. The residue was purified by flash chromatography (PE: EtOAc=5:1 to 1:1) to give the title compound (2.2 g, 49.8% yield) as colorless oil. LC/MS (ESI) m/z: 169 $(M+H)^+$. $^1H$-NMR (400 MHz, $CDCl_3$) δ 8.49 (d, J=5.2 Hz, 1H), 7.11 (d, J=5.2 Hz, 1H), 3.70-3.53 (m, 1H), 2.41-2.30 (m, 4H), 2.15-2.03 (m, 1H), 1.99-1.92 (m, 1H).

Intermediate 43: 2-chloro-4-isopropylpyrimidine intermediate 43

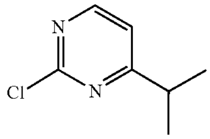

Intermediate 43 was prepared from 2-chloropyrimidine and isobutyric acid using the same synthetic method as intermediate 42. LC/MS (ESI) m/z: 157 $(M+H)^+$. $^1H$ NMR (400 MHz, $CD_3OD$) δ 8.52 (d, J=5.1 Hz, 1H), 7.17 (d, J=5.1 Hz, 1H), 3.06-2.99 (m, 1H), 1.32 (d, J=7.0 Hz, 6H).

Intermediate 44: 2-chloro-4-cyclopropylpyrimidine intermediate 44

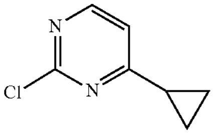

Intermediate 44 was prepared from 2-chloropyrimidine and cyclopropanecarboxylic acid using the same synthetic method as intermediate 42. LC/MS (ESI) m/z: 155 $(M+H)^+$.

Intermediate 45: 4-chloro-6-cyclobutylpyrimidine

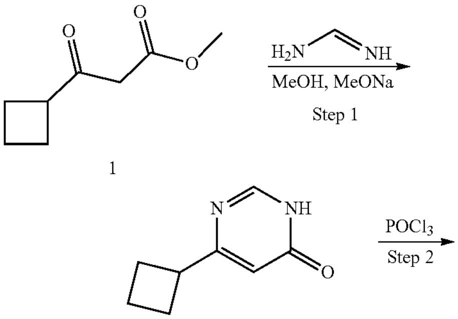

1

2

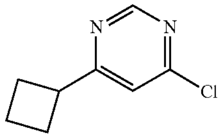

Intermediate 45

Step 1: 6-propyl-3,4-dihydropyrimidin-4-one

To a solution of methyl 3-cyclobutyl-3-oxopropanoate (2 g, 12.81 mmol) and formamidine acetate salt (1.33 g, 19.98 mmol) in MeOH (30 mL) was added 5N MeONa/MeOH solution (7.7 mL, 38.5 mmol) drop-wisely at 0° C. After the addition, the mixture was stirred at 70° C. for 4 hrs. After cooling to 0° C., the reaction was filtered and was treated with DCM (100 mL) and water (100 mL), the organic layer was separated and the aqueous layer was extracted with DCM (50 mL). The combined organic was concentrated to dryness and the residue was purified by flash chromatography (0~80% of EtOAc in PE) to give the title compound (400 mg, 29.0% yield) as white solid. LC/MS (ESI) m/z: 151 $(M+H)^+$.

Step 2: 4-chloro-6-cyclobutylpyrimidine

A stirred solution of 6-cyclobutyl-3,4-dihydropyrimidin-4-one (100 mg, 0.666 mmol) in $POCl_3$ (2 mL) was stirred at 120° C. for 2 hrs. The solution was concentrated under reduced pressure to dryness. The residue was purified by flash chromatography (0~10% of EtOAc in PE) to give the title compound (70 mg, 62.3% yield) as light yellow oil. LC/MS (ESI) m/z: 169 $(M+H)^+$. $^1H$ NMR (400 MHz, $CDCl_3$) δ 8.91 (s, 1H), 7.20 (s, 1H), 3.63-3.59 (m, 1H), 2.40-2.30 (m, 4H), 2.12-2.07 (m, 1H), 1.96-1.93 (m, 1H).

Intermediate 46: 3-chloro-5-cyclopropyl-1,2,4-oxadiazole

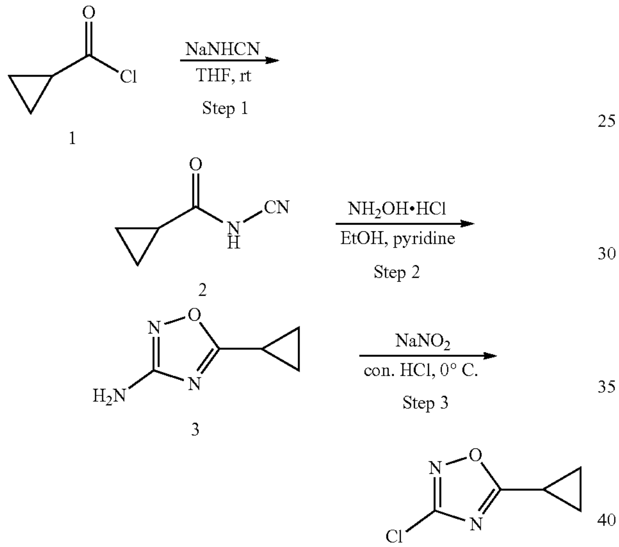

Intermediate 46

Step 1: N-cyanocyclopropanecarboxamide

To a solution of sodium hydrogen cyanamide (1.25 g, 19.51 mmol) in THF (10 mL) was added cyclopropanecarbonyl chloride (1.02 g, 9.76 mmol) at 0° C. under $N_2$ atmosphere and the mixture was stirred at 25° C. for 16 hrs. The mixture was concentrated to dryness and the residue was dissolved in $H_2O$ (10 mL). The mixture was washed with EtOAc (2×3 mL), acidified with 1N aq·HCl to pH-2 and extracted with DCM (3×5 mL). The combined organic layers were washed with brine, dried over anhydrous $Na_2SO_4$, filtered and concentrated to dryness to give the title compound (564 mg, 52.5% yield) as colorless oil, which was used in next step directly.

Step 2: 5-cyclopropyl-1,2,4-oxadiazol-3-amine

To a mixture of N-cyanocyclopropanecarboxamide (525 mg, 4.77 mmol) and hydroxylamine hydrochloride (497.0 mg, 7.15 mmol) in EtOH (6 mL) was added pyridine (1.51 g, 19.07 mmol) under $N_2$ atmosphere and the mixture was stirred at 25° C. for 16 hrs. The mixture was diluted with water (10 mL) and extracted with DCM (3×5 mL). The combined organic layers were washed with brine, dried over anhydrous $Na_2SO_4$, filtered and concentrated to dryness give the title compound (429 mg, 71.9% yield) as white solid, which was used in next step directly. LC/MS (ESI) m/z: 126 $(M+H)^+$. $^1H$ NMR (400 MHz, $CDCl_3$) δ 4.28 (s, 1H), 2.05 (tt, J=7.0, 6.0 Hz, 1H), 1.19-1.12 (m, 2H).

Step 3: 3-chloro-5-cyclopropyl-1,2,4-oxadiazole

To a solution of 5-cyclopropyl-1,2,4-oxadiazol-3-amine (200 mg, 1.60 mmol) in aq·HCl (2 mL, 36% wt) was added dropwise a solution of $NaNO_2$ (276 mg, 4.00 mmol) in water (2 mL) and the mixture was stirred at 0° C. for 2 hrs. The mixture was diluted with water and extracted with DCM (2×5 mL). The combined organic layers were washed with brine, dried over anhydrous $Na_2SO_4$, filtered and concentrated to dryness. The residue was purified by flash chromatography (eluted with PE:EtOAc=200:1 to 20:1) to give the title compound (78 mg, 33.8% yield) as yellow oil. $^1H$ NMR (400 MHz, $CDCl_3$) δ 2.24-2.15 (m, 1H), 1.34-1.25 (m, 5H).

Intermediate 47: 3-chloro-5-(cyclopropylmethyl)-1,2,4-oxadiazole intermediate 47

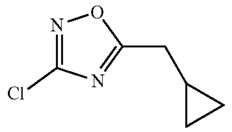

The title compound was prepared from 2-cyclopropylacetyl chloride using the same procedure as intermediate 46. LC/MS (ESI) m/z: 159 $(M+H)^+$.

Intermediate 48: 3-chloro-5-cyclobutyl-1,2,4-oxadiazole intermediate 48

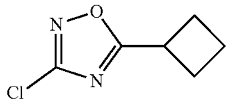

The title compound was prepared from cyclobutanecarbonyl chloride using the same procedure as intermediate 46. LC/MS (ESI) m/z: 159 $(M+H)^+$.

Intermediate 49: 5-bromo-1-propyl-1H-1,2,4-triazole

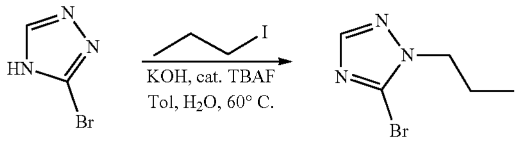

intermediate 49

To a mixture of 3-bromo-4H-1,2,4-triazole (1 g, 6.76 mmol), 1-iodopropane (1.0 mL, 10.13 mmol) and TBAF (10 mg, cat.) in toluene (10 mL) was added a solution of KOH (750 mg, 13.5 mmol) in water (2 mL) and the mixture was stirred at 60° C. for 16 hrs. The mixture was diluted with water (10 mL) and extracted with EtOAc (2×10 mL). The combined organic layers were washed with brine, dried over anhydrous $Na_2SO_4$, filtered and concentrated to dryness. The residue was purified by chromatography on silica gel (eluted with PE:EtOAc=6:1) to give the title compound (400 mg, 31.3% yield) as yellow oil. LC/MS (ESI) m/z: 190/192 $(M+H)^+$. $^1H$-NMR (400 MHz, $CDCl_3$) δ 7.89 (s, 1H), 4.14 (t, J=2.4 Hz, 2H), 1.91 (m, 2H), 0.95 (t, J=2.4 Hz, 2H).

Intermediate 50: 5-bromo-1-(cyclopropylmethyl)-1H-1,2,4-triazole

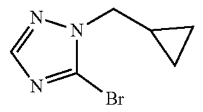

intermediate 50

The title compound was prepare from 3-bromo-4H-1,2,4-triazole and (bromomethyl)cyclopropane using the same procedure as intermediate 49. LC/MS (ESI) m/z: 202/204 $(M+H)^+$.

Intermediate 51: 5-bromo-1-isobutyl-1H-1,2,4-triazole

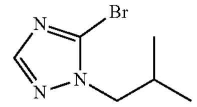

intermediate 51

The title compound was prepare from 3-bromo-4H-1,2,4-triazole and 1-iodo-2-methylpropane using the same procedure as intermediate 49. LC/MS (ESI) m/z: 204/206 $(M+H)^+$. $^1H$-NMR (400 MHz, $CDCl_3$) δ 7.89 (s, 1H), 3.97 (d, J=7.2 Hz, 2H), 2.35-2.86 (m, 1H), 0.95 (d, J=6.8 Hz, 6H).

Example 1: (S)-2-(5,5-difluoro-1-(2-methyl-6-(1-methyl-5-((3-methyl-2-oxo-5-propylpyridin-1(2H)-yl)methyl)-1H-1,2,3-triazol-4-yl)pyridin-3-yl)piperidin-3-yl)acetic acid

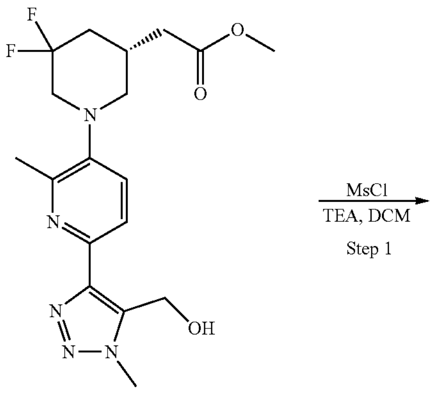

1

-continued

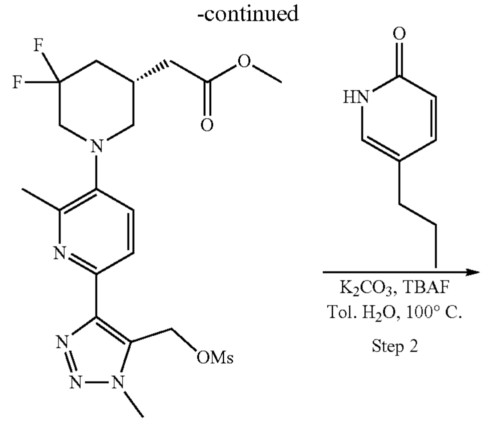

2

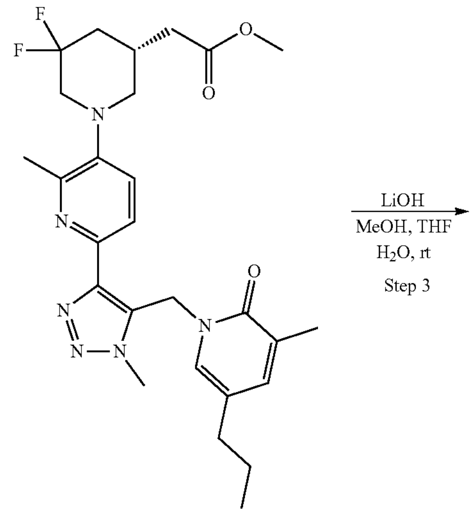

3

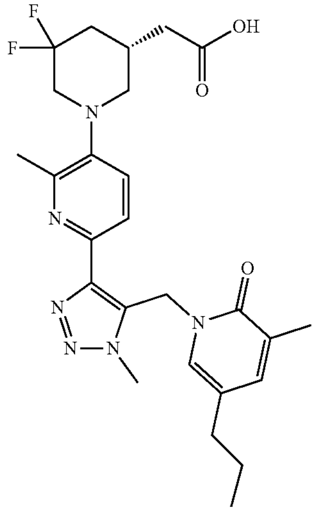

Example 1

Step 1: methyl (S)-2-(5,5-difluoro-1-(2-methyl-6-(1-methyl-5-(((methylsulfonyl)oxy)methyl)-1H-1,2,3-triazol-4-yl)pyridin-3-yl)piperidin-3-yl)acetate To a solution of methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate (40 mg, 0.1 mmol) in DCM (1 mL) was added TEA (20 mg, 0.2 mmol) followed by MsCl (17 mg, 0.15 mmol) at 0° C. and the mixture was stirred at this temperature for 2 hrs. The mixture was diluted with DCM (2 mL), washed with saturated aq·$NaHCO_3$ solution and brine, dried over $Na_2SO_4$, filtered and concentrated to dryness to give the title compound (43 mg, 91% yield) as light yellow solid, which was directly used in the next reaction without purification. LC/MS (ESI) (m/z): 474 $(M+H)^+$.

Step 2: methyl (S)-2-(5,5-difluoro-1-(2-methyl-6-(1-methyl-5-((3-methyl-2-oxo-5-propylpyridin-1(2H)-yl)methyl)-1H-1,2,3-triazol-4-yl)pyridin-3-yl)piperidin-3-yl)acetate To a mixture of methyl (S)-2-(5,5-difluoro-1-(2-methyl-6-(1-methyl-5-(((methylsulfonyl)oxy)methyl)-1H-1,2,3-triazol-4-yl)pyridin-3-yl)piperidin-3-yl)acetate (43 mg, 0.091 mmol) and 3-methyl-5-propyl-1,2-dihydropyridin-2-one (16.5 mg, 0.11 mmol) in toluene (3 mL) and water (1 mL) were added $K_2CO_3$ (25 mg, 0.182 mmol) and TBAF (3 mg, cat. amount) and the reaction mixture was stirred at 100° C. for 16 hrs. The reaction mixture was diluted with water (3 mL) and extracted with EtOAc (2×3 mL). The combined organic layers were washed with brine, dried over anhydrous $Na_2SO_4$, filtered and concentrated to dryness to give the title compound (35 mg, 72.9% yield) as light yellow solid. LC/MS (ESI) (m/z): 529 $(M+H)^+$.

Step 3: (S)-2-(5,5-difluoro-1-(2-methyl-6-(1-methyl-5-((3-methyl-2-oxo-5-propylpyridin-1(2H)-yl)methyl)-1H-1,2,3-triazol-4-yl)pyridin-3-yl)piperidin-3-yl)acetic acid To a solution of methyl (S)-2-(5,5-difluoro-1-(2-methyl-6-(1-methyl-5-((3-methyl-2-oxo-5-propylpyridin-1(2H)-yl)methyl)-1H-1,2,3-triazol-4-yl)pyridin-3-yl)piperidin-3-yl)acetate (35 mg, 0.066 mmol) in THE (1 mL) and methanol (2 mL) was added a solution of LiOH (15.8 mg, 0.66 mmol) in water (1 mL) at 0° C. After stirring at room temperature for 2 hrs, the reaction mixture was concentrated to dryness and the residue was dissolved in water (3 mL). The mixture was washed with MTBE twice and the aqueous layer was acidified with 1N aq·HCl to pH~2 and extracted with EtOAc (2×2 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (22 mg, 64.6% yield) as white solid. LC/MS (ESI) (m/z): 515 $(M+H)^+$. $^1H$ NMR (400 MHz, DMSO-$d_6$) δ 7.82 (d, J=8.3 Hz, 1H), 7.62 (d, J=1.7 Hz, 1H), 7.55 (d, J=8.4 Hz, 1H), 7.17-7.16 (m, 1H), 5.56 (s, 2H), 4.23 (s, 3H), 3.20-3.04 (m, 4H), 2.60-2.55 (m, 4H), 2.39-2.27 (m, 4H), 2.15 (t, J=7.4 Hz, 2H), 1.95 (s, 3H), 1.84-1.68 (m, 1H), 1.35-1.26 (m, 2H), 0.71 (t, J=7.3 Hz, 3H).

Example 2: (S)-2-(1-(6-(5-((4-(cyclopropylmethyl)-3-methyl-2-oxopyridin-1(2H)-yl)methyl)-1-methyl-1H-1,2,3-triazol-4-yl)-2-methylpyridin-3-yl)-5,5-difluoropiperidin-3-yl)acetic acid

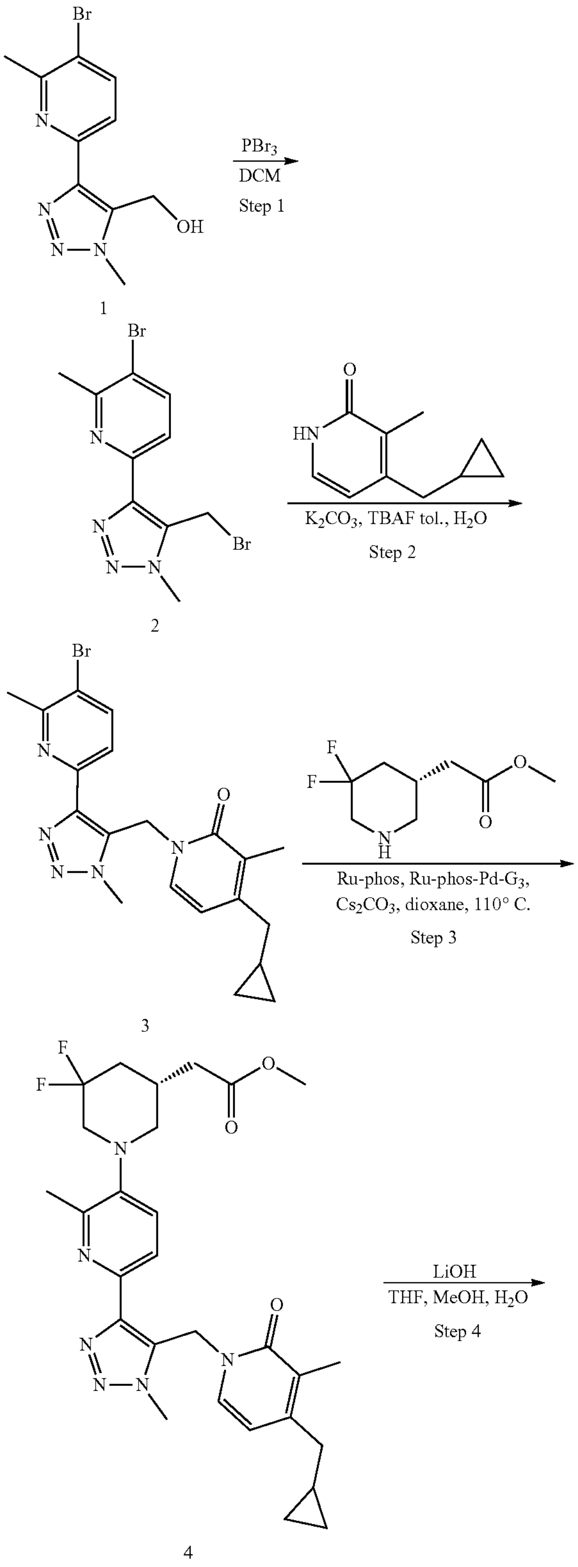

-continued

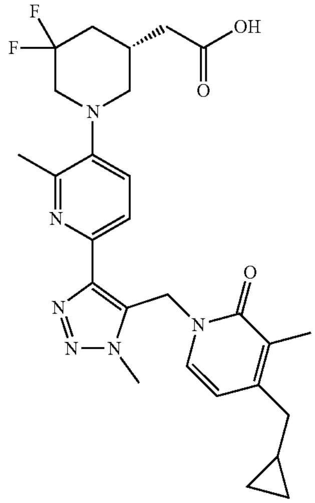

Example 2

Step 1: 3-bromo-6-(5-(bromomethyl)-1-methyl-1H-1,2,3-triazol-4-yl)-2-methylpyridine To a solution of (4-(5-bromo-6-methylpyridin-2-yl)-1-methyl-1H-1,2,3-triazol-5-yl)methanol (500 mg, 1.76 mmol) in DCM (10 mL) was added $PBr_3$ (717 mg, 2.65 mmol) drop-wisely at 0° C. and the mixture was stirred at 0° C. to r.t. for 3 hrs. The mixture was diluted with DCM (10 mL), washed with ice-cooled saturated aq·$NaHCO_3$ solution and brine, dried over anhydrous $Na_2SO_4$, filtered and concentrated to dryness to give crude product, which was purified by flash chromatography (silica gel, 0-30% EtOAc in PE) to give the title compound (510 mg, 83.7% yield) as white solid. LC/MS (ESI) m/z: 347 $(M+H)^+$.

Step 2: 1-((4-(5-bromo-6-methylpyridin-2-yl)-1-methyl-1H-1,2,3-triazol-5-yl)methyl)-4-(cyclopropylmethyl)-3-methylpyridin-2(1H)-one To a mixture of 3-bromo-6-(5-(bromomethyl)-1-methyl-1H-1,2,3-triazol-4-yl)-2-methylpyridine (200 mg, 0.58 mmol) and 4-(cyclopropylmethyl)-3-methyl-1,2-dihydropyridin-2-one (136 mg, 0.83 mmol) in toluene (5 mL) and $H_2O$ (1 mL) was added $K_2CO_3$ (230 mg, 1.66 mmol) and TBAF (10 mg, cat.) and the mixture was stirred at 100° C. for 3 hrs. The reaction mixture was diluted with EtOAc (5 mL), washed with brine, dried over anhydrous $Na_2SO_4$, filtered and concentrated to dryness. The residue was purified by flash chromatography (silica gel, 0-56% EtOAc in PE) to give the title compound (220 mg, 88.9% yield) as white solid. LC/MS (ESI) m/z: 428/430 $(M+H)^+$.

Step 3: methyl (S)-2-(1-(6-(5-((4-(cyclopropylmethyl)-3-methyl-2-oxopyridin-1(2H)-yl)methyl)-1-methyl-1H-1,2,3-triazol-4-yl)-2-methylpyridin-3-yl)-5,5-difluoropiperidin-3-yl)acetate To a mixture of 1-((4-(5-bromo-6-methylpyridin-2-yl)-1-methyl-1H-1,2,3-triazol-5-yl)methyl)-4-(cyclopropylmethyl)-3-methylpyridin-2(1H)-one (78 mg, 0.18 mmol), methyl 2-[(3S)-5,5-difluoropiperidin-3-yl]acetate (35 mg, 0.18 mmol), $Cs_2CO_3$ (177 mg, 0.54 mmol) and Ru-phos (17 mg, 0.036 mmol) in 1,4-dioxane (2 mL) was added Ru-phos-Pd-G3 (30 mg, 0.036 mmol). Then the mixture was degassed under $N_2$ atmosphere for three times and stirred at 110° C. under $N_2$ atmosphere for 16 hrs. The reaction mixture was poured into ice-water and extracted with EtOAc (2×5 mL). The combined organic layers were washed with brine, dried over anhydrous $Na_2SO_4$, filtered and concentrated to dryness. The residue was purified by flash chromatography (silica gel, 0-50% EtOAc in PE) to give the title compound (35 mg, 35.5% yield) as yellow solid. LC/MS (ESI) m/z: 541 $(M+H)^+$.

Step 4: (S)-2-(I-(6-(5-((4-(cyclopropylmethyl)-3-methyl-2-oxopyridin-1(2H)-yl)methyl)-1-methyl-1H-1,2,3-triazol-4-yl)-2-methylpyridin-3-yl)-5,5-difluoropiperidin-3-yl)acetic acid To a solution of methyl (S)-2-(1-(6-(5-((4-(cyclopropylmethyl)-3-methyl-2-oxopyridin-1(2H)-yl)methyl)-1-methyl-1H-1,2,3-triazol-4-yl)-2-methylpyridin-3-yl)-5,5-difluoropiperidin-3-yl)acetate (35 mg, 0.065 mmol) in MeOH (1 mL), $H_2O$ (1 mL), THE (4 mL) was added LiOH (50 mg, 2.1 mmol) and the mixture was stirred at 25° C. for 1 hr. The reaction mixture was acidified with 1N aq·HCl to pH-3 and extracted with DCM (2×5 mL). The combined organic layers were washed with brine, dried over anhydrous $Na_2SO_4$, filtered and concentrated to dryness. The residue was purified by prep·HPLC (C18, 10-95%, MeCN in $H_2O$ with 0.1% HCOOH) to give the title compound (15 mg, 43.8 yield) as white solid. LC/MS (ESI) m/z: 527 (M+H). H NMR (400 MHz, $CD_3OD$) δ 7.83 (d, J=8.4 Hz, 1H), 7.75 (d, J=7.1 Hz, 1H), 7.52 (d, J=8.4 Hz, 1H), 6.30 (d, J=7.2 Hz, 1H), 5.73 (s, 2H), 4.21 (s, 3H), 3.28-3.23 (m, 2H), 3.15-3.00 (m, 1H), 2.62-2.56 (m, 1H), 2.59 (s, 3H), 2.54-2.48 (i, 1H), 2.43-2.39 (i, 4H), 2.36-2.26 (m, 1H), 2.04 (s, 3H), 1.81-1.64 (m, 1H), 0.90-0.87 (m, 1H), 0.52-0.46 (m, 2H), 0.18-0.14 (m, 2H).

The examples in the following table were prepared by the indicated method using analogous reactants.

| Ex# | Structure & name | Analytical & biological data | Method |
| --- | --- | --- | --- |
| 3 | 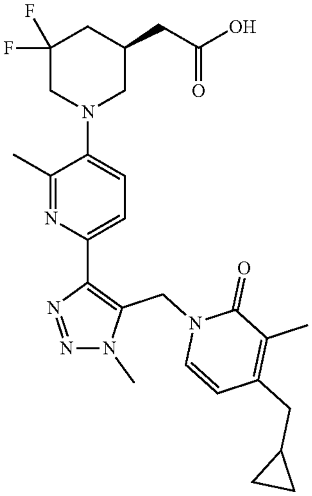 [SMILES: Cc1nc(-c2nnn(C)c2Cn2ccc(CC3CC3)c(C)c2=O)ccc1N1C[C@H](CC(=O)O)CC(F)(F)C1] (S)-2-(1-(6-(5-((4-(cyclopropylmethyl)-3-methyl-2-oxopyridin-1(2H)-yl)methyl)-1-methyl-1H-1,2,3-triazol-4-yl)-2-methylpyridin-3-yl)-5,5-difluoropiperidin-3-yl)acetic acid | LC/MS (ESI) m/z: 527 $(M + H)^+$. $^1H$ NMR (400 MHz, DMSO-$d_6$) δ 7.73 (d, J = 8.4 Hz, 1H), 7.62 (d, J = 7.2 Hz, 1H), 7.41 (d, J = 8.4 Hz, 1H), 6.04 (d, J = 7.2 Hz, 1H), 5.43 (s, 2H), 4.02 (s, 3H), 3.16-2.86 (m, 3H), 2.54-2.36 (m, 3H), 2.31-2.09 (m, 7H), 1.80 (s, 3H), 1.69-1.56 (m, 1H), 0.75-0.67 (m, 1H), 0.30-0.25 (m, 2H), 0.02-0.00 (m, 2H). | Example 2 |
| 4 | 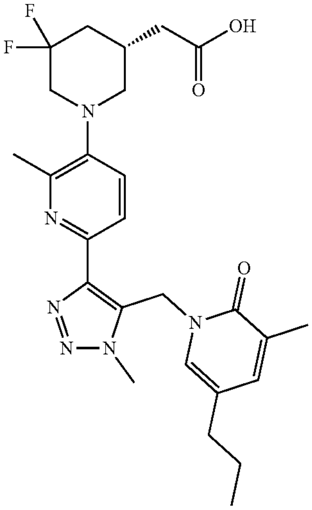 (S)-2-(5,5-difluoro-1-(2-methyl-6-(1-methyl-5-((2-oxo-5-propylpyridin-1(2H)-yl)methyl)-1H-1,2,3-triazol-4-yl)pyridin-3-yl)piperidin-3-yl)acetic acid | LC/MS (ESI) m/z: 501 $(M + H)^+$. $^1H$ NMR (400 MHz, $CD_3OD$) δ 7.83 (d, J = 4.5 Hz, 1H), 7.81 (d, J = 9.2, 2.5 Hz, 1H), 7.54 (d, J = 8.4 Hz, 1H), 7.36 (dd, J = 9.2, 2.5 Hz, 1H), 6.46 (d, J = 9.2 Hz, 1H), 5.74 (s, 2H), 4.24 (s, 3H), 3.31-3.28 (m, 2H), 3.13-3.03 (m, 1H), 2.63 (s, 3H), 2.61-2.57 (m, 1H), 2.56-2.49 (m, 1H), 2.43-2.38 (m, 2H), 2.36-2.30 (m, 1H), 2.25 (d, J = 7.6, 2H), 1.83-1.66 (m, 1H), 1.43-1.33 (m, 2H), 0.78 (t, J = 7.6 Hz, 3H). | Example 1 |

-continued

| Ex# | Structure & name | Analytical & biological data | Method |
|---|---|---|---|
| 5 | 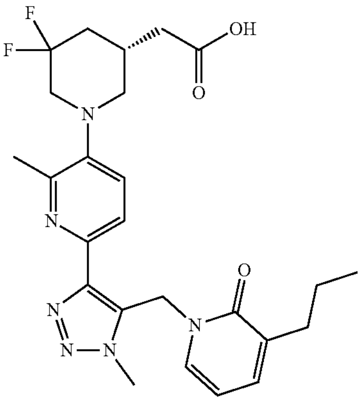 [SMILES: CCCc1cccn(Cc2c(-c3ccc(N4C[C@@H](CC(=O)O)CC(F)(F)C4)c(C)n3)nnn2C)c1=O] (S)-2-(5,5-difluoro-1-(2-methyl-6-(1-methyl-5-((2-oxo-3-propylpyridin-1(2H)-yl)methyl)-1H-1,2,3-triazol-4-yl)pyridin-3-yl)piperidin-3-yl)acetic acid | LC/MS (ESI) m/z: 501 $(M + H)^+$. $^1H$ NMR (400 MHz, $CD_3OD$) δ 7.85 (dd, J = 6.8, 2.0 Hz, 1H), 7.83 (d, J = 8.4 Hz, 1H), 7.52 (d, J = 8.4 Hz, 1H), 7.28 (dd, J = 6.8, 1.9 Hz, 1H), 6.21 (t, J = 6.9 Hz, 1H), 5.77 (s, 2H), 4.19 (s, 3H), 3.31-3.28 (m, 2H), 3.13-2.96 (m, 1H), 2.63-2.56 (m, 1H), 2.58 (s, 3H), 2.55-2.48 (m, 1H), 2.46-2.36 (m, 4H), 2.36-2.25 (m, 1H), 1.80-1.64 (m, 1H), 1.61-1.49 (m, 2H), 0.92 (d, J = 9.6, 3H). | Example 1 |
| 6 | 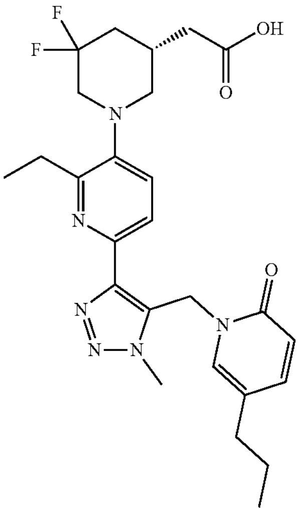 [SMILES: CCCc1ccc(=O)n(Cc2c(-c3ccc(N4C[C@@H](CC(=O)O)CC(F)(F)C4)c(CC)n3)nnn2C)c1] (S)-2-(1-(2-ethyl-6-(1-methyl-5-((2-oxo-5-propylpyridin-1(2H)-yl)methyl)-1 H-1,2,3-triazol-4-yl)pyridin-3-yl)-5,5-difluoropiperidin-3-yl)acetic acid | LC/MS (ESI) m/z: 515 $(M + H)^+$. $^1H$ NMR (400 MHz, $CD_3OD$) δ 7.89 (d, J = 8.4 Hz, 1H), 7.66 (d, J = 2.2 Hz, 1H), 7.61 (d, J = 8.4 Hz, 1H), 7.38 (dd, J = 9.2, 2.5 Hz, 1H), 6.52 (d, J = 9.4 Hz, 1H), 5.86 (s, 2H), 3.25 (dd, J = 8.4, 6.0 Hz, 2H), 3.14-3.06 (m, 2H), 2.99 (q, J = 7.5 Hz, 2H), 2.65-2.58 (m, 1H), 2.53 (dd, J = 10.8, 4.5 Hz, 1H), 2.40 (d, J = 6.8 Hz, 2H), 2.35-2.26 (m, 1H), 2.22 (t, J = 7.6 Hz, 2H), 1.82-1.62 (m, 1H), 1.41-1.26 (m, 5H), 0.76 (t, J = 7.2 Hz, 3H). | Example 1 |

-continued

| Ex# | Structure & name | Analytical & biological data | Method |
|---|---|---|---|
| 7 | 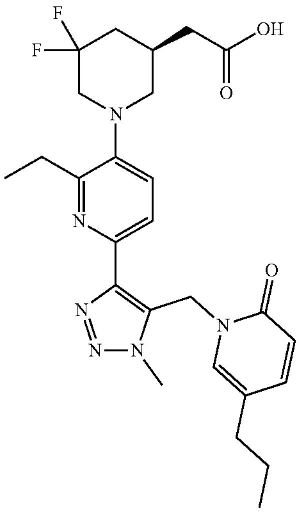 [SMILES: CCCc1ccc(=O)n(Cc2c(-c3ccc(N4C[C@H](CC(=O)O)CC(F)(F)C4)c(CC)n3)nnn2C)c1] (R)-2-(1-(2-ethyl-6-(1-methyl-5-((2-oxo-5-propylpyridin-1(2H)-yl)methyl)- 1H-1,2,3-triazol-4-yl)pyridin-3-yl)-5,5-difluoropiperidin-3-yl)acetic acid | LC/MS (ESI) m/z: 515 $(M + H)^+$. $^1H$ NMR (400 MHz, $CD_3OD$) δ 7.88 (d, J = 8.3 Hz, 1H), 7.66 (d, J = 2.0 Hz, 1H), 7.61 (d, J = 8.4 Hz, 1H), 7.38 (dd, J = 9.3, 2.5 Hz, 1H), 6.52 (d, J = 9.2 Hz, 1H), 5.86 (s, 2H), 4.17 (s, 3H), 3.26-3.23 (m, 2H), 3.14-3.05 (m, 1H), 2.99 (q, J = 7.5 Hz, 2H), 2.66-2.59 (m, 1H), 2.55-2.49 (m, 1H), 2.39-2.30 (m, 3H), 2.22 (t, J = 7.5 Hz, 2H), 1.85-1.67 (m, 1H), 1.40-1.34 (m, 2H), 1.31 (t, J = 7.5 Hz, 3H), 0.76 (t, J = 7.3 Hz, 3H). | Example 2 |
| 8 | 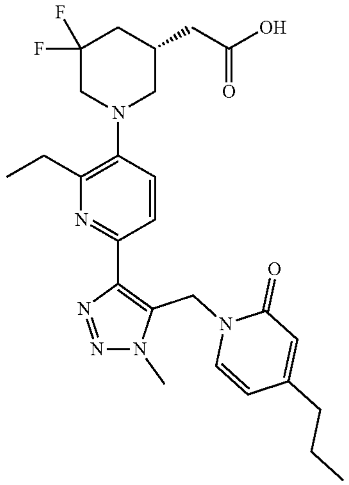 [SMILES: CCCc1ccn(Cc2c(-c3ccc(N4C[C@@H](CC(=O)O)CC(F)(F)C4)c(CC)n3)nnn2C)c(=O)c1] (S)-2-(1-(2-ethyl-6-(1-methyl-5-((2-oxo-4-propylpyridin-1(2H)-yl)methyl)- 1 H-1,2,3-triazol-4-yl)pyridin-3-yl)-5,5-difluoropiperidin-3-yl)acetic acid | LC/MS (ESI) m/z: 515 $(M + H)^+$. $^1H$ NMR (400 MHz, $CD_3OD$) δ 7.90 (d, J = 8.3 Hz, 1H), 7.77 (d, J = 7.1 Hz, 1H), 7.60 (d, J = 8.4 Hz, 1H), 6.36 (s, 1H), 6.19 (dd, J = 7.1, 1.9 Hz, 1H), 5.84 (s, 2H), 4.14 (s, 3H), 3.29-3.21 (m, 2H), 3.13-3.04 (m, 1H), 2.96 (q, J = 7.5 Hz, 2H), 2.65-2.57 (m, 1H), 2.54-2.48 (m, 1H), 2.45-2.40 (m, 4H), 2.35-2.25 (m, 1H), 1.82-1.66 (m, 1H), 1.64-1.54 (m, 2H), 1.28 (t, J = 7.5 Hz, 3H), 0.92 (t, J = 7.4 Hz, 3H). | Example 1 |

-continued

| Ex# | Structure & name | Analytical & biological data | Method |
|---|---|---|---|
| 9 | 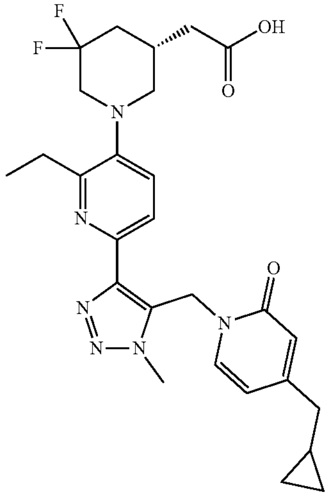 [SMILES: CCc1nc(-c2nnn(C)c2Cn2ccc(CC3CC3)cc2=O)ccc1N1C[C@@H](CC(=O)O)CC(F)(F)C1] (S)-2-(1-(6-(5-((4-(cyclopropylmethyl)-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 527 $(M+H)^+$. $^1H$ NMR (400 MHz, $CD_3OD$) δ 7.91 (d, J = 8.3 Hz, 1H), 7.78 (d, J = 7.1 Hz, 1H), 7.60 (d, J = 8.4 Hz, 1H), 6.49 (s, 1H), 6.26 (dd, J = 7.1, 1.9 Hz, 1H), 5.86 (s, 2H), 4.15 (s, 3H), 3.28-3.20 (m, 2H), 3.15-3.03 (m, 1H), 2.96 (q, J = 7.5 Hz, 2H), 2.68-2.58 (m, 1H), 2.56-2.50 (m, 1H), 2.44-2.34 (m, 4H), 2.31-2.20 (m, 1H), 1.82-1.66 (m, 1H), 1.29 (t, J = 7.5 Hz, 3H), 0.98-0.84 (m, 1H), 0.58-0.48 (m, 2H), 0.20-0.12 (m, 2H). | Example 1 |
| 10 | 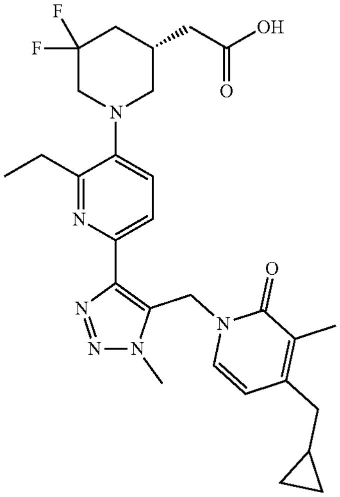 [SMILES: CCc1nc(-c2nnn(C)c2Cn2ccc(CC3CC3)c(C)c2=O)ccc1N1C[C@@H](CC(=O)O)CC(F)(F)C1] (S)-2-(1-(6-(5-((4-(cyclopropylmethyl)-3-methyl-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 541 $(M+H)^+$. $^1H$ NMR (400 MHz, $CD_3OD$) δ 7.89 (d, J = 8.4 Hz, 1H), 7.62 (d, J = 7.2 Hz, 1H), 7.59 (d, J = 8.4 Hz, 1H), 6.29 (d, J = 7.2 Hz, 1H), 5.87 (s, 2H), 4.14 (s, 3H), 3.29-3.21 (m, 2H), 3.13-3.03 (m, 1H), 2.96 (q, J = 7.4 Hz, 2H), 2.63-2.57 (m, 1H), 2.55-2.48 (m, 1H), 2.44 (d, J = 6.9 Hz, 2H), 2.38-2.35 (m, 2H), 2.34-2.25 (m, 1H), 2.09 (s, 3H), 1.81-1.62 (m, 1H), 1.27 (t, J = 7.5 Hz, 3H), 0.94-0.85 (m, 1H), 0.53-0.46 (m, 2H), 0.19-0.15 (m, 2H). | Example 2 |

-continued

| Ex# | Structure & name | Analytical & biological data | Method |
|---|---|---|---|
| 11 | 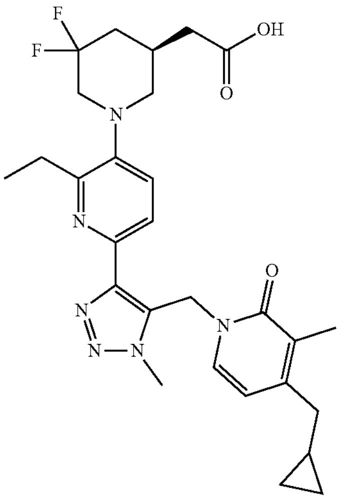 [SMILES: CCc1nc(-c2nnn(C)c2Cn2ccc(CC3CC3)c(C)c2=O)ccc1N1C[C@H](CC(=O)O)CC(F)(F)C1] (R)-2-(1-(6-(5-((4-(cyclopropylmethyl)-3-methyl-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 541 $(M + H)^+$. $^1H$ NMR (400 MHz, $CD_3OD$) δ 7.89 (d, J = 8.4 Hz, 1H), 7.62 (d, J = 7.2 Hz, 1H), 7.59 (d, J = 8.4 Hz, 1H), 6.29 (d, J = 7.2 Hz, 1H), 5.87 (s, 2H), 4.14 (s, 3H), 3.29-3.21 (m, 2H), 3.13-3.03 (m, 1H), 2.95 (q, J = 7.6 Hz, 2H), 2.63-2.57 (m, 1H), 2.56-2.48 (m, 1H), 2.44 (d, J = 6.8 Hz, 2H), 2.38-2.35 (m, 2H), 2.33-2.22 (m, 1H), 2.09 (s, 3H), 1.79-1.64 (m, 1H), 1.27 (t, J = 7.6 Hz, 3H), 0.99-0.83 (m, 1H), 0.54-0.44 (m, 2H), 0.19-0.14 (m, 2H). | Example 2 |
| 12 | 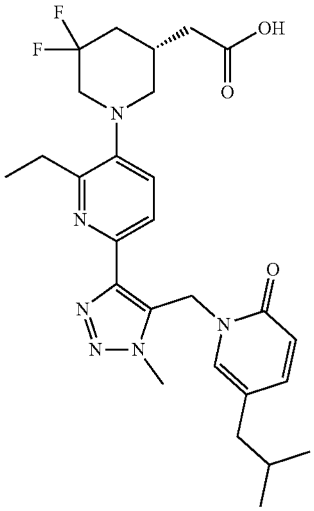 [SMILES: CCc1nc(-c2nnn(C)c2Cn2cc(CC(C)C)ccc2=O)ccc1N1C[C@@H](CC(=O)O)CC(F)(F)C1] (S)-2-(1-(2-ethyl-6-(5-((5-isobutyl-2-oxopyridin-1(2H)-yl)methyl)-l-methyl-1H-1,2,3-triazol-4-yl)pyridin-3-yl)-5,5-difluoropiperidin-3-y)acetic acid | LC/MS (ESI) m/z: 529 $(M + H)^+$. $^1H$ NMR (400 MHz, $CD_3OD$) δ 7.89 (d, J = 8.4 Hz, 1H), 7.61 (d, J = 8.4 Hz, 1H), 7.60 (d, J = 2.4 Hz, 1H), 7.36 (dd, J = 7.2, 2.4 Hz, 1H), 6.52 (d, J = 7.2 Hz, 1H), 5.87 (s, 2H), 4.17 (s, 3H), 3.29-3.22 (m, 2H), 3.16-3.02 (m, 1H), 2.96 (q, J = 7.6 Hz, 2H), 2.70-2.61 (m, 1H), 2.56-2.48 (m, 1H), 2.40-2.27 (m, 3H), 2.09 (d, J = 6.8 Hz, 1H), 1.80-1.66 (m, 1H), 1.62-1.53 (m, 2H), 1.32(t, J = 7.6 Hz, 3H), 0.72 (d, J = 6.4 Hz, 6H). | Example 1 |

-continued

| Ex# | Structure & name | Analytical & biological data | Method |
|---|---|---|---|
| 13 | 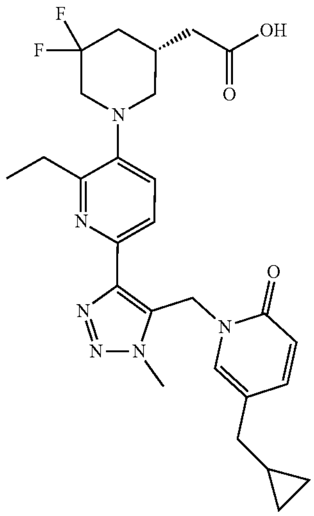 [SMILES: CCc1nc(-c2nnn(C)c2Cn2cc(CC3CC3)ccc2=O)ccc1N1C[C@@H](CC(=O)O)CC(F)(F)C1] (S)-2-(1-(6-(5-((5-(cyclopropylmethyl)-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 527 $(M + H)^+$. $^1H$ NMR (400 MHz, $CD_3OD$) δ 7.98 (d, J = 8.4 Hz, 1H), 7.74 (d, J = 2.4 Hz, 1H), 7.67 (d, J = 8.4 Hz, 1H), 7.49 (dd, J = 7.2, 2.4 Hz, 1H), 6.59 (d, J = 7.2 Hz, 1H), 5.99 (s, 2H), 4.22 (s, 3H), 3.30-3.26 (m, 2H), 3.21-3.10 (m, 1H), 3.03 (q, J = 7.6 Hz, 2H), 2.70-2.62 (m, 1H), 2.60-2.49 (m, 1H), 2.48-2.43 (m, 2H), 2.41-2.31 (m, 1H), 2.22 (d, J = 6.8 Hz, 1H), 1.88-1.72 (m, 1H), 1.36 (t, J = 7.6 Hz, 3H), 0.72-0.64 (m, 1H), 0.36-0.28 (m, 2H), 0.03-0.00 (m, 2H). | Example 1 |
| 14 | 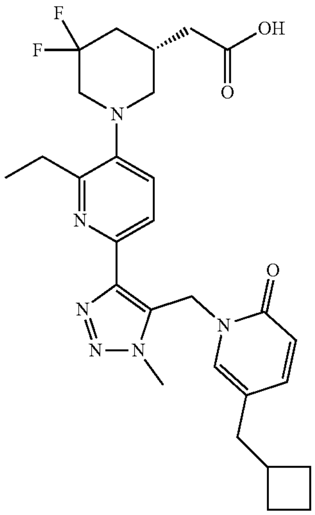 [SMILES: CCc1nc(-c2nnn(C)c2Cn2cc(CC3CCC3)ccc2=O)ccc1N1C[C@@H](CC(=O)O)CC(F)(F)C1] (S)-2-(1-(6-(5-((5-(cyclobutylmethyl)-2-oxopyridin-1(2H)-y)methyl)-1-methyl-1H-1,2,3-triazol-4-yl)-2-ethylpyridin-3-yl)-5,5-difluoropiperidin-3-yl)acetic acid | LC/MS (ESI) m/z: 541 $(M + H)^+$. $^1H$ NMR (400 MHz, $CD_3OD$) δ 7.91 (d, J = 8.4 Hz, 1H), 7.62 (d, J = 8.4 Hz, 1H), 7.55 (d, J = 2.4 Hz, 1H), 7.34 (dd, J = 7.2, 2.4 Hz, 1H), 6.51 (d, J = 7.2 Hz, 1H), 5.89 (s, 2H), 4.16 (s, 3H), 3.29-3.24 (m, 2H), 3.16-3.06 (m, 1H), 2.99 (q, J = 7.6 Hz, 2H), 2.65-2.59 (m, 1H), 2.56-2.48 (m, 1H), 2.41-2.37 (m, 2H), 2.34-2.20 (m, 4H), 1.83-1.65 (m, 5H), 1.48-1.39 (m, 2H), 1.32 (t, J = 7.6 Hz, 3H). | Example 1 |

-continued

| Ex# | Structure & name | Analytical & biological data | Method |
| --- | --- | --- | --- |
| 15 | 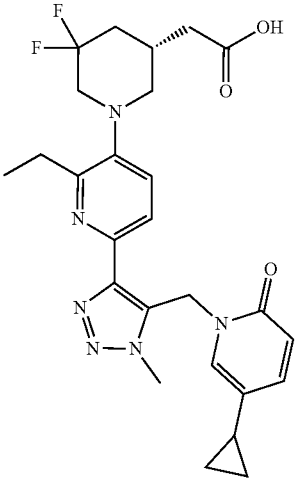 [SMILES: CCc1nc(-c2nnn(C)c2Cn2cc(C3CC3)ccc2=O)ccc1N1C[C@@H](CC(=O)O)CC(F)(F)C1] (S)-2-(1-(6-(5-((5-cyclopropyl-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 513 $(M + H)^+$. $^1H$ NMR (400 MHz, $CD_3OD$) δ 7.88 (d, J = 8.4 Hz, 1H), 7.68 (d, J = 2.8 Hz, 1H), 7.62 (d, J = 8.4 Hz, 1H), 7.28 (dd, J = 7.2, 2.8 Hz, 1H), 6.48 (d, J = 7.2 Hz, 1H), 5.84 (s, 2H), 4.18 (s, 3H), 3.28-3.21 (m, 2H), 3.16-3.09 (m, 1H), 2.99 (q, J = 7.6 Hz, 2H), 2.65-2.59 (m, 1H), 2.56-2.48 (m, 1H), 2.41-2.37 (m, 2H), 2.37-2.27 (m, 1H), 1.81-1.65 (m, 1H), 1.61-1.53 (m, 1H), 1.33 (t, J = 7.6 Hz, 3H), 0.78-0.72 (m, 2H), 0.31-0.26 (m, 2H). | Example 1 |
| 16 | 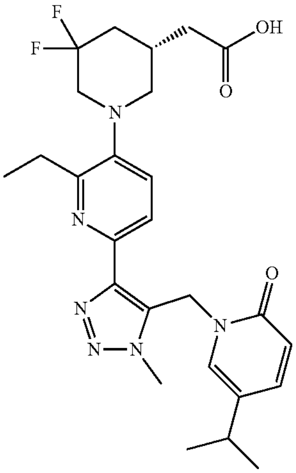 [SMILES: CCc1nc(-c2nnn(C)c2Cn2cc(C(C)C)ccc2=O)ccc1N1C[C@@H](CC(=O)O)CC(F)(F)C1] (S)-2-(1-(2-ethyl-6-(5-((5-isopropyl-2-oxopyridin-1(2H)-yl)methyl)-1-methyl-1H-1,2,3-triazol-4-yl)pyridin-3-yl)-5,5-difluoropiperidin-3-yl)acetic acid | LC/MS (ESI) m/z: 515 $(M + H)^+$. $^1H$ NMR (400 MHz, $CD_3OD$) δ 7.89 (d, J = 8.4 Hz, 1H), 7.64 (d, J = 2.4 Hz, 1H), 7.62 (d, J = 8.4 Hz, 1H), 7.45 (dd, J = 7.2, 2.4 Hz, 1H), 6.53 (d, J = 7.2 Hz, 1H), 5.89 (s, 2H), 4.18 (s, 3H), 3.26-3.22 (m, 2H), 3.14-3.08 (m, 1H), 2.99 (q, J = 7.6 Hz, 2H), 2.64-2.47 (m, 3H), 2.40-2.36 (m, 2H), 2.35-2.26 (m, 1H), 1.81-1.65 (m, 1H), 1.33 (t, J = 7.6 Hz, 3H), 0.97 (d, J = 6.8 Hz, 6H). | Example 1 |

-continued

| Ex# | Structure & name | Analytical & biological data | Method |
|---|---|---|---|
| 17 | 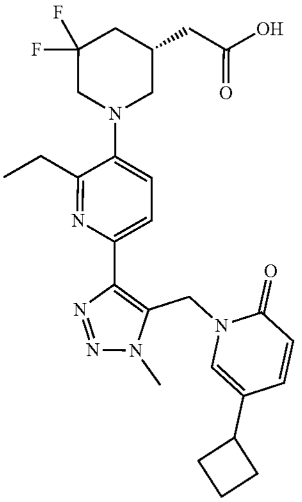 [SMILES: CCc1nc(-c2nnn(C)c2Cn2cc(C3CCC3)ccc2=O)ccc1N1C[C@@H](CC(=O)O)CC(F)(F)C1] (S)-2-(1-(6-(5-((5-cyclobutyl-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 527 $(M + H)^+$. $^1H$ NMR (400 MHz, $CD_3OD$) δ 7.89 (d, J = 8.4 Hz, 1H), 7.64 (d, J = 2.4 Hz, 1H), 7.61 (d, J = 8.4 Hz, 1H), 7.44 (dd, J = 9.6, 2.4 Hz, 1H), 6.53 (d, J = 9.6 Hz, 1H), 5.89 (s, 2H), 4.17 (s, 3H), 3.29-3.24 (m, 2H), 3.20-3.04 (m, 2H), 2.99 (q, J = 7.6 Hz, 2H), 2.65-2.58 (m, 1H), 2.55-2.49 (m, 1H), 2.42-2.40 (m, 2H), 2.35-2.26 (m, 1H), 2.14-2.06 (m, 2H), 1.95-1.85 (m, 1H), 1.82-1.65 (m, 4H), 1.32 (t, J = 7.6 Hz, 3H). | Example 1 |
| 18 | 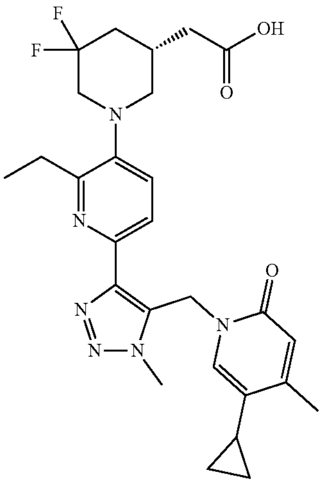 [SMILES: CCc1nc(-c2nnn(C)c2Cn2cc(C3CC3)c(C)cc2=O)ccc1N1C[C@@H](CC(=O)O)CC(F)(F)C1] (S)-2-(1-(6-(5-((5-cyclopropyl-4-methyl-2-oxopyridin-1(2H)-ylmethyl)-1-methyl-1H-1,2,3-triazol-4-yl)-2-ethylpyridin-3-yl)-5,5-difluoropiperidin-3-yl)acetic acid | LC/MS (ESI) m/z: 527 $(M + H)^+$. $^1H$ NMR (400 MHz, $CD_3OD$) δ 7.88 (d, J = 8.4 Hz, 1H), 7.62 (d, J = 8.4 Hz, 1H), 7.52 (s, 1H), 6.37 (s, 1H), 5.82 (s, 2H), 4.17 (s, 3H), 3.29-3.24 (m, 2H), 3.13-3.05 (m, 1H), 3.00 (q, J = 7.6 Hz, 2H), 2.65-2.60 (m, 1H), 2.56-2.50 (m, 1H), 2.41-2.28 (m, 3H), 2.27 (s, 3H), 1.80-1.70 (m, 1H), 1.55-1.49 (m, 1H), 1.32 (t, J = 7.6 Hz, 3H), 0.73-0.68 (m, 2H), 0.12-0.08 (m, 2H). | Example 1 |

-continued

| Ex# | Structure & name | Analytical & biological data | Method |
| --- | --- | --- | --- |
| 19 | 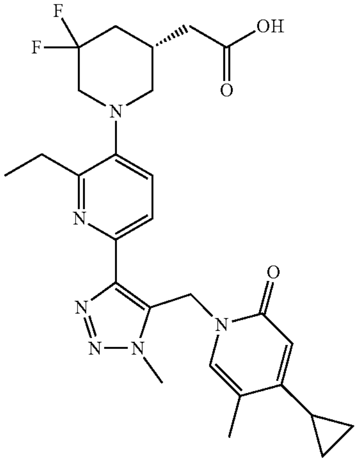 [SMILES: CCc1nc(-c2nnn(C)c2Cn2cc(C)c(C3CC3)cc2=O)ccc1N1C[C@@H](CC(=O)O)CC(F)(F)C1] (S)-2-(1-(6-(5-((4-cyclopropyl-5-methyl-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 527 $(M + H)^+$. $^1H$ NMR (400 MHz, $CD_3OD$) δ 7.88 (d, J = 8.4 Hz, 1H), 7.63 (s, 1H), 7.60 (d, J = 8.4 Hz, 1H), 7.52 (s, 1H), 6.06 (s, 1H), 5.79 (s, 2H), 4.12 (s, 3H), 3.29-3.20 (m, 2H), 3.15-3.05 (m, 1H), 2.99 (q, J = 7.6 Hz, 2H), 2.65-2.58 (m, 1H), 2.56-2.55 (m, 1H), 2.40-2.38 (m, 2H), 2.36-2.27 (m, 1H), 2.04 (s, 3H), 1.83-1.65 (m, 2H), 1.31 (t, J = 7.6 Hz, 3H) , 1.05-1.00 (m, 2H), 0.73-0.66 (m, 2H). | Example 1 |
| 20 | 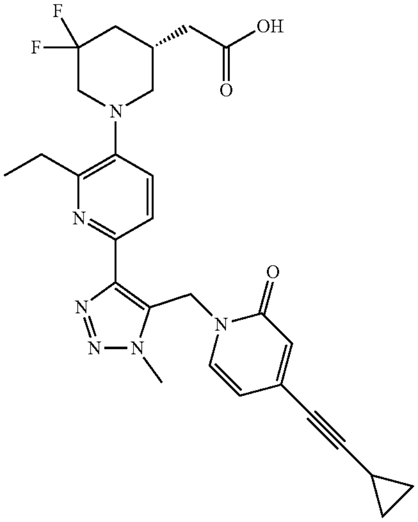 [SMILES: CCc1nc(-c2nnn(C)c2Cn2ccc(C#CC3CC3)cc2=O)ccc1N1C[C@@H](CC(=O)O)CC(F)(F)C1] (S)-2-(1-(6-(5-((4-(cyclopropylethynyl)-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 537 $(M + H)^+$. $^1H$ NMR (400 MHz, $CD_3OD$) δ 7.89 (d, J = 8.4 Hz, 1H), 7.79 (d, J = 7.2 Hz, 1H), 7.59 (d, J = 8.4 Hz, 1H), 6.46 (d, J = 1.6 Hz, 1H), 6.16 (dd, J = 7.2, 1.6 Hz, 1H), 5.82 (s, 2H), 4.13 (s, 3H), 3.29-3.21 (m, 2H), 3.13-3.03 (m, 1H), 2.95 (q, J = 7.6 Hz, 2H), 2.66-2.58 (m, 1H), 2.55-2.48 (m, 1H), 2.40-2.26 (m, 3H), 1.80-1.65 (m, 1H), 1.52-1.44 (m, 1H), 1.28 (t, J = 7.6 Hz, 3H), 0.96-0.87 (m, 2H), 0.79-0.75 (m, 2H). | Example 1 |

-continued

| Ex# | Structure & name | Analytical & biological data | Method |
| --- | --- | --- | --- |
| 21 | 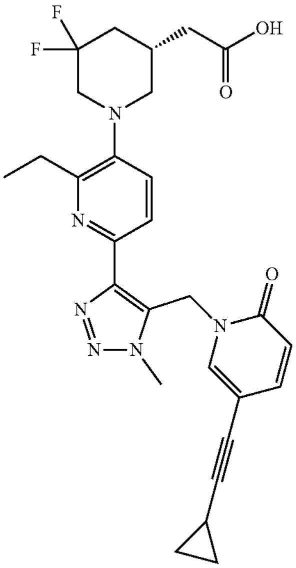 [SMILES: CCc1nc(-c2nnn(C)c2Cn2cc(C#CC3CC3)ccc2=O)ccc1N1C[C@@H](CC(=O)O)CC(F)(F)C1] (S)-2-(1-(6-(5-((5-(cyclopropylethynyl)-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 537 $(M + H)^+$. $^1$H NMR (400 MHz, $CD_3OD$) δ 8.19 (d, J = 2.4 Hz, 1H), 7.86 (d, J = 8.4 Hz, 1H), 7.61 (d, J = 8.4 Hz, 1H), 7.35 (dd, J = 7.2, 2.4 Hz, 1H), 6.42 (d, J = 7.2 Hz, 1H), 5.71 (s, 2H), 4.22 (s, 3H), 3.29-3.21 (m, 2H), 3.13-2.98 (m, 3H), 2.70-2.63 (m, 1H), 2.56-2.49 (m, 1H), 2.44-2.26 (m, 3H), 1.83-1.66 (m, 1H), 1.42-1.28(m, 1H), 1.35 (t, J = 7.6 Hz, 3H), 0.86-0.77 (m, 2H), 0.66-0.61(m, 2H). | Example 1 |
| 22 | 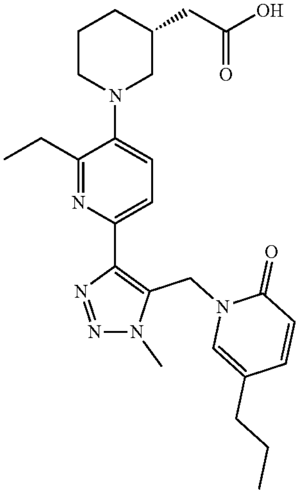 [SMILES: CCCc1ccc(=O)n(Cc2c(-c3ccc(N4CCC[C@H](CC(=O)O)C4)c(CC)n3)nnn2C)c1] (R)-2-(1-(2-ethyl-6-(1-methyl-5-((2-oxo-5-propylpyridin-1(2H)-yl)methyl)-1H-1,2,3-triazol-4-yl)pyridin-3-yl)piperidin-3-yl)acetic acid | LC/MS (ESI) m/z: 479 $(M + H)^+$. $^1$H NMR (400 MHz, $CD_3OD$) δ 7.85 (d, J = 8.4 Hz, 1H), 7.66 (d, J = 2.4 Hz, 1H), 7.55 (d, J = 8.4 Hz, 1H), 7.37 (dd, J = 9.2, 2.4 Hz, 1H), 6.52 (d, J = 9.2 Hz, 1H), 5.87 (s, 2H), 4.16 (s, 3H), 3.20-3.17 (m, 1H), 3.08-3.03 (m, 1H), 2.95 (q, J = 7.6 Hz, 2H), 2.78-2.71 (m, 1H), 2.49-2.43 (m, 1H), 2.33-2.18 (m, 5H), 1.93-1.73 (m, 3H), 1.40-1.29 (m, 5H), 1.28-1.17 (m, 1H), 0.75 (t, J = 7.6 Hz, 3H). | Example 2 |

-continued

| Ex# | Structure & name | Analytical & biological data | Method |
|---|---|---|---|
| 23 | 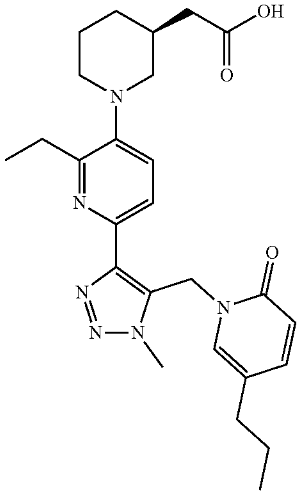 [SMILES: CCCc1ccc(=O)n(Cc2c(-c3ccc(N4CCC[C@@H](CC(=O)O)C4)c(CC)n3)nnn2C)c1] (S)-2-(1-(2-ethyl-6-(1-methyl-5-((2-oxo-5-propylpyridin-1(2H)-yl)methyl)-1H-1,2,3-triazol-4-yl)pyridin-3-yl)piperidin-3-yl)acetic acid | LC/MS (ESI) m/z: 479 (M + H)$^+$. $^1$H NMR (400 MHz, $CD_3OD$) δ 7.84 (d, J = 8.4 Hz, 1H), 7.66 (d, J = 2.4 Hz, 1H), 7.55 (d, J = 8.4 Hz, 1H), 7.37 (dd, J = 9.2, 2.4 Hz, 1H), 6.52 (d, J = 9.2 Hz, 1H), 5.87 (s, 2H), 4.16 (s, 3H), 3.24-3.03 (m, 2H), 2.95 (q, J = 7.6 Hz, 2H), 2.78-2.71 (m, 1H), 2.49-2.41 (m, 1H), 2.33-2.18 (m, 5H), 1.92-1.73 (m, 3H), 1.42-1.29 (m, 5H), 1.27-1.17 (m, 1H), 0.75 (t, J = 7.6 Hz, 3H). | Example 2 |
| 24 | 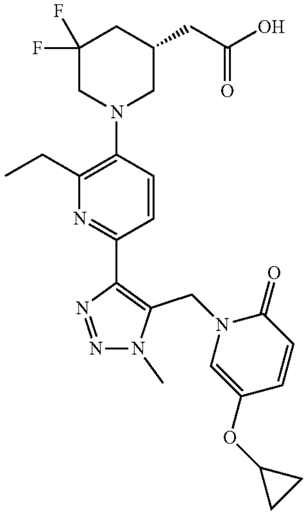 [SMILES: CCc1nc(-c2nnn(C)c2Cn2cc(OC3CC3)ccc2=O)ccc1N1C[C@@H](CC(=O)O)CC(F)(F)C1] (S)-2-(1-(6-(5-((5-cyclopropoxy-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 529 (M + H)$^+$. $^1$H NMR (400 MHz, $CD_3OD$) δ 7.96 (d, J = 8.3 Hz, 1H), 7.61 (dd, J = 14.4, 5.8 Hz, 2H), 7.30 (dd, J = 9.8, 3.2 Hz, 1H), 6.55 (d, J = 9.8 Hz, 1H), 6.00 (s, 2H), 4.16 (s, 3H), 3.28-3.19 (m, 2H), 3.14-3.04 (m, 2H), 3.04-2.91 (m, 2H), 2.63-2.47 (m, 2H), 2.42-2.23 (m, 3H), 1.77-1.63 (m, 1H), 1.33 (t, J = 7.5 Hz, 3H), 0.48-0.39 (m, 2H), 0.36-0.20 (m, 2H). | Example 1 |

-continued

| Ex# | Structure & name | Analytical & biological data | Method |
| --- | --- | --- | --- |
| 25 | 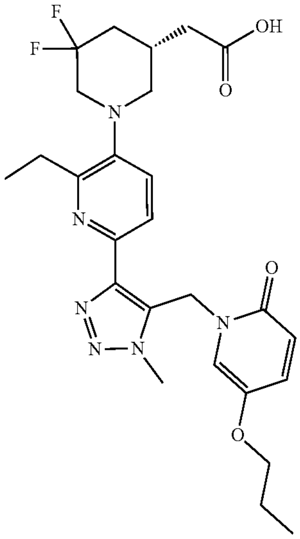 [SMILES: CCCOc1ccc(=O)n(Cc2c(-c3ccc(N4C[C@@H](CC(=O)O)CC(F)(F)C4)c(CC)n3)nnn2C)c1] (S)-2-(1-(2-ethyl-6-(1-methyl-5-((2-oxo-5-propoxypyridin-1 (2H)-yl)methyl)-1H-1,2,3-triazol-4-yl)pyridin-3-yl)-5,5-difluoropiperidin-3-yl)acetic acid | LC/MS (ESI) m/z: 531 $(M + H)^+$. $^1H$ NMR (400 MHz, $CD_3OD$) δ 7.93-7.91 (d, J = 8.4 Hz, 1H), 7.64-7.62 (d, J = 8.4 Hz, 1H), 7.48-7.47 (d, J = 3.1 Hz, 1H), 7.34-7.30 (dd, J = 9.8, 3.2 Hz, 1H), 6.55-6.53 (d, J = 9.8 Hz, 1H), 5.90 (s, 2H), 4.17 (s, 3H), 3.46-3.44 (m, 2H), 3.30-3.26 (m, 2H), 3.14-3.05 (m, 1H), 3.02-2.97 (q, J = 7.3 Hz, 2H), 2.69-2.47 (m, 2H), 2.34-2.27 (m, 3H), 1.80-1.65 (m, 1H) 1.62-1.53 (m, 2H), 1.34 (t, J = 7.5 Hz, 3H), 0.85 (t, J = 7.4 Hz, 3H). | Example 1 |
| 26 | 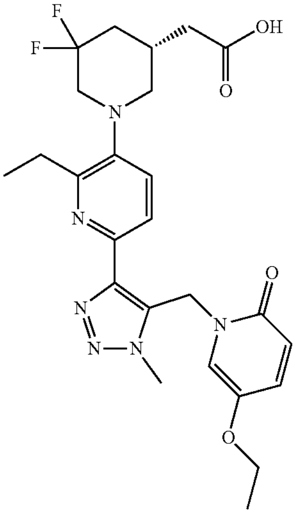 [SMILES: CCOc1ccc(=O)n(Cc2c(-c3ccc(N4C[C@@H](CC(=O)O)CC(F)(F)C4)c(CC)n3)nnn2C)c1] (S)-2-(1-(6-(5-((5-ethoxy-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 517 $(M + H)^+$. $^1H$ NMR (400 MHz, $CD_3OD$) δ 7.91 (d, J = 8.3 Hz, 1H), 7.63 (d, J = 8.4 Hz, 1H), 7.46 (d, J = 3.1 Hz, 1H), 7.34-7.29 (m, 1H), 6.54 (d, J = 9.8 Hz, 1H), 5.89 (s, 2H), 4.17 (s, 3H), 3.55 (q, J = 7.0 Hz, 2H), 3.28-3.21 (m, 2H), 3.17-3.08 (m, 1H), 2.99 (q, J = 7.5 Hz, 2H), 2.65-2.58 (m, 1H), 2.56-2.48 (m, 1H), 2.43-2.38 (m, 2H), 2.36-2.26 (m, 1H), 1.82-1.66 (m, 1H), 1.33 (t, J = 7.5 Hz, 3H), 1.18 (t, J = 7.0 Hz, 3H). | Example 1 |

-continued

| Ex# | Structure & name | Analytical & biological data | Method |
|---|---|---|---|
| 27 | 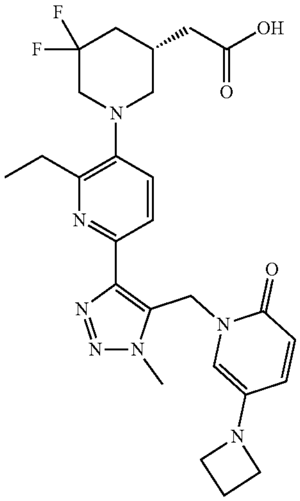 [SMILES: CCc1nc(-c2nnn(C)c2Cn2cc(N3CCC3)ccc2=O)ccc1N1C[C@@H](CC(=O)O)CC(F)(F)C1] (S)-2-(1-(6-(5-((5-(azetidin-1-yl)-2-oxopyridin-1(2H)-yl)methyl)-1-methyl-1H-1,2,3-triazol-4-yl)-2-ethylpyridin-3-yl)-5,5-difluoropiperidin-3-yl)acetic acid | LC-MS (ESI) m/z 528 $(M + H)^+$. $^1H$ NMR (400 MHz, $CD_3OD$) δ7.80-7.79 (d, J = 8.3 Hz, 1H), 7.53-7.51 (d, J = 8.4 Hz, 1H), 7.01-6.98 (dd, J = 9.6, 3.0 Hz, 1H), 6.82 (d, J = 3.0 Hz, 1H), 6.44-6.41 (d, J = 9.6 Hz, 1H), 5.81 (s, 2H), 4.07 (s, 3H), 3.38-3.34 (m, 4H), 3.7-3.11 (m, 2H), 3.05-2.98 (m, 1H), 2.93-2.87 (m, 2H), 2.54-2.48 (m, 1H), 2.4-2.39 (m, 1H), 2.30 (d, J = 6.9 Hz, 2H), 2.26-2.20 (m, 1H), 2.14-2.06 (m, 2H), 1.71-1.59 (m, 1H), 1.26-1.22 (t, J = 7.5 Hz, 3H). | Example 1 |
| 28 | 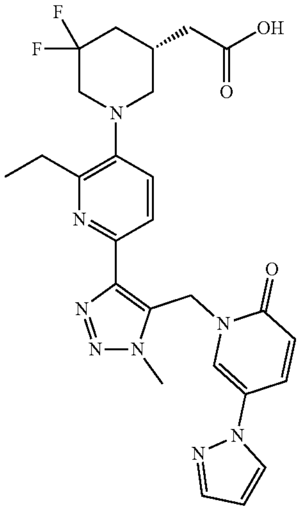 [SMILES: CCc1nc(-c2nnn(C)c2Cn2cc(-n3cccn3)ccc2=O)ccc1N1C[C@@H](CC(=O)O)CC(F)(F)C1] (S)-2-(1-(2-ethyl-6-(1-methyl-5-((2-oxo-5-(1H-pyrazol-1-yl)pyridin-1 (2H)-y)methyl)-1H-1,2,3-triazol-4-yl)pyridin-3-yl)-5,5-difluoropiperidin-3-yl)acetic acid | LC/MS (ESI) m/z: 539 $(M + H)^+$. $^1H$ NMR (400 MHz, $CD_3OD$) δ 8.41 (d, J = 2.8 Hz, 1H), 7.85-7.76 (m, 3H), 7.64 (s, 1H), 7.54 (d, J = 1.7 Hz, 1H), 6.57 (d, J = 9.7 Hz, 1H), 6.41-6.30 (m, 1H), 5.70 (s, 2H), 4.17 (s, 3H), 3.13 (d, J = 9.7 Hz, 2H), 3.04-2.92 (m, 1H), 2.85 (q, J = 7.5 Hz, 2H), 2.57-2.48 (m, 1H), 2.45-2.35 (m, 1H), 2.31 (d, J = 7.0 Hz, 2H), 2.26-2.14 (m, 1H), 1.74-1.56 (m, 1H), 1.16 (t, J = 7.5 Hz, 3H). | Example 1 |

-continued

| Ex# | Structure & name | Analytical & biological data | Method |
|---|---|---|---|
| 29 | 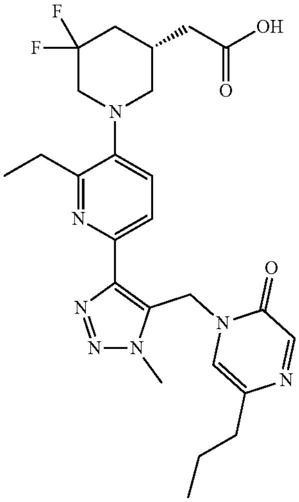 [SMILES: CCCc1cn(Cc2c(-c3ccc(N4C[C@@H](CC(=O)O)CC(F)(F)C4)c(CC)n3)nnn2C)c(=O)cn1] (S)-2-(1-(2-ethyl-6-(1-methyl-5-((2-oxo-5-propylpyrazin-1(2H)-yl)methyl)-1H-1,2,3-triazol-4-yl)pyridin-3-yl)-5,5-difluoropiperidin-3-yl)acetic acid | LC/MS (ESI) m/z: 516 $(M + H)^+$. $^1$H NMR (400 MHz, $CD_3OD$) δ 8.05 (s, 1H), 7.91 (d, J = 8.4 Hz, 1H), 7.62 (d, J = 8.4 Hz, 1H), 7.57 (s, 1H), 5.79 (s, 2H), 4.19 (s, 3H), 3.30-3.22 (s, 2H), 3.15-3.05 (m, 1H), 2.97 (d, J = 7.6 Hz, 1H), 2.64-2.27 (m, 7H), 1.81-1.66 (m, 1H), 1.52-1.42 (m, 2H), 1.29 (t, J = 7.6 Hz, 3H), 0.78 (t, J = 7.6 Hz, 3H). | Example 1 |
| 30 | 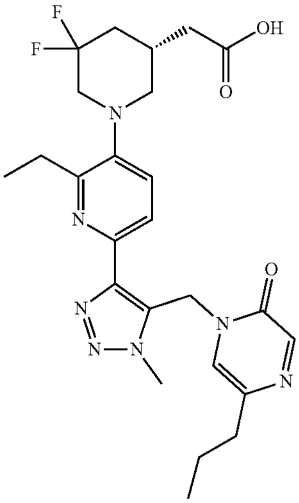 [SMILES: CCCc1cn(Cc2c(-c3ccc(N4C[C@@H](CC(=O)O)CC(F)(F)C4)c(CC)n3)nnn2C)c(=O)cn1] (S)-2-(1-(2-ethyl-6-(1-methyl-5-((2-oxo-5-propylpyrimidin-1(2H)-yl)methyl)-1H-1,2,3-triazol-4-yl)pyridin-3-yl)-5,5-difluoropiperidin-3-yl)acetic acid | LC/MS (ESI) m/z: 515 $(M + H)^+$. $^1$H NMR (400 MHz, $CD_3OD$) δ 8.46 (d, J = 3.2 Hz, 1H), 8.14 (d, J = 3.2 Hz, 1H), 7.90 (d, J = 8.4 Hz, 1H), 7.61 (d, J = 8.4 Hz, 1H), 5.74 (s, 2H), 4.24 (s, 3H), 3.25-3.22 (m, 2H), 3.13-3.05 (m, 1H), 2.97 (q, J = 7.2 Hz, 2H), 2.64-2.28 (m, 7H), 1.82-1.65 (m, 1H), 1.44-1.31 (m, 2H), 1.28 (t, J = 7.2 Hz, 3H), 0.79 (t, J = 7.6 Hz, 3H). | Example 1 |

-continued

| Ex# | Structure & name | Analytical & biological data | Method |
| --- | --- | --- | --- |
| 31 | 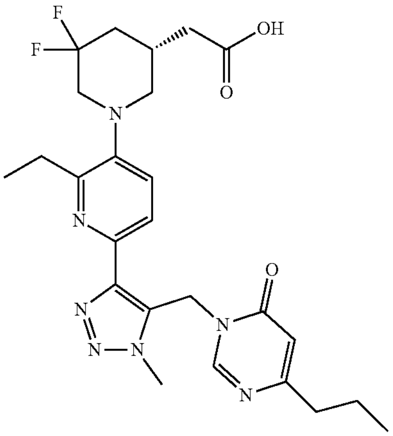 [SMILES: CCCc1cc(=O)n(Cc2c(-c3ccc(N4C[C@@H](CC(=O)O)CC(F)(F)C4)c(CC)n3)nnn2C)cn1] (S)-2-(1-(2-ethyl-6-(1-methyl-5-((6-oxo-4-propylpyrimidin-1(6H)-yl)methyl)-1H-1,2,3-triazol-4-ypyridin-3-yl)-5,5-difluoropiperidin-3-yl)acetic acid | LC/MS (ESI) m/z: 516 $[M + 1]^+$. $^1H$ NMR (400 MHz, $CD_3OD$) δ 8.68 (s, 1H), 7.89 (d, J = 8.3 Hz, 1H), 7.59 (d, J = 8.4 Hz, 1H), 6.25 (s, 1H), 5.67 (s, 2H), 4.25 (s, 3H), 3.26-3.19 (m, 2H), 3.13-3.05 (m, 1H), 2.99 (t, J = 7.5 Hz, 2H), 2.66-2.58 (m, 1H), 2.57-2.48 (m, 1H), 2.46-2.37 (m, 4H), 2.35-2.25 (m, 1H), 1.86-1.67 (m, 1H), 1.62 (dd, J = 14.9, 7.4 Hz, 2H), 1.31 (t, J = 7.5 Hz, 3H), 0.89 (t, J = 7.4 Hz, 3H). | Example 1 |
| 32 | 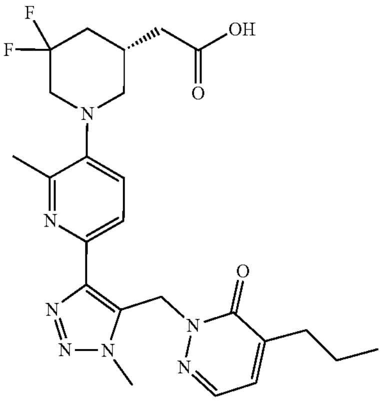 [SMILES: CCCc1ccnn(Cc2c(-c3ccc(N4C[C@@H](CC(=O)O)CC(F)(F)C4)c(C)n3)nnn2C)c1=O] (S)-2-(5,5-difluoro-1-(2-methyl-6-(1-methyl-5-((6-0xo-5-propylpyridazin-1(6H)-yl)methyl)-1H-1,2,3-triazol-4-yl)pyridin-3-yl)piperidin-3-yl)acetic acid | LC/MS (ESI) m/z: 502 $(M + H)^+$. $^1H$ NMR (400 MHz, DMSO-$d_6$) δ 7.76 (d, J = 8.3 Hz, 1H), 7.61 (d, J = 4.0 Hz, 1H), 7.43 (d, J = 8.4 Hz, 1H), 7.11 (d, J = 4.0 Hz, 1H), 5.83-5.72 (m, 2H), 3.96 (s, 3H), 3.10-2.85 (m, 3H), 2.41-2.39 (m, 2H), 2.29 (s, 3H), 2.31-2.29 (m, 7H), 1.96-1.90 (m, 1H), 1.69-1.60 (m, 1H), 1.56-1.44 (m, 2H), 0.83 (t, J = 7.4 Hz, 3H). | Example 1 |

-continued

| Ex# | Structure & name | Analytical & biological data | Method |
| --- | --- | --- | --- |
| 33 | 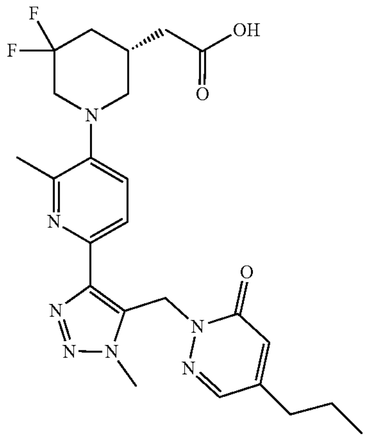 [SMILES: CCCc1cnn(Cc2c(-c3ccc(N4C[C@@H](CC(=O)O)CC(F)(F)C4)c(C)n3)nnn2C)c(=O)c1] (S)-2-(5,5-difluoro-1-(2-methyl-6-(1-methyl-5-((6-oxo-4-propylpyridazin-1(6H)-yl)methyl)-1H-1,2,3-triazol-4-yl)pyridin-3-yl)piperidin-3-yl)acetic acid | LC/MS (ESI) m/z: 502 $(M + H)^+$. $^1H$ NMR (400 MHz, $CD_3OD$) δ 7.77 (d, J = 8.2 Hz, 1H), 7.69 (d, J = 2.0 Hz, 1H), 7.48 (d, J = 8.2 Hz, 1H), 6.74 (d, J = 2.0 Hz, 1H), 5.88 (s, 2H), 4.15 (s, 3H), 3.27-3.20 (m, 2H), 3.09-2.97 (m, 1H), 2.60-2.50 (m, 2H), 2.49-2.45 (m, 6H), 2.42-2.36 (m, 2H), 2.32-2.25 (m, 1H), 1.80-1.65 (m, 1H), 1.60 (dd, J = 15.2, 7.5 Hz, 2H), 0.93 (t, J = 7.4 Hz, 3H). | Example 1 |
| 34 | 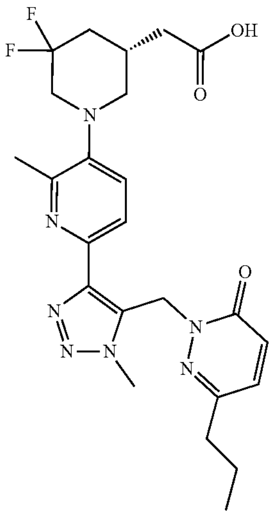 [SMILES: CCCc1ccc(=O)n(Cc2c(-c3ccc(N4C[C@@H](CC(=O)O)CC(F)(F)C4)c(C)n3)nnn2C)n1] (S)-2-(5,5-difluoro-1-(2-methyl-6-(1-methyl-5-((6-oxo-3-propylpyridazin-1(6H)-yl)methyl)-1H-1,2,3-triazol-4-yl)pyridin-3-yl)piperidin-3-yl)acetic acid | LC/MS (ESI) (m/z): 502 $(M + H)^+$. $^1H$ NMR (400 MHz, $CD_3OD$) δ 7.76 (d, J = 8.3 Hz, 1H), 7.49 (d, J = 8.3 Hz, 1H), 7.28 (d, J = 9.5 Hz, 1H), 6.91 (d, J = 9.5 Hz, 1H), 5.88 (s, 2H), 4.18 (s, 3H), 3.25 (d, J = 10.3 Hz, 2H), 3.08-2.99 (m, 1H), 2.60-2.55 (m, 1H), 2.49 (s, 3H), 2.41-2.38 (m, 3H), 1.79-1.59 (m, 2H), 1.45-1.42 (m, 4H), 0.75 (t, J = 7.4 Hz, 3H). | Example 1 |

-continued

| Ex# | Structure & name | Analytical & biological data | Method |
|---|---|---|---|
| 35 | 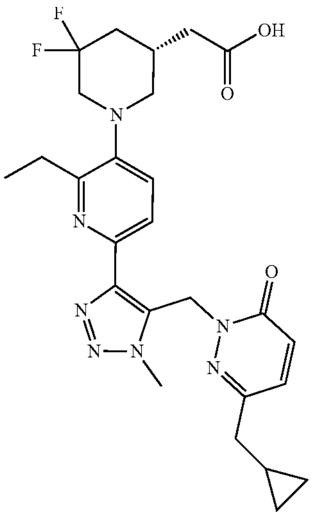 [SMILES: CCc1nc(-c2nnn(C)c2Cn2nc(CC3CC3)ccc2=O)ccc1N1C[C@@H](CC(=O)O)CC(F)(F)C1] (S)-2-(1-(6-(5-((3-(cyclopropylmethyl)-6-oxopyridazin-1(6H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 528 $(M + H)^+$. $^1H$ NMR (400 MHz, $CD_3OD$) δ 7.80 (d, J = 8.4 Hz, 1H), 7.54 (d, J = 8.3 Hz, 1H), 7.38 (d, J = 9.5 Hz, 1H), 6.93 (d, J = 9.4 Hz, 1H), 5.97 (s, 2H), 4.13 (s, 3H), 3.22-3.16 (m, 2H), 3.11-3.00 (m, 1H), 2.87 (d, J = 7.5 Hz, 2H), 2.62-2.54 (m, 1H), 2.53-2.45 (m, 1H), 2.39-2.35 (m, 2H), 2.31 (d, J = 7.1 Hz, 3H), 1.78-1.64 (m, 1H), 1.21 (t, J = 7.4 Hz, 3H), 0.78-0.70 (m, 1H), 0.37 (d, J = 7.0 Hz, 2H), 0.03-0.01 (m, 2H). | Example 1 |
| 36 | 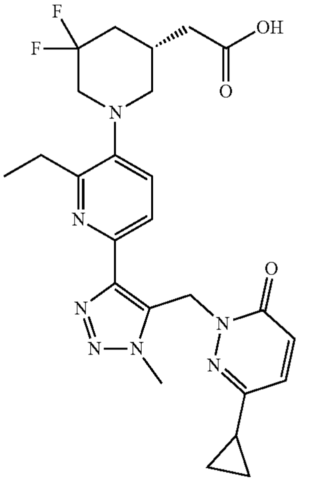 [SMILES: CCc1nc(-c2nnn(C)c2Cn2nc(C3CC3)ccc2=O)ccc1N1C[C@@H](CC(=O)O)CC(F)(F)C1] (S)2-(1-(6-(5-((3-cyclopropyl-6-oxopyridazin-1(6H)-yl)methyl)-1-methyl-1H-1,2,3-triazol-4-yl)-2-ethylpyridin-3-yl)-5,5-difluoropiperidin-3-yl)acetic acid | LC/MS (ESI) m/z: 514 $[M + 1]^+$. $^1H$ NMR (400 MHz, $CD_3OD$) δ 7.80 (d, J = 8.4 Hz, 1H), 7.56 (d, J = 8.4 Hz, 1H), 7.27 (d, J = 9.5 Hz, 1H), 6.88 (d, J = 9.4 Hz, 1H), 5.95(s, 2H), 4.13 (s, 3H), 3.21 (d, J = 10.5 Hz, 2H), 3.09 (d, J = 28.7 Hz, 1H), 2.87 (t, J = 7.4 Hz, 2H), 2.59 (d, J = 10.9 Hz, 1H), 2.50 (dd, J = 8.5, 4.8 Hz, 1H), 2.41-2.36 (m, 2H), 2.34-2.26 (m, 1H), 1.82-1.67 (m, 2H), 1.21 (t, J = 7.5 Hz, 3H), 0.78 (dd, J = 8.2, 2.5 Hz, 2H), 0.41 (d, J = 4.9 Hz, 2H). | Example 1 |

-continued

| Ex# | Structure & name | Analytical & biological data | Method |
|---|---|---|---|
| 37 | 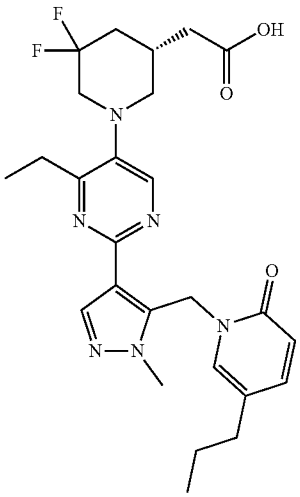 [SMILES: CCCc1ccc(=O)n(Cc2c(-c3ncc(N4C[C@@H](CC(=O)O)CC(F)(F)C4)c(CC)n3)cnn2C)c1] (S)-2-(1-(4-ethyl-2-(1-methyl-5-((2-oxo-5-propylpyridin-1(2H)-yl)methyl)-1H-pyrazol-4-yl)pyrimidin-5-yl)-5,5-difluoropiperidin-3-yl)acetic acid | LC/MS (ESI) (m/z): 515 $(M + H)^+$. $^1H$ NMR (400 MHz, $CD_3OD$) δ 8.44 (s, 1H), 8.13 (s, 1H), 7.47 (d, J = 2.1 Hz, 1H), 7.40 (dd, J = 9.2, 2.5 Hz, 1H), 6.56 (d, J = 9.2 Hz, 1H), 5.84 (s, 2H), 3.91 (s, 3H), 3.66 (d, J = 11.2 Hz, 2H), 3.61 (s, 2H), 3.58 (s, 2H), 3.23-3.17 (m, 2H), 2.92-2.87 (m, 2H), 2.73-2.68 (m, 1H), 2.52-2.46 (m, 1H), 2.41 (d, J = 7.4 Hz, 2H), 2.24 (t, J = 7.5 Hz, 2H), 1.43-1.36 (m, 3H), 0.77 (t, J = 7.3 Hz, 3H). | Example 1 |
| 38 | 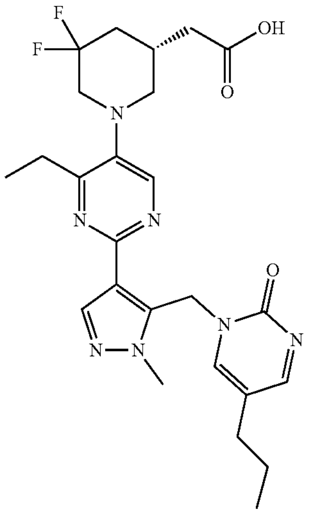 [SMILES: CCCc1cnc(=O)n(Cc2c(-c3ncc(N4C[C@@H](CC(=O)O)CC(F)(F)C4)c(CC)n3)cnn2C)c1] (S)-2-(1-(4-ethyl-2-(1-methyl-5-((2-oxo-5-propylpyrimidin-1(2H)-yl)methyl)-1H-pyrazol-4-yl)pyrimidin-5-yl)-5,5-difluoropiperidin-3-yl)acetic acid | LC-MS: m/z 516 $(M + H)^+$. $^1H$ NMR (400 MHz, $CD_3OD$) δ 8.46 (d, J = 2.2 Hz, 1H), 8.42 (s, 1H), 8.14 (s, 1H), 8.01 (d, J = 3.1 Hz, 1H), 5.68 (s, 2H), 4.02 (s, 3H), 3.30-3.28 (m, 1H), 3.26-3.13 (m, 2H), 2.89-2.84 (m, 2H), 2.73-2.66 (m, 1H), 2.54-2.45 (m, 1H), 2.36-2.41 (d, 2H), 2.38-2.28 (m, 3H), 1.84-1.66 (m, 1H), 1.48-1.40 (m, 2H), 1.27-1.23 (t, J = 7.5 Hz, 3H), 0.83-0.79 (t, J = 7.3 Hz, 3H). | Example 1 |

-continued

| Ex# | Structure & name | Analytical & biological data | Method |
|---|---|---|---|
| 39 | 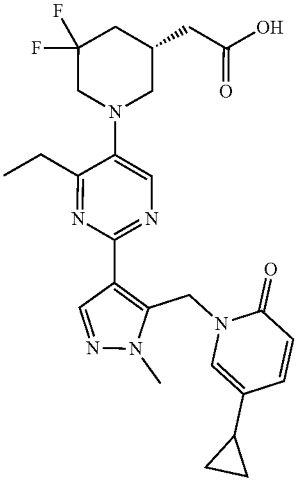 [SMILES: CCc1nc(-c2cnn(C)c2Cn2cc(C3CC3)ccc2=O)ncc1N1C[C@@H](CC(=O)O)CC(F)(F)C1] (S)-2-(1-(2-(5-((5-cyclopropyl-2-oxopyridin-1(2H)-yl)methyl)-1-methyl-1H-pyrazol-4-yl)-4-ethylpyrimidin-5-yl)-5,5-difluoropiperidin-3-yl)acetic acid | LC/MS (ESI) (m/z): 513 (M + H)$^+$. $^1$H-NMR (400 MHz, $CD_3OD$) δ 8.45 (s, 1H), 8.13 (s, 1H), 7.55 (d, J = 2.5 Hz, 1H), 7.29 (dd, J = 9.3, 2.6 Hz, 1H), 6.52 (d, J = 9.3 Hz, 1H) 5.83 (s, 2H), 3.92 (s, 3H), 3.38-3.35 (m, 2H), 3.24-3.13 (m, 1H), 2.95-2.89 (m, 2H), 2.70 (t, J = 10.9 Hz, 1H), 2.55-2.47(m, 1H), 2.40-2.38 (m, 2H), 2.34-2.27 (m, 1H), 1.82-1.67 (m, 1H), 1.63-1.56 (m, 1H), 1.29 (t, J = 7.5 Hz, 3H), 0.79-0.74 (m, 2H), 0.36-0.32 (m, 2H). | Example 1 |
| 40 | 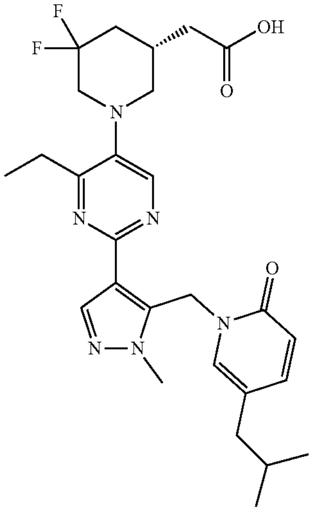 [SMILES: CCc1nc(-c2cnn(C)c2Cn2cc(CC(C)C)ccc2=O)ncc1N1C[C@@H](CC(=O)O)CC(F)(F)C1] (S)-2-(1-(4-ethyl-2-(5-((5-isobutyl-2-oxopyridin-1(2H)-yl)methyl)-1-methyl-1H-pyrazol-4-yl)pyrimidin-5-yl)-5,5-difluoropiperidin-3-yl)acetic acid | LC/MS (ESI) m/z: 529 (M + H)$^+$. $^1$H NMR (400 MHz, $CD_3OD$) δ 8.43 (s, 1H), 8.14 (s, 1H), 7.40-7.37 (m, 2H), 6.56 (d, J = 9.3 Hz, 1H), 5.85 (s, 2H), 3.92 (s, 3H), 3.23-3.13 (m, 1H), 2.89 (q, J = 7.4 Hz, 2H), 2.72-2.67 (m, 1H), 2.55-2.45 (m, 1H), 2.37 (d, J = 7.2 Hz, 2H), 2.35-2.25 (m, 1H), 2.12 (d, J = 7.1 Hz, 2H), 1.80-1.65 (m, 1H), 1.60 (dt, J = 13.4, 6.7 Hz, 1H), 1.27 (t, J = 7.5 Hz, 3H), 0.73 (d, J = 6.6 Hz, 6H). | Example 1 |

-continued

| Ex# | Structure & name | Analytical & biological data | Method |
|---|---|---|---|
| 41 | 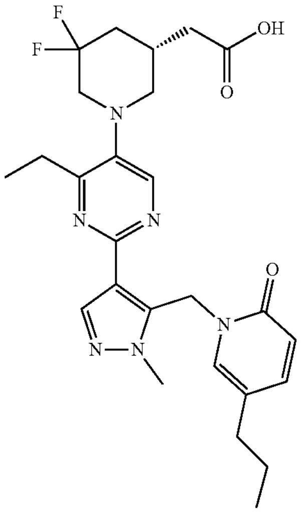 [SMILES: CCCc1ccc(=O)n(Cc2c(-c3ncc(N4C[C@@H](CC(=O)O)CC(F)(F)C4)c(CC)n3)cnn2C)c1] (S)-2-(1-(2-ethyl-6-(1-methyl-5-((2-oxo-5-propylpyridin-1(2H)-yl)methyl)-1H-pyrazol-4-yl)pyridin-3-yl)-5,5-difluoropiperidin-3-yl)acetic acid | LC-MS: m/z 514 $(M + H)^+$. $^1H$ NMR (400 MHz, $CD_3OD$) δ 7.80 (s, 1H), 7.44 (d, J = 8.3 Hz, 1H), 7.42 (d, J = 1.9 Hz, 1H), 7.39 (d, J = 8.3 Hz, 1H), 7.29 (dd, J = 9.2, 2.5 Hz, 1H), 6.45 (d, J = 9.2 Hz, 1H), 5.73 (s, 2H), 3.80 (s, 3H), 3.14-3.07 (m, 2H), 3.02-2.92 (m, 1H), 2.84-2.78 (m, 2H), 2.53-2.46 (m, 1H), 2.44-2.36 (m, 1H), 2.31-2.29 (d, J = 7.1 Hz, 2H), 2.23-2.16 (m, 1H), 2.12-2.08 (t, J = 7.4 Hz, 2H), 1.70-1.56 (m, 1H), 1.31-1.22 (m, 2H), 1.15-1.11 (t, J = 7.5 Hz, 3H), 0.68-0.64 (t, J = 7.3 Hz, 3H). | Example 1 |
| 42 | 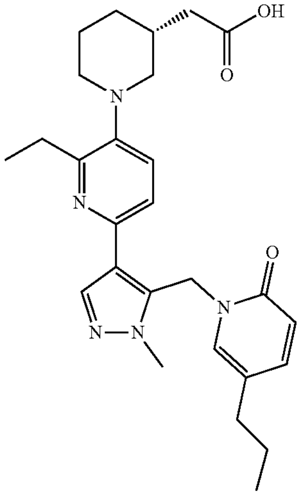 [SMILES: CCCc1ccc(=O)n(Cc2c(-c3ccc(N4CCC[C@H](CC(=O)O)C4)c(CC)n3)cnn2C)c1] (R)-2-(1-(2-ethyl-6-(1-methyl-5-((2-oxo-5-propylpyridin-1(2H)-yl)methyl)-1H-pyrazol-4-yl)pyridin-3-yl)piperidin-3-yl)acetic acid | LC/MS (ESI) (m/z): 478 $(M + H)^+$. $^1H$-NMR (400 MHz, $CD_3OD$) δ 7.87 (s, 1H), 7.51-7.53 (d, J = 2.0 Hz, 1H), 7.43-7.49 (m, 2H), 7.37-7.40 (dd, J = 9.2, 2.5 Hz, 1H), 6.53-6.55 (d, J = 9.2 Hz, 1H), 5.82 (s, 2H), 3.89 (s, 3H), 3.12-3.15 (d, J = 9.9 Hz, 1H), 3.00-3.02 (d, J = 11.2 Hz, 1H), 2.85-2.91 (m, 2H), 2.67-2.73 (m, 1H), 2.41-2.46 (m, 1H), 2.29-2.31 (d, J = 6.8 Hz, 2H), 2.17-2.21 (m, 3H), 2.00-2.05 (m, 1H), 1.73-1.91 (m, 3H), 1.20-1.24 (m, 4H), 0.89-0.92 (m, 1H), 0.74-0.77 (t, J = 7.3 Hz, 3H). | Example 1 |

Example 43: (S)-2-(5,5-difluoro-1-(2-methyl-6-(1-methyl-5-((4-oxo-3-propylpyridin-1(4H)-yl)methyl)-1H-1,2,3-triazol-4-yl)pyridin-3-yl)piperidin-3-yl) acetic acid

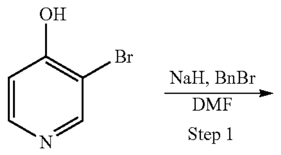

1

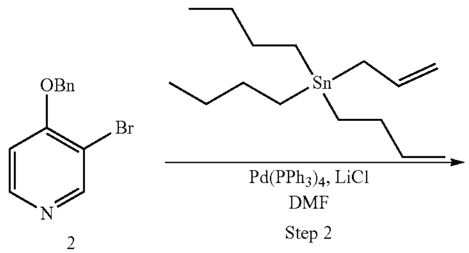

2

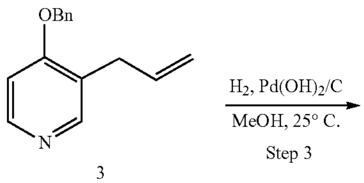

3

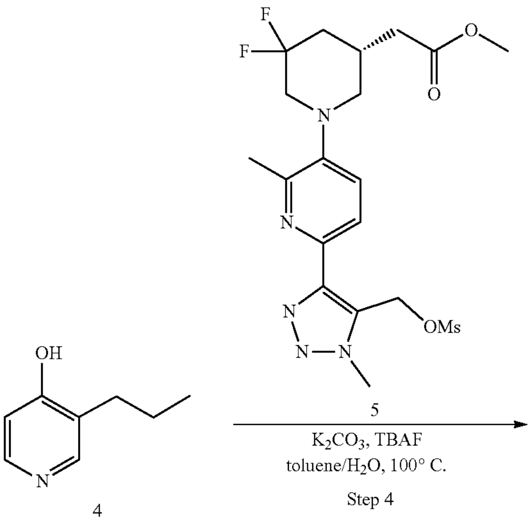

5

4

-continued

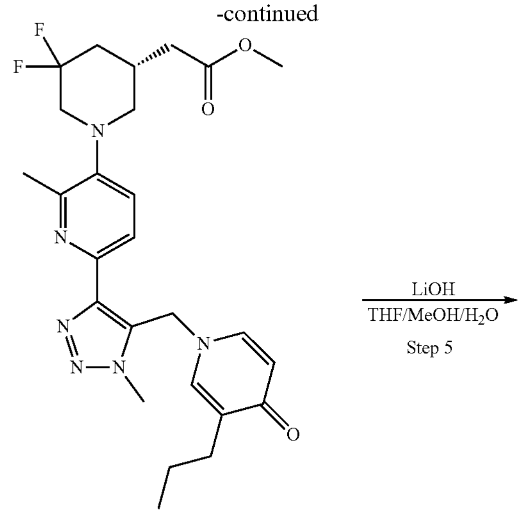

6

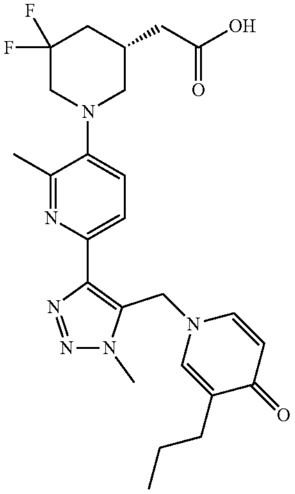

Example 43

Step 1: 4-(benzyloxy)-3-bromopyridine

To a solution of 3-bromopyridin-4-ol (0.13 mL, 1.16 mmol) in DMF (2 mL) was added NaH (92 mg, 2.30 mmol, 60% dispersion in mineral oil) in portions at 0° C. under $N_2$ atmosphere and the reaction was stirred at 0° C. for 20 min. BnBr (0.21 mL, 1.76 mmol) was added to the above mixture and the resulting mixture was stirred at 25° C. for 16 hrs. The reaction was quenched with water (20 mL) at 0° C. and the mixture was extracted with EtOAc (3×15 mL). The combined organic layers were washed with water and brine, dried over $Na_2SO_4$, filtered and concentrated to dryness. The residue was purified by column chromatography (PE:EtOAc=50:1 to 20:1) to give the title compound (300 mg, 98.6% yield) as light yellow solid. LC/MS (ESI) m/z: 264 $(M+H)^+$.

Step 2: 3-allyl-4-(benzyloxy)pyridine

To a mixture of 4-(benzyloxy)-3-bromopyridine (300 mg, 1.14 mmol), Tibutyl(vinyl)tin (0.53 mL, 1.71 mmol) and LiCl (121 mg, 2.85 mmol) was added $Pd(PPh_3)_4$ (132 mg, 0.114 mmol) under $N_2$ atmosphere. After addition, the mixture was degassed under $N_2$ atmosphere at 100° C. for 16 hrs. The mixture was diluted with EtOAc (10 mL), washed with saturated aq·KF solution and brine, dried over $Na_2SO_4$, filtered and concentrated to dryness. The residue was purified by column chromatography (DCM:MeOH=50:1 to 20:1) to give the title compound 3 (205 mg, 80.2% yield) as yellow oil. LC/MS (ESI) m/z: 226 $(M+H)^+$.

Step 3: 3-propylpyridin-4-ol

To a solution of 3-allyl-4-(benzyloxy)pyridine (150 mg, 0.67 mmol) in MeOH (3 mL) was added $Pd(OH)_2/C$ (20 mg, 10% wt) at 25° C. under $N_2$ atmosphere and the mixture was degassed under $N_2$ atmosphere for three times, stirred under a $H_2$ balloon at 25° C. for 5 hrs. The mixture was filtered and the filter cake was washed with MeOH (2×5 mL). The filtrate was concentrated to dryness and the residue was purified by column chromatography (DCM:MeOH=20:1 to 10:1) to give compound 4 (50 mg, 54.7% yield) as colorless oil. LC/MS (ESI) m/z: 138 $(M+H)^+$.

Step 4: methyl (R)-2-(5,5-difluoro-1-(2-methyl-6-(1-methyl-5-((4-oxo-3-propylpyridin-1(4H)-yl)methyl)-1H-1,2,3-triazol-4-yl)pyridin-3-yl)piperidin-3-yl)acetate To a mixture of 3-propylpyridin-4-ol (15.7 mg, 0.114 mmol) and methyl (S)-2-(5,5-difluoro-1-(2-methyl-6-(1-methyl-5-(((methylsulfonyl)oxy)methyl)-1H-1,2,3-triazol-4-yl)pyridin-3-yl)piperidin-3-yl)acetate (36 mg, 0.076 mmol) in toluene (2 mL) and $H_2O$ (1 mL) was added $K_2CO_3$ (31.5 mg, 0.23 mmol) followed by TBAF (2 mg, 0.008 mmol) and the reaction mixture was heated to 80° C. for 16 hrs. The mixture was diluted with EtOAc (3 mL), washed with water and brine, dried over anhydrous $Na_2SO_4$, filtered and concentrated to dryness to give the title compound (50 mg, 100% yield) as yellow solid, which was used in next reaction directly. LC/MS (ESI) m/z: 515 $(M+H)^+$.

Step 5: (R)-2-(5,5-difluoro-1-(2-methyl-6-(1-methyl-5-((4-oxo-3-propylpyridin-1(4H)-yl)methyl)-1H-1,2,3-triazol-4-yl)pyridin-3-yl)piperidin-3-yl) acetic acid To a solution of methyl (R)-2-(5,5-difluoro-1-(2-methyl-6-(1-methyl-5-((4-oxo-3-propylpyridin-1(4H)-yl)methyl)-1H-1,2,3-triazol-4-yl)pyridin-3-yl)piperidin-3-yl)acetate (50 mg, 0.097 mmol) in THE (2 mL), MeOH (0.50 mL) and water (0.5 mL) was added $LiOH·H_2O$ (42 mg, 1.00 mmol) at 25° C. and the mixture was stirred at 25° C. for 16 hrs. The reaction was concentrated to dryness and the residue was diluted with water (5 mL). The mixture was basified with 1N aq·NaOH to pH~14 and washed with EtOAc (2×2 mL). The aqueous layer was acidified with 1N aq·HCl to pH~3 and extracted with DCM (2×3 mL). The combined organic layers were washed with brine, dried over anhydrous $Na_2SO_4$, filtered and concentrated to dryness. The residue was purified by prep-HPLC to give the title compound (5.2 mg, 10.7%) as white solid. LC/MS (ESI) m/z: 501 $(M+H)^+$. $^1H$ NMR (400 MHz, DMSO) δ 7.90 (d, J=8.3 Hz, 1H), 7.84-7.75 (m, 2H), 7.59 (d, J=8.4 Hz, 1H), 6.03 (d, J=7.3 Hz, 1H), 5.69 (s, 2H), 4.10 (s, 3H), 3.21-3.07 (m, 3H), 2.59-2.56 (m, 1H), 2.52 (s, 3H), 2.40-2.25 (m, 4H), 2.22-2.15 (m, 2H), 2.03-1.95 (m, 1H), 1.80-1.73 (m, 1H), 1.40-1.31 (m, 2H), 0.78 (t, J=7.4 Hz, 3H).

Example 44: 2-[5,5-difluoro-1-(2-methyl-6-{1-methyl-5-[2-(6-oxo-5-propyl-1,6-dihydropyridazin-1-yl)ethyl]-1H-1,2,3-triazol-4-yl}pyridin-3-yl)piperidin-3-yl]acetic acid

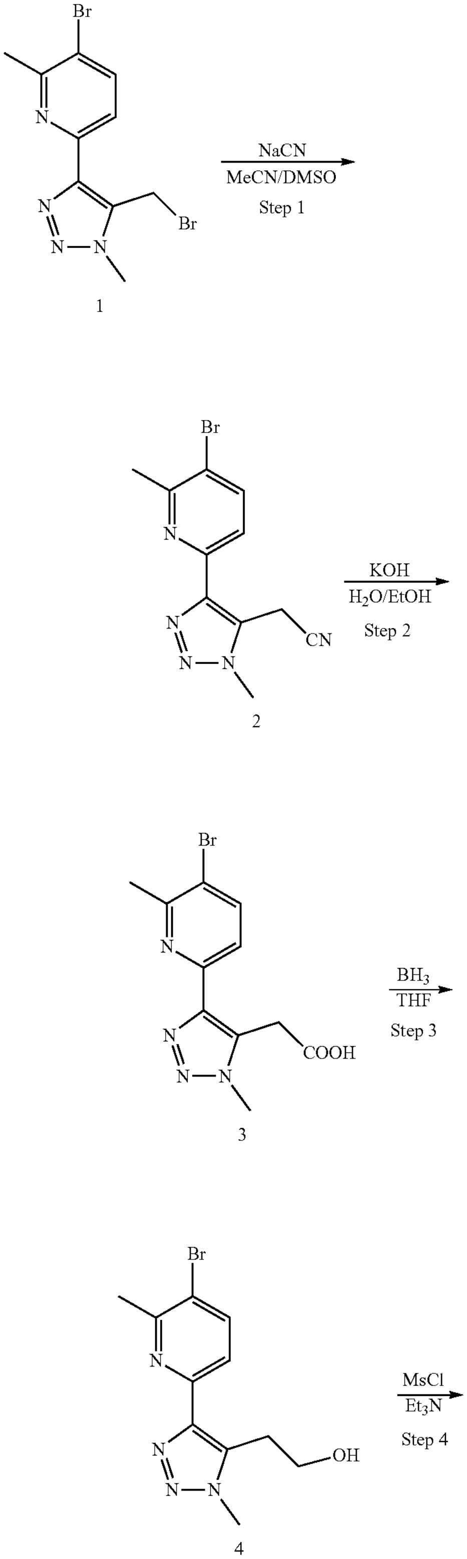

-continued

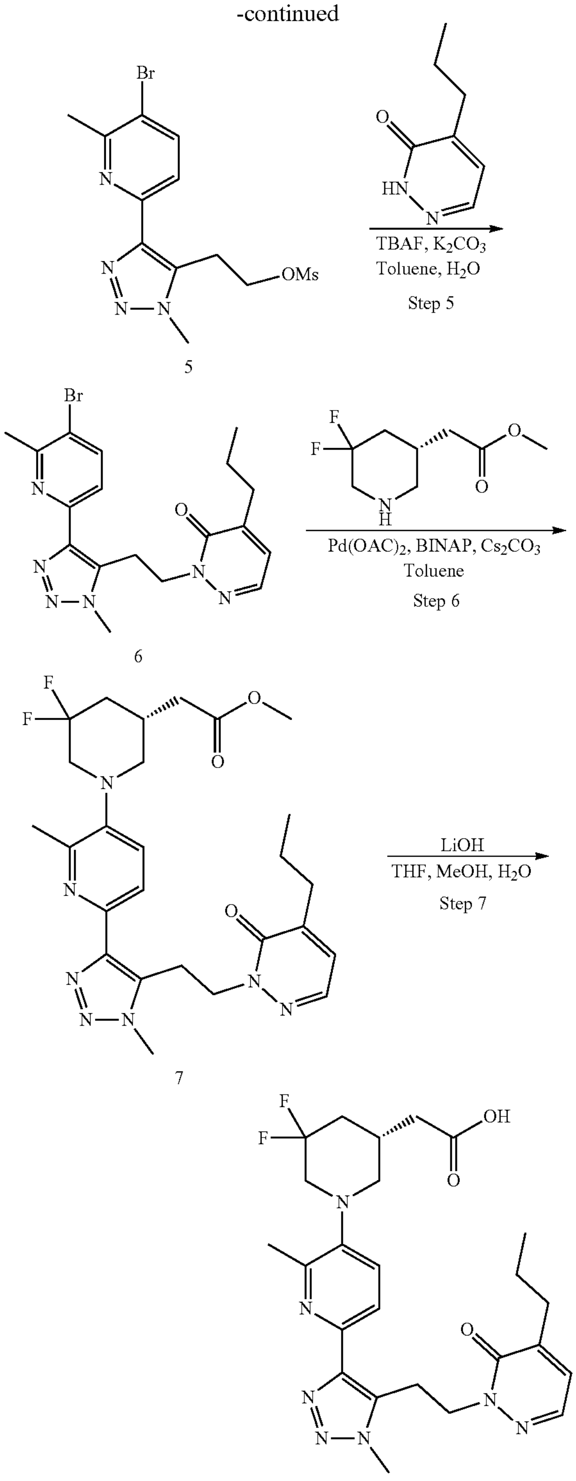

5

6

7

Example 44

Step 1: 2-[4-(5-bromo-6-methylpyridin-2-yl)-1-methyl-1H-1,2,3-triazol-5-yl]acetonitrile To a solution of 3-bromo-6-[5-(bromomethyl)-1-methyl-1H-1,2,3-triazol-4-yl]-2-methylpyridine (1.1 g, 3.18 mmol) in $CH_3CN$ (10 mL) was added NaCN (260 mg, 5.31 mmol) in DMSO (10 mL) and the reaction mixture was stirred at r.t. for 30 min, then was partitioned between EtOAc and water. The aqueous phase was extracted with EtOAc (3×20 mL). The combined organic extracts were concentrated washed with brine, dried over anhydrous $Na_2SO_4$, filtered and concentrated to dryness. The residue was purified by flash chromatography (0% to 100% EtOAc in PE) to give the title compound (680 mg, 73.2% yield) as white solid. $^1H$ NMR (400 MHz, $CDCl_3$) δ 7.92 (q, J=8.4 Hz, 2H), 4.64 (s, 2H), 4.19 (s, 3H), 2.69 (s, 3H), 1.66 (s, 2H).

Step 2: 2-[4-(5-bromo-6-methylpyridin-2-yl)-1-methyl-11H-1,2,3-triazol-5-yl]acetic acid To a solution of 2-[4-(5-bromo-6-methylpyridin-2-yl)-1-methyl-1H-1,2,3-triazol-5-yl]acetonitrile (630 mg, 2.16 mmol) in ethanol (10 mL) and $H_2O$ (10 mL) was added KOH (483 mg, 8.63 mmol) and the resulting mixture was refluxed for 16 hrs. The ethanol was removed under reduced pressure, and then the solution was cooled to below 10° C. and acidified with concentrated aq·HCl to pH~1. The mixture was extracted with EtOAc (2×10 mL) and the combined organic extracts were concentrated washed with brine, dried over anhydrous $Na_2SO_4$, filtered and concentrated to dryness to give the title compound (680 mg, 101.4% yield) as white solid. LC/MS (ESI) m/z: 312/314 $(M+H)^+$.

Step 3: 2-[4-(5-bromo-6-methylpyridin-2-yl)-1-methyl-11H-1,2,3-triazol-5-yl]ethan-1-ol To a mixture of 2-[4-(5-bromo-6-methylpyridin-2-yl)-1-methyl-1H-1,2,3-triazol-5-yl]acetic acid (450 mg, 1.45 mmol) in THE was added $BH_3$·THF complex (4.3 mL, 1 M in THF) drop-wisely at 0° C. and the mixture was stirred at r.t. for 6 hrs. The reaction mixture was quenched by drop-wise addition of MeOH (5 mL) at 0° C. and the resulting mixture was concentrated to dryness to give the title compound (250 mg, 58.2% yield) as white solid. LC/MS (ESI) m/z: 298/300 $(M+H)^+$.

Step 4: 2-[4-(5-bromo-6-methylpyridin-2-yl)-1-methyl-1H-1,2,3-triazol-5-yl]ethyl methanesulfonate To a stirred solution of 2-[4-(5-bromo-6-methylpyridin-2-yl)-1-methyl-1H-1,2,3-triazol-5-yl]ethan-1-ol (250 mg, 0.84 mmol) in DCM (10 mL) was added MsCl (0.1 mL, 1.26 mmol) and TEA (0.35 mL, 2.52 mmol) at 0° C. under $N_2$ atmosphere. After stirring at r.t. for 3 hrs, the reaction mixture was quenched with $H_2O$ (10 mL), extracted with DCM (2×10 mL). The combined organic layers were washed with brine, dried over $Na_2SO_4$, filtered and concentrated to dryness. The residue was purified by silica gel chromatography (PE:EtOAc=9:1 to 4:1) to give the title compound (270 mg, 85.5% yield) as yellow solid. LC/MS (ESI) m/z: 376/378 $(M+H)^+$.

Step 5: 2-{2-[4-(5-bromo-6-methylpyridin-2-yl)-1-methyl-1H-1,2,3-triazol-5-yl]ethyl}-4-propyl-2,3-dihydropyridazin-3-one To a solution of 2-[4-(5-bromo-6-methylpyridin-2-yl)-1-methyl-1H-1,2,3-triazol-5-yl]ethyl methanesulfonate (120 mg, 0.32 mmol) and 4-propyl-2,3-dihydropyridazin-3-one (66 mg, 0.48 mmol) in toluene (2 mL) was added $K_2CO_3$ (132 mg, 0.96 mmol) in $H_2O$ (2 mL) followed by TBAF (8 mg, 0.03 mmol) and the mixture was stirred at 100° C. for 16 hrs. The reaction mixture diluted with EtOAc (10 mL), washed with water and brine, dried over anhydrous $Na_2SO_4$, filtered and concentrated to dryness. The residue was purified by flash chromatography (0-25% EtOAc in PE) to give the title compound (40 mg, 30.0% yield) as brown solid. LC/MS (ESI) m/z: 418/420 $(M+H)^+$.

Step 6: methyl 2-[(3R)-5,5-difluoro-1-(2-methyl-6-{1-methyl-5-[2-(6-oxo-5-propyl-1,6-dihydro-pyridazin-1-yl)ethyl]-1H-1,2,3-triazol-4-yl}pyridin-3-yl)piperidin-3-yl]acetate To mixture of 2-{2-[4-(5-bromo-6-methylpyridin-2-yl)-1-methyl-1H-1,2,3-triazol-5-yl]ethyl}-4-propyl-2,3-dihydro-pyridazin-3-one (40 mg, 0.10 mmol) and methyl 2-[(3R)-5,5-difluoropiperidin-3-yl]acetate (22 mg, 0.12 mmol) in toluene (2 mL) were added $Cs_2CO_3$ (62 mg, 0.19 mmol) followed by the addition of BINAP (6 mg, 0.01 mmol) and $Pd(OAc)_2$ (2 mg, 0.01 mmol) under $N_2$ atmosphere. The reaction was degassed under $N_2$ atmosphere for three times and stirred at 110° C. in a CEM microwave reactor for 2 hrs. The mixture was diluted with EtOAc (5 mL), washed with water and brine, dried over anhydrous $Na_2SO_4$, filtered and concentrated to dryness. The residue was purified by flash chromatography (0~55% EtOAc in PE) to give the title compound (10 mg, 19.7% yield) as yellow solid. LC/MS (ESI) m/z: 531 $(M+H)^+$.

Step 7: 2-[5,5-difluoro-1-(2-methyl-6-{1-methyl-5-[2-(6-oxo-5-propyl-1,6-dihydropyridazin-1-yl)ethyl]-1H-1,2,3-triazol-4-yl}pyridin-3-yl)piperidin-3-yl]acetic acid To a solution of methyl 2-[5,5-difluoro-1-(2-methyl-6-{1-methyl-5-[2-(6-oxo-5-propyl-1,6-dihydropyridazin-1-yl)ethyl]-1H-1,2,3-triazol-4-yl}pyridin-3-yl)piperidin-3-yl]acetate (10 mg, 0.02 mmol) in THE (5 mL) and MeOH (1 mL) was added a solution of LiOH (8 mg, 0.2 mmol) in $H_2O$ (1 mL). The mixture was stirred at r.t. for 2 hrs. The mixture was acidified with 1N aq·HCl to pH~3 and extracted with DCM (2×2 mL). The combined organic layers were washed with brine and concentrated to dryness. The residue was purified by prep·HPLC (C18, 0~90% acetonitrile in $H_2O$ with 0.1% formic acid) to give 2-[5,5-difluoro-1-(2-methyl-6-{1-methyl-5-[2-(6-oxo-5-propyl-1,6-dihydropyridazin-1-yl)ethyl]-1H-1,2,3-triazol-4-yl}pyridin-3-yl)piperidin-3-yl] acetic acid (2.2 mg, 22.6% yield) as white solid. LC/MS (ESI) m/z: 517 $(M+H)^+$. $^1H$ NMR (400 MHz, $CD_3OD$) δ 7.65 (d, J=8.3 Hz, 1H), 7.57 (d, J=4.2 Hz, 1H), 7.44 (d, J=8.3 Hz, 1H), 6.99 (d, J=4.2 Hz, 1H), 4.61 (s, 3H), 4.50 (t, J=7.3 Hz, 2H), 4.06 (s, 3H), 3.78 (t, J=6.6 Hz, 2H), 3.14-2.99 (m, 1H), 2.56 (s, 3H), 2.54-2.47 (m, 1H), 2.42-2.35 (m, 4H), 2.34-2.25 (m, 1H), 1.83-1.64 (m, 1H), 1.57-1.45 (m, 2H), 0.92 (t, J=7.4 Hz, 3H).

Example 45 and 46:2-((3R,5R) or (3S,5S)-1-(2-ethyl-6-(1-methyl-5-((2-oxo-5-propylpyridin-1(2H)-yl)methyl)-1H-1,2,3-triazol-4-yl)pyridin-3-yl)-5-fluoropiperidin-3-yl)acetic acid and 2-((3S,5S) or (3R,5R)-1-(2-ethyl-6-(1-methyl-5-((2-oxo-5-propylpyridin-1(2H)-yl)methyl)-1H-1,2,3-triazol-4-yl)pyridin-3-yl)-5-fluoropiperidin-3-yl)acetic acid

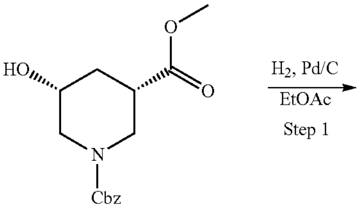

cis-mixture
1

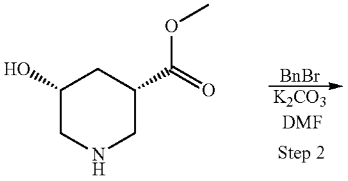

cis-mixture
2

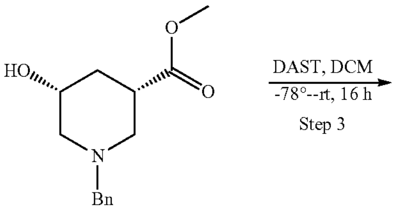

cis-mixture
3

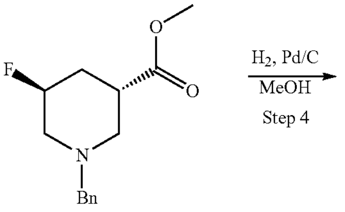

trans-mixture
4

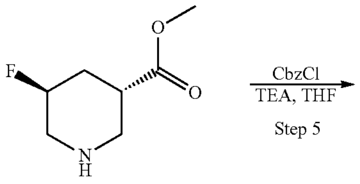

trans-mixture
5

-continued

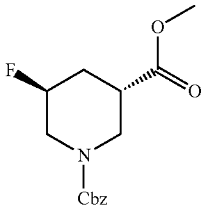

trans-mixture
6

LiOH, THF
MeOH, $H_2O$
Step 6

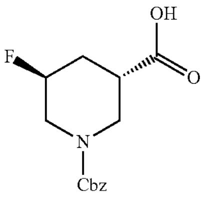

trans-mixture
7

1) Oxalyl chloride
DCM, DMF cat.
2) $TMSCHN_2$, THF
Step 7

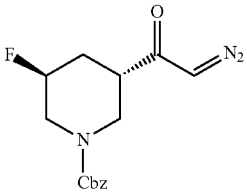

trans-mixture
8

$CF_3COOAg$
TEA, MeOH
Step 8

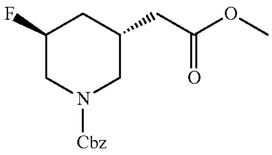

trans-mixture
9

$H_2$, Pd/C
EtOAc
Step 9

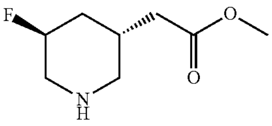

trans-mixture
10

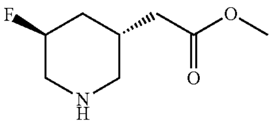

trans-mixture
11

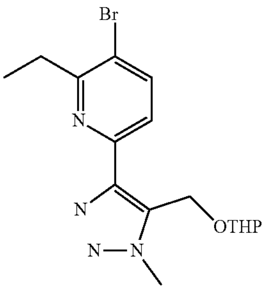

12

Ru-phos, $Pd_2(dba)_3$
$C_sCO_3$, dioxane
Step 10

-continued

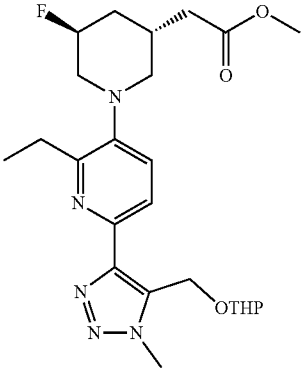

trans-mixture
13

PPTS, MeOH
50° C., 16 h
Step 11

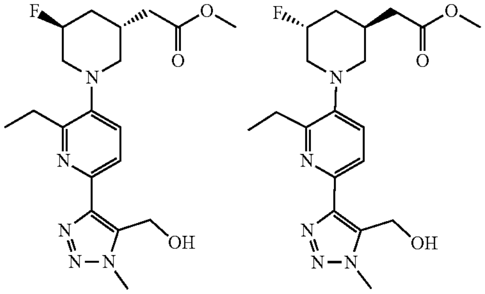

Stereochemistry not assigned
14-P1 and 14-P2

MsCl,
TEA,
DCM
Step 12

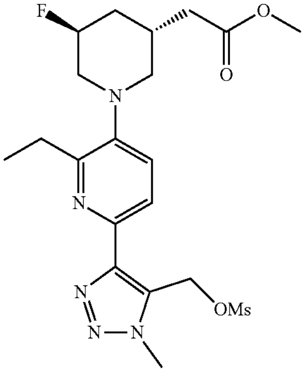

single isomer
15

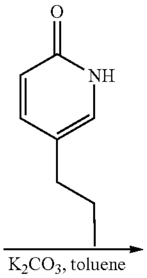

$K_2CO_3$, toluene
$H_2O$
Step 13

-continued

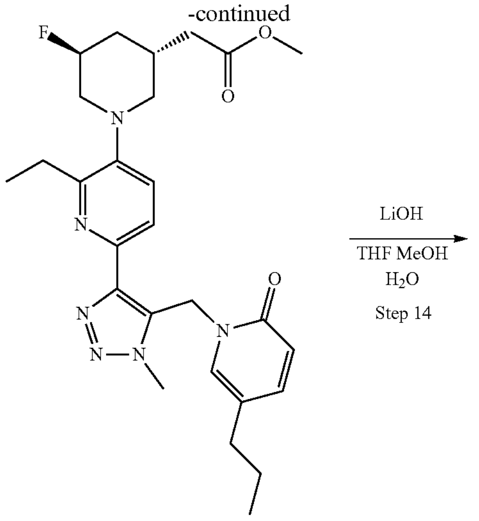

single isomer

16

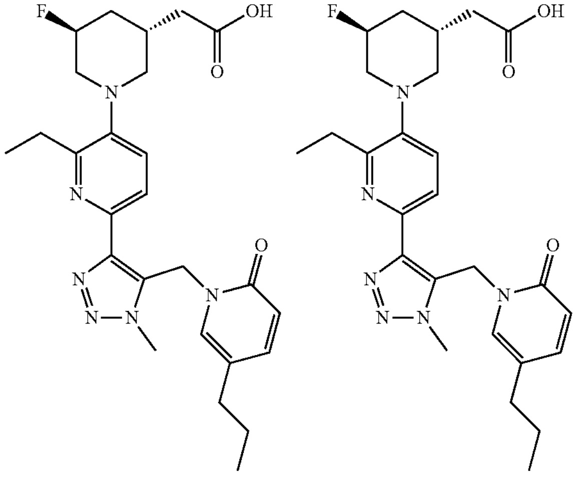

Stereochemistry not assigned

Example 45 and 46

Step 1: Cis-methyl 5-hydroxypiperidine-3-carboxylate

To a solution of cis-1-benzyl 3-methyl 5-hydroxypiperidine-1,3-dicarboxylate (8 g, 27.3 mmol) in EtOAc (100 mL) was added Pd/C (1 g, 10% wt) and the mixture was degassed under $N_2$ atmosphere for three times, stirred under a $H_2$ balloon at room temperature for 16 hrs. The mixture was filtered and the filtrate was concentrated to dryness to give the title compound (4.3 g, 99% yield) as colorless oil. LC/MS (ESI) m/z: 160 $(M+1)^+$.

Step 2: Cis-methyl 1-benzyl-5-hydroxypiperidine-3-carboxylate

To a mixture of cis-methyl 5-hydroxypiperidine-3-carboxylate (4.3 g, 27.0 mmol) and $K_2CO_3$ (7.5 g, 54.1 mmol) in DMF (50 mL) was added BnBr (7.4 g, 40.5 mmol) and the mixture was stirred at r.t. for 2 hrs. The mixture was diluted with EtOAc (100 mL), washed with water and brine, dried over $Na_2SO_4$, filtered and concentrated to dryness. The residue was purified by flash chromatography (0-100%, EtOAc in PE) to give the title compound (3.85 g, 57.2% yield) as yellow oil. LC/MS (ESI) m/z: 250 $(M+1)^+$.

Step 3: Trans-methyl 1-benzyl-5-fluoropiperidine-3-carboxylate

To a mixture of cis-methyl 1-benzyl-5-hydroxypiperidine-3-carboxylate (3.85 g, 15.4 mmol) in DCM (50 mL) was added DAST (4.1 mL, 30.9 mmol) drop-wisely at −78° C. and the mixture was stirred at −78° C. to r.t. for 16 hrs. The mixture was quenched with saturated aq·$NaHCO_3$ solution at 0° C. and extracted with DCM (3×20 mL). The combined organic layers were washed with brine, dried over $Na_2SO_4$, filtered and concentrated to dryness. The residue was purified by flash chromatography (0-100%, EtOAc in PE) to give the title compound (3.2 g, 82.5% yield) as yellow oil. LC/MS (ESI) m/z: 252 $(M+1)^+$.

Step 4: Trans-methyl 5-fluoropiperidine-3-carboxylate

To a mixture of trans-methyl 1-benzyl-5-fluoropiperidine-3-carboxylate (3.2 g, 12.7 mmol) in MeOH (50 mL) was added $Pd(OH)_2$ (400 mg, 10% wt) and AcOH (3 drops) and the mixture was degassed under $N_2$ for three times and stirred under a $H_2$ balloon at r.t. for 16 hrs. The mixture was filtered and the filtrate was concentrated to dryness to give the title compound (2.5 g, 100% yield) as colorless oil. LC/MS (ESI) m/z: 162 $(M+1)^+$.

Step 5: Trans-1-benzyl 3-methyl 5-fluoropiperidine-1,3-dicarboxylate

To a mixture of trans-methyl 5-fluoropiperidine-3-carboxylate (2.5 g, 15.5 mmol) in THE (30 mL) and saturated aq·$NaHCO_3$ solution (15 mL) was added CbzCl (5.27 g, 31.0 mmol) drop-wisely at 0° C. and the mixture was stirred at r.t. for 16 hrs. The mixture was extracted with EtOAc (2×20 mL) and the combined organic layers were washed with brine, dried over $Na_2SO_4$, filtered and concentrated to dryness. The residue was purified by flash chromatography (0-50%, EtOAc in PE) to give the title compound (3.7 g, 80.8% yield) as yellow oil. LC/MS (ESI) m/z: 296 $(M+1)^+$.

Step 6: Trans-1-((benzyloxy)carbonyl)-5-fluoropiperidine-3-carboxylic acid

To a solution of trans-1-benzyl 3-methyl 5-fluoropiperidine-1,3-dicarboxylate (3.7 g, 12.5 mmol) in MeOH (40 mL), THE (20 mL) and $H_2O$ (20 mL) was added LiOH $H_2O$ (2.63 g, 62.6 mmol) and the mixture was stirred at r.t. for 16 hrs. The mixture was concentrated to dryness and the residue was dissolved in water (50 mL), washed with EtOAc (2×10 mL). The aqueous layer was acidified with 1N aq·HCl to pH~4 and extracted with DCM (3×30 mL). The combined organic layers were washed brine, dried over $Na_2SO_4$, filtered and concentrated to dryness to give the title compound (3.1 g, 88% yield) as white solid. LC/MS (ESI) m/z: 282 $(M+1)^+$.

Step 7: Trans-benzyl 3-(chlorocarbonyl)-5-fluoropiperidine-1-carboxylate

To a solution of 1-[(benzyloxy)carbonyl]-5-fluoropiperidine-3-carboxylic acid (3.1 g, 11.0 mmol) and DMF (0.085 mL, 1.10 mmol) in DCM (31 mL) was added Oxalyl chloride (2.80 g, 22.0 mmol) drop-wisely at 0° C. and the mixture was stirred at r.t. for 2 hrs. The mixture was concentrated to dryness and the residue was dissolved in THF (40 mL). A solution of $TMSCHN_2$ (16.5 mL, 2M in toluene) was added to the above mixture and the mixture was stirred at r.t. for 16 hrs. The reaction mixture was quenched with AcOH (6 mL) and concentrated to dryness to give a yellow residue. The residue was dissolved in MeOH (50 mL) and $F_3CCOOAg$ (0.48 g, 2.16 mmol) and TEA (6 mL) were added. The reaction mixture was sonicated with ultrasound at room temperature for 1 hr. The mixture was concentrated to dryness and the residue was purified by flash chromatography (silica gel (40 g), 0-100%, EtOAc in PE) to give the title compound (2.0 g, 60% yield) as yellow oil. LC/MS (ESI) m/z: 310 $(M+1)^+$.

Step 8: Trans-methyl 2-(5-fluoropiperidin-3-yl)acetate

To a mixture of trans-benzyl 3-fluoro-5-(2-methoxy-2-oxoethyl)piperidine-1-carboxylate (2 g, 6.46 mmol) in EtOAc (50 mL) was added Pd/C (200 mg, 10% wt), the mixture was degassed under $N_2$ atmosphere for three times and stirred under a $H_2$ balloon at r.t. for 2 hrs. The reaction mixture was filtered and the filtrate was concentrated to dryness to give the title compound (1.1 g, yield 97%) as off-white solid. LC/MS (ESI) m/z: 176 $(M+1)^+$.

Step 9: Trans-methyl 2-(1-(2-ethyl-6-(1-methyl-5-(((tetrahydro-2H-pyran-2-yl)oxy)methyl)-1H-1,2,3-triazol-4-yl)pyridin-3-yl)-5-fluoropiperidin-3-yl) acetate To a mixture of 3-bromo-2-ethyl-6-{1-methyl-5-[(oxan-2-yloxy)methyl]-1H-1,2,3-triazol-4-yl}pyridine (600 mg, 1.57 mmol), trans-methyl 2-(5-fluoropiperidin-3-yl)acetate (276 mg, 1.58 mmol), Ru-phos (147 mg, 0.315 mmol) and $Cs_2CO_3$ (1.0 mg, 3.14 mmol) in 1,4-dioxane (15 mL) was added $Pd_2(dba)_3$ (216 mg, 0.236 mmol) under $N_2$ atmosphere, the mixture was degassed under $N_2$ for three times and stirred at 120° C. for 3 hrs. The mixture was filtered and the filtrate was concentrated to dryness. The residue was purified by flash chromatography (silica gel, 0-40% EtOAc in PE) to give the title compound (430 mg, 57.5% yield) as yellow solid. LC/MS (ESI) m/z: 476 $(M+1)^+$.

Step 10: Methyl 2-((3S,5S) or (3R,5R)-1-(2-ethyl-6-(5-(hydroxymethyl)-1-methyl-11H-1,2,3-triazol-4-yl)pyridin-3-yl)-5-fluoropiperidin-3-yl)acetate (14-P1) & methyl 2-((3R,5R) or (3S,5S)-1-(2-ethyl-6-(5-(hydroxymethyl)-1-methyl-1H-1,2,3-triazol-4-yl) pyridin-3-yl)-5-fluoropiperidin-3-yl)acetate (14-P2)

To a mixture of methyl 2-[1-(2-ethyl-6-{1-methyl-5-[(oxan-2-yloxy)methyl]-1H-1,2,3-triazol-4-yl}pyridin-3-yl)-5-fluoropiperidin-3-yl]acetate (430 mg, 0.904 mmol) in MeOH (10 mL) was added PPTS (454 mg, 1.81 mmol). After stirred at 50° C. for 16 hrs, the mixture was poured into saturated aq·$NH_4Cl$ solution and extracted with EtOAc (3×10 mL). The combined organic phase was washed brine, dried over $Na_2SO_4$, filtered and concentrated to dryness. The residue was purified by prep-HPLC (Cis, 10-95%, MeCN in $H_2O$ with 0.1% HCOOH) to give the racemic product, which was purified by chiral SFC to give compound 14-Pt (peak 1, retention time: 5.48 min) (64 mg, yield 18%) and 14-P2 (peak 2, retention time: 5.83 min) (92 mg, yield 26%) as white solid. LC/MS (ESI) m/z: 392.5 $(M+1)^+$. SFC condition: Column: ChiralPak OJ, 250×21.2 mm I.D., 5 μm; Mobile phase: A for $C_{02}$ and B for Methanol (0.1% $NH_4OH$); Gradient: B 40%; Flow rate: 50 mL/min; Column temperature: 35° C.

Step 11: methyl 2-((3S,5S) or (3R,5R)-1-(2-ethyl-6-(1-methyl-5-(((methylsulfonyl)oxy) methyl)-1H-1,2,3-triazol-4-yl)pyridin-3-yl)-5-fluoropiperidin-3-yl) acetate To a mixture of compound 14-P1 (64 mg, 0.16 mmol) and TEA (0.07 mL, 0.510 mmol) in DCM (3 mL) was added MsCl (0.025 mL, 0.33 mmol) at 0° C. After stirring at 0° C. for 1 hr, the reaction mixture was diluted with DCM (5 mL), washed with saturated aq·$NaHCO_3$ solution and brine, dried over anhydrous $Na_2SO_4$, filtered and concentrated to dryness to give the title compound (76 mg, 99% yield) as yellow solid. LC/MS (ESI) m/z: 470 (M+1)*.

Step 12: methyl 2-((3S,5S) or (3R,5R)-1-(2-ethyl-6-(1-methyl-5-((2-oxo-5-propylpyridin-1(2H)-yl) methyl)-1H-1,2,3-triazol-4-yl)pyridin-3-yl)-5-fluoropiperidin-3-yl)acetate To a mixture of compound 15 (35 mg, 0.075 mmol) and $K_2CO_3$ (21 mg, 0.151 mmol) in toluene (2 mL) and $H_2O$ (0.4 mL) was added 5-propyl-1,2-dihydropyridin-2-one (12 mg, 0.089 mmol). After stirring at 100° C. for 2 hrs, the reaction mixture was diluted with EtOAc (5 mL), washed with water and brine, dried over $Na_2SO_4$, filtered and concentrated to give the title compound (38 mg, 99.8% yield) as yellow solid. LC/MS (ESI) m/z: 511 (M+1)*.

Step 13: 2-((3S,5S) or (3R,5R)-1-(2-ethyl-6-(1-methyl-5-((2-oxo-5-propylpyridin-1(2H)-yl)methyl)-1H-1,2,3-triazol-4-yl)pyridin-3-yl)-5-fluoropiperidin-3-yl)acetic acid To a solution of compound 16 (38 mg, 0.074 mmol) in THE (2 mL), $H_2O$ (0.5 mL) and MeOH (0.5 mL) was added LiOH—$H_2O$ (31 mg, 0.740 mmol). After stirring at r.t. for 16 hrs, the reaction mixture was acidified with 1N aq·HCl to pH~6 and extracted with DCM (3×5 mL). The combined organic layers were washed brine, dried over $Na_2SO_4$, filtered and concentrated to dryness. The residue was purified by prep-HPLC (Cis, 10-95%, MeCN in $H_2O$ with 0.1% HCOOH) to give the title compound (8.5 mg, 23% yield) as white solid. LC/MS (ESI) m/z: 497 $(M+1)^+$. $^1H$ NMR (400 MHz, $CD_3OD$) δ 7.88 (d, J=8.3 Hz, 1H), 7.66 (d, J=1.7 Hz, 1H), 7.60 (d, J=8.4 Hz, 1H), 7.38 (dd, J=9.3, 2.4 Hz, 1H), 6.52 (d, J=9.2 Hz, 1H), 5.87 (s, 2H), 4.82-4.63 (m, 1H), 4.16 (s, 3H), 3.21-3.12 (m, 1H), 3.02-2.90 (m, 2H), 2.89-2.79 (m, 1H), 2.54-2.40 (m, 3H), 2.39-2.27 (m, 2H), 2.21 (t, J=7.5 Hz, 2H), 1.48-1.28 (m, 7H), 0.76 (t, J=7.3 Hz, 3H).

Example 46: 2-((3R,5R) or (33,5S)-1-(2-ethyl-6-(1-methyl-5-((2-oxo-5-propylpyridin-1(2H)-yl)methyl)-1H-1,2,3-triazol-4-yl)pyridin-3-yl)-5-fluoropiperidin-3-yl)acetic acid The title compound was prepared from compound 14-P2 as the same sequence for the synthesis of example 45. LC/MS (ESI) m/z: 497 $(M+1)^+$. $^1H$ NMR (400 MHz, $CD_3OD$) δ 7.88 (d, J=8.4 Hz, 1H), 7.66 (d, J=2.0 Hz, 1H), 7.60 (d, J=8.4 Hz, 1H), 7.38 (dd, J=9.3, 2.5 Hz, 1H), 6.52 (d, J=9.2 Hz, 1H), 5.87 (s, 2H), 4.73 (d, J=4.6 Hz, 1H), 4.16 (s, 3H), 3.33 (s, 1H), 3.20-3.14 (m, 1H), 3.01-2.90 (m, 2H), 2.88-2.81 (m, 1H), 2.54-2.40 (m, 3H), 2.39-2.26 (m, 2H), 2.21 (t, J=7.6 Hz, 2H), 1.50-1.40 (m, 1H), 1.39-1.33 (m, 2H), 1.31 (t, J=7.5 Hz, 3H), 0.76 (t, J=7.3 Hz, 3H).
Example 47: 2-(1-(4-fluoro-2-methyl-6-(1-methyl-5-((2-oxo-5-propylpyridin-1(2H)-yl)methyl)-1H-1,2,3-triazol-4-yl)pyridin-3-yl)piperidin-3-yl)acetic acid
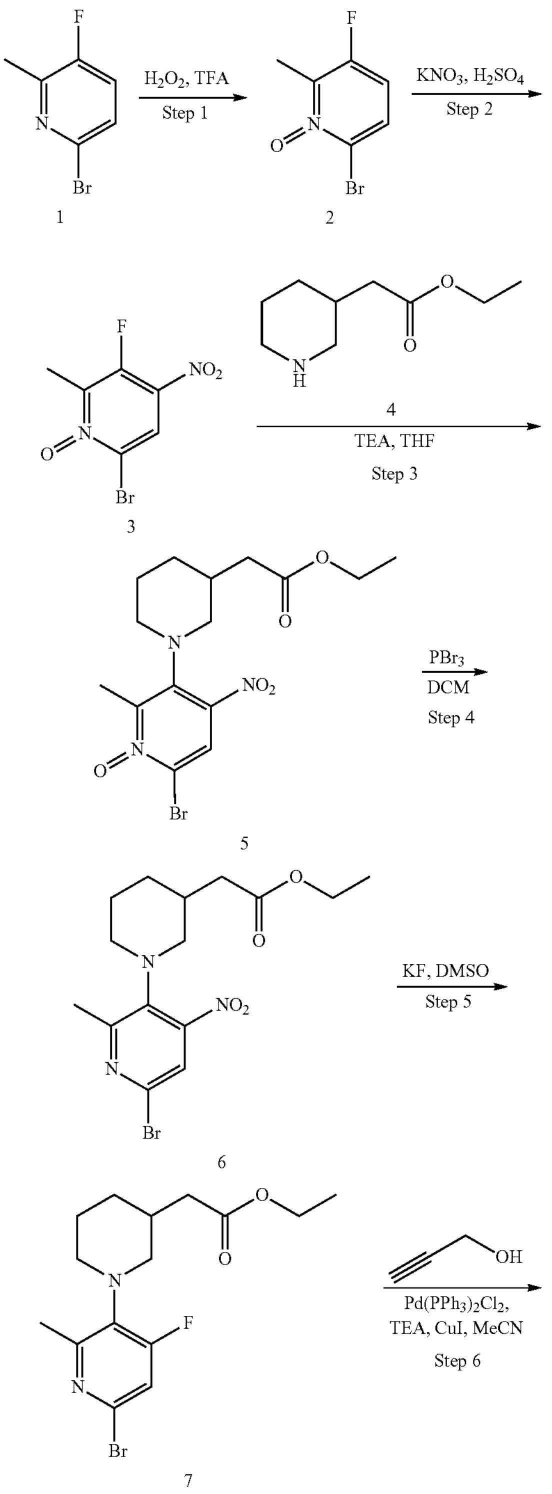
1 2 3 4 5 6 7
-continued
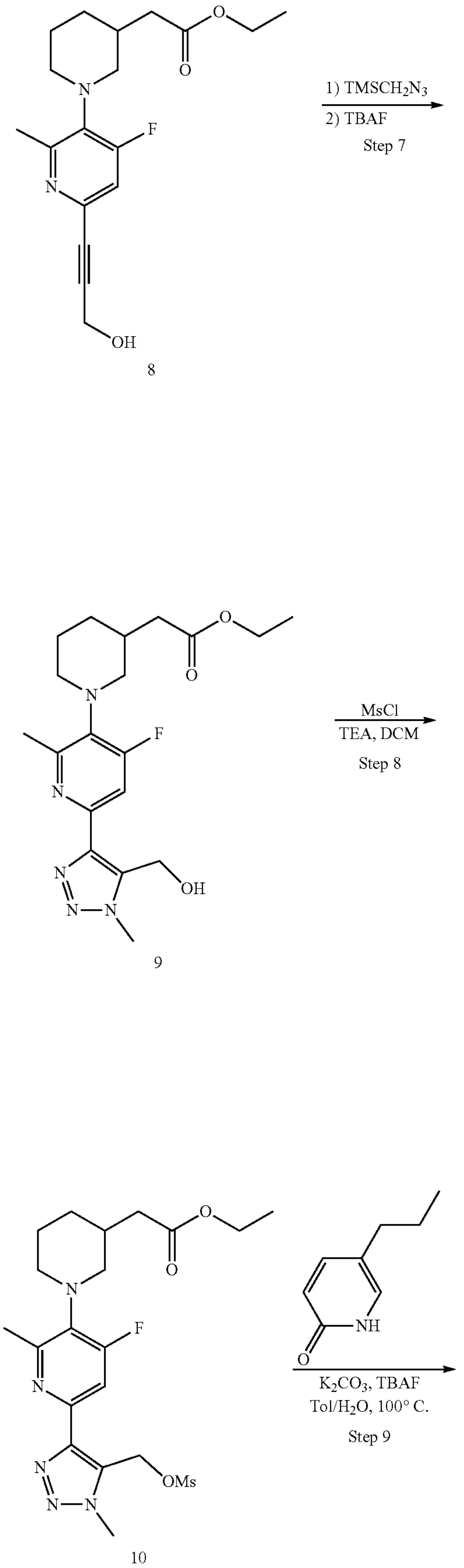
8 9 10

-continued

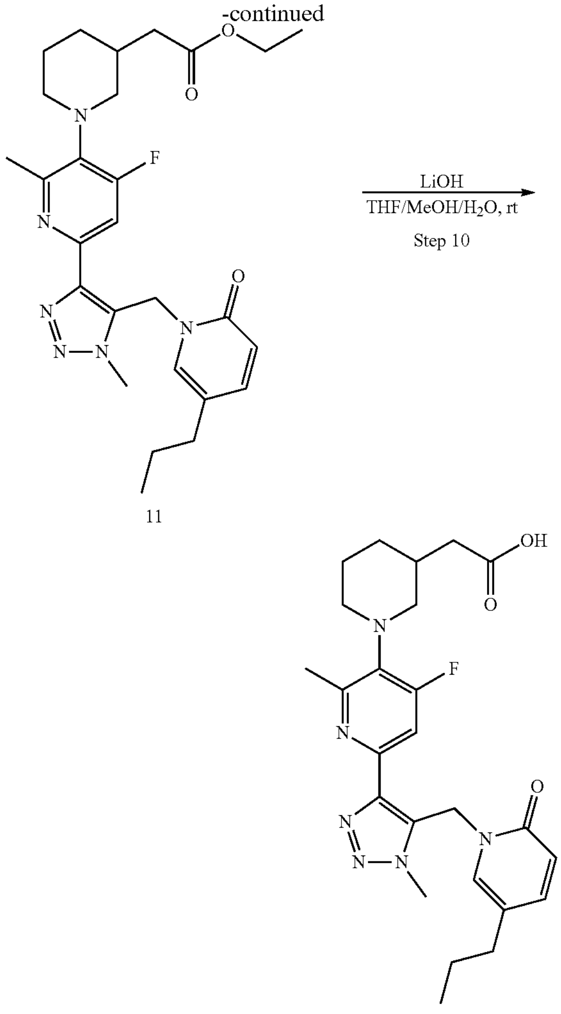

11

Example 47

Step 1: 6-bromo-3-fluoro-2-methylpyridine 1-oxide

To solution of 6-bromo-3-fluoro-2-methylpyridine (10 g, 52.6 mmol) in TFA (100 mL) was added $H_2O_2$ (40 mL, 353 mmol) at 0° C. under $N_2$ atmosphere and the mixture was stirred at 70° C. for 20 hrs. The reaction was cooled to 0° C. and quenched with saturated aq·$Na_2$S203 solution. The mixture was extracted with EtOAc (3×100 mL) and the combined organic layers were washed with saturated aq·$NaHCO_3$ solution and brine, dried over anhydrous $Na_2SO_4$, filtered and concentrated to dryness. The residue was purified by silica gel chromatography (PE:EtOAc=10:1 to 0:1) to give the title compound (8.2 g, 75.6% yield) as yellow solid.

Step 2: 6-bromo-3-fluoro-2-methyl-4-nitropyridine 1-oxide

To a solution of 6-bromo-3-fluoro-2-methylpyridine 1-oxide (7 g, 34.0 mmol) in conc·$H_2SO_4$ (70 mL, 731 mmol) was added $KNO_3$ (1.96 g, 19.4 mmol) in portions at 0° C. and the mixture was stirred at 120° C. for 6 hrs. The reaction mixture was poured into ice-water and extracted with EtOAc (3×100 mL). The combined organic layers were washed with saturated aq·$NaHCO_3$ solution and brine, dried over $Na_2SO_4$, filtered and concentrated to dryness. The residue was recrystallized in EtOAc to give the title compound (2.57 g, 30.1% yield) as yellow solid. LC/MS (ESI) m/z: 251 $(M+H)^+$.

Step 3: 6-bromo-3-(3-(2-ethoxy-2-oxoethyl)piperidin-1-yl)-2-methyl-4-nitropyridine 1-oxide To a solution of 6-bromo-3-fluoro-2-methyl-4-nitropyridine 1-oxide (1.2 g, 4.78 mmol) in THE (5 mL) was added TEA (0.7 mL, 5.04 mmol) and a solution of ethyl 2-(piperidin-3-yl)acetate (0.9 g, 5.26 mmol) in THE (5 mL) at 0° C. and the reaction was stirred at 25° C. for 24 hrs. The mixture was diluted with EtOAc (20 mL), washed with water and brine, dried over $Na_2SO_4$, filtered and concentrated to dryness. The residue was purified by silica gel chromatography (PE:EtOAc=10:1 to 3:1) to give the title compound (1.55 g, 82.8% yield) as red solid. LC/MS (ESI) m/z: 402 $(M+H)^+$.

Step 4: ethyl 2-(1-(6-bromo-2-methyl-4-nitropyridin-3-yl)piperidin-3-yl)acetate

To a solution of 6-bromo-3-(3-(2-ethoxy-2-oxoethyl)piperidin-1-yl)-2-methyl-4-nitropyridine 1-oxide (1.55 g, 4.13 mmol) in DCM (15 mL) was added a solution of $PBr_3$ (0.91 mL, 9.63 mmol) in DCM (2 mL) at 0° C. under $N_2$ atmosphere and the mixture was stirred at 16° C. for 3 hrs. The reaction was poured into ice-cooled saturated aq·$NaHCO_3$ solution and extracted with DCM (3×50 mL). The combined organic layers were washed with brine, dried over anhydrous $Na_2SO_4$, filtered and concentrated to dryness. The residue was purified by silica gel chromatography (PE:EtOAc=30:1 to 10:1) to give the title compound (1.52 g, 93.9% yield) as red oil. LC/MS (ESI) m/z: 386 $(M+H)^+$.

Step 5: ethyl 2-(1-(6-bromo-4-fluoro-2-methylpyridin-3-yl)piperidin-3-yl)acetate To solution of ethyl 2-(1-(6-bromo-2-methyl-4-nitropyridin-3-yl)piperidin-3-yl)acetate (1.5 g, 3.88 mmol) in DMSO (15 mL) was added KF (1.13 g, 19.4 mmol) and the reaction mixture was stirred at 140° C. under $N_2$ atmosphere for 3 hrs. The mixture was poured into ice-water and extracted with EtOAc (3×50 mL). The combined organic layers were washed with brine, dried over anhydrous $Na_2SO_4$, filtered and concentrated to dryness. The residue was purified by silica gel chromatography (PE:EtOAc=20:1 to 10:1) to give the title compound (700 mg, 50.2% yield) as yellow solid. LC/MS (ESI) m/z: 359 $(M+H)^+$.

Step 6: ethyl 2-(1-(4-fluoro-6-(3-hydroxyprop-1-yn-1-yl)-2-methylpyridin-3-yl)piperidin-3-yl)acetate To a mixture of ethyl 2-(1-(6-bromo-4-fluoro-2-methylpyridin-3-yl)piperidin-3-yl)acetate (830 mg, 2.31 mmol) and TEA (0.96 mL, 6.93 mmol) in MeCN (8 mL) were added CuI (10 mg, 0.046 mmol) and $Pd(PPh_3)_2Cl_2$ (32.4 mg, 0.046 mmol) at 16° C. under $N_2$ atmosphere. Then prop-2-yn-1-ol (0.27 mL, 4.62 mmol) was added and the resulting mixture was degassed under $N_2$ atmosphere for three times and stirred at 25° C. for 22 hrs. The mixture was diluted with EtOAc (20 mL) and filtered. The filtrate was concentrated to dryness and the residue was purified by silica gel chromatography (PE:EtOAc=10:1 to 1:1) to give the title compound (430 mg, 55.7% yield) as yellow oil. LC/MS (ESI) m/z: 335 $(M+H)^+$.

Step 7: ethyl 2-(1-(4-fluoro-6-(5-(hydroxymethyl)-1-methyl-11H-1,2,3-triazol-4-yl)-2-methylpyridin-3-yl)piperidin-3-yl)acetate To a solution of ethyl 2-(1-(4-fluoro-6-(3-hydroxyprop-1-yn-1-yl)-2-methylpyridin-3-yl)piperidin-3-yl)acetate (430 mg, 1.29 mmol) in 1,4-dioxane (10 mL) were added $TMSCH_2N_3$ (332 mg, 2.57 mmol), $Cp^*RuCl(PPh_3)_2$ (51 mg, 0.064 mmol) and cuprous iodide (12.25 mg, 0.064 mmol) under $N_2$ atmosphere. The mixture reaction was degassed under $N_2$ atmosphere for three times and stirred at 50° C. under $N_2$ atmosphere for 16 hrs. The mixture was concentrated to dryness and the residue was dissolved in THE (10 mL) and TBAF (336 mg, 1.29 mmol) was added. The mixture was stirred at room temperature for 1 hr. The mixture was diluted with EtOAc (10 mL), washed with water and brine, dried over $Na_2SO_4$, filtered and concentrated to dryness. The residue was purified by silica gel chromatography (DCM:EtOAc=6:1) to give the title compound (200 mg, 39.7% yield) as yellow solid. LC/MS (ESI) (m/z): 392 $(M+H)^+$.

Step 8: ethyl 2-(1-(4-fluoro-2-methyl-6-(1-methyl-5-(((methylsulfonyl)oxy)methyl)-1H-1,2,3-triazol-4-yl)pyridin-3-yl)piperidin-3-yl)acetate To a solution of ethyl 2-(1-(4-fluoro-6-(5-(hydroxymethyl)-1-methyl-1H-1,2,3-triazol-4-yl)-2-methylpyridin-3-yl)piperidin-3-yl)acetate (200 mg, 0.511 mmol) in DCM (10 mL) were added TEA (0.213 mL, 1.53 mmol) and MsCl (0.079 mL, 1.02 mmol) at 0° C. and the mixture was stirred at room temperature for 1 hr. The mixture was diluted with water and extracted with DCM (2x5 mL). The combined organic layers were washed with brine, dried over anhydrous $Na_2SO_4$, filtered and concentrated under reduced pressure to give the title compound (210 mg, 87.5% yield) as yellow solid. LC/MS (ESI) (m/z): 470 $(M+H)^+$.

Step 9: ethyl 2-(1-(4-fluoro-2-methyl-6-(1-methyl-5-((2-oxo-5-propylpyridin-1(2H)-yl)methyl)-1H-1,2,3-triazol-4-yl)pyridin-3-yl)piperidin-3-yl)acetate To a mixture of ethyl 2-(1-(4-fluoro-2-methyl-6-(1-methyl-5-(((methylsulfonyl)oxy)methyl)-1H-1,2,3-triazol-4-yl)pyridin-3-yl)piperidin-3-yl)acetate (135 mg, 0.29 mmol) and 5-propyl-1,2-dihydropyridin-2-one (59 mg, 0.43 mmol) in toluene (4 mL) and $H_2O$ (1 mL) were added $K_2CO_3$ (80 mg, 0.57 mmol) and TBAF (7.5 mg, 0.03 mmol) under $N_2$ atmosphere and the mixture was stirred at 70° C. for 3 hrs. The reaction mixture was diluted with water and extracted with EtOAc (2x5 mL). The combined organic layers were washed with brine, dried over anhydrous $Na_2SO_4$, filtered and concentrated under reduced pressure. The residue was purified by silica gel chromatography (PE:EtOAc=5:1 to 2:1) to give the title compound (70 mg, 47.7% yield) as yellow oil. LC/MS (ESI) (m/z): 511 $(M+H)^+$.

Step 10: 2-(1-(4-fluoro-2-methyl-6-(1-methyl-5-((2-oxo-5-propylpyridin-1(2H)-yl)methyl)-1H-1,2,3-triazol-4-yl)pyridin-3-yl)piperidin-3-yl)acetic acid To a solution of ethyl 2-(1-(4-fluoro-2-methyl-6-(1-methyl-5-((2-oxo-5-propylpyridin-1(2H)-yl)methyl)-1H-1,2,3-triazol-4-yl)pyridin-3-yl)piperidin-3-yl)acetate (50 mg, 0.098 mmol) in THE (2 mL) and MeOH (3 mL) was added a solution of LiOH (23.5 mg, 0.98 mmol) in water (1 mL) at 0° C. and the mixture was stirred at room temperature for 1 hr. The mixture was concentrated to ⅕ volume, diluted with water and washed with ethyl acetate twice. The aqueous layer was acidified with 1N aq·HCl to pH~3 and extracted with EtOAc (2x5 mL). The combined organic layers were washed with brine, dried over anhydrous $Na_2SO_4$, filtered and concentrated under reduced pressure to dryness. The residue was purified by prep-HPLC (C18, 25-95%, MeCN in $H_2O$ with 0.1% HCOOH) to give the title compound (10 mg, 21.2% yield) as white solid. LC/MS (ESI) m/z: 483 $(M+H)^+$. $^1H$ NMR (400 MHz, $CD_3OD$) δ 7.83 (d, J=2.1 Hz, 1H), 7.60 (d, J=13.0 Hz, 1H), 7.38 (dd, J=9.2, 2.5 Hz, 1H), 6.47 (d, J=9.2 Hz, 1H), 5.72 (s, 2H), 4.23 (s, 3H), 3.14 (t, J=11.7 Hz, 2H), 3.06-3.03 (m, 2H), 2.63 (s, 3H), 2.31-2.26 (m, 4H), 1.96-1.90 (m, 1H), 1.84 (d, J=12.9 Hz, 2H), 1.51-1.36 (m, 4H), 0.80 (t, J=7.3 Hz, 3H).

Example 48: 2-(1-(2-ethyl-4-fluoro-6-(1-methyl-5-((2-oxo-5-propylpyridin-1(2H)-yl)methyl)-1H-1,2,3-triazol-4-yl)pyridin-3-yl)piperidin-3-yl)acetic acid

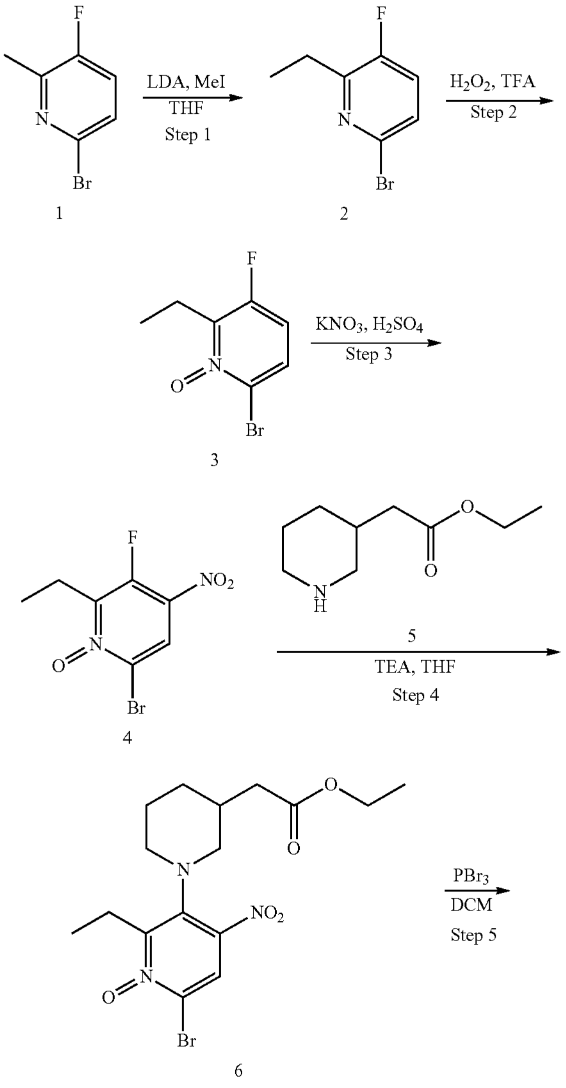

1 2 3 4 5 6

-continued

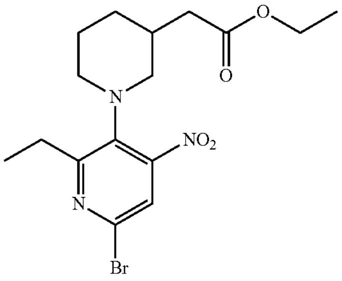

7

TBAF

THF

Step 6

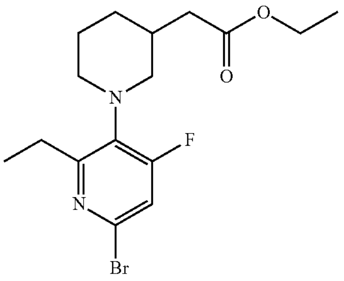

8

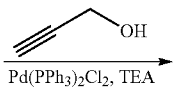

Pd($PPh_3$)$_2$$Cl_2$, TEA

CuI, MeCN

Step 7

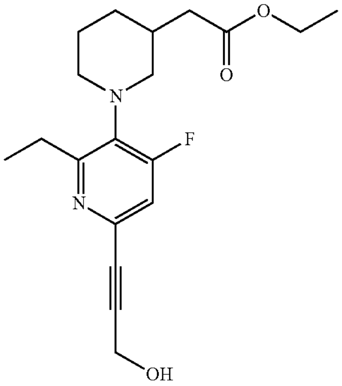

9

1) $TMSCH_2N_3$

2) TBAF

Step 8

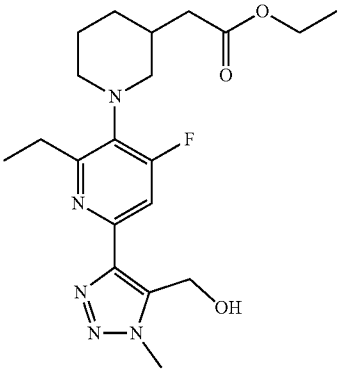

10

MsCl, TEA

DCM

Step 9

-continued

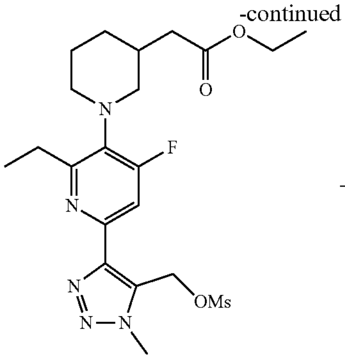

11

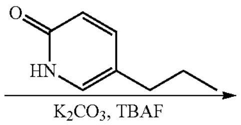

$K_2CO_3$, TBAF tol. $H_2O$

Step 10

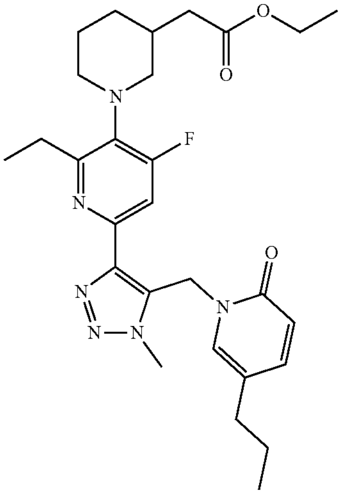

12 aq. LiOH

THF, MeOH

Step 11

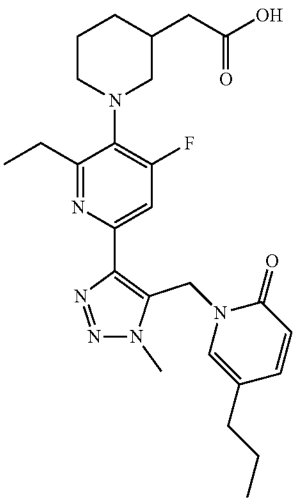

Example 48

Step 1: 6-bromo-2-ethyl-3-fluoropyridine

To a mixture of 6-bromo-3-fluoro-2-methylpyridine (7.9 g, 41.6 mmol) and DMPU (6.5 mL, 54.1 mmol) in THE (80 mL) was added LDA (27 mL, 54.1 mmol, 2M in THF) drop-wisely at −70° C. under $N_2$ atmosphere and the mixture was stirred at −70° C. for 1 hr. MeI (3.37 mL, 54.1 mmol) was added to the above mixture and the resulting mixture was stirred at −70° C. for 3 hrs and r.t. for 16 hrs. The reaction was quenched with saturated aq·$NH_4Cl$ solution and extracted with EtOAc (3×20 mL). The combined organic layers were washed with water and brine, dried over anhydrous $Na_2SO_4$, filtered and concentrated to dryness. The residue was purified by silica gel chromatography (eluted with PE) to give the title compound (2 g, 21.2% yield) as colorless oil. LC/MS (ESI) m/z: 204/206 $(M+H)^+$.

Step 2: 6-bromo-2-ethyl-3-fluoropyridine 1-oxide

To a solution of 6-bromo-2-ethyl-3-fluoropyridine (2 g, 10.5 mmol) in TFA (20 mL) was added $H_2O_2$ (8 mL, 70.6 mmol) and the mixture was stirred at 70° C. under $N_2$ atmosphere for 16 hrs. The reaction was cooled to 0° C. and quenched with saturated aq·$Na_2S_2O_3$ solution. The mixture was extracted with EtOAc (3×50 mL) and the combined organic layers were washed saturated aq·$NaHCO_3$ solution and brine (50 mL), dried over $Na_2SO_4$, filtered and concentrated to dryness. The residue was purified by column chromatography (PE:EtOAc=10:1 to 5:1) to give the title compound (1.5 g, 65.0% yield) as yellow solid. LC/MS (ESI) m/z: 220/222 $(M+H)^+$.

Step 3: 6-bromo-2-ethyl-3-fluoro-4-nitropyridine 1-oxide

To a solution of 6-bromo-2-ethyl-3-fluoropyridine 1-oxide (5.0 g, 22.7 mmol) in conc·$H_2SO_4$ (50 mL) was added $KNO_3$ (9.19 g, 90.9 mmol) in portions at 0° C. and the mixture was stirred at 120° C. for 4 hrs. The mixture was poured into ice-water and extracted with EtOAc (3×50 mL). The combined organic layers were washed with saturated aq·$NaHCO_3$ solution and brine (20 mL), dried over anhydrous $Na_2SO_4$, filtered and concentrated to dryness. The residue was purified by silica gel chromatography (PE: EtOAc=5:1 to 3:1) to give the title compound (380 mg, 6.31% yield) as yellow solid. LC/MS (ESI) m/z: 265/267 $(M+H)^+$.

Step 4: 6-bromo-3-(3-(2-ethoxy-2-oxoethyl)piperidin-1-yl)-2-ethyl-4-nitropyridine 1-oxide To a solution of 6-bromo-2-ethyl-3-fluoro-4-nitropyridine 1-oxide (380 mg, 1.43 mmol) and ethyl 2-(piperidin-3-yl) acetate (318 mg, 1.86 mmol) in THE (5 mL) was added TEA (0.60 mL, 4.30 mmol) and the mixture was stirred at 25° C. for 4 hrs. The mixture was concentrated to dryness and the residue was purified by silica gel chromatography (PE: EtOAc=10:1 to 3:1) to give the title compound (480 mg, 80.4% yield) as yellow oil. LC/MS (ESI) m/z: 416/418 $(M+H)^+$.

Step 5: ethyl 2-(1-(6-bromo-2-ethyl-4-nitropyridin-3-yl)piperidin-3-yl)acetate

To a solution of 6-bromo-3-(3-(2-ethoxy-2-oxoethyl)piperidin-1-yl)-2-ethyl-4-nitropyridine 1-oxide (480 mg, 1.15 mmol) in DCM (5 mL) was added a solution of $PBr_3$ (0.11 mL, 1.15 mmol) in DCM (1 mL) at 0° C. under $N_2$ atmosphere and the mixture was stirred at r.t. for 5 hrs. The reaction mixture was poured into ice-cooled saturated aq·$NaHCO_3$ solution and extracted with DCM (3×20 mL). The combined organic layers were washed with brine, dried over $Na_2SO_4$, filtered and concentrated to dryness. The residue was purified by silica gel chromatography (PE: EtOAc=30:1 to 20:1) to give the title compound (435 mg, 94.3% yield) as yellow solid. LC/MS (ESI) m/z: 400/402 $(M+H)^+$.

Step 6: ethyl 2-(1-(6-bromo-2-ethyl-4-fluoropyridin-3-yl)piperidin-3-yl)acetate

To a solution of ethyl 2-(1-(6-bromo-2-ethyl-4-nitropyridin-3-yl)piperidin-3-yl)acetate (435 mg, 1.09 mmol) in DMF (5 mL) was added TBAF (5.43 mL, 5.43 mmol, 1M in THF) and the reaction was stirred at 50° C. for 1 hr. The mixture was poured into ice-water and extracted with EtOAc (2×10 mL). The combined organic layers were washed brine, dried over $Na_2S04$, filtered and concentrated to dryness. The residue was purified by silica gel chromatography (PE:EtOAc=30:1 to 20:1) to give the title compound (220 mg, 54.2% yield) as yellow solid. LC/MS (ESI) m/z: 373/375 $(M+H)^+$.

Step 7: ethyl 2-(1-(2-ethyl-4-fluoro-6-(3-hydroxyprop-1-yn-1-yl)pyridin-3-yl)piperidin-3-yl)acetate To a mixture of ethyl 2-(1-(6-bromo-2-ethyl-4-fluoropyridin-3-yl)piperidin-3-yl)acetate (220 mg, 0.59 mmol) and prop-2-yn-1-ol (0.10 mL, 1.77 mmol) in $CH_3CN$ (5 mL) was added TEA (0.25 mL, 1.77 mmol), $Pd(PPh_3)_2Cl_2$ (41.4 mg, 0.059 mmol) and CuI (11.2 mg, 0.059 mmol) at 0° C. under $N_2$ atmosphere and the mixture was stirred under $N_2$ atmosphere at 25° C. for 16 hrs. The mixture was concentrated to dryness and the residue was purified by silica gel chromatography (PE:EtOAc=10:1 to 2:1) to give the title compound (167 mg, 81.3% yield) as yellow solid. LC/MS (ESI) m/z: 349 $(M+H)^+$.

Step 8: ethyl 2-(1-(2-ethyl-4-fluoro-6-(5-(hydroxymethyl)-1-methyl-11H-1,2,3-triazol-4-yl)pyridin-3-yl)piperidin-3-yl)acetate To a mixture of ethyl 2-(1-(2-ethyl-4-fluoro-6-(3-hydroxyprop-1-yn-1-yl)pyridin-3-yl)piperidin-3-yl)acetate (167 mg, 0.48 mmol) and $TMSCH_2N_3$ (0.14 mL, 0.96 mmol) in 1,4-dioxane (3 mL) were added $Cp^*RuCl(PPh_3)_2$ (38 mg, 0.05 mmol) and CuI (9.1 mg, 0.05 mmol) under $N_2$ atmosphere. The reaction mixture was degassed and stirred under $N_2$ atmosphere at 50° C. for 16 hrs. The mixture was concentrated to dryness and the residue was dissolved in THE (10 mL) followed by the addition of TBAF (1.5 mL, 3 mmol, 2M in THF). The mixture was diluted with EtOAc (10 mL), washed with water and brine, dried over anhydrous $Na_2SO_4$, filtered and concentrated to dryness. The residue was purified by silica gel chromatography (DCM: EtOAc=100:0 to 1:1) to give the title compound (100 mg, 51.4% yield) as yellow oil. LC/MS (ESI) m/z: 406 $(M+H)^+$.

Step 9: ethyl 2-(1-(2-ethyl-4-fluoro-6-(1-methyl-5-(((methylsulfonyl)oxy)methyl)-1H-1,2,3-triazol-4-yl)pyridin-3-yl)piperidin-3-yl)acetate To a solution of ethyl 2-(1-(2-ethyl-4-fluoro-6-(5-(hydroxymethyl)-1-methyl-1H-1,2,3-triazol-4-yl)pyridin-3-yl) piperidin-3-yl)acetate (40 mg, 0.099 mmol) in DCM (2 mL) was added TEA (0.10 mL, 0.719 mmol) and MsCl (0.05 mL, 0.646 mmol) at 0° C. under $N_2$ atmosphere and the mixture was stirred at r.t. for 30 min. The mixture was diluted with DCM (5 mL) and washed with water and brine, dried over $Na_2SO_4$, filtered and concentrated to dryness to give the title compound (50 mg, 100% yield), which was directly used to next step directly. LC/MS (ESI) m/z: 484 $(M+H)^+$.

Step 10: 2-(1-(2-ethyl-4-fluoro-6-(1-methyl-5-((2-oxo-5-propylpyridin-1(2H)-yl)methyl)-1H-1,2,3-triazol-4-yl)pyridin-3-yl)piperidin-3-yl)acetic acid The title compound was prepared as the procedure described for the synthesis of Example 47. LC/MS (ESI) m/z: 497 $(M+H)^+$. $^1H$ NMR (400 MHz, $CD_3OD$) δ 7.69-7.62 (m, 2H), 7.48-7.30 (m, 1H), 6.53-6.49 (d, J=9.2 Hz, 1H), 5.84 (s, 2H), 4.16 (s, 3H), 3.21-3.13 (m, 2H), 3.06-2.98 (m, 4H), 2.31-2.28 (d, J=7.0 Hz, 2H), 2.21-2.26 (m, 2H), 1.98-1.88 (m, 1H), 1.80-1.86 (m, 2H), 1.51-1.36 (m, 4H), 1.32-1.26 (m, 3H), 0.80-0.75 (m, 3H).

Example 49: (S)-2-(1-(2-cyano-6-(1-methyl-5-((2-oxo-5-propylpyridin-1(2H)-yl)methyl)-1H-1,2,3-triazol-4-yl)pyridin-3-yl)-5,5-difluoropiperidin-3-yl)acetic acid

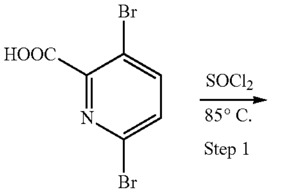

1

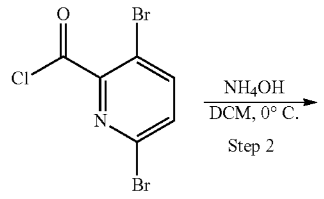

2

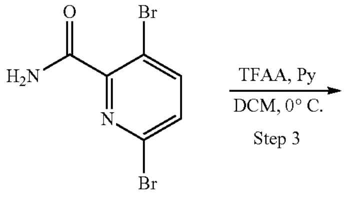

3

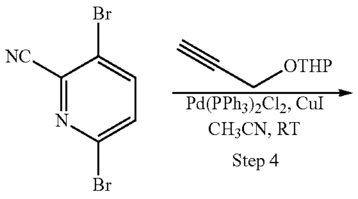

4

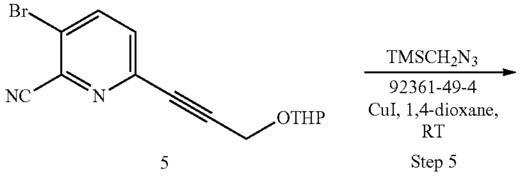

5

-continued

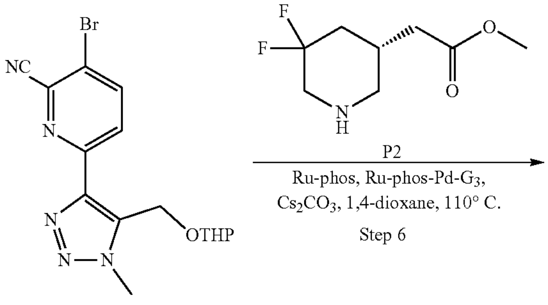

6

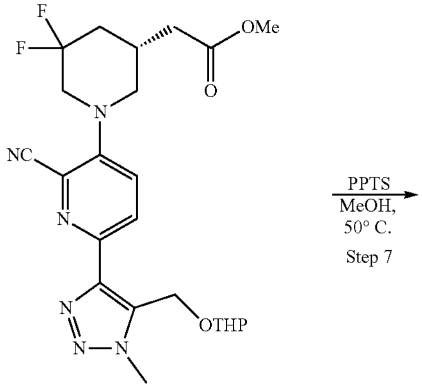

7

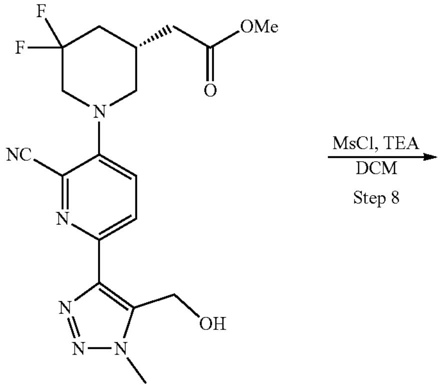

8

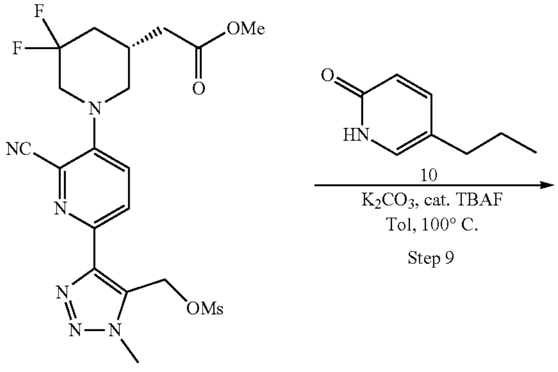

9

-continued

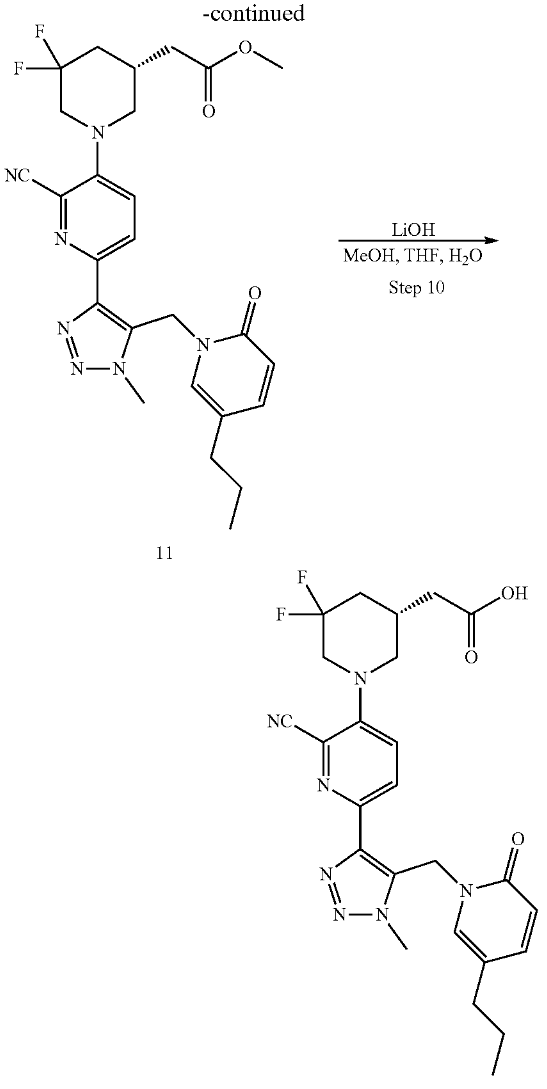

11

Example 49

Step 1: 3,6-dibromopicolinoyl chloride

A solution of 3,6-dibromopicolinic acid (1 g, 3.56 mmol) in $SOCl_2$ (10 mL) was stirred at 85° C. for 3 hrs. The reaction mixture was concentrated to dryness to give the title compound (1.0 g, 95.0% yield) as yellow oil, which was directly used in the next step.

Step 2: 3,6-dibromopicolinamide

To a solution of 3,6-dibromopyridine-2-carbonyl chloride (1 g, 3.34 mmol) in DCM (10 mL) was added drop-wisely $NH_4OH$ (10 mL) at 0° C. and the mixture was stirred at 0° C. for 1 hr. The mixture was poured into ice water and extracted with DCM (2×10 mL). The combined organic layers were washed with brine, dried with anhydrous $Na_2SO_4$, filtered and concentrated to dryness to give the title compound (900 mg, 90% yield). $^1H$ NMR (400 MHz, $CDCl_3$) δ 7.88 (d, J=8.4 Hz, 1H), 7.45 (d, J=8.4 Hz, 1H), 5.59 (s, 2H). LC/MS (ESI) m/z: 281 $(M+H)^+$.

Step 3: 3,6-dibromopicolinonitrile

To a solution of 3,6-dibromopicolinamide (900 mg, 3.21 mmol) in DCM (10 mL) was added pyridine (1.3 mL, 16 mmol), followed by TFAA (1.25 mL, 9 mmol) at 0° C. and the mixture was stirred at this temperature for 1 hr. The mixture was poured into ice water and extracted with DCM (2×5 mL). The combined organic layers were washed with brine, dried with anhydrous $Na_2SO_4$, filtered and concentrated to dryness. The residue was purified by chromatography on silica gel (eluted with PE:EtOAc=30:1 to 5:1) to give the title compound (650 mg, 77.2% yield) as white solid. $^1H$ NMR (400 MHz, $CDCl_3$) δ 7.85 (d, J=8.4 Hz, 1H), 7.58 (d, J=8.4 Hz, 1H).

Step 3: 3-bromo-6-(3-((tetrahydro-2H-pyran-2-yl)oxy)prop-1-yn-1-yl)picolinonitrile To a mixture of 3,6-dibromopicolinonitrile (2.3 g, 8.7 mmol) and 2-(prop-2-yn-1-yloxy)oxane (1.5 g, 10.54 mmol) in MeCN (20 mL) was added TEA (3.7 mL, 26.34 mmol), CuI (84 mg, 0.44 mmol) and $Pd(PPh_3)_2Cl_2$ (310 mg, 0.44 mmol). The mixture was degassed under $N_2$ atmosphere for three times and stirred under $N_2$ atmosphere at room temperature for 16 hrs. The mixture was diluted with ice water and extracted with EtOAc (2×10 mL). The combined organic layers were washed with brine, dried over anhydrous $Na_2SO_4$, filtered and concentrated to dryness. The residue was purified by chromatography on silica gel (PE:EtOAc=2:1) to give the title compound (2.2 g, 54.4% yield) as yellow solid. $^1H$ NMR (400 MHz, $CDCl_3$) δ 7.97 (d, J=8.4 Hz, 1H), 7.48 (d, J=8.4 Hz, 1H), 4.86 (t, J=3.2 Hz, 1H), 4.50 (q, J=16.4 Hz, 2H), 3.93-3.81 (m, 1H), 3.62-3.51 (m, 1H), 1.91-1.72 (m, 2H), 1.75-1.60 (m, 3H). LC (ESI) m/z: 238 (M+H−84)*.

Step 4: 3-bromo-6-(1-methyl-5-(((tetrahydro-2H-pyran-2-yl)oxy)methyl)-1H-1,2,3-triazol-4-yl)picolinonitrile To a solution of 3-bromo-6-(3-((tetrahydro-2H-pyran-2-yl)oxy)prop-1-yn-1-yl)picolinonitrile (2.2 g, 6.85 mmol) in 1,4-dioxane (5 mL) were added (azidomethyl)trimethylsilane (1.1 g, 8.22 mmol), CuI (65 mg, 0.34 mmol), Cp*RuCl $(PPh_3)_2$ (270 mg, 0.34 mmol). The mixture was degassed under $N_2$ atmosphere for three times and stirred under $N_2$ atmosphere at 50° C. for 16 hrs. The mixture was concentrated to dryness and the residue was dissolved in THE (10 mL). TBAF (1.8 g, 13.7 mmol) was added to the above mixture and the resulting mixture was stirred at 0° C. for 10 min. The mixture was diluted with EtOAc (5 mL) and washed with water and brine, dried over anhydrous $Na_2SO_4$, filtered and concentrated to dryness to give crude product, which was purified by flash chromatography (PE:EtOAc=4:1) to give the title compound (1.6 g, 51.8% yield) as white solid. LC/MS (ESI) (m/z): 294 (M+H−84)*.

Step 6: methyl 2-((3S)-1-(2-cyano-6-(1-methyl-5-(((tetrahydro-2H-pyran-2-yl)oxy)methyl)-1H-1,2,3-triazol-4-yl)pyridin-3-yl)-5,5-difluoropiperidin-3-yl)acetate To a mixture of 3-bromo-6-(1-methyl-5-(((tetrahydro-2H-pyran-2-yl)oxy)methyl)-1H-1,2,3-triazol-4-yl)picolinonitrile (80 mg, 0.21 mmol) and methyl (S)-2-(5,5-difluoropiperidin-3-yl)acetate (40.9 mg, 0.21 mmol) in 1,4-dioxane (7.5 mL) were added $Cs_2CO_3$ (137.8 mg, 0.42 mmol), Ru-Phos Pd G3 (35 mg, 0.04 mmol), Ru-phos (20 mg, 0.04 mmol) under $N_2$ atmosphere. The mixture was degassed under $N_2$ atmosphere for three times and stirred under $N_2$ atmosphere at 110° C. overnight. The mixture was diluted with EtOAc (5 mL) and washed with water, brine, dried over anhydrous $Na_2SO_4$, filtered and concentrated to dryness. The residue was purified by flash chromatography (PE: EtOAc=2:1) to give the title compound (70 mg, 67.5% yield) as yellow solid. LC/MS (ESI) m/z: 491 $(M+H)^+$.

Step 7: methyl (S)-2-(1-(2-cyano-6-(5-(hydroxymethyl)-1-methyl-1H-1,2,3-triazol-4-yl)pyridin-3-yl)-5,5-difluoropiperidin-3-yl)acetate To a solution of methyl 2-((3S)-1-(2-cyano-6-(1-methyl-5-(((tetrahydro-2H-pyran-2-yl)oxy)methyl)-1H-1,2,3-triazol-4-yl)pyridin-3-yl)-5,5-difluoropiperidin-3-yl)acetate (70 mg, 0.14 mmol) in MeOH (5 mL) was added PPTS (72 mg, 0.28 mmol) and the mixture was stirred at 50° C. for 16 hrs. The mixture was concentrated to dryness and the residue was purified by chromatography on silica gel (eluted with PE:EtOAc=1:1) to give the title compound (55 mg, 94.8% yield) as yellow solid. LC/MS (ESI) m/z: 407 $(M+H)^+$.

Step 8: methyl (S)-2-(1-(2-cyano-6-(1-methyl-5-(((methylsulfonyl)oxy)methyl)-1H-1,2,3-triazol-4-yl)pyridin-3-yl)-5,5-difluoropiperidin-3-yl)acetate To a solution of methyl (S)-2-(1-(2-cyano-6-(5-(hydroxymethyl)-1-methyl-1H-1,2,3-triazol-4-yl)pyridin-3-yl)-5,5-difluoropiperidin-3-yl)acetate (60 mg, 0.15 mmol) in DCM (2 mL) was added TEA (0.06 mL, 0.44 mmol), followed by MsCl (25 mg, 0.22 mmol) at 0° C. and the reaction mixture was stirred at 0° C. for 1 hr. The mixture was diluted with ice water and extracted with DCM (2×3 mL). The combined organic layers were washed with brine, dried over anhydrous $Na_2SO_4$, filtered and concentrated to dryness give the title compound (65 mg, 90.8% yield) as yellow solid. LC/MS (ESI) m/z: 485 $(M+H)^+$.

Step 9: methyl (S)-2-(1-(2-cyano-6-(1-methyl-5-((2-oxo-5-propylpyridin-1(2H)-yl)methyl)-1H-1,2,3-triazol-4-yl)pyridin-3-yl)-5,5-difluoropiperidin-3-yl) acetate To a mixture of methyl (S)-2-(1-(2-cyano-6-(1-methyl-5-(((methylsulfonyl)oxy)methyl)-1H-1,2,3-triazol-4-yl)pyridin-3-yl)-5,5-difluoropiperidin-3-yl)acetate (70 mg, 0.14 mmol) and 5-propylpyridin-2(1H)-one (20 mg, 0.14 mmol) in toluene (5 mL) and water (1 mL) was added $K_2CO_3$ (40 mg, 0.29 mmol) and TBAF (3.4 mg, cat.) and the mixture was stirred at 110° C. for 1.5 hrs. The reaction mixture was diluted with EtOAc (5 mL) and washed with brine, dried over anhydrous $Na_2SO_4$, filtered and concentrated to dryness to give the title compound (65 mg, 88.4% yield) as yellow solid. LC/MS (ESI) m/z: 526 $(M+H)^+$.

Step 10: (S)-2-(1-(2-cyano-6-(1-methyl-5-((2-oxo-5-propylpyridin-1(2H)-yl)methyl)-1H-1,2,3-triazol-4-yl)pyridin-3-yl)-5,5-difluoropiperidin-3-yl)acetic acid (12)

To a solution of methyl (S)-2-(1-(2-cyano-6-(1-methyl-5-((2-oxo-5-propylpyridin-1(2H)-yl)methyl)-1H-1,2,3-triazol-4-yl)pyridin-3-yl)-5,5-difluoropiperidin-3-yl)acetate (35 mg, 0.067 mmol) in MeOH (1 mL), water (1 mL) and THE (4 mL) was added LiOH (28 mg, 0.67 mmol) and the mixture was stirred at 25° C. for 1 hr. The reaction mixture was acidified with 1M aq·HCl and extracted with EtOAc (3×3 mL). The combined organic layers were washed with brine, dried over $Na_2SO_4$, filtered and concentrated to dryness. The residue was purified by prep-HPLC to give the title compound (20 mg, 58.7% yield) as white solid. $^1H$ NMR (400 MHz, $CD_3OD$) δ 8.21 (d, J=9.2 Hz, 1H), 7.91 (d, J=2.0

Hz, 1H), 7.80 (d, J=9.2 Hz, 1H), 7.39 (dd, J=9.2, 2.0 Hz, 1H), 6.41 (d, J=9.2 Hz, 1H), 5.55 (s, 2H), 4.31 (s, 3H), 3.98-3.74 (m, 2H), 3.57-3.32 (m, 4H), 3.03-2.91 (m, 1H), 2.59-2.32 (m, 6H), 1.90-1.74 (m, 6H), 1.55-1.45 (m, 1H), 0.88 (t, J=7.2, 3H). LC/MS (ESI) m/z: 512 $(M+H)^+$.

Example 50: (R)-2-(1-(2-cyano-6-(1-methyl-5-((2-oxo-5-propylpyridin-1(2H)-yl)methyl)-1H-1,2,3-triazol-4-yl)pyridin-3-yl)piperidin-3-yl)acetic acid Example 50

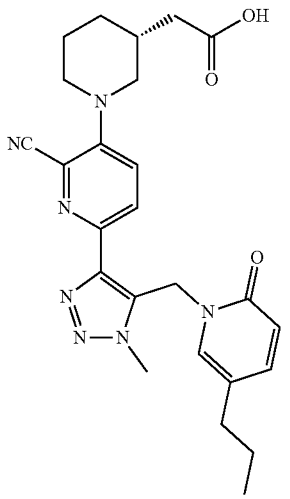

The title compound was prepared as the procedure described for the synthesis of example 49. LC/MS (ESI) m/z: 476 $(M+H)^+$. $^1H$ NMR (400 MHz, $CD_3OD$) δ 8.17-8.14 (d, J=8.9 Hz, 1H), 7.91 (s, 1H), 7.71-7.68 (d, J=9.0 Hz, 1H), 7.41-7.37 (m, 1H), 6.42-6.39 (d, J=9.2 Hz, 1H), 5.54 (s, 2H), 4.30 (s, 3H), 3.77-3.65 (m, 2H), 3.02-2.96 (m, 1H), 2.81-2.74 (m, 1H), 2.46-2.39 (m, 3H), 2.27-2.24 (m, 2H), 1.99-1.81 (m, 3H), 1.59-1.46 (m, 3H), 0.89-0.85 (m, 3H).

Example 51: (S)-2-(1-(2-cyano-6-(1-methyl-5-((2-oxo-5-propylpyridin-1(2H)-yl)methyl)-1H-1,2,3-triazol-4-yl)pyridin-3-yl)piperidin-3-yl)acetic acid

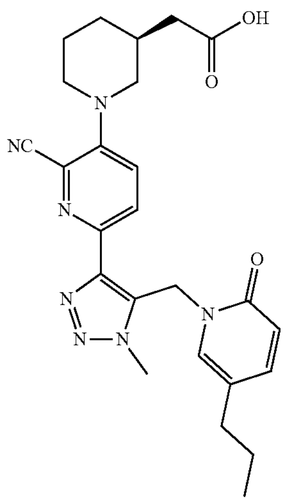 [SMILES: CCCc1ccc(=O)n(Cc2c(-c3ccc(N4CCC[C@@H](CC(=O)O)C4)c(C#N)n3)nnn2C)c1]

The title compound was prepared as the procedure described for the synthesis of example 49. LC/MS (ESI) m/z: 476 $(M+H)^+$. $^1H$ NMR (400 MHz, $CD_3OD$) δ 8.21 (d, J=9.2 Hz, 1H), 7.91 (d, J=2.0 Hz, 1H), 7.80 (d, J=9.2 Hz, 1H), 7.39 (dd, J=9.2, 2.0 Hz, 1H), 6.41 (d, J=9.2 Hz, 1H), 5.55 (s, 2H), 4.31 (s, 3H), 3.98-3.74 (m, 2H), 3.57-3.32 (m, 4H), 3.03-2.91 (m, 1H), 2.59-2.32 (m, 6H), 1.90-1.74 (m, 6H), 1.55-1.45 (m, 1H), 0.88 (t, J=7.2, 3H).

Example 52 and 53: (R) or (S)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetic acid and (S) or (R)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetic acid

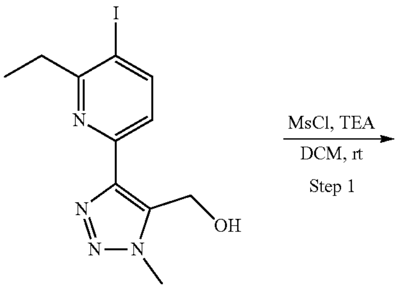

1

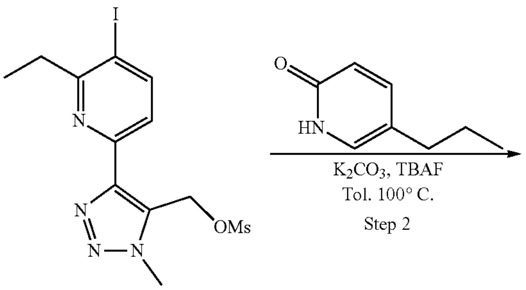

2

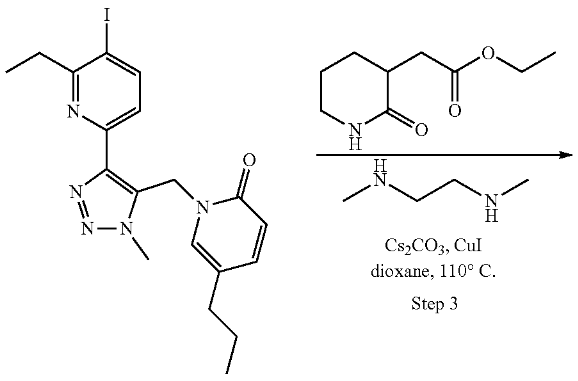

3

-continued

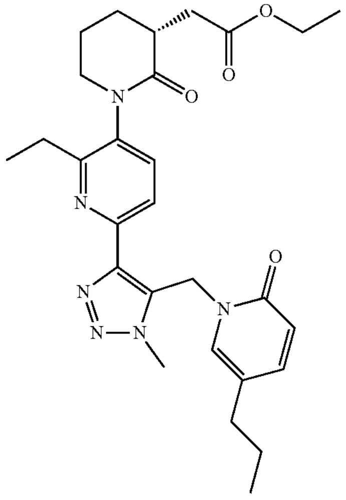

4A

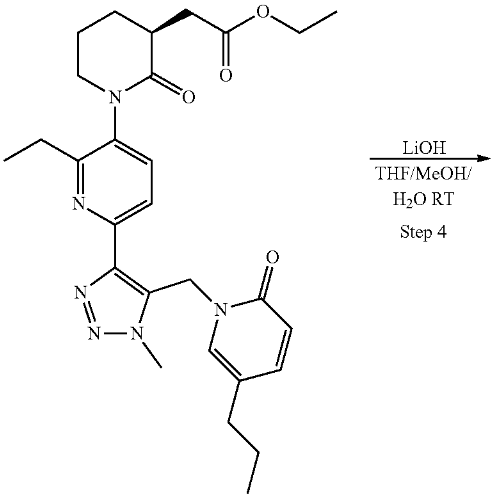

4B

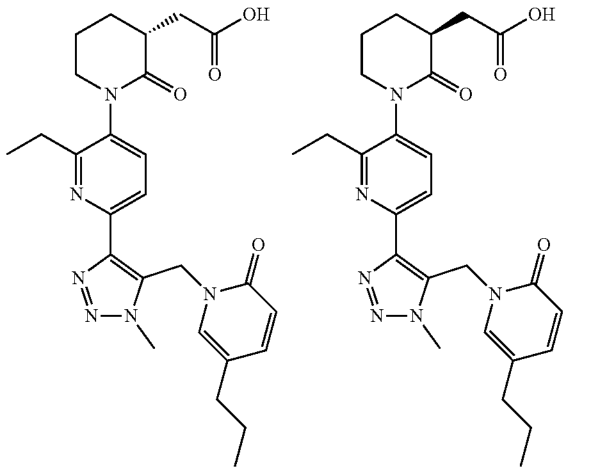

Stereochemistry not assigned

Example 52 and 53

Step 1: (4-(6-ethyl-5-iodopyridin-2-yl)-1-methyl-1H-1,2,3-triazol-5-yl)methyl methanesulfonate To a solution of (4-(6-ethyl-5-iodopyridin-2-yl)-1-methyl-1H-1,2,3-triazol-5-yl)methanol (1 g, 2.91 mmol) in DCM (10 mL) were added TEA (590 mg, 5.8 mmol) followed by drop-wise addition of MsCl (0.40 g, 3.49 mmol) at 0° C., and the mixture was stirred at 0° C. for 2 hrs. The mixture was quenched with saturated aq·$NaHCO_3$ solution and extracted with DCM (2×20 mL). The combined organic layers were washed with brine, dried over anhydrous $Na_2SO_4$, filtered and concentrated to dryness to give the title compound (1.27 g, 103.5% yield) as yellow oil, which was used in next step directly. LC/MS (ESI) m/z: 423 $(M+H)^+$.

Step 2: 1-((4-(6-ethyl-5-iodopyridin-2-yl)-1-methyl-1H-1,2,3-triazol-5-yl)methyl)-5-propylpyridin-2(1H)-one To a mixture of (4-(6-ethyl-5-iodopyridin-2-yl)-1-methyl-1H-1,2,3-triazol-5-yl)methyl methanesulfonate (1.27 g, 3.01 mmol) and 5-propylpyridin-2(1H)-one (0.54 g, 3.91 mmol) in toluene (15 mL) and water (3 mL) were added $K_2CO_3$ (1.25 g, 9.02 mmol), TBAF (80 mg, 0.30 mmol) and the mixture was stirred at 100° C. for 16 hrs. The mixture was diluted EtOAc (20 mL), washed with water and brine, dried over anhydrous $Na_2SO_4$, filtered and concentrated to dryness. The residue was purified by flash chromatography (eluted with PE:EtOAc=20:1 to 1:1) to give the title compound (1.06 g, 76.1% yield) as yellow solid. LC/MS (ESI) m/z: 464 $(M+H)^+$.

Step 3: ethyl (R)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetate and ethyl (S)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetate To a mixture of 1-((4-(6-ethyl-5-iodopyridin-2-yl)-1-methyl-1H-1,2,3-triazol-5-yl)methyl)-5-propylpyridin-2(1H)-one (120 mg, 0.26 mmol) and ethyl 2-(2-oxopiperidin-3-yl)acetate (48 mg, 0.26 mmol) in 1,4-dioxane (3 mL) was added $Cs_2CO_3$ (253 mg, 0.78 mmol), $N_1$,$N_2$-dimethylethane-1,2-diamine (2.3 mg, 0.026 mmol), CuI (9.9 mg, 0.052 mmol) under $N_2$ atmosphere, after addition, the mixture was degassed under $N_2$ atmosphere for three times and stirred under $N_2$ atmosphere at 110° C. for 16 hrs. The mixture was diluted with EtOAc (10 mL), washed with water and brine, dried over anhydrous $Na_2SO_4$, filtered and concentrated to dryness. The residue was purified by chiral SFC to give arbitrarily assigned: ethyl (R)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetate (Peak 1, retention time: 6.782 min) (37 mg, yield 27.4%) and ethyl (S)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetate (Peak 2, retention time: 7.367 min) (37 mg, yield 27.4%) as white solid. LC/MS (ESI) m/z: 521 $(M+H)^+$. SFC Instrument: Waters Thar 80 preparative SFC, Column: ChiralPak IA, 250×21.2 mm I.D., 5 μm, Mobile phase: A for $CO_2$ and B for MEOH+0.1% $NH_3H_2O$, Gradient: B 35%, Flow rate: 50 mL/min, Column temperature: 35° C., Wavelength: 220 nm.

Step 4: (R) or (S)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetic acid To a solution of ethyl (R)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetate (37 mg, 0.071 mmol) in THE (2 mL), MeOH (0.5 mL) and water (0.5 mL) was added lithium hydroxide monohydrate (30 mg, 0.71 mmol) and the reaction mixture was stirred at 25° C. for 2 hrs. The mixture was concentrated to dryness and the residue was dissolved in water. The mixture was washed with EtOAc (2×3 mL) and the aqueous layer was acidified with 1N aq·HCl to pH=3 and extracted with EtOAc (3×3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (14.7 mg, 42.0% yield) as white solid. LC/MS (ESI) m/z: 493 $(M+H)^+$. $^1$H NMR (400 MHz, $CD_3OD$) δ 8.03 (dd, J=8.2, 1.9 Hz, 1H), 7.76-7.65 (m, 1H), 7.41 (dd, J=9.3, 2.5 Hz, 1H), 6.55 (d, J=9.2 Hz, 1H), 5.91 (s, 1H), 4.14 (s, 1H), 3.82-3.46 (m, 1H), 2.88-2.68 (m, 2H), 2.27-2.22 (m, 1H), 2.15-1.96 (m, 1H), 1.47-1.36 (m, 1H), 1.31-1.25 (m, 1H), 0.79 (t, J=7.2 Hz, 1H).

Example 53: (S) or (R)-2-(1-(2-ethyl-6-(1-methyl-5-((2-oxo-5-propylpyridin-1(2H)-yl)methyl)-1H-1,2,3-triazol-4-yl)pyridin-3-yl)-2-oxopiperidin-3-yl)acetic acid The title compound was prepared according to the procedure described for the synthesis of example 53. LC/MS (ESI) m/z: 493 $(M+H)^+$. $^1$H NMR (400 MHz, $CD_3OD$) δ 8.03 (dd, J=8.3, 1.8 Hz, 1H), 7.77-7.64 (m, 2H), 7.41 (dd, J=9.2, 2.5 Hz, 1H), 6.55 (d, J=9.2 Hz, 1H), 5.91 (s, 2H), 4.14 (s, 3H), 3.81-3.46 (m, 2H), 2.89-2.70 (m, 5H), 2.25 (t, J=7.6 Hz, 2H), 2.16-1.93 (m, 4H), 1.47-1.37 (m, 2H), 1.31-1.25 (m, 3H), 0.79 (t, J=7.2 Hz, 3H).

Example 54 and 55: (R) or (S)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetic acid and (S) or (R)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetic acid

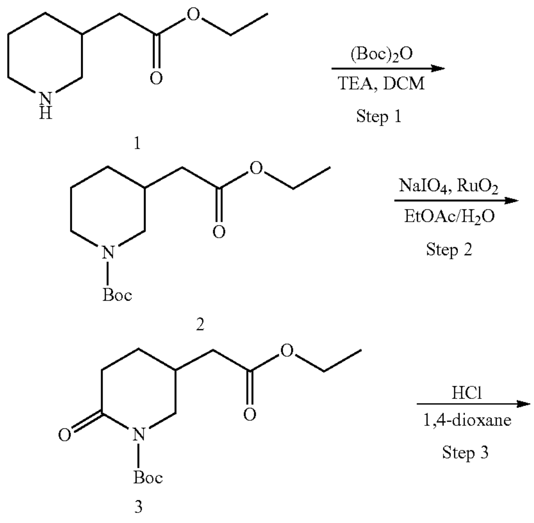

-continued

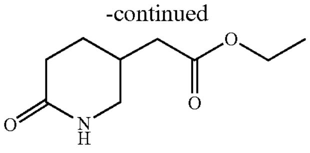

4

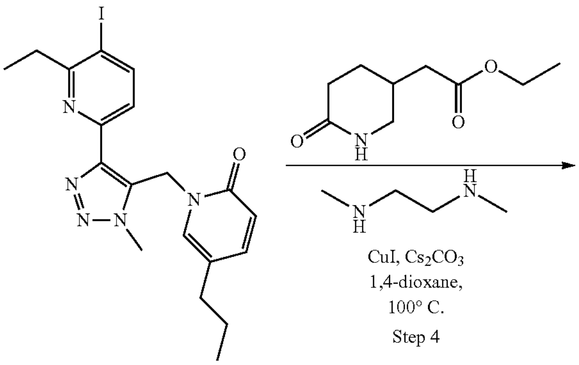

5

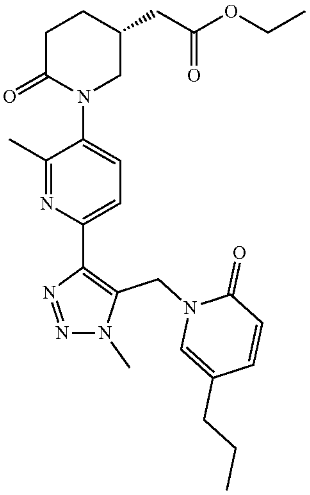

6A

+

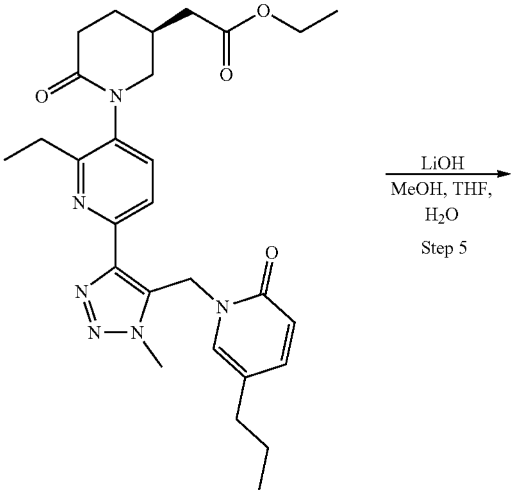

6B

-continued

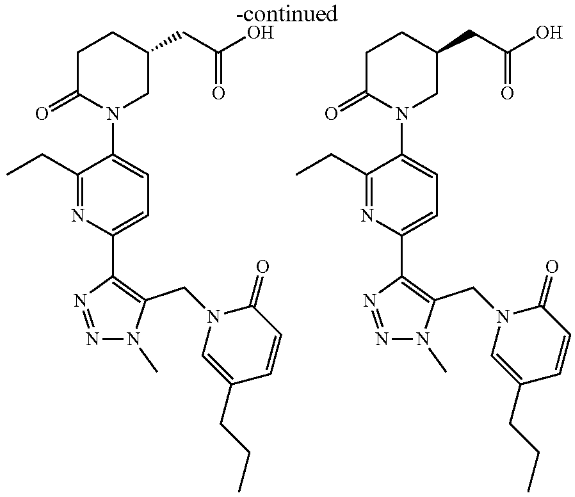

Stereochemistry not assigned

Example 54 and 55

Step 1: tert-butyl 3-(2-ethoxy-2-oxoethyl)piperidine-1-carboxylate

To a mixture of ethyl 2-(piperidin-3-yl)acetate (1 g, 5.8 mmol) in DCM (25 mL) and di-tert-butyl dicarbonate (1.9 mL, 8.8 mmol) was added TEA (1.6 mL, 11.7 mmol) at 0° C. and the mixture was stirred at r.t. for 16 hrs. The mixture was concentrated to dryness and the residue was purified by flash chromatography (0~20% EtOAc in PE) to give the title compound (1.3 g, 82.3% yield) as yellow oil. LC-MS (ESI) m/z 272 $(M+H)^+$.

Step 2: tert-butyl 5-(2-ethoxy-2-oxoethyl)-2-oxopiperidine-1-carboxylate

To solution of tert-butyl 3-(2-ethoxy-2-oxoethyl)piperidine-1-carboxylate (1.3 g, 4.8 mmol) in EtOAc (10 mL) was added a solution of $NaIO_4$ (5.1 g, 24.0 mmol) in $H_2O$ (10 mL) followed by Ruthenium(IV) oxide hydrate (70 mg, 0.45 mmol) at 0° C. and the reaction mixture was stirred at r.t. for 2 hrs. The reaction mixture was filtered through a celite pad and the filter cake was washed with EtOAc (2×5 mL). The filtrate was washed with saturated aq·$Na_2SO_3$ solution and brine, dried over anhydrous $Na_2SO_4$, filtered and was concentrated to dryness. The residue was purified by flash chromatography (0~30% EtOAc in PE) to give the title compound (1.1 g, 80.1% yield) as yellow oil. LC-MS (ESI) m/z 286 $(M+H)^+$.

Step 3: ethyl 2-(6-oxopiperidin-3-yl)acetate

To a solution of tert-butyl 5-(2-ethoxy-2-oxoethyl)-2-oxopiperidine-1-carboxylate (1.1 g, 3.9 mmol) in 1,4-dioxane (5 mL) was added HCl/1,4-dioxane (4.8 mL, 4M) at 0° C. and the reaction mixture was stirred at r.t. for 1 hr. The mixture was concentrated to dryness and the residue was basified with saturated aq·$NaHCO_3$ solution. The mixture was extracted with EtOAc (2×10 mL) and the combined organic layers were washed with brine, dried over $Na_2SO_4$, filtered and concentrated to dryness to give the title compound (640 mg, 89.6% yield) as yellow syrup. LC-MS (ESI) m/z 186 $(M+H)^+$.

Step 4: ethyl (R)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetate and ethyl (S)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetate To a solution of 1-{[4-(6-ethyl-5-iodopyridin-2-yl)-1-methyl-1H-1,2,3-triazol-5-yl]methyl}-5-propyl-1,2-dihydropyridin-2-one (250 mg, 0.5 mmol) in 1,4-dioxane (10 mL) were added ethyl 2-(6-oxopiperidin-3-yl)acetate (150 mg, 0.8 mmol) followed by the addition of $Cs_2CO_3$ (527 mg, 1.6 mmol), CuI (21 mg, 0.11 mmol) and $N_1$,$N_2$-dimethylethane-1,2-diamine (15 mg, 0.11 mmol) and the reaction mixture was stirred at 120° C. for 16 hrs. The mixture was filtered through a Celite pad and the filter cake was washed with EtOAc (10 mL). The filtrate was washed with water and brine, dried over $Na_2SO_4$, filtered and concentrated to dryness. The residue was purified by flash chromatography (0~50% EtOAc in PE) and further separated by chiral SFC to give arbitrarily assigned: ethyl 2-[(3R)-1-(2-ethyl-6-{1-methyl-5-[(2-oxo-5-propyl-1,2-dihydropyridin-1-yl)methyl]-1H-1,2,3-triazol-4-yl}pyridin-3-yl)-6-oxopiperidin-3-yl]acetate (peak 1 retention time: 4.123 min) (35 mg, 9.2% yield) and ethyl 2-[(3S)-1-(2-ethyl-6-{1-methyl-5-[(2-oxo-5-propyl-1,2-dihydropyridin-1-yl)methyl]-1H-1,2,3-triazol-4-yl}pyridin-3-yl)-6-oxopiperidin-3-yl]acetate (peak 2, retention time:4.669 min) (40 mg, 10.3% yield) as white solid. LC-MS (ESI) m/z 521 $(M+H)^+$. SFC condition: Column: ChiralPak IA, 250×21.2 mm I.D., 5 μm; Mobile phase: A for $CO_2$ and B for Methanol (0.1% $NH_4OH$); Gradient: B 30%; Flow rate: 50 mL/min; Column temperature: 35° C.

Step 5: (R) or (S)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetic acid To solution of ethyl 2-[(3R)-1-(2-ethyl-6-{1-methyl-5-[(2-oxo-5-propyl-1,2-dihydropyridin-1-yl)methyl]-1H-1,2,3-triazol-4-yl}pyridin-3-yl)-6-oxopiperidin-3-yl]acetate (35 mg, 0.06 mmol) in THE (4 mL) and MeOH (1 mL) was added LiOH (28 mg, 0.7 mmol) in $H_2O$ (1 mL) at 0° C. and the reaction was stirred at r.t. for 2 hrs. The mixture was concentrated to dryness and the residue was diluted with water (5 mL) and washed with EtOAc (2×3 mL) twice. The aqueous layer was acidified with 1N aq·HCl to pH ~3 and extracted with DCM (2×5 mL). The combined organic layers were washed with brine, dried over $Na_2SO_4$, filtered and concentrated to dryness. The residue was purified by perp-HPLC (C18, 0~90% acetonitrile in $H_2O$ with 0.1% formic acid) to give the title compound (7 mg, 21.2% yield) as white solid. LC-MS (ESI) m/z 493 $(M+H)^+$. $^1H$ NMR (400 MHz, $CD_3OD$) δ 8.06-8.03 (m, 1H), 7.78-7.71 (m, 1H), 7.66-7.65 (t, J=2.6 Hz, 1H), 7.442-7.29 (dd, J=9.3, 2.5 Hz, 1H), 6.55 (d, J=9.3 Hz, 1H), 5.91 (d, J=1.8 Hz, 2H), 4.15 (s, 3H), 3.87-3.41 (m, 2H), 2.81-2.67 (m, 3H), 2.62-2.49 (m, 1H), 2.45-2.43 (m, 2H), 2.35-2.32 (m, 1H), 2.26-2.22 (t, J=7.5 Hz, 2H), 2.20-2.09 (m, 1H), 1.89-1.78 (m, 1H), 1.47-1.36 (m, 2H), 1.32-1.26 (q, J=7.6 Hz, 3H), 0.80-0.77 (t, J=7.3 Hz, 3H).

Example 55: (S) or (R)-2-(1-(2-ethyl-6-(1-methyl-5-((2-oxo-5-propylpyridin-1(2H)-yl)methyl)-1H-1,2,3-triazol-4-yl)pyridin-3-yl)-6-oxopiperidin-3-yl)acetic acid The title compound was prepared according to the procedure described for the synthesis of Example 54. $^1H$ NMR (400 MHz, $CD_3OD$) δ 7.98-7.91 (m, 1H), 7.67-7.60 (m, 1H), 7.56 (t, J=2.6 Hz, 1H), 7.34-7.27 (m, 1H), 6.45 (d, J=9.3 Hz, 1H), 5.81 (d, J=1.7 Hz, 2H), 4.05 (s, 3H), 3.76-3.34 (m, 2H), 2.72-2.58 (m, 3H), 2.53-2.39 (m, 1H), 2.39-2.32 (m, 2H), 2.28-2.18 (m, 1H), 2.15 (t, J=7.5 Hz, 2H), 2.06 (d, J=13.6 Hz, 1H), 1.82-1.65 (m, 1H), 1.38-1.26 (m, 2H), 1.19 (q, J=7.6 Hz, 3H), 0.69 (t, J=7.3 Hz, 3H). LC/MS (ESI) m/z: 493 $(M+H)^+$.

Example 56: (R)-2-(5,5-difluoro-1-(5-(1-methyl-5-((2-oxo-5-propylpyridin-1(2H)-yl)methyl)-1H-1,2,3-triazol-4-yl)pyrazin-2-yl)piperidin-3-yl)acetic acid

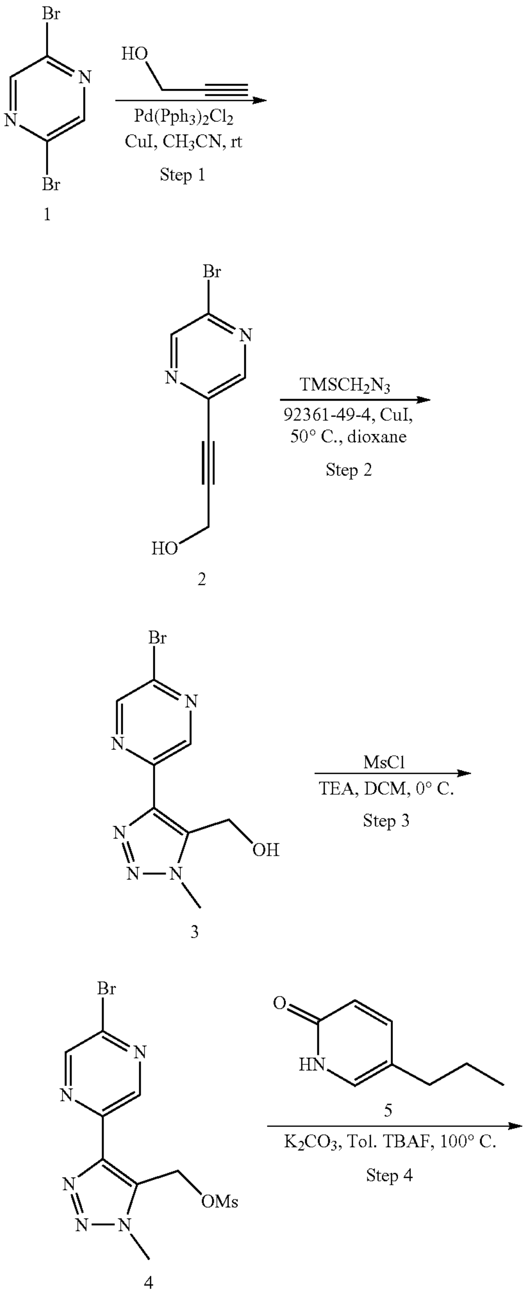

1
2
3
4
5

-continued

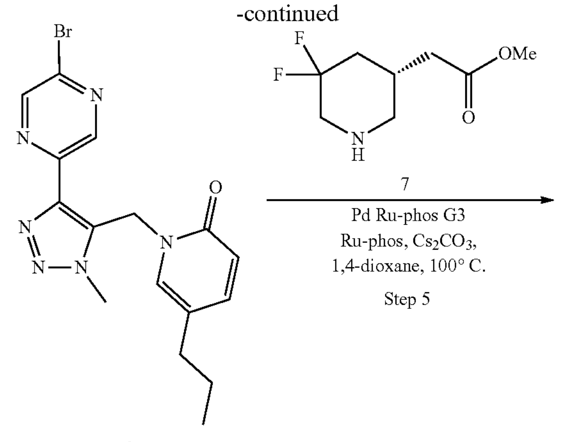

6

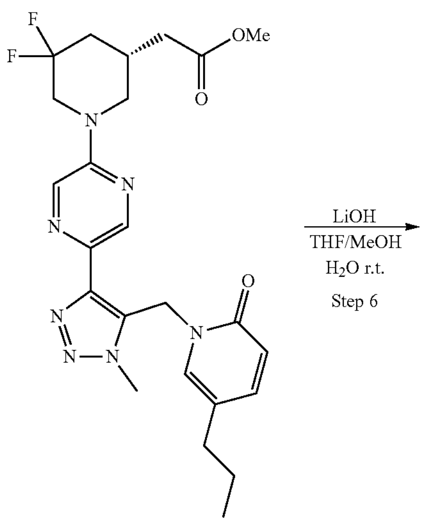

8

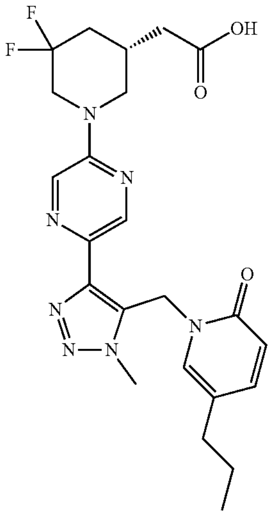

Example 56

Step 1: 3-(5-bromopyrazin-2-yl)prop-2-yn-1-ol

To a solution of 2,5-dibromopyrazine (1.6 g, 6.73 mmol) and prop-2-yn-1-ol (0.38 g, 6.73 mmol) in MeCN (16 mL) were added TEA (2.0 g, 20.18 mmol), CuI (30 mg, 0.14 mmol), $Pd(PPh_3)_2Cl_2$ (90 mg, 0.14 mmol) under $N_2$ atmosphere, after addition, the mixture was degassed under $N_2$ atmosphere for three times and stirred at 25° C. for 16 hrs. The mixture was diluted with water and extracted with EtOAc (2×15 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound (453 mg, 31.6% yield) as yellow solid. LC/MS (ESI) m/z: 213/215 $(M+H)^+$.

Step 2: (4-(5-bromopyrazin-2-yl)-1-methyl-1H-1,2,3-triazol-5-yl)methanol

To a solution of 3-(5-bromopyrazin-2-yl)prop-2-yn-1-ol (453 mg, 2.13 mmol) and $TMSCH_2N_3$ (493.76 mg, 3.83 mmol) in 1,4-dioxane (5 mL) were added CuI (20.3 mg, 0.11 mmol), chloro(pentamethylcyclopentadienyl)bis(triphenylphosphine)ruthenium(II) (84.7 mg, 0.11 mmol) under $N_2$ atmosphere, after addition, the mixture was degassed under $N_2$ atmosphere for three times and stirred at 50° C. for 16 hrs. The mixture was concentrated to dryness and the residue was dissolved in THE (5 mL). TBAF (1 M in THF, 4.3 mL) was added and the resulting mixture was stirred at 25° C. for 1 hr. The mixture was diluted with water (10 mL) and extracted with EtOAc (2×10 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound (205 mg, 35.7% yield) as yellow solid. LC/MS (ESI) m/z: 270/272 $(M+H)^+$.

Step 3: (4-(5-bromopyrazin-2-yl)-1-methyl-1H-1,2,3-triazol-5-yl)methyl methanesulfonate To a solution of (4-(5-bromopyrazin-2-yl)-1-methyl-1H-1,2,3-triazol-5-yl)methanol (205 mg, 0.76 mmol) in DCM (2 mL) were added TEA (230.4 mg, 2.28 mmol) and MsCl (104.3 mg, 0.91 mmol) at 0° C. under $N_2$ atmosphere and the mixture was stirred at 0° C. for 2 hrs. The mixture was quenched with saturated aq·$NaHCO_3$ solution and extracted with DCM (2×5 mL). The combined organic layers were washed with brine, dried over anhydrous $Na_2SO_4$, filtered and concentrated to dryness to give the title compound (295 mg, 111.6% yield) as yellow solid, which was used in next step directly. LC/MS (ESI) m/z: 348/350 $(M+H)^+$.

Step 4: 1-((4-(5-bromopyrazin-2-yl)-1-methyl-1H-1,2,3-triazol-5-yl)methyl)-5-propylpyridin-2(1H)-one To a solution of (4-(5-bromopyrazin-2-yl)-1-methyl-1H-1,2,3-triazol-5-yl)methyl methanesulfonate (295 mg, 0.85 mmol) and 5-propylpyridin-2(1H)-one (174.3 mg, 1.27 mmol) in toluene (5 mL) and $H_2O$ (1 mL) were added $K_2CO_3$ (351 mg, 2.54 mmol), TBAF (22 mg, 0.085 mmol) at r.t. under $N_2$ atmosphere and the mixture was stirred at 100° C. for 16 hrs. The mixture was diluted with water (10 mL) and extracted with EtOAc (2×5 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound 6 (130 mg, 39.4% yield) as yellow solid. LC/MS (ESI) m/z: 389/391 $(M+H)^+$.

Step 5: methyl (S)-2-(5,5-difluoro-1-(5-(1-methyl-5-((2-oxo-5-propylpyridin-1(2H)-yl)methyl)-1H-1,2,3-triazol-4-yl)pyrazin-2-yl)piperidin-3-yl)acetate To a solution of 1-((4-(5-bromopyrazin-2-yl)-1-methyl-1H-1,2,3-triazol-5-yl)methyl)-5-propylpyridin-2(1H)-one (30 mg, 0.077 mmol) and methyl (S)-2-(5,5-difluoropiperidin-3-yl)acetate (14.9 mg, 0.077 mmol) in 1,4-dioxane (2 mL) were added $Cs_2CO_3$ (49 mg, 0.15 mmol), Ru-Phos Pd G3 (13 mg, 0.015 mmol), Ru-Phos (7.2 mg, 0.015 mmol) under $N_2$ atmosphere, after addition, the mixture was degassed under $N_2$ atmosphere for three times and stirred at 110° C. for 16 hrs. The mixture was diluted with water (10 mL) and extracted with EtOAc (2×10 mL). The combined organic layers were washed with brine, dried over anhydrous $Na_2SO_4$, filtered and concentrated to dryness to give the title compound (30 mg, 77.6% yield) as white solid, which was used in next step directly. LC/MS (ESI) m/z: 502 $(M+H)^+$.

Step 6: (S)-2-(5,5-difluoro-1-(5-(1-methyl-5-((2-oxo-5-propylpyridin-1(2H)-yl)methyl)-1H-1,2,3-triazol-4-yl)pyrazin-2-yl)piperidin-3-yl)acetic acid To a solution of methyl (S)-2-(5,5-difluoro-1-(5-(1-methyl-5-((2-oxo-5-propylpyridin-1(2H)-yl)methyl)-1H-1,2,3-triazol-4-yl)pyrazin-2-yl)piperidin-3-yl)acetate (30 mg, 0.06 mmol) in THE (2 mL), MeOH (0.5 mL) and $H_2O$ (0.5 mL) was added $LiOH{\cdot}H_2O$ (25 mg, 0.60 mmol) at 25° C. The reaction was stirred at 25° C. for 2 hrs. The mixture was concentrated to dryness and the residue was dissolved in water (5 mL). The mixture was washed with EtOAc (2×3 mL) and the aqueous layer was acidified with 1N aq·HCl to pH=4 and extracted with EtOAc (3×3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (3.6 mg, 12.3% yield) as white solid. LC/MS (ESI) m/z: 488 $(M+H)^+$. $^1H$ NMR (400 MHz, $CD_3OD$) δ 8.68 (s, 1H), 8.41 (s, 1H), 7.71 (d, J=2.4 Hz, 1H), 7.37 (dd, J=12.0, 2.6 Hz, 1H), 6.43 (d, J=9.6 Hz, 1H), 5.60 (s, 2H), 4.25 (s, 4H), 3.29-3.19 (m, 3H), 3.02-2.91 (m, 1H), 2.40-2.27 (m, 7H), 1.91-1.75 (m, 1H), 1.49-1.40 (m, 2H), 0.86-0.78 (m, 3H).

Example 57: 2-(1-(5-(1-methyl-5-((2-oxo-5-propylpyridin-1(2H)-yl)methyl)-1H-1,2,3-triazol-4-yl)pyrazin-2-yl)piperidin-3-yl)acetic acid

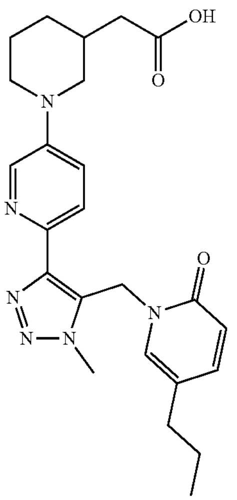 [SMILES: CCCc1ccc(=O)n(Cc2c(-c3ccc(N4CCCC(CC(=O)O)C4)cn3)nnn2C)c1]

The title compound was prepared according to the procedure described for the synthesis of example 56. LC/MS (ESI) m/z: 452 $(M+H)^+$. $^1H$ NMR (400 MHz, $CD_3OD$) δ 8.63 (d, J=1.2 Hz, 1H), 8.30 (s, 1H), 7.70 (d, J=2.0 Hz, 1H), 7.35 (dd, J=9.2 Hz, d, J=2.8 Hz, 1H), 6.44 (d, J=9.2 Hz, 1H), 5.59 (s, 2H), 4.47-4.41 (m, 2H), 4.24 (s, 3H), 3.02-2.95 (m, 2H), 2.34-2.24 (m, 4H), 2.11-2.02 (m, 1H), 1.93-1.84 (m, 2H), 1.51-1.40 (m, 2H), 1.36-1.24 (m, 2H), 0.83 (d, J=7.2 Hz, 3H).

Example 58: 2-[(3R)-1-(6-{1-methyl-5-[(2-oxo-5-propyl-1,2-dihydropyridin-1-yl)methyl]-1H-1,2,3-triazol-4-yl}-2-(trifluoromethyl)pyridin-3-yl)piperidin-3-yl]acetic acid

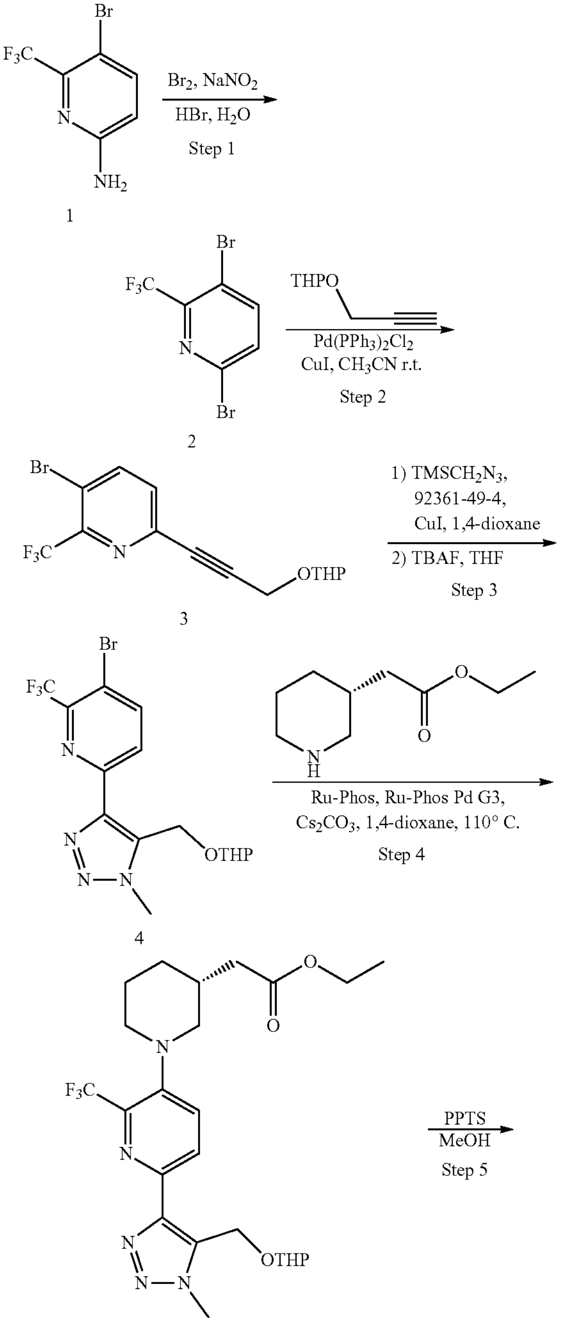

-continued

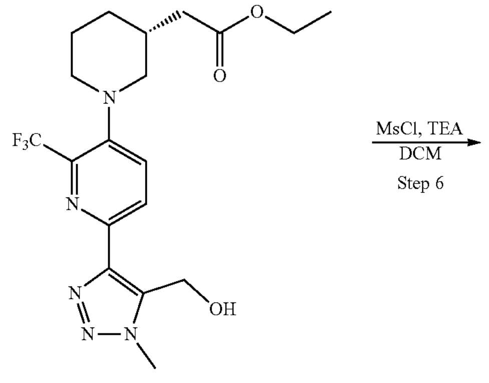

6

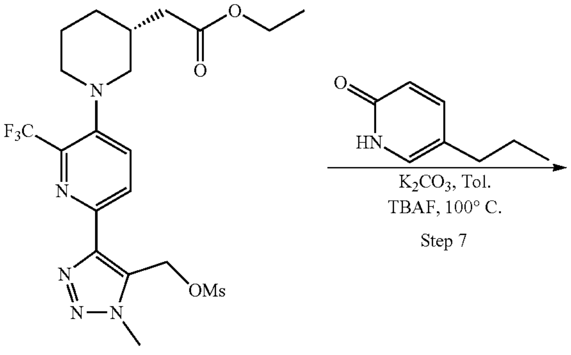

7

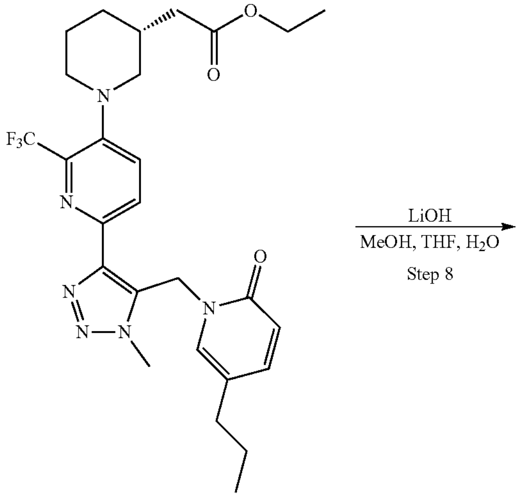

8

-continued

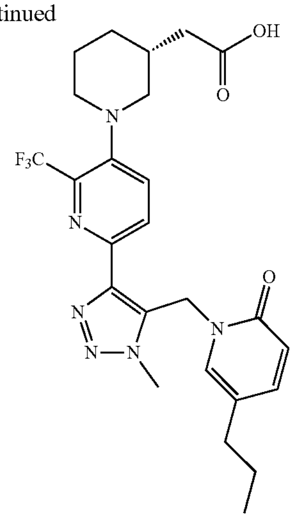

Example 58

Step 1: 3,6-dibromo-2-(trifluoromethyl)pyridine

To a solution of 5-bromo-6-(trifluoromethyl)pyridin-2-amine (1.01 g, 4.14 mmol) in aq·HBr (1.34 g, 16.59 mmol, 40% wt) was added $Br_2$ (0.59 mL, 11.61 mmol), $NaNO_2$ (0.72 g, 10.37 mmol) in water (10 mL) at 0° C., and the mixture was stirred at 0° C. for 1 hr. The reaction mixture was diluted with EtOAc (20 mL), washed with water and brine, dried over anhydrous $Na_2SO_4$, filtered and concentrated to dryness. The residue was purified by flash chromatography (silica gel, 0-10% EtOAc in PE) to give the title compound (720 mg, 56.9% yield) as white solid. $^1H$ NMR (400 MHz, DMSO) δ 8.34 (d, J=8.4 Hz, 1H), 7.95 (d, J=8.4 Hz, 1H).

Step 2: 3-bromo-6-[3-(oxan-2-yloxy)prop-1-yn-1-yl]-2-(trifluoromethyl)pyridine

To a solution of 3,6-dibromo-2-(trifluoromethyl)pyridine (720 mg, 2.36 mmol) in acetonitrile (10 mL) was added 2-(prop-2-yn-1-yloxy)oxane (397 mg, 2.83 mmol), CuI (22 mg, 0.11 mmol), triethylamine (0.98 mL, 7.08 mmol), $Pd(PPh_3)_2Cl_2$ (83 mg, 0.11 mmol), and the mixture was degassed under $N_2$ for 3 times and stirred at 25° C. for 16 hrs. The reaction mixture was concentrated to dryness and the residue was purified by flash chromatography (silica gel, 0-20% EtOAc in PE) to give the title compound (696 mg, 80.9% yield) as yellow oil. LC/MS (ESI) m/z: 364 $(M+H)^+$. $^1H$ NMR (400 MHz, DMSO-$d_6$) δ 8.42 (d, J=8.4 Hz, 1H), 7.78 (d, J=8.3 Hz, 1H), 4.82 (d, J=3.2 Hz, 1H), 4.59-4.43 (m, 2H), 3.81-3.72 (m, 1H), 3.53-3.46 (m, 1H), 1.74-1.63 (m, 2H), 1.56-1.47 (m, 4H).

Step 3: 3-bromo-6-(1-methyl-5-(((tetrahydro-2H-pyran-2-yl)oxy)methyl)-1H-1,2,3-triazol-4-yl)-2-(trifluoromethyl)pyridine To a solution of 3-bromo-6-[3-(oxan-2-yloxy)prop-1-yn-1-yl]-2-(trifluoromethyl)pyridine (696 mg, 1.91 mmol) in 1,4-dioxane (7 mL) was added $TMSCH_2N_3$ (246 mg, 1.91 mmol), CuI (18 mg, 0.096 mmol), pentamethylcyclopentadienylbis(triphenylphosphine)ruthenium(II) chloride (76 mg, 0.096 mmol), and the mixture was degassed under $N_2$ for three times and stirred at 50° C. for 16 hrs. Then the reaction mixture was concentrated to dryness and the residue was dissolved in THE (7 mL). TBAF (1.49 g, 5.73 mmol) was added to the mixture and the resulting mixture was stirred at r.t. for 1 hr. The mixture was diluted with EtOAc (10 mL), washed with saturated aq·$NH_4Cl$ solution and brine, dried over anhydrous $Na_2SO_4$, filtered and concentrated to dryness. The residue was purified by flash chromatography (silica gel, 0-60% EtOAc in PE) to give the title compound (306 mg, 38.0% yield) as white solid. $^1H$ NMR (400 MHz, DMSO-$d_6$) δ 8.52 (d, J=8.5 Hz, 1H), 8.30 (d, J=8.5 Hz, 1H), 5.36 (d, J=12.5 Hz, 1H), 5.19 (d, J=12.5 Hz, 1H), 4.77-4.72 (m, 1H), 4.18 (s, 3H), 3.77-3.68 (m, 1H), 3.46-3.41 (m, 1H), 1.73-1.61 (m, 2H), 1.57-1.44 (m, 4H).

Step 4: ethyl 2-((3R)-1-(6-(1-methyl-5-(((tetrahydro-2H-pyran-2-yl)oxy)methyl)-1H-1,2,3-triazol-4-yl)-2-(trifluoromethyl)pyridin-3-yl)piperidin-3-yl) acetate To a solution of 3-bromo-6-{1-methyl-5-[(oxan-2-yloxy)methyl]-1H-1,2,3-triazol-4-yl}-2-(trifluoromethyl)pyridine (180 mg, 0.42 mmol) in 1,4-dioxane (5 mL) was added $Cs_2CO_3$ (417 mg, 1.28 mmol), ethyl 2-[(3R)-piperidin-3-yl] acetate (73 mg, 0.42 mmol), RuPhos Pd G3 (71 mg, 0.085 mmol), RuPhos (40 mg, 0.085 mmol) and the mixture was degassed under $N_2$ for 3 times and stirred at 120° C. for 16 hrs. The reaction mixture was diluted with EtOAc (10 mL) and washed with brine, dried over anhydrous $Na_2SO_4$, filtered and concentrated to dryness. The residue was purified by flash chromatography (silica gel, 0-60% EtOAc in PE) to give the title compound (125 mg, 57.2% yield) as yellow solid. LC/MS (ESI) m/z: 512 $(M+H)^+$.

Step 5: ethyl (R)-2-(1-(6-(5-(hydroxymethyl)-1-methyl-1H-1,2,3-triazol-4-yl)-2-(trifluoromethyl) pyridin-3-yl)piperidin-3-yl)acetate To a solution of ethyl 2-[(3S)-1-(6-{1-methyl-5-[(oxan-2-yloxy)methyl]-1H-1,2,3-triazol-4-yl}-2-(trifluoromethyl) pyridin-3-yl)piperidin-3-yl]acetate (125 mg, 0.24 mmol) in MeOH (5 mL) was added PPTS (184 mg, 0.73 mmol) and the mixture was stirred at 60° C. for 2 hrs. The reaction mixture was concentrated to dryness and the residue was diluted with DCM (10 mL), washed with saturated aq. $NH_4Cl$ solution and brine, dried over anhydrous $Na_2SO_4$, filtered and concentrated to dryness. The residue was purified by flash chromatography (silica gel, 0-80% EtOAc in PE) to give the title compound (102 mg, 97.7% yield) as yellow solid. LC/MS (ESI) m/z: 428 $(M+H)^+$.

Step 6: ethyl (R)-2-(1-(6-(1-methyl-5-(((methylsulfonyl)oxy)methyl)-1H-1,2,3-triazol-4-yl)-2-(trifluoromethyl)pyridin-3-yl)piperidin-3-yl)acetate To a solution of ethyl 2-[(3R)-1-{6-[5-(hydroxymethyl)-1-methyl-1H-1,2,3-triazol-4-yl]-2-(trifluoromethyl)pyridin-3-yl}piperidin-3-yl]acetate (50 mg, 0.11 mmol) in DCM (3 mL) was added TEA (0.081 mL, 0.58 mmol), MsCl (0.011 mL, 0.14 mmol), and then the mixture was stirred at 0° C. for 30 mins. The reaction mixture was diluted with DCM (5 mL) and washed with brine, dried over anhydrous $Na_2SO_4$, filtered and concentrated to dryness to the title compound (62 mg, 94.4% yield) as yellow oil. LC/MS (ESI) m/z: 506 $(M+H)^+$.

Step 7: ethyl 2-[(3R)-1-(6-{1-methyl-5-[(2-oxo-5-propyl-1,2-dihydropyridin-1-yl)methyl]-1H-1,2,3-triazol-4-yl}-2-(trifluoromethyl)pyridin-3-yl)piperidin-3-yl]acetate To a solution of ethyl 2-[(3S)-1-(6-{5-[(methanesulfonyloxy)methyl]-1-methyl-1H-1,2,3-triazol-4-yl}-2-(trifluoromethyl)pyridin-3-yl)piperidin-3-yl]acetate (62 mg, 0.12 mmol) in toluene (5 mL) and water (1 mL) was added 5-propyl-1,2-dihydropyridin-2-one (34 mg, 0.24 mmol), $K_2CO_3$ (51 mg, 0.36 mmol), and then the mixture was stirred at 110° C. for 16 hrs. The mixture was diluted with EtOAc (5 mL), washed with water and brine, dried over $Na_2SO_4$, filtered and concentrated to dryness to give the title compound (71 mg, 95.1% yield) as yellow solid. LC/MS (ESI) m/z: 547 $(M+H)^+$.

Step 8: 2-[(3R)-1-(6-{1-methyl-5-[(2-oxo-5-propyl-1,2-dihydropyridin-1-yl)methyl]-1H-1,2,3-triazol-4-yl}-2-(trifluoromethyl)pyridin-3-yl)piperidin-3-yl] acetic acid To a solution of ethyl 2-[(3R)-1-(6-{1-methyl-5-[(2-oxo-5-propyl-1,2-dihydropyridin-1-yl)methyl]-1H-1,2,3-triazol-4-yl}-2-(trifluoromethyl)pyridin-3-yl)piperidin-3-yl]acetate (69 mg, 0.12 mmol) in THE (2 mL) was added MeOH (0.5 mL), water (0.5 mL), LiOH (30 mg, 1.26 mmol) and the mixture was stirred at 25° C. for 1 hr. The reaction mixture was concentrated to dryness and the residue was dissolved in $H_2O$ (5 mL). The mixture was acidified with 1N aq·HCl and extracted with EtOAc (2×5 mL). The combined organic layers were washed with brine, dried over anhydrous $Na_2SO_4$, filtered and concentrated to dryness. The residue was purified by prep·HPLC to give the title compound (28 mg, 42.8% yield) as white solid. LC/MS (ESI) m/z: 519 $(M+H)^+$. $^1H$ NMR (400 MHz, $CD_3OD$) δ 8.27 (d, J=8.6 Hz, 1H), 8.01 (d, J=8.6 Hz, 1H), 7.73 (d, J=2.1 Hz, 1H), 7.40-7.35 (m, 1H), 6.49 (d, J=9.2 Hz, 1H), 5.76 (s, 2H), 4.22 (s, 3H), 3.23-3.18 (m, 1H), 3.11-3.05 (m, 1H), 2.88-2.80 (m, 1H), 2.66-2.59 (m, 1H), 2.35-2.28 (m, 2H), 2.27-2.19 (m, 3H), 1.94-1.72 (m, 3H), 1.43-1.33 (m, 2H), 1.31-1.20 (m, 1H), 0.76 (t, J=7.3 Hz, 3H).

Example 59: (R)-2-(1-(6-(5-((5-cyclopropyl-2-oxopyridin-1(2H)-yl)methyl)-1-methyl-1H-1,2,3-triazol-4-yl)-2-(trifluoromethyl)pyridin-3-yl)piperidin-3-yl)acetic acid Example 59

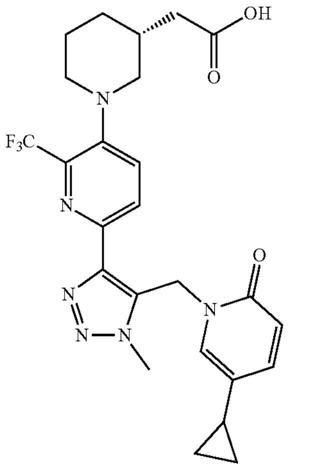

The title compound was prepared according to the procedure described for the synthesis of example 58. LC/MS (ESI) m/z: 519 $(M+H)^+$. $^1H$ NMR (400 MHz, $CD_3OD$) δ 8.29 (d, J=8.5 Hz, 1H), 8.04 (d, J=8.7 Hz, 1H), 7.74-7.71 (m, 1H), 7.31-7.26 (m, 1H), 6.49 (d, J=9.3 Hz, 1H), 5.79 (s, 2H), 4.22 (s, 3H), 3.26-3.22 (m, 1H), 3.16-3.10 (m, 1H), 2.90-2.84 (m, 1H), 2.68-2.62 (m, 1H), 2.35-2.30 (m, 2H), 2.28-2.21 (m, 1H), 1.96-1.89 (m, 1H), 1.85-1.76 (m, 2H), 1.64-1.56 (m, 1H), 1.33-1.24 (m, 1H), 0.80-0.74 (m, 2H), 0.37-0.31 (m, 2H).
Example 60: (R)-2-(1-(2-(difluoromethyl)-6-(1-methyl-5-((2-oxo-5-propylpyridin-1(2H)-yl)methyl)-1H-1,2,3-triazol-4-yl)pyridin-3-yl)piperidin-3-yl) acetic acid
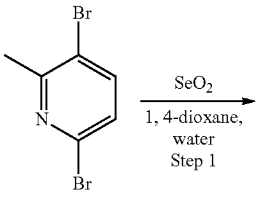
1
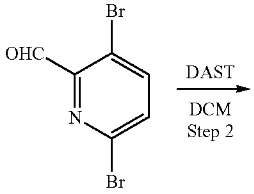
2
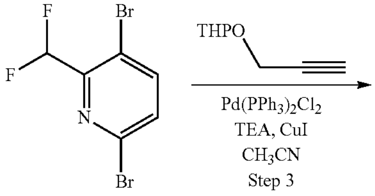
3
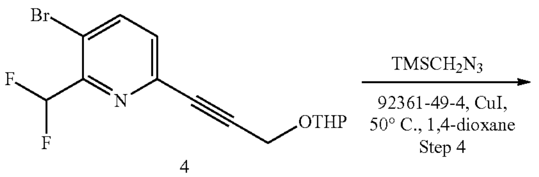
4
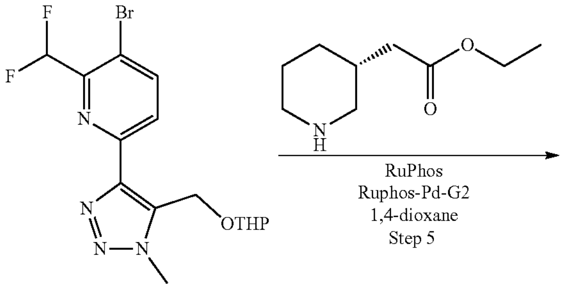
5
-continued
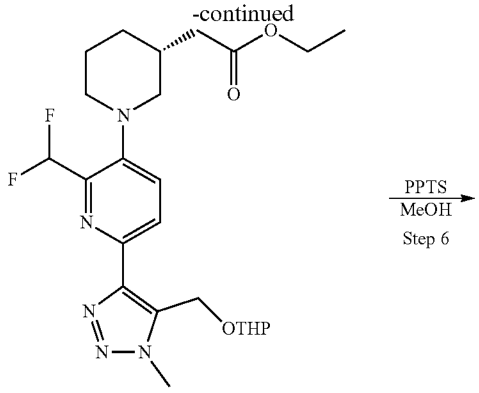
6
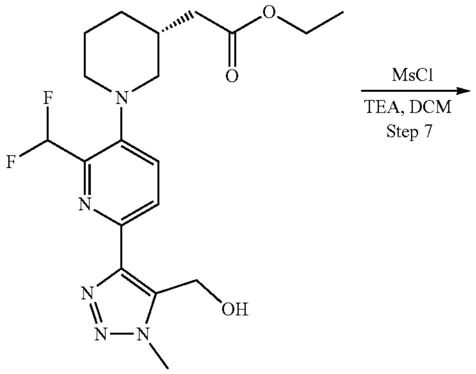
7
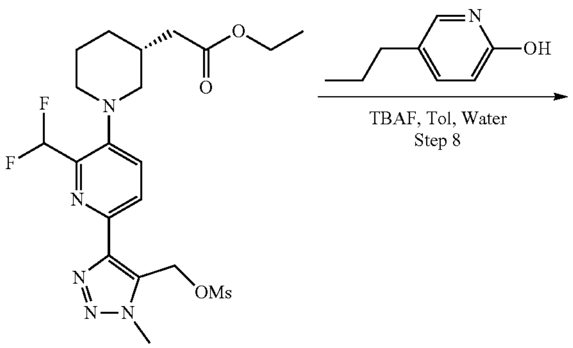
8
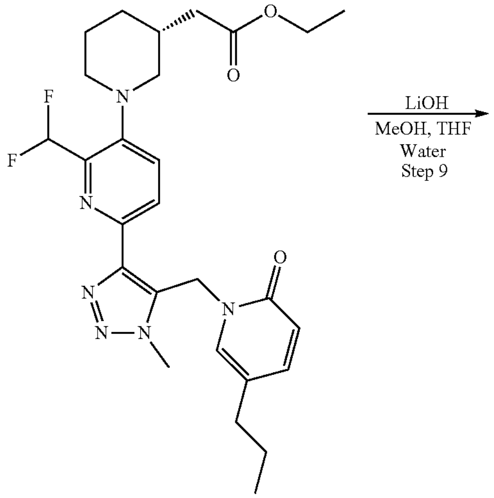
9

-continued

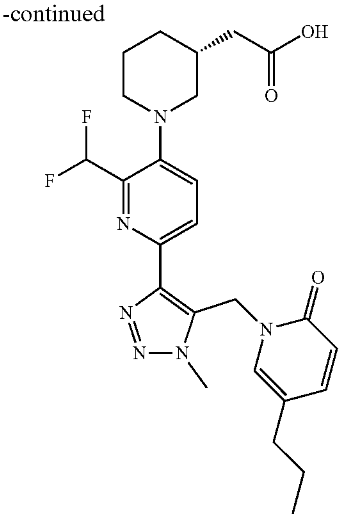

Example 59

Step 1: 3,6-dibromopicolinaldehyde

To a solution of 3,6-dibromo-2-methylpyridine (2 g, 7.9 mmol) in 1,4-dioxane (20 mL) was added $SeO_2$ (3.54 g, 31.9 mmol) and $H_2O$ (0.5 mL) the mixture was stirred at 120° C. for 16 hrs. The mixture was diluted with ice water (10 mL) and extracted with EtOAc (2×10 mL). The combined organic layers were washed with brine, dried over anhydrous $Na_2SO_4$, filtered and concentrated to dryness. The residue was purified by chromatography on silica gel (PE:EtOAc=10:1) to give the title compound (1.2 g, 56.8% yield) as white solid. LC/MS (ESI) (m/z): 266 $(M+H)^+$. $^1H$ NMR (400 MHz, $CDCl_3$) δ 10.09 (s, 1H), 7.87 (d, J=8.4 Hz, 1H), 7.54 (d, J=8.4 Hz, 1H).

Step 2: 3,6-dibromo-2-(difluoromethyl)pyridine

To a solution of 3,6-dibromopyridine-2-carbaldehyde (500 mg, 1.8 mmol) in DCM (10 mL) was added DAST (0.6 mL, 4.7 mmol) at 0° C. and the mixture was stirred at 25° C. for 1 hr. The mixture was diluted with DCM (10 mL) and washed with saturated aq·$NaHCO_3$ solution and brine, dried over anhydrous $Na_2SO_4$, filtered and concentrated to dryness. The residue was purified by chromatography on silica gel (PE:EtOAc=10:1) to give the title compound (400 mg, 73.8% yield) as white solid. LC/MS (ESI) (m/z): 288 $(M+H)^+$. $^1H$ NMR (400 MHz, $CDCl_3$) δ 7.81 (d, J=8.4 Hz, 1H), 7.49 (d, J=8.4 Hz, 1H), 6.80 (t, J=53.6 Hz, 1H) Step 3: 3-bromo-2-(difluoromethyl)-6-[3-(oxan-2 yloxy)prop-1-yn-1-yl]pyridine To a mixture of 3,6-dibromo-2-(difluoromethyl)pyridine (400 mg, 1.3 mmol) and (prop-2-yn-1-yloxy)tetrahydro-2H-pyran (195 mg, 1.3 mmol) in MeCN (10 mL) was added TEA (423 mg, 4.1 mmol), CuI (13.2 mg, 0.07 mmol) and $Pd(PPh_3)_2Cl_2$ (49 mg, 0.07 mmol). The mixture was degassed under $N_2$ atmosphere for three times and stirred under $N_2$ atmosphere at r.t. overnight. The mixture was diluted with EtOAc (10 mL), washed with water and brine, dried over anhydrous $Na_2SO_4$, filtered and concentrated to dryness. The residue was purified by chromatography on silica gel (PE:EtOAc=2:1) to give the title compound (400 mg, 82.9% yield) as yellow solid. $^1H$ NMR (400 MHz, $CDCl_3$) δ 7.92 (s, 1H), 7.40 (t, J=7.8 Hz, 1H), 6.82 (s, 1H), 4.87 (t, J=3.3 Hz, 1H), 4.50 (d, J=11.6 Hz, 2H), 3.89-3.80 (m, 1H), 3.59-3.52 (m, 1H), 1.88-1.58 (m, 6H).

Step 4: 3-bromo-2-(difluoromethyl)-6-{1-methyl-5-[(oxan-2-yloxy)methyl]-1H-1,2,3-triazol-4-yl}pyridine To a solution of 3-bromo-2-(difluoromethyl)-6-[3-(oxan-2-yloxy)prop-1-yn-1-yl]pyridine (1.5 g, 4.3 mmol) in 1,4-dioxane (10 mL) were added (azidomethyl)trimethylsilane (0.56 g, 4.3 mmol), CuI (0.007 mL, 0.2 mmol), Cp*RuCl $(PPh_3)_2$ (0.17 g, 0.2 mmol). The mixture was degassed under $N_2$ atmosphere for three times and stirred under $N_2$ atmosphere at 50° C. for 16 hrs. The mixture was concentrated to dryness and the residue was dissolved in THE (10 mL). TBAF (1.8 g, 13.7 mmol) was added to the above mixture and the resulting mixture was stirred at 0° C. for 10 mins. The mixture was diluted with EtOAc (10 mL) and washed with water, brine, dried over anhydrous $Na_2SO_4$, filtered and concentrated to dryness. The residue was purified by flash chromatography (PE:EtOAc=4:1) to give the title compound (1.25 g, 71.5% yield) as white solid. LC/MS (ESI) (m/z): 403 $(M+H)^+$. $^1H$ NMR (400 MHz, $CDCl_3$) δ 8.21 (d, J=8.5 Hz, 1H), 8.00 (t, J=10.1 Hz, 1H), 7.06-6.79 (m, 1H), 5.38-5.25 (m, 2H), 4.76 (t, J=3.4 Hz, 1H), 4.17 (s, 3H), 3.88-3.75 (m, 1H), 3.51 (dd, J=10.9, 4.9 Hz, 1H), 1.83-1.68 (m, 3H), 1.51 (d, J=4.9 Hz, 2H).

Step 5: ethyl 2-[(3R)-1-[2-(difluoromethyl)-6-{1-methyl-5-[(oxan-2-yloxy)methyl]-1H-1,2,3-triazol-4-yl}pyridin-3-yl]piperidin-3-yl]acetate To a mixture of 3-bromo-2-(difluoromethyl)-6-{1-methyl-5-[(oxan-2-yloxy)methyl]-1H-1,2,3-triazol-4-yl}pyridine (100 mg, 0.24 mmol) and ethyl 2-[(3R)-piperidin-3-yl]acetate (42 mg, 0.248 mmol) in 1,4-dioxane (7.5 mL) were added $Cs_2CO_3$ (242 mg, 0.74 mmol), Ru-Phos Pd G3 (42 mg, 0.04 mmol), Ru-phos (23 mg, 0.04 mmol) under $N_2$ atmosphere. The mixture was degassed under $N_2$ atmosphere for three times and stirred at 110° C. for 16 hrs. The mixture was diluted with EtOAc (10 mL) and washed with water and brine, dried over anhydrous $Na_2SO_4$, filtered and concentrated to dryness. The residue was purified by flash chromatography (PE:EtOAc=4:1) to give the title compound (100 mg, 81.6% yield). LC/MS (ESI) m/z: 494 $(M+H)^+$.

Step 6: ethyl (S)-2-(1-(2-cyano-6-(1-methyl-5-(((methylsulfonyl)oxy)methyl)-1H-1,2,3-triazol-4-yl)pyridin-3-yl)piperidin-3-yl)acetate To a solution of ethyl give ethyl 2-[(3R)-1-[2-(difluoromethyl)-6-{1-methyl-5-[(oxan-2-yloxy)methyl]-1H-1,2,3-triazol-4-yl}pyridin-3-yl]piperidin-3-yl]acetate (80 mg, 0.162 mmol) in MeOH (10 mL) was added PPTS (203 mg, 0.810 mmol) and the mixture was stirred at 50° C. for 16 hrs. The mixture was concentrated to dryness and the residue was purified by chromatography on silica gel (eluted with PE:EtOAc=1:1) to give the title compound (65 mg, 97% yield). LC/MS (ESI) m/z: 410 $(M+H)^+$.

Step 7: ethyl (S)-2-(1-(2-cyano-6-(1-methyl-5-(((methylsulfonyl)oxy)methyl)-1H-1,2,3-triazol-4-yl)pyridin-3-yl)piperidin-3-yl)acetate To a solution of ethyl 2-[(3R)-1-[2-(difluoromethyl)-6-[5-(hydroxymethyl)-1-methyl-1H-1,2,3-triazol-4-yl]pyridin-3-yl]piperidin-3-yl]acetate (65 mg, 0.159 mmol) in DCM (10 mL) was added TEA (0.1 mL, 0.4 mmol) followed by MsCl (0.1 mL, 0.2 mmol) at 0° C. and the reaction mixture was stirred at 0° C. for 1 hr. The mixture was diluted with ice water and extracted with DCM (2×3 mL). The combined organic layers were washed with brine, dried over anhydrous $Na_2SO_4$, filtered and concentrated to dryness give the title compound (70 mg, 90% yield) as yellow solid. LC/MS (ESI) m/z: 488 $(M+H)^+$.

Step 8: [(3R)-1-[2-(difluoromethyl)-6-{1-methyl-5-[(2-oxo-5-propyl-1,2-dihydropyridin-1-yl)methyl]-1H-1,2,3-triazol-4-yl}pyridin-3-yl]piperidin-3-yl] acetate To a mixture of 2-{4-[6-(difluoromethyl)-5-[(3R)-3-(2-ethoxy-2-oxoethyl)piperidin-1-yl]pyridin-2-yl]-1-methyl-1H-1,2,3-triazol-5-yl}ethane-1-sulfonic acid (60 mg, 0.1 mmol) and 5-propylpyridin-2-ol (17 mg, 0.1 mmol) in toluene (5 mL) and water (1 mL) was added $K_2CO_3$ (51 mg, 0.3 mmol) and TBAF (0.6 mg, 0.002 mmol) and the mixture was stirred at 110° C. for 1.5 hrs. The reaction mixture was diluted with EtOAc (5 mL) and washed with brine, dried over anhydrous $Na_2SO_4$, filtered and concentrated to dryness to give the title compound (60 mg, 92.2% yield) as yellow solid. LC/MS (ESI) m/z: 529 $(M+H)^+$.

Step 9: 2-[(3R)-1-[2-(difluoromethyl)-6-{1-methyl-5-[(2-oxo-5-propyl-1,2-dihydropyridin-1-yl)methyl]-1H-1,2,3-triazol-4-yl}pyridin-3-yl]piperidin-3-yl] acetic acid To a solution of 2-{4-[6-(difluoromethyl)-5-[(3R)-3-(2-ethoxy-2-oxoethyl)piperidin-1-yl]pyridin-2-yl]-1-methyl-1H-1,2,3-triazol-5-yl}ethane-1-sulfonic acid (65 mg, 0.13 mmol) in MeOH (1 mL), water (1 mL) and THE (4 mL) was added LiOH (5.5 mg, 0.13 mmol) and the mixture was stirred at 25° C. for 1.5 hrs. The reaction mixture was acidified with 1M aq·HCl to pH=4 and extracted with EtOAc (2×5 mL). The combined organic layers were washed with brine, dried over $Na_2SO_4$, filtered and concentrated to dryness. The residue was purified by prep-HPLC to give the title compound (30 mg, 44.9% yield) as white solid. LC/MS (ESI) m/z: 501 $(M+H)^+$. $^1H$ NMR (400 MHz, $CD_3OD$) δ 8.15 (d, J=8.7 Hz, 1H), 8.00 (d, J=2.0 Hz, 1H), 7.84 (d, J=8.6 Hz, 1H), 7.37 (dd, J=9.2, 2.4 Hz, 1H), 7.20 (t, J=54.4 Hz, 1H), 6.48 (d, J=9.2 Hz, 1H), 5.78 (s, 2H), 4.26 (s, 3H), 3.23 (d, J=11.5 Hz, 1H), 3.12 (d, J=10.8 Hz, 1H), 2.89-2.79 (m, 1H), 2.65-2.57 (m, 1H), 2.25 (dd, J=20.7, 13.4 Hz, 5H), 1.96-1.80 (m, 3H), 1.37 (dd, J=14.9, 7.4 Hz, 2H), 1.31-1.22 (m, 1H), 0.75 (t, J=7.3 Hz, 3H).

Example 61: 2-((S)-1-(6-(5-(((S)-4-(cyclopropylmethyl)-3-methyl-2-oxoimidazolidin-1-yl)methyl)-1-methyl-1H-1,2,3-triazol-4-yl)-2-ethylpyridin-3-yl)-5,5-difluoropiperidin-3-yl)acetic acid

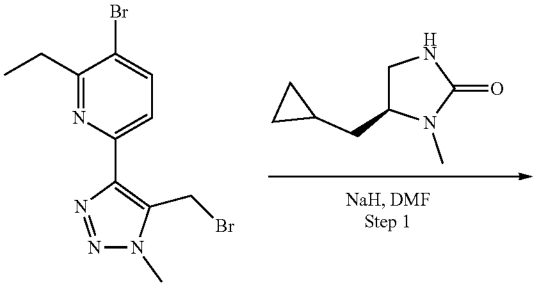

1

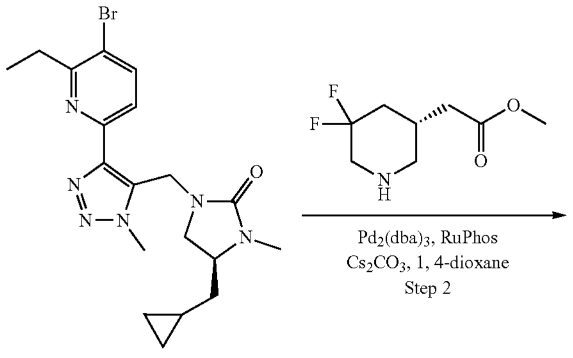

2

-continued

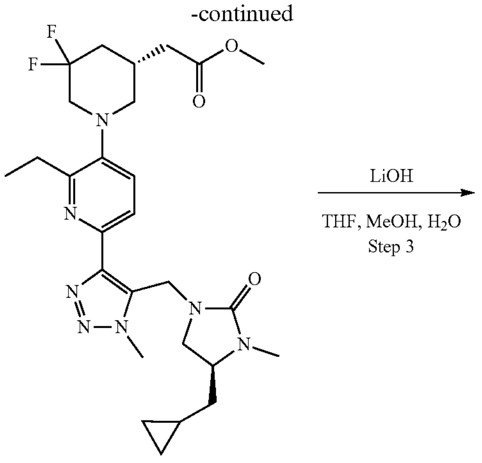

3

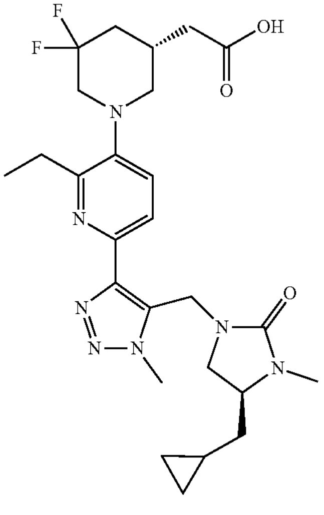

Example 61

Step 1: (4S)-1-{[4-(5-bromo-6-ethylpyridin-2-yl)-1-methyl-1H-1,2,3-triazol-5-yl]methyl}-4-(cyclopropylmethyl)-3-methylimidazolidin-2-one To a mixture of 3-bromo-6-[5-(bromomethyl)-1-methyl-1H-1,2,3-triazol-4-yl]-2-ethylpyridine (140 mg, 0.39 mmol) and (5S)-5-(cyclopropylmethyl)-1-methylimidazolidin-2-one (90 mg, 0.58 mmol) in DMF (10 mL) was added NaH (47 mg, 1.17 mmol, 60% dispersion in mineral oil) at 0° C. and the mixture was stirred at r.t for 16 hrs. The reaction mixture was quenched with ice-water and the mixture was extracted with EtOAc (2x5 mL). The combined organic layers were washed with brine, dried over $Na_2SO_4$, filtered and evaporated to dryness. The residue was purified by flash chromatography (silica gel, 0~35% EtOAc in PE) to give the title compound (90 mg, 53.4% yield) as white solid. LC/MS (ESI) m/z: 434/436 $(M+H)^+$.

Step 2: methyl 2-[(3S)-1-[6-(5-{[(4S)-4-(cyclopropylmethyl)-3-methyl-2-oxoimidazolidin-1-yl]methyl}-1-methyl-1H-1,2,3-triazol-4-yl)-2-ethylpyridin-3-yl]-5,5-difluoropiperidin-3-yl]acetate To a mixture of (4S)-1-{[4-(5-bromo-6-ethylpyridin-2-yl)-1-methyl-1H-1,2,3-triazol-5-yl]methyl}-4-(cyclopropylmethyl)-3-methylimidazolidin-2-one (45 mg, 0.10 mmol) and methyl 2-[(3S)-5,5-difluoropiperidin-3-yl]acetate (30 mg, 0.16 mmol) in 1,4-dioxane (5 mL) was added $Cs_2CO_3$ (104 mg 0.32 mmol) and $Pd_2(dba)_3$ (9 mg, 0.01 mmol) and RuPhos (5 mg, 0.01 mmol) under $N_2$ atmosphere and the mixture was stirred at 110° C. for 16 hrs. The mixture was diluted with EtOAc (5 mL), washed with water and brine, dried over $Na_2SO_4$, filtered and concentrated to dryness. The residue was purified by flash chromatography (silica gel, 0~50% EtOAc in PE) to give the title compound (22 mg, 40.3% yield) as yellow solid. LC/MS (ESI) m/z: 546 $(M+H)^+$.

Step 3: 2-[(3S)-1-[6-(5-{[(4S)-4-(cyclopropylmethyl)-3-methyl-2-oxoimidazolidin-1-yl]methyl}-1-methyl-1H-1,2,3-triazol-4-yl)-2-ethylpyridin-3-yl]-5,5-difluoropiperidin-3-yl]acetic acid To a solution of methyl 2-[(3R)-1-[6-(5-{[(4S)-4-(cyclopropylmethyl)-3-methyl-2-oxoimidazolidin-1-yl]methyl}-1-methyl-1H-1,2,3-triazol-4-yl)-2-ethylpyridin-3-yl]-5,5-difluoropiperidin-3-yl]acetate (22 mg, 0.04 mmol) in THE (5 mL) and MeOH (1 mL) was added a solution of LiOH (4 mg 0.18 mmol) in $H_2O$ (1 mL) and the mixture was stirred at r.t. for 3 hrs. The mixture was acidified with 1N aq·HCl to pH~4 and extracted with DCM (3x3 mL). The combined organic layers were washed with brine, dried over $Na_2SO_4$, filtered and concentrated to dryness. The residue was purified by perp-HPLC (C18, 0~90% acetonitrile in $H_2O$ with 0.1% HCOOH) to give the title compound (11 mg, 50.9% yield) as white solid. $^1H$ NMR (400 MHz, $CD_3OD$) δ 7.87 (d, J=8.3 Hz, 1H), 7.58 (d, J=8.4 Hz, 1H), 5.13 (s, 2H), 4.11 (s, 3H), 3.54-3.47 (m, 1H), 3.41 (t, J=8.8 Hz, 1H), 3.22 (d, J=10.1 Hz, 2H), 3.10-2.93 (m, 4H), 2.76 (s, 3H), 2.63-2.48 (m, 2H), 2.38-2.23 (m, 3H), 1.95 (s, 3H), 1.77-1.62 (m, 1H), 1.46-1.30 (m, 6H), 0.54-0.42 (m, 1H), 0.40-0.29 (m, 2H). LC/MS (ESI) m/z: 532 $(M+H)^+$. The examples in the following table were prepared by using method analogous to the examples as indicated in the method column in the table.

| Ex# | Structure & name | Analytical & biological data | Method |
|---|---|---|---|
| 62 | 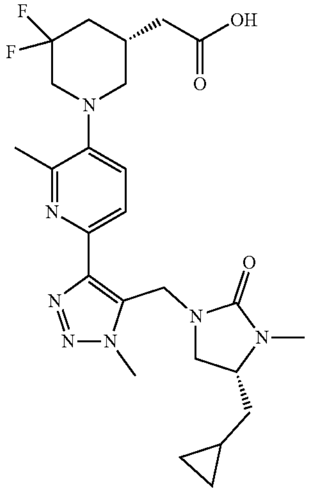 [SMILES: Cc1nc(-c2nnn(C)c2CN2C[C@@H](CC3CC3)N(C)C2=O)ccc1N1C[C@@H](CC(=O)O)CC(F)(F)C1] 2-((S)-1-(6-(5-(((R)-4-(cyclopropylmethyl)-3-methyl-2-oxoimidazolidin-1-yl)methyl)-1-methyl-1H-1,2,3-triazol-4-yl)-2-methylpyridin-3-yl)-5,5-difluoropiperidin-3-yl)acetic acid | LC/MS (ESI) m/z: 519 $(M + H)^+$. $^1H$ NMR (400 MHz, $CD_3OD$) δ 7.86 (d, J = 8.3 Hz, 1H), 7.55 (d, J = 8.4 Hz, 1H), 5.05 (d, J = 1.1 Hz, 2H), 4.14 (s, 3H), 3.57-3.43 (m, 2H), 3.29-3.18 (m, 2H), 3.16-3.04 (m, 2H), 2.76 (s, 3H), 2.63-2.57 (m, 1H), 2.59 (s, 3H), 2.52-2.49 (m, 1H), 2.46-2.38 (m, 2H), 2.38-2.26 (m, 1H), 1.87-1.64 (m, 1H), 1.55-1.45 (m, 1H), 1.44-1.33 (m, 1H), 0.56-0.43 (m, 1H), 0.42-0.31 (m, 2H), 0.01--0.03 (m, 2H). | Example 61 |
| 63 | 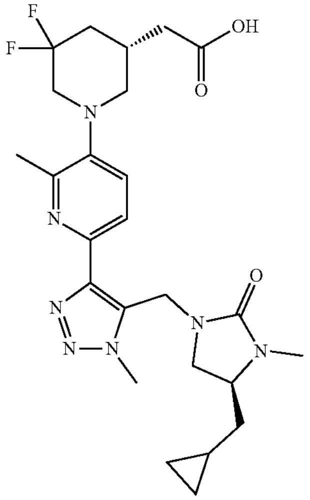 [SMILES: Cc1nc(-c2nnn(C)c2CN2C[C@H](CC3CC3)N(C)C2=O)ccc1N1C[C@@H](CC(=O)O)CC(F)(F)C1] 2-((S)-1-(6-(5-(((S)-4-(cyclopropylmethyl)-3-methyl-2-oxoimidazolidin-1-yl)methyl)-1-methyl-1H-1,2,3-triazol-4-yl)-2-methylpyridin-3-yl)-5,5-difluoropiperidin-3-yl)acetic acid | LC/MS (ESI) m/z: 518 $(M + H)^+$. $^1H$ NMR (400 MHz, $CD_3OD$) δ 7.84 (d, J = 8.3 Hz, 1H), 7.53 (d, J = 8.4 Hz, 1H), 5.03 (s, 2H), 4.12 (s, 3H), 3.45-3.47 (m, 2H), 3.29-3.18 (m, 1H), 3.13-3.02 (m, 2H), 2.75 (s, 3H), 2.60-2.63 (m, 1H), 2.59 (s, 3H), 2.48-2.54 ( m, 1H), 2.45-2.36 (m, 2H), 2.30-2.32 (m, 1H), 1.81-1.65 (m, 1H), 1.53-1.44 (m, 1H), 1.34-1.40 (m, 1H), 0.53-0.44 (m, 1H), 0.40-0.29 (m, 2H), 0.02-0.03 (m, 2H). | Example 61 |

-continued

| Ex# | Structure & name | Analytical & biological data | Method |
|---|---|---|---|
| 64 | 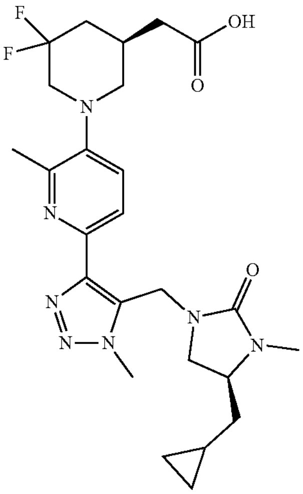 [SMILES: Cc1nc(-c2nnn(C)c2CN2C[C@H](CC3CC3)N(C)C2=O)ccc1N1C[C@H](CC(=O)O)CC(F)(F)C1]<br>2-((R)-1-(6-(5-(((S)-4-(cyclopropylmethyl)-3-methyl-2-oxoimidazolidin-1-yl)methyl)-1-methyl-1H-1,2,3-triazol-4-yl)-2-methylpyridin-3-yl)-5,5-difluoropiperidin-3-yl)acetic acid | LC/MS (ESI) m/z: 519 $(M + H)^+$. $^1H$ NMR (400 MHz, $CD_3OD$) δ 7.86 (d, J = 8.3 Hz, 1H), 7.55 (d, J = 8.4 Hz, 1H), 5.05 (d, J = 1.1 Hz, 2H), 4.14 (s, 3H), 3.57-3.43 (m, 2H), 3.29-3.18 (m, 2H), 3.16-3.04 (m, 2H), 2.76 (s, 3H), 2.63-2.57 (m, 1H), 2.59 (s, 3H), 2.52-2.49 (m, 1H), 2.47-2.38 (m, 2H), 2.38-2.26 (m, 1H), 1.87-1.64 (m, 1H), 1.55-1.45 (m, 1H), 1.44-1.33 (m, 1H), 0.56-0.43 (m, 1H), 0.42-0.31 (m, 2H), 0.01--0.03 (m, 2H). | Example 61 |

Example 65: 2-((S)-1-(6-(5-(((S)-4-(cyclopropylmethyl)-2-oxoimidazolidin-1-yl)methyl)-1-methyl-1H-1,2,3-triazol-4-yl)-2-ethylpyridin-3-yl)-5,5-difluoropiperidin-3-yl)acetic acid

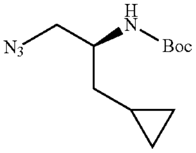

1

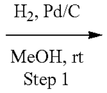

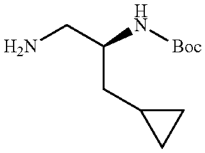

2

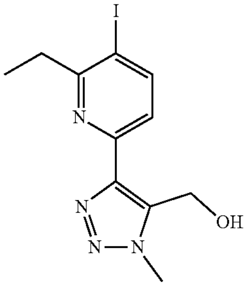

3

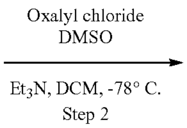

-continued

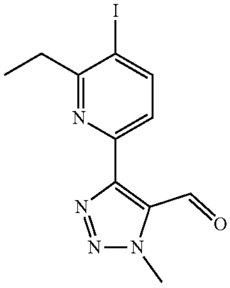

4

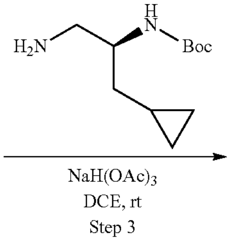

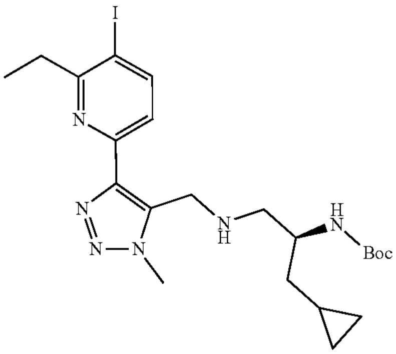

5

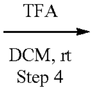

-continued

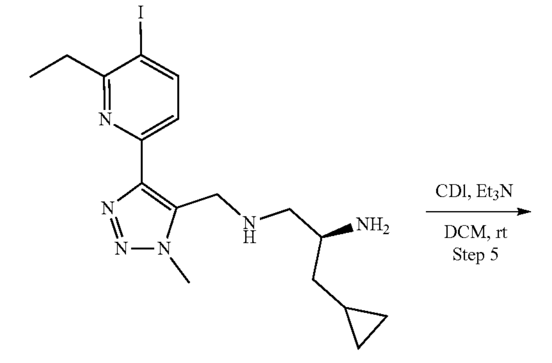

6

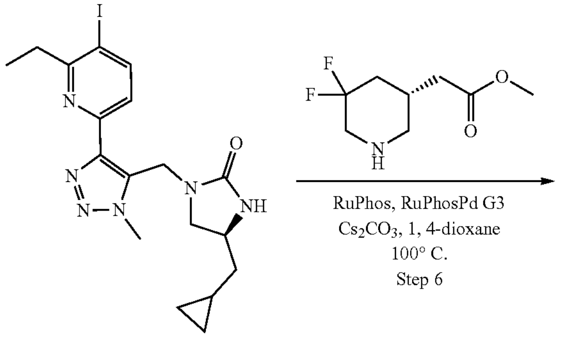

7

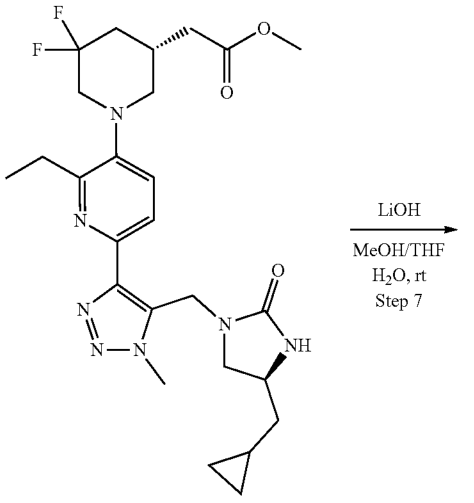

8

-continued

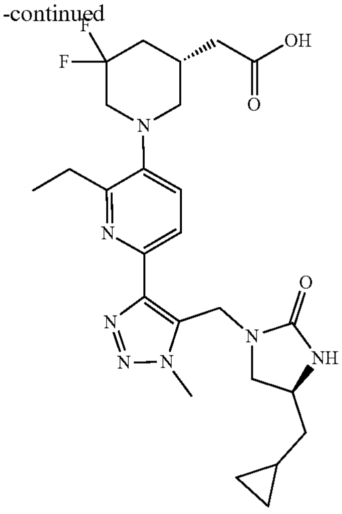

Example 65

Step 1: tert-butyl (S)-(1-amino-3-cyclopropylpropan-2-yl)carbamate

To a solution of tert-butyl (S)-(1-azido-3-cyclopropylpropan-2-yl)carbamate (580 mg, 2.4 mmol) in MeOH (8 mL) was added Pd/C (100 mg, 5% wt) at 0° C. and the mixture was degassed under $N_2$ atmosphere for three times and stirred under a $H_2$ balloon at room temperature for 2 hrs. The mixture was filtered and the filtrate was concentrated to dryness to give the title compound (500 mg, 96.6% yield) as yellow solid. LC/MS (ESI) (m/z): 215 $(M+H)^+$.

Step 2: 4-(6-ethyl-5-iodopyridin-2-yl)-1-methyl-11H-1,2,3-triazole-5-carbaldehyde To a solution of oxalyl chloride (0.15 mL, 1.74 mmol) in DCM (10 mL) was added a solution of DMSO (0.19 mL, 2.6 mmol) in DCM (2 mL) at −78° C. After stirring for 20 minutes, a solution of (4-(6-ethyl-5-iodopyridin-2-yl)-1-methyl-1H-1,2,3-triazol-5-yl)methanol (300 mg, 0.87 mmol) in DCM (5 mL) was added and the mixture was stirred at −78° C. for 2 hrs. TEA (0.47 mL, 3.4 mmol) was added drop-wisely at −78° C. and the resulting mixture was stirred from −78° C. to r.t. for 2 hrs. The mixture was diluted with DCM (5 mL) and washed with water and brine, dried over anhydrous $Na_2SO_4$, filtered and concentrated under reduced pressure to dryness. The residue was purified by chromatography on silica gel (PE:EtOAc=3:1) to give the title compound (170 mg, 57.0% yield) as white solid. LC/MS (ESI) (m/z): 343 $(M+H)^+$.

Step 3: tert-butyl (S)-(1-cyclopropyl-3-(((4-(6-ethyl-5-iodopyridin-2-yl)-1-methyl-1H-1,2,3-triazol-5-yl)methyl)amino)propan-2-yl)carbamate To a mixture of 4-(6-ethyl-5-iodopyridin-2-yl)-1-methyl-1H-1,2,3-triazole-5-carbaldehyde (173 mg, 0.51 mmol) and tert-butyl (S)-(1-amino-3-cyclopropylpropan-2-yl)carbamate (108 mg, 0.5 mmol) in DCE (5 mL) was added sodium triacetoxyborohydride (160 mg, 0.76 mmol) and the reaction was stirred at room temperature under $N_2$ atmosphere for 4 hrs. The reaction mixture was quenched with saturated aq·$NaHCO_3$ solution (5 mL) and extracted with DCM (2×5 mL). The combined organic layers were washed with brine, dried over anhydrous $Na_2SO_4$, filtered and concentrated under reduced pressure to dryness. The residue was purified by chromatography on silica gel (PE:EtOAc=2:1) to give the title compound (160 mg, 58.6% yield) as white solid. LC/MS (ESI) (m/z): 541 $(M+H)^+$.

Step 4: (S)-3-cyclopropyl-N1-((4-(6-ethyl-5-iodopyridin-2-yl)-1-methyl-11H-1,2,3-triazol-5-yl)methyl)propane-1,2-diamine TFA salt To a solution of tert-butyl (S)-(1-cyclopropyl-3-(((4-(6-ethyl-5-iodopyridin-2-yl)-1-methyl-1H-1,2,3-triazol-5-yl)methyl)amino)propan-2-yl)carbamate (160 mg, 0.3 mmol) in DCM (5 mL) was added TFA (5 mL, 67.3 mmol) at 0° C. and the reaction mixture was stirred at room temperature for 2 hrs. The reaction mixture was concentrated under reduced pressure to give the title compound (160 mg, yield 100%) as yellow oil, which was directly used in the next step. LC/MS (ESI) (m/z): 441 $(M+H)^+$.

Step 5: (S)-4-(cyclopropylmethyl)-1-((4-(6-ethyl-5-iodopyridin-2-yl)-1-methyl-1H-1,2,3-triazol-5-yl)methyl)imidazolidin-2-one To a solution of (S)-3-cyclopropyl-$N_1$-((4-(6-ethyl-5-iodopyridin-2-yl)-1-methyl-1H-1,2,3-triazol-5-yl)methyl)propane-1,2-diamine TFA salt (160 mg, 0.34 mmol) in DCM (6 mL) were added TEA (0.13 mL, 0.91 mmol) and CDI (49.3 mg, 0.3 mmol) and the mixture was stirred at room temperature for 16 hrs. The reaction mixture was washed with water and brine, dried over anhydrous $Na_2SO_4$, filtered and concentrated under reduced pressure to dryness. The residue was purified by chromatography on silica gel (PE:EtOAc=3:1) to give the title compound (110 mg, 77.5% yield) as white solid. LC/MS (ESI) (m/z): 467 $(M+H)^+$.

Step 6: methyl 2-((S)-1-(6-(5-(((S)-4-(cyclopropylmethyl)-2-oxoimidazolidin-1-yl)methyl)-1-methyl-1H-1,2,3-triazol-4-yl)-2-ethylpyridin-3-yl)-5,5-difluoropiperidin-3-yl)acetate To a mixture of (S)-4-(cyclopropylmethyl)-1-((4-(6-ethyl-5-iodopyridin-2-yl)-1-methyl-1H-1,2,3-triazol-5-yl)methyl)imidazolidin-2-one (30 mg, 0.064 mmol) and methyl (S)-2-(5,5-difluoropiperidin-3-yl)acetate (12.4 mg, 0.064 mmol) in 1,4-dioxane (2 mL) were added $Cs_2CO_3$ (42 mg, 0.128 mmol), RuPhos (15 mg, 0.032 mmol) and RuPhos Pd G3 (15 mg, 0.064 mmol) under $N_2$ atmosphere and the mixture reaction was stirred at 100° C. under $N_2$ atmosphere for 16 hrs. The reaction mixture was diluted with EtOAc (5 mL), washed with water and brine, dried over $Na_2SO_4$, filtered and concentrated to dryness. The residue was purified by prep-TLC (PE:EtOAc=2:1) to give the title compound (15 mg, 43.9% yield) as yellow solid. LC/MS (ESI) (m/z): 532 $(M+H)^+$.

Step 7: 2-((S)-1-(6-(5-(((S)-4-(cyclopropylmethyl)-2-oxoimidazolidin-1-yl)methyl)-1-methyl-1H-1,2,3-triazol-4-yl)-2-ethylpyridin-3-yl)-5,5-difluoropiperidin-3-yl)acetic acid To a solution of methyl 2-((S)-1-(6-(5-(((S)-4-(cyclopropylmethyl)-2-oxoimidazolidin-1-yl)methyl)-1-methyl-1H-1,2,3-triazol-4-yl)-2-ethylpyridin-3-yl)-5,5-difluoropiperidin-3-yl)acetate (15 mg, 0.028 mmol) in THE (1 mL) and MeOH (2 mL) was added a solution of LiOH (6.7 mg, 0.28 mmol) in water (1 mL) at 0° C. After stirring at room temperature for 2 hrs, the reaction mixture was concentrated to dryness and the residue was dissolved in water (3 mL). The mixture was washed with EtOAc twice and the aqueous layer was acidified with 1N aq·HCl to pH~2 and extracted with EtOAc (2×3 mL). The combined organic layers were washed with brine, dried over anhydrous $Na_2SO_4$, filtered and concentrated to dryness. The residue was purified by prep-HPLC (C18, 25-95%, MeCN in $H_2O$ with 0.1% HCOOH) to give the title compound (4.3 mg, 29.6% yield) as white solid. LC/MS (ESI) (m/z): 518 $(M+H)^+$. $^1H$ NMR (400 MHz, $CD_3OD$) δ 7.88 (d, J=8.4 Hz, 1H), 7.58 (d, J=8.4 Hz, 1H), 5.12 (s, 2H), 4.12 (s, 3H), 3.72-3.65 (m, 1H), 3.44 (t, J=8.9 Hz, 1H), 3.26-3.21 (m, 2H), 3.13-3.07 (m, 1H), 3.06-3.02 (m, 1H), 3.0-2.94 (m, 2H), 2.61 (t, J=10.3 Hz, 1H), 2.55-2.46 (m, 1H), 2.41-2.39 (m, 2H), 2.33-2.25 (m, 1H), 1.81-1.67 (m, 1H), 1.42-1.22 (m, 8H), 0.61-0.55 (m, 1H), 0.38-0.36 (m, 2H).

Example 66: 2-[(3R)-1-[2-ethyl-6-(1-methyl-5-{[3-methyl-4-(2-methylpropyl)-2-oxo-2,3-dihydro-1H-imidazol-1-yl]methyl}-1H-1,2,3-triazol-4-yl)pyridin-3-yl]-5,5-difluoropiperidin-3-yl]acetic acid

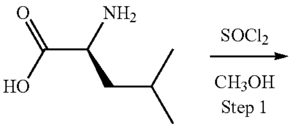

1

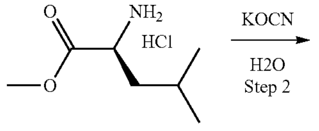

2

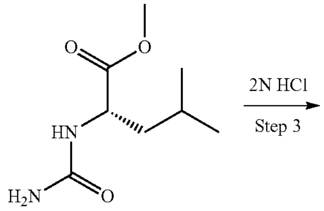

3

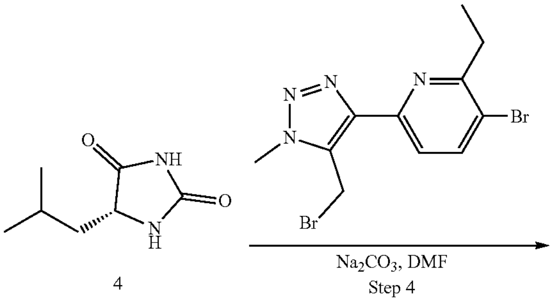

4

-continued

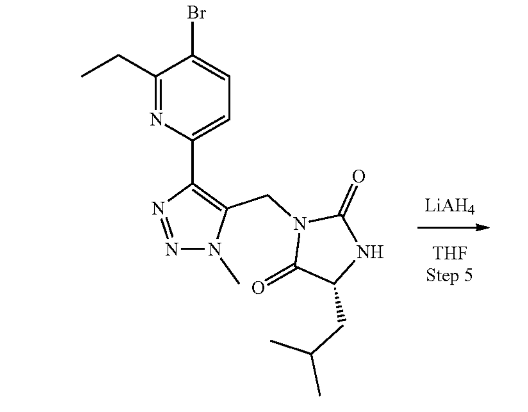

5

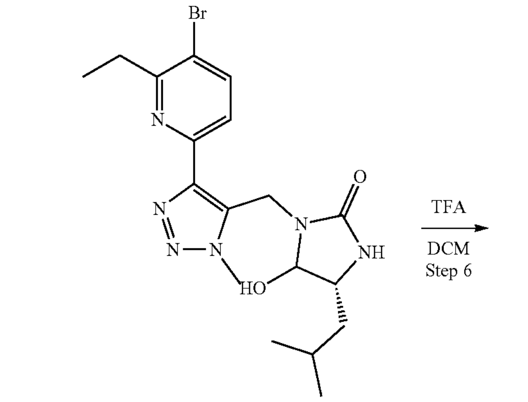

6

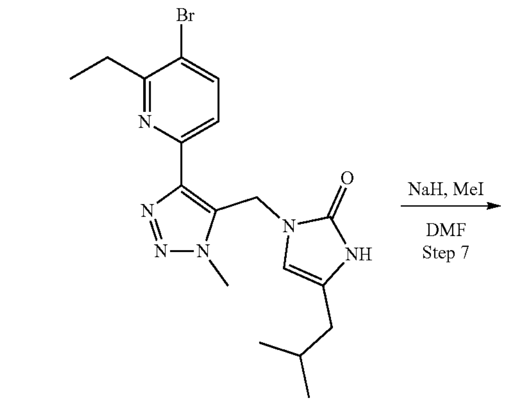

7

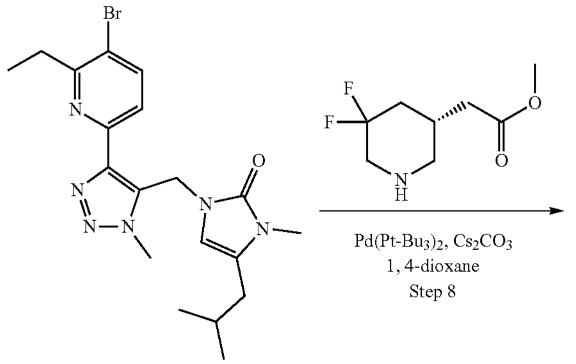

8

-continued

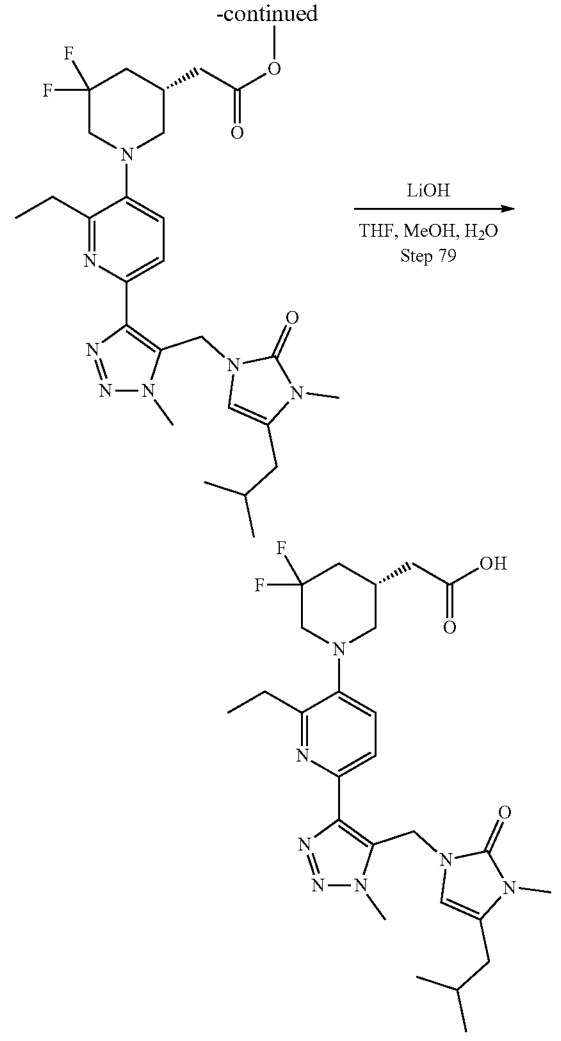

Example 66

Step 1: methyl (2S)-2-amino-4-methylpentanoate hydrochloride

To a solution of L-leucine (5 g, 38.12 mmol) in MeOH (50 mL) was added sulfuryl dichloride (6.2 mL, 76.24 mmol) and the reaction mixture was stirred at r.t. for 16 hrs. The mixture was concentrated to dryness to give the title compound (5 g, 90.3% yield) as white solid.

Step 2: (5R)-5-(2-methylpropyl)imidazolidine-2,4-dione

To a solution of methyl (2S)-2-amino-4-methylpentanoate (4 g, 27.6 mmol) in water (50 mL) was added KOCN (2.35 g, 28.9 mmol) and the mixture was stirred at r.t. for 1 hr. The mixture was extracted with EtOAc (2×20 mL) and the combined organic layers were washed with brine, dried over $Na_2SO_4$, filtered and concentrated to dryness. The residue was dissolved in 2N aq·HCl (20 mL) and the mixture was stirred at reflux for 1 hr. The mixture was extracted with EtOAc (3×10 mL) and the combined organic phases were dried over $Na_2SO_4$, filtered and concentrated to dryness to give the title compound (2.3 g, 53.5% yield). LC/MS (ESI) m/z: 157 $(M+H)^+$.

Step 3: 3-{[4-(5-bromo-6-ethylpyridin-2-yl)-1-methyl-1H-1,2,3-triazol-5-yl]methyl}-5-(2-methylpropyl)imidazolidine-2,4-dione To a stirred mixture of 3-bromo-6-[5-(bromomethyl)-1-methyl-1H-1,2,3-triazol-4-yl]-2-ethylpyridine (500 mg, 1.39 mmol) and 5-(2-methylpropyl)imidazolidine-2,4-dione (434 mg, 2.78 mmol) in DMF (10 mL) was added $Na_2CO_3$ (442 mg, 4.17 mmol) in portions at r.t., and the mixture was stirred at 50° C. for 16 hrs. The reaction mixture was quenched with $H_2O$ (10 mL) and extracted with EtOAc (3×5 mL). The combined organic phase was washed with brine, dried over $Na_2SO_4$, filtered and concentrated to dryness. The residue was purified by flash chromatography flash chromatography (silica gel, EtOAc:PE=1:2) to give the title compound (200 mg, 33.1% yield) as white solid. LC/MS (ESI) m/z: 436/438 $(M+H)^+$.

Step 4: 1-{[4-(5-bromo-6-ethylpyridin-2-yl)-1-methyl-1H-1,2,3-triazol-5-yl]methyl}-5-hydroxy-4-(2-methylpropyl)imidazolidin-2-one To a stirred solution of 3-{[4-(5-bromo-6-ethylpyridin-2-yl)-1-methyl-1H-1,2,3-triazol-5-yl]methyl}-5-(2-methylpropyl)imidazolidine-2,4-dione (50 mg, 0.12 mmol) in THF (5 mL) was added $LiAlH_4$ (9 mg, 0.23 mmol) at 0° C. and the mixture was stirred at this temperature for 30 mins. The reaction mixture was quenched with $Na_2SO_4 \cdot 9H_2O$ and stirred at r.t. for 10 mins. The mixture was filtered and the filtrate was concentrated to dryness to give the title compound (50 mg, 79.6% yield) as white solid. LC/MS (ESI) m/z: 438/440 $(M+H)^+$.

Step 5: (S)-2-(N-methyl-4-nitrophenylsulfonamido)hex-5-enoic acid

To a stirred solution of 1-{[4-(5-bromo-6-ethylpyridin-2-yl)-1-methyl-1H-1,2,3-triazol-5-yl]methyl}-5-hydroxy-4-(2-methylpropyl)imidazolidin-2-one (50 mg, 0.11 mmol) in DCM (5 mL) was added TFA (0.5 mL) at r.t. After stirring at r.t. for 3 hrs, the reaction mixture was concentrated to dryness under reduced pressure to give the title compound (50 mg, 104.3% yield) as yellow oil, which was used directly without further purification. LC/MS (ESI) m/z: 420/422 $(M+H)^+$.

Step 6: 1-{[4-(5-bromo-6-ethylpyridin-2-yl)-1-methyl-1H-1,2,3-triazol-5-yl]methyl}-3-methyl-4-(2-methylpropyl)-2,3-dihydro-1H-imidazol-2-one To a stirred solution of 1-{[4-(5-bromo-6-ethylpyridin-2-yl)-1-methyl-1H-1,2,3-triazol-5-yl]methyl}-4-(2-methylpropyl)-2,3-dihydro-1H-imidazol-2-one (50 mg, 0.12 mmol) in DMF (5 mL) was added NaH (14 mg 0.36 mmol, 60% dispersion in mineral oil) in portions at 0° C., and the mixture was stirred at this temperature for 30 mins. MeI (0.015 mL, 0.24 mmol) was added to the mixture and the resulting mixture was stirred at r.t. for 3 hrs. The reaction mixture was quenched with sat·$NH_4Cl$ solution and extracted with EtOAc (3×5 mL). The combined organic phase was washed with brine, dried over $Na_2SO_4$ and concentrated. The residue was purified by flash chromatography (silica gel, EtOAc:PE=1:3) to give the title compound (50 mg, 96.8% yield) as white solid. LC/MS (ESI) m/z: 434/436 $(M+H)^+$.

Step 7: methyl 2-[(3R)-1-[2-ethyl-6-(1-methyl-5-{[3-methyl-4-(2-methylpropyl)-2-oxo-2,3-dihydro-1H-imidazol-1-yl]methyl}-1H-1,2,3-triazol-4-yl)pyridin-3-yl]-5,5-difluoropiperidin-3-yl]acetate To a solution of 1-{[4-(5-bromo-6-ethylpyridin-2-yl)-1-methyl-1H-1,2,3-triazol-5-yl]methyl}-3-methyl-4-(2-methylpropyl)-2,3-dihydro-1H-imidazol-2-one (50 mg, 0.12 mmol) in 1,4-dioxane (5 mL) was added methyl 2-[(3R)-5,5-difluoropiperidin-3-yl]acetate (27 mg, 0.14 mmol) followed by the addition of $CS_2CO_3$ (114 mg, 0.35 mmol) and Bis(tri-tert-butylphosphine)palladium (6 mg, 0.012 mmol) under $N_2$ atmosphere with stirring and the mixture was stirred at 100° C. for 16 hrs. The reaction mixture was filtered through a Celite pad and the filtrate was concentrated to dryness. The residue was purified by flash chromatography (silica gel, 0~50% EtOAc in PE) to give the title compound (28 mg, 44.4% yield) as yellow solid. LC/MS (ESI) m/z: 546 $(M+H)^+$.

Step 8: 2-[(3R)-1-[2-ethyl-6-(1-methyl-5-{[3-methyl-4-(2-methylpropyl)-2-oxo-2,3-dihydro-1H-imidazol-1-yl]methyl}-1H-1,2,3-triazol-4-yl)pyridin-3-yl]-5,5-difluoropiperidin-3-yl]acetic acid To a solution of methyl 2-[(3R)-1-[2-ethyl-6-(1-methyl-5-{[3-methyl-4-(2-methylpropyl)-2-oxo-2,3-dihydro-1H-imidazol-1-yl]methyl}-1H-1,2,3-triazol-4-yl)pyridin-3-yl]-5,5-difluoropiperidin-3-yl]acetate (28 mg, 0.051 mmol) in THE (5 mL) and MeOH (1 mL) was added LiOH (8 mg, 0.33 mmol) in $H_2O$ (1 mL) and the reaction was stirred at r.t. for 3 hrs. The mixture was concentrated to dryness and the residue was dissolved in $H_2O$ (3 mL). The mixture was acidified with 1 N aq·HCl to pH~4 and extracted with DCM (2×5 mL). The combined organic layers were washed with brine, dried over $Na_2SO_4$, filtered and concentrated to dryness. The residue was purified by perp-HPLC (C18, 0~90% acetonitrile in $H_2O$ with 0.1% formic acid) to give the title compound (6 mg, 22% yield) as white solid. LC/MS (ESI) m/z: 532 $(M+H)^+$. $^1H$ NMR (400 MHz, $CD_3OD$) δ 7.90 (d, J=8.3 Hz, 1H), 7.60 (d, J=8.4 Hz, 1H), 6.29 (s, 1H), 5.50 (s, 2H), 4.12 (s, 3H), 3.28-3.21 (m, 2H), 3.19 (s, 3H), 3.17-3.04 (m, 1H), 2.98 (q, J=7.5 Hz, 2H), 2.61 (t, J=10.6 Hz, 1H), 2.57-2.46 (m, 1H), 2.40 (d, J=6.9 Hz, 2H), 2.36-2.26 (m, 1H), 2.23-2.16 (m, 2H), 1.83-1.64 (m, 2H), 1.33 (t, J=7.5 Hz, 3H), 0.86 (d, J=6.6 Hz, 6H).

Example 67: Preparation of (S)-2-(1-(6-(5-((4-(cyclopropylmethyl)-3-methyl-2-oxo-2,3-dihydro-1H-imidazol-1-yl)methyl)-1-methyl-1H-1,2,3-triazol-4-yl)-2-methylpyridin-3-yl)-5,5-difluoropiperidin-3-yl) acetic acid Example 67

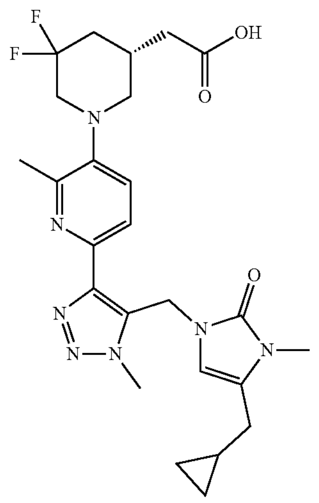

The title compound was prepared from (S)-2-amino-3-cyclopropylpropanoic acid using the same synthetic sequence that was used to synthesize example 66. LC/MS (ESI) m/z: 517 $(M+H)^+$. $^1H$ NMR (400 MHz, DMSO-$d_6$) δ 7.88 (d, J=8.3 Hz, 1H), 7.58 (d, J=8.4 Hz, 1H), 6.50 (s, 1H), 5.26 (s, 2H), 4.14 (s, 3H), 3.22-3.07 (m, 2H), 3.05 (s, 3H), 2.60 (d, J=10.0 Hz, 1H), 2.55 (s, 3H), 2.39-2.25 (m, 4H), 2.21 (d, J=5.9 Hz, 2H), 1.81-1.74 (m, 1H), 0.79-0.75 (m, 1H), 0.46-0.33 (m, 2H), 0.09-0.01 (m, 2H).

Example 68: (S)-2-(1-(6-(5-((3-(cyclopropylmethyl)-4-methyl-5-oxo-4,5-dihydro-1H-1,2,4-triazol-1-yl)methyl)-1-methyl-1H-1,2,3-triazol-4-yl)-2-ethylpyridin-3-yl)-5,5-difluoropiperidin-3-yl)acetic acid

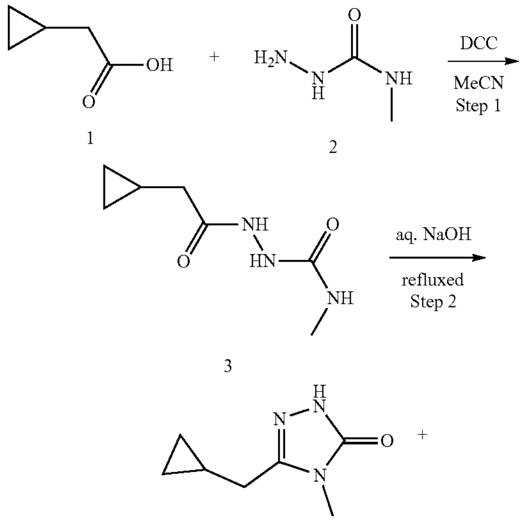

1 2 3 4

-continued

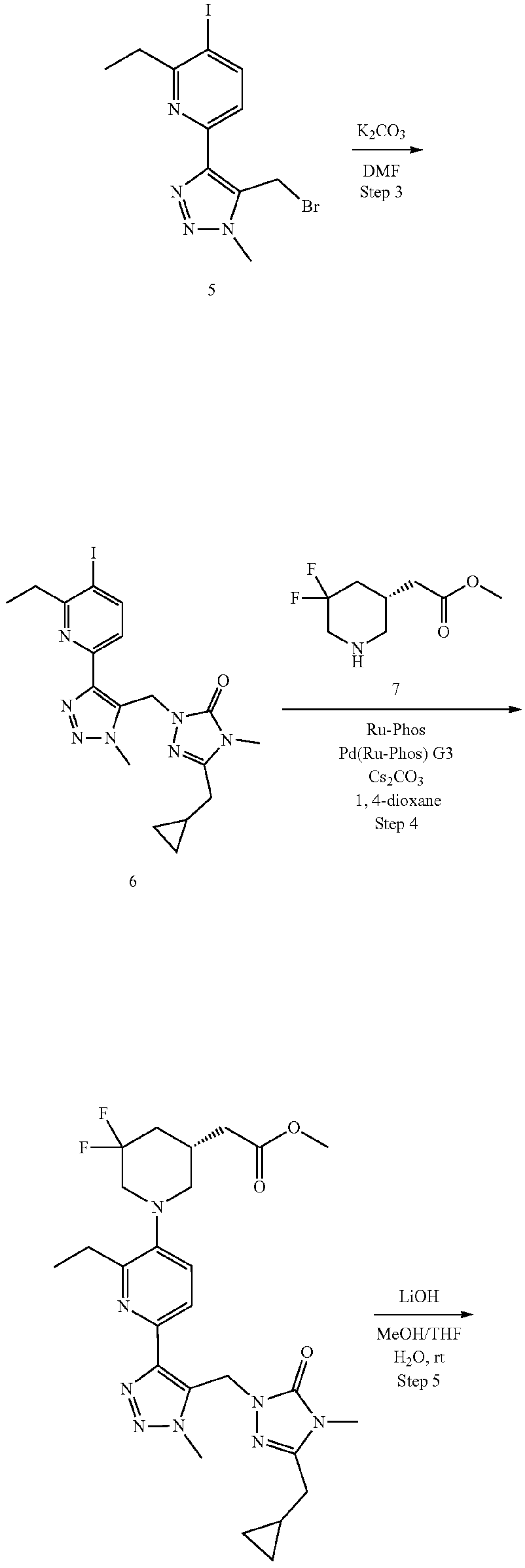

5 6 7 8

-continued

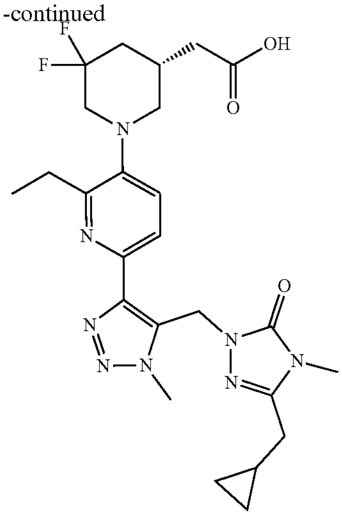

Example 68

Step 1: 2-cyclopropyl-N-[(methylcarbamoyl)amino] acetamide

To a solution of 2-cyclopropylacetic acid (500 mg, 5.0 mmol) and 1-amino-3-methylurea (370 mg, 4.2 mmol) in MeCN (10 mL) was added DCC (1.03 g, 5.0 mmol) at 0° C. under $N_2$ atmosphere. After the addition, the resulting solution was stirred at r.t. for 3 hrs. The mixture was diluted with EtOAc (10 mL) and washed with water and brine, dried over anhydrous $Na_2SO_4$, filtered and concentrated to dryness to give the title compound (560 mg, 78.6% yield) as white solid. LC/MS (ESI) m/z: 172 $(M+1)^+$.

Step 2: 3-(cyclopropylmethyl)-4-methyl-4,5-dihydro-1H-1,2,4-triazol-5-one

A solution of 2-cyclopropyl-N-[(methylcarbamoyl)amino]acetamide (514 mg, 3.0 mmol) in aq·NaOH solution (12 mL, 24.0 mmol, 2 M in water) was stirred at 100° C. for 16 hrs. The mixture was washed with EtOAc (30 mL) and the aqueous layer was treated with 1N aq·HCl to adjust pH=1. The aqueous layer was concentrated under vacuum to dryness and the residue was purified by flash chromatography (eluent: 0~50% of MeOH in $H_2O$) to give the title compound (220 mg, 47.8% yield) as white solid. LC/MS (ESI) m/z: 154 (M+1)*.

Step 3: 3-(cyclopropylmethyl)-1-{[4-(6-ethyl-5-iodopyridin-2-yl)-1-methyl-1H-1,2,3-triazol-5-yl]methyl}-4-methyl-4,5-dihydro-1H-1,2,4-triazol-5-one To a mixture of 6-[5-(bromomethyl)-1-methyl-1H-1,2,3-triazol-4-yl]-2-ethyl-3-iodopyridine (50 mg, 0.12 mmol) and $K_2CO_3$ (51 mg, 0.37 mmol) in DMF (5 mL) was added 3-(cyclopropylmethyl)-4-methyl-4,5-dihydro-1H-1,2,4-triazol-5-one (28 mg, 0.18 mmol) under $N_2$ atmosphere. After the addition, the resulting solution was stirred at 60° C. for 3 hrs. The mixture was diluted with EtOAc (5 mL) and washed with water and brine, dried over anhydrous $Na_2SO_4$, filtered and concentrated to dryness. The residue was purified by flash chromatography (eluent: 0~100% of EtOAc in PE) to give the title compound (36 mg, 61.1% yield) as white solid. LC/MS (ESI) m/z: 480 $(M+1)^+$.

Step 4: methyl (S)-2-(1-(6-(5-((3-(cyclopropylmethyl)-4-methyl-5-oxo-4,5-dihydro-1H-1,2,4-triazol-1-yl)methyl)-1-methyl-1H-1,2,3-triazol-4-yl)-2-ethylpyridin-3-yl)-5,5-difluoropiperidin-3-yl)acetate To a mixture of 5-(cyclopropylmethyl)-2-((4-(6-ethyl-5-iodopyridin-2-yl)-1-methyl-1H-1,2,3-triazol-5-yl)methyl)-4-methyl-2,4-dihydro-3H-1,2,4-triazol-3-one (36 mg, 0.075 mmol) and methyl (S)-2-(5,5-difluoropiperidin-3-yl)acetate (14.5 mg, 0.075 mmol) in 1,4-dioxane (8 mL) were added $Cs_2CO_3$ (49 mg, 0.15 mmol), Ru-Phos Pd G3 (14 mg, 0.015 mmol), Ru-phos (7 mg, 0.017 mmol) under $N_2$ atmosphere. The mixture was degassed under $N_2$ atmosphere for three times and stirred under $N_2$ atmosphere at 110° C. for 16 hrs. The mixture was diluted with EtOAc (5 mL) and washed with water, brine, dried over anhydrous $Na_2SO_4$, filtered and concentrated to dryness. The residue was purified by flash chromatography (eluent: 0-50% of EtOAc in PE) to give the title compound (26 mg, 61.1% yield) as yellow solid. LC/MS (ESI) m/z: 545 $(M+H)^+$.

Step 5: (S)-2-(1-(6-(5-((3-(cyclopropylmethyl)-4-methyl-5-oxo-4,5-dihydro-1H-1,2,4-triazol-1-yl)methyl)-1-methyl-1H-1,2,3-triazol-4-yl)-2-ethylpyridin-3-yl)-5,5-difluoropiperidin-3-yl)acetic acid To a solution of (S)-2-(1-(6-(5-((3-(cyclopropylmethyl)-4-methyl-5-oxo-4,5-dihydro-1H-1,2,4-triazol-1-yl)methyl)-1-methyl-1H-1,2,3-triazol-4-yl)-2-ethylpyridin-3-yl)-5,5-difluoropiperidin-3-yl)acetate (26 mg, 0.05 mmol) in MeOH (1 mL), water (1 mL) and THF (4 mL) was added LiOH (14 mg, 0.34 mmol) and the mixture was stirred at 25° C. for 1 hr. The reaction mixture was acidified with 1M aq·HCl and extracted with DCM (2x3 mL). The combined organic layers were washed with brine, dried over $Na_2SO_4$, filtered and concentrated to dryness. The residue was purified by prep-HPLC to give the title compound (8.9 mg, 41.6% yield) as white solid. LC/MS (ESI) m/z: 531 [M+1]+. $^1$H NMR (400 MHz, $CD_3OD$) δ 7.83 (d, J=8.1 Hz, 1H), 7.55 (d, J=8.2 Hz, 1H), 5.72 (s, 2H), 4.13 (s, 3H), 3.52-3.45 (m, 1H), 3.25-3.23 (m, 1H), 3.23 (s, 3H), 3.22-3.19 (m, 1H), 3.13 (d, J=1.6 Hz, 2H), 2.95 (q, J=7.6 Hz, 2H), 2.64-2.54 (m, 1H), 2.53-2.45 (m, 1H), 2.42 (d, J=6.9 Hz, 2H), 2.38 (dd, J=6.7, 2.8 Hz, 2H), 1.32 (t, J=7.5 Hz, 3H), 0.96 (m, 1H), 0.52-0.47 (m, 2H), 0.15-0.12 (m, 2H).

Example 69: 2-((R)-1-(6-(5-(((S)-5-(cyclopropylmethyl)-2-oxooxazolidin-3-yl)methyl)-1-methyl-1H-1,2,3-triazol-4-yl)-2-ethylpyridin-3-yl)-5,5-difluoropiperidin-3-yl)acetic acid

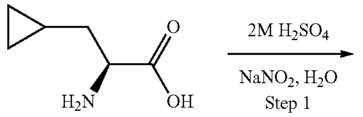

1

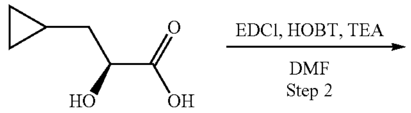

2

-continued
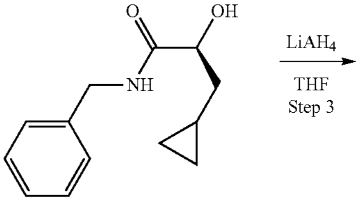
3
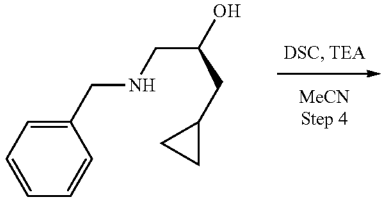
4
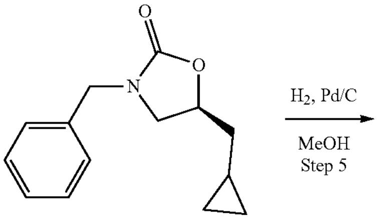
5
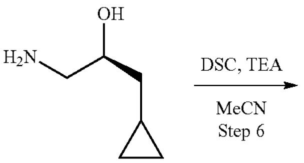
6
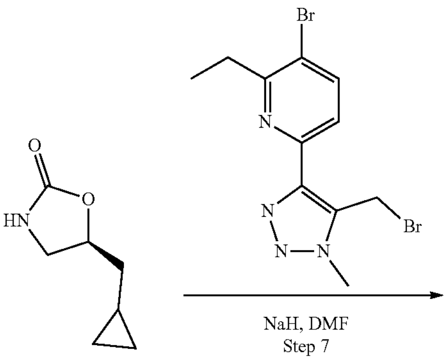
7
-continued
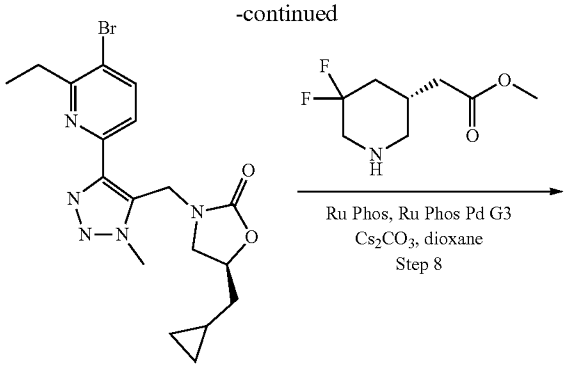
8
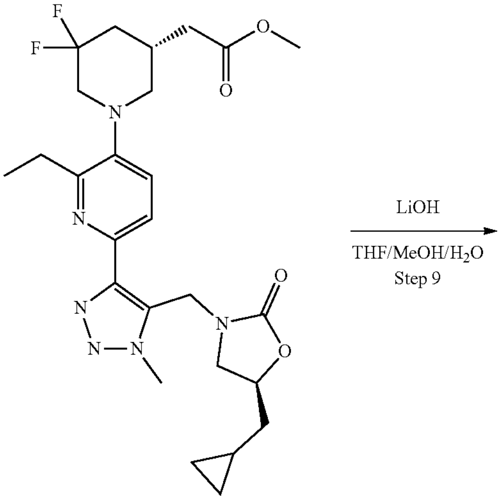
9
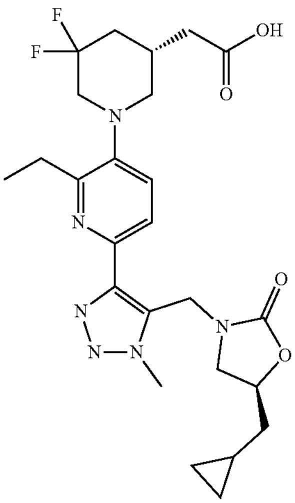
Example 69
Step 1: (S)-3-cyclopropyl-2-hydroxypropanoic acid
To suspension of (S)-2-amino-3-cyclopropylpropanoic acid (5 g, 38.7 mmol) in $H_2O$ (30 mL) was added 2N $H_2SO_4$ (22 mL, 44 mmol) and the mixture was cooled to 0° C. To the above mixture, 2N aq·$NaNO_2$ solution (19.5 mL, 39.0 mmol) were added drop-wisely while maintaining the internal temperature below than 5° C. The reaction was stirred at 0° C. for 3 hrs and r.t. for 16 hrs. The reaction mixture was saturated with NaCl and extracted with EtOAc (5×30 mL). The combined organic layers were dried over $Na_2SO_4$, filtered and concentrated to dryness to give the title compound (2.14 g, 42.5% yield) as yellow oil.

Step 2: (S)—N-benzyl-3-cyclopropyl-2-hydroxypropanamide

To a mixture of (S)-3-cyclopropyl-2-hydroxypropanoic acid (2.14 g, 16.4 mmol), phenylmethanamine (2.16 mL, 19.7 mmol), TEA (6.86 mL, 49.3 mmol) and HOBt (3.33 g, 24.7 mmol) in DMF (20 mL) was added EDCI (4.37 mL, 24.7 mmol) at 0° C. under $N_2$ atmosphere and the reaction was stirred at 25° C. for 2 hrs. Water (50 mL) was added and the mixture was extracted with EtOAc (3×20 mL). The combined organic layers were washed with brine, dried over $Na_2SO_4$, filtered and concentrated to dryness. The residue was purified by column chromatography on silica (DCM: MeOH=100:1 to 30:1) to give the title compound (2.6 g, 72.1% yield) as yellow oil. LC/MS (ESI) m/z: 220 $(M+H)^+$.

Step 3: (S)-1-(benzylamino)-3-cyclopropylpropan-2-ol

To suspension of $LiAlH_4$ (1.35 g, 35.6 mmol) in THE (10 mL) was added solution of (S)—N-benzyl-3-cyclopropyl-2-hydroxypropanamide (2.6 g, 11.8 mmol) in THE (10 mL) drop-wisely at 0° C. under $N_2$ atmosphere and the mixture was stirred at 70° C. for 16 hrs. The reaction was cooled to 0° C. and quenched with 1.5 mL water, 1.5 mL 15% NaOH solution and 4.5 mL water. The mixture was filtered and the filtrate was concentrated to dryness. The residue was purified by column chromatography on silica (DCM: MeOH=100:1 to 20:1) to give the title compound (1.53 g, 62.8% yield) as yellow solid. LC/MS (ESI) m/z: 206 $(M+H)^+$.

Step 4: (S)-3-benzyl-5-(cyclopropylmethyl)oxazolidin-2-one

To a solution of (S)-1-(benzylamino)-3-cyclopropylpropan-2-ol (1.5 g, 7.31 mmol) in $CH_3CN$ (15 mL) were added TEA (1.05 mL, 7.55 mmol) and N,N'-disuccinimidyl carbonate (1.87 g, 7.30 mmol) at 0° C. and the mixture was stirred at 25° C. for 16 hrs. The reaction mixture concentrated to dryness and the residue was purified by column chromatography on silica (DCM:MeOH=100:1 to 50:1) to give the title compound (1.3 g, 76.9% yield) as yellow oil. LC/MS (ESI) m/z: 232 $(M+H)^+$.

Step 5: (S)-1-amino-3-cyclopropylpropan-2-ol

To a solution of (S)-3-benzyl-5-(cyclopropylmethyl)oxazolidin-2-one (900 mg, 3.89 mmol) in MeOH (7 mL) was added Pd/C (100 mg, 10% wt) at 25° C. under $N_2$ atmosphere and the mixture was stirred under a $H_2$ balloon at 25° C. for 3 hrs. The mixture was filtered and the filtrate was concentrated to dryness to give the title compound (450 mg, 100% yield) as yellow oil. LC/MS (ESI) m/z: 116 $(M+H)^+$.

Step 6: (S)-5-(cyclopropylmethyl)oxazolidin-2-one

To a mixture of (S)-1-amino-3-cyclopropylpropan-2-ol (450 mg, 3.9 mmol) and TEA (1.21 mL, 8.7 mmol) in $CH_3CN$ (10 mL) was added DSC (1.2 g, 4.69 mmol) at 0° C. under $N_2$ atmosphere and the mixture was stirred at 25° C. for 16 hrs. The reaction was concentrated to dryness and the residue was purified by column chromatography on silica (DCM:MeOH=100:1 to 20:1) to give the title compound (460 mg, 83.5% yield) as white solid. LC/MS (ESI) m/z: 142 $(M+H)^+$.

Step 7: (S)-3-((4-(5-bromo-6-ethylpyridin-2-yl)-1-methyl-1H-1,2,3-triazol-5-yl)methyl)-5-(cyclopropylmethyl)oxazolidin-2-one To a solution of (S)-5-(cyclopropylmethyl)oxazolidin-2-one (102 mg, 0.722 mmol) in DMF (2 mL) was added NaH (44.4 mg, 1.11 mmol, 60% dispersion in mineral oil) at 0° C. under $N_2$ atmosphere and the mixture was stirred at 0° C. for 0.5 hr. A solution of 3-bromo-6-(5-(bromomethyl)-1-methyl-1H-1,2,3-triazol-4-yl)-2-ethylpyridine (200 mg, 0.555 mmol) in DMF (2 mL) was added to the mixture and the resulting mixture was stirred at r.t. for 2 hrs. The mixture was quenched with saturated aq·$NH_4Cl$ solution and extracted with EtOAc (2×10 mL). The combined organic layers were washed with brine, dried over $Na_2SO_4$, filtered and concentrated to dryness. The residue was purified by column chromatography on silica gel (PE:EtOAc=3:1 to 1:1) to give the title compound (175 mg, 75.0% yield) as white solid. LC/MS (ESI) m/z: 420 $(M+H)^+$.

Step 8: methyl 2-((S)-1-(6-(5-(((S)-5-(cyclopropylmethyl)-2-oxooxazolidin-3-yl)methyl)-1-methyl-1H-1,2,3-triazol-4-yl)-2-ethylpyridin-3-yl)-5,5-difluoropiperidin-3-yl)acetate To a mixture of (S)-3-((4-(5-bromo-6-ethylpyridin-2-yl)-1-methyl-1H-1,2,3-triazol-5-yl)methyl)-5-(cyclopropylmethyl)oxazolidin-2-one (130 mg, 0.309 mmol) and methyl (S)-2-(5,5-difluoropiperidin-3-yl)acetate (59.8 mg, 0.309 mmol) and $Cs_2CO_3$ (101 mg, 0.309 mmol) in 1,4-dioxane (4 mL) was added Ru PHOS (65 mg, 0.139 mmol) and RuPhos Pd G3 (65 mg, 0.078 mmol), the mixture was degassed under $N_2$ atmosphere for three times and stirred at 110° C. for 16 hrs. The mixture was filtered and the filtrate was concentrated to dryness. The residue was purified by column chromatography on silica gel (PE:EtOAc=3:1 to 1:1) to give the title compound (100 mg, 60.8% yield) as yellow solid. LC/MS (ESI) m/z: 543 $(M+H)^+$.

Step 9: 2-((S)-1-(6-(5-(((S)-5-(cyclopropylmethyl)-2-oxooxazolidin-3-yl)methyl)-1-methyl-1H-1,2,3-triazol-4-yl)-2-ethylpyridin-3-yl)-5,5-difluoropiperidin-3-yl)acetic acid To a solution of methyl 2-((S)-1-(6-(5-(((S)-5-(cyclopropylmethyl)-2-oxooxazolidin-3-yl)methyl)-1-methyl-1H-1,2,3-triazol-4-yl)-2-ethylpyridin-3-yl)-5,5-difluoropiperidin-3-yl)acetate (100 mg, 0.188 mmol) in THE (2 mL), MeOH (0.5 mL) and $H_2O$ (0.5 mL) was added LiOH—$H_2O$ (150 mg, 3.58 mmol) and the mixture was stirred at 25° C. for 2 hrs. The reaction mixture was concentrated to dryness and the residue was dissolved in $H_2O$ (5 mL). The mixture was washed with EtOAc (2×3 mL), acidified with 1N aq·HCl to pH~4 and extracted with DCM (2×3 mL). The combined organic layers were washed with brine, dried over $Na_2SO_4$, filtered and concentrated to dryness. The residue was purified by prep-HPLC to give the title compound (11.4 mg, 11.7% yield) as white solid. LC/MS (ESI) m/z: 519 $(M+H)^+$. $^1H$ NMR (400 MHz, $CD_3OD$) δ 7.89 (d, J=8.3 Hz, 1H), 7.57 (d, J=8.4 Hz, 1H), 5.27-5.11 (m, 2H), 4.58 (dt, J=13.6, 6.6 Hz, 1H), 4.14 (s, 3H), 3.60 (t, J=8.8 Hz, 1H), 3.26-3.20 (m, 3H), 3.15-3.01 (m, 1H), 2.97 (q, J=7.5 Hz, 2H), 2.65-2.55 (m, 1H), 2.52-2.50 (m, 1H), 2.43-2.36 (m, 2H), 2.31-2.29 (m, 1H), 1.81-1.66 (m, 1H), 1.65-1.58 (m, 1H), 1.42-1.33 (m, 4H), 0.70-0.59 (m, 1H), 0.45-0.33 (m, 2H), 0.09-0.04 (m, 2H).

Example 70: (R)-2-(1-(6-(5-((3-(cyclopropylmethyl)-2-oxoimidazolidin-1-yl)methyl)-1-methyl-1H-1,2,3-triazol-4-yl)-2-methylpyridin-3-yl)-5,5-difluoropiperidin-3-yl)acetic acid

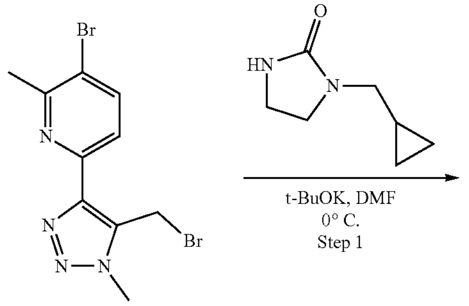

1

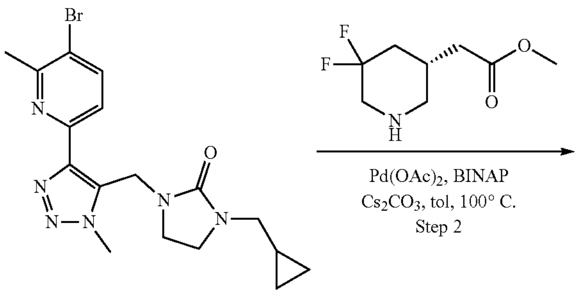

2

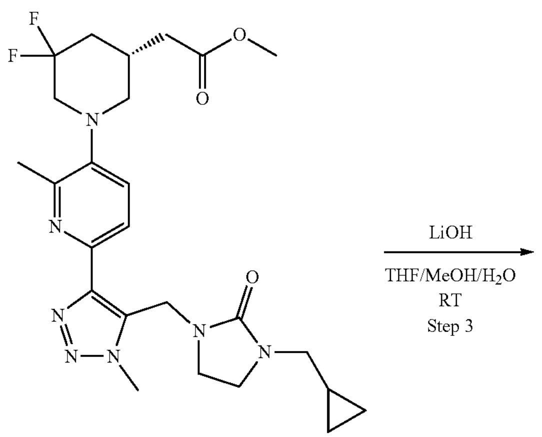

3

-continued

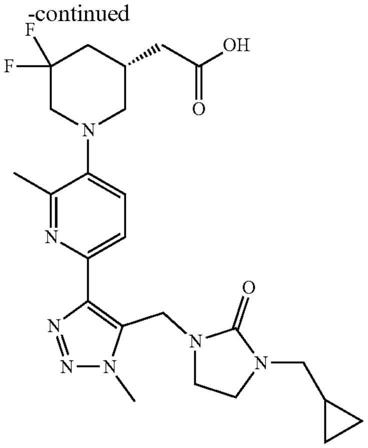

Example 70

Step 1: 1-((4-(5-bromo-6-methylpyridin-2-yl)-1-methyl-1H-1,2,3-triazol-5-yl)methyl)-3-(cyclopropylmethyl)imidazolidin-2-one To a solution of 3-bromo-6-(5-(bromomethyl)-1-methyl-1H-1,2,3-triazol-4-yl)-2-methylpyridine (100 mg, 0.29 mmol) and 1-(cyclopropylmethyl)imidazolidin-2-one (48.6 mg, 0.35 mmol) in DMF (2 mL) was added t-BuOK (1 M in THF, 0.58 mL, 0.58 mmol) at 0° C. under $N_2$ and the mixture was stirred at 0° C. for 1 hr. The mixture was quenched with water and extracted with EtOAc (2×3 mL). The combined organic layers were washed with brine, dried over anhydrous $Na_2SO_4$, filtered and concentrated to dryness. The residue was purified by flash chromatography (eluted with PE:EtOAc=30:1 to 3:1) to give the title compound (90 mg, 76.8% yield) as white solid. LC/MS (ESI) m/z: 405/407 $(M+H)^+$.

Step 2: methyl (S)-2-(1-(6-(5-((3-(cyclopropylmethyl)-2-oxoimidazolidin-1-yl)methyl)-1-methyl-1H-1,2,3-triazol-4-yl)-2-methylpyridin-3-yl)-5,5-difluoropiperidin-3-yl)acetate To a mixture of 1-((4-(5-bromo-6-methylpyridin-2-yl)-1-methyl-1H-1,2,3-triazol-5-yl)methyl)-3-(cyclopropylmethyl)imidazolidin-2-one (90 mg, 0.22 mmol) and methyl (S)-2-(5,5-difluoropiperidin-3-yl)acetate (64.4 mg, 0.33 mmol) in toluene (2 mL) were added $Cs_2CO_3$ (144.7 mg, 0.44 mmol), BINAP (27.7 mg, 0.044 mmol), $Pd(OAc)_2$ (5.0 mg, 0.022 mmol) under $N_2$ atmosphere, after addition, the mixture was degassed under $N_2$ atmosphere for three times and stirred at 100° C. for 16 hrs. The mixture was filtered and the filtrate was concentrated to dryness. The residue was purified by flash chromatography (PE:EtOAc=10:1 to 1:1) to give the title compound (95 mg, 82.7% yield) as white solid. LC/MS (ESI) m/z: 518 $(M+H)^+$.

Step 3: (S)-2-(1-(6-(5-((3-(cyclopropylmethyl)-2-oxoimidazolidin-1-yl)methyl)-1-methyl-1H-1,2,3-triazol-4-yl)-2-methylpyridin-3-yl)-5,5-difluoropiperidin-3-yl)acetic acid To a solution of methyl (S)-2-(1-(6-(5-((3-(cyclopropylmethyl)-2-oxoimidazolidin-1-yl)methyl)-1-methyl-1H-1,2,3-triazol-4-yl)-2-methylpyridin-3-yl)-5,5-difluoropiperidin-3-yl)acetate (95 mg, 0.18 mmol) in THE (2 mL), MeOH (0.5 mL) and $H_2O$ (0.5 mL) was added $LiOH \cdot H_2O$ (77 mg, 1.84 mmol) at 25° C. The reaction was stirred at 25° C. for 2 hrs. The mixture was concentrated to dryness and the residue was dissolved in water (5 mL). The mixture was washed with EtOAc twice and the aqueous layer was acidified with 1N aq·HCl to pH=2 and extracted with DCM (2×3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (14 mg, 15.1% yield) as white solid. LC/MS (ESI) m/z: 504 $(M+H)^+$. $^1H$ NMR (400 MHz, $CD_3OD$) δ 7.85 (d, J=8.2 Hz, 1H), 7.53 (d, J=8.4 Hz, 1H), 5.06 (s, 2H), 4.12 (s, 3H), 3.46-3.38 (m, 3H), 3.37-3.34 (m, 1H), 3.28-3.22 (m, 2H), 3.11-2.96 (m, 3H), 2.58 (s, 4H), 2.54-2.44 (m, 1H), 2.42-2.33 (m, 2H), 2.33-2.25 (m, 1H), 0.94-0.87 (m, 1H), 0.55-0.48 (m, 2H), 0.23-0.18 (m, 2H).

Example 71: (S)-2-(5,5-difluoro-1-(6-(5-((3-isobutyl-2-oxo-2,3-dihydro-1H-imidazol-1-yl)methyl)-1-methyl-1H-1,2,3-triazol-4-yl)-2-methylpyridin-3-yl)piperidin-3-yl)acetic acid

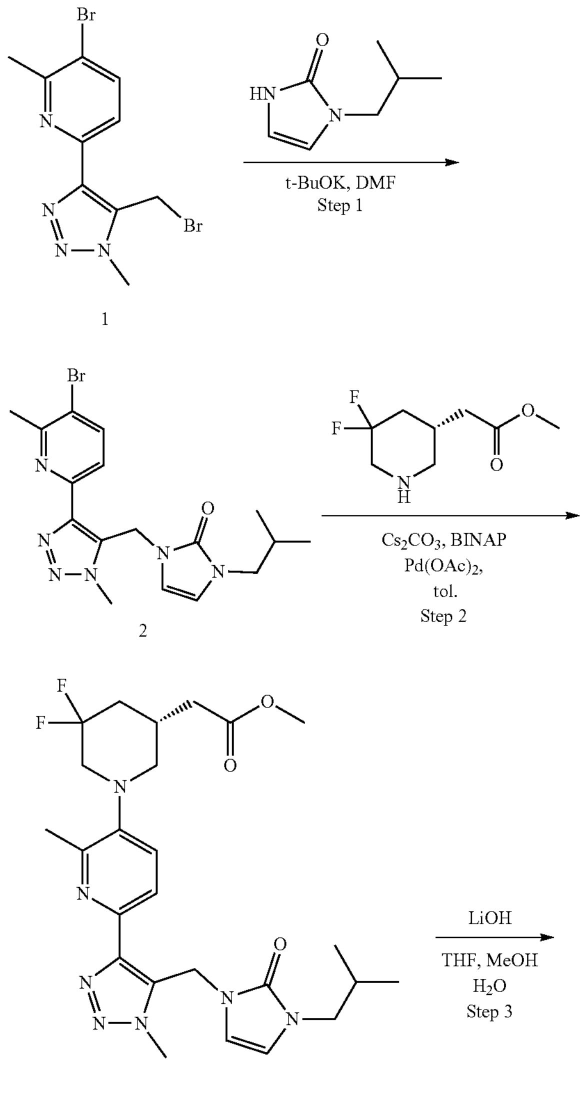

1

2

3

-continued

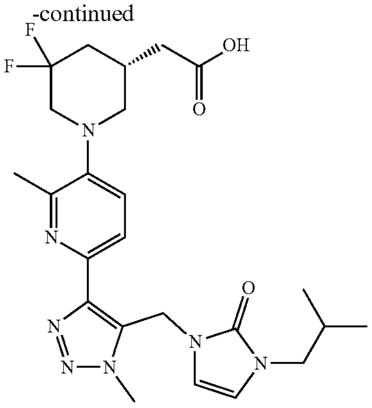

Example 73

Step 1: 1-((4-(5-bromo-6-methylpyridin-2-yl)-1-methyl-1H-1,2,3-triazol-5-yl)methyl)-3-isobutyl-1,3-dihydro-2H-imidazol-2-one To a mixture of 3-bromo-6-(5-(bromomethyl)-1-methyl-1H-1,2,3-triazol-4-yl)-2-methylpyridine (100 mg, 0.29 mmol) and 1-(2-methylpropyl)-2,3-dihydro-1H-imidazol-2-one (60 mg, 0.43 mmol) in DMF (2 mL) was added t-BuOK (0.58 mL, 0.58 mmol, 1M in THF) drop-wisely at 0° C. and the mixture was stirred at 0° C. for 2 hrs. The mixture was quenched with saturated aq·$NH_4Cl$ solution and extracted with EtOAc (2×10 mL). The combined organic layers were washed with brine, dried over $Na_2SO_4$, filtered and concentrated to dryness. The residue was purified by column silica chromatography on silica (PE:EtOAc=5:1 to 3:1) to give the title compound (90 mg, 76.8% yield) as yellow solid. LC/MS (ESI) m/z: 406 $(M+H)^+$.

Step 2: methyl (S)-2-(5,5-difluoro-1-(6-(5-((3-isobutyl-2-oxo-2,3-dihydro-1H-imidazol-1-yl)methyl)-1-methyl-1H-1,2,3-triazol-4-yl)-2-methylpyridin-3-yl)piperidin-3-yl)acetate To the mixture of 1-((4-(5-bromo-6-methylpyridin-2-yl)-1-methyl-1H-1,2,3-triazol-5-yl)methyl)-3-isobutyl-1,3-dihydro-2H-imidazol-2-one (40 mg, 0.10 mmol) and methyl (S)-2-(5,5-difluoropiperidin-3-yl)acetate (17 mg, 0.10 mmol) in toluene (2 mL) was added $Cs_2CO_3$ (96 mg, 0.30 mmol), BINAP (24 mg, 0.04 mmol) and $Pd(OAc)_2$ (9 mg, 0.04 mmol) under $N_2$ atmosphere. The mixture was degassed under $N_2$ atmosphere for three times and stirred at 110° C. for 16 hrs. The mixture was diluted with EtOAc (10 mL) and washed with water and brine, dried over $Na_2SO_4$, filtered and concentrated to dryness. The residue was purified by column chromatography on silica (PE:EtOAc=3:1) to give the title compound (40 mg, 78.3% yield). LC/MS (ESI) m/z: 518 $(M+H)^+$.

Step 3: (S)-2-(5,5-difluoro-1-(6-(5-((3-isobutyl-2-oxo-2,3-dihydro-1H-imidazol-1-yl)methyl)-1-methyl-1H-1,2,3-triazol-4-yl)-2-methylpyridin-3-yl)piperidin-3-yl)acetic acid To a solution of methyl (S)-2-(5,5-difluoro-1-(6-(5-((3-isobutyl-2-oxo-2,3-dihydro-1H-imidazol-1-yl)methyl)-1-methyl-1H-1,2,3-triazol-4-yl)-2-methylpyridin-3-yl)piperidin-3-yl)acetate (40 mg, 0.08 mmol) in THF (2 mL) and MeOH (1 mL) was added a solution of LiOH (7 mg, 0.29 mmol) in $H_2O$ (1 mL) and the mixture was stirred at r.t. for 2 hrs. The mixture was concentrated to dryness and the residue was dissolved in $H_2O$ (5 mL). The mixture was washed with EtOAc (2×3 mL), acidified with 1N aq·HCl to pH~4 and extracted with DCM (2×5 mL). The combined organic layers were washed with brine, dried over $Na_2SO_4$, filtered and concentrated to dryness. The residue was purified by perp-HPLC (C18, 0~90% acetonitrile in $H_2O$ with 0.1% formic acid) to give the title compound (20 mg, 51.4% yield) as white solid. LC/MS (ESI) m/z: 504 $(M+H)^+$. $^1H$ NMR (400 MHz, $CD_3OD$) δ 7.88 (d, J=8.3 Hz, 1H), 7.55 (d, J=8.4 Hz, 1H), 6.67 (d, J=3.0 Hz, 1H), 6.40 (d, J=3.0 Hz, 1H), 5.47 (s, 2H), 4.15 (s, 3H), 3.42 (d, J=7.3 Hz, 2H), 3.00-3.20 (m, 2H), 2.62-2.67 (m, 1H), 2.61 (s, 3H), 2.42-2.58 (m, 2H), 2.36-2.41 (m, 2H), 2.28-2.35 (m, 1H), 1.90-2.10 (m, 1H), 1.66-1.79 (m, 1H), 0.89 (d, J=6.7 Hz, 6H).

Example 72: (S)-2-(1-(6-(5-((3-(cyclopropylmethyl)-2-oxo-2,3-dihydro-1H-imidazol-1-yl)methyl)-1-methyl-1H-1,2,3-triazol-4-yl)-2-methylpyridin-3-yl)-5,5-difluoropiperidin-3-yl)acetic acid Example 72

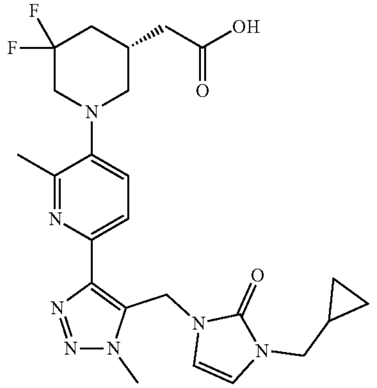

The title compound was prepared from 1-(cyclopropylmethyl)-1,3-dihydro-2H-imidazol-2-one using the same synthetic sequence that was used to synthesize example 71. LC/MS (ESI) (m/z): 502 $(M+H)^+$. $^1H$ NMR (400 MHz, $CD_3OD$) δ 7.89 (d, J=8.4 Hz, 1H), 7.55 (d, J=8.4 Hz, 1H), 6.67 (d, J=3.0 Hz, 1H), 6.51 (d, J=3.0 Hz, 1H), 5.47 (s, 2H), 4.16 (s, 3H), 3.47 (d, J=7.1 Hz, 2H), 3.37-3.31 (m, 2H), 3.14-3.01 (m, 1H), 2.63-2.55 (m, 4H), 2.53-2.45 (m, 1H), 2.45-2.36 (m, 2H), 2.35-2.25 (m, 1H), 1.82-1.63 (m, 1H), 1.14-1.04 (m, 1H), 0.57-0.50 (m, 2H), 0.32 (q, J=4.7 Hz, 2H).

Example 73: 2-((3S)-1-(6-(5-((3-(sec-butyl)-2-oxo-2,3-dihydro-1H-imidazol-1-yl)methyl)-1-methyl-1H-1,2,3-triazol-4-yl)-2-methylpyridin-3-yl)-5,5-difluoropiperidin-3-yl)acetic acid Example 73

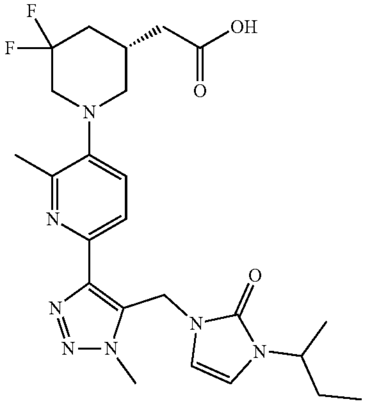

The title compound was prepared from 1-(sec-butyl)-1,3-dihydro-2H-imidazol-2-one using the same synthetic sequence that was used to synthesize example 71. LC/MS (ESI) m/z: 504 $(M+H)^+$. $^1H$ NMR (400 MHz, $CD_3OD$) δ 7.90-7.86 (d, J=8.4 Hz, 1H), 7.57-7.53 (d, J=8.4 Hz, 1H), 6.73-6.66 (d, J=3.0 Hz, 1H), 6.49-6.42 (d, J=3.0 Hz, 1H), 5.54-5.43 (m, 2H), 4.16 (s, 3H), 4.11-4.04 (m, 1H), 3.31 (s, 2H), 3.13-3.00 (m, 1H), 2.61 (s, 3H), 2.59-2.50 (d, J=11.0 Hz, 2H), 2.35-2.26 (d, J=6.8 Hz, 3H), 1.74-1.60 (m, 3H), 1.29-1.26 (d, J=6.8 Hz, 3H), 0.83-0.79 (m, 3H).

Example 74: (R)-2-(1-(6-(5-(((4-cyclobutylpyrimidin-2-yl)oxy)methyl)-1-methyl-11H-1,2,3-triazol-4-yl)-2-ethylpyridin-3-yl)piperidin-3-yl)acetic acid

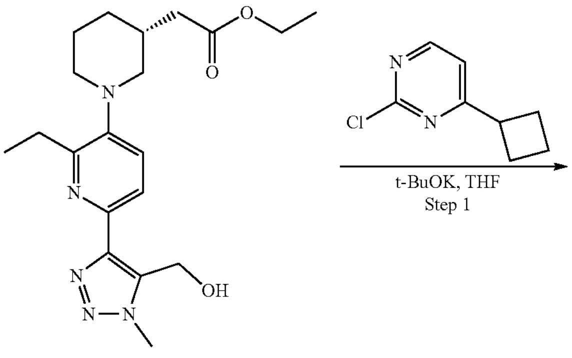

1

-continued

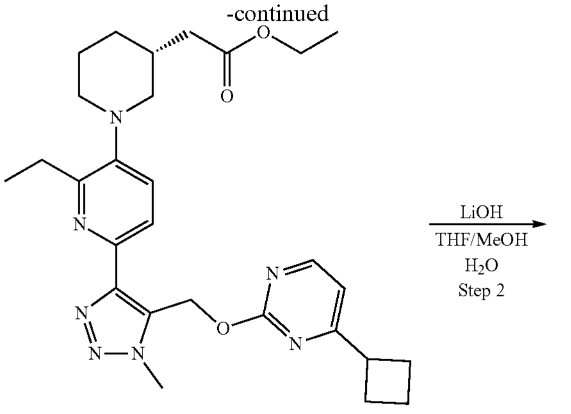

2

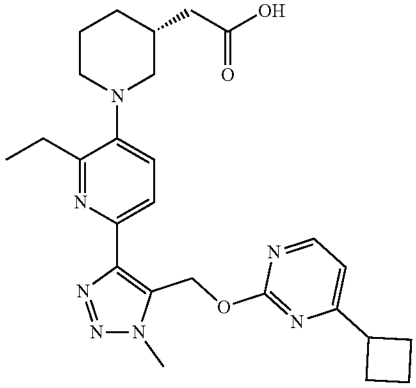

Example 74

Step 1: ethyl (R)-2-(1-(6-(5-(((4-cyclobutylpyrimidin-2-yl)oxy)methyl)-1-methyl-1H-1,2,3-triazol-4-yl)-2-ethylpyridin-3-yl)piperidin-3-yl)acetate To a mixture of ethyl 2-[(3R)-1-{2-ethyl-6-[5-(hydroxymethyl)-1-methyl-1H-1,2,3-triazol-4-yl]pyridin-3-yl}piperidin-3-yl]acetate (60 mg, 0.16 mmol) and 2-chloro-4-cyclobutylpyrimidine (34 mg, 0.2 mmol) in THF (5 mL) was t-BuOK (0.20 mL, 1M in THF) drop-wisely at 0° C. After the addition, the mixture was stirred at r.t. for 16 hrs. The reaction mixture was diluted with EtOAc (5 mL) and washed with water and brine, dried over anhydrous $Na_2SO_4$, filtered and concentrated to dryness. The residue was purified by flash chromatography (0-50% of EtOAc in PE) to give the title compound (62 mg, 77% yield) as white solid. LC-MS (ESI) m/z: 520 $[M+1]^+$.

Step 2: (R)-2-(1-(6-(5-(((4-cyclobutylpyrimidin-2-yl)oxy)methyl)-1-methyl-1H-1,2,3-triazol-4-yl)-2-ethylpyridin-3-yl)piperidin-3-yl)acetic acid To a solution of ethyl (R)-2-(1-(6-(5-(((4-cyclobutylpyrimidin-2-yl)oxy)methyl)-1-methyl-1H-1,2,3-triazol-4-yl)-2-ethylpyridin-3-yl)piperidin-3-yl)acetate (62 mg, 0.12 mmol) in MeOH (1 mL), water (1 mL) and THE (4 mL) was added LUGH (34 mg, 1 mmol) and the mixture was stirred at 25 #C for 1 hr. The reaction mixture was acidified with M aq·HCl to pH=3 and extracted with DCM (3x3 mL). The combined organic layers were washed with brine, dried over $Na_2SO_4$, filtered and concentrated to dryness. The residue was purified by prep-HPLC to give the title compound (31 mg, 55.20 yield) as white solid. LC/MS (ESI) m/z: 492 $[M+1]^+$. $^1$H NMR (400 MHz, $CD_3OD$) δ 8.41 (d, J=5.1 Hz, 1H), 7.84 (d, J=8.0 Hz, 1H), 7.51 (d, J=8.4 Hz, 1H), 6.98 (d, J=5.1 Hz, 1H), 6.21 (t, J=7.8 Hz, 2H), 4.23 (s, 3H), 3.54-3.47 (m, 1H), 3.17-3.10 (m, 1H), 3.07-2.97 (m, 1H), 2.84 (q, J==7.4 Hz, 2H), 2.71 (td, J=10.9, 2.9 Hz, 1H), 2.48-2.40 (m, 3H), 2.30 (d, J=6.7 Hz, 2H), 2.25-2.18 (m, 5H), 2.02 (dd, J=10.5, 7.5 Hz, 1H), 1.92-1.74 (m, 4H), 1.24-1.20 (t, J=72, 6.8 Hz, 3H).

The examples in the following table were prepared by using method analogous to the examples as indicated in the method column in the table.

| Ex# | Structure & name | Analytical & biological data | Method |
| --- | --- | --- | --- |
| 75 | 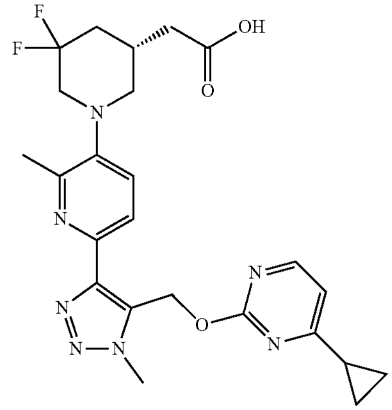 [SMILES: Cc1nc(-c2nnn(C)c2COc2nccc(C3CC3)n2)ccc1N1C[C@@H](CC(=O)O)CC(F)(F)C1] (S)-2-(1-(6-(5-(((4-cyclopropylpyrimidin-2-yl)oxy)methyl)-1-methyl-1H-1,2,3-triazol-4-yl)-2-methylpyridin-3-yl)-5,5-difluoropiperidin-3-yl)acetic acid | LC/MS (ESI) m/z: 500 $(M + H)^+$. $^1$H-NMR (400 MHz, $CD_3OD$) δ 8.27 (d, J = 4.2 Hz, 1H), 7.84 (d, J = 8.4 Hz, 1H), 7.54 (d, J = 8.4 Hz, 1H), 6.98 (d, J = 4.2 Hz, 1H), 6.18 (q, J = 10.4 Hz 2H), 4.21 (s, 3H), 3.31-3.29 (m, 2H), 3.09-3.02 (m, 1H), 2.55-2.52 (m, 1H), 2.51-2.49 (m, 1H), 2.50 (s, 3H), 2.39-2.26 (m, 3H), 1.98-1.91 (m, 1H), 1.78-1.67 (m, 1H), 0.99-0.93 (m, 2H), 0.90-0.83 (m, 2H). | Example 74 |

-continued

| Ex# | Structure & name | Analytical & biological data | Method |
|---|---|---|---|
| 76 | 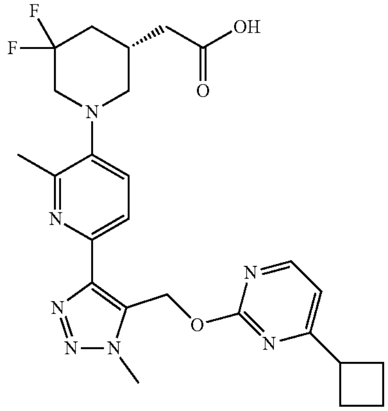 [SMILES: Cc1nc(-c2nnn(C)c2COc2nccc(C3CCC3)n2)ccc1N1C[C@@H](CC(=O)O)CC(F)(F)C1] (S)-2-(1-(6-(5-(((4-cyclobutylpyrimidin-2-yl)oxy)methyl)-1-methyl-1H-1,2,3-triazol-4-yl)-2-methylpyridin-3-yl)-5,5-difluoropiperidin-3-yl)acetic acid | LC/MS (ESI) m/z: 514 (M + H)$^+$. $^1$H-NMR (400 MHz, $CD_3OD$) δ 8.40 (d, J = 4.8 Hz, 1H), 7.85 (d, J = 8.4 Hz, 1H), 7.55 (d, J = 8.4 Hz, 1H), 6.98 (d, J = 5.2 Hz, 1H), 6.16 (s, 2H), 4.23 (s, 3H), 3.54-3.45 (m, 1H), 3.37-3.25 (m, 2H), 3.14-3.01 (m, 1H), 2.62-2.57 (m, 1H), 2.48 (s, 3H), 2.49-2.44 (m, 1H), 2.40-2.28 (m, 3H), 2.26-2.14 (m, 4H), 2.06-1.97 (m, 1H), 1.82-1.67 (m, 2H). | Example 74 |
| 77 | 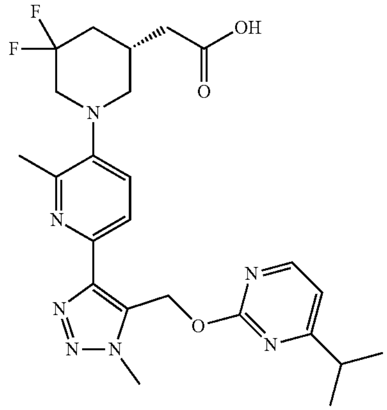 [SMILES: Cc1nc(-c2nnn(C)c2COc2nccc(C(C)C)n2)ccc1N1C[C@@H](CC(=O)O)CC(F)(F)C1] (S)-2-(5,5-difluoro-1-(6-(5-(((4-isopropylpyrimidin-2-yl)oxy)methyl)-1-methyl-1H-1,2,3-triazol-4-yl)-2-methylpyridin-3-yl)piperidin-3-yl)acetic acid | LC/MS (ESI) m/z: 502 (M + H)$^+$. $^1$H NMR (400 MHz, $CD_3OD$) δ 8.42 (d, J = 5.1 Hz, 1H), 7.84 (d, J = 8.3 Hz, 1H), 7.54 (d, J = 8.4 Hz, 1H), 7.01 (d, J = 5.1 Hz, 1H), 6.17-6.07 (m, 2H), 4.23 (s, 3H), 3.26-3.22 (m, 2H), 3.16-3.00 (m, 1H), 2.89-2.73 (m, 1H), 2.70-2.56 (m, 1H), 2.49-2.47 (m, 1H), 2.48 (s, 3H), 2.44-2.36 (m, 2H), 2.36-2.23 (m, 1H), 1.82-1.63 (m, 1H), 1.16 (d, J = 6.9 Hz, 6H). | Example 74 |
| 78 | 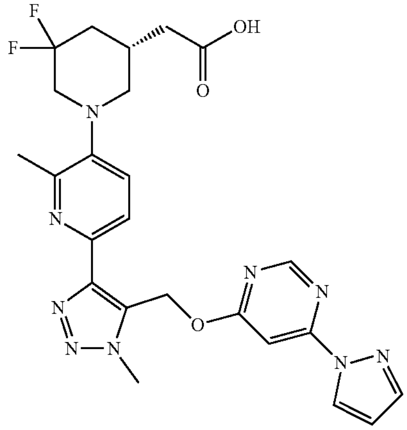 [SMILES: Cc1nc(-c2nnn(C)c2COc2cc(-n3cccn3)ncn2)ccc1N1C[C@@H](CC(=O)O)CC(F)(F)C1] (S)-2-(1-(6-(5-(((6-(1H-pyrazol-1-yl)pyrimidin-4-yl)oxy)methyl)-1-methyl-1H-1,2,3-triazol-4-yl)-2-methylpyridin-3-yl)-5,5-difluoropiperidin-3-yl)acetic acid | LC/MS (ESI) m/z: 526 (M + H)$^+$. $^1$H-NMR (400 MHz, $CD_3OD$) δ: 8.64-8.59 (m, 2H), 7.84 (d, J = 8.4 Hz, 1H), 7.77 (s, 1H), 7.53 (d, J = 8.4 Hz, 1H), 7.29 (s, 1H), 6.54 (t, J = 1.6 Hz, 1H), 6.16 (s, 2H), 4.22 (s, 3H), 3.31-3.25 (m, 2H), 3.14-3.00 (m, 1H), 2.62-2.55 (m, 1H), 2.52-2.49 (m, 1H), 2.48 (s, 3H), 2.36-2.48 (m, 3H), 1.80-1.64 (m, 1H). | Example 74 |

-continued

| Ex# | Structure & name | Analytical & biological data | Method |
|---|---|---|---|
| 79 | 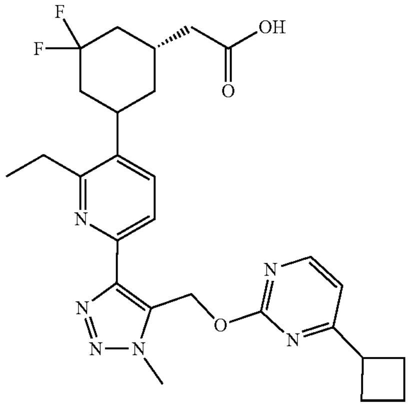 [SMILES: CCc1nc(-c2nnn(C)c2COc2nccc(C3CCC3)n2)ccc1C1C[C@@H](CC(=O)O)CC(F)(F)C1] (S)-2-(1-(6-(5-(((4-cyclobutylpyrimidin-2-yl)oxy)methyl)-1-methyl-1H-1,2,3-triazol-4-yl)-2-ethylpyridin-3-yl)-5,5-difluoropiperidin-3-yl)acetic acid | LC/MS (ESI) m/z: 528 (M + H)$^+$. $^1$H NMR (400 MHz, $CD_3OD$) δ 8.41 (d, J = 5.2 Hz, 1H), 7.88 (d, J = 8.2 Hz, 1H), 7.57 (d, J = 8.4 Hz, 1H), 6.99 (d, J = 5.0 Hz, 1H), 6.20 (s, 2H), 4.23 (s, 3H), 3.54-3.49 (m, 1H), 3.25-3.17 (m, 2H), 3.11-3.01 (m, 1H), 2.87 (q, J = 7.6 Hz, 2H), 2.62-2.56 (m, 1H), 2.53-2.44 (m, 1H), 2.40-2.34 (m, 2H), 2.33-2.27 (m, 1H), 2.26-2.18 (m, 4H), 2.08-1.98 (m, 1H), 1.84-1.74 (m, 1H), 1.73-1.65 (m, 1H), 1.23 (t, J = 7.6 Hz, 3H). | Example 74 |
| 80 | 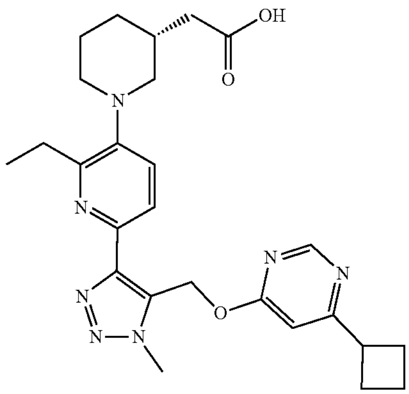 [SMILES: CCc1nc(-c2nnn(C)c2COc2cc(C3CCC3)ncn2)ccc1N1CCC[C@H](CC(=O)O)C1] (R)-2-(1-(6-(5-(((6-cyclobutylpyrimidin-4-yl)oxy)methyl)-1-methyl-1H-1,2,3-triazol-4-yl)-2-ethylpyridin-3-yl)piperidin-3-yl)acetic acid | LC/MS (ESI) m/z: 492 (M + H)$^+$. $^1$H NMR (400 MHz, $CD_3OD$) δ 8.66 (d, J = 0.9 Hz, 1H), 7.85 (d, J = 8.3 Hz, 1H), 7.54 (d, J = 8.4 Hz, 1H), 6.79 (s, 1H), 6.12 (s, 2H), 4.20 (s, 3H), 3.61-3.51 (m, 1H), 3.16 (d, J = 11.0 Hz, 1H), 3.03 (d, J = 11.2 Hz, 1H), 2.82 (t, J = 7.5 Hz, 2H), 2.76-2.66 (m, 1H), 2.49-2.39 (m, 1H), 2.33-2.19 (m, 7H), 2.11-2.02 (m, 1H), 1.91-1.72 (m, 4H), 1.21 (t, J = 7.5 Hz, 4H). | Example 74 |
| 81 | 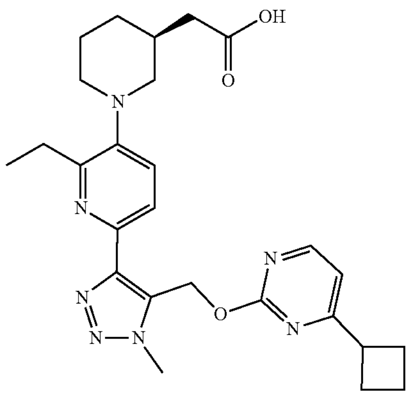 (S)-2-(1-(6-(5-(((4-cyclobutylpyrimidin-2-yl)oxy)methyl)-1-methyl-1H-1,2,3-triazol-4-yl)-2-ethylpyridin-3-yl)piperidin-3-yl)acetic acid | LC/MS (ESI) (m/z): 515 (M + H)$^+$. $^1$H NMR (400 MHz, $CD_3OD$) δ 8.60-8.61 (m, 2H), 7.84 (s, 1H), 7.77-7.78 (d, J = 1.1 Hz, 1H), 7.41-7.44 (m, 2H), 7.25-7.26 (m, 1H), 6.54-6.55 (m, 1H), 5.98 (s, 2H), 4.01 (s, 3H), 3.20-3.24 (m, 2H), 2.97-3.07 (m, 1H), 2.54-2.59 (m, 1H), 2.46 (s, 3H), 2.37-2.39 (m, 2H), 2.24-2.30 (m, 1H), 1.59-1.76 (m, 2H). | Example 74 |

-continued

| Ex# | Structure & name | Analytical & biological data | Method |
|---|---|---|---|
| 82 | 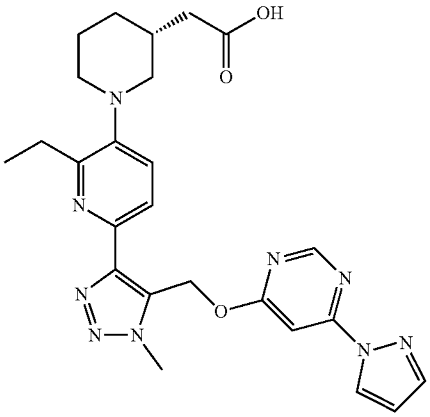 [SMILES: CCc1nc(-c2nnn(C)c2COc2cc(-n3cccn3)ncn2)ccc1N1CCC[C@H](CC(=O)O)C1] (R)-2-(1-(6-(5-(((6-(1H-pyrazol-1-yl)pyrimidin-4-yl)oxy)methyl)-1-methyl-1H-1,2,3-triazol-4-yl)-2-ethylpyridin-3-yl)piperidin-3-yl)acetic acid | LC/MS (ESI) m/z: 504 $(M + H)^+$. $^1H$ NMR (400 MHz, $CD_3OD$) δ 8.62-8.64 (d, J = 0.9 Hz, 1H), 8.59-8.61 (dd, J = 2.7, 0.5 Hz, 1H), 7.82-7.84 (d, J= 8.3 Hz, 1H), 7.76-7.78 (d, J = 1.1 Hz, 1H), 7.48-7.50 (d, J = 8.4 Hz, 1H), 7.28-7.30 (d, J = 0.9 Hz, 1H), 6.53-6.55 (dd, J = 2.7, 1.6 Hz, 1H), 6.20 (s, 2H), 4.23 (s, 3H), 3.12-3.18 (m, 1H), 3.00-3.06 (m, 1H), 2.80-2.86 (q, J = 7.5 Hz, 2H), 2.66-2.74 (m, 1H), 2.39-2.47 (m, 1H), 2.27-2.33 (m, 2H), 2.15-2.26 (m, 1H), 2.03 (s, 1H), 1.73-1.91 (m, 3H), 1.27-1.19 (m, 1H), 1.24-1.20 (t, J = 7.5 Hz, 3H). | Example 74 |
| 83 | 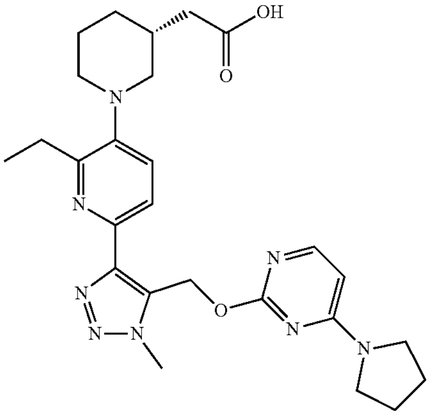 [SMILES: CCc1nc(-c2nnn(C)c2COc2nccc(N3CCCC3)n2)ccc1N1CCC[C@H](CC(=O)O)C1] (R)-2-(1-(2-ethyl-6-(1-methyl-5-(((4-(pyrrolidin-1-yl)pyrimidin-2-yl)oxy)methyl)-1H-1,2,3-triazol-4-yl)pyridin-3-yl)piperidin-3-yl)acetic acid | LC/MS (ESI) m/z: 507 $[M+1]^+$ $^1H$ NMR (400 MHz, $CD_3OD$) δ 7.87 (d, J = 6.1 Hz, 1H), 7.82 (d, J = 8.3 Hz, 1H), 7.50 (d, J = 8.4 Hz, 1H), 6.12 (dt, J = 15.4, 13.3 Hz, 3H), 4.20 (s, 3H), 3.32 (s, 2H), 3.17 (d, J = 11.8 Hz, 3H), 3.03 (d, J = 11.3 Hz, 1H), 2.87 (q, J = 7.5 Hz, 2H), 2.77-2.68 (m, 1H), 2.50-2.41 (m, 1H), 2.36-2.18 (m, 3H), 2.06-1.93 (m, 2H), 1.92-1.74 (m, 5H), 1.28 (t, J = 7.5 Hz, 3H), 1.25-1.17 (m, 1H). | Example 74 |
| 84 | 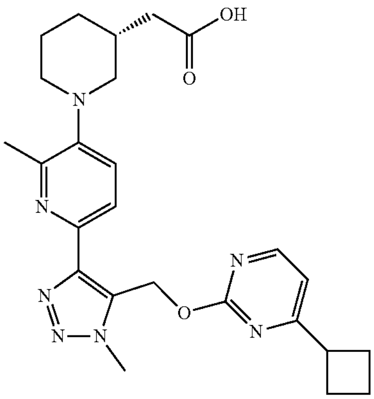 (R)-2-(1-(6-(5-(((4-cyclobutylpyrimidin-2-yl)oxy)methyl)-1-methyl-1H-1,2,3-triazol-4-yl)-2-methylpyridin-3-yl)piperidin-3-yl)acetic acid | LC/MS (ESI) m/z: 504 $(M + H)^+$. $^1H$ NMR (400 MHz, $CD_3OD$) δ 8.41 (d, J = 5.1 Hz, 1H), 8.12 (s, 2H), 7.03 (d, J = 5.2 Hz, 1H), 5.86 (s, 2H), 4.33 (s, 3H), 3.56-3.54 (m, 1H), 3.52-3.50 (m, 1H), 3.28-3.25 (m, 1H), 2.93-2.91 (m, 1H), 2.78 (s, 3H), 2.64-2.59 (m, 1H), 2.34-2.27 (m, 7H), 1.89-1.84 (m, 4H), 1.33-1.29 (m, 2H). | Example 74 |

-continued

| Ex# | Structure & name | Analytical & biological data | Method |
| --- | --- | --- | --- |
| 85 | 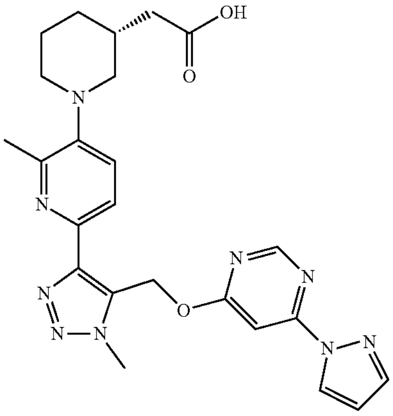 (R)-2-(1-(6-(5-(((6-(1H-pyrazol-1-yl)pyrimidin-4-yl)oxy)methyl)-1-methyl-1H-1,2,3-triazol-4-yl)-2-methylpyridin-3-yl)piperidin-3-yl)acetic acid | LC/MS (ESI) m/z: 481 (M + H)$^+$. $^1$H NMR (400 MHz, $CD_3OD$) δ 8.64-8.56 (m, 2H), 7.99-7.92 (m, 1H), 7.82-7.75 (m, 2H), 7.29 (s, 1H), 6.57-6.52 (m, 1H), 6.03 (s, 2H), 4.27 (s, 3H), 3.29-3.27 (m, 1H), 3.20-3.14 (m, 1H), 2.83-2.75 (m, 1H), 2.60 (s, 3H), 2.54-2.47 (m, 1H), 2.35-2.30 (m, 2H), 2.29-2.18 (m, 1H), 1.94-1.76 (m, 3H), 1.30-1.19 (m, 1H). | Example 74 |
| 86 | 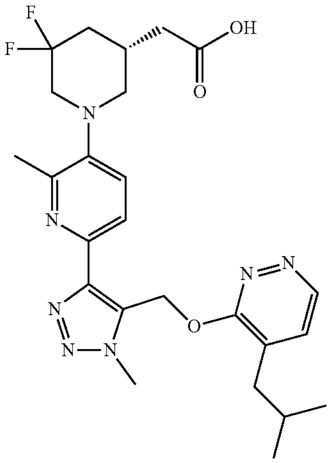 [SMILES: Cc1nc(-c2nnn(C)c2COc2nnccc2CC(C)C)ccc1N1C[C@@H](CC(=O)O)CC(F)(F)C1] (S)-2-(5,5-difluoro-1-(6-(5-(((4-isobutylpyridazin-3-yl)oxy)methyl)-1-methyl-1H-1,2,3-triazol-4-yl)-2-methylpyridin-3-yl)piperidin-3-yl)acetic acid | $^1$H NMR (400 MHz, $CD_3OD$) δ 8.71 (d, J = 4.7 Hz, 1H), 7.82 (d, J = 8.3 Hz, 1H), 7.51 (d, J = 8.3 Hz, 1H), 7.39 (d, J = 4.7 Hz, 1H), 6.15 (s, 2H), 4.28 (s, 3H), 3.25 (d, J = 11.2 Hz, 2H), 3.15-3.00 (m, 1H), 2.63-2.45 (m, 2H), 2.43-2.26 (m, 8H), 1.78-1.62 (m, 2H), 0.72 (d, J = 6.6 Hz, 6H). LC/MS (ESI) m/z: 516 (M + H)$^+$. | Example 74 |

-continued

| Ex# | Structure & name | Analytical & biological data | Method |
|---|---|---|---|
| 87 | 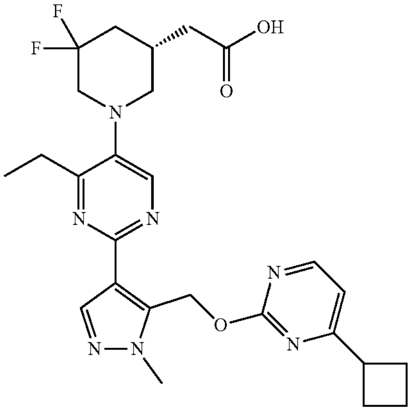 [SMILES: CCc1nc(-c2cnn(C)c2COc2nccc(C3CCC3)n2)ncc1N1C[C@@H](CC(=O)O)CC(F)(F)C1] (S)-2-(1-(2-(5-(((4-cyclobutylpyrimidin-2-yl)oxy)methyl)-1-methyl-1H-pyrazol-4-yl)-4-ethylpyrimidin-5-yl)-5,5-difluoropiperidin-3-yl)acetic acid | LC/MS (ESI) m/z: 528 $(M + H)^+$. $^1H$ NMR (400 MHz, $CD_3OD$) δ 8.42 (d, J = 5.1 Hz, 1H), 8.38 (s, 1H), 8.08 (s, 1H), 6.99 (d, J = 5.1 Hz, 1H), 6.16 (s, 2H), 4.02 (s, 3H), 3.58-3.51 (m, 1H), 3.28-3.10 (m, 3H), 2.79-2.86 (m, 2H), 2.70-2.64 (m, 1H), 2.42-2.51(m, 1H), 2.37-2.41(d, J = 6.9 Hz, 2H), 2.22-2.30 (m, 5H), 2.00-2.08 (m, 8.2 Hz, 1H), 1.68-1.86 (m, 2H), 1.20-1.24 (m, 3H). | Example 74 |
| 88 | 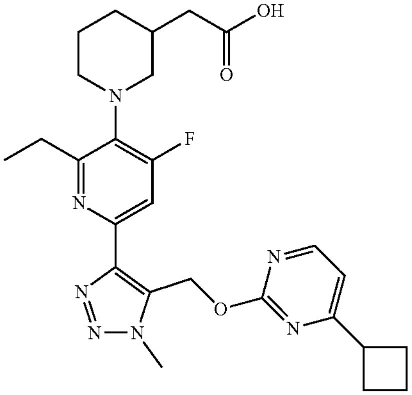 [SMILES: CCc1nc(-c2nnn(C)c2COc2nccc(C3CCC3)n2)cc(F)c1N1CCCC(CC(=O)O)C1] 2-(1-(6-(5-(((4-cyclobutylpyrimidin-2-yl)oxy)methyl)-1-methyl-1H-1,2,3-triazol-4-yl)-2-ethyl-4-fluoropyridin-3-yl)piperidin-3-yl)acetic acid | LC/MS (ESI) m/z: 510 $(M + H)^+$. $^1H$-NMR (400 MHz, $CD_3OD$) δ 8.41 (d, J = 5.1 Hz, 1H), 7.63 (d, J = 13.1 Hz, 1H), 6.99 (d, J = 5.1 Hz, 1H), 6.19 (s, 2H), 4.23 (s, 3H), 3.57-3.48 (m, 1H), 3.15 (t, J = 11.7 Hz, 2H), 3.01-2.98 (m, 2H), 2.89 (q, J = 7.5 Hz, 2H), 2.29 (d, J = 7.0 Hz, 2H), 2.26-2.19 (m, 4H), 2.06-1.99 (m, 1H), 1.94-1.87 (m, 1H), 1.84-1.76 (m, 3H), 1.48-1.38 (m, 2H), 1.19 (t, J = 7.5 Hz, 3H). | Example 74 |
| 89 | 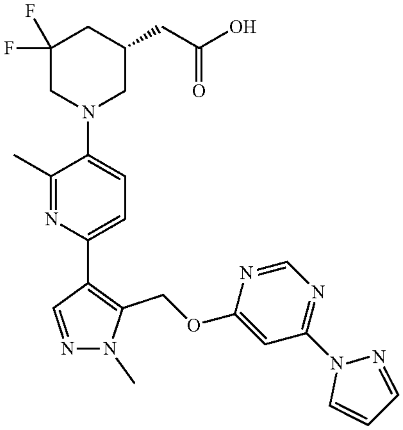 (S)-2-(1-(6-(5-(((6-(1H-pyrazol-1-yl)pyrimidin-4-yl)oxy)methyl)-1-methyl-1H-pyrazol-4-yl)-2-methylpyridin-3-yl)-5,5-difluoropiperidin-3-yl)acetic acid | LC/MS (ESI) (m/z): 515 $(M + H)^+$. $^1H$ NMR (400 MHz, $CD_3OD$) δ 8.60-8.61 (m, 2H), 7.84 (s, 1H), 7.77-7.78 (d, J = 1.1 Hz, 1H), 7.41-7.44 (m, 2H), 7.25-7.26 (m, 1H), 6.54-6.55 (m, 1H), 5.98 (s, 2H), 4.01 (s, 3H), 3.20-3.24 (m, 2H), 2.97-3.07 (m, 1H), 2.54-2.59 (m, 1H), 2.46 (s, 3H), 2.37-2.39 (m, 2H), 2.24-2.30 (m, 1H), 1.59-1.76 (m, 2H). | Example 74 |

-continued

| Ex# | Structure & name | Analytical & biological data | Method |
|---|---|---|---|
| 90 | 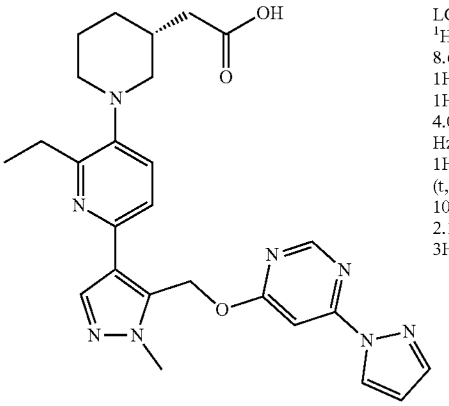 (R)-2-(1-(6-(5-(((6-(1H-pyrazol-1-yl)pyrimidin-4-yl)oxy)methyl)-1-methyl-1H-pyrazol-4-yl)-2-ethylpyridin-3-yl)piperidin-3-yl)acetic acid | LC/MS (ESI) (m/z): 503 $(M + H)^+$ $^1H$ NMR (400 MHz, $CD_3OD$) δ 8.60 (s, 2H), 7.85 (s, 1H), 7.77 (s, 1H), 7.39-7.45 (m, 2H), 7.27 (s, 1H), 6.55 (s, 1H), 6.05 (s, 2H), 4.01 (s, 3H), 3.09-3.11 (d, J = 11.0 Hz, 1H), 2.97-2.99 (d, J = 10.9 Hz, 1H), 2.78-2.83 (m, 2H), 2.65-2.70 (t, J = 9.5 Hz, 1H), 2.39-2.44 (t, J = 10.3 Hz, 1H), 2.28-2.30 (m, 2H), 2.17-2.20 (m, 1H), 1.73-1.89 (m, 3H), 1.18-1.21 (m, 4H). | Example 74 |
| 91 | 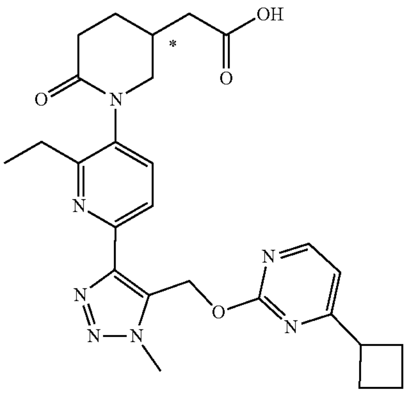 [SMILES: CCc1nc(-c2nnn(C)c2COc2nccc(C3CCC3)n2)ccc1N1CC(CC(=O)O)CCC1=O] arbitrarily assigned enantiomer A: (R) or (S)-2-(1-(6-(5-(((4-cyclobutylpyrimidin-2-yl)oxy)methyl)-1-methyl-1H-1,2,3-triazol-4-yl)-2-ethylpyridin-3-yl)-6-oxopiperidin-3-yl)acetic acid | LC-MS (ESI) m/z 506 $(M + H)^+$. $^1H$ NMR (400 MHz, $CD_3OD$) δ 8.42-8.41(d, 1H), 8.03-8.00 (m, 1H), 7.72-7.67 (m, 1H), 7.00 (d, J = 5.1 Hz, 1H), 6.28-6.27 (m, 1H), 6.17-6.14 (d, J = 13.0 Hz, 1H), 4.24 (s, 3H), 3.79-3.53 (m, 3H), 2.69-2.62 (m, 3H), 2.52-2.41(m, 3H), 2.32-2.21 (m, 5H), 2.14 (d, J = 13.0 Hz, 1H), 2.08-1.97 (m, 1H), 1.8-1.81 (m, 2H), 1.24-1.18 (m, 3H). | Example 74 |
| 92 | 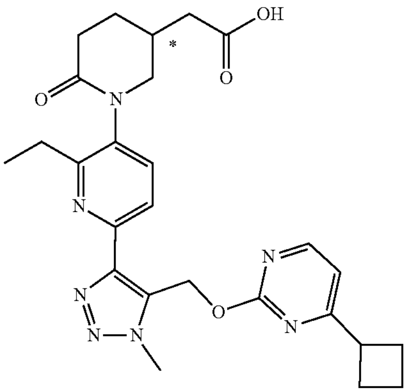 [SMILES: CCc1nc(-c2nnn(C)c2COc2nccc(C3CCC3)n2)ccc1N1CC(CC(=O)O)CCC1=O] arbitrarily assigned enantiomer B: (S) or (R)-2-(1-(6-(5-(((4-cyclobutylpyrimidin-2-yl)oxy)methyl)-1-methyl-1H-1,2,3-triazol-4-yl)-2-ethylpyridin-3-yl)-6-oxopiperidin-3-yl)acetic acid | LC/MS (ESI) m/z: 507 $(M + H)^+$. $^1H$ NMR (400 MHz, $CD_3OD$) δ 8.32 (d, J = 5.1 Hz, 1H), 7.91 (dd, J = 8.2, 5.3 Hz, 1H), 7.59 (dd, J = 12.5, 8.2 Hz, 1H), 6.90 (d, J = 5.1 Hz, 1H), 6.20-6.12 (m, 1H), 6.06 (d, J = 13.0 Hz, 1H), 4.14 (s, 3H), 3.71-3.30 (m, 3H), 2.66-2.52 (m, 3H), 2.47-2.36 (m, 1H), 2.36-2.29 (m, 2H), 2.24-2.12 (m, 5H), 2.07-1.99 (m, 1H), 1.99-1.90 (m, 1H), 1.79-1.62 (m, 2H), 1.11 (q, J = 7.4 Hz, 3H). | Example 74 |

-continued

| Ex# | Structure & name | Analytical & biological data | Method |
| --- | --- | --- | --- |
| 93 | 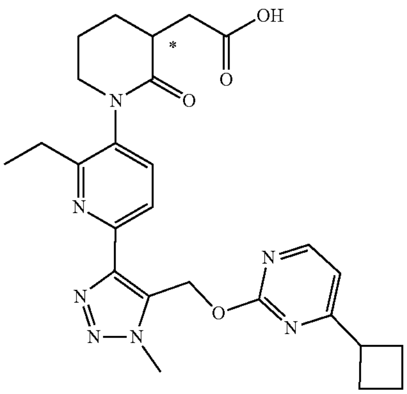 [SMILES: CCc1nc(-c2nnn(C)c2COc2nccc(C3CCC3)n2)ccc1N1CCCC(CC(=O)O)C1=O] arbitrarily assigned enantiomer A: (R) or (S)-2-(1-(6-(5-(((4-cyclobutylpyrimidin-2-yl)oxy)methyl)-1-methyl-1H-1,2,3-triazol-4-yl)-2-ethylpyridin-3-yl)-2-oxopiperidin-3-yl)acetic acid | LC/MS (ESI) m/z: 506 $(M + H)^+$ $^1H$ NMR (400 MHz, $CD_3OD$) δ 8.42 (d, J = 5.1 Hz, 1H), 8.00 (dd, J = 8.3, 2.9 Hz, 1H), 7.68 (dd, J = 14.4, 8.2 Hz, 1H), 7.00 (d, J = 5.1 Hz, 1H), 6.28 (dd, J = 13.0, 3.9 Hz, 1H), 6.13 (d, J = 13.0 Hz, 1H), 4.24 (s, 3H), 3.80-3.71 (m, 1H), 3.64-3.52 (m, 2H), 3.43 (d, J = 12.1 Hz, 1H), 2.89-2.79 (m, 1H), 2.76-2.65 (m, 4H), 2.31-2.23 (m, 4H), 2.14-2.00 (m, 4H), 1.98-1.89 (m, 1H), 1.88-1.79 (m, 1H), 1.20 (td, J = 7.5, 2.8 Hz, 3H). | Example 74 |
| 94 | 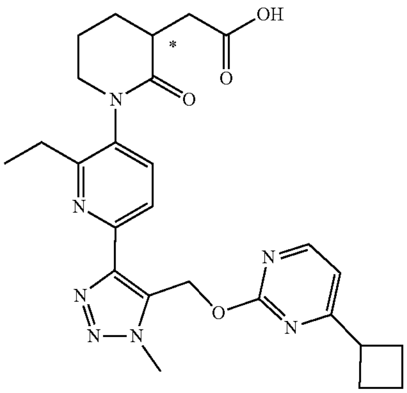 [SMILES: CCc1nc(-c2nnn(C)c2COc2nccc(C3CCC3)n2)ccc1N1CCCC(CC(=O)O)C1=O] arbitrarily assigned enantiomer B: (S) or (R)-2-(1-(6-(5-(((4-cyclobutylpyrimidin-2-yl)oxy)methyl)-1-methyl-1H-1,2,3-triazol-4-yl)-2-ethylpyridin-3-yl)-2-oxopiperidin-3-yl)acetic acid | LC/MS (ESI) m/z: 506 $(M + H)^+$. $^1H$ NMR (400 MHz, $CD_3OD$) δ 8.42 (d, J = 5.1 Hz, 1H), 7.99 (dd, J = 8.2, 3.3 Hz, 1H), 7.69 (dd, J = 20.3, 8.2 Hz, 1H), 7.00 (d, J = 5.1 Hz, 1H), 6.28 (dd, J = 13.0, 3.3 Hz, 1H), 6.13 (d, J = 13.0 Hz, 1H), 4.24 (s, 3H), 3.80-3.72 (m, 1H), 3.65-3.53 (m, 2H), 3.44-3.39 (m, 1H), 2.86-2.65 (m, 4H), 2.63-2.48 (m, 1H), 2.31-2.23 (m, 4H), 2.16-2.09 (m, 1H), 2.09-1.98 (m, 3H), 1.93-1.79 (m, 2H), 1.20 (td, J = 7.5, 2.4 Hz, 3H). | Example 74 |

Example 95: (R)-2-(1-(6-(5-(((4-cyclobutyl-1,3,5-triazin-2-yl)oxy)methyl)-1-methyl-1H-1,2,3-triazol-4-yl)-2-ethylpyridin-3-yl)piperidin-3-yl)acetic acid

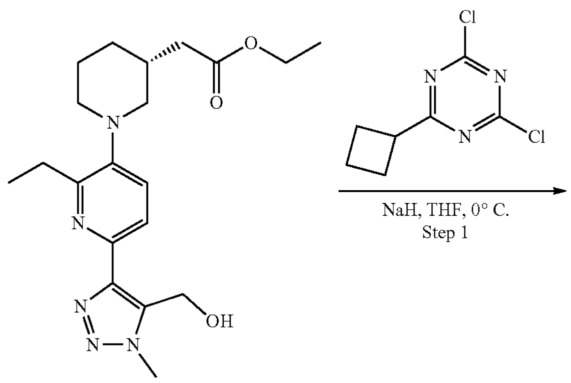

1

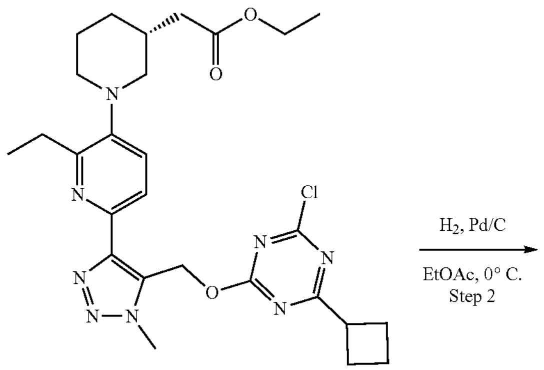

2

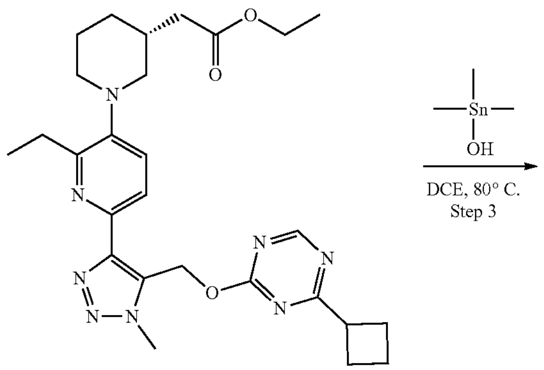

3

-continued

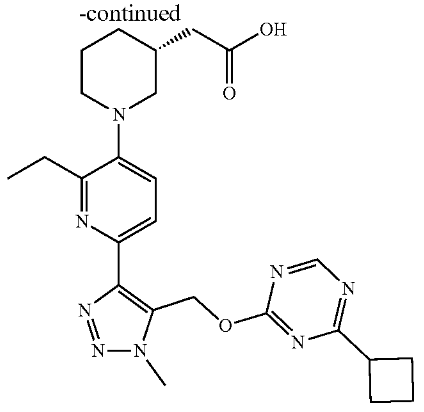

Example 95

Step 1: ethyl (R)-2-(l-(6-(5-(((4-chloro-6-cyclobutyl-1,3,5-triazin-2-yl)oxy)methyl)-1-methyl-1H-1,2,3-triazol-4-yl)-2-ethylpyridin-3-yl)piperidin-3-yl)acetate To a solution of ethyl (R)-2-(1-(2-ethyl-6-(5-(hydroxymethyl)-1-methyl-1H-1,2,3-triazol-4-yl)pyridin-3-yl)piperidin-3-yl)acetate (60 mg, 0.155 mmol) in THF (3 mL) was added NaH (12.4 mg, 0.31 mmol, 60% dispersion in mineral oil) under $N_2$ atmosphere at 0° C. and the mixture was stirred at 0° C. for 30 mins. Then 2,4-dichloro-6-cyclobutyl-1,3,5-triazine (38 mg, 0.186 mmol) was added and the resulting mixture was stirred at 0° C. for 2 hrs. The mixture was diluted with saturated aq·$NH_4Cl$ solution and extracted with EtOAc (2×5 mL). The combined organic layers were washed with brine, dried over anhydrous $Na_2SO_4$, filtered and concentrated under reduced pressure to dryness. The residue was purified by chromatography on silica gel (PE: EtOAc=3:1) to give the title compound (60 mg, 69.8% yield) as white solid. LC/MS (ESI) (m/z): 555 $(M+H)^+$.

Step 2: ethyl (R)-2-(1-(6-(5-(((4-cyclobutyl-1,3,5-triazin-2-yl)oxy)methyl)-1-methyl-1H-1,2,3-triazol-4-yl)-2-ethylpyridin-3-yl)piperidin-3-yl)acetate To a solution of ethyl (R)-2-(1-(6-(5-(((4-chloro-6-cyclobutyl-1,3,5-triazin-2-yl)oxy)methyl)-1-methyl-1H-1,2,3-triazol-4-yl)-2-ethylpyridin-3-yl)piperidin-3-yl)acetate (60 mg, 0.108 mmol) in EtOAc (3 mL) were added TEA (0.075 mL, 0.540 mmol) and Pd/C (10 mg, 10% wt) at 0° C. and the mixture was degassed under $N_2$ atmosphere for three times and stirred under a $H_2$ balloon at room temperature for 2 hrs. The mixture was filtered and the filtrate was concentrated to dryness to give title compound (52 mg, 92.4% yield) as yellow oil. LC/MS (ESI) (m/z): 521 $(M+H)^+$.

Step 3: (R)-2-(1-(6-(5-(((4-cyclobutyl-1,3,5-triazin-2-yl)oxy)methyl)-1-methyl-11H-1,2,3-triazol-4-yl)-2-ethylpyridin-3-yl)piperidin-3-yl)acetic acid To a solution of ethyl (R)-2-(1-(6-(5-(((4-cyclobutyl-1,3,5-triazin-2-yl)oxy)methyl)-1-methyl-1H-1,2,3-triazol-4-yl)-2-ethylpyridin-3-yl)piperidin-3-yl)acetate (20 mg, 0.038 mmol) in 1,2-dichloroethane (2 mL) was added trimethyltin hydroxide (69 mg, 0.38 mmol) at room temperature. After stirring at 80° C. for 16 hrs, the mixture was filtered and the filtrate was concentrated to dryness. The residue was purified by prep-HPLC (C18, 25-95%, MeCN in $H_2O$ with 0.1% HCOOH) to give the title compound (5.5 mg, 29% yield) as white solid. LC/MS (ESI) (m/z): 493 $(M+H)^+$. $^1$H-NMR (400 MHz, $CD_3OD$) δ 8.82 (s, 1H), 7.84-7.86 (d, J=8.3 Hz, 1H), 7.50-7.52 (d, J=8.4 Hz, 1H), 6.23-6.30 (m, 2H), 4.22 (s, 3H), 3.54-3.58 (m, 1H), 3.14-3.17 (d, J=10.8 Hz, 1H), 3.02-3.05 (d, J=11.5 Hz, 1H), 2.81-2.87 (m, 2H), 2.69-2.74 (m, 1H), 2.41-2.46 (m, 1H), 2.17-2.37 (m, 8H), 2.01-2.09 (m, 2H), 1.74-1.91 (m, 4H), 1.20-1.24 (m, 4H).

Example 96: (R)-2-(1-(6-(5-(((4-cyclobutyl-6-morpholino-1,3,5-triazin-2-yl)oxy)methyl)-1-methyl-1H-1,2,3-triazol-4-yl)-2-ethylpyridin-3-yl)piperidin-3-yl)acetic acid

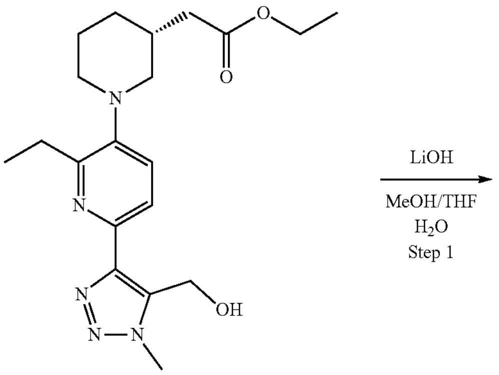

1

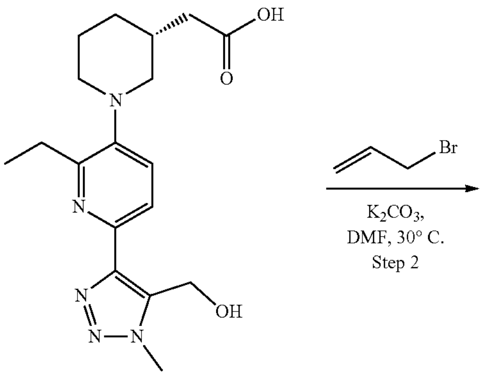

2

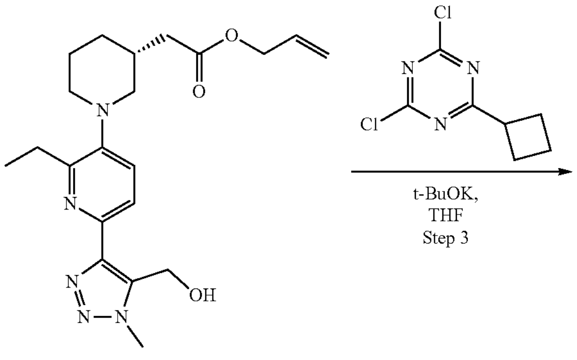

3

-continued

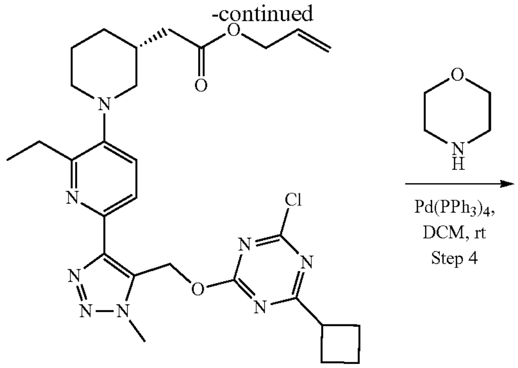

4

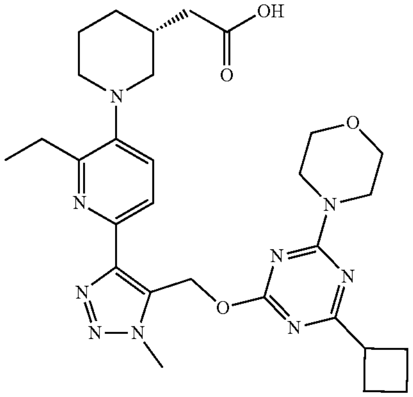

Example 96

Step 1: (R)-2-(1-(2-ethyl-6-(5-(hydroxymethyl)-1-methyl-11H-1,2,3-triazol-4-yl)pyridin-3-yl)piperidin-3-yl)acetic acid To a solution of ethyl (R)-2-(1-(2-ethyl-6-(5-(hydroxymethyl)-1-methyl-1H-1,2,3-triazol-4-yl)pyridin-3-yl)piperidin-3-yl)acetate (200 mg, 0.516 mmol) in THF (2 mL) and MeOH (6 mL) was added a solution of LiOH (16.6 mg, 0.51 mmol) in water (2 mL) at 0° C. After stirring at room temperature for 2 hrs, the reaction mixture was concentrated to dryness and the residue was dissolved in water. The mixture was washed with EtOAc (2×3 mL) and the aqueous layer was acidified with 1N aq·HCl to pH~2 and extracted with DCM (2×3 mL). The combined organic layers were washed with brine, dried over anhydrous $Na_2SO_4$, filtered and concentrated to dryness give the title compound (180 mg, 97% yield) as white solid. LC/MS (ESI) (m/z): 360 $(M+H)^+$.

Step 2: allyl (R)-2-(1-(2-ethyl-6-(5-(hydroxymethyl)-1-methyl-1H-1,2,3-triazol-4-yl)pyridin-3-yl)piperidin-3-yl)acetate To a mixture of (R)-2-(1-(2-ethyl-6-(5-(hydroxymethyl)-1-methyl-1H-1,2,3-triazol-4-yl)pyridin-3-yl)piperidin-3-yl)acetic acid (180 mg, 0.501 mmol) and 3-bromoprop-1-ene (0.065 mL, 0.751 mmol) in DMF (6 mL) was added $K_2CO_3$ (138 mg, 1.002 mmol) at room temperature and the reaction mixture was stirred at 30° C. for 4 hrs. The mixture was diluted with water and extracted with EtOAc (2×5 mL). The combined organic layers were washed with brine, dried with anhydrous $Na_2SO_4$, filtered and concentrated under reduced pressure to dryness. The residue was purified by chromatography on silica gel (PE:EtOAc=1:1) to give the title compound (130 mg, 65% yield) as yellow solid. LC/MS (ESI) (m/z): 400 $(M+H)^+$.

Step 3: allyl (R)-2-(1-(6-(5-(((4-chloro-6-cyclobutyl-1,3,5-triazin-2-yl)oxy)methyl)-1-methyl-1H-1,2,3-triazol-4-yl)-2-ethylpyridin-3-yl)piperidin-3-yl)acetate To a mixture of allyl (R)-2-(1-(2-ethyl-6-(5-(hydroxymethyl)-1-methyl-1H-1,2,3-triazol-4-yl)pyridin-3-yl)piperidin-3-yl)acetate (130 mg, 0.325 mmol) and 2,4-dichloro-6-cyclobutyl-1,3,5-triazine (80 mg, 0.39 mmol) in THE (6 mL) was added t-BuOK (0.65 mL, 0.65 mmol, 1M in THF) under $N_2$ atmosphere at 0° C. and the mixture was stirred at 0° C. for 2 hrs. The mixture was poured into ice-cooled saturated aq·$NH_4Cl$ solution and extracted with EtOAc (2×5 mL). The combined organic layers were washed with brine, dried with anhydrous $Na_2SO_4$, filtered and concentrated to dryness. The residue was purified by chromatography on silica gel (PE:EtOAc=5:1) to give the title compound (150 mg, 81.4% yield) as yellow oil. LC/MS (ESI) (m/z): 568 $(M+H)^+$.

Step 4: (R)-2-(1-(6-(5-(((4-cyclobutyl-6-morpholino-1,3,5-triazin-2-yl)oxy)methyl)-1-methyl-1H-1,2,3-triazol-4-yl)-2-ethylpyridin-3-yl)piperidin-3-yl)acetic acid To a solution of allyl (R)-2-(1-(6-(5-(((4-chloro-6-cyclobutyl-1,3,5-triazin-2-yl)oxy)methyl)-1-methyl-1H-1,2,3-triazol-4-yl)-2-ethylpyridin-3-yl)piperidin-3-yl)acetate (120 mg, 0.21 mmol) in DCM (5 mL) were added morpholine (0.037 mL, 0.423 mmol) and tetrakis(triphenylphosphine) palladium (122 mg, 0.106 mmol) under $N_2$ atmosphere and the reaction mixture was stirred at r.t. for 2 hrs. The reaction mixture was diluted with DCM (5 mL), washed with water and brine, dried with anhydrous $Na_2SO_4$, filtered and concentrated to dryness. The residue was purified by prep-HPLC (C18, 45-95%, MeCN in $H_2O$ with 0.1% HCOOH) to give the title compound (50 mg, 40.9% yield) as white solid. LC/MS (ESI) (m/z): 578 $(M+H)^+$. $^1H$ NMR (400 MHz, $CD_3OD$) δ 7.84-7.86 (d, J=8.3 Hz, 1H), 7.50-7.52 (d, J=8.4 Hz, 1H), 6.13-6.20 (m, 2H), 4.19 (s, 3H), 3.88 (s, 2H), 3.67 (s, 2H), 3.52 (m, 4H), 3.33-3.42 (m, 1H), 3.16-3.18 (d, J=11.1 Hz, 1H), 3.02-3.04 (d, J=11.5 Hz, 1H), 2.84-2.89 (m, 2H), 2.70-2.76 (m, 1H), 2.42-4.47 (m, 1H), 2.28-2.36 (m, 4H), 2.17-2.25 (m, 3H), 1.97-2.05 (m, 1H), 1.80-1.92 (m, 3H), 1.25-1.29 (m, 4H).

Example 97: 2-[(3R)-1-{2-ethyl-6-[1-methyl-5-({[6-(1H-1,2,3-triazol-1-yl)pyrimidin-4-yl]oxy}methyl)-1H-1,2,3-triazol-4-yl]pyridin-3-yl}piperidin-3-yl] acetic acid

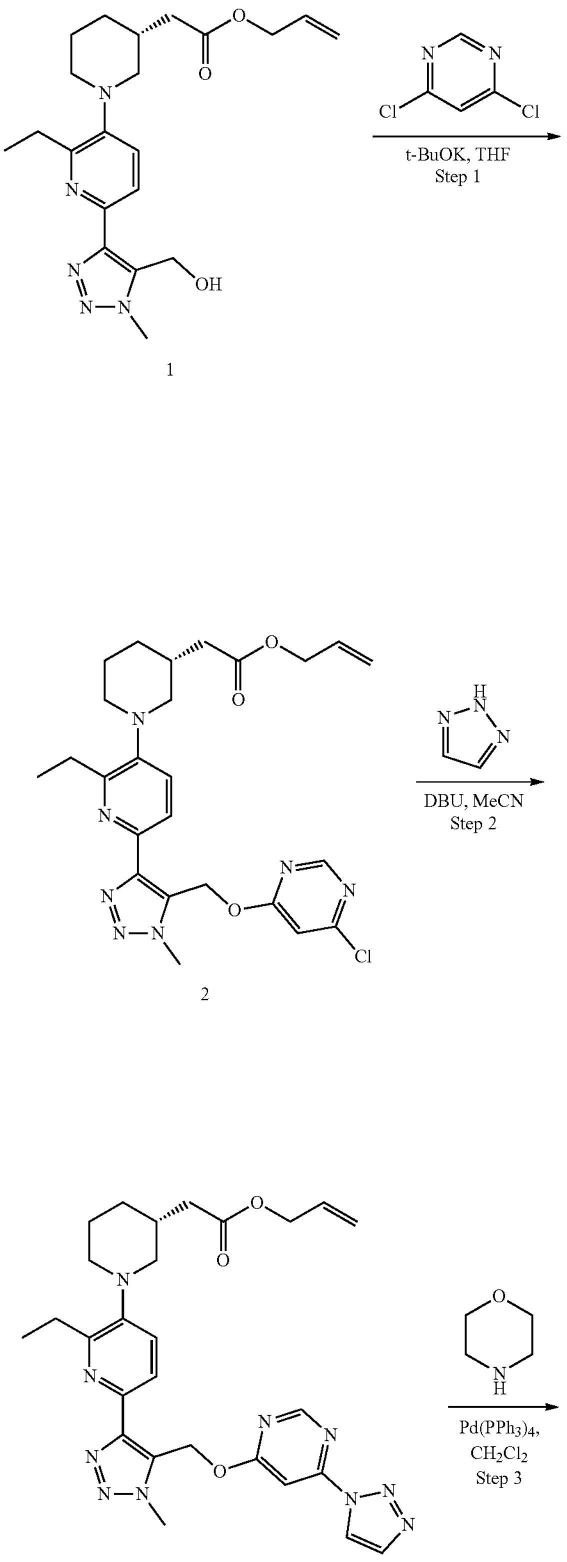

1

2

-continued

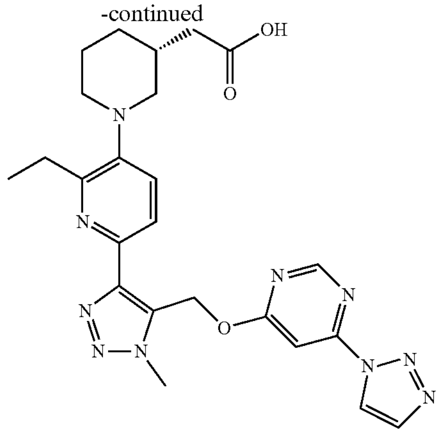

Example 97

Step 1: prop-2-en-1-yl 2-[(3R)-1-[6-(5-{[(6-chloro-pyrimidin-4-yl)oxy]methyl}-1-methyl-1H-1,2,3-triazol-4-yl)-2-ethylpyridin-3-yl]piperidin-3-yl]acetate To a solution of prop-2-en-1-yl 2-[(3R)-1-{2-ethyl-6-[5-(hydroxymethyl)-1-methyl-1H-1,2,3-triazol-4-yl]pyridin-3-yl}piperidin-3-yl]acetate (135 mg, 0.34 mmol) in THE (10 mL) was added t-BuOK (114 mg, 1.01 mmol) and 4,6-dichloropyrimidine (101 mg, 0.68 mmol) at 0° C. under $N_2$ atmosphere and the mixture was stirred at r.t. for 1 hr. The reaction mixture was quenched with ice-water (10 mL), extracted with EtOAc (2×10 mL). The combined organic layers were washed with water and brine, dried over $Na_2SO_4$, filtered and evaporated to dryness. The residue was purified by flash chromatography (silica gel, 0~35% EtOAc in PE) to give the title compound (140 mg, 80.9% yield) as white solid. LC/MS (ESI) m/z: 513 $(M+H)^+$.

Step 2: allyl (R)-2-(1-(6-(5-(((6-(1H-1,2,3-triazol-1-yl)pyrimidin-4-yl)oxy)methyl)-1-methyl-1H-1,2,3-triazol-4-yl)-2-ethylpyridin-3-yl)piperidin-3-yl)acetate To a solution of prop-2-en-1-yl 2-[(3R)-1-[6-(5-{[(6-chloropyrimidin-4-yl)oxy]methyl}-1-methyl-1H-1,2,3-triazol-4-yl)-2-ethylpyridin-3-yl]piperidin-3-yl]acetate (140 mg, 0.27 mmol) in $CH_3CN$ (3 mL) was added DBU (125 mg, 0.82 mmol) and 2H-1,2,3-triazole (94 mg, 1.37 mmol) and the mixture was stirred in a CEM microwave reactor at 105° C. for 3 hrs. The reaction mixture was evaporated to dryness and the residue was purified by prep-TLC (EtOAc:PE=1:2) to give allyl (R)-2-(1-(6-(5-(((6-(1H-1,2,3-triazol-1-yl)pyrimidin-4-yl)oxy)methyl)-1-methyl-1H-1,2,3-triazol-4-yl)-2-ethylpyridin-3-yl)piperidin-3-yl)acetate (50 mg, 33.6% yield) (45 mg, 29% yield) as white solid. LC/MS (ESI) m/z: 545 $(M+H)^+$.

Step 3: 2-[(3R)-1-{2-ethyl-6-[1-methyl-5-({[6-(1H-1,2,3-triazol-1-yl)pyrimidin-4-yl]oxy}methyl)-1H-1,2,3-triazol-4-yl]pyridin-3-yl}piperidin-3-yl]acetic acid To a solution of prop-2-en-1-yl 2-[(3R)-1-{2-ethyl-6-[1-methyl-5-({[6-(1H-1,2,3-triazol-1-yl)pyrimidin-4-yl]oxy}methyl)-1H-1,2,3-triazol-4-yl]pyridin-3-yl}piperidin-3-yl]acetate (50 mg, 0.10 mmol) in DCM (3 mL) was added $Pd(PPh_3)_4$ (5 mg, 0.005 mmol) and morpholine (16 mg, 0.2 mmol) and the mixture was degassed under $N_2$ atmosphere for three times and stirred at r.t. for 4 hrs. The reaction mixture was evaporated to dryness and the residue was purified by perp-HPLC (C18, 0~90% acetonitrile in $H_2O$ with 0.1% HCOOH) to give the title compound (12 mg, 25.9% yield) as white solid. $^1H$ NMR (400 MHz, $CD_3OD$) δ 8.80 (d, J=1.3 Hz, 1H), 8.79 (d, J=0.9 Hz, 1H), 7.91 (d, J=1.3 Hz, 1H), 7.84 (d, J=8.3 Hz, 1H), 7.59 (d, J=0.9 Hz, 1H), 7.50 (d, J=8.4 Hz, 1H), 6.27 (s, 2H), 4.24 (s, 3H), 3.18-3.12 (m, 1H), 3.07-2.99 (m, 1H), 2.83 (q, J=7.5 Hz, 2H), 2.76-2.65 (m, 1H), 2.46-2.38 (m, 1H), 2.30 (d, J=6.4 Hz, 2H), 2.24-2.14 (m, 1H), 1.92-1.72 (m, 3H), 1.23 (t, J=7.5 Hz, 4H). LC/MS (ESI) m/z: 505 $(M+H)^+$.

Example 98: (R)-2-(1-(6-(5-(((6-(2H-1,2,3-triazol-2-yl)pyrimidin-4-yl)oxy)methyl)-1-methyl-1H-1,2,3-triazol-4-yl)-2-ethylpyridin-3-yl)piperidin-3-yl)acetic acid Example 98

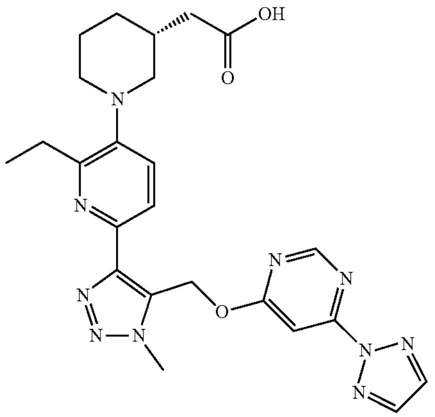

The title compound was prepared using the same procedure as example 97. LC/MS (ESI) m/z: 505 $(M+H)^+$. $^1H$ NMR (400 MHz, $CD_3OD$) δ 8.76 (d, J=0.8 Hz, 1H), 8.07 (s, 2H), 7.84 (d, J=8.3 Hz, 1H), 7.50 (dd, J=4.6, 3.8 Hz, 2H), 6.26 (s, 2H), 4.24 (s, 3H), 3.17-3.11 (m, 1H), 3.06-2.98 (m, 1H), 2.83 (q, J=7.5 Hz, 2H), 2.74-2.66 (m, 1H), 2.48-2.39 (m, 1H), 2.29 (d, J=6.7 Hz, 2H), 2.25-2.15 (m, 1H), 1.91-1.70 (m, 3H), 1.22 (t, J=7.5 Hz, 3H).

Example 99: (S)-2-(1-(6-(5-(((6-(1H-1,2,3-triazol-1-yl)pyrimidin-4-yl)oxy)methyl)-1-methyl-1H-1,2,3-triazol-4-yl)-2-methylpyridin-3-yl)-5,5-difluoropiperidin-3-yl)acetic acid Example 99

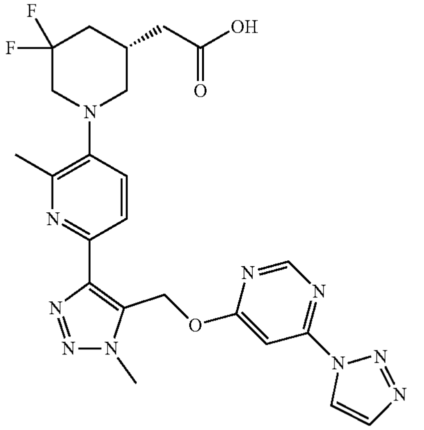

The title compound was prepared from methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate using the same sequence that was synthesized example 97. $^1$H NMR (400 MHz, $CD_3OD$) δ 8.79 (t, J=1.1 Hz, 2H), 7.91 (d, J=1.3 Hz, 1H), 7.85 (d, J=8.3 Hz, 1H), 7.59 (d, J=0.9 Hz, 1H), 7.53 (d, J=8.4 Hz, 1H), 6.26-6.18 (m, 2H), 4.24 (s, 3H), 3.27 (d, J=13.2 Hz, 2H), 3.11-2.96 (m, 1H), 2.64-2.54 (m, 1H), 2.53-2.44 (m, 4H), 2.43-2.23 (m, 3H), 1.80-1.61 (m, 1H). LC/MS (ESI) m/z: 527 $(M+H)^+$.

Example 100: (S)-2-(1-(6-(5-(((6-(1H-1,2,3-triazol-2-yl)pyrimidin-4-yl)oxy)methyl)-1-methyl-1H-1,2,3-triazol-4-yl)-2-methylpyridin-3-yl)-5,5-difluoropiperidin-3-yl)acetic acid Example 100

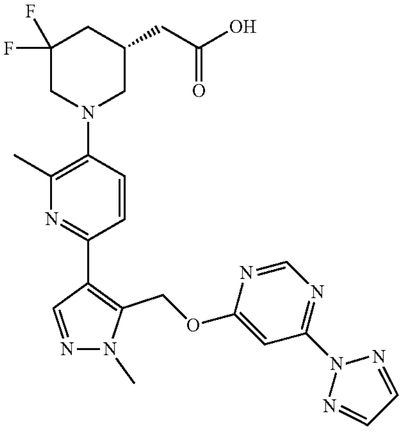

The title compound was prepared from methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate using the same sequence that was synthesized example 97. LC/MS (ESI) m/z: 527 $(M+H)^+$. $^1$H NMR (400 MHz, $CD_3OD$) δ 8.74 (s, 1H), 8.09 (s, 2H), 7.99 (d, J=8.4 Hz, 1H), 7.80 (d, J=8.4 Hz, 1H), 7.51 (s, 1H), 6.12 (s, 2H), 4.28 (s, 3H), 3.37 (s, 2H), 3.17-3.09 (m, 1H), 2.70-2.64 (m, 1H), 2.60 (s, 3H), 2.55-2.47 (m, 1H), 2.42 (d, J=7.1 Hz, 2H), 2.35-2.27 (m, 1H), 1.82-1.70 (m, 1H).

Example 101: (R)-2-(1-(6-(5-(((4-(1H-pyrazol-1-yl)pyrimidin-2-yl)oxy)methyl)-1-methyl-1H-1,2,3-triazol-4-yl)-2-ethylpyridin-3-yl)piperidin-3-yl)acetic acid

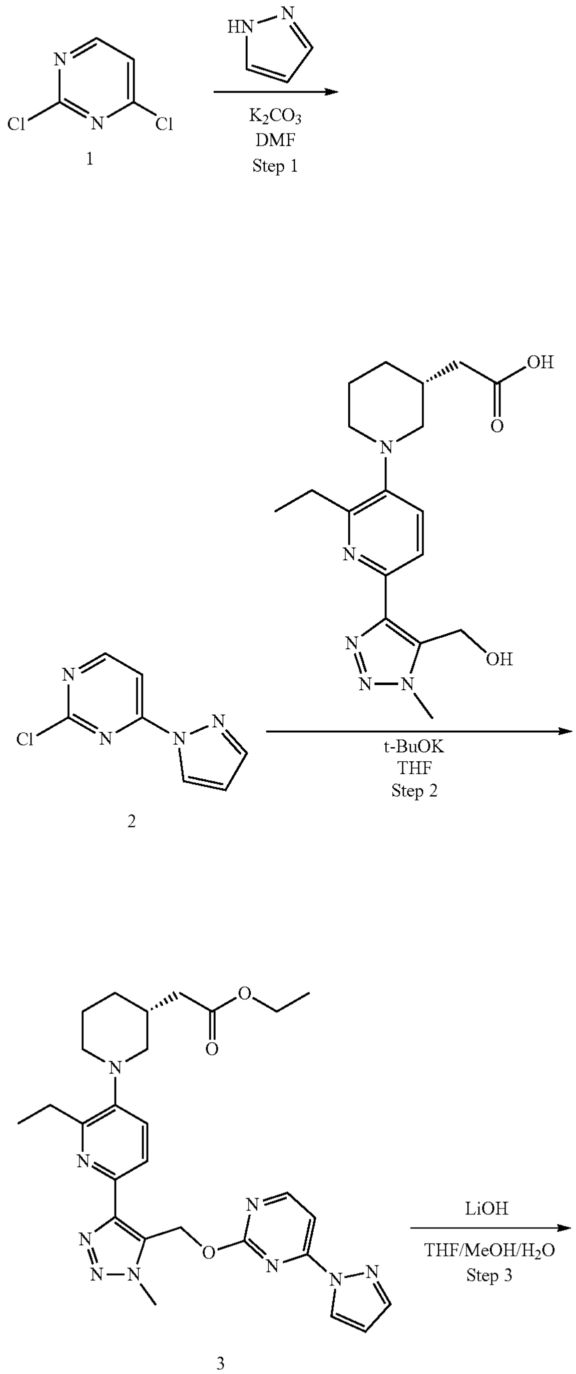

-continued

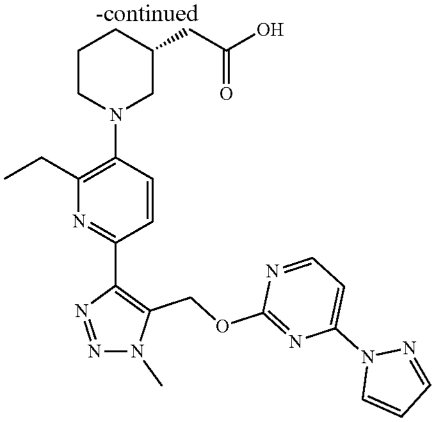

Example 101

Step 1: 2-chloro-4-(1H-pyrazol-1-yl)pyrimidine

To a solution of 2,4-dichloropyrimidine (5.0 g, 33.6 mmol) in DMF (50 mL) was added 1H-pyrazole (2.28 g, 33.6 mmol) followed by $K_2CO_3$ (9.28 g, 67.1 mmol) and the reaction was stirred at r.t. for 16 hrs. The mixture was diluted with EtOAc (50 mL), washed with brine, dried over anhydrous $Na_2SO_4$, filtered and concentrated under reduced pressure to dryness. The residue was purified by flash chromatography (0~5% EtOAc in PE) to give the title compound (1.2 g, 19.8% yield) as yellow solid. LC/MS (ESI) (m/z): 181 $(M+H)^+$. $^1H$ NMR (400 MHz, $CDCl_3$) δ 8.63 (d, J=5.5 Hz, 1H), 8.58 (d, J=2.4 Hz, 1H), 7.86 (d, J=5.5 Hz, 1H), 7.82 (d, J=0.8 Hz, 1H), 6.54 (dd, J=2.7, 1.6 Hz, 1H).

Step 2: ethyl (R)-2-(1-(6-(5-(((4-(1H-pyrazol-1-yl)pyrimidin-2-yl)oxy)methyl)-1-methyl-1H-1,2,3-triazol-4-yl)-2-ethylpyridin-3-yl)piperidin-3-yl)acetate To a mixture of ethyl ethyl (R)-2-(1-(2-ethyl-6-(5-(hydroxymethyl)-1-methyl-1H-1,2,3-triazol-4-yl)pyridin-3-yl)piperidin-3-yl)acetate (40 mg, 0.11 mmol) and 2-chloro-4-(1H-pyrazol-1-yl)pyrimidine (30 mg, 0.16 mmol) in THE (5 mL) was added t-BuOK (0.22 mL, 0.22 mmol, 1.0 M in THF) drop-wisely at 0° C. and the reaction was stirred at 0° C. for 1 hr. The mixture was quenched with saturated aq·$NH_4Cl$ solution at 0° C. and extracted with EtOAc (3×5 mL). The combined organic layers were washed with brine, dried over anhydrous $Na_2SO_4$, filtered and concentrated to dryness. The residue was purified by flash chromatography (0~60% EtOAc in PE) to give the title compound (35 mg, 59.5% yield) as yellow oil. LC/MS (ESI) (m/z): 532 $(M+H)^+$.

Step 3: (R)-2-(1-(6-(5-(((4-(1H-pyrazol-1-yl)pyrimidin-2-yl)oxy)methyl)-1-methyl-1H-1,2,3-triazol-4-yl)-2-ethylpyridin-3-yl)piperidin-3-yl)acetic acid To a solution of ethyl (R)-2-(1-(6-(5-(((4-(1H-pyrazol-1-yl)pyrimidin-2-yl)oxy)methyl)-1-methyl-1H-1,2,3-triazol-4-yl)-2-ethylpyridin-3-yl)piperidin-3-yl)acetate (36 mg, 0.065 mmol) in THF (4 mL)/$H_2O$ (4 mL)/MeOH (4 mL) was added LiOH·$H_2O$ (28 mg, 0.66 mmol), and the reaction was stirred at r.t. for 2 hrs. Volatiles were removed under vacuum and the residue was diluted with $H_2O$ (5 mL). The mixture was adjusted with 1N aq·HCl to pH~4. The mixture was extracted with EtOAc (3×5 mL) and the combined organic layers were washed with brine, dried over anhydrous $Na_2SO_4$, filtered and concentrated to dryness. The residue was purified by prep-HPLC (C18, 5-95%, MeCN in $H_2O$ with 0.1% HCOOH) to give the title compound (15 mg, 45.2% yield) as white solid. LC/MS (ESI) (m/z): 504 $(M+H)^+$. 1H NMR (400 MHz, $CD_3OD$) δ 8.57 (d, J=5.5 Hz, 1H), 8.34 (d, J=2.6 Hz, 1H), 7.96 (d, J=8.5 Hz, 1H), 7.81-7.74 (m, 2H), 7.61 (d, J=5.5 Hz, 1H), 6.51-6.50 (m, 1H), 6.16-6.09 (m, 2H), 4.27 (s, 3H), 3.25 (d, J=13.1 Hz, 3H), 3.11 (d, J=11.0 Hz, 1H), 2.98-2.92 (m, 2H), 2.84-2.78 m, 1H), 2.56-2.51 (m, 1H), 2.33-2.31 (m, 2H), 2.27-2.21 (m, 1H), 1.93-1.76 (m, 3H), 1.30-1.26 (m, 4H).

Example 102: (R)-2-(1-(6-(5-(((4-(1H-pyrazol-1-yl)pyrimidin-2-yl)oxy)methyl)-1-methyl-1H-1,2,3-triazol-4-yl)-2-methylpyridin-3-yl)piperidin-3-yl)acetic acid

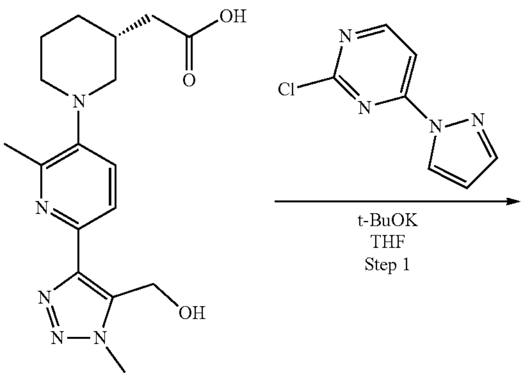

1

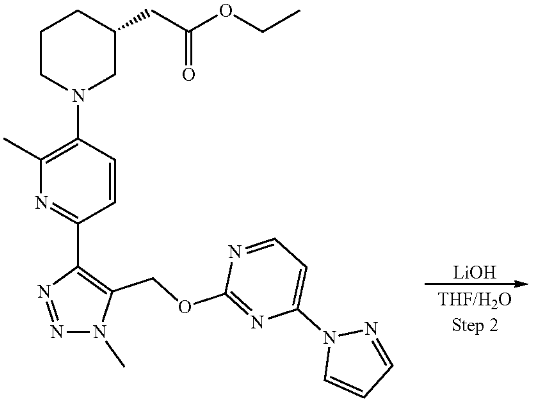

2

-continued

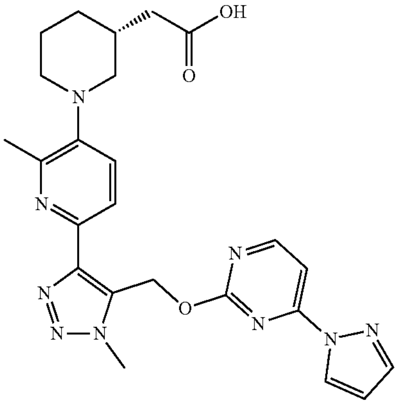

Example 102

The title compound was synthesized from Intermediate 2A of example 101 according to the same sequence as was used for the synthesis of example 101. LC/MS (ESI) m/z: 490 $(M+H)^+$. $^1H$ NMR (400 MHz, DMSO-$d_6$) δ 8.72 (d, J=5.5 Hz, 1H), 8.42 (d, J=2.2 Hz, 1H), 7.93 (d, J=1.0 Hz, 1H), 7.88 (d, J=8.3 Hz, 1H), 7.59 (d, J=5.5 Hz, 1H), 7.50 (d, J=8.4 Hz, 1H), 6.57 (dd, J=2.7, 1.6 Hz, 1H), 6.14 (s, 2H), 4.16 (s, 3H), 3.10 (d, J=10.4 Hz, 1H), 3.02 (d, J=11.5 Hz, 1H), 2.67-2.61 (m, 1H), 2.43-2.37 (m, 1H), 2.32 (s, 3H), 2.27-2.19 (m, 2H), 2.10-2.03 (m, 1H), 1.82-1.71 (m, 2H), 1.67-1.59 (m, 1H), 1.16-1.08 (m, 1H).

Example 103: (R)-2-(1-(6-(5-(((4-(1H-pyrazol-1-yl)pyridin-2-yl)oxy)methyl)-1-methyl-1H-1,2,3-triazol-4-yl)-2-methylpyridin-3-yl)piperidin-3-yl)acetic acid

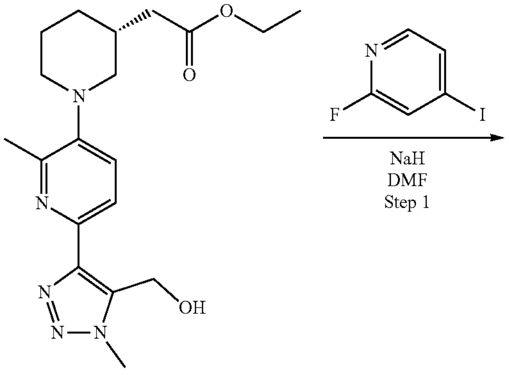

1

-continued

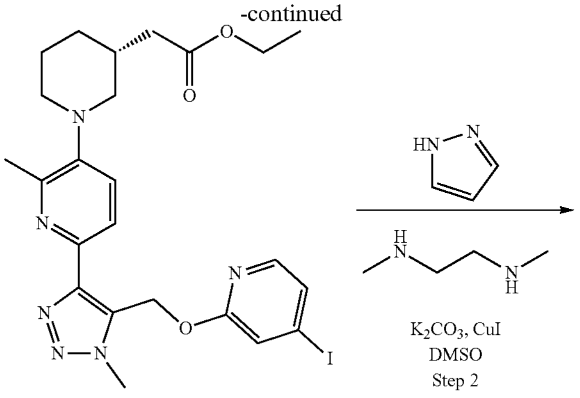

2

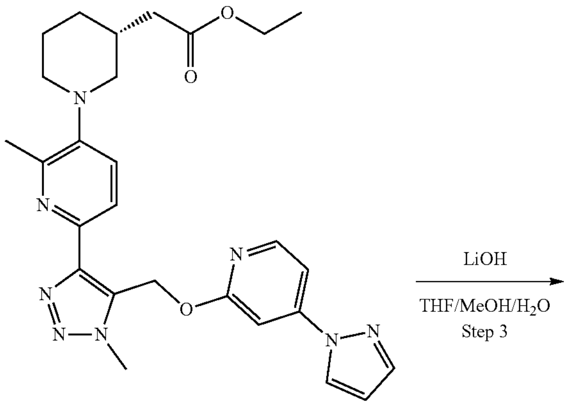

3

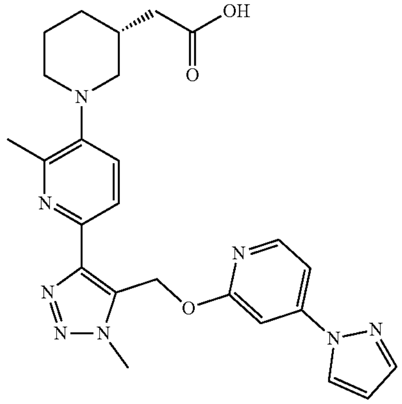

Example 103

Step 1: ethyl (R)-2-(1-(6-(5-(((4-iodopyridin-2-yl)oxy)methyl)-1-methyl-1H-1,2,3-triazol-4-yl)-2-methylpyridin-3-yl)piperidin-3-yl)acetate To a solution of ethyl (R)-2-(1-(6-(5-(hydroxymethyl)-1-methyl-1H-1,2,3-triazol-4-yl)-2-methylpyridin-3-yl)piperidin-3-yl)acetate (200 mg, 0.53 mmol) in DMF (10 mL) was added NaH (43 mg, 1.07 mmol, 60% dispersion in mineral oil) at 0° C. and the mixture was stirred at 0° C. for 30 min. A solution of 2-fluoro-4-iodopyridine (240 mg, 1.07 mmol) in DMF (2 mL) was added drop-wisely to the above mixture and the resulting mixture was stirred at r.t. for 30 min. The mixture was quenched with saturated aq·$NH_4Cl$ solution at 0° C. and was extracted with EtOAc (3×10 mL). The combined organic layers were washed with brine, dried over anhydrous $Na_2SO_4$, filtered and concentrated to dryness. The residue was purified by flash chromatography (silica gel, 0~45% EtOAc in PE) to give the title compound (120 mg, 38.9% yield) as yellow solid. LC/MS (ESI) (m/z): 577 $(M+H)^+$.

Step 2: ethyl (R)-2-(1-(6-(5-(((4-(1H-pyrazol-1-yl)pyridin-2-yl)oxy)methyl)-1-methyl-1H-1,2,3-triazol-4-yl)-2-methylpyridin-3-yl)piperidin-3-yl)acetate To a solution of ethyl (R)-2-(1-(6-(5-(((4-iodopyridin-2-yl)oxy)methyl)-1-methyl-1H-1,2,3-triazol-4-yl)-2-methylpyridin-3-yl)piperidin-3-yl)acetate (120 mg, 0.21 mmol) in DMSO (5 mL) was added 1H-pyrazole (28 mg, 0.42 mmol) followed by $K_2CO_3$ (58 mg, 0.42 mmol), CuI (8 mg, 0.04 mmol) and N,N'-Dimethyl-1,2-ethanediamine (4 mg, 0.04 mmol). The reaction was stirred at 120° C. for 16 hrs. The mixture was diluted with EtOAc (15 mL), washed with water and brine, dried over anhydrous $Na_2SO_4$, filtered and concentrated under reduced pressure to dryness. The residue was purified by flash chromatography (0~40% EtOAc in PE) to give the title compound (50 mg, 46.5% yield) as yellow solid. LC/MS (ESI) m/z: 517 $(M+H)^+$.

Step 3: (R)-2-(1-(6-(5-(((4-(1H-pyrazol-1-yl)pyridin-2-yl)oxy)methyl)-1-methyl-11H-1,2,3-triazol-4-yl)-2-methylpyridin-3-yl)piperidin-3-yl)acetic acid The title compounds was synthesized from compound 3 according to the same sequence as was used for the synthesis of example 101. LC/MS (ESI) m/z: 489 $(M+H)^+$. $^1H$ NMR (400 MHz, $CD_3OD$) δ 8.31 (d, J=2.6 Hz, 1H), 8.18 (d, J=5.8 Hz, 1H), 7.79 (d, J=8.4 Hz, 1H), 7.74 (d, J=1.6 Hz, 1H), 7.51-7.42 (m, 2H), 7.24 (d, J=1.7 Hz, 1H), 6.57-6.44 (m, 1H), 6.03 (d, J=2.1 Hz, 2H), 4.22 (s, 3H), 3.20 (d, J=11.0 Hz, 1H), 3.08 (d, J=11.3 Hz, 1H), 2.75-2.65 (m, 1H), 2.46 (s, 3H), 2.42 (d, J=11.2 Hz, 1H), 2.33-2.27 (m, 2H), 2.25-2.17 (m, 1H), 1.93-1.86 (m, 1H), 1.85-1.72 (m, 2H), 1.22-1.15 (m, 1H).

Example 104: (R)-2-(1-(6-(5-(((4-(2H-1,2,3-triazol-2-yl)pyridin-2-yl)oxy)methyl)-1-methyl-1H-1,2,3-triazol-4-yl)-2-methylpyridin-3-yl)piperidin-3-yl) acetic acid

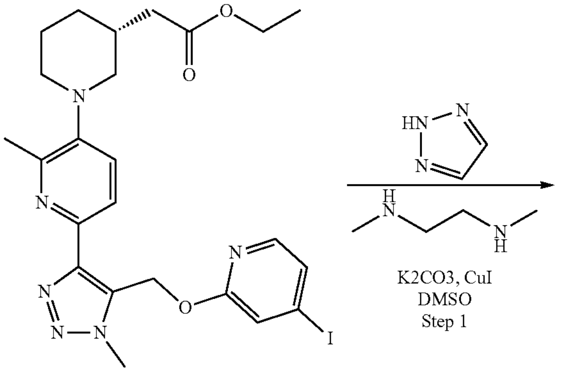

1

-continued

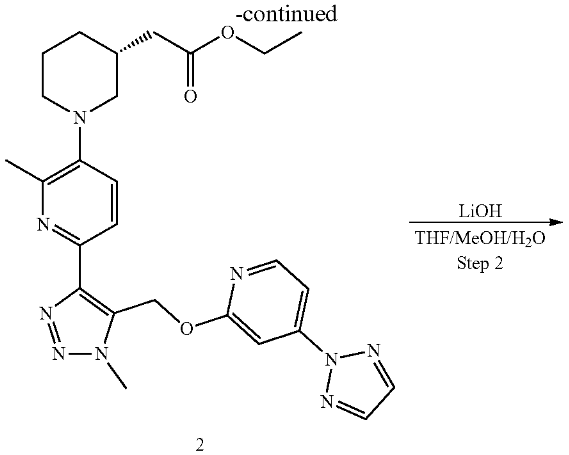

2

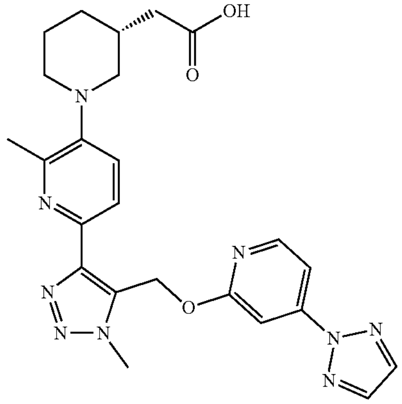

Example 104

Step 1: ethyl (R)-2-(1-(6-(5-(((4-(2H-1,2,3-triazol-2-yl)pyridin-2-yl)oxy)methyl)-1-methyl-1H-1,2,3-triazol-4-yl)-2-methylpyridin-3-yl)piperidin-3-yl) acetate To a solution of ethyl (R)-2-(1-(6-(5-(((4-iodopyridin-2-yl)oxy)methyl)-1-methyl-1H-1,2,3-triazol-4-yl)-2-methylpyridin-3-yl)piperidin-3-yl)acetate (120 mg, 0.21 mmol) in DMSO (5 mL) was added 1,2,3-1H-Triazole (29 mg, 0.42 mmol) followed by $K_2CO_3$ (58 mg, 0.42 mmol), CuI (8 mg, 0.04 mmol) and N,N'-Dimethyl-1,2-ethanediamine (4 mg, 0.04 mmol). The reaction was stirred at 120° C. for 16 hrs. The mixture was diluted with EtOAc (10 mL), washed with water and brine, dried over anhydrous $Na_2SO_4$, filtered and concentrated under reduced pressure to dryness. The residue was purified by flash chromatography (silica gel, 0~50% EtOAc in PE) to give the title compound (65 mg, 69.8% yield) as yellow solid. LC/MS (ESI) m/z: 518 $(M+H)^+$. $^1H$ NMR (400 MHz, $CDCl_3$) δ 8.20 (d, J=5.6 Hz, 1H), 7.87 (d, J=8.3 Hz, 1H), 7.77 (s, 2H), 7.60 (dd, J=5.6, 1.8 Hz, 1H), 7.40 (d, J=1.8 Hz, 1H), 7.26 (d, J=8.3 Hz, 1H), 6.04 (s, 2H), 4.10 (s, 3H), 4.05-4.03 (m, 2H), 3.02-2.95 (m, 1H), 2.97 (d, J=11.4 Hz, 1H), 2.64-2.54 (m, 1H), 2.44-2.38 (m, 3H), 2.37-2.30 (m, 1H), 2.21-2.16 (m, 1H), 1.84 7 1.75 (m, 1H), 1.18 (dd, J=4.7, 2.4 Hz, 3H), 1.13-1.05 (m, 1H).

Step 2: (R)-2-(1-(6-(5-(((4-(2H-1,2,3-triazol-2-yl)pyridin-2-yl)oxy)methyl)-1-methyl-1H-1,2,3-triazol-4-yl)-2-methylpyridin-3-yl)piperidin-3-yl)acetic acid The title compounds was synthesized according to the same sequence as was used for the synthesis of example 103.

LC/MS (ESI) m/z:490 $(M+H)^+$. $^1H$ NMR (400 MHz, $CD_3OD$) δ 8.24 (d, J=5.7 Hz, 1H), 7.97 (s, 2H), 7.78 (d, J=8.3 Hz, 1H), 7.70 (dd, J=5.7, 1.8 Hz, 1H), 7.48 (d, J=8.3 Hz, 1H), 7.47 (d, J=1.8 Hz, 1H), 6.06 (s, 2H), 4.22 (s, 3H), 3.22-3.19 (m, 1H), 3.10-3.05 (m, 1H), 2.73-2.66 (m, 1H), 2.46 (s, 3H), 2.44-2.40 (m, 1H), 2.32-2.28 (m, 2H), 2.25-2.18 (m, 1H), 1.93-1.87 (m, 1H), 1.84-1.72 (m, 2H), 1.26-1.18 (m, 1H).
Example 105: (S)-2-(1-(6-(4-(((6-(1H-pyrazol-1-yl)pyrimidin-4-yl)oxy)methyl)-3-methylisoxazol-5-yl)-2-methylpyridin-3-yl)-5,5-difluoropiperidin-3-yl)acetic acid
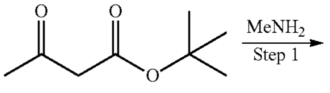
1
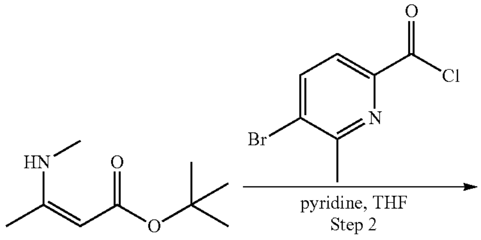
2
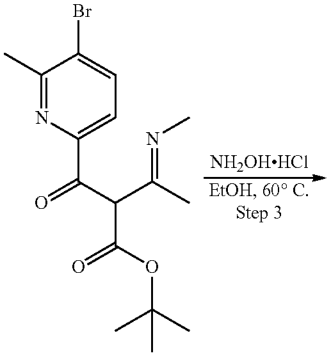
3
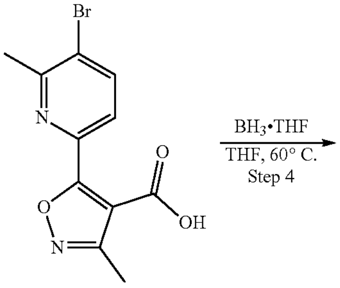
4
-continued
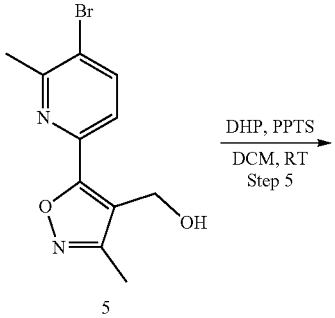
5
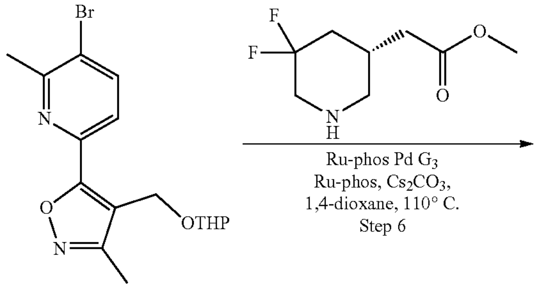
6
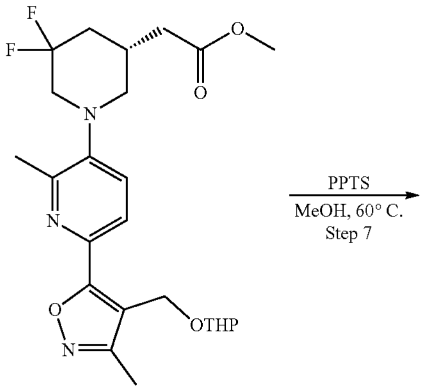
7
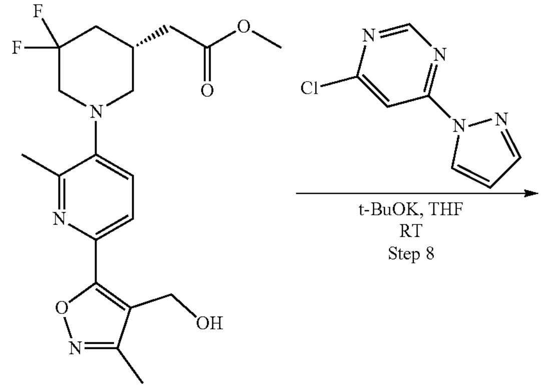
8

-continued

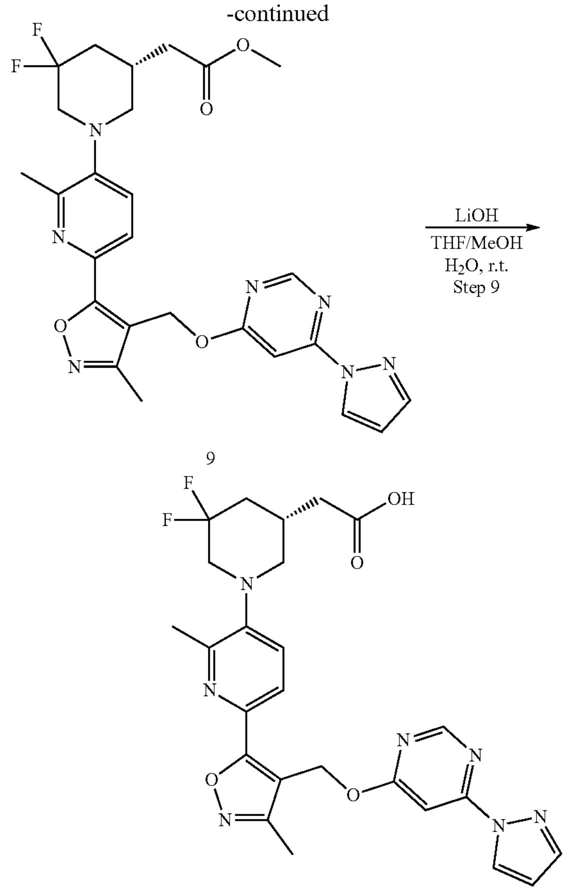

9

Example 105

Step 1: tert-butyl (Z)-3-(methylamino)but-2-enoate

To aq·$MeNH_2$ solution (40% wt in water) (5.9 g, 190 mmol) was added tert-butyl 3-oxobutanoate (10 g, 63.2 mmol) drop-wisely at 0° C. and the mixture was stirred at r.t. for 2 hrs. The mixture was diluted with DCM (50 mL) and washed with water and brine, dried over anhydrous $Na_2SO_4$, filtered and concentrated to dryness. The residue was purified by flash chromatography (eluted with PE:EtOAc=20:1 to 2:1) to give the title compound (10.8 g, 99.8% yield) as yellow oil. LC/MS (ESI) m/z: 172 $(M+H)^+$.

Step 2: tert-butyl (E)-2-(5-bromo-6-methylpicolinoyl)-3-(methylimino)butanoate

To a mixture of 5-bromo-6-methylpicolinoyl chloride (1 g, 4.27 mmol) and tert-butyl (Z)-3-(methylamino)but-2-enoate (0.80 g, 4.69 mmol) in THE (10 mL) was added pyridine (1.69 g, 21.3 mmol) drop-wisely at 0° C. and the mixture was stirred at r.t. for 16 hrs. The mixture was diluted EtOAc (20 mL), washed with water and brine, dried over anhydrous $Na_2SO_4$, filtered and concentrated to dryness. The residue was purified by flash chromatography (eluted with PE:EtOAc=20:1 to 2:1) to give title compound (964 mg, 61.2% yield) as yellow solid. LC/MS (ESI) m/z: 369/371 $(M+H)^+$.

Step 3: 5-(5-bromo-6-methylpyridin-2-yl)-3-methylisoxazole-4-carboxylic acid

To a solution of tert-butyl (E)-2-(5-bromo-6-methylpicolinoyl)-3-(methylimino)butanoate (964 mg, 2.61 mmol) in EtOH (10 mL) was added hydroxylamine hydrochloride (272 mg, 3.92 mmol) and the mixture was stirred at 60° C. for 3 hrs. The mixture was diluted with water and extracted with EtOAc (2×10 mL). The combined organic layers were washed with brine, dried over anhydrous $Na_2SO_4$, filtered and concentrated to dryness. The residue was purified by flash chromatography (eluted with DCM:MeOH=200:1 to 20:1) to give the title compound (353 mg, 45.5% yield) as white solid. LC/MS (ESI) m/z: 297/299 $(M+H)^+$.

Step 4: (5-(5-bromo-6-methylpyridin-2-yl)-3-methylisoxazol-4-yl)methanol

To a solution of 5-(5-bromo-6-methylpyridin-2-yl)-3-methylisoxazole-4-carboxylic acid (353 mg, 1.19 mmol) in THF (5 mL) was added $BH_3$-THF (3 mL, 3 mmol, 1 M in THF) drop-wisely at 0° C. and the mixture was stirred at 60° C. for 2 hrs. The mixture was quenched with MeOH at 0° C. and concentrated to dryness. The residue was purified by flash chromatography (PE:EtOAc=30:1 to 3:1) to give the title compound (163 mg, 48.5% yield) as white solid. LC/MS (ESI) m/z: 283/285 $(M+H)^+$.

Step 5: 5-(5-bromo-6-methylpyridin-2-yl)-3-methyl-4-(((tetrahydro-2H-pyran-2-yl)oxy)methyl)isoxazole To a solution of (5-(5-bromo-6-methylpyridin-2-yl)-3-methylisoxazol-4-yl)methanol (163 mg, 0.58 mmol) in DCM (3 mL) were added DHP (121 mg, 1.44 mmol), PPTS (7.2 mg, 0.029 mmol) and the mixture was stirred at r.t. for 16 hrs. The mixture was quenched with saturated aq·$NaHCO_3$ and extracted with EtOAc (2×10 mL). The combined organic layers were washed with brine, dried over anhydrous $Na_2SO_4$, filtered and concentrated to dryness. The residue was purified by flash chromatography (eluted with DCM:MeOH=200:1 to 20:1) to give the title compound (200 mg, 94.6% yield) as yellow oil. LC/MS (ESI) m/z: 367/369 $(M+H)^+$.

Step 6: methyl 2-((3S)-5,5-difluoro-1-(2-methyl-6-(3-methyl-4-(((tetrahydro-2H-pyran-2-yl)oxy)methyl)isoxazol-5-yl)pyridin-3-yl)piperidin-3-yl)acetate To a mixture of 5-(5-bromo-6-methylpyridin-2-yl)-3-methyl-4-(((tetrahydro-2H-pyran-2-yl)oxy)methyl)isoxazole (95 mg, 0.26 mmol) and methyl (S)-2-(5,5-difluoropiperidin-3-yl)acetate (50.0 mg, 0.26 mmol) in 1,4-dioxane (2 mL) were added $Cs_2CO_3$ (253 mg, 0.78 mmol), $Pd_2(dba)_3$ (24 mg, 0.026 mmol), Ru-Phos (12 mg, 0.026 mmol) under $N_2$ atmosphere, after addition, the mixture was degassed under $N_2$ atmosphere for three times and stirred at 110° C. for 16 hrs. The mixture was diluted with water and extracted with EtOAc (2×5 mL). The combined organic layers were washed with brine, dried over anhydrous $Na_2SO_4$, filtered and concentrated to dryness. The residue was purified by flash chromatography (eluted with PE:EtOAc=20:1 to 1:1) to give the title compound (45 mg, 36.2% yield) as yellow solid. LC/MS (ESI) m/z: 480 $(M+H)^+$.

Step 7: methyl (S)-2-(5,5-difluoro-1-(6-(4-(hydroxymethyl)-3-methylisoxazol-5-yl)-2-methylpyridin-3-yl)piperidin-3-yl)acetate To a solution of methyl 2-((3S)-5,5-difluoro-1-(2-methyl-6-(3-methyl-4-(((tetrahydro-2H-pyran-2-yl)oxy)methyl)isoxazol-5-yl)pyridin-3-yl)piperidin-3-yl)acetate (45 mg, 0.094 mmol) in MeOH (2 mL) was added PPTS (47 mg, 0.19 mmol) and the mixture was stirred at 60° C. for 2 hrs. The mixture was diluted with EtOAc (5 mL) and washed with saturated aq·$NaHCO_3$ solution and brine, dried over anhydrous $Na_2SO_4$, filtered and concentrated to dryness. The residue was purified by flash chromatography (eluted with PE:EtOAc=20:1 to 1:1) to give the title compound (30 mg, 80.9% yield) as yellow oil. LC/MS (ESI) m/z: 396 $(M+H)^+$.

Step 8: methyl (S)-2-(1-(6-(4-(((6-(1H-pyrazol-1-yl)pyrimidin-4-yl)oxy)methyl)-3-methylisoxazol-5-yl)-2-methylpyridin-3-yl)-5,5-difluoropiperidin-3-yl)acetate To a solution of methyl (S)-2-(5,5-difluoro-1-(6-(4-(hydroxymethyl)-3-methylisoxazol-5-yl)-2-methylpyridin-3-yl)piperidin-3-yl)acetate (30 mg, 0.076 mmol) and 4-chloro-6-(1H-pyrazol-1-yl)pyrimidine (20.6 mg, 0.11 mmol) in THF (2 mL) was added t-BuOK (0.15 mL, 0.15 mmol, 1 M in THF) drop-wisely at 0° C. under $N_2$ atmosphere and the mixture was stirred at 25° C. for 2 hrs. The mixture was quenched with water and extracted with EtOAc (3x3 mL). The combined organic layers were washed with brine, dried over anhydrous $Na_2SO_4$, filtered and concentrated to dryness to give the title compound (30 mg, yield 73.3%) as yellow oil, which was used in next step directly. LC/MS (ESI) m/z: 540 $(M+H)^+$.

Step 9: (S)-2-(1-(6-(4-(((6-(1H-pyrazol-1-yl)pyrimidin-4-yl)oxy)methyl)-3-methylisoxazol-5-yl)-2-methylpyridin-3-yl)-5,5-difluoropiperidin-3-yl)acetic acid To a solution of methyl (S)-2-(1-(6-(4-(((6-(1H-pyrazol-1-yl)pyrimidin-4-yl)oxy)methyl)-3-methylisoxazol-5-yl)-2-methylpyridin-3-yl)-5,5-difluoropiperidin-3-yl)acetate (30 mg, 0.056 mmol) in THE (2 mL), MeOH (0.5 mL) and $H_2O$ (0.5 mL) was added LiOH·$H_2O$ (23.3 mg, 0.56 mmol) at 25° C. and the mixture was stirred at 25° C. for 2 hrs. The mixture was concentrated to dryness and the residue was dissolved in water (5 mL). The mixture was washed with EtOAc (2x3 mL) and the aqueous layer was acidified with 1N aq·HCl to pH=4 and extracted with DCM (3x3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (5 mg, 17.1% yield) as white solid. $^1H$ NMR (400 MHz, $CD_3OD$) δ 8.63 (s, 1H), 8.59 (d, J=2.6 Hz, 1H), 7.76 (d, J=1.0 Hz, 1H), 7.73 (d, J=8.2 Hz, 1H), 7.53 (d, J=8.4 Hz, 1H), 7.27 (s, 1H), 6.54 (dd, J=2.6, 1.7 Hz, 1H), 5.89 (s, 2H), 3.40-3.33 (m, 2H), 3.15-3.03 (m, 1H), 2.64-2.57 (m, 1H), 2.55-2.50 (m, 1H), 2.48 (s, 3H), 2.41 (s, 3H), 2.41-2.38 (m, 2H), 2.36-2.27 (m, 1H), 1.80-1.66 (m, 1H). LC/MS (ESI) m/z: 526 $(M+H)^+$.

Example 106: (S)-2-(5,5-difluoro-1-(2-methyl-6-(1-methyl-5-(((3-oxo-4-propyl-3,4-dihydropyrazin-2-yl)oxy)methyl)-1H-1,2,3-triazol-4-yl)pyridin-3-yl)piperidin-3-yl)acetic acid

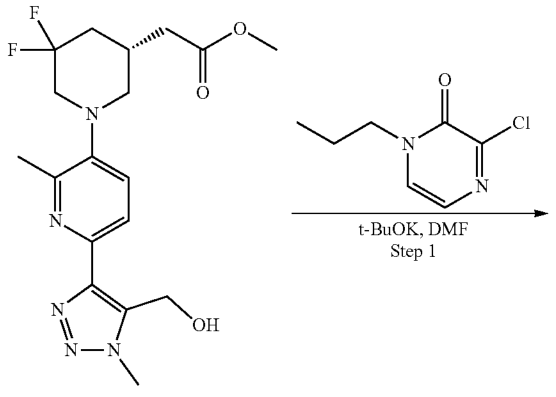

1

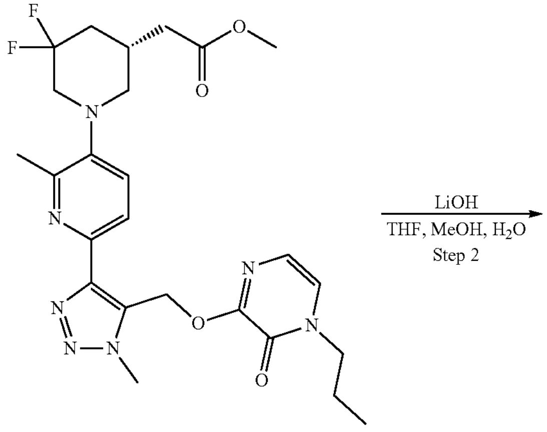

2

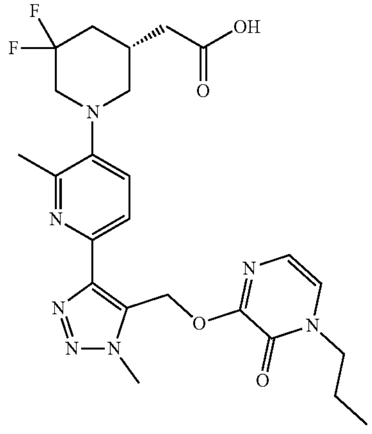

Example 106

Step 1: methyl (S)-2-(5,5-difluoro-1-(2-methyl-6-(1-methyl-5-(((3-oxo-4-propyl-3,4-dihydropyrazin-2-yl)oxy)methyl)-1H-1,2,3-triazol-4-yl)pyridin-3-yl)piperidin-3-yl)acetate To a mixture of methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate (55 mg, 0.14 mmol) and 3-chloro-1-propylpyrazin-2(1H)-one (27 mg, 0.15 mmol) in DMF (5 mL) was added t-BuOK (0.42 mL, 0.42 mmol, 1 M in THF) at 0° C. and the mixture was stirred at room temperature overnight. The mixture was diluted with EtOAc and washed with saturated aq·$NH_4Cl$ solution and brine, dried over anhydrous $Na_2SO_4$ filtered and concentrated to dryness to give the title compound (70 mg, 94.2% yield). LC/MS (ESI) (m/z): 532 $(M+H)^+$.

Step 2: (S)-2-(5,5-difluoro-1-(2-methyl-6-(1-methyl-5-(((3-oxo-4-propyl-3,4-dihydropyrazin-2-yl)oxy)methyl)-1H-1,2,3-triazol-4-yl)pyridin-3-yl)piperidin-3-yl)acetic acid To a solution of methyl (S)-2-(5,5-difluoro-1-(2-methyl-6-(1-methyl-5-(((3-oxo-4-propyl-3,4-dihydropyrazin-2-yl)oxy)methyl)-1H-1,2,3-triazol-4-yl)pyridin-3-yl)piperidin-3-yl)acetate (74 mg, 0.14 mmol) in MeOH (1 mL), water (1 mL) and THE (4 mL) was added LiOH (29 mg, 0.7 mmol) and the mixture was stirred at 25° C. for 1 hr. The reaction mixture was concentrated to dryness. The residue was diluted with water (5 mL) and washed with EtOAc (2x3 mL). The aqueous layer was acidified with 1N aq·HCl to pH~3 and extracted with DCM (3x3 mL). The combined organic layers were washed with brine, dried over $Na_2SO_4$, filtered and concentrated to dryness. The residue was purified by prep-HPLC to give the title compound (15 mg, 20.8% yield) as white solid. LC/MS (ESI) m/z: 518 $(M+H)^+$. $^1$H-NMR (400 MHz, $CD_3OD$) δ 7.83 (d, J=8.4 Hz, 1H), 7.53 (d, J=8.4 Hz, 1H), 7.16 (d, J=4.4 Hz, 1H), 6.92 (d, J=4.4 Hz, 1H), 5.99 (s, 2H), 4.21 (s, 3H), 3.90 (t, J=8.4 Hz, 2H), 3.30-3.24 (m, 2H), 3.14-3.00 (m, 1H), 2.64-2.51 (m, 1H), 2.47-2.26 (m, 7H), 1.81-1.62 (m, 3H), 0.94 (t, J=7.2 Hz, 3H).

Example 107: (S)-2-(1-(2-ethyl-6-(1-methyl-5-(((4-oxo-1-propyl-1,4-dihydropyridin-3-yl)oxy)methyl)-1H-1,2,3-triazol-4-yl)pyridin-3-yl)-5,5-difluoropiperidin-3-yl)acetic acid

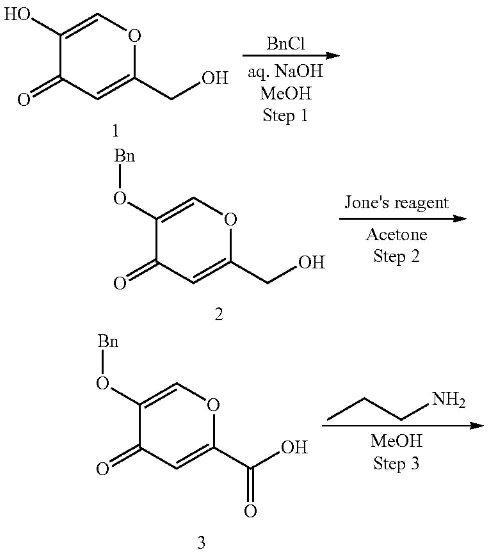

1, 2, 3

-continued

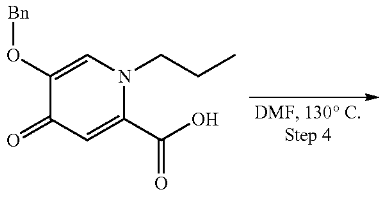

4

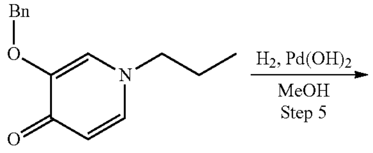

5

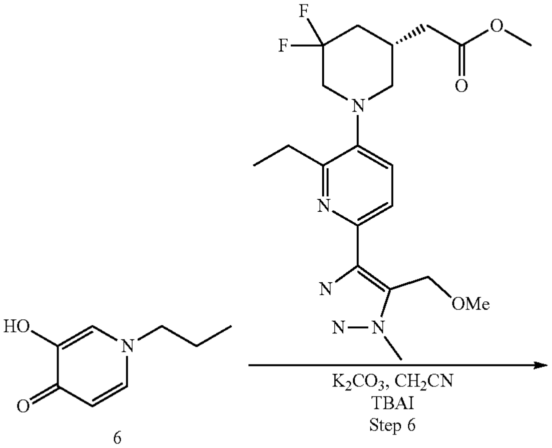

6

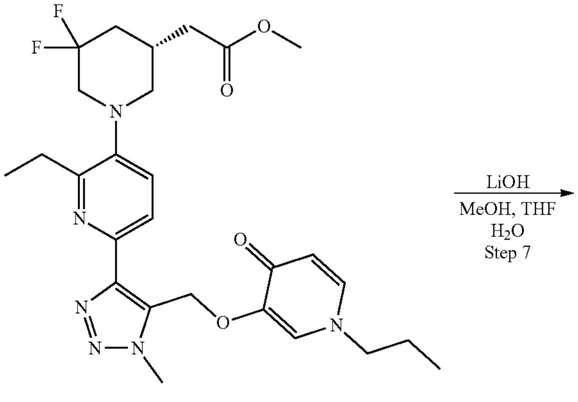

7

-continued

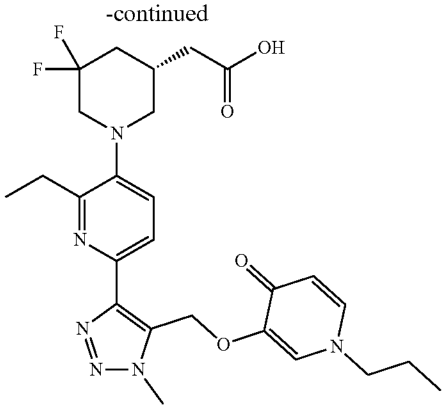

Example 107

Step 1: 5-(benzyloxy)-2-(hydroxymethyl)-4H-pyran-4-one

To a solution of 5-hydroxy-2-(hydroxymethyl)-4H-pyran-4-one (5 g, 35.2 mmol) in MeOH (100 mL) was added a solution of NaOH (1.41 g, 35.2 mmol) in $H_2O$ (10 mL) and the reaction was stirred at 80° C. for 30 min. (Chloromethyl) benzene (4.05 mL, 35.2 mmol) was added drop-wisely to the above mixture and the resulting mixture was stirred at 80° C. for 16 hrs. The mixture was diluted with $H_2O$ (20 mL) and extracted with EtOAc (3×20 mL). The combined organic layers were washed with brine, dried over $Na_2SO_4$, filtered and concentrated to dryness to give the title compound (800 mg, 9.8% yield) as brown yellow solid, which was directly used in the next step. LC/MS (ESI) m/z: 233 $(M+H)^+$.

Step 2: 5-(benzyloxy)-4-oxo-4H-pyran-2-carboxylic acid

To a solution of 5-(benzyloxy)-2-(hydroxymethyl)-4H-pyran-4-one (800 mg, 3.44 mmol) in acetone (50 mL) was added newly prepared Jone's-reagent (2.6 mL, 5.2 mmol) at 0° C. and the mixture was stirred at r.t. for 1 hr. The mixture was poured into ice-water and extracted with EtOAc (3×10 mL). The combined organic layers were washed with saturated aq·$Na_2SO_3$ solution and brine, dried over $Na_2SO_4$, filtered and concentrated to dryness to give the title compound (850 mg, 100% yield) as yellow oil, which was directly used in the next reaction without purification. LC/MS (ESI) m/z: 247 $(M+H)^+$.

Step 3: 5-(benzyloxy)-4-oxo-1-propyl-1,4-dihydropyridine-2-carboxylic acid

A mixture of 5-(benzyloxy)-4-oxo-4H-pyran-2-carboxylic acid (850 mg, 3.44 mmol) and propan-1-amine (816 mg, 13.8 mmol) in MeOH (10 mL) was stirred at r.t. for 16 hrs. The reaction mixture was concentrated to dryness and the residue was dissolved in $H_2O$ (10 mL). The mixture was acidified with 3N aq·HCl to pH~2 and filtered. The filter cake was washed with water, dried under vacuum to give the title compound (390 mg, 39.3% yield) as light yellow solid. LC/MS (ESI) m/z: 288 $(M+H)^+$.

Step 4: 3-(benzyloxy)-1-propyl-1,4-dihydropyridin-4-one

The solution of 5-(benzyloxy)-4-oxo-1-propyl-1,4-dihydropyridine-2-carboxylic acid (250 mg, 0.87 mmol) in DMF (5 mL) was stirred at 130° C. for 1 hr. The mixture was diluted with EtOAc (10 mL), washed with water and brine, dried over $Na_2SO_4$, filtered and concentrated to dryness to give the title compound (150 mg, 70.9% yield) as yellow solid. LC/MS (ESI) m/z: 244 $(M+H)^+$.

Step 5: 3-hydroxy-1-propylpyridin-4(1H)-one

To a solution of 3-(benzyloxy)-1-propyl-1,4-dihydropyridin-4-one (150 mg, 0.62 mmol) in MeOH (3 mL) was added $Pd(OH)_2$ (30 mg, 10% wt), the mixture was degassed under $N_2$ atmosphere for three times and stirred under a $H_2$ balloon at r.t. for 1 hr. The mixture was filtered and the filtrate was concentrated to dryness to give the title compound (90 mg, 95.3% yield) as white solid. LC/MS (ESI) (m/z):154 $(M+H)^+$. $^1H$ NMR (400 MHz, $CDCl_3$) δ 7.18-7.24 (m, 2H), 6.43 (d, J=6.9 Hz, 1H), 3.74-3.80 (m, 2H), 1.89-1.78 (m, 2H), 0.92-0.98 (m, 3H).

Step 6: methyl (S)-2-(1-(2-ethyl-6-(1-methyl-5-(((4-oxo-1-propyl-1,4-dihydropyridin-3-yl)oxy)methyl)-1H-1,2,3-triazol-4-yl)pyridin-3-yl)-5,5-difluoropiperidin-3-yl)acetate To a mixture of methyl (S)-2-(1-(2-ethyl-6-(1-methyl-5-(((methylsulfonyl)oxy)methyl)-1H-1,2,3-triazol-4-yl)pyridin-3-yl)-5,5-difluoropiperidin-3-yl)acetate (30 mg, 0.062 mmol) and 3-hydroxy-1-propylpyridin-4(1H)-one (14 mg, 0.092 mmol) in $CH_3CN$ (1 mL) was added $K_2CO_3$ (25 mg, 0.18 mmol) and TBAI (4 mg, 0.01 mmol) and the mixture was stirred at 70° C. for 16 hrs. The mixture was diluted with EtOAc (5 mL), washed with water and brine, dried over $Na_2SO_4$, filtered and concentrated to dryness to give the title compound (32 mg, 94.8% yield) as yellow solid. LC/MS (ESI) (m/z): 545 $(M+H)^+$.

Step 7: (S)-2-(1-(2-ethyl-6-(1-methyl-5-(((4-oxo-1-propyl-1,4-dihydropyridin-3-yl)oxy)methyl)-1H-1,2,3-triazol-4-yl)pyridin-3-yl)-5,5-difluoropiperidin-3-yl)acetic acid To a solution of methyl (S)-2-(1-(2-ethyl-6-(1-methyl-5-(((4-oxo-1-propyl-1,4-dihydropyridin-3-yl)oxy)methyl)-1H-1,2,3-triazol-4-yl)pyridin-3-yl)-5,5-difluoropiperidin-3-yl)acetate (32 mg, 0.059 mmol) in MeOH (1 mL), water (1 mL) and THE (2 mL) was added LiOH·$H_2O$ (12 mg, 0.29 mmol) and the mixture was stirred at 25° C. for 1 hr. The reaction mixture was concentrated to dryness. The residue was diluted with water (3 mL) and washed with EtOAc (2×3 mL). The aqueous layer was acidified with 1M aq·HCl to pH~3 and extracted with DCM (3×3 mL). The combined organic layers were washed with brine, dried over $Na_2SO_4$, filtered and concentrated to dryness. The residue was purified by prep HPLC to give the title compound (9 mg, 28.9% yield) as white solid. LC/MS (ESI) (m/z): 531 $(M+H)^+$. $^1H$ NMR (400 MHz, $CD_3OD$) δ 7.93 (d, J=8.4 Hz, 1H), 7.77 (d, J=2.1 Hz, 1H), 7.63-7.58 (m, 2H), 6.42 (d, J=7.2 Hz, 1H), 6.01-5.82 (m, 2H), 4.22 (s, 3H), 3.71-3.68 (t, J=7.2 Hz, 2H), 3.2-3.20 (m, 2H), 3.14-3.05 (m, 1H), 2.9-2.93 (m, 2H), 2.65-2.57 (m, 1H), 2.63-2.58 (m, 1H), 2.40 (d, J=7.0 Hz, 2H), 2.34-2.25 (m, 1H), 1.80-1.64 (m, 1H), 1.5-1.49 (m, 2H), 1.33-1.29 (t, J=7.5 Hz, 3H), 0.73-0.96 (t, J=7.4 Hz, 3H).

Example 108: 2-[(1S)-5-(6-{5-[(5-cyclobutyl-2-oxo-1,2-dihydropyridin-1-yl)methyl]-1-methyl-1H-1,2,3-triazol-4-yl}-2-ethylpyridin-3-yl)-3,3-difluorocyclohexyl]acetic acid

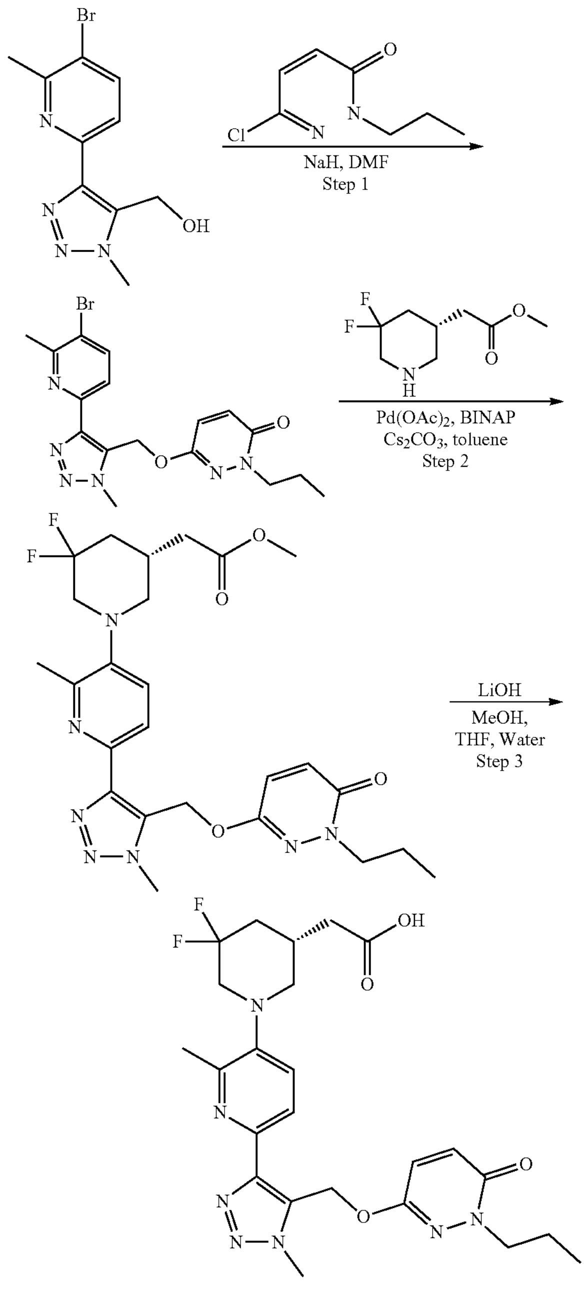

Example 108

Step 1: 6-((4-(5-bromo-6-methylpyridin-2-yl)-1-methyl-1H-1,2,3-triazol-5-yl)methoxy)-2-propylpyridazin-3(2H)-one To a solution of [4-(5-bromo-6-methylpyridin-2-yl)-1-methyl-1H-1,2,3-triazol-5yl]methanol (150 mg, 0.5 mmol) in DMF (4 mL) was added NaH (42 mg, 1.1 mmol, 60% dispersion in mineral oil) at 0° C. and the mixture was stirred at this temperature for 30 min. 3-Chloro-1-propyl-1,2-dihydropyrazin-2-one (101 mg, 0.6 mmol) was added to the above mixture and the resulting mixture was stirred at r.t. for 1.5 hrs. The reaction was quenched with saturated aq·$NH_4Cl$ solution and extracted with EtOAc (2×5 mL). The combined organic layers were washed with brine, dried over anhydrous $Na_2SO_4$, filtered and concentrated to dryness. The residue was purified by chromatography on silica gel (PE:EtOAc=4:1) to give the title compound (120 mg, 54.0% yield) as off-white solid. LC/MS (ESI) (m/z): 420 $(M+H)^+$.

Step 2: methyl (S)-2-(5,5-difluoro-1-(2-methyl-6-(1-methyl-5-(((6-oxo-1-propyl-1,6-dihydropyridazin-3-yl)oxy)methyl)-1H-1,2,3-triazol-4-yl)pyridin-3-yl)piperidin-3-yl)acetate To a solution of 6-((4-(5-bromo-6-methylpyridin-2-yl)-1-methyl-1H-1,2,3-triazol-5-yl)methoxy)-2-propylpyridazin-3(2H)-one (120 mg, 0.28 mmol) and methyl (S)-2-(5,5-difluoropiperidin-3-yl)acetate (55 mg, 0.28 mmol) in toluene (3 mL) were added $Cs_2CO_3$ (234 mg, 0.71 mmol), BINAP (35.7 mg, 0.05 mmol), $Pd(OAc)_2$ (6.4 mg, 0.028 mmol) under $N_2$ atmosphere, after addition, the mixture was degassed under $N_2$ atmosphere for three times and stirred at 100° C. for 16 hrs. The mixture was filtered and the filtrate was concentrated to dryness. The residue was purified by flash chromatography (eluted with PE:EtOAc=10:1 to 1:1) to give the title compound (100 mg, 67.2% yield) as white solid. LC/MS (ESI) m/z: 534 $(M+H)^+$.

Step 3: (S)-2-(5,5-difluoro-1-(2-methyl-6-(1-methyl-5-(((6-oxo-1-propyl-1,6 dihydropyridazin-3-yl)oxy)methyl)-1H-1,2,3-triazol-4-yl)pyridin-3-yl)piperidin-3-yl)acetic acid To a solution of (S)-2-(5,5-difluoro-1-(2-methyl-6-(1-methyl-5-(((6-oxo-1-propyl-1,6-dihydropyridazin-3-yl)oxy)methyl)-1H-1,2,3-triazol-4-yl)pyridin-3-yl)piperidin-3-yl)acetate (50 mg, 0.094 mmol) in THE (2 mL), MeOH (1 mL) and water (1 mL) was added LiOH·$H_2O$ (40 mg, 0.1 mmol) and the mixture was stirred at 25° C. for 3 hrs. The reaction mixture was acidified with 1M aq·HCl to pH~4 and extracted with DCM (2×5 mL). The combined organic layers were washed with brine, dried over $Na_2SO_4$, filtered and concentrated to dryness. The residue was purified by prep-HPLC to give the title compound (15 mg, 30.8% yield) as white solid. LC/MS (ESI) m/z: 518 $(M+H)^+$. $^1H$ NMR (400 MHz, $CD_3OD$) δ 7.86 (d, J=8.3 Hz, 1H), 7.55 (d, J=8.4 Hz, 1H), 7.16 (d, J=9.7 Hz, 1H), 6.94 (d, J=9.7 Hz, 1H), 5.97 (s, 2H), 4.19 (s, 3H), 3.79-3.72 (m, 2H), 3.30-3.25 (m, 2H), 3.14-3.03 (m, 1H), 2.60 (t, J=10.5 Hz, 1H), 2.52 (s, 3H), 2.51-2.42 (m, 1H), 2.39 (d, J=6.5 Hz, 2H), 2.30 (s, 1H), 1.82-1.66 (m, 1H), 1.65-1.55 (m, 2H), 0.83 (t, J=7.4 Hz, 3H).

Example 109: (S)-2-(1-(2-ethyl-6-(1-methyl-5-(((5-oxo-2-propyl-2,5-dihydropyridazin-4-yl)oxy)methyl)-1H-1,2,3-triazol-4-yl)pyridin-3-yl)-5,5-difluoropiperidin-3-yl)acetic acid

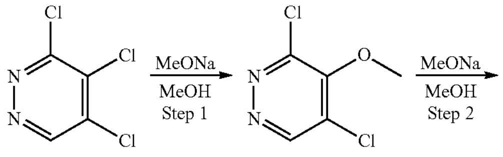

1 2

-continued

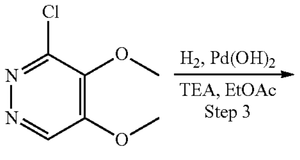

3

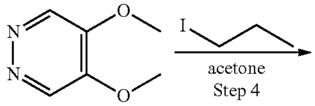

4

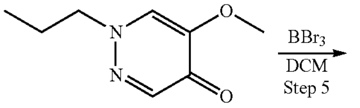

5

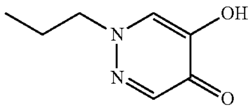

6

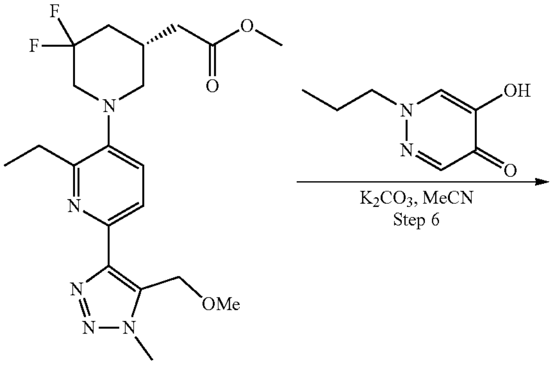

7

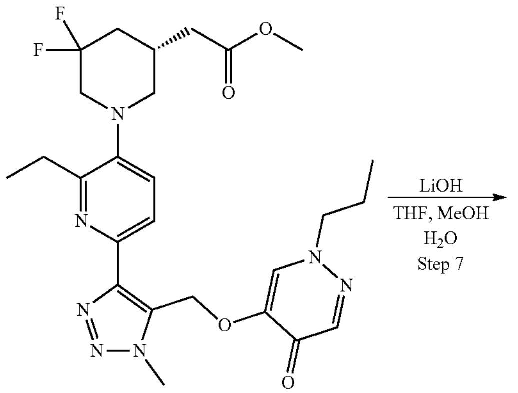

8

-continued

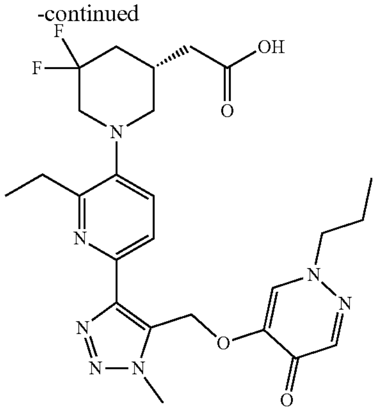

Example 109

Step 1: 3,5-dichloro-4-methoxypyridazine

To a solution of 3,4,5-trichloropyridazine (5 g, 27.26 mmol) in MeOH (50 mL) was added MeONa/MeOH solution (5.5 mL, 5 M) drop-wisely at −10° C. and the mixture was stirred at 0° C. for 1 hr. The mixture was concentrated to dryness and the residue was dissolved in $H_2O$ (50 mL). The mixture was extracted with DCM (2×30 mL) and the combined organic layers were washed with brine, dried over $Na_2SO_4$, filtered and concentrated to dryness. The residue was purified by silica gel column chromatography (PE:EtOAc=20:1) to give the title compound (1.5 g, 30.7% yield) as yellow solid. LC/MS (ESI) m/z: 179 $(M+H)^+$. $^1H$ NMR (400 MHz, $CDCl_3$) δ 9.01 (s, 1H), 4.15 (s, 3H).

Step 2: 3-chloro-4,5-dimethoxypyridazine

To a solution of 3,5-dichloro-4-methoxypyridazine (2.8 g, 15.64 mmol) in MeOH (30 mL) was MeONa/MeOH solution (3.2 mL, 16 mmol, 5 M) drop-wisely at r.t. and the mixture was stirred at 80° C. for 1 hr. The mixture was concentrated to dryness and the residue was dissolved in $H_2O$ (50 mL). The mixture was extracted with DCM (2×30 mL) and the combined organic layers were washed with brine, dried over $Na_2SO_4$, filtered and concentrated to dryness. The residue was purified by silica gel column chromatography (PE:EtOAc=10:1) to give the title compound (1.6 g, 58.6% yield) as yellow solid. LC/MS (ESI) m/z: 175 $(M+H)^+$.

Step 3: 4,5-dimethoxypyridazine

To a solution of 3-chloro-4,5-dimethoxypyridazine (600 mg, 3.44 mmol) in EtOAc (20 mL) were added TEA (695 mg, 6.87 mmol) and $Pd(OH)_2/C$ (48 mg, 0.03 mmol, 10% wt) and the mixture was degassed under $N_2$ atmosphere for three times and stirred under a $H_2$ balloon at 25° C. for 1 hr. The mixture was filtered and the filtrate was concentrated to dryness to give the title compound (210 mg, 43.6% yield) as white solid. LC/MS (ESI) m/z: 141 $(M+H)^+$. $^1H$ NMR (400 MHz, $CDCl_3$) δ 8.78 (s, 2H), 3.96 (s, 6H).

Step 4:
5-methoxy-1-propyl-1,4-dihydropyridazin-4-one

To a solution of 4,5-dimethoxypyridazine (200 mg, 1.43 mmol) in acetone (5 mL) was added 1-iodopropane (485 mg, 2.85 mmol) and the mixture was stirred at 50° C. for 18 hrs. The mixture was concentrated to dryness and the residue was purified by silica gel column chromatography (PE:EtOAc=3:1) to give the title compound (80 mg, 33.3% yield). LC/MS (ESI) (m/z): 169 $(M+H)^+$. $^1H$ NMR (400 MHz, $CDCl_3$) δ 7.86 (s, 1H), 7.42 (s, 1H), 3.93-3.98 (m, 2H), 3.80 (s, 3H), 1.81-1.89 (m, 2H), 0.87-0.93 (m, 3H).

Step 5: 5-hydroxy-1-propyl-1,4-dihydropyridazin-4-one

To a solution of 5-methoxy-1-propyl-1,4-dihydropyridazin-4-one (80 mg, 0.48 mmol) in DCM (3 mL) was $BBr_3$ (0.18 mL, 1.90 mmol) drop-wisely at 0° C. and the mixture was stirred at r.t. for 2 hrs. The mixture was quenched with MeOH at 0° C. and poured into ice-cooled saturated aq·$NaHCO_3$ solution. The mixture was extracted with DCM (2×5 mL) and the combined organic layers were washed with brine, dried over $Na_2SO_4$, filtered and concentrated to dryness. The residue was purified by silica gel chromatography (PE:EtOAc=1:1) to give the title compound (30 mg, 40.9% yield) as yellow solid. LC/MS (ESI) m/z: 155 $(M+H)^+$.

Step 6: methyl (S)-2-(1-(2-ethyl-6-(1-methyl-5-(((5-oxo-2-propyl-2,5-dihydropyridazin-4-yl)oxy)methyl)-1H-1,2,3-triazol-4-yl)pyridin-3-yl)-5,5-difluoropiperidin-3-yl)acetate To the mixture of 5-hydroxy-1-propyl-1,4-dihydropyridazin-4-one (14 mg, 0.09 mmol) and methyl (S)-2-(1-(2-ethyl-6-(1-methyl-5-(((methylsulfonyl)oxy)methyl)-1H-1,2,3-triazol-4-yl)pyridin-3-yl)-5,5-difluoropiperidin-3-yl)acetate (30 mg, 0.06 mmol) in MeCN (3 mL) was added $K_2CO_3$ (25 mg, 0.18 mmol) and TBAI (5 mg, 0.01 mmol) and the mixture was stirred at 70° C. for 16 hrs. The mixture was diluted with EtOAc (5 mL), washed with water and brine, dried over $Na_2SO_4$, filtered and concentrated to dryness. The residue was purified by silica gel chromatography (PE:EtOAc=5:1 to 1:1) to give the title compound (20 mg, 59.7% yield) as yellow solid. LC/MS (ESI) m/z: 546 $(M+H)^+$.

Step 7: (S)-2-(1-(2-ethyl-6-(1-methyl-5-(((5-oxo-2-propyl-2,5-dihydropyridazin-4-yl)oxy)methyl)-1H-1,2,3-triazol-4-yl)pyridin-3-yl)-5,5-difluoropiperidin-3-yl)acetic acid To a solution of methyl (S)-2-(1-(2-ethyl-6-(1-methyl-5-(((5-oxo-2-propyl-2,5-dihydropyridazin-4-yl)oxy)methyl)-1H-1,2,3-triazol-4-yl)pyridin-3-yl)-5, 5-difluoropiperidin-3-yl)acetate (20 mg, 0.037 mmol) in THF (1 mL) and MeOH (1 mL) was added a solution of LiOH (15 mg, 0.37 mmol) in $H_2O$ (0.5 mL), and the mixture was stirred at r.t. for 2 hrs. The mixture was acidified with 1N aq·HCl to pH~4 and extracted with DCM (2×3 mL). The combined organic layers were washed with brine, dried over $Na_2SO_4$, filtered and concentrated to dryness. The residue was purified by perp-HPLC (C18, 0~90% acetonitrile in $H_2O$ with 0.1% HCOOH) to give the title compound (9 mg, 46.2% yield) as white solid. LC/MS (ESI) m/z: 532 $(M+H)^+$. $^1H$ NMR (400 MHz, $CD_3OD$) δ 8.54 (s, 1H), 7.94 (d, J=9.5 Hz, 2H), 7.61 (d, J=8.4 Hz, 1H), 6.04-5.94 (m, 2H), 4.22 (s, 3H), 3.91-3.96 (t, J=7.1 Hz, 2H), 3.25-3.22 (m, 2H), 3.14-3.05 (m, 1H), 2.99-2.92 (q, J=7.7 Hz, 2H), 2.63-2.58 (t, J=10.8 Hz, 1H), 2.53-2.50 (m, 1H), 2.41-2.39 (m, 2H), 2.31-2.26 (m, 1H), 1.80-1.63 (m, 3H), 1.26-1.32 (t, J=7.5 Hz, 3H), 0.72-0.78 (t, J=7.4 Hz, 3H).

Example 110: (S)-2-(1-(2-ethyl-6-(1-methyl-5-(((4-methyl-3-oxo-6-propyl-3,4-dihydropyrazin-2-yl)oxy)methyl)-1H-1,2,3-triazol-4-yl)pyridin-3-yl)-5,5-difluoropiperidin-3-yl)acetic acid

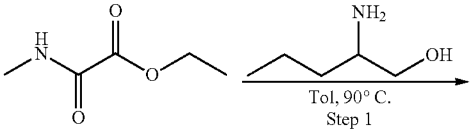

1

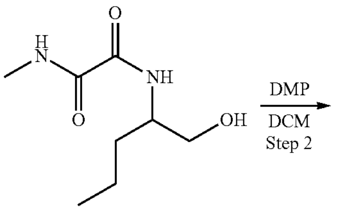

2

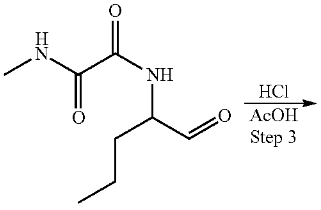

3

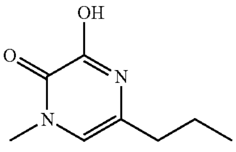

4

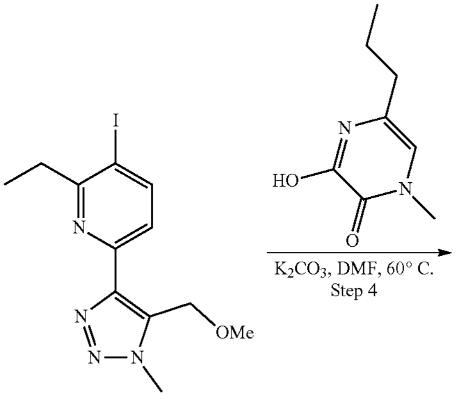

5

-continued

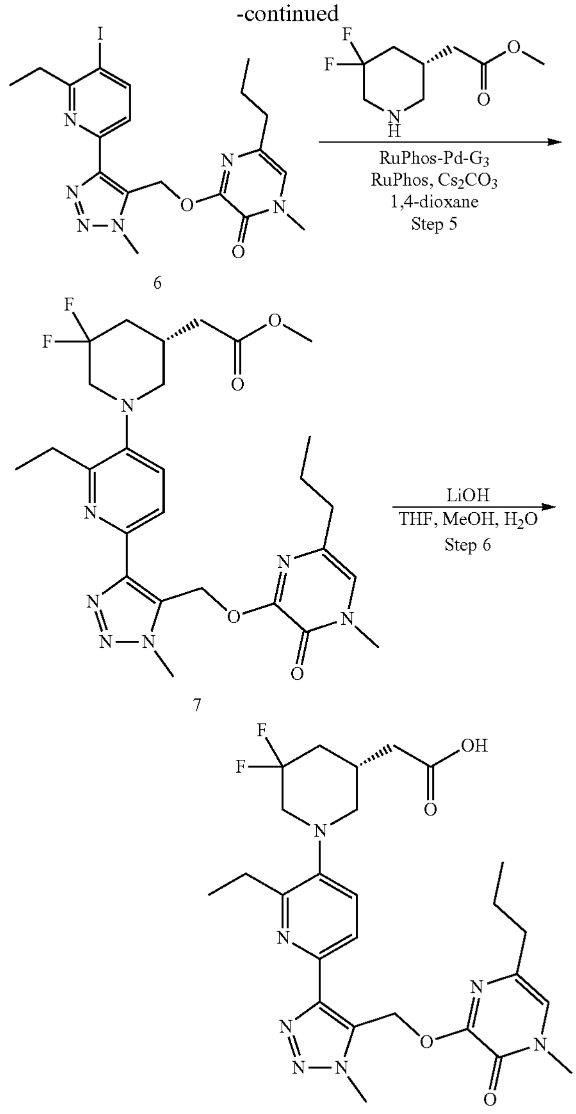

6

7

Example 110

Step 1: N-(1-hydroxypentan-2-yl)-N'-methylethane-diamide

To a solution of 2-aminopentan-1-ol (1.21 g, 11.63 mmol) in toluene (15 mL) and EtOAc was added ethyl (methylcarbamoyl)formate (1.67 g, 12.79 mmol), and the mixture was stirred at 90° C. for 16 hrs. The reaction mixture was concentrated to dryness and the solid was washed with PE, dried under vacuum to give the title compound (2.06 g, 94.1% yield) as white solid. LC/MS (ESI) m/z: 189 $(M+H)^+$.

Step 2: N'-methyl-N-(1-oxopentan-2-yl)ethanediamide

To a solution of N-(1-hydroxypentan-2-yl)-N'-methyl-ethanediamide (400 mg, 2.12 mmol) in DCM (15 mL) was added Dess-Martin periodinane (900 mg, 2.12 mmol) and the mixture was stirred at r.t. for 3 hrs. The mixture was washed with saturated aq·$NaHCO_3$ solution and brine, dried over $Na_2SO_4$, filtered and concentrated to dryness to give the title compound (405 mg, 81.9% yield) as white solid. LC/MS (ESI) m/z: 187 $(M+H)^+$.

Step 3: 3-hydroxy-1-methyl-5-propyl-1,2-dihydro-pyrazin-2-one

To a solution of N'-methyl-N-(1-oxopentan-2-yl)ethane-diamide (405 mg, 2.14 mmol) in AcOH (5 mL) was added conc·HCl (0.5 mL) and the mixture was stirred at 100° C. for 1 hr. The reaction mixture was concentrated to dryness and the residue was purified by flash chromatography (silica gel, 0-15% MeOH in DCM) to give the title compound (121 mg, 33.5% yield) as yellow solid. LC/MS (ESI) m/z: 169 $(M+H)^+$. $^1H$ NMR (400 MHz, DMSO-$d_6$) δ 11.25 (s, 1H), 6.29 (s, 1H), 3.23 (s, 3H), 2.16 (t, J=7.4 Hz, 2H), 1.49 (dt, J=14.5, 7.3 Hz, 2H), 0.86 (t, J=7.3 Hz, 3H).

Step 4: 3-{[4-(6-ethyl-5-iodopyridin-2-yl)-1-methyl-1H-1,2,3-triazol-5-yl]methoxy}-1-methyl-5-propyl-1,2-dihydropyrazin-2-one To a solution of (4-(6-ethyl-5-iodopyridin-2-yl)-1-methyl-1H-1,2,3-triazol-5-yl)methyl methanesulfonate (207 mg, 0.49 mmol) in DMF (5 mL) was added 3-hydroxy-1-methyl-5-propyl-1,2-dihydropyrazin-2-one (115 mg, 0.68 mmol), $K_2CO_3$ (203 mg, 1.47 mmol) and the mixture was stirred at 60° C. for 2 hrs. The reaction mixture was diluted with EtOAc (10 mL), washed with saturated aq·$NH_4Cl$ solution and brine, dried over anhydrous $Na_2SO_4$, filtered and concentrated to dryness. The residue was purified by flash chromatography (silica gel, 0-100% EtOAc in PE) to give the title compound (58 mg, 23.9% yield) as white solid. LC/MS (ESI) m/z: 495 $(M+H)^+$.

Step 5: methyl 2-[(3S)-1-[2-ethyl-6-(1-methyl-5-{[(4-methyl-3-oxo-6-propyl-3,4-dihydropyrazin-2-yl)oxy]methyl}-1H-1,2,3-triazol-4-yl)pyridin-3-yl]-5,5-difluoropiperidin-3-yl]acetate To a solution of 3-{[4-(6-ethyl-5-iodopyridin-2-yl)-1-methyl-1H-1,2,3-triazol-5-yl]methoxy}-1-methyl-5-propyl-1,2-dihydropyrazin-2-one (58 mg, 0.12 mmol) in 1,4-dioxane (2 mL) was added $Cs_2CO_3$ (118 mg, 0.36 mmol), methyl 2-[(3S)-5,5-difluoropiperidin-3-yl]acetate (23 mg, 0.12 mmol), Ruphos-Pd-G3 (30 mg, 0.036 mmol), RuPhos (11 mg, 0.024 mmol) and the mixture was degassed under $N_2$ for 3 times and stirred at 110° C. for 16 hrs. The reaction mixture was diluted with EtOAc (10 mL), washed with water and brine, dried over anhydrous $Na_2SO_4$, filtered and concentrated to dryness to give the title compound (75 mg, 88.3% yield) as yellow solid, which was directly used to the next reaction without purification. LC/MS (ESI) m/z: 560 $(M+H)^+$.

Step 6: 2-[(3S)-1-[2-ethyl-6-(1-methyl-5-{[(4-methyl-3-oxo-6-propyl-3,4-dihydropyrazin-2-yl)oxy]methyl}-1H-1,2,3-triazol-4-yl)pyridin-3-yl]-5,5-difluoropiperidin-3-yl]acetic acid To a solution of methyl 2-[(3S)-1-[2-ethyl-6-(1-methyl-5-{[(4-methyl-3-oxo-6-propyl-3,4-dihydropyrazin-2-yl)oxy]methyl}-1H-1,2,3-triazol-4-yl)pyridin-3-yl]-5,5-difluoropiperidin-3-yl]acetate (75 mg, 0.11 mmol) in THE (2 mL), MeOH (0.5 mL), $H_2O$ (1 mL) was added LiOH (26 mg, 1.07 mmol) and the mixture was stirred at 25° C. for 1 hr. The reaction mixture was concentrated to dryness and the residue was dissolved in $H_2O$ (5 mL). The mixture was washed with MTBE (3×5 mL), acidified with 1N aq·HCl to pH~3 and extracted with DCM (3×5 mL). The combined organic layers were washed with brine, dried over anhydrous $Na_2SO_4$, filtered and concentrated to dryness. The residue was purified by prep·HPLC to give the title compound (18 mg, 30% yield) as white solid. LC/MS (ESI) m/z: 546 $(M+H)^+$. $^1$H NMR (400 MHz, $CD_3OD$) δ 7.86 (d, J=8.3 Hz, 1H), 7.56 (d, J=8.4 Hz, 1H), 6.94 (s, 1H), 6.12 (s, 2H), 4.21 (s, 3H), 3.48 (s, 3H), 3.22 (d, J=10.2 Hz, 2H), 3.07 (dd, J=24.7, 9.4 Hz, 1H), 2.89 (q, J=7.4 Hz, 2H), 2.59 (t, J=10.5 Hz, 1H), 2.54-2.46 (m, 1H), 2.36 (d, J=7.0 Hz, 2H), 2.34-2.27 (m, 1H), 2.26-2.22 (m, 2H), 1.71 (dt, J=24.4, 15.7 Hz, 1H), 1.46 (dt, J=13.8, 6.9 Hz, 2H), 1.27 (t, J=7.5 Hz, 3H), 0.85 (t, J=7.4 Hz, 3H).

Example 111: (S)-2-(1-(2-ethyl-6-(1-methyl-5-(((4-oxo-1-propyl-1,4-dihydropyridazin-3-yl)oxy)methyl)-1H-1,2,3-triazol-4-yl)pyridin-3-yl)-5,5-difluoropiperidin-3-yl)acetic acid

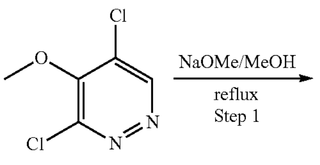

1

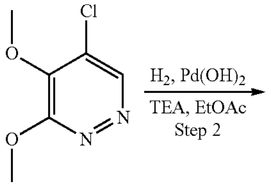

2

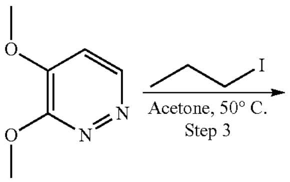

3

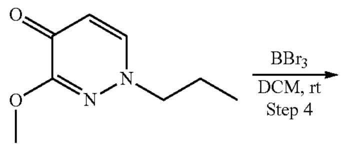

4

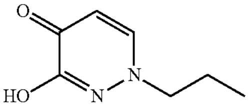

5

-continued

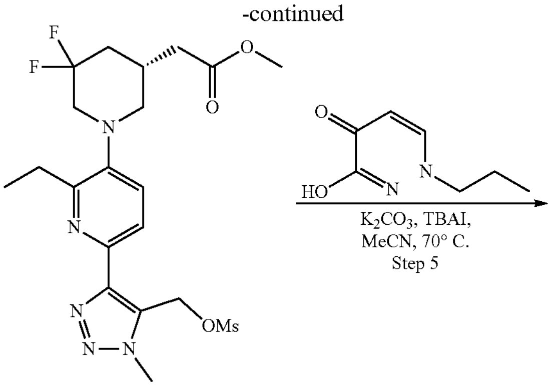

6

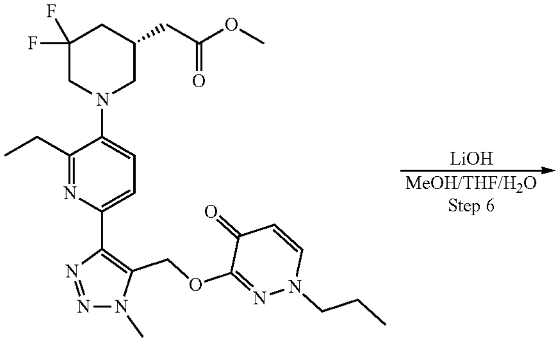

7

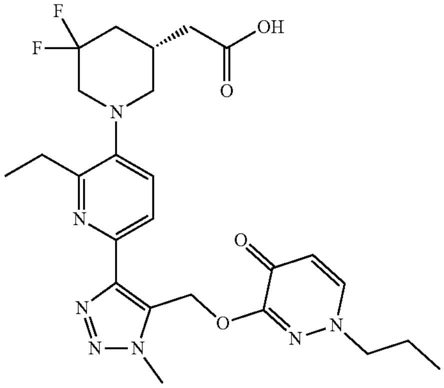

Example 111

Step 1: 5-chloro-3,4-dimethoxypyridazine

To a solution of 3,5-dichloro-4-methoxypyridazine (3.2 g, 17.9 mmol) in MeOH (20 mL) was added sodium methoxide solution (30% in methanol) (3.22 g, 17.9 mmol) at room temperature under $N_2$ atmosphere and the reaction was stirred at 90° C. for 3 hrs. The mixture was diluted with water (20 mL) and extracted with EtOAc (2×20 mL). The combined organic layers were washed with brine, dried over anhydrous $Na_2SO_4$, filtered and concentrated to dryness. The residue was purified by chromatography on silica gel (PE:EtOAc=10:1) to give the title compound (0.74 g, 23.7% yield) as white solid. LCMS (ESI) m/z: 175 $(M+H)^+$.

Step 2: 3,4-dimethoxypyridazine

To a solution of 5-chloro-3,4-dimethoxypyridazine (740 mg, 4.24 mmol) in EtOAc (10 mL) was added TEA (1.18 mL, 8.4 mmol) and $Pd(OH)_2/C$ (120 mg, 10% wt) at 0° C. and the mixture was degassed under $N_2$ atmosphere for three times and stirred under a $H_2$ balloon at room temperature for 4 hrs. The mixture was filtered and the filtrate was concentrated to dryness to give the title compound (500 mg, 84.2% yield) as white solid. LC/MS (ESI) (m/z): 141 $(M+H)^+$.

Step 3: 3-methoxy-1-propylpyridazin-4(1H)-one

To a solution of 3,4-dimethoxypyridazine (500 mg, 3.57 mmol) in acetone (10 mL) was added 1-iodopropane (0.52 mL, 5.35 mmol) at room temperature and the reaction mixture was stirred at 50° C. for 16 hrs. The mixture was diluted with water (5 mL) and extracted with DCM (2×5 mL). The combined organic layers were washed with brine, dried over anhydrous $Na_2SO_4$, and concentrated under reduced pressure to dryness. The residue was purified by chromatography on silica gel (PE:EtOAc=20:1) to give the title compound (80 mg, 13.3% yield) as white solid. LC/MS (ESI) (m/z): 169 $(M+H)^+$.

Step 4: 3-hydroxy-1-propylpyridazin-4(1H)-one

To a solution of 3-methoxy-1-propylpyridazin-4(1H)-one (80 mg, 0.476 mmol) in DCM (5 mL) was added $BBr_3$ (0.135 mL, 1.43 mmol) at 0° C. and the mixture was stirred at r.t. for 1 hr. The reaction was quenched with MeOH at 0° C. and the mixture was basified with saturated aq·$NaHCO_3$ solution. The mixture was extracted with DCM (2×5 mL) and the combined organic layers were washed with brine, dried over anhydrous $Na_2SO_4$, filtered and concentrated to dryness to give the title compound (30 mg, 40.9% yield) as yellow solid. LC/MS (ESI) (m/z): 155 $(M+H)^+$.

Step 5: methyl (S)-2-(1-(2-ethyl-6-(1-methyl-5-(((4-oxo-1-propyl-1,4-dihydropyridazin-3-yl)oxy)methyl)-1H-1,2,3-triazol-4-yl)pyridin-3-yl)-5,5-difluoropiperidin-3-yl)acetate To a mixture of methyl (S)-2-(1-(2-ethyl-6-(1-methyl-5-(((methylsulfonyl)oxy)methyl)-1H-1,2,3-triazol-4-yl)pyridin-3-yl)-5,5-difluoropiperidin-3-yl)acetate (30 mg, 0.062 mmol) and 3-hydroxy-1-propylpyridazin-4(1H)-one (14.3 mg, 0.093 mmol) in $CH_3CN$ (2 mL) were added $K_2CO_3$ (17 mg, 0.124 mmol) and TBAI (2.3 mg, 0.006 mmol) and the mixture reaction was stirred at 70° C. under $N_2$ atmosphere for 16 hrs. The mixture was diluted with EtOAc (5 mL), washed with water and brine, dried over $Na_2SO_4$, filtered and concentrated to dryness to give crude product, which was purified by prep·TLC (PE:EtOAc=2:1) to give the title compound (15 mg, 44% yield) as yellow oil. LC/MS (ESI) (m/z): 546 $(M+H)^+$.

Step 6: (S)-2-(1-(2-ethyl-6-(1-methyl-5-(((4-oxo-1-propyl-1,4-dihydropyridazin-3-yl)oxy)methyl)-1H-1,2,3-triazol-4-yl)pyridin-3-yl)-5,5-difluoropiperidin-3-yl)acetic acid To a solution of methyl (S)-2-(1-(2-ethyl-6-(1-methyl-5-(((4-oxo-1-propyl-1,4-dihydropyridazin-3-yl)oxy)methyl)-1H-1,2,3-triazol-4-yl)pyridin-3-yl)-5,5-difluoropiperidin-3-yl)acetate (10 mg, 0.018 mmol) in THE (0.5 mL) and MeOH (1 mL) was added a solution of LiOH (4.3 mg, 0.18 mmol) in water (0.5 mL) at 0° C. After stirring at room temperature for 2 hrs, the reaction mixture was acidified with 1N aq·HCl to pH~3 and extracted with DCM (2×3 mL). The combined organic layers were washed with brine, dried over anhydrous $Na_2SO_4$, filtered and concentrated to dryness. The residue was purified by prep-HPLC (C18, 25-95%, MeCN in $H_2O$ with 0.1% HCOOH) to give the title compound (1.4 mg, 14.4% yield) as white solid. LC/MS (ESI) (m/z): 532 $(M+H)^+$. $^1H$ NMR (400 MHz, $CD_3OD$) δ 8.19 (d, J=7.1 Hz, 1H), 7.90 (d, J=8.3 Hz, 1H), 7.58 (d, J=8.3 Hz, 1H), 6.41 (d, J=7.0 Hz, 1H), 6.12 (s, 2H), 4.21 (s, 3H), 3.83 (t, J=7.0 Hz, 2H), 3.23 (d, J=11.8 Hz, 2H), 3.13-3.03 (m, 1H), 2.94-2.89 (m, 2H), 2.60 (t, J=10.7 Hz, 1H), 2.54-2.47 (m, 1H), 2.39-2.38 (m, 2H), 2.32-2.25 (m, 1H), 1.73-1.67 (m, 3H), 1.36-1.30 (m, 3H), 0.83 (t, J=7.4 Hz, 3H).

Example 112: (R)-2-(1-(6-(5-(((5-cyclopropyl-1,2,4-triazin-3-yl)amino)methyl)-1-methyl-1H-1,2,3-triazol-4-yl)-2-ethylpyridin-3-yl)-5,5-difluoropiperidin-3-yl)acetic acid

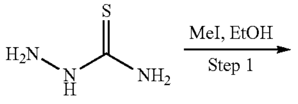

1

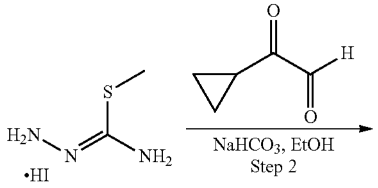

2

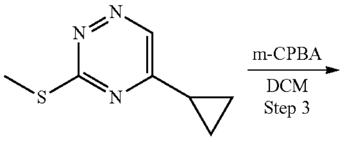

3

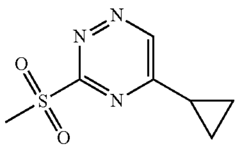

4

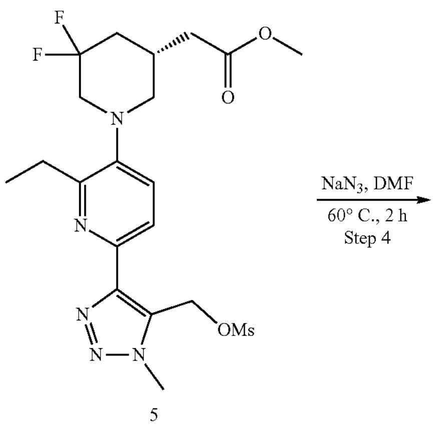

5

-continued

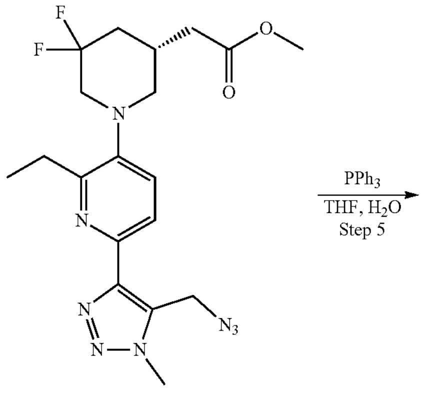

6

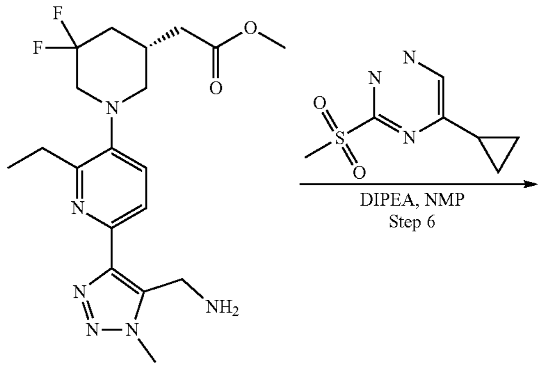

7

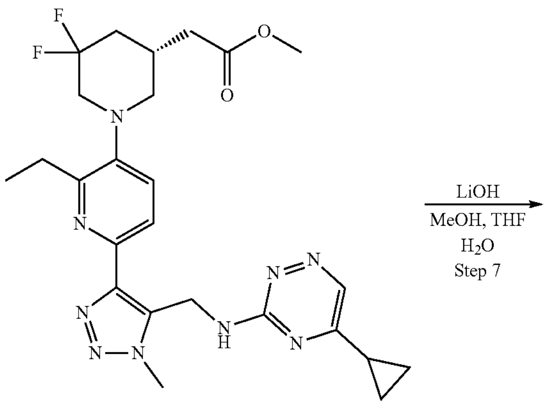

8

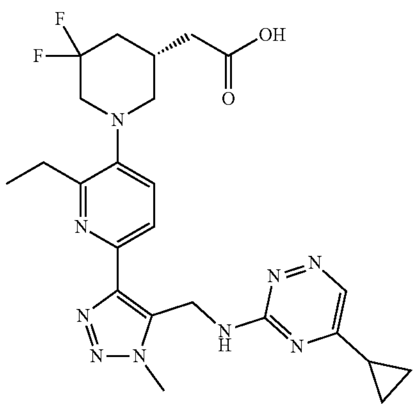

Example 112

Step 1: methyl (Z)-carbamohydrazonothioate hydroiodide

To a solution of aminothiourea (5 g, 54.9 mmol) in EtOH (30 mL) was added Mel (4.1 mL, 65.8 mmol). After stirring at 75° C. for 16 hrs, the reaction mixture was cooled to 0° C. and filtered. Then filter cake was concentrated to dryness to give the title compound (4.2 g, 72.8% yield) as white solid, which was directly used in the next reaction without purification.

Step 2: 5-cyclopropyl-3-(methylthio)-1,2,4-triazine

To a solution of methyl (Z)-carbamohydrazonothioate hydroiodide (4 g, 38.0 mmol) in EtOH (80 mL) was added 2-cyclopropyl-2-oxoacetaldehyde (5.6 g, 57.05 mmol). After stirring at 75° C. for 16 hrs, the reaction mixture was poured into ice-water and extracted with DCM (3×50 mL). The combined organic layers were washed brine, dried over anhydrous $Na_2SO_4$, filtered and concentrated to dryness. The residue was purified by flash chromatography (silica gel, 0-50% EtOAc in PE) to give the title compound (2.8 g, 44% yield) as yellow oil. LC/MS (ESI) m/z: 168 $(M+H)^+$.

Step 3: 5-cyclopropyl-3-(methylsulfonyl)-1,2,4-triazine

To a solution of 5-cyclopropyl-3-(methylthio)-1,2,4-triazine (2.6 g, 15.5 mmol) in DCM (40 mL) was added m-CPBA (8.05 g, 46.6 mmol) at 0° C. After stirring at r.t. for 1 hr, the reaction mixture was quenched with saturated aq·$Na_2$S203 solution and extracted with DCM (3×20 mL). The combined organic layers were washed with brine, dried over anhydrous $Na_2SO_4$, filtered and concentrated to dryness. The residue was triturated with EtOAc and the slurry was filtered. The filter cake was dried under vacuum to give the title compound (1.3 g, 42% yield) as yellow solid. LC/MS (ESI) m/z: 200 $(M+H)^+$.

Step 4: methyl (R)-2-(1-(6-(5-(azidomethyl)-1-methyl-1H-1,2,3-triazol-4-yl)-2-ethylpyridin-3-yl)-5,5-difluoropiperidin-3-yl)acetate To a solution of methyl 2-[(3R)-1-(2-ethyl-6-{5-[(methanesulfonyloxy)methyl]-1-methyl-1H-1,2,3-triazol-4-yl}pyridin-3-yl)-5,5-difluoropiperidin-3-yl]acetate (40 mg, 0.082 mmol) in DMF (3 mL) was added $NaN_3$ (20 mg, 0.41 mmol). After stirring at 60° C. for 2 hrs, the reaction mixture was poured into water and extracted with EtOAc (3×5 mL). The combined organic phases were washed brine, dried over $Na_2SO_4$, filtered and concentrated to give the title compound (31 mg, 96.3% yield) as yellow oil, which was directly used in the next reaction without purification.

Step 5: methyl (R)-2-(1-(6-(5-(aminomethyl)-1-methyl-11H-1,2,3-triazol-4-yl)-2-ethylpyridin-3-yl)-5,5-difluoropiperidin-3-yl)acetate To a solution of methyl (R)-2-(1-(6-(5-(azidomethyl)-1-methyl-1H-1,2,3-triazol-4-yl)-2-ethylpyridin-3-yl)-5,5-difluoropiperidin-3-yl)acetate (31 mg, 0.079 mmol) in THF (2 mL) and water (0.2 mL) was added $PPh_3$ (103 mg, 0.4 mmol). After stirring at r.t. for 16 hrs, the reaction mixture was concentrated to dryness. The residue was purified by flash chromatography (silica gel, 0-50%, MeOH in DCM) to give the title compound (31 mg, 96% yield) as yellow solid. LC/MS (ESI) m/z: 409 $(M+1)^+$.

Step 6: methyl (R)-2-(1-(6-(5-(((5-cyclopropyl-1,2,4-triazin-3-yl)amino)methyl)-1-methyl-1H-1,2,3-triazol-4-yl)-2-ethylpyridin-3-yl)-5,5-difluoropiperidin-3-yl)acetate To a solution of methyl (R)-2-(1-(6-(5-(aminomethyl)-1-methyl-1H-1,2,3-triazol-4-yl)-2-ethylpyridin-3-yl)-5,5-difluoropiperidin-3-yl)acetate (31 mg, 0.076 mmol) and DIPEA (29 mg, 0.23 mmol) in NMP (2 mL) was added 5-cyclopropyl-3-(methylsulfonyl)-1,2,4-triazine (30 mg, 0.15 mmol). After stirring at 100° C. for 2 hrs, the reaction mixture was poured into water and extracted with EtOAc (3×5 mL). The combined organic phases were washed brine, dried over $Na_2SO_4$, filtered and concentrated to dryness. The residue was purified by flash chromatography (silica gel, 0-100% EtOAc in PE) to give the title compound (20 mg, 50% yield) as yellow solid. LC/MS (ESI) m/z: 528 $(M+1)^+$.

Step 8: (R)-2-(1-(6-(5-(((5-cyclopropyl-1,2,4-triazin-3-yl)amino)methyl)-1-methyl-1H-1,2,3-triazol-4-yl)-2-ethylpyridin-3-yl)-5,5-difluoropiperidin-3-yl) acetic acid To a solution of methyl (R)-2-(1-(6-(5-(((5-cyclopropyl-1,2,4-triazin-3-yl)amino)methyl)-1-methyl-1H-1,2,3-triazol-4-yl)-2-ethylpyridin-3-yl)-5,5-difluoropiperidin-3-yl) acetate (20 mg, 0.038 mmol) in THE (2 mL), water (0.5 mL) and MeOH (0.5 mL) was added LiOH (8 mg, 0.19 mmol). After stirring at r.t. for 2 hrs, the reaction mixture was poured into water and washed with MTBE (3×2 mL). The aqueous layer was acidified with 1N aq·HCl to pH~4 and extracted with DCM (3×3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (3 mg, 15.4% yield) as white solid. LC/MS (ESI) m/z: 514 $(M+1)^+$. $^1H$ NMR (400 MHz, $CD_3OD$) δ 8.50 (s, 1H), 7.90 (d, J=8.4 Hz, 1H), 7.61 (d, J=8.4 Hz, 1H), 5.10 (d, J=2.2 Hz, 2H), 4.22 (s, 3H), 3.28-3.20 (m, 2H), 3.15-3.05 (m, 1H), 3.03-2.96 (m, 2H), 2.62 (dd, J=12.1, 9.7 Hz, 1H), 2.57-2.46 (m, 1H), 2.44-2.37 (m, 2H), 2.36-2.27 (m, 1H), 1.96-1.89 (m, 1H), 1.79-1.68 (m, 1H), 1.35 (t, J=7.5 Hz, 3H), 1.11-1.06 (m, 2H), 1.02-0.94 (m, 2H).

Example 113: 2-(3,3-difluoro-1-(2-methyl-6-(1-methyl-5-(((3-propylpyridin-2-yl)oxy)methyl)-1H-1,2,3-triazol-4-yl)pyridin-3-yl)piperidin-4-yl)acetic acid

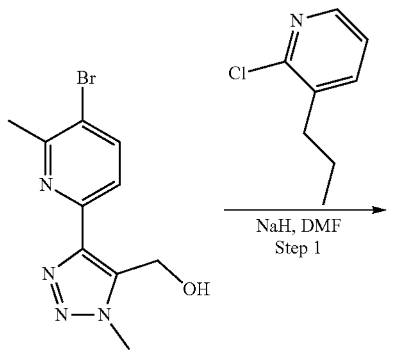

1

-continued

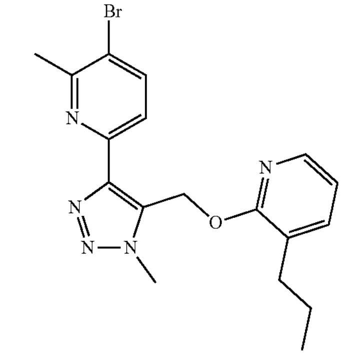

2

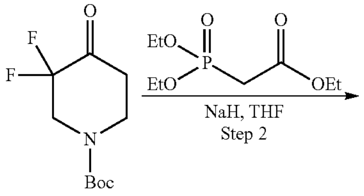

3

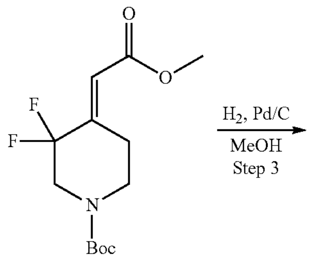

4

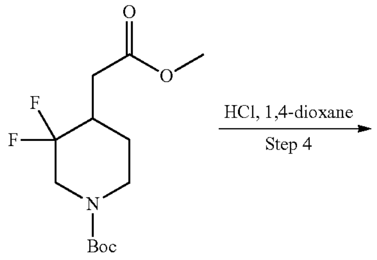

5

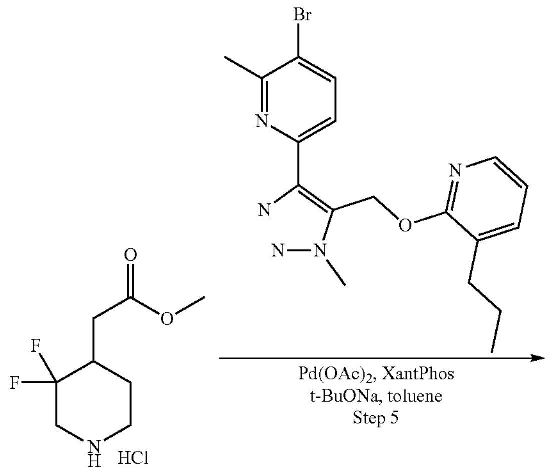

6

-continued

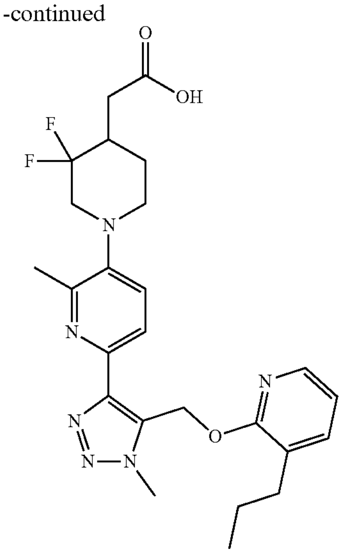

Example 113

Step 1: 3-bromo-2-methyl-6-(1-methyl-5-(((3-propylpyridin-2-yl)oxy)methyl)-1H-1,2,3-triazol-4-yl)pyridine To a solution of (4-(5-bromo-6-methylpyridin-2-yl)-1-methyl-1H-1,2,3-triazol-5-yl)methanol (500 mg, 1.76 mmol) in DMF (10 mL) was added NaH (106 mg, 2.65 mmol, 60% dispersion in mineral oil) in portions at 0° C. and the mixture was stirred this temperature for 30 min. A solution of 2-chloro-3-propylpyridine (300 mg, 1.92 mmol) in DMF (3 mL) was added to the above mixture drop-wise at 0° C. and the resulting mixture was stirred at r.t. for 4 hrs. The mixture was quenched with saturated aq·$NH_4Cl$ solution and extracted with EtOAc (3×10 mL). The combined organic layers were washed with brine, dried over $Na_2SO_4$, filtered and concentrated to dryness. The residue was purified by flash chromatography (silica gel, 0-30 EtOAc in PE) to give the title compound (620 mg, 86.1% yield) as white solid. LC/MS (ESI) m/z: 402 $(M+H)^+$.

Step 2: tert-butyl (E)-3,3-difluoro-4-(2-methoxy-2-oxoethylidene)piperidine-1-carboxylate To a solution of ethyl 2-(diethoxyphosphoryl)acetate (500 mg, 2.23 mmol) in THE (10 mL) was added NaH (116 mg, 2.9 mmol, 60% dispersion in mineral oil) in portions at 0° C. and the mixture was stirred this temperature for 30 min. A solution of tert-butyl 3,3-difluoro-4-oxopiperidine-1-carboxylate (524 mg, 2.23 mmol) in THE (5 mL) was added drop-wise at 0° C. to the above mixture and the resulting mixture was stirred at r.t. for 2 hrs. The mixture was quenched with ice-cooled saturated aq·$NH_4Cl$ solution and extracted with EtOAc (2×10 mL). The combined organic layers were washed with brine, dried over $Na_2SO_4$, filtered and concentrated to dryness. The residue was purified by flash chromatography (silica gel, 0-40 EtOAc in PE) to give the title compound (260 mg, 40% yield) as light-yellow oil. LC/MS (ESI) m/z: 292 $(M+H)^+$.

Step 3: tert-butyl 3,3-difluoro-4-(2-methoxy-2-oxoethyl)piperidine-1-carboxylate To a solution of tert-butyl (E)-3,3-difluoro-4-(2-methoxy-2-oxoethylidene)piperidine-1-carboxylate (260 mg, 0.89 mmol) in MeOH (5 mL) was added Pd/C (30 mg, 10% wt) and the mixture was degassed under $N_2$ atmosphere for three times and stirred under a $H_2$ balloon at r.t. for 3 hrs. The mixture was filtered and the filtrate was concentrated to dryness to give the title compound (240 mg, 92% yield) as light yellow oil. LC/MS (ESI) m/z: 294 $(M+H)^+$.

Step 4: methyl 2-(3,3-difluoropiperidin-4-yl)acetate hydrochloride

To a solution of tert-butyl 3,3-difluoro-4-(2-methoxy-2-oxoethyl)piperidine-1-carboxylate (240 mg, 0.82 mmol) in 1,4-dioxane (3 mL) was added 4N HCl/1,4-dioxane solution (2 mL) and the mixture was stirred at r.t. for 3 hrs. The mixture was concentrated to dryness and the residue was washed with MTBE, dried under vacuum to give the title compound (170 mg, 90% yield) as yellow solid. LC/MS (ESI) m/z: 194 $(M+H)^+$.

Step 5: 2-(3,3-difluoro-1-(2-methyl-6-(1-methyl-5-(((3-propylpyridin-2-yl)oxy)methyl)-1H-1,2,3-triazol-4-yl)pyridin-3-yl)piperidin-4-yl)acetic acid To a mixture of 3-bromo-2-methyl-6-(1-methyl-5-(((3-propylpyridin-2-yl)oxy)methyl)-1H-1,2,3-triazol-4-yl)pyridine (50 mg, 0.12 mmol) and methyl 2-(3,3-difluoropiperidin-4-yl)acetate hydrochloride (29 mg, 0.12 mmol) in 1,4-dioxane (10 mL) was added t-BuONa (36 mg, 0.37 mmol), the mixture was degassed under $N_2$ for three times and $Pd(OAc)_2$ (10 mg, 0.044 mmol) and XantPhos (26 mg, 0.044 mmol) were added under $N_2$ atmosphere. The resulting mixture was stirred at 110° C. for 16 hrs. $H_2O$ (10 mL) was added and the mixture was stirred at r.t. for 1 hr. The mixture was washed with MTBE (2×5 mL) and the aqueous layer was acidified with 1 N aq·HCl to pH~4, extracted with DCM (3×5 mL). The combined organic layers were washed with brine, dried over $Na_2SO_4$, filtered and concentrated to dryness. The residue was purified by prep·HPLC to give the title compound (11 mg, 17.7% yield) as white solid. LC/MS (ESI) m/z: 501 $(M+H)^+$. 1H NMR (400 MHz, $CD_3OD$) δ 7.96-7.94 (dd, J=5.2, 2 Hz, 1H), 7.81-7.78 (d, J=7.6 Hz, 1H), 7.54-7.52 (d, J=8.0 Hz, 1H), 7.47-7.45 (dd, J=7.2, 1.6 Hz, 1H), 6.91-6.88 (m, 1H), 5.95 (s, 2H), 4.22 (s, 3H), 3.35-3.33 (m, 1H), 3.19-3.01 (m, 3H), 2.86-2.75 (m, 2H), 2.44-2.40 (m, 1H), 2.42 (s, 3H), 2.31-2.27 (m, 1H), 2.06-2.00 (m, 1H), 1.75-1.69 (m, 2H), 1.46-1.40 (m, 2H), 0.80-0.76 (t, J=7.6 Hz, 3H).

Example 114: (R)-2-(1-(6-(5-(((5-cyclopropyl-1,2,4-oxadiazol-3-yl)oxy)methyl)-1-methyl-11H-1,2,3-triazol-4-yl)-2-ethylpyridin-3-yl)-5,5-difluoropiperidin-3-yl)acetic acid

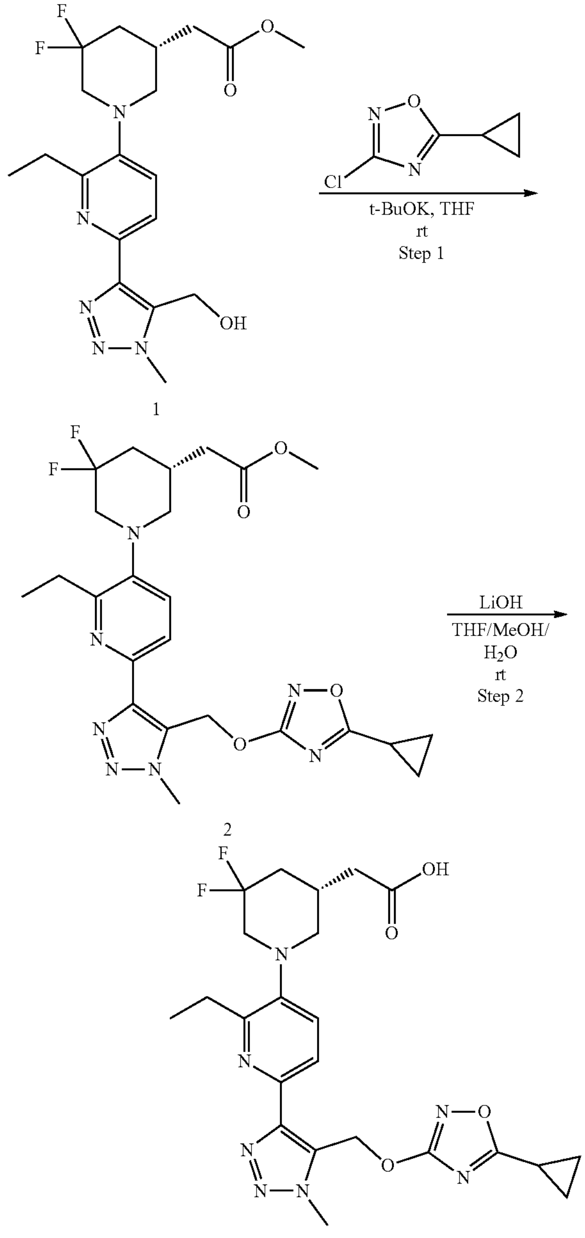

1
2
Example 114

Step 1: methyl (R)-2-(1-(6-(5-(((5-cyclopropyl-1,2,4-oxadiazol-3-yl)oxy)methyl)-1-methyl-1H-1,2,3-triazol-4-yl)-2-ethylpyridin-3-yl)-5,5-difluoropiperidin-3-yl)acetate To a mixture of methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate (40 mg, 0.098 mmol) and 3-chloro-5-cyclopropyl-1,2,4-oxadiazole (21.2 mg, 0.15 mmol) in THE (2 mL) was added t-BuOK (0.2 mL, 0.20 mmol, 1M in THF) drop-wisely at 0° C. and the mixture was stirred at r.t. for 2 hrs. The mixture was quenched with ice-water and extracted with EtOAc (2×3 mL). The combined organic layers were washed with brine, dried over anhydrous $Na_2SO_4$, filtered and concentrated to dryness to give the title compound (50 mg, 98.9% yield) as yellow solid, which was used in next step directly. LC/MS (ESI) m/z: 518 $(M+H)^+$.

Step 2: (R)-2-(1-(6-(5-(((5-cyclopropyl-1,2,4-oxadiazol-3-yl)oxy)methyl)-1-methyl-1H-1,2,3-triazol-4-yl)-2-ethylpyridin-3-yl)-5,5-difluoropiperidin-3-yl) acetic acid To a solution of methyl (R)-2-(1-(6-(5-(((5-cyclopropyl-1,2,4-oxadiazol-3-yl)oxy)methyl)-1-methyl-1H-1,2,3-triazol-4-yl)-2-ethylpyridin-3-yl)-5,5-difluoropiperidin-3-yl) acetate (50 mg, 0.097 mmol) in THE (2 mL), MeOH (0.5 mL) and $H_2O$ (0.5 mL) was added $LiOH \cdot H_2O$ (40.5 mg, 0.97 mmol) and the mixture was stirred at 25° C. for 2 hrs. The mixture was concentrated to dryness and the residue was dissolved in water (5 mL). The mixture was washed with EtOAc (2×3 mL), acidified with 1N aq·HCl to pH=4 and extracted with DCM (2×5 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (6.7 mg, 13.8% yield) as white solid. LC/MS (ESI) m/z: 504 $(M+H)^+$. $^1H$ NMR (400 MHz, $CD_3OD$) δ 7.88 (d, J=8.2 Hz, 1H), 7.56 (d, J=8.2 Hz, 1H), 6.05 (s, 2H), 4.20 (s, 3H), 3.23 (t, J=10.2 Hz, 2H), 3.12-3.01 (m, 1H), 2.92-2.84 (m, 2H), 2.64-2.56 (m, 1H), 2.53-2.45 (m, 1H), 2.43-2.36 (m, 2H), 2.34-2.24 (m, 1H), 2.17-2.09 (m, 1H), 1.79-1.65 (m, 1H), 1.29-1.20 (m, 5H), 1.11-1.04 (m, 2H).

Example 115: (R)-2-(1-(6-(5-(((5-cyclopropyl-1,2,4-oxadiazol-3-yl)amino)methyl)-1-methyl-1H-1,2,3-triazol-4-yl)-2-ethylpyridin-3-yl)-5,5-difluoropiperidin-3-yl)acetic acid

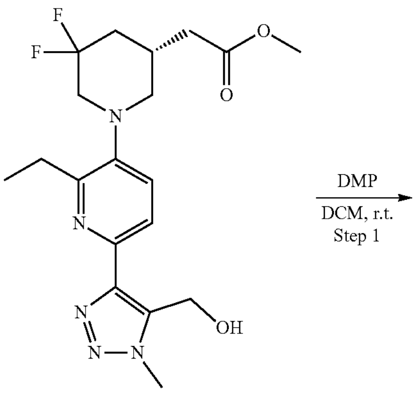

1

-continued

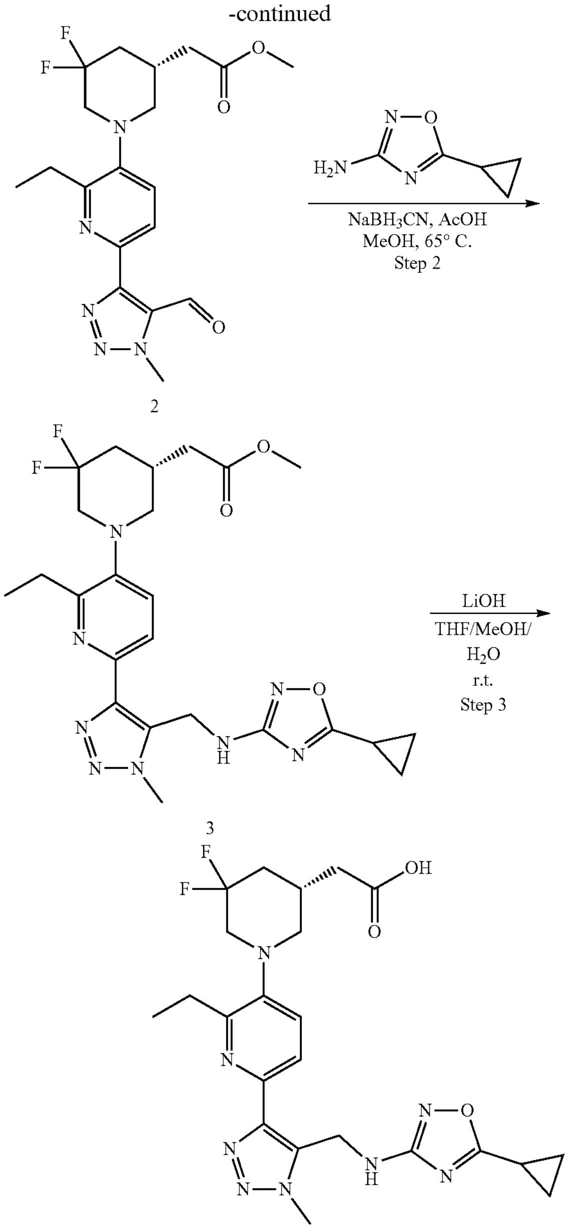

2

3

Example 115

Step 1: methyl (R)-2-(1-(2-ethyl-6-(5-formyl-1-methyl-1H-1,2,3-triazol-4-yl)pyridin-3-yl)-5,5-difluoropiperidin-3-yl)acetate To a solution of methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate (80 mg, 0.20 mmol) in DCM (5 mL) was added DMP (331 mg, 0.78 mmol) and the mixture was stirred at 25° C. for 1 hr. The mixture was quenched with saturated aq·$NaHCO_3$ solution and extracted with DCM (3x5 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound (50 mg, 62.8% yield) as yellow oil. LC/MS (ESI) m/z: 408 $(M+H)^+$.

Step 2: methyl (R)-2-(1-(6-(5-(((5-cyclopropyl-1,2,4-oxadiazol-3-yl)amino)methyl)-1-methyl-1H-1,2,3-triazol-4-yl)-2-ethylpyridin-3-yl)-5,5-difluoropiperidin-3-yl)acetate To a solution of methyl (R)-2-(1-(2-ethyl-6-(5-formyl-1-methyl-1H-1,2,3-triazol-4-yl)pyridin-3-yl)-5,5-difluoropiperidin-3-yl)acetate (25 mg, 0.061 mmol) and 5-cyclopropyl-1,2,4-oxadiazol-3-amine (15.4 mg, 0.12 mmol) in MeOH (2 mL) was added AcOH (3 drops) under $N_2$ atmosphere and the mixture was stirred at 65° C. for 16 hrs. $NaBH_3CN$ (38 mg, 0.61 mmol) was added to the above mixture at 25° C. and the resulting mixture was continued to stir at 25° C. for 2 hrs. The mixture was quenched with saturated aq·$NaHCO_3$ solution and extracted with DCM (2x3 mL). The combined organic layers were washed with brine, dried over anhydrous $Na_2SO_4$, filtered and concentrated to dryness to give the title compound (35 mg, 110.4% yield) as yellow oil, which was used in the next step directly. LC/MS (ESI) m/z: 517 $(M+H)^+$.

Step 2: (R)-2-(1-(6-(5-(((5-cyclopropyl-1,2,4-oxadiazol-3-yl)amino)methyl)-1-methyl-1H-1,2,3-triazol-4-yl)-2-ethylpyridin-3-yl)-5,5-difluoropiperidin-3-yl) acetic acid To a solution of methyl (R)-2-(1-(6-(5-(((5-cyclopropyl-1,2,4-oxadiazol-3-yl)amino)methyl)-1-methyl-1H-1,2,3-triazol-4-yl)-2-ethylpyridin-3-yl)-5,5-difluoropiperidin-3-yl) acetate (35 mg, 0.068 mmol) in THE (2 mL), MeOH (0.5 mL) and $H_2O$ (0.5 mL) was added LiOH·$H_2O$ (28.4 mg, 0.68 mmol) and the reaction mixture was stirred at 25° C. for 2 hrs. The mixture was concentrated to dryness and the residue was dissolved in water (5 mL). The aqueous solution was washed with EtOAc (2x3 mL), acidified with 1N aq·HCl to pH~3 and extracted with DCM (3x3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (12.5 mg, 36.5% yield) as white solid. LC/MS (ESI) m/z: 503 $(M+H)^+$. $^1H$ NMR (400 MHz, $CD_3OD$) δ 7.90 (d, J=8.2 Hz, 1H), 7.60 (d, J=8.4 Hz, 1H), 4.78 (s, 2H), 4.21 (s, 3H), 3.27-3.20 (m, 2H), 3.14-3.06 (m, 1H), 3.02-2.96 (m, 2H), 2.65-2.58 (m, 1H), 2.55-2.46 (m, 1H), 2.43-2.37 (m, 2H), 2.34-2.25 (m, 1H), 2.09-2.01 (m, 1H), 1.81-1.65 (m, 1H), 1.38-1.31 (m, 4H), 1.18-1.10 (m, 2H), 1.07-1.02 (m, 2H).

The examples list in the table were prepared according to the same method as described for the synthesis of example 114 and 115.

| EX# | Structure & name | Analytical data | Method |
|---|---|---|---|
| 116 | 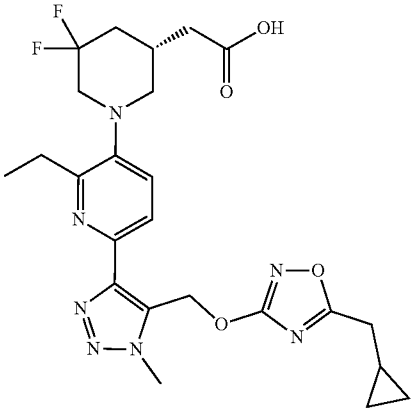 [SMILES: CCc1nc(-c2nnn(C)c2COc2noc(CC3CC3)n2)ccc1N1C[C@@H](CC(=O)O)CC(F)(F)C1] (S)-2-(1-(6-(5-(((5-(cyclopropylmethyl)-1,2,4-oxadiazol-3-yl)oxy)methyl)-1-methyl-1H-1,2,3-triazol-4-yl)-2-ethylpyridin-3-yl)-5,5-difluoropiperidin-3-yl)acetic acid | LC/MS (ESI) m/z: 518 $(M + H)^+$. $^1H$ NMR (400 MHz, $CD_3OD$) δ 7.89 (d, J = 8.4 Hz, 1H), 7.56 (d, J = 8.3 Hz, 1H), 6.09 (s, 2H), 4.22 (s, 3H), 3.26-3.22 (m, 1H), 3.13-3.01 (m, 1H), 2.89 (q, J = 7.6 Hz, 2H), 2.73 (d, J = 7.1 Hz, 2H), 2.64-2.56 (m, 1H), 2.55-2.46 (m, 1H), 2.41-2.36 (m, 2H), 2.35-2.27 (m, 1H), 1.81-1.65 (m, 1H), 1.26 (t, J = 7.5 Hz, 3H), 1.14-1.07 (m, 1H), 0.60 (t, J = 6.3 Hz, 2H), 0.31-0.24 (m, 2H). | Example 114 |
| 117 | 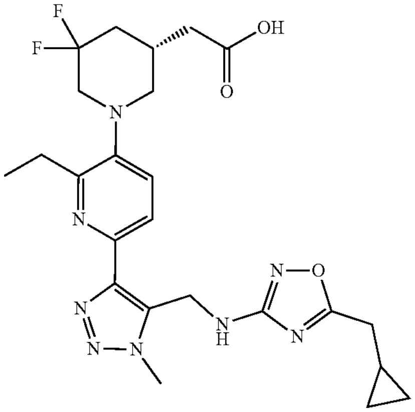 [SMILES: CCc1nc(-c2nnn(C)c2CNc2noc(CC3CC3)n2)ccc1N1C[C@@H](CC(=O)O)CC(F)(F)C1] (S)-2-(1-(6-(5-(((5-(cyclopropylmethyl)-1,2,4-oxadiazol-3-yl)amino)methyl)-1-methyl-1H-1,2,3-triazol-4-yl)-2-ethylpyridin-3-yl)-5,5-difluoropiperidin-3-yl)acetic acid | LC/MS (ESI) m/z: 517 $(M + 1)^+$ $^1H$-NMR (400 MHz, $CD_3OD$) δ 7.91 (d, J = 8.3 Hz, 1H), 7.61 (d, J = 8.4 Hz, 1H), 4.81 (s, 2H), 4.24 (s, 3H), 3.25 (t, J = 10.3 Hz, 2H), 3.16-3.04 (m, 1H), 3.00 (q, J = 7.6 Hz, 2H), 2.67-2.39 (m, 6H), 2.36-2.24 (m, 1H), 1.84-1.65 (m, 1H), 1.36 (t, J = 7.5 Hz, 3H), 1.13-1.02 (m, 1H), 0.57 (q, J = 5.5 Hz, 2H), 0.24 (q, J = 4.9 Hz, 2H). | Example 115 |
| 118 | 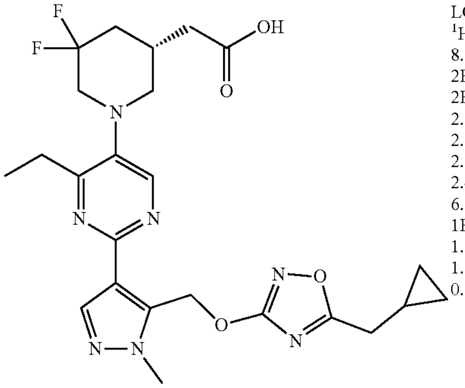 (S)-2-(1-(2-(5-(((5-(cyclopropylmethyl)-1,2,4-oxadiazol-3-yl)oxy)methyl)-1-methyl-1H-pyrazol-4-yl)-4-ethylpyrimidin-5-yl)-5,5-difluoropiperidin-3-yl)acetic acid | LC/MS (ESI) m/z: 518 $(M + H)^+$. $^1H$ NMR (400 MHz, $CD_3OD$) δ 8.38 (s, 1H), 8.10 (s, 1H), 6.04 (s, 2H), 4.01 (s, 3H), 3.30-3.23 (m, 2H), 3.21-3.11 (m, 1H), 2.89-2.83 (q, J = 7.5 Hz, 2H), 2.74-2.72 (d, J = 7.1 Hz, 2H), 2.69-2.66 (d, J = 10.7 Hz, 1H), 2.51-2.44 (m, 1H), 2.41-2.39 (dd, J = 6.9, 3.4 Hz, 2H), 2.36-2.27 (m, 1H), 1.81-1.66 (m, 1H), 1.29-1.25 (t, J = 7.5 Hz, 3H), 1.14-1.07 (m, 1H), 0.62-0.57 (m, 2H), 0.230-0.25 (m, 2H). | Example 114 |

-continued

| EX# | Structure & name | Analytical data | Method |
|---|---|---|---|
| 119 | 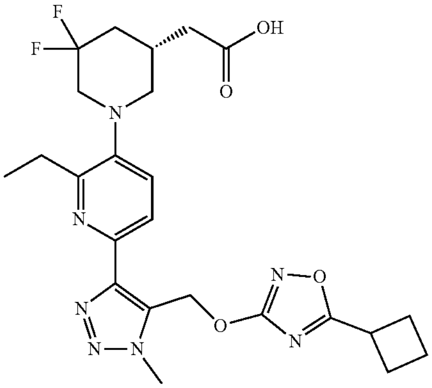 [SMILES: CCc1nc(-c2nnn(C)c2COc2noc(C3CCC3)n2)ccc1N1C[C@@H](CC(=O)O)CC(F)(F)C1] (S)-2-(1-(6-(5-(((5-cyclobutyl-1,2,4-oxadiazol-3-yl)oxy)methyl)-1-methyl-1H-1,2,3-triazol-4-yl)-2-ethylpyridin-3-yl)-5,5-difluoropiperidin-3-yl)acetic acid | LC/MS (ESI) m/z: 518 $(M + H)^+$. $^1$H-NMR (400 MHz, $CD_3OD$) δ 7.89 (d, J = 8.6 Hz, 1H), 7.56 (d, J = 8.4 Hz, 1H), 6.09 (s, 2H), 4.22 (s, 3H), 3.71-3.67 (m, 1H), 3.23-3.20 (m, 3H), 3.12 -3.02 (m, 2H), 2.91-2.86 (m, 2H), 2.63-2.58 (m, 1H), 2.44-2.26 (m, 6H), 2.18-2.09 (m, 1H), 2.05-1.96 (m, 1H), 1.81-1.64 (m, 1H), 1.26 (t, J = 7.5 Hz, 3H). | Example 114 |
| 120 | 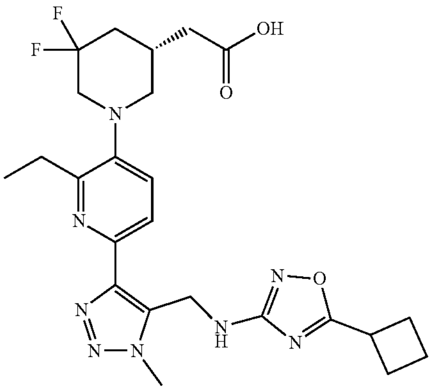 [SMILES: CCc1nc(-c2nnn(C)c2CNc2noc(C3CCC3)n2)ccc1N1C[C@@H](CC(=O)O)CC(F)(F)C1] (S)-2-(1-(6-(5-(((5-cyclobutyl-1,2,4-oxadiazol-3-yl)amino)methyl)-1-methyl-1H-1,2,3-triazol-4-yl)-2-ethylpyridin-3-yl)-5,5-difluoropiperidin-3-yl)acetic acid | LC/MS (ESI) m/z: 517 $(M + H)^+$. $^1$H-NMR (400 MHz, $CD_3OD$) δ 7.91 (d, J = 8.4 Hz, 1H), 7.61 (d, J = 8.4 Hz, 1H), 4.81 (s, 2H), 4.58 (s, 1H), 4.24 (s, 3H), 3.66-3.57 (m, 1H), 3.24 (d, J = 10.2 Hz, 2H), 3.13-3.07 (m, 1H), 3.03-2.98 (m, 2H), 2.62 (t, J = 10.6 Hz, 1H), 2.55-2.49 (m, 1H), 2.41-2.23 (m, 7H), 2.14-2.06 (m, 1H), 2.04-1.93 (m, 1H), 1.81-1.67 (m, 1H), 1.36 (t, J = 7.5 Hz, 3H). | Example 115 |

Example 121: (S)-2-(1-(2-ethyl-6-(1-methyl-5-(((1-propyl-1H-1,2,4-triazol-5-yl)oxy)methyl)-1H-1,2,3-triazol-4-yl)pyridin-3-yl)-5,5-difluoropiperidin-3-yl) acetic acid

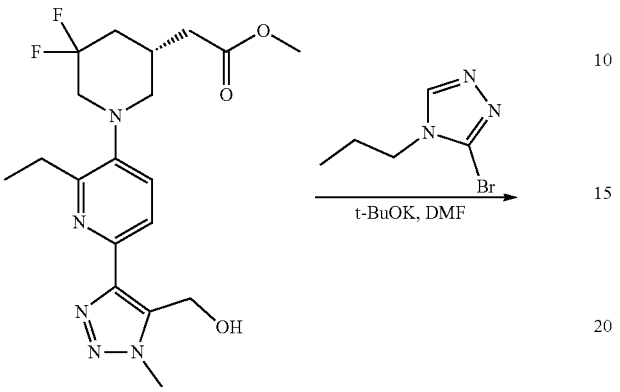

1

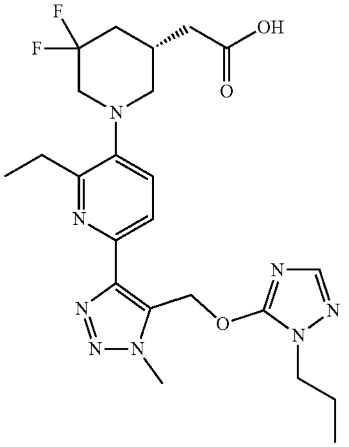

Example 121

To a solution of methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate (30 mg, 0.073 mmol) and 3-bromo-4-propyl-4H-1,2,4-triazole (21 mg, 0.11 mmol) in DMF (1 mL) was added t-BuOK (0.15 mL, 0.15 mmol, 1 M in THF) at 0° C. and the mixture was stirred at r.t. for 16 hrs. The reaction was quenched with ice water (5 mL) and the mixture was stirred at r.t. for 1 hr. The mixture was washed MTBE (2×3 mL) and the aqueous layer was acidified with 1N aq·HCl and extracted with DCM (2×5 mL). The combined organic layers were washed with brine, dried over $Na_2SO_4$, filtered and concentrated to dryness. The residue was purified by prep-HPLC to give the title compound (10 mg, 27.20 yield) as white solid. LC/MS (ESI) m/z: 505 $(M+H)^+$. $^1H$ NMR (400 MHz, $CD_3OD$) δ 7.88 (d, J=8.4 Hz, 1H), 7.60 (s, 1H), 7.56 (d, J=8.4 Hz, 1H), 6.11 (s, 2H), 4.24 (s, 3H), 3.79 (t, J=6.8 Hz, 2H), 3.25-3.18 (m, 2H), 3.13-2.99 (m, 1H), 2.84 (t, J=7.2 Hz, 2H), 2.61-2.26 (m, 5H), 1.74-1.59 (m, 3H), 1.22 (t, J=7.2 Hz, 3H), 0.73 (t, J=7.6 Hz, 3H).

The examples list in the below table were prepared according to the same method as described for the synthesis of example 121.

| Ex# | Structure & name | Analytical data | Method |
|---|---|---|---|
| 122 | 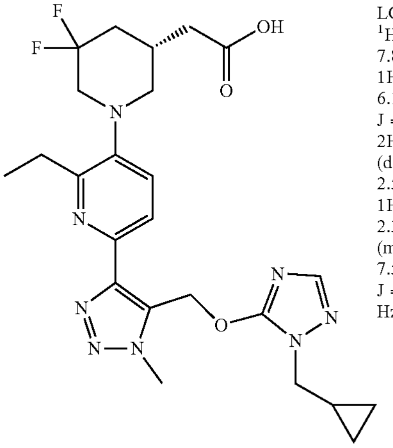 (S)-2-(1-(6-(5-(((1-(cyclopropylmethyl)-1H-1,2,4-triazol-5-yl)oxy)methyl)-1-methyl-1H-1,2,3-triazol-4-yl)-2-ethylpyridin-3-yl)-5,5-difluoropiperidin-3-yl)acetic acid | LC/MS (ESI) m/z: 517(M + H)$^+$. $^1$H NMR (400 MHz, $CD_3OD$) δ 7.89 (d, J = 8.3 Hz, 1H), 7.60 (s, 1H), 7.56 (d, J = 8.3 Hz, 1H), 6.10 (s, 2H), 4.24 (s, 3H), 3.69 (d, J = 7.1 Hz, 2H), 3.23-3.18 (m, 2H), 3.09-3.02 (m, 1H), 2.84 (dd, J = 14.9, 7.4 Hz, 2H), 2.62-2.56 (m, 1H), 2.50-2.44 (m, 1H), 2.39 (d, J = 6.8 Hz, 1H), 2.33-2.25 (m, 1H), 1.84-1.62 (m, 1H), 1.30 (s, 1H), 1.21 (t, J = 7.5 Hz, 3H), 1.04 (s, 1H), 0.36 (d, J = 6.9 Hz, 2H), 0.14 (d, J = 5.2 Hz, 2H). | Example 121 |
| 123 | 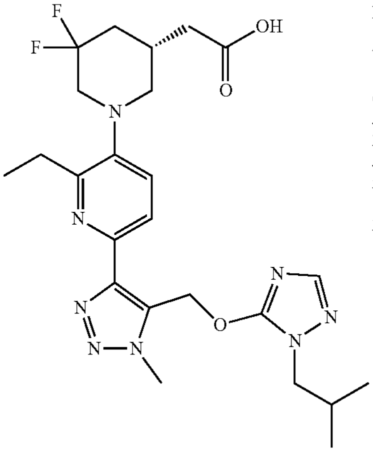 [SMILES: CCc1nc(-c2nnn(C)c2COc2ncnn2CC(C)C)ccc1N1C[C@@H](CC(=O)O)CC(F)(F)C1] (S)-2-(1-(2-ethyl-6-(5-(((1-isobutyl-1H-1,2,4-triazol-5-yl)oxy)methyl)-1-methyl-1H-1,2,3-triazol-4-yl)pyridin-3-yl)-5,5-difluoropiperidin-3-yl)acetic acid | LC/MS (ESI) m/z: 519 (M + H)$^+$. $^1$H-NMR (400 MHz, $CD_3OD$) δ 7.88 (d, J = 8.4 Hz, 1H), 7.60 (s, 1H), 7.56 (d, J = 8.4 Hz, 1H), 6.11 (s, 2H), 4.24 (s, 3H), 3.62 (d, J = 7.2 Hz, 2H), 3.30-3.19 (m, 2H), 3.13-3.02 (s, 1H), 2.86 (q, J = 7.6 Hz, 2H), 2.62-2.25 (m, 5H), 2.03-1.91 (m, 1H), 1.80-1.64 (m, 1H), 1.23 (t, J = 7.6 Hz, 3H), 0.73 (d, J = 6.8 Hz, 6H). | Example 121 |

Example 124: (S)-2-(1-(2-ethyl-6-(5-(((2-isobutyl-2H-tetrazol-5-yl)oxy)methyl)-1-methyl-ill-1,2,3-triazol-4-yl)pyridin-3-yl)-5,5-difluoropiperidin-3-yl) acetic acid

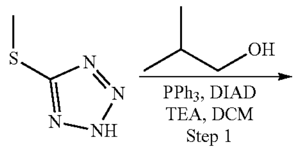

1

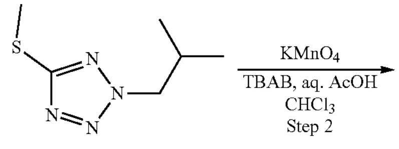

2

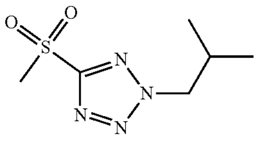

3

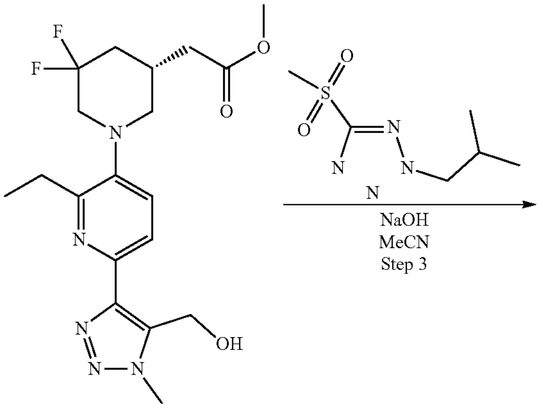

4

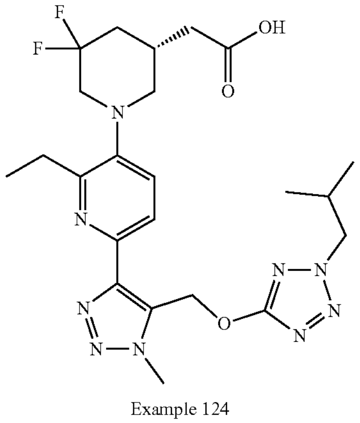

Example 124

Step 1: 2-(2-methylpropyl)-5-(methylsulfanyl)-2H-1,2,3,4-tetrazole

To a mixture of 5-(Methylthio)-1H-tetrazole (1 g, 8.61 mmol), 2-methyl-1-propanol (1.28 g, 17.2 mmol) and $PPh_3$ (4.06 g, 15.5 mmol) in DCM (50 mL) was added TEA (1.31 g, 12.92 mmol) followed by drop-wise addition of DIAD (1.74 g, 8.61 mmol) at 0° C. under $N_2$ atmosphere and the mixture was stirred at r.t. for 16 hrs. The mixture was concentrated to dryness and the residue was purified by silica gel chromatography (PE:EtOAc=2:1) to give the title compound (810 mg, 54.6% yield) as white solid. LC/MS (ESI) m/z: 173 $(M+H)^+$. $^1H$ NMR (400 MHz, $CDCl_3$) δ 4.37 (d, J=7.2 Hz, 2H), 2.68 (s, 3H), 2.31-2.43 (m, 1H), 0.97 (d, J=6.7 Hz, 6H).

Step 2: 5-methanesulfonyl-2-(2-methylpropyl)-2H-1,2,3,4-tetrazole

To a solution of 2-(2-methylpropyl)-5-(methylsulfanyl)-2H-1,2,3,4-tetrazole (800 mg, 4.64 mmol) in chloroform (40 mL) was added TBAB (75 mg, 0.23 mmol), aq·AcOH (25 mL, 10% wt) followed by $KMnO_4$ (1.47 g, 9.29 mmol) and the mixture was stirred at r.t. for 18 hrs. The mixture was diluted with DCM (20 mL) and washed with water (3×10 mL) and brine, dried over $Na_2SO_4$, filtered and concentrated to dryness to give the title compound (530 mg, 55.9% yield) as white solid. LC/MS (ESI) m/z: 205 $(M+H)^+$.

Step 3: (S)-2-(1-(2-ethyl-6-(5-(((2-isobutyl-2H-tetrazol-5-yl)oxy)methyl)-1-methyl-1H-1,2,3-triazol-4-yl)pyridin-3-yl)-5,5-difluoropiperidin-3-yl)acetic acid To a solution of methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate (30 mg, 0.073 mmol) and 5-methanesulfonyl-2-(2-methylpropyl)-2H-1,2,3,4-tetrazole (29 mg, 0.15 mmol) in $CH_3CN$ (1 mL) was added NaOH (14 mg, 0.37 mmol) and the mixture was stirred at 80° C. for 3 hrs. The mixture was diluted with water (10 mL), washed with MTBE (2x3 mL), acidified with 1N aq·HCl to pH~4 and extracted with DCM (3×5 mL). The combined organic layers were washed with brine, dried over $Na_2SO_4$, filtered and concentrated to dryness. The residue was purified by perp-HPLC (C18, 0~90% acetonitrile in $H_2O$ with 0.1% HCOOH) to give the title compound (11 mg, 29.0% yield) as white solid. LC/MS (ESI) m/z: 520 $(M+H)^+$. $^1H$ NMR (400 MHz, $CD_3OD$) δ 7.87 (d, J=8.4 Hz, 1H), 7.56 (d, J=8.0 Hz, 1H), 6.17 (s, 2H), 4.28 (d, J=7.2 Hz, 2H), 4.23 (s, 3H), 3.25-3.20 (m, 2H), 3.12-3.02 (m, 1H), 2.90-2.84 (q, J=7.7 Hz, 2H), 2.62-2.57 (t, J=10.8 Hz, 1H), 2.52-2.38 (m, 3H), 2.31-2.15 (m, 2H), 1.72-1.68 (m, 1H), 1.25-1.21 (t, J=7.5 Hz, 3H), 0.89 (d, J=7.2 Hz, 6H).

Example 125: (S)-2-(1-(6-(5-(((2-(cyclopropylmethyl)-2H-tetrazol-5-yl)oxy)methyl)-1-methyl-1H-1,2,3-triazol-4-yl)-2-ethylpyridin-3-yl)-5,5-difluoropiperidin-3-yl)acetic acid Example 125

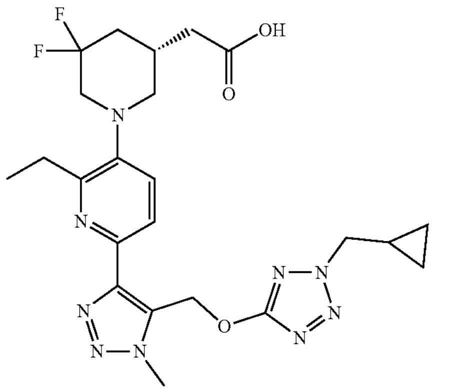

The title compound was prepared from cyclopropylmethanol using the same sequence that was synthesized example 124. LC/MS (ESI) m/z: 518 $(M+H)^+$. $^1H$ NMR (400 MHz, $CD_3OD$) δ 7.89-7.86 (d, J=8.3 Hz, 1H), 7.57-7.54 (d, J=8.3 Hz, 1H), 6.18 (s, 2H), 4.32-4.29 (d, J=7.4 Hz, 2H), 4.23 (s, 3H), 3.27-3.19 (m, 2H), 3.15-3.07 (m, 1H), 2.91-2.84 (m, 2H), 2.63-2.56 (m, 1H), 2.54-2.46 (m, 1H), 2.39-2.26 (d, J=6.0 Hz, 2H), 2.33-2.26 (m, 1H), 1.79-1.64 (m, 1H), 1.32-1.28 (m, 1H), 1.25-1.21 (t, J=7.2 Hz, 3H), 0.64-0.59 (m, 2H), 0.45-0.37 (m, 2H).

Example 126: (S)-2-(1-(6-(5-(((1-(cyclopropylmethyl)-1H-1,2,3-triazol-4-yl)oxy)methyl)-1-methyl-1H-1,2,3-triazol-4-yl)-2-ethylpyridin-3-yl)-5,5-difluoropiperidin-3-yl)acetic acid

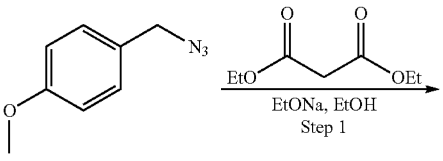

1

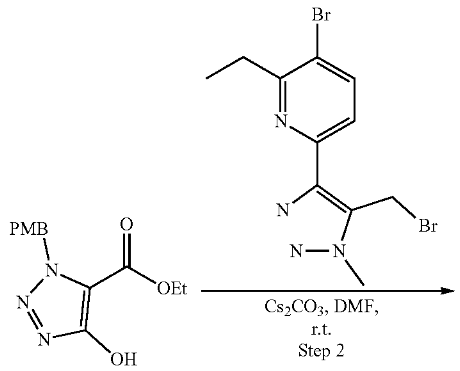

2

-continued

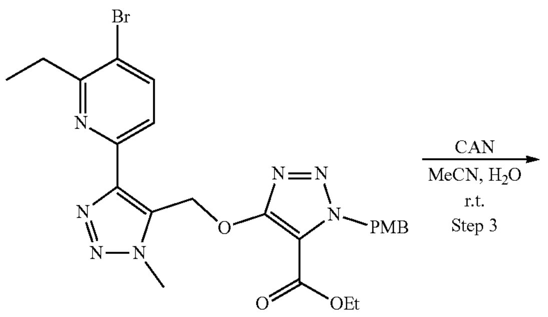

3

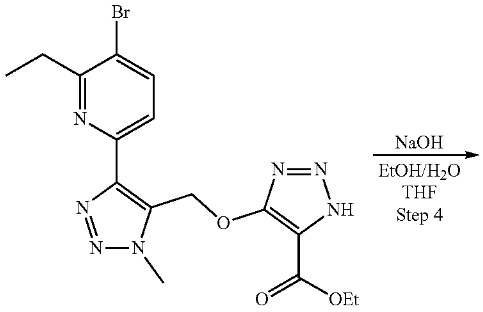

4

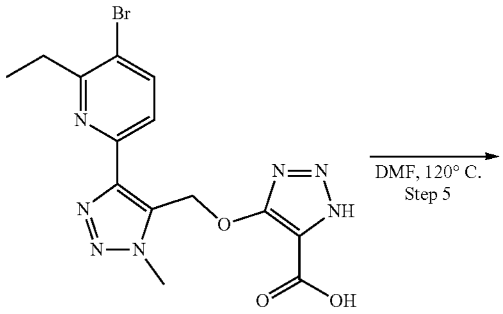

5

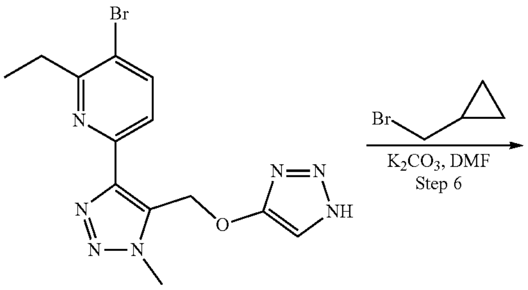

6

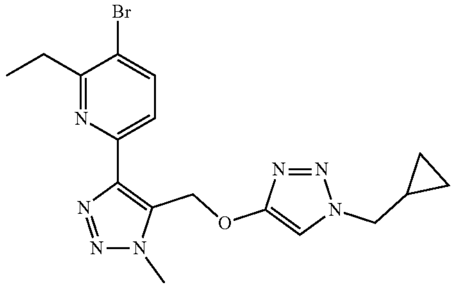

7A

-continued

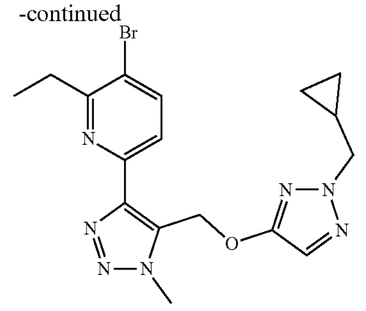

7B

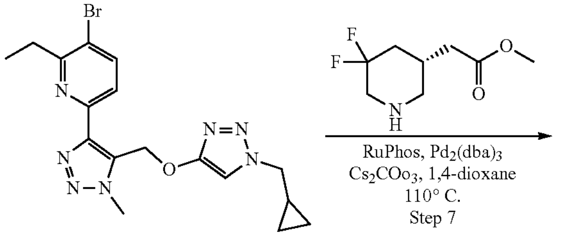

7A

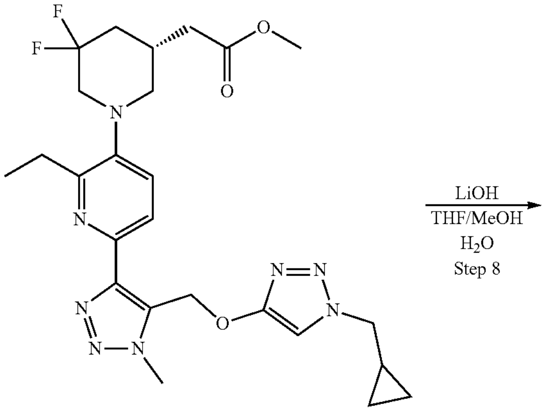

8

8

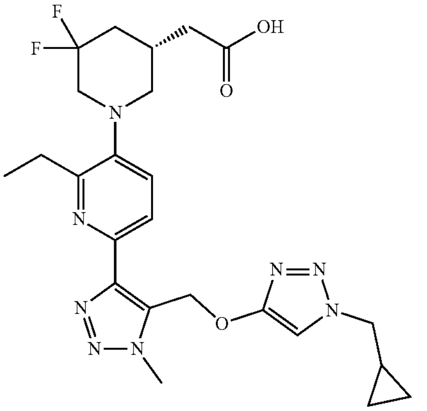

Example 126

Step 1: ethyl 4-hydroxy-1-(4-methoxybenzyl)-1H-1,2,3-triazole-5-carboxylate

To a newly prepared EtONa/EtOH solution (22 mmol in 50 mL of EtOH) was added diethyl malonate (3.54 g, 22 mmol) under $N_2$ atmosphere and the mixture was stirred at r.t. for 0.5 hr. To the above mixture, a solution of 1-(azidomethyl)-4-methoxybenzene (2.4 g, 14.7 mmol) in ethanol (4 mL) was added drop-wisely and the resulting mixture was stirred at 85° C. for 5 hrs. The mixture was concentrated to dryness and diluted with water, the aqueous solution was acidified with 1N aq·HCl to pH=2 and extracted with DCM (2×10 mL). The combined organic layers were washed with brine, dried over anhydrous $Na_2SO_4$, filtered and concentrated to dryness. The residue was purified by flash chromatography (eluted with PE:EtOAc=20:1 to 1:1) to give the title compound (1.82 g, 50.1% yield) as red solid. LC/MS (ESI) m/z: 278 $(M+H)^+$.

Step 2: ethyl 4-((4-(5-bromo-6-ethylpyridin-2-yl)-1-methyl-1H-1,2,3-triazol-5-yl)methoxy)-1-(4-methoxybenzyl)-1H-1,2,3-triazole-5-carboxylate To a solution of 3-bromo-6-(5-(bromomethyl)-1-methyl-1H-1,2,3-triazol-4-yl)-2-ethylpyridine (970 mg, 2.7 mmol) and ethyl 4-hydroxy-1-(4-methoxybenzyl)-1H-1,2,3-triazole-5-carboxylate (747 mg, 2.7 mmol) in DMF (10 mL) was added $Cs_2CO_3$ (2.63 g, 8.08 mmol) under $N_2$ atmosphere and the mixture was stirred at r.t. for 1 hr. The mixture was diluted with water (20 mL) and extracted with EtOAc (2×15 mL). The combined organic layers were washed with saturated aq·$NH_4Cl$ solution and brine, dried over anhydrous $Na_2SO_4$, filtered and concentrated to dryness. The residue was purified by flash chromatography (eluted with PE:EtOAc=20:1 to 2:1) to give the title compound (839 mg, 56% yield) as white solid. LC/MS (ESI) m/z: 556/558 $(M+H)^+$.

Step 3: ethyl 4-((4-(5-bromo-6-ethylpyridin-2-yl)-1-methyl-11H-1,2,3-triazol-5-yl)methoxy)-1H-1,2,3-triazole-5-carboxylate To a solution of ethyl 4-((4-(5-bromo-6-ethylpyridin-2-yl)-1-methyl-1H-1,2,3-triazol-5-yl)methoxy)-1-(4-methoxybenzyl)-1H-1,2,3-triazole-5-carboxylate (800 mg, 1.44 mmol) in MeCN (20 mL) was added a solution of CAN (1.97 g, 3.59 mmol) in water (20 mL) drop-wisely at 0° C. and the mixture was stirred at r.t. for 16 hrs. The slurry was filtered and the filter cake was washed with water, dried under vacuum to give the title compound (600 mg, 76.5% yield) as white solid. LC/MS (ESI) m/z: 436/438 $(M+H)^+$.

Step 4: 4-((4-(5-bromo-6-ethylpyridin-2-yl)-1-methyl-11H-1,2,3-triazol-5-yl)methoxy)-1H-1,2,3-triazole-5-carboxylic acid To a solution of ethyl 4-((4-(5-bromo-6-ethylpyridin-2-yl)-1-methyl-1H-1,2,3-triazol-5-yl)methoxy)-1H-1,2,3-triazole-5-carboxylate (600 mg, 1.17 mmol) in THE (10 mL), EtOH (10 mL) and $H_2O$ (5 mL) was added NaOH (468 mg, 11.69 mmol) and the mixture was stirred at 60° C. for 5 hrs. The mixture was concentrated to dryness and the residue was dissolved in water (10 mL). The aqueous layer was acidified with 1N aq·HCl to pH=3 and extracted with DCM (2×10 mL). The combined organic layers were washed with brine, dried over anhydrous $Na_2SO_4$, filtered and concentrated to dryness. The residue was purified by flash chromatography (eluted with PE:EtOAc=20:1 to 1:1) to give the title compound (500 mg, 83.8% yield) as white solid. LC/MS (ESI) m/z: 408/410 $(M+H)^+$.

Step 5: 6-(5-(((1H-1,2,3-triazol-4-yl)oxy)methyl)-1-methyl-1H-1,2,3-triazol-4-yl)-3-bromo-2-ethylpyridine A solution of 4-((4-(5-bromo-6-ethylpyridin-2-yl)-1-methyl-1H-1,2,3-triazol-5-yl)methoxy)-1H-1,2,3-triazole-5-carboxylic acid (500 mg, 0.98 mmol) in DMF (10 mL) was stirred at 120° C. for 16 hrs. The mixture was diluted with EtOAc (20 mL), washed with water and brine, dried over anhydrous $Na_2SO_4$, filtered and concentrated to dryness. The residue was purified by flash chromatography (eluted with PE:EtOAc=20:1 to 2:1) to give title compound (290 mg, 77.2% yield) as white solid. LC/MS (ESI) m/z: 364/366 $(M+H)^+$.

Step 6: 3-bromo-6-(5-(((1-(cyclopropylmethyl)-1H-1,2,3-triazol-4-yl)oxy)methyl)-1-methyl-1H-1,2,3-triazol-4-yl)-2-ethylpyridine (7A) & 3-bromo-6-(5-(((2-(cyclopropylmethyl)-2H-1,2,3-triazol-4-yl)oxy)methyl)-1-methyl-1H-1,2,3-triazol-4-yl)-2-ethylpyridine (7B)

To a solution of 3-bromo-2-ethyl-6-{1-methyl-5-[(1H-1,2,3-triazol-4-yloxy)methyl]-1H-1,2,3-triazol-4-yl}pyridine (140 mg, 0.38 mmol) in DMF (5 mL) was added $K_2CO_3$ (159 mg, 1.15 mmol) followed by (bromomethyl)cyclopropane (0.18 mL, 1.92 mmol). After stirring at r.t. for 2 hrs, the reaction mixture was diluted with ice-water and extracted with EtOAc (2×10 mL). The combined organic layers were washed with brine, dried over anhydrous $Na_2SO_4$, filtered and concentrated to dryness. The residue was purified by flash chromatography (silica gel, 0-100% EtOAc in PE) to give 3-bromo-6-(5-(((1-(cyclopropylmethyl)-1H-1,2,3-triazol-4-yl)oxy)methyl)-1-methyl-1H-1,2,3-triazol-4-yl)-2-ethylpyridine 7A (45 mg, yield 28.0%) and 3-bromo-6-(5-(((2-(cyclopropylmethyl)-2H-1,2,3-triazol-4-yl)oxy)methyl)-1-methyl-1H-1,2,3-triazol-4-yl)-2-ethylpyridine 7B (85 mg, yield 52.9%) as white solid. 7A: $^1H$ NMR (400 MHz, DMSO-$d_6$) δ 8.12 (d, J=8.4 Hz, 1H), 7.87 (d, J=8.4 Hz, 1H), 7.71 (s, 1H), 5.89 (s, 2H), 4.16 (s, 3H), 4.10 (d, J=7.2 Hz, 2H), 2.87 (q, J=7.6 Hz, 2H), 1.24-1.15 (m, 1H), 1.18 (t, J=7.6 Hz, 3H), 0.53-0.48 (m, 2H), 0.37-0.32 (m, 2H). 7B: $^1H$-NMR (400 MHz, DMSO-$d_6$) δ 8.11 (d, J=8.4 Hz, 1H), 7.86 (d, J=8.4 Hz, 1H), 7.31 (s, 1H), 5.90 (s, 2H), 4.16 (s, 3H), 4.06 (d, J=7.2 Hz, 2H), 2.87 (q, J=7.6 Hz, 2H), 1.20-1.14 (m, 1H), 1.16 (t, J=7.6 Hz, 3H), 0.52-0.46 (m, 2H), 0.33-0.30 (m, 2H). LC/MS (ESI) m/z: 420/422 $(M+H)^+$.

Step 7: methyl (S)-2-(1-(6-(5-(((1-(cyclopropylmethyl)-1H-1,2,3-triazol-4-yl)oxy)methyl)-1-methyl-1H-1,2,3-triazol-4-yl)-2-ethylpyridin-3-yl)-5,5-difluoropiperidin-3-yl)acetate To a mixture of 3-bromo-6-(5-(((1-(cyclopropylmethyl)-1H-1,2,3-triazol-4-yl)oxy)methyl)-1-methyl-1H-1,2,3-triazol-4-yl)-2-ethylpyridine (45 mg, 0.11 mmol), methyl 2-[(3S)-5,5-difluoropiperidin-3-yl]acetate (21 mg, 0.11 mmol) and $Cs_2CO_3$ (105 mg, 0.32 mmol) in 1,4-dioxane (2 mL) was added Ru-Phos (5 mg, 0.011 mmol) followed by Ru-Phos Pd G3 (9 mg, 0.011 mmol). Then the mixture was degassed under $N_2$ atmosphere for three times and stirred at 120° C. under $N_2$ atmosphere for 16 hrs. The mixture was diluted with ice-water and extracted with EtOAc (2×5 mL). The combined organic layers were washed with brine, dried over anhydrous $Na_2SO_4$, filtered and concentrated to dryness. The residue was purified by prep·TLC (PE:EtOAc=2:1) to give the title compound (35 mg, 61.3% yield) as yellow solid. LC/MS (ESI) m/z: 531$(M+H)^+$.

Step 8: (S)-2-(1-(6-(5-(((1-(cyclopropylmethyl)-1H-1,2,3-triazol-4-yl)oxy)methyl)-1-methyl-1H-1,2,3-triazol-4-yl)-2-ethylpyridin-3-yl)-5,5-difluoropiperidin-3-yl)acetic acid To a solution of methyl (S)-2-(1-(6-(5-(((1-(cyclopropylmethyl)-1H-1,2,3-triazol-4-yl)oxy)methyl)-1-methyl-1H-1,2,3-triazol-4-yl)-2-ethylpyridin-3-yl)-5,5-difluoropiperidin-3-yl)acetate (35 mg, 0.066 mmol) in THF (1 mL) and MeOH (0.5 mL) was added a solution of LiOH (8 mg, 0.33 mmol) in water (0.5 mL) at 0° C. and the mixture was stirred at r.t. for 1 hr. The reaction mixture was acidified with 1N aq·HCl to pH=3 and extracted with EtOAc (2×5 mL). The combined organic layers were washed with brine, dried over anhydrous $Na_2SO_4$, filtered and concentrated to dryness. The residue was purified by flash chromatography (silica gel, 0-10% MeOH in DCM) and further purified by prep-HPLC to give the title compound (10 mg, 27.9% yield) as white solid. LC/MS (ESI) m/z: 517 $(M+H)^+$. $^1H$ NMR (400 MHz, $CD_3OD$) δ 7.89 (d, J=8.4 Hz, 1H), 7.57 (d, J=8.4 Hz, 1H), 7.56 (s, 1H), 5.98 (s, 2H), 4.21 (s, 3H), 4.10 (d, J=7.6 Hz, 2H), 3.28-3.20 (m, 2H), 3.13-3.02 (m, 1H), 2.90 (q, J=7.6 Hz, 2H), 2.63-2.26 (m, 5H), 1.80-1.65 (m, 1H), 1.25 (t, J=7.6 Hz, 3H), 1.21-1.13 (m, 1H), 0.58-0.53 (m, 2H), 0.35-0.30 (m, 2H).

Example 127: ((S)-2-(1-(6-(5-(((2-(cyclopropylmethyl)-2H-1,2,3-triazol-4-yl)oxy)methyl)-1-methyl-1H-1,2,3-triazol-4-yl)-2-ethylpyridin-3-yl)-5,5-difluoropiperidin-3-yl)acetic acid Example 127

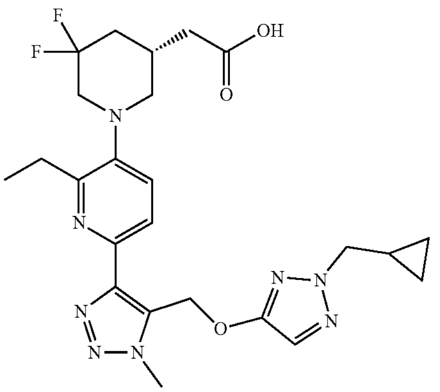

The title compound was prepared from 3-bromo-6-(5-(((2-(cyclopropylmethyl)-2H-1,2,3-triazol-4-yl)oxy)methyl)-1-methyl-1H-1,2,3-triazol-4-yl)-2-ethylpyridine using the same procedure as the synthesis of example 126. LC/MS (ESI) m/z: 517 $(M+H)^+$. $^1H$-NMR (400 MHz, $CD_3OD$) δ 7.86 (d, J=8.4 Hz, 1H), 7.56 (d, J=8.4 Hz, 1H), 7.14 (s, 1H), 5.99 (s, 2H), 4.20 (s, 3H), 4.01 (d, J=7.2 Hz, 2H), 3.26-3.20 (m, 2H), 3.13-3.02 (m, 1H), 2.90 (q, J=7.6 Hz, 2H), 2.63-2.28 (m, 5H), 1.80-1.65 (m, 1H), 1.27 (t, J=7.6 Hz, 3H), 1.24-1.14 (m, 1H), 0.55-0.50 (m, 2H), 0.34-0.29 (m, 2H).

Example 128: (S)-2-(1-(2-ethyl-6-(5-(((1-isobutyl-1H-1,2,3-triazol-4-yl)oxy)methyl)-1-methyl-1H-1,2,3-triazol-4-yl)pyridin-3-yl)-5,5-difluoropiperidin-3-yl)acetic acid Example 128

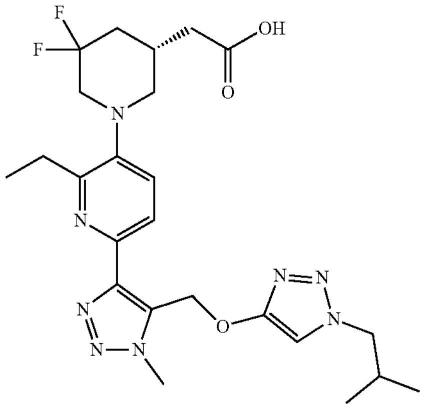

The title compound was prepared according the same sequence for the synthesis of example 126. LC/MS (ESI) m/z: 519 $(M+H)^+$. $^1H$ NMR (400 MHz, $CD_3OD$) δ 7.88 (d, J=8.2 Hz, 1H), 7.57 (d, J=8.4 Hz, 1H), 7.49 (s, 1H), 5.97 (s, 2H), 4.21 (s, 3H), 4.07 (d, J=7.2 Hz, 2H), 3.26-3.19 (m, 2H), 3.13-3.01 (m, 1H), 2.94-2.86 (m, 2H), 2.59 (t, J=10.8 Hz, 1H), 2.55-2.46 (m, 1H), 2.40-2.24 (m, 3H), 2.11-2.00 (m, 1H), 1.80-1.64 (m, 1H), 1.25 (t, J=7.6 Hz, 3H), 0.84 (d, J=6.8 Hz, 6H).

Example 129: (S)-2-(1-(2-ethyl-6-(5-(((2-isobutyl-2H-1,2,3-triazol-4-yl)oxy)methyl)-1-methyl-1H-1,2,3-triazol-4-yl)pyridin-3-yl)-5,5-difluoropiperidin-3-yl)acetic acid Example 129

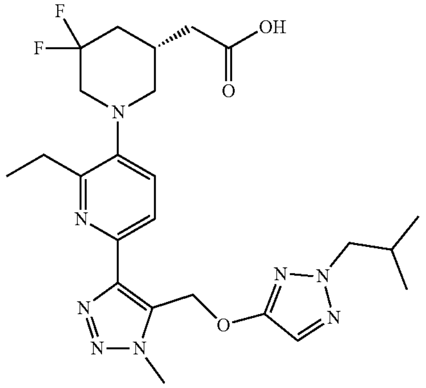

The title compound was prepared according the same sequence for the synthesis of example 126. LC/MS (ESI) m/z: 519 $(M+H)^+$. $^1H$ NMR (400 MHz, $CD_3OD$) δ 7.86 (d, J=8.4 Hz, 1H), 7.56 (d, J=8.4 Hz, 1H), 7.13 (s, 1H), 5.99 (s, 2H), 4.20 (s, 3H), 3.97 (d, J=7.2 Hz, 2H), 3.26-3.18 (m, 2H), 3.11-3.00 (m, 1H), 2.94-2.87 (m, 2H), 2.59 (t, J=10.6 Hz, 1H), 2.54-2.42 (m, 1H), 2.38-2.25 (m, 3H), 2.17-2.06 (m, 1H), 1.79-1.59 (m, 1H), 1.27 (t, J=7.6 Hz, 3H), 0.83 (d, J=6.8 Hz, 6H).

Example 130: (S)-2-(1-(6-(5-((4-(cyclopropylmethyl)-2H-1,2,3-triazol-2-yl)methyl)-1-methyl-1H-1,2,3-triazol-4-yl)-2-ethylpyridin-3-yl)-5,5-difluoropiperidin-3-yl)acetic acid

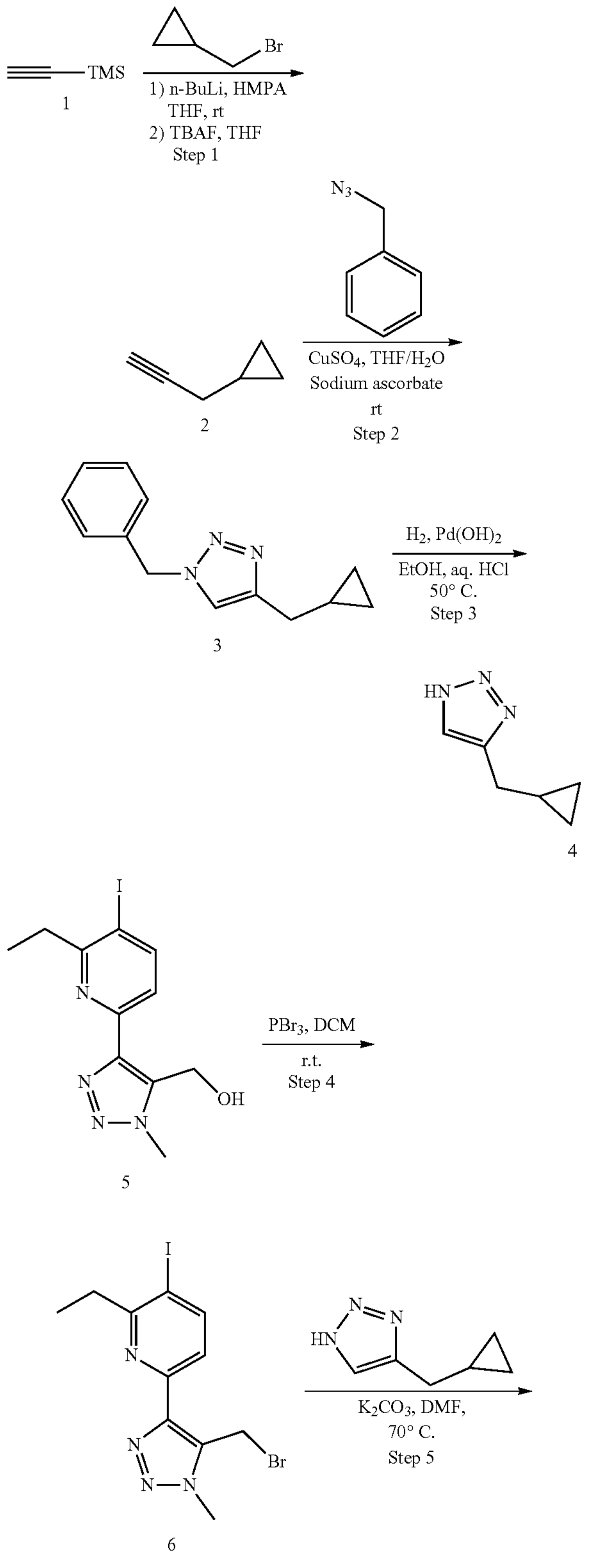

-continued

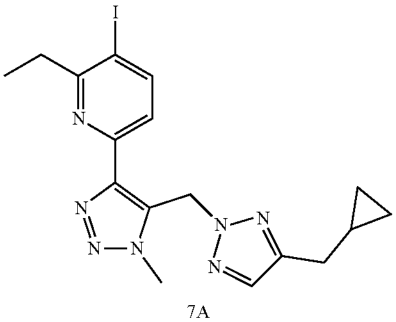

7A

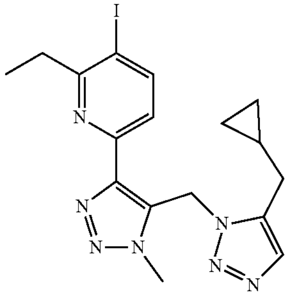

7B

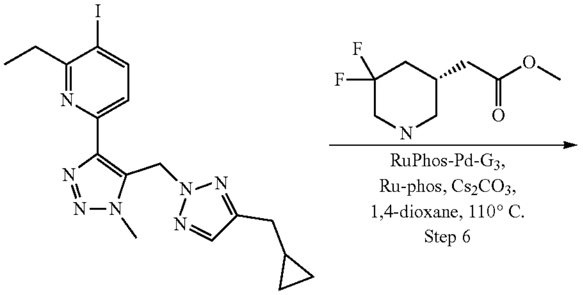

7C

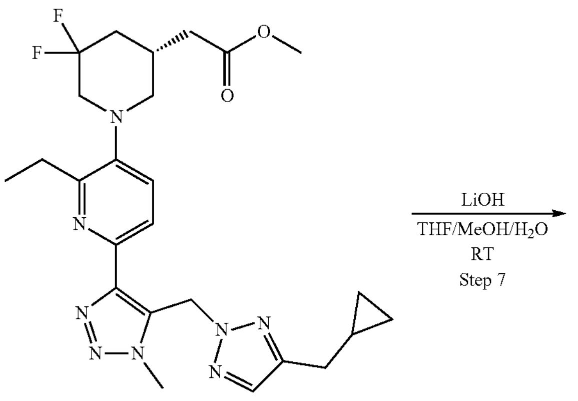

8

-continued

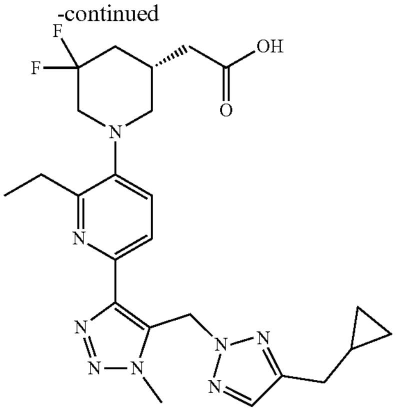

Example 130

Step 1: prop-2-yn-1-ylcyclopropane

To a solution of ethynyltrimethylsilane (3 g, 30.5 mmol) in anhydrous THF (15 mL) was added n-BuLi (16 mL, 40 mmol, 2.5 M in THF) drop-wisely at −70° C. under $N_2$ atmosphere and the mixture was stirred at 0° C. for 10 min. The mixture was re-cooled to −70° C. and HMPA (8.0 mL, 45.8 mmol) was added. Then the mixture was stirred at −70° C. for 30 min. (Bromomethyl)cyclopropane (3.0 mL, 30.54 mmol) was added to the above mixture and the resulting mixture was stirred at −70° C. to r.t. for 16 hrs. The mixture was quenched with water and extracted with EtOAc (2×20 mL). The combined organic layers were washed with brine, dried over anhydrous $Na_2SO_4$, filtered and concentrated to dryness to give (3-cyclopropylprop-1-yn-1-yl) trimethylsilane (3.2 g, 68.8% yield) as colorless oil. To a solution of (3-cyclopropylprop-1-yn-1-yl) trimethylsilane (3.2 g, 21 mmol) in THF (9 mL) was added TBAF (15 mL, 30 mmol, 2M in THF) and the mixture was stirred at room temperature for 4 hrs. The mixture was washed with saturated aq·$NH_4Cl$ solution (10 mL) once and the solution was used to next step directly.

Step 2: 1-benzyl-4-(cyclopropylmethyl)-1H-1,2,3-triazole

To the above solution was added a solution of (azidomethyl)benzene (4 g, 29.8 mmol) in THF (10 mL) followed by a solution of sodium ascorbate (1.2 g, 6 mmol) in water (10 ml) and $CuSO_4$ (0.5 g, 3 mmol) and the resulting mixture was stirred at 25° C. for 16 hrs. The mixture was diluted with EtOAc (10 mL), washed with water and brine, dried over anhydrous $Na_2SO_4$, filtered and concentrated to dryness. The residue was purified by flash chromatography (eluted with PE:EtOAc=50:1 to 1:1) to give the title compound (2 g, 31.4% yield) as yellow oil. LC/MS (ESI) m/z: 214 $(M+H)^+$.

Step 3: 4-(cyclopropylmethyl)-1H-1,2,3-triazole

To a solution of 1-benzyl-4-(cyclopropylmethyl)-1H-1,2,3-triazole (2 g, 9.38 mmol) in EtOH (20 mL) were added $Pd(OH)_2$ (300 mg, 10% wt) and aq·HCl (0.5 mL, 36% wt). After addition, the mixture was degassed under $N_2$ atmosphere for three times and stirred under a $H_2$ balloon at 50° C. for 16 hrs. The mixture was filtered and the filtrate was concentrated to dryness to give the title compound (1.52 g, 100% yield) as colorless oil, which was used to next step directly. LC/MS (ESI) m/z: 124 $(M+H)^+$.

Step 4: 6-(5-(bromomethyl)-1-methyl-1H-1,2,3-triazol-4-yl)-2-ethyl-3-iodopyridine To a solution of (4-(6-ethyl-5-iodopyridin-2-yl)-1-methyl-1H-1,2,3-triazol-5-yl) methanol (500 mg, 1.45 mmol) in DCM (5 mL) was added $PBr_3$ (984 mg, 3.63 mmol) drop-wisely at 0° C. under $N_2$ atmosphere and the mixture was stirred at 25° C. for 2 hrs. The mixture was quenched with saturated aq·$NaHCO_3$ solution and extracted with DCM (2×10 mL). The combined organic layers were washed with brine, dried over anhydrous $Na_2SO_4$, filtered and concentrated to dryness. The residue was purified by flash chromatography (eluted with PE:EtOAc=20:1 to 2:1) to give the title compound (529 mg, 89.5% yield) as white solid. LC/MS (ESI) m/z: 407/409 $(M+H)^+$.

Step 5: 6-(5-((4-(cyclopropylmethyl)-2H-1,2,3-triazol-2-yl)methyl)-1-methyl-11H-1,2,3-triazol-4-yl)-2-ethyl-3-iodopyridine (7A) & 6-(5-((5-(cyclopropylmethyl)-1H-1,2,3-triazol-1-yl)methyl)-1-methyl-1H-1,2,3-triazol-4-yl)-2-ethyl-3-iodopyridine (7B) & 6-(5-((4-(cyclopropylmethyl)-1H-1,2,3-triazol-1-yl)methyl)-1-methyl-11H-1,2,3-triazol-4-yl)-2-ethyl-3-iodopyridine (7C)

To a solution of 6-(5-(bromomethyl)-1-methyl-1H-1,2,3-triazol-4-yl)-2-ethyl-3-iodopyridine (300 mg, 0.74 mmol) and 4-(cyclopropylmethyl)-1H-1,2,3-triazole (136 mg, 1.11 mmol) in DMF (3 mL) was added $K_2CO_3$ (306 mg, 2.21 mmo 1) under $N_2$ atmosphere and the mixture was stirred at 70° C. for 16 hrs. The mixture was diluted with EtOAc (10 mL), washed with water and brine, dried over anhydrous $Na_2SO_4$, filtered and concentrated to dryness. The residue was purified by flash chromatography (eluted with PE:EtOAc=20:1 to 2:1) to give compound 7A (103 mg, yield 31.1%) and a mixture of 7B and 7C (190 mg, 57.1% yield) as white solid. The mixture of 7B&7C was isolated by prep·HPLC to give 7B (35 mg, 10.6% yield) and 7C (80 mg, 24.1% yield) as white solid. LC/MS (ESI) m/z: 450 $(M+H)^+$. The absolute configurations were confirmed by NOE. 6-(5-((4-(cyclopropylmethyl)-2H-1,2,3-triazol-2-yl)methyl)-1-methyl-1H-1,2,3-triazol-4-yl)-2-ethyl-3-iodopyridine (7A): $^1H$ NMR (400 MHz, $CDCl_3$) δ 7.76 (d, J=8.4 Hz, 1H), 7.69 (d, J=8.4 Hz, 1H), 7.26 (s, 1H), 6.19 (s, 2H), 3.88 (s, 3H), 2.83 (q, J=7.6 Hz, 2H), 2.37 (d, J=7.2 Hz, 2H), 1.16 (t, J=7.6 Hz, 3H), 0.83-0.73 (m, 1H), 0.36-0.31 (m, 2H), 0.02-0.00 (m, 2H). 6-(5-((5-(cyclopropylmethyl)-1H-1,2,3-triazol-1-yl)methyl)-1-methyl-1H-1,2,3-triazol-4-yl)-2-ethyl-3-iodopyridine (7B): $^1H$ NMR (400 MHz, $CD_3OD$) δ 8.29 (d, J=8.4 Hz, 1H), 7.70 (d, J=8.4 Hz, 1H), 7.64 (s, 1H), 6.34 (s, 2H), 4.07 (s, 3H), 3.00 (q, J=7.6 Hz, 2H), 2.54 (d, J=7.2 Hz, 2H), 1.25 (t, J=7.6 Hz, 3H), 0.90-0.82 (m, 1H), 0.54-0.48 (m, 2H), 0.07-0.02 (m, 2H). 6-(5-((4-(cyclopropylmethyl)-1H-1,2,3-triazol-1-yl)methyl)-1-methyl-1H-1,2,3-triazol-4-yl)-2-ethyl-3-iodopyridine (7C): $^1H$ NMR (400 MHz, $CD_3OD$) δ 8.29 (d, J=8.4 Hz, 1H), 7.71 (d, J=8.4 Hz, 1H), 7.64 (s, 1H), 6.34 (s, 2H), 4.07 (s, 3H), 3.06 (q, J=7.6 Hz, 2H), 2.56 (d, J=7.2 Hz, 2H), 1.27 (t, J=7.6 Hz, 3H), 0.90-0.82 (m, 1H), 0.54-0.48 (m, 2H), 0.07-0.02 (m, 2H).

Step 6: methyl (S)-2-(1-(6-(5-((4-(cyclopropylmethyl)-2H-1,2,3-triazol-2-yl)methyl)-1-methyl-1H-1,2,3-triazol-4-yl)-2-ethylpyridin-3-yl)-5,5-difluoropiperidin-3-yl)acetate To a solution of 6-(5-((4-(cyclopropylmethyl)-2H-1,2,3-triazol-2-yl)methyl)-1-methyl-1H-1,2,3-triazol-4-yl)-2-ethyl-3-iodopyridine (103 mg, 0.23 mmol) and methyl (S)-2-(5,5-difluoropiperidin-3-yl)acetate (44 mg, 0.23 mmol) in 1,4-dioxane (3 mL) were added $Cs_2CO_3$ (149.4 mg, 0.46 mmol), RuPhos-Pd-G3 (11.2 mg, 0.013 mmol) and RuPhos (21.4 mg, 0.046 mmol) under $N_2$ atmosphere, after addition, the mixture was degassed under $N_2$ atmosphere for three times and stirred at 110° C. for 16 hrs. The mixture was diluted EtOAc (10 mL), washed with water and brine, dried over anhydrous $Na_2SO_4$, filtered and concentrated to dryness to give title compound (120 mg, yield 100%) as yellow solid, which was used in next step directly. LC/MS (ESI) m/z: 515 $(M+H)^+$.

Step 8: (S)-2-(1-(6-(5-((4-(cyclopropylmethyl)-2H-1,2,3-triazol-2-yl)methyl)-1-methyl-1H-1,2,3-triazol-4-yl)-2-ethylpyridin-3-yl)-5,5-difluoropiperidin-3-yl) acetic acid To a solution of methyl (S)-2-(1-(6-(5-((4-(cyclopropylmethyl)-2H-1,2,3-triazol-2-yl)methyl)-1-methyl-1H-1,2,3-triazol-4-yl)-2-ethylpyridin-3-yl)-5,5-difluoropiperidin-3-yl)acetate (120 mg, 0.23 mmol) in THE (2 mL), MeOH (0.5 mL) and water (0.5 mL) was added lithium hydroxide monohydrate (98 mg, 2.33 mmol) and the reaction mixture was stirred at 25° C. for 2 hrs. The mixture was concentrated to dryness and the residue was dissolved in water. The mixture was washed with EtOAc twice and the aqueous layer was acidified with 1M aq·HCl to pH=4 and extracted with EtOAc twice. The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (19.2 mg, 13.2% yield) as white solid. LC/MS (ESI) m/z: 501 $(M+H)^+$. $^1H$ NMR (400 MHz, $CD_3OD$) δ 7.72 (d, J=8.2 Hz, 1H), 7.39 (d, J=8.4 Hz, 1H), 7.34 (s, 1H), 6.23 (s, 2H), 3.96 (s, 3H), 3.13-3.03 (m, 2H), 2.91 (m, 1H), 2.77 (q, J=7.4 Hz, 2H), 2.47-2.41 (m, 1H), 2.37 (d, J=7.0 Hz, 2H), 2.35-2.29 (m, 1H), 2.28-2.22 (m, 2H), 2.19-2.09 (m, 1H), 1.66-1.48 (m, 1H), 1.15 (t, J=7.4 Hz, 3H), 0.85-0.76 (m, 1H), 0.35-0.29 (m, 2H), 0.02-0.00 (m, 2H).

The examples in the following table were prepared by using method analogous to the examples as indicated in the method column in the table.

| Ex# | Structure & name | Analytical data | Method |
| --- | --- | --- | --- |
| 131 | 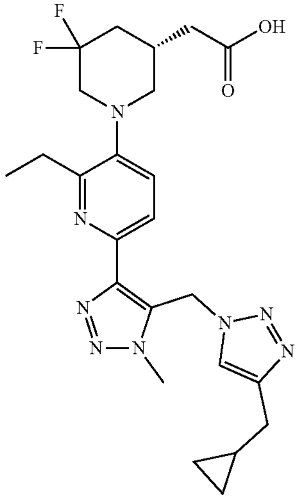 [SMILES: CCc1nc(-c2nnn(C)c2Cn2cc(CC3CC3)nn2)ccc1N1C[C@@H](CC(=O)O)CC(F)(F)C1] (S)-2-(1-(6-(5-((4-(cyclopropylmethyl)-1H-1,2,3-triazol-1-yl)methyl)-1-methyl-1H-1,2,3-triazol-4-yl)-2-ethylpyridin-3-yl)-5,5-difluoropiperidin-3-yl)acetic acid | LC/MS (ESI) m/z: 501 $(M + H)^+$. $^1H$ NMR (400 MHz, $CD_3OD$) δ 7.80 (d, J = 8.2 Hz, 1H), 7.75 (s, 1H), 7.45 (d, J = 8.4 Hz, 1H), 6.17 (s, 2H), 4.03 (s, 3H), 3.28-3.10 (m, 2H), 3.01-2.88 (m, 1H), 2.84 (q, J = 7.6 Hz, 2H), 2.51-2.44 (m, 1H), 2.41 (d, J = 7.0 Hz, 2H), 2.39-2.31 (m, 1H), 2.29-2.23 (m, 2H), 2.19-2.11 (m, 1H), 1.67-1.51 (m, 1H), 1.16 (t, J = 7.6 Hz, 3H), 0.85-0.75 (m, 1H), 0.35-0.29 (m, 2H), 0.02-0.00 (m, 2H). | Example 130 |
| 132 | 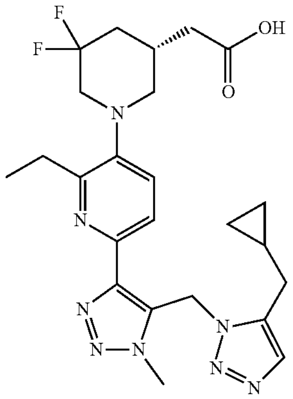 [SMILES: CCc1nc(-c2nnn(C)c2Cn2nncc2CC2CC2)ccc1N1C[C@@H](CC(=O)O)CC(F)(F)C1] (S)-2-(1-(6-(5-((5-(cyclopropylmethyl)-1H-1,2,3-triazol-1-yl)methyl)-1-methyl-1H-1,2,3-triazol-4-yl)-2-ethylpyridin-3-yl)-5,5-difluoropiperidin-3-yl)acetic acid | LC/MS (ESI) m/z: 501 $(M + H)^+$. $^1H$ NMR (400 MHz, $CD_3OD$) δ 7.92 (d, J = 8.4 Hz, 1H), 7.62 (s, 1H), 7.61 (d, J = 8.2 Hz, 1H), 6.39 (d, J = 4.4 Hz, 2H), 4.08 (s, 3H), 3.28-3.21 (m, 2H), 3.16-3.05 (m, 1H), 2.95 (q, J = 7.6 Hz, 2H), 2.65-2.57 (m, 1H), 2.56-2.51 (m, 1H), 2.49 (d, J = 6.8 Hz, 2H), 2.44-2.37 (m, 2H), 2.36-2.27 (m, 1H), 1.81-1.66 (m, 1H), 1.28 (t, J = 7.6 Hz, 3H), 0.88-0.79 (m, 1H), 0.52-0.44 (m, 2H), 0.02-0.00 (m, 2H). | Example 130 |

-continued

| Ex# | Structure & name | Analytical data | Method |
| --- | --- | --- | --- |
| 133 | 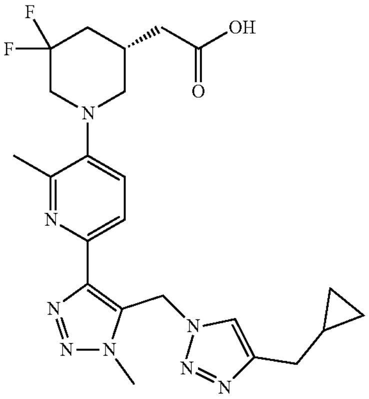 [SMILES: Cc1nc(-c2nnn(C)c2Cn2cc(CC3CC3)nn2)ccc1N1C[C@@H](CC(=O)O)CC(F)(F)C1] (S)-2-(1-(6-(5-((4-(cyclopropylmethyl)-1H-1,2,3-triazol-1-yl)methyl)-1-methyl-1H-1,2,3-triazol-4-yl)-2-methylpyridin-3-yl)-5,5-difluoropiperidin-3-yl)acetic acid | LC/MS (ESI) m/z: 487 (M + H)$^+$. $^1$H NMR (400 MHz, $CD_3OD$) δ 8.04 (s, 1H), 7.92 (d, J = 8.4 Hz, 1H), 7.56 (d, J = 8.4 Hz, 1H), 6.24 (s, 2H), 4.22 (s, 3H), 3.28-3.23 (m, 2H), 3.13-3.03 (m, 1H), 2.63 (s, 3H), 2.62-2.58 (m, 1H), 2.56 (d, J = 6.8 Hz, 2H), 2.54-2.49 (m, 1H), 2.43-2.39 (m, 2H), 2.37-2.27 (m, 1H), 1.82-1.64 (m, 1H), 1.00-0.91 (m, 1H), 0.51-0.46 (m, 2H), 0.18-0.13 (m, 2H). | Example 130 |
| 134 | 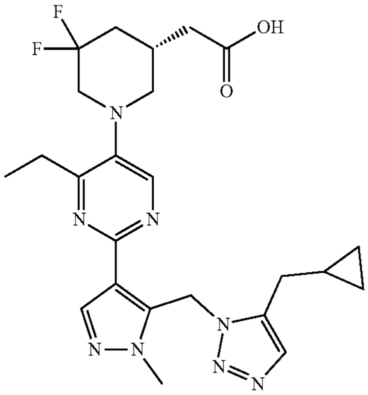 [SMILES: CCc1nc(-c2cnn(C)c2Cn2nncc2CC2CC2)ncc1N1C[C@@H](CC(=O)O)CC(F)(F)C1] (S)-2-(1-(2-(5-((5-(cyclopropylmethyl)-1H-1,2,3-triazol-1-yl)methyl)-1-methyl-1H-pyrazol-4-yl)-4-ethylpyrimidin-5-yl)-5,5-difluoropiperidin-3-yl)acetic acid | LC/MS (ESI) m/z: 501 (M + H)$^+$. $^1$H NMR (400 MHz, $CD_3OD$) δ 8.41 (s, 1H), 8.12 (s, 1H), 7.62 (s, 1H), 6.32 (s, 2H), 3.88 (s, 3H), 3.28-3.24 (m, 2H), 3.22-3.12 (m, 1H), 2.90 (q, J = 7.6 Hz, 2H), 2.73-2.67 (m, 1H), 2.58 (d, J = 6.8 Hz, 2H), 2.56-2.41 (m, 1H), 2.40-2.38 (m, 2H), 2.36-2.26 (m, 1H), 1.82-1.66 (m, 1H), 1.30 (t, J = 7.6 Hz, 3H), 0.94-0.85 (m, 1H), 0.54-0.49 (m, 2H), 0.09-0.05 (m, 2H). | Example 130 |

-continued

| Ex# | Structure & name | Analytical data | Method |
|---|---|---|---|
| 135 | 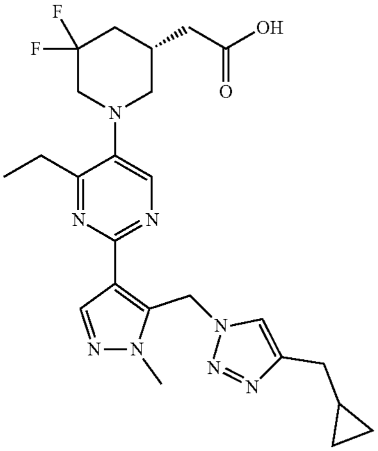 [SMILES: CCc1nc(-c2cnn(C)c2Cn2cc(CC3CC3)nn2)ncc1N1C[C@@H](CC(=O)O)CC(F)(F)C1] (S)-2-(1-(2-(5-((4-(cyclopropylmethyl)-1H-1,2,3-triazol-1-yl)methyl)-1-methyl-1H-pyrazol-4-yl)-4-ethylpyrimidin-5-yl)-5,5-difluoropiperidin-3-yl)acetic acid | LC/MS (ESI) m/z: 501 $(M + H)^+$. $^1$H NMR (400 MHz, $CD_3OD$) δ 8.46 (s, 1H), 8.13 (s, 1H), 7.84 (s, 1H), 6.28 (s, 2H), 3.98 (s, 3H), 3.28-3.24 (m, 2H), 3.23-3.12 (m, 1H), 2.92 (q, J = 7.6 Hz, 2H), 2.74-2.68 (m, 1H), 2.55 (d, J = 6.8 Hz, 2H), 2.54-2.45 (m, 1H), 2.42-2.38 (m, 2H), 2.36-2.26 (m, 1H), 1.82-1.66 (m, 1H), 1.31 (t, J = 7.6 Hz, 3H), 0.99-0.86 (m, 1H), 0.49-0.43 (m, 2H), 0.16-0.12 (m, 2H). | Example 130 |
| 136 | 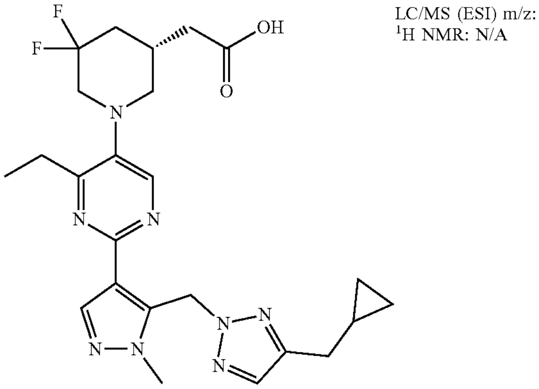 (S)-2-(1-(2-(5-((4-(cyclopropylmethyl)-2H-1,2,3-triazol-2-yl)methyl)-1-methyl-1H-pyrazol-4-yl)-4-ethylpyrimidin-5-yl)-5,5-difluoropiperidin-3-yl)acetic acid | LC/MS (ESI) m/z: 501 $(M + H)^+$. $^1$H NMR: N/A | Example 130 |

Example 137: 2-[(3S)-1-[6-(5-{[5-(cyclopropylmethyl)-1H-1,2,3,4-tetrazol-1-yl]methyl}-1-methyl-1H-1,2,3-triazol-4-yl)-2-ethylpyridin-3-yl]-5,5-difluoropiperidin-3-yl]acetic acid & example 138 2-[(3S)-1-[6-(5-{[5-(cyclopropylmethyl)-1H-1,2,3,4-tetrazol-1-yl]methyl}-1-methyl-1H-1,2,3-triazol-4-yl)-2-ethylpyridin-3-yl]-5,5-difluoropiperidin-3-yl] acetic acid

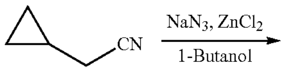

1

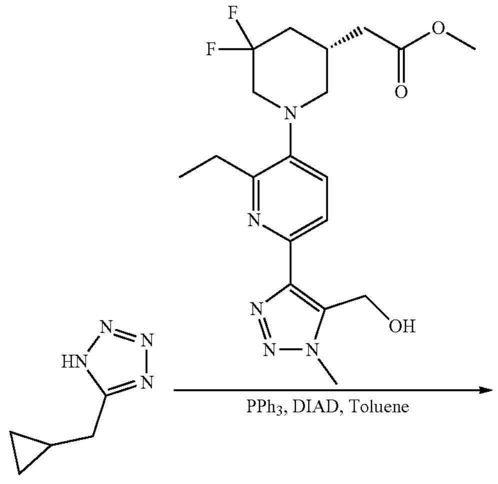

2

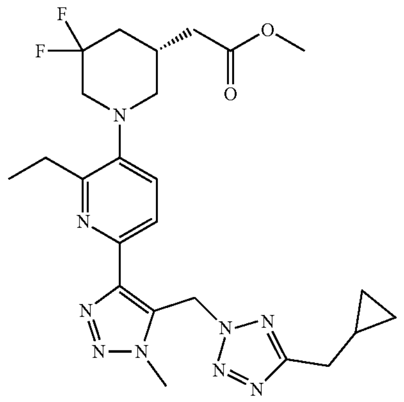

3A

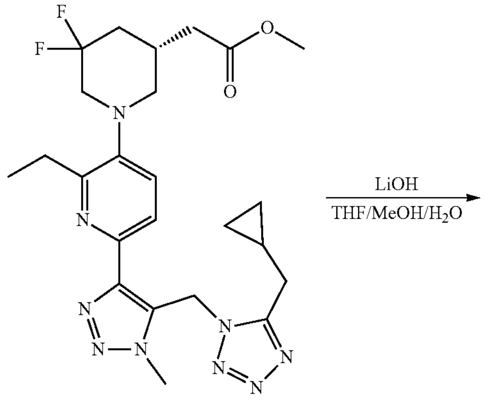

3B

-continued

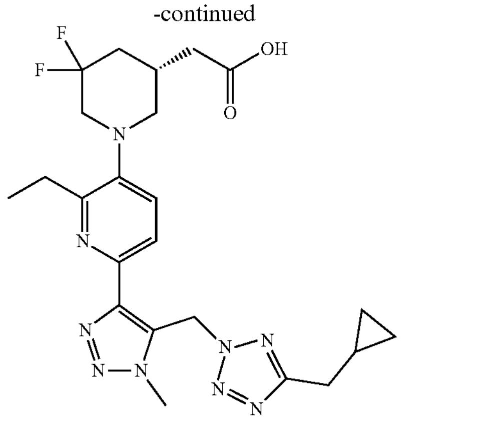

Example 137

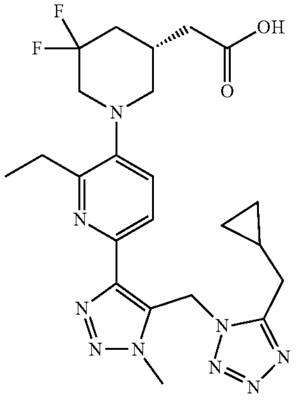

Example 138

Step 1: 5-(cyclopropylmethyl)-1H-1,2,3,4-tetrazole (2)

To a solution of 2-cyclopropylacetonitrile (1 g, 12.33 mmol) in 1-Butanol (20 mL) was added $NaN_3$ (0.96 g, 14.80 mmol) and $ZnCl_2$ (1.7 g, 12.33 mmol). The reaction mixture was stirred under $N_2$ atmosphere at 110° C. for 16 hrs. After cooling to room temperature, 1-Butanol was removed under reduced pressure. To the mixture was added 0.5M aq·NaOH (2.0 eq) and the resulting suspension was filtered. The filtrate was acidified with 1M aq·HCl to pH=4 and extracted with EtOAc (2×10 mL). The combined organic layers were dried over anhydrous $Na_2SO_4$, filtered and concentrated to dryness to give the title compound (800 mg, 52.3% yield) as white solid. LC/MS (ESI) m/z: 125 $(M+H)^+$.

Step 2: methyl 2-[(3S)-1-[6-(5-{[5-(cyclopropylmethyl)-1H-1,2,3,4-tetrazol-1-yl]methyl}-1-methyl-1H-1,2,3-triazol-4-yl)-2-ethylpyridin-3-yl]-5,5-difluoropiperidin-3-yl]acetate (3A) and methyl (S)-2-(1-(6-(5-((5-(cyclopropylmethyl)-1H-tetrazol-1-yl)methyl)-1-methyl-1H-1,2,3-triazol-4-yl)-2-ethylpyridin-3-yl)-5,5-difluoropiperidin-3-yl)acetate (3B)

To a solution of methyl (S)-2-(1-(2-ethyl-6-(5-(hydroxymethyl)-1-methyl-1H-1,2,3-triazol-4-yl)pyridin-3-yl)-5,5-difluoropiperidin-3-yl)acetate (80 mg, 0.20 mmol) in toluene (10 mL) was added 5-(cyclopropylmethyl)-1H-1,2,3,4-tetrazole (49 mg, 0.39 mmol) followed by $PPh_3$ (102 mg, 0.39 mmol) and DIAD (79 mg, 0.39 mmol) under $N_2$ atmosphere at 0° C. and the reaction mixture was stirred at 60° C. for 16 hrs. The mixture was concentrated to dryness and the residue was purified by prep-TLC (PE:EtOAc=1:1) to give compound 3A (20 mg, yield 19.9%) and compound 3B (40 mg, yield 39.7%) as white solid. LC/MS (ESI) m/z: 516 $(M+H)^+$. The configuration of two isolated products was confirmed in the next reaction.

Step 3: 2-[(3S)-1-[6-(5-{[5-(cyclopropylmethyl)-2H-1,2,3,4-tetrazol-2-yl]methyl}-1-methyl-1H-1,2,3-triazol-4-yl)-2-ethylpyridin-3-yl]-5,5-difluoropiperidin-3-yl]acetic acid To a solution of methyl 2-[(3S)-1-[6-(5-{[5-(cyclopropylmethyl)-1H-1,2,3,4-tetrazol-1-yl]methyl}-1-methyl-1H-1,2,3-triazol-4-yl)-2-ethylpyridin-3-yl]-5,5-difluoropiperidin-3-yl]acetate (20 mg, 0.04 mmol) in THE (4 mL), MeOH (1 mL) and water (1 mL) was added LiOH (16 mg, 0.39 mmol) and the reaction mixture was stirred at 25° C. for 2 hrs. The mixture was concentrated to dryness and the residue was dissolved in water (10 mL). The mixture was washed with EtOAc (2×3 mL) and the aqueous layer was acidified with 1M aq·HCl to pH=4 and extracted with DCM (2×5 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (5 mg, 25.7% yield) as white solid. LC/MS (ESI) m/z: 502 $(M+H)^+$. $^1H$ NMR (400 MHz, $CD_3OD$) δ 7.90 (d, J=8.4 Hz, 1H), 7.55 (d, J=8.4 Hz, 1H), 6.65 (s, 2H), 4.24 (s, 3H), 3.28-3.19 (m, 2H), 3.13-3.01 (m, 1H), 2.91 (q, J=7.6 Hz, 2H), 2.73 (d, J=7.0 Hz, 2H), 2.64-2.55 (m, 1H), 2.54-2.45 (m, 1H), 2.44-2.36 (m, 2H), 2.31-2.26 (m, 1H), 1.80-1.63 (m, 1H), 1.29 (t, J=7.6 Hz, 3H), 1.12-1.00 (m, 1H), 0.56-0.45 (m, 2H), 0.22-0.17 (m, 2H).

Example 138: 2-[(3S)-1-[6-(5-{[5-(cyclopropylmethyl)-1H-1,2,3,4-tetrazol-1-yl]methyl}-1-methyl-1H-1,2,3-triazol-4-yl)-2-ethylpyridin-3-yl]-5,5-difluoropiperidin-3-yl]acetic acid The title compound was prepared using the same method for the synthesis of example 137. LC/MS (ESI) m/z: 502 $(M+H)^+$. $^1H$ NMR (400 MHz, $CD_3OD$) δ 7.94 (d, J=8.3 Hz, 1H), 7.62 (d, J=8.4 Hz, 1H), 6.43 (d, J=8.8 Hz, 2H), 4.09 (s, 3H), 3.22-3.13 (m, 2H), 3.06-2.99 (m, 1H), 3.90-2.88 (m, 2H), 2.71 (d, J=7.0 Hz, 2H), 2.58-2.50 (m, 1H), 2.48-2.40 (m, 1H), 2.34-2.30 (m, 2H), 2.28-2.17 (m, 1H), 1.72-1.57 (m, 1H), 1.16 (t, J=7.5 Hz, 3H), 0.91-0.82 (m, 1H), 0.43-0.38 (m, 2H), 0.02-0.00 (m, 2H).

Example 139: (S)-2-(5,5-difluoro-1-(2-methyl-6-(1-methyl-5-(((methyl(propyl)carbamoyl)oxy)methyl)-1H-1,2,3-triazol-4-yl)pyridin-3-yl)piperidin-3-yl) acetic acid

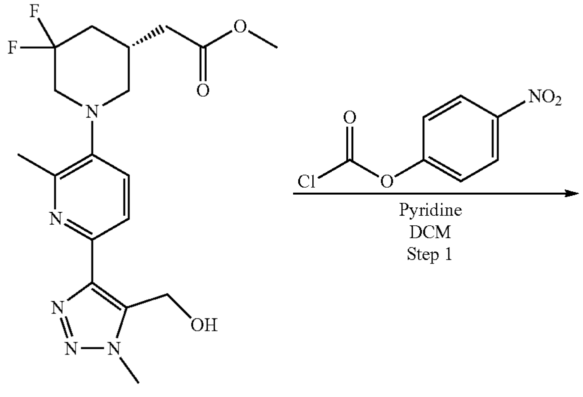

1

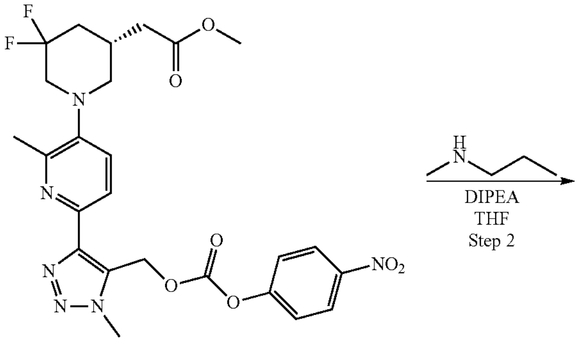

2

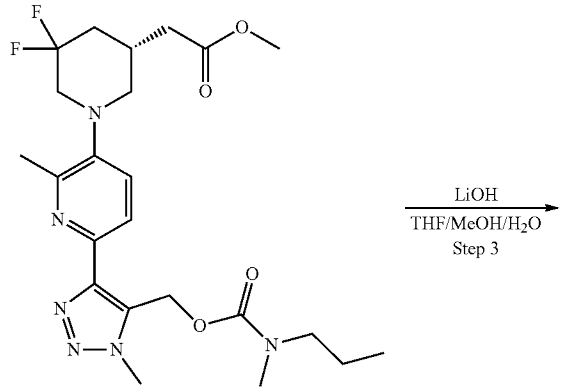

3

-continued

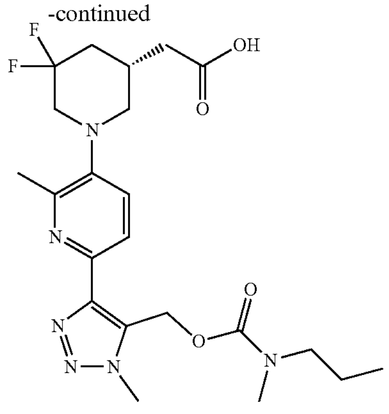

Example 139

Step 1: Methyl (S)-2-(5,5-difluoro-1-(2-methyl-6-(1-methyl-5-((((4-nitrophenoxy)carbonyl)oxy)methyl)-1H-1,2,3-triazol-4-yl)pyridin-3-yl)piperidin-3-yl)acetate To a mixture of methyl (S)-2-(5,5-difluoro-1-(6-(5-(hydroxymethyl)-1-methyl-1H-1,2,3-triazol-4-yl)-2-methylpyridin-3-yl)piperidin-3-yl)acetate (350 mg, 0.89 mmol) and 4-nitrophenyl chloroformate (535 mg, 2.67 mmol) in DCM (15 mL) was added pyridine (348 mg, 4.41 mmol) and the reaction was stirred at r.t. for 1 hr. The mixture was diluted with DCM (20 mL) and was washed with saturated aq·$NaHCO_3$ solution and brine, dried over $Na_2SO_4$, filtered and concentrated to dryness. The residue was purified via silica gel chromatography (eluted with PE:EtOAc=5:1 to 3:1) to give the title compound (460 mg, 92.8% yield) as yellow solid. LC/MS (ESI) (m/z): 561 $(M+H)^+$.

Step 2: Methyl (S)-2-(5,5-difluoro-1-(2-methyl-6-(1-methyl-5-(((methyl(propyl)carbamoyl)oxy)methyl)-1H-1,2,3-triazol-4-yl)pyridin-3-yl)piperidin-3-yl)acetate To a solution of methyl (S)-2-(5,5-difluoro-1-(2-methyl-6-(1-methyl-5-((((4-nitrophenoxy)carbonyl)oxy)methyl)-1H-1,2,3-triazol-4-yl)pyridin-3-yl)piperidin-3-yl)acetate (120 mg, 0.21 mmol) in THF (10 mL) was added DIPEA (135 mg, 1.04 mmol) followed by methyl(propyl)amine (76 mg, 1.04 mmol) at 0° C. and the reaction was stirred at r.t. for 2 hrs. The mixture was diluted with EtOAc (10 mL) and was washed with 1M aq·NaOH solution and brine, dried over $Na_2SO_4$, filtered and concentrated to dryness. The residue was purified by perp-TLC (50% EtOAc in PE) to give the title compound (55 mg, 52.0% yield) as yellow solid. LC/MS (ESI) (m/z): 495 $(M+H)^+$.

Step 3: (S)-2-(5,5-difluoro-1-(2-methyl-6-(1-methyl-5-(((methyl(propyl)carbamoyl)oxy)methyl)-1H-1,2,3-triazol-4-yl)pyridin-3-yl)piperidin-3-yl)acetic acid To a solution of methyl (S)-2-(5,5-difluoro-(2-methyl-6-(1-methyl-5-(((methyl(propyl)carbamoyl)oxy)methyl)-1H-1,2,3-triazol-4-yl)pyridin-3-yl)piperidin-3-yl)acetate (55 mg, 0.11 mmol) in THE (4 mL)/S20 (4 mL)/MeOH (4 mL) was added $LiOH·H_2O$ (47 mg, 1.11 mmol) and the reaction mixture was stirred at r.t. for 2 hrs. The reaction mixture was concentrated to dryness and the residue was dissolved in $H_2O$ (5 mL). The mixture was washed with EtOAc (2×5 mL), acidified with 1N aq·HCl to pH~4 and extracted with DCM (2×3 mL). The combined organic layers were washed with brine, dried over $Na_2SO_4$, filtered and concentrated to dryness. The residue was purified by prep-HPLC to give the title compound (28.7 mg, 53.8% yield) as white solid. LC/MS (ESI) (m/z): 481 $(M+H)^+$. $^1$H NMR (400 MH z, $CD_3OD$) δ 7.82 (d, J=8.3 Hz, 1H), 7.53 (d, J=8.3 Hz, 1H), 5.70 (d, J=5.1 Hz, 2H), 4.17 (s, 3H), 3.30-3.20 (m, 3H), 3.15-3.00 (m, 2H), 2.84 (d, J=20.0 Hz, 3H), 2.64-2.57 (m, 1H), 2.56 (s, 3H), 2.54-2.46 (m, 1H), 2.44-2.38 (m, 2H), 2.36-2.25 (m, 1H), 1.82-1.64 (m, 1H), 1.59-1.32 (m, 2H), 0.89-0.67 (in, 3H).

The Examples in the following table were synthesized according to the procedures described as the synthesis of example from appropriate starting materials.

| Ex# | Structure & name | Analytical data | Method |
|---|---|---|---|
| 140 | 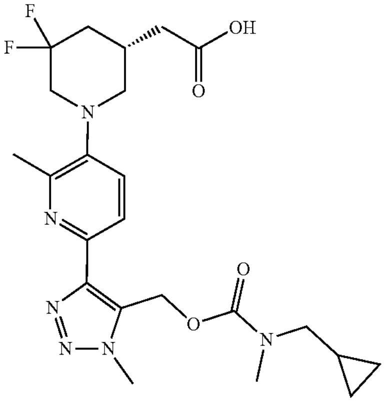 [SMILES: Cc1nc(-c2nnn(C)c2COC(=O)N(C)CC2CC2)ccc1N1C[C@@H](CC(=O)O)CC(F)(F)C1] (S)-2-(1-(6-(5-((((cyclopropylmethyl)(methyl)carbamoyl)oxy)methyl)-1-methyl-1H-1,2,3-triazol-4-yl)-2-methylpyridin-3-yl)-5,5-difluoropiperidin-3-yl)acetic acid | LC/MS (ESI ) (m/z): 493, $(M + H)^+$. $^1$H NMR (400 MHz, CD3OD) 8 7.82 (d, J = 8.0 Hz, 1H), 7.53 (d, J = 8.0 Hz, 1H), 5.70 (s, 2H), 3.29-3.23 (m, 2H), 3.17-3.01 (m, 3H), 2.91 (d, J = 16.2 Hz, 3H), 2.65-2.48 (m, 2H), 2.56 (s, 3H), 2.45-2.37 (m, 2H), 2.35-2.25 (m, 1H), 1.84-1.65 (m, 1H), 1.05-0.73 (m, 1H), 0.40-0.12 (m, 4H). | Example 139 |

-continued

| Ex# | Structure & name | Analytical data | Method |
|---|---|---|---|
| 141 | 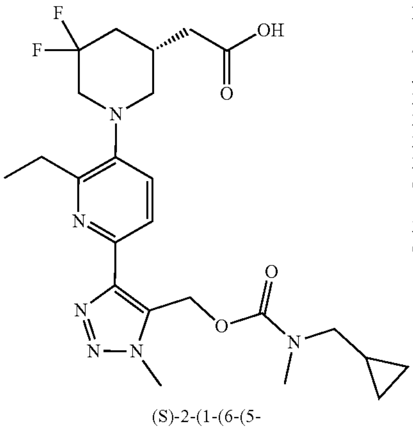 (S)-2-(1-(6-(5-((((cyclopropylmethyl)(methyl) carbamoyl)oxy)methyl)-1-methyl-1H-1,2,3-triazol-4-yl)-2-ethylpyridin-3-yl)-5,5-difluoropiperidin-3-yl)acetic acid | LC/MS (ESI) (m/z): 506, $(M + H)^+$. $^1H$ NMR (400 MHz, $CD_3OD$) δ 7.85 (d, J = 8.3 Hz, 1H), 7.55 (d, J = 8.3 Hz, 1H), 5.76 (d, J = 9.0 Hz, 2H), 4.19 (s, 3H), 3.27-3.18 (m, 2H), 3.16-3.00 (m, 3H), 2.97 - 2.87 (m, 5H), 2.63-2.55 (m, 1H), 2.55-2.45 (m, 1H), 2.43-2.36 (m, 2H), 2.35-2.25 (m, 1H), 1.80-1.64 (m, 1H), 1.34 (t, J = 7.4 Hz, 3H), 1.04-0.72 (m, 1H), 0.55-0.01 (m, 1H). | Example 139 |
| 142 | 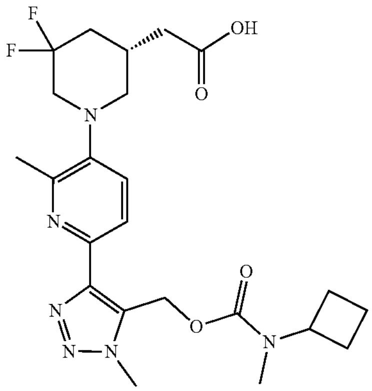 [SMILES: Cc1nc(-c2nnn(C)c2COC(=O)N(C)C2CCC2)ccc1N1C[C@@H](CC(=O)O)CC(F)(F)C1] (S)-2-(1-(6-(5-(((cyclobutyl(methyl) carbamoyl)oxy)methyl)-1-methyl-1H-1,2,3-triazol-4-yl)-2-methylpyridin-3-yl)-5,5-difluoropiperidin-3-yl)acetic acid | LC/MS (ESI) m/z: 493 $(M + H)^+$. $^1H$ NMR (400 MHz, $CD_3OD$) δ 7.82 (d, J = 8.4 Hz, 1H), 7.53 (d, J = 8.4 Hz, 1H), 5.69 (s, 2H), 4.17 (s, 3H), 3.29-3.24 (m, 2H), 3. 15- 3.00 (m, 1H), 2.81 (s, 3H), 2.64-2.46 (m, 2H), 2.55 (s, 3H), 2.44-2.28 (m, 3H), 2.18-1.87 (m, 4H), 1.80-1.50 (m, 3H), 1.17 (t, J = 7.1 Hz, 1H). | Example 139 |
| 143 | 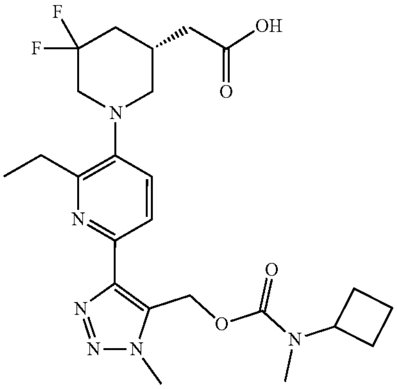 [SMILES: CCc1nc(-c2nnn(C)c2COC(=O)N(C)C2CCC2)ccc1N1C[C@@H](CC(=O)O)CC(F)(F)C1] (S)-2-(1-(6-(5-(((cyclobutyl (methyl)carbamoyl)oxy) methyl)-1-methyl-1H-1,2,3-triazol-4-yl)-2-ethylpyridin-3-yl)-5,5-difluoropiperidin-3-yl)acetic acid | LC/MS (ESI) m/z: 507 $(M + H)^+$. $^1H$ NMR (400 MHz, $CD_3OD$) δ 7.85 (d, J = 8.3 Hz, 1H), 7.56 (d, J = 8.3 Hz, 1H), 5.75 (s, 2H), 4.17 (s, 3H), 3.27-3.19 (m, 2H), 3.13-3.04 (m, 1H), 2.93 (q, J = 7.4 Hz, 2H), 2.81 (s, 3H), 2.63-2.57 (m, 1H), 2.51 (s, 1H), 2.43-2.38 (m, 2H), 2.36-2.24 (m, 1H), 2.23-1.77 (m, 4H), 1.69 (d, J = 29.6 Hz, 3H), 1.33 (t, J = 7.5 Hz, 3H). | Example 139 |

-continued

| Ex# | Structure & name | Analytical data | Method |
| --- | --- | --- | --- |
| 144 | 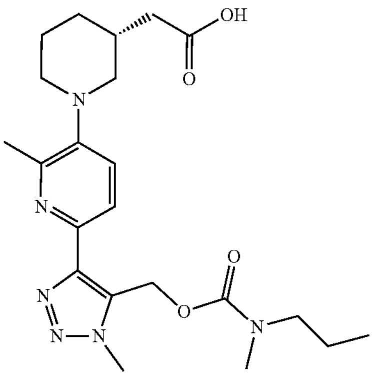 [SMILES: CCCN(C)C(=O)OCc1c(-c2ccc(N3CCC[C@H](CC(=O)O)C3)c(C)n2)nnn1C] (R)-2-(1-(2-methyl-6-(1-methyl-5-(((methyl(propyl)carbamoyl)oxy)methyl)-1H-1,2,3-triazol-4-yl)pyridin-3-yl)piperidin-3-yl)acetic acid | LC/MS (ESI) m/z: 445 $(M + H)^+$. $^1H$ NMR (400 MHz, $CD_3OD$) δ 7.77 (d, J = 8.3 Hz, 1H), 7.47 (d, J = 8.3 Hz, 1H), 5.69 (s, 2H), 4.17 (s, 3H), 3.25-3.19 (m, 2H), 3.13-3.06 (m, 2H), 2.88-2.78 (m, 3H), 2.74-2.67 (m, 1H), 2.54 (s, 3H), 2.47-2.39 (m, 1H), 2.32-2.19 (m, 3H), 1.94-1.74 (m, 3H), 1.60-1.48 (m, 1H), 1.41-1.32 (m, 1H), 1.27-1.16 (m, 1H), 0.90-0.66 (m, 3H). | Example 139 |
| 145 | 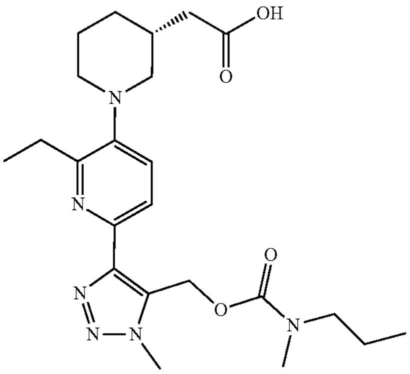 [SMILES: CCCN(C)C(=O)OCc1c(-c2ccc(N3CCC[C@H](CC(=O)O)C3)c(CC)n2)nnn1C] (R)-2-(1-(2-ethyl-6-(1-methyl-5-(((methyl(propyl)carbamoyl)oxy)methyl)-1H-1,2,3-triazol-4-yl)pyridin-3-yl)piperidin-3-yl)acetic acid | LC/MS (ESI) m/z: 459 $(M + H)^+$. $^1H$ NMR (400 MHz, $CD_3OD$) δ 7.80 (d, J = 8.2 Hz, 1H), 7.49 (d, J = 8.2 Hz, 1H), 5.75 (s, 2H), 4.18 (s, 3H), 3.24-3.00 (m, 4H), 2.90 (q, J = 7.5 Hz, 2H), 2.83 (d, J = 17.4 Hz, 3H), 2.76-2.66 (m, 1H), 2.48-2.39 (m, 1H), 2.36-2.18 (m, 3H), 1.94-1.74 (m, 3H), 1.61-1.50 (m, 1H), 1.38-1.31 (m, 1H), 1.34 (t, J = 7.1 Hz, 3H) 1.27-1.17 (m, 1H), 0.77 (dt, J = 77.5, 7.1 Hz, 3H). | Example 139 |
| 146 | 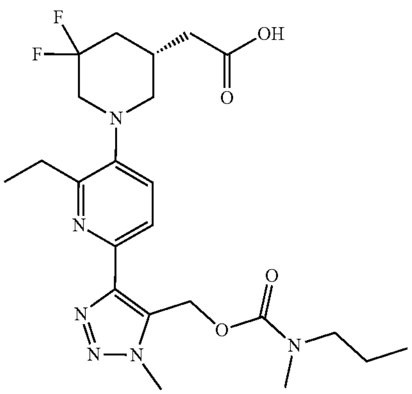 (S)-2-(1-(2-ethyl-6-(1-methyl-5-(((methyl(propyl)carbamoyl)oxy)methyl)-1H-1,2,3-triazol-4-yl)pyridin-3-yl)-5,5-difluoropiperidin-3-yl)acetic acid | LC/MS (ESI) m/z: 459 $(M + H)^+$. $^1H$ NMR (400 MHz, $CD_3OD$) δ 7.85 (d, J = 7.8 Hz, 1H), 7.56 (d, J = 7.8 Hz, 1H), 5.76 (s, 2H), 4.18 (s, 3H), 3.26-3.18 (m, 3H), 3.14-3.06 (m, 2H), 2.94 (q, J = 7.2 Hz, 2H), 2.83 (d, J = 17.3 Hz, 3H), 2.65 - 2.46 (m, 2H), 2.39-2.28 (m, 3H), 1.78-1.64 (m, 1H), 1.60-1.50 (m, 1H), 1.34 (t, J = 7.5 Hz, 3H), 0.78 (dt, J = 14.2, 6.5 Hz, 3H). | Example 139 |

Example 147 and 148: (S) and (R)-1-((6-(5-(((4-cyclobutylpyrimidin-2-yl)oxy)methyl)-1-methyl-1H-1,2,3-triazol-4-yl)-2-methylpyridin-3-yl)methyl)-5,5-difluoropiperidine-3-carboxylic acid

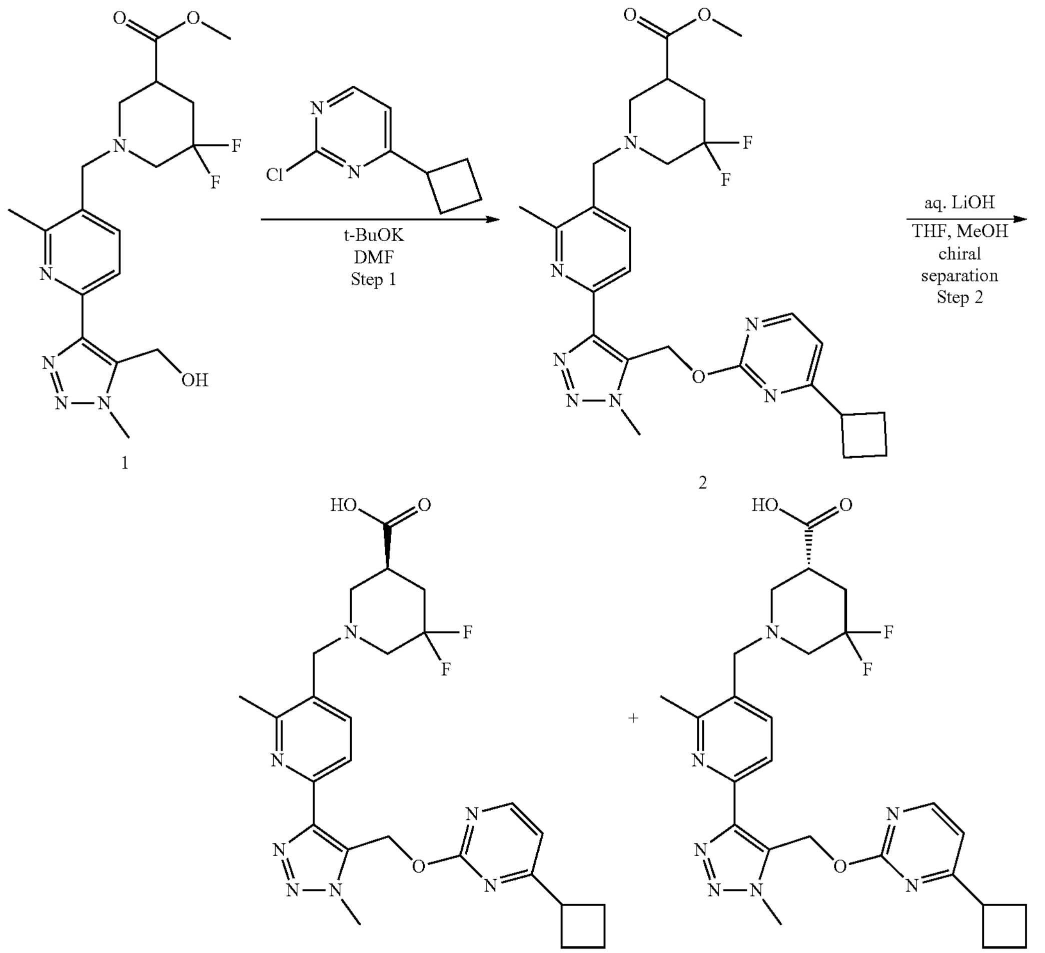

Example 147 and 148
Stereochemisry not assigned

Step 1: Methyl 1-((6-(5-(((4-cyclobutylpyrimidin-2-yl)oxy)methyl)-1-methyl-1H-1,2,3-triazol-4-yl)-2-methylpyridin-3-yl)methyl)-5,5-difluoropiperidine-3-carboxylate To a mixture of Methyl 5,5-difluoro-1-((6-(5-(hydroxymethyl)-1-methyl-1H-1,2,3-triazol-4-yl)-2-methylpyridin-3-yl)methyl)piperidine-3-carb oxyl ate (50 mg, 0.13 mmol) and 2-chloro-4-cyclobutylpyrimidine (21 mg, 0.13 mmol) in DMF (5 mL) was added t-BuOK (0.25 mL, 0.25 mmol, 1.0 M in THF) drop-wisely at 0° C. and the reaction was stirred at 0° C. for 2 hrs. The mixture was quenched with saturated aq·$NH_4Cl$ solution at 0° C. and acidified with 1N aq·HCl to pH~4. The mixture was extracted with EtOAc (3x5 mL) and the combined organic layers were washed with brine, dried over anhydrous $Na_2SO_4$, filtered and concentrated to dryness. The residue was purified by flash chromatography (0~50% EtOAc in PE) to give the title compound (40 mg, 60.0% yield) as yellow solid. LC/MS (ESI) (m/z): 528 $(M+H)^+$.

Step 2: (S) or (R)-1-((6-(5-(((4-cyclobutylpyrimidin-2-yl)oxy)methyl)-1-methyl-1H-1,2,3-triazol-4-yl)-2-methylpyridin-3-yl)methyl)-5,5-difluoropiperidine-3-carboxylic acid and (R) or (S)-1-((6-(5-(((4-cyclobutylpyrimidin-2-yl)oxy)methyl)-1-methyl-1H-1,2,3-triazol-4-yl)-2-methylpyridin-3-yl)methyl)-5,5-difluoropiperidine-3-carboxylic acid To a solution of methyl 1-((6-(5-(((4-cyclobutylpyrimidin-2-yl)oxy)methyl)-1-methyl-1H-1,2,3-triazol-4-yl)-2-methylpyridin-3-yl)methyl)-5,5-difluoropiperidine-3-carboxylate (40 mg, 0.076 mmol) in THE (4 mL)/$H_2O$ (4 mL)/MeOH (4 mL) was added LiOH·$H_2O$ (32 mg, 0.76 mmol) and the reaction was stirred at r.t. for 2 hrs. Volatiles were removed under vacuum and the residue was diluted with $H_2O$ (5 mL). The mixture was adjusted with 1N aq·HCl to pH~4 and extracted with EtOAc (3x5 mL). The combined organic layers were washed with brine, dried over anhydrous $Na_2SO_4$, filtered and concentrated to dryness. The residue was firstly purified by prep-HPLC (C18, 5-95%, MeCN in $H_2O$ with 0.1% HCOOH) and further purified by chiral SFC to give example 147 (Peak 1, retention time: 6.433 min) (6.5 mg, 16.7% yield) as white solid and example 148 (Peak 2, retention time: 6.662 min) (5.5 mg, 14.1% yield) as white solid. Absolute stereochemistry of these two isomers has not been assigned.

Example 147: LC/MS (ESI) (m/z): 514 $(M+H)^+$. $^1H$ NMR (400 MHz, DMSO-$d_6$) δ 8.55 (d, J=5.0 Hz, 1H), 7.97 (d, J=7.9 Hz, 1H), 7.79 (d, J=7.9 Hz, 1H), 7.09 (d, J=5.1 Hz, 1H), 6.17 (d, J=1.6 Hz, 2H), 4.22 (s, 3H), 3.67 (s, 2H), 3.61-3.54 (m, 2H), 3.05-2.95 (m, 2H), 2.76-2.67 (m, 1H), 2.44 (s, 3H), 2.25-2.20 (m, 2H), 2.27-2.20 (m, 4H), 2.05-1.93 (m, 2H), 1.83-1.74 (m, 1H).

Example 148: LC/MS (ESI) (m/z): 514 $(M+H)^+$. $^1H$ NMR (400 MHz, DMSO-$d_6$) δ 8.55 (d, J=5.0 Hz, 1H), 7.97 (d, J=7.9 Hz, 1H), 7.79 (d, J=7.9 Hz, 1H), 7.09 (d, J=5.1 Hz, 1H), 6.24-6.08 (m, 2H), 4.22 (s, 3H), 3.67 (s, 2H), 3.62-3.55 (m, 2H), 3.04-2.96 (m, 2H), 2.76-2.70 (m, 1H), 2.44 (s, 3H), 2.34-2.28 (m, 2H), 2.26-2.20 (m, 4H), 2.06-1.95 (m, 2H), 1.82-1.75 (m, 1H).

SFC condition: Column: ChiralPak AD, 250×21.2 mm I.D., 5 μm; Mobile phase: A for $CO_2$ and B for Methanol (0.1% $NH_4OH$); Gradient: B 30%; Flow rate: 50 mL/min; Column temperature: 35° C.

Example 149 and 150: (S) and (R)-1-((2-ethyl-6-(1-methyl-5-((2-oxo-5-propylpyridin-1(2H)-yl)methyl)-1H-1,2,3-triazol-4-yl)pyridin-3-yl)methyl)-5,5-difluoropiperidine-3-carboxylic acid

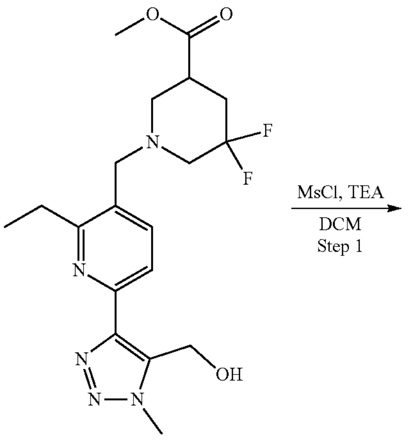

1

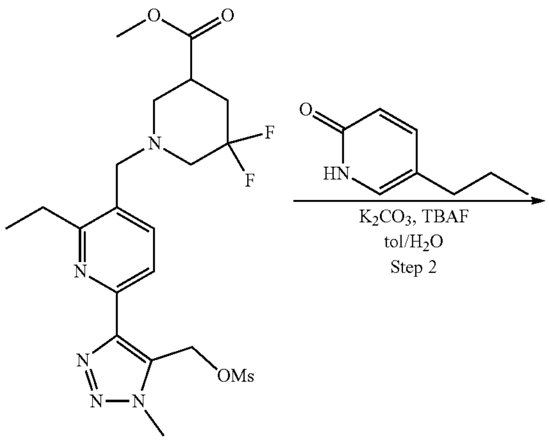

2

-continued

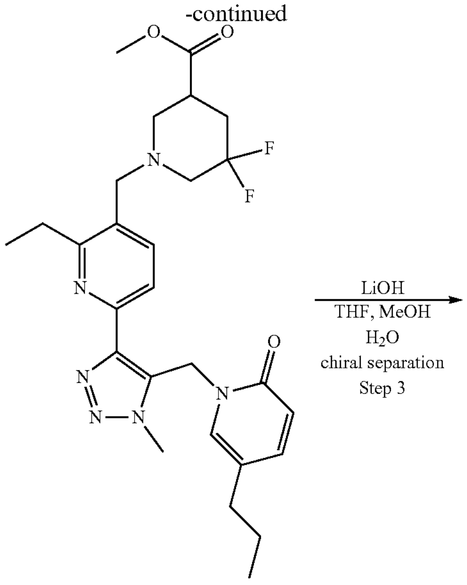

3

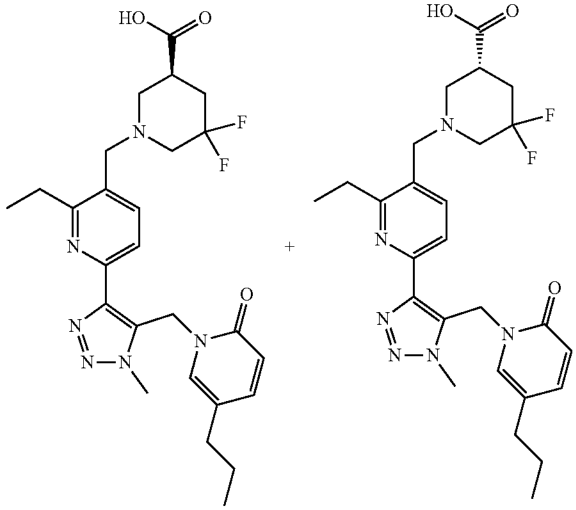

Example 149 and 150
Stereochemisry not assigned

Step 1: Methyl 1-((2-ethyl-6-(1-methyl-5-(((methylsulfonyl)oxy)methyl)-1H-1,2,3-triazol-4-yl)pyridin-3-yl)methyl)-5,5-difluoropiperidine-3-carboxylate To a solution of methyl 1-((2-ethyl-6-(5-(hydroxymethyl)-1-methyl-1H-1,2,3-triazol-4-yl)pyridin-3-yl)methyl)-5,5-difluoropiperidine-3-carboxylate (100 mg, 0.25 mmol) in DCM (10 mL) were added TEA (51 mg, 0.51 mmol) and MsCl (43 mg, 0.38 mmol) at 0° C. and the reaction was stirred at r.t. for 2 hrs. The mixture was washed with saturated aq·$NaHCO_3$ solution and brine, dried over anhydrous $Na_2SO_4$, filtered and concentrated under reduced pressure to dryness. The crude product was used in the next reaction without further purification. LC/MS (ESI) (m/z): 488 $(M+H)^+$.

Step 2: Methyl 1-((2-ethyl-6-(1-methyl-5-((2-oxo-5-propylpyridin-1(2H)-yl)methyl)-1H-1,2,3-triazol-4-yl)pyridin-3-yl)methyl)-5,5-difluoropiperidine-3-carboxylate To a mixture of methyl 1-((2-ethyl-6-(1-methyl-5-(((methylsulfonyl)oxy)methyl)-1H-1,2,3-triazol-4-yl)pyridin-3-yl)methyl)-5,5-difluoropiperidine-3-carboxylate (90 mg, 0.190 mmol) and 4-propylpyridin-2(1H)-one (39 mg, 0.285 mmol) in toluene (5 mL)/$H_2O$ (1 mL) was added $K_2CO_3$ (53 mg, 0.380 mmol) followed by TBAF (5 mg, 0.019 mmol) and the reaction mixture was stirred at 100° C. for 16 hrs. The mixture was partitioned between EtOAc (10 mL) and water (5 mL). The organic layer was washed with brine, dried over anhydrous $Na_2SO_4$, filtered and concentrated to dryness. The residue was purified by flash chromatography (0~40% EtOAc in PE) to give the title compound (75 mg, 76.7% yield) as yellow solid. LC/MS (ESI) (m/z): 529 $(M+H)^+$.

Step 3: (S) or (R)-1-((2-ethyl-6-(1-methyl-5-((2-oxo-5-propylpyridin-1(2H)-yl)methyl)-1H-1,2,3-triazol-4-yl)pyridin-3-yl)methyl)-5,5-difluoropiperidine-3-carboxylic acid and (R) or (S)-1-((2-ethyl-6-(1-methyl-5-((2-oxo-5-propylpyridin-1(2H)-yl)methyl)-1H-1,2,3-triazol-4-yl)pyridin-3-yl)methyl)-5,5-difluoropiperidine-3-carboxylic acid The title compounds were synthesized according the same procedure as example 147 and 148. The final product was purified by chiral SFC to give example 149 (Peak 1, retention time: 3.513 min) (6.5 mg, 28.5% yield) as white solid and example 150 (Peak 2, retention time: 3.839 min) (4.4 mg, 19.3% yield) as white solid.

Example 149: LC/MS (ESI) (m/z): 515 $(M+H)^+$. $^1H$ NMR (400 MHz, $CD_3OD$) δ 7.90 (d, J=7.8 Hz, 1H), 7.80 (d, J=7.8 Hz, 1H), 7.70 (d, J=2.4 Hz, 1H), 7.39 (dd, J=9.2, 2.4 Hz, 1H), 6.53 (d, J=9.2 Hz, 1H), 5.91 (s, 2H), 3.70 (d, J=4.4 Hz, 2H), 3.14-3.02 (m, 1H), 3.00 (t, J=7.5 Hz, 2H), 3.04-2.92 (m, 1H), 2.88-2.66 (m, 1H), 2.38-2.28 (m, 2H), 2.21 (t, J=7.6 Hz, 2H), 1.38 (q, J=14.7, 7.4 Hz, 2H), 1.30 (t, J=7.5 Hz, 3H), 0.75 (t, J=7.4 Hz, 3H).

Example 150: LC/MS (ESI) (m/z): 515 $(M+H)^+$. $^1H$ NMR (400 MHz, $CD_3OD$) δ 7.90 (d, J=7.9 Hz, 1H), 7.80 (d, J=8.0 Hz, 1H), 7.70 (s, 1H), 7.39 (dd, J=9.2, 2.5 Hz, 1H), 6.53 (d, J=9.2 Hz, 1H), 5.91 (s, 2H), 4.17 (s, 3H), 3.70 (s, 2H), 3.14-3.09 (m, 1H), 2.99 (t, J=7.4 Hz, 2H), 2.99-2.94 (m, 1H), 2.82-2.74 (m, 1H), 2.50-2.30 (m, 3H), 2.21 (t, J=7.4 Hz, 2H), 2.05-1.92 (m, 1H), 1.38 (q, J=7.4 Hz, 2H), 1.30 (t, J=7.4 Hz, 3H), 0.75 (t, J=7.4 Hz, 3H). SFC condition: Column: ChiralPak IG, 250×21.2 mm I.D., 5 μm; Mobile phase: A for $CO_2$ and B for Methanol (0.1% $NH_4OH$); Gradient: B 30%; Flow rate: 50 mL/min; Column temperature: 35° C.

Example 151: 1-((6-(5-(((4-cyclopropylpyrimidin-2-yl)amino)methyl)-1-methyl-1H-1,2,3-triazol-4-yl)-2-ethylpyridin-3-yl)methyl)-5,5-difluoropiperidine-3-carboxylic acid

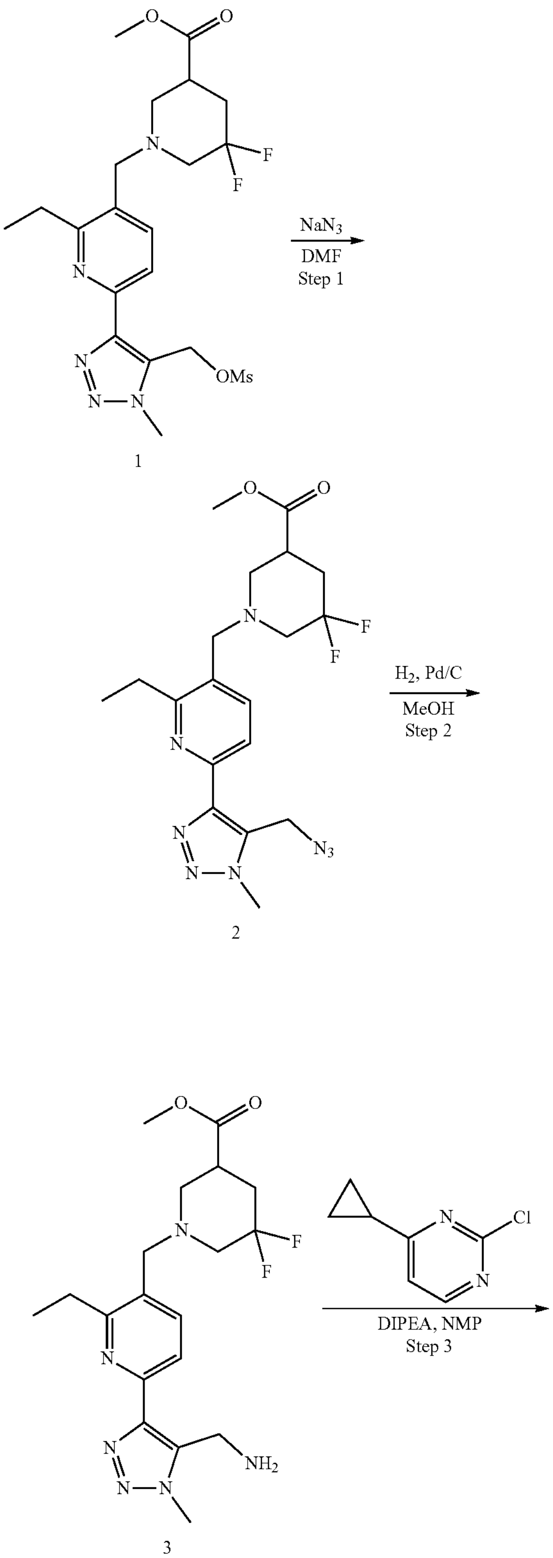

-continued

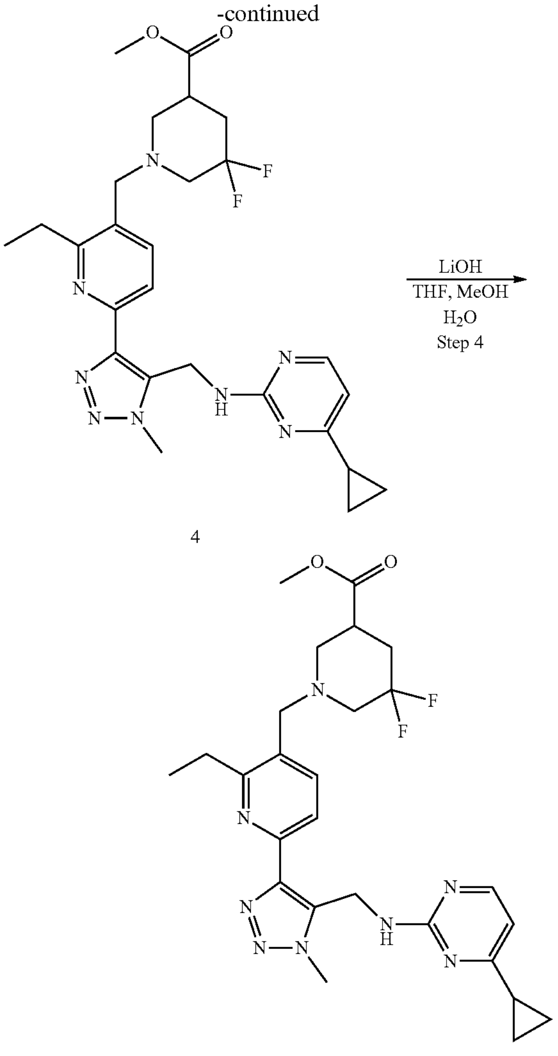

4

Example 151

Step 1: Methyl 1-((6-(5-(azidomethyl)-1-methyl-11H-1,2,3-triazol-4-yl)-2-ethylpyridin-3-yl)methyl)-5,5-difluoropiperidine-3-carboxylate To a solution of methyl 1-((2-ethyl-6-(5-(hydroxymethyl)-1-methyl-1H-1,2,3-triazol-4-yl)pyridin-3-yl)methyl)-5,5-difluoropiperidine-3-carboxylate (300 mg, 0.62 mmol) in DMF (5 mL) was added $NaN_3$ (60 mg, 0.923 mmol) and the reaction was stirred at 60° C. for 16 hrs. The mixture was diluted with EtOAc (10 mL) and was washed with water and brine, dried over anhydrous $Na_2SO_4$, filtered and concentrated under reduced pressure to dryness. The residue was purified by flash chromatography (0~30% EtOAc in PE) to give the title compound (208 mg, 77.8% yield) as yellow solid. LC/MS (ESI) (m/z): 435 $(M+H)^+$. $^1H$ NMR (400 MHz, $CDCl_3$) δ 8.03 (d, J=7.9 Hz, 1H), 7.66 (d, J=7.9 Hz, 1H), 5.17 (s, 2H), 4.13 (s, 3H), 3.69 (s, 3H), 3.64-3.60 (m, 2H), 3.13-2.99 (m, 2H), 2.92 (q, J=7.4 Hz, 2H), 2.94-2.89 (m, 1H), 2.46-2.37 (m, 1H), 2.35-2.25 (m, 1H), 2.23-2.21 (m, 1H), 2.02-1.98 (m, 1H), 1.36 (t, J=7.4, 3H).

Step 2: Methyl 1-((6-(5-(aminomethyl)-1-methyl-11H-1,2,3-triazol-4-yl)-2-ethylpyridin-3-yl)methyl)-5,5-difluoropiperidine-3-carboxylate To a solution of methyl 1-((6-(5-(azidomethyl)-1-methyl-1H-1,2,3-triazol-4-yl)-2-ethylpyridin-3-yl)methyl)-5,5-difluoropiperidine-3-carboxylate (200 mg, 0.46 mmol) in EtOAc (5 mL) was added 10% Pd/C (40 mg, 0.038 mmol) and the mixture was degassed under $N_2$ for three times and stirred under a $H_2$ balloon at r.t. for 2 hrs. The reaction mixture was filtered through a pad of Celite and the filtrate was concentrated to dryness to give the title compound (190 mg, 100% yield), which was used in the next step without further purification. LC/MS (ESI) (m/z): 409 $(M+H)^+$.

Step 3: Methyl 1-((6-(5-(((4-cyclopropylpyrimidin-2-yl)amino)methyl)-1-methyl-11H-1,2,3-triazol-4-yl)-2-ethylpyridin-3-yl)methyl)-5,5-difluoropiperidine-3-carboxylate To a mixture of methyl 1-((6-(5-(aminomethyl)-1-methyl-1H-1,2,3-triazol-4-yl)-2-ethylpyridin-3-yl)methyl)-5,5-difluoropiperidine-3-carboxylate (70 mg, 0.17 mmol) and 2-chloro-4-cyclobutylpyrimidine (29 mg, 0.17 mmol) in NMP (2 mL) was added DIPEA (44 mg, 0.34 mmol) and the reaction was stirred in a CEM microwave reactor at 150° C. for 2 hrs. The mixture was diluted with EtOAc (10 mL) and was washed with brine, dried over anhydrous $Na_2SO_4$, filtered and concentrated under reduced pressure to dryness. The residue was purified by perp-TLC (40% EtOAc in PE) to give the title compound (50 mg, 54.0% yield) as yellow oil. LC/MS (ESI) (m/z): 527 $(M+H)^+$.

Step 4: methyl 1-((6-(5-(((4-cyclopropylpyrimidin-2-yl)amino)methyl)-1-methyl-11H-1,2,3-triazol-4-yl)-2-ethylpyridin-3-yl)methyl)-5,5-difluoropiperidine-3-carboxylate The title compound was synthesized according to the same procedure as Example 149. LC/MS (ESI)(m/z): 513 $(M+H)^+$. $^1H$ NMR (400 MHz, $CD_3OD$) δ 8.02 (d, J=5.2 Hz, 1H), 7.89 (d, J=8.0 Hz, 1H), 7.77 (d, J=8.0 Hz, 1H), 6.51 (d, J=5.2 Hz, 1H), 5.06 (s, 2H), 4.23 (s, 3H), 3.70 (s, 2H), 3.14-3.09 (m, 1H), 3.05-2.99 (q, J=7.5 Hz, 2H), 3.00-2.94 (m, 1H), 2.83-2.73 (m, 1H), 2.50-2.38 (m, 1H), 2.36-2.26 (m, 2H), 2.04-1.88 (m, 1H), 1.87-1.80 (m, 1H), 1.36 (t, J=7.5 Hz, 3H), 0.94-0.86 (m, 4H).

The Examples in the below Table were synthesized and separated by chiral SFC by the same methods exemplified by the preparation of the examples as indicated. As a conversion, the faster-eluting enantiomer is always listed as enantiomer P1 and the slower-eluting enantiomer is listed as enantiomer P2. The symbol * at the chiral centre denotes that this chiral center has been resolved and the absolute stereochemistry at that center has not been determined.

| Ex# | Structure & name | Analytical data | Method |
|---|---|---|---|
| 152 | 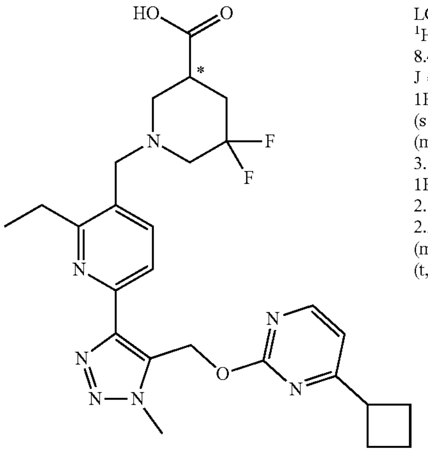 enantiomer P1: (S) or (R)-1-((6-(5-(((4-cyclobutylpyrimidin-2-yl)oxy)methyl)-1-methyl-1H-1,2,3-triazol-4-yl)-2-ethylpyridin-3-yl)methyl)-5,5-difluoropiperidine-3-carboxylic acid | LC/MS (ESI) (m/z): 528 $(M + H)^+$. $^1H$ NMR (400 MHz, $CD_3OD$) δ 8.40 (d, J = 5.1 Hz, 1H), 7.88 (d, J = 7.8 Hz, 1H), 7.75 (d, J = 8.1 Hz, 1H), 6.98 (d, J = 5.1 Hz, 1H), 6.23 (s, 2H), 4.24 (s, 3H), 3.68-3.62 (m, 2H), 3.54-3.48 (m, 2H), 3.14-3.11 (m, 1H), 3.03-2.92 (m, 1H), 2.87 (q, J = 7.5 Hz, 2H), 2.79-2.64 (m, 1H), 2.42-2.28(m, 2H), 2.27-2.18 (m, 5H), 2.06-1.98 (m, 1H), 1.84-1.71 (m, 1H), 1.21 (t, J = 7.5 Hz, 3H). | Example 147 |
| 153 | 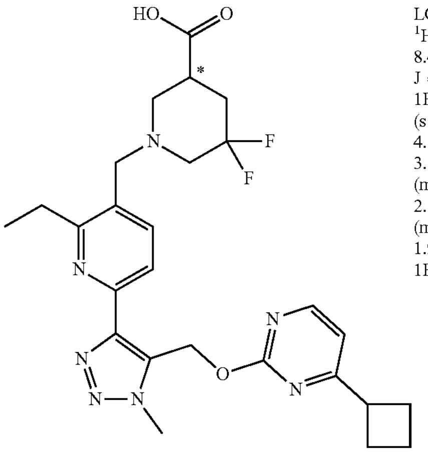 enantiomer P2: (R) or (S)-1-((6-(5-(((4-cyclobutylpyrimidin-2-yl)oxy)methyl)-1-methyl-1H-1,2,3-triazol-4-yl)-2-ethylpyridin-3-yl)methyl)-5,5-difluoropiperidine-3-carboxylic acid | LC/MS (ESI) (m/z): 528 $(M + H)^+$. $^1H$ NMR (400 MHz, $CD_3OD$) δ 8.40 (d, J = 5.1 Hz, 1H), 7.88 (d, J = 7.8 Hz, 1H), 7.75 (d, J = 7.8 Hz, 1H), 6.98 (d, J = 5.1 Hz, 1H), 6.23 (s, 2H), 4.24 (s, 3H), 3.66 (d, J = 4.1 Hz, 2H), 3.58-3.46 (m, 2H), 3.15-3.10 (m, 1H), 3.00-2.92 (m, 1H), 2.88 (q, J = 7.5 Hz, 2H), 2.82-2.65 (m, 1H), 2.41-2.28 (m, 2H), 2.27-2.16 (m, 5H), 2.05-1.98 (m, 1H), 1.82-1.72 (m, 1H), 1.21 (t, J = 7.5 Hz, 3H). | Example 147 |

-continued

| Ex# | Structure & name | Analytical data | Method |
| --- | --- | --- | --- |
| 154 | 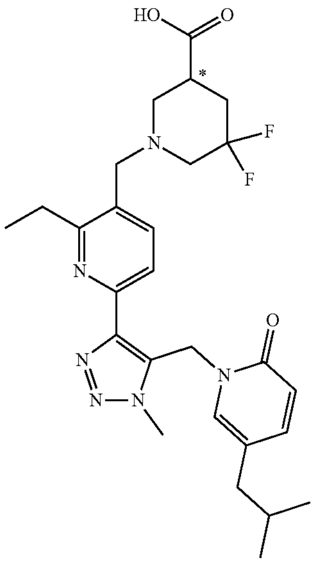 [SMILES: CCc1nc(-c2nnn(C)c2Cn2cc(CC(C)C)ccc2=O)ccc1CN1CC(C(=O)O)CC(F)(F)C1] enantiomer P1: (S) or (R)-1-((2-ethyl-6-(5-((5-isobutyl-2-oxopyridin-1(2H)-yl)methyl)-1-methyl-1H-1,2,3-triazol-4-yl)pyridin-3-yl)methyl)-5,5-difluoropiperidine-3-carboxylic acid | LC/MS (ESI) (m/z): 529 $(M + H)^+$. $^1H$ NMR (400 MHz, $CD_3OD$) δ 7.90 (d, J = 8.0 Hz, 1H), 7.79 (d, J = 8.0 Hz, 1H), 7.65 (d, J = 2.1 Hz, 1H), 7.36 (dd, J = 9.2, 2.1 Hz, 1H), 6.53 (d, J = 9.2 Hz, 1H), 5.92 (s, 2H), 4.18 (s, 3H), 3.70 (s, 2H), 3.14-3.10 (m, 1H), 2.99 (q, J = 7.6 Hz, 2H), 2.97-2.91 (m, 1H), 2.85-2.67 (m, 1H), 2.49-2.28 (m, 3H), 2.09 (d, J = 6.6 Hz, 2H), 2.02-1.85 (m, 1H), 1.62-1.55 (m, 1H), 1.30 (t, J = 7.4 Hz, 6H), 1.02 (t, J = 7.4 Hz, 1H), 0.72 (d, J = 6.6 Hz, 6H). | Example 148 |
| 155 | 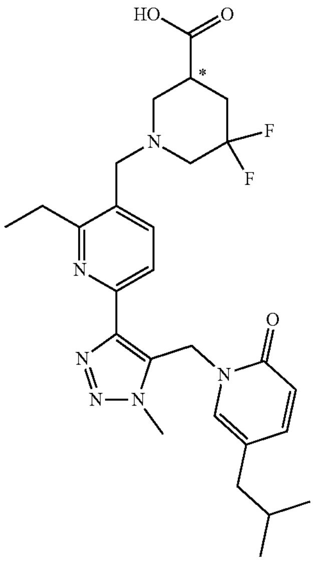 [SMILES: CCc1nc(-c2nnn(C)c2Cn2cc(CC(C)C)ccc2=O)ccc1CN1CC(C(=O)O)CC(F)(F)C1] enantiomer P2: (R) or (S)-1-((2-ethyl-6-(5-((5-isobutyl-2-oxopyridin-1(2H)-yl)methyl)-1-methyl-1H-1,2,3-triazol-4-yl)pyridin-3-yl)methyl)-5,5-difluoropiperidine-3-carboxylic acid | LC/MS (ESI) (m/z): 529 $(M + H)^+$. $^1H$ NMR (400 MHz, $CD_3OD$) δ 7.90 (d, J = 7.9 Hz, 1H), 7.79 (d, J = 7.9 Hz, 1H), 7.65 (d, J = 2.0 Hz, 1H), 7.36 (dd, J = 9.2, 2.0 Hz, 1H), 6.53 (d, J = 9.2 Hz, 1H), 5.92 (s, 2H), 4.18 (s, 3H), 3.70 (s, 2H), 3.14-3.07 (m, 1H), 2.99 (q, J = 7.5 Hz, 3H), 2.97-2.90 (m, 1H), 2.86-2.74 (m, 1H), 2.49-2.26 (m, 3H), 2.09 (d, J = 7.1 Hz, 2H), 2.04-1.89 (m, 1H), 1.62-1.55 (m, 1H), 1.30 (t, J = 7.1 Hz, 1H), 0.72 (d, J = 6.6 Hz, 6H). | Example 149 |

-continued

| Ex# | Structure & name | Analytical data | Method |
|---|---|---|---|
| 156 | 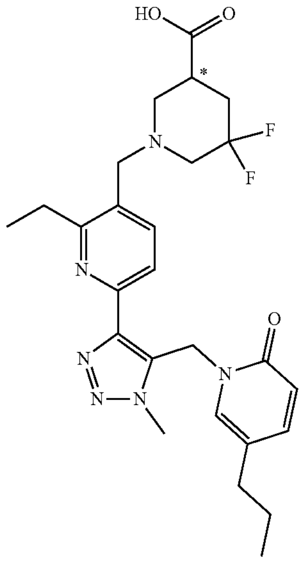 enantiomer P1: (S) or (R)-5,5-difluoro-1-((2-methyl-6-(1-methyl-5-((2-oxo-5-propylpyridin-1(2H)-yl)methyl)-1H-1,2,3-triazol-4-yl)pyridin-3-yl)methyl)piperidine-3-carboxylic acid | LC/MS (ESI) (m/z): 501 $(M + H)^+$. $^1H$ NMR (400 MHz, $CD_3OD$) δ 7.88 (d, J = 2.1 Hz, 1H), 7.86 (d, J = 7.9 Hz, 1H), 7.75 (d, J = 8.0 Hz, 1H), 7.36 (dd, J = 9.2, 2.5 Hz, 1H), 6.47 (d, J = 9.2 Hz, 1H), 5.79 (s, 2H), 4.24 (s, 3H), 3.68 (s, 2H), 3.12-3.06 (m, 1H),3.00-2.92 (m, 1H), 2.83-2.74 (m, 1H), 2.67 (s, 3H), 2.48-2.38 (m, 1H), 2.36-2.29 (m, 2H), 2.25 (t, J = 7.5 Hz, 2H), 2.04-1.89 (m, 1H), 1.45-1.36 (m, 2H), 0.77 (t, J = 7.3 Hz, 3H). | Example 149 |
| 157 | 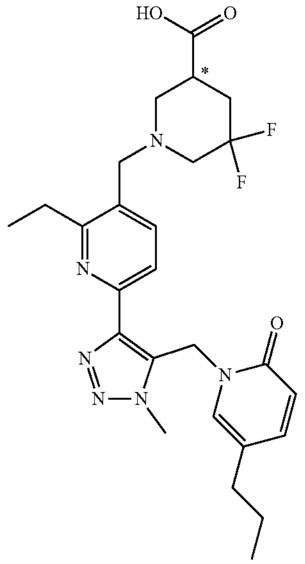 enantiomer P2: (R) or (S)-5,5-difluoro-1-((2-methyl-6-(1-methyl-5-((2-oxo-5-propylpyridin-1(2H)-yl)methyl)-1H-1,2,3-triazol-4-yl)pyridin-3-yl)methyl)piperidine-3-carboxylic acid | LC/MS (ESI) (m/z): 501 $(M + H)^+$. $^1H$ NMR (400 MHz, $CD_3OD$) δ 7.89 (d, J = 2.3 Hz, 1H), 7.86 (d, J = 8.0 Hz, 1H), 7.76 (d, J = 8.0 Hz, 1H), 7.37 (dd, J = 9.2, 2.5 Hz, 1H), 6.48 (d, J = 9.2 Hz, 1H), 5.79 (s, 2H), 4.24 (s, 3H), 3.67 (d, J = 8.3 Hz, 2H), 3.15-3.07 (m, 1H), 3.00-2.91 (m, 1H), 2.79-2.71 (m, 1H), 2.67 (s, 3H), 2.47-2.37 (m, 1H), 2.36-2.29 (m, 2H), 2.27-2.21 (m, 2H), 2.05-2.00 (m, 1H), 1.44-1.38 (m, 2H), 0.78 (t, J = 7.3 Hz, 3H). | Example 149 |

-continued

| Ex# | Structure & name | Analytical data | Method |
|---|---|---|---|
| 158 | 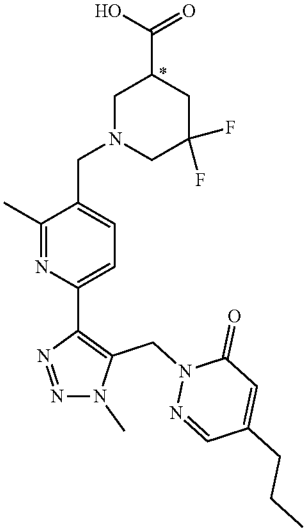 [SMILES: CCCc1cnn(Cc2c(-c3ccc(CN4CC(C(=O)O)CC(F)(F)C4)c(C)n3)nnn2C)c(=O)c1] enantiomer P1: (S) or (R)-5,5-difluoro-1-((2-methyl-6-(1-methyl-5-((6-oxo-4-propylpyridazin-1(6H)-yl)methyl)-1H-1,2,3-triazol-4-yl)pyridin-3-yl)methyl)piperidine-3-carboxylic acid | LC/MS (ESI) (m/z): 502 $(M + H)^+$ $^1H$ NMR (400 MHz, $CD_3OD$) δ 7.78 (d, J = 7.9 Hz, 1H), 7.69 (d, J = 7.9 Hz, 2H), 7.68 (s, 1H), 6.83-6.69 (m, 1H), 5.91 (s, 2H), 4.16 (s, 3H), 3.61 (q, J = 13.7 Hz, 2H), 3.11-3.03 (m, 1H), 2.97-2.88 (m, 1H), 2.76-2.66 (m, 1H), 2.52 (s, 3H), 2.50-2.43 (m, 2H), 2.42-2.21 (m, 3H), 1.99-1.82 (m, 1H), 1.65-1.54 (m, 2H), 0.93 (t, J = 7.4 Hz, 3H). | Example 149 |
| 159 | 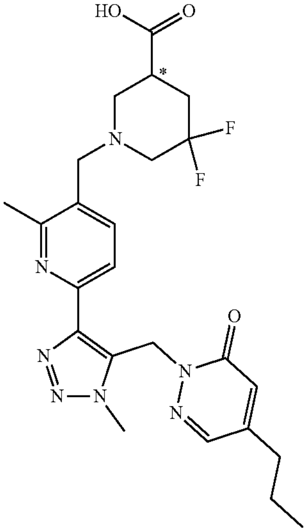 [SMILES: CCCc1cnn(Cc2c(-c3ccc(CN4CC(C(=O)O)CC(F)(F)C4)c(C)n3)nnn2C)c(=O)c1] enantiomer P2: (R) or (S)-5,5-difluoro-1-((2-methyl-6-(1-methyl-5-((6-oxo-4-propylpyridazin-1(6H)-yl)methyl)-1H-1,2,3-triazol-4-yl)pyridin-3-yl)methyl)piperidine-3-carboxylic acid | LC/MS (ESI) (m/z): 502 $(M + H)^+$. $^1H$ NMR (400 MHz, $CD_3OD$) δ 7.79 (d, J = 7.9 Hz, 1H), 7.69 (d, J = 7.9 Hz, 1H), 7.68 (s, 2H), 6.82-6.68 (m, 1H), 5.91 (s, 2H), 4.16 (s, 3H), 3.62 (d, J = 3.6 Hz, 2H), 3.11-2.99 (m, 1H), 2.98-2.87 (m, 1H), 2.82-2.70 (m, 1H), 2.52 (s, 3H), 2.49-2.44 (m, 2H), 2.42-2.25 (m, 3H), 2.02-1.84 (m, 1H), 1.65-1.55 (m, 2H), 0.93 (t, J = 7.4 Hz, 3H). | Example 149 |

-continued

| Ex# | Structure & name | Analytical data | Method |
|---|---|---|---|
| 160 | 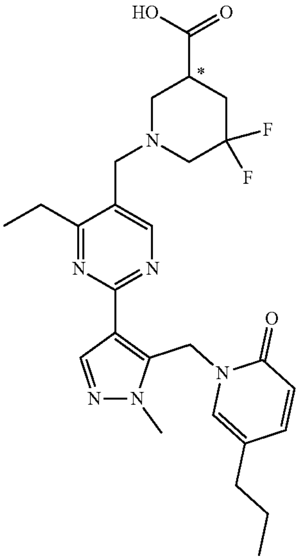 [SMILES: CCCc1ccc(=O)n(Cc2c(-c3ncc(CN4CC(C(=O)O)CC(F)(F)C4)c(CC)n3)cnn2C)c1] enantiomer P1: (S) or (R)-1-((4-ethyl-2-(1-methyl-5-((2-oxo-5-propylpyridin-1(2H)-yl)methyl)-1H-pyrazol-4-yl)pyrimidin-5-yl)methyl)-5,5-difluoropiperidine-3-carboxylic acid | LC/MS (ESI) (m/z): 515 $(M + H)^+$. $^1H$ NMR (400 MHz, $CD_3OD$) δ 8.54 (s, 1H), 8.20 (s, 1H), 7.51 (d, J = 2.5 Hz, 1H), 7.40 (dd, J = 9.1, 2.5 Hz, 1H), 6.55 (d, J = 9.1 Hz, 1H), 5.88 (s, 2H), 3.93 (s, 3H), 3.67 (s, 2H), 3.10-3.03 (m, 1H), 2.92 (q, J = 7.5 Hz, 3H), 2.80-2.75 (m, 1H), 2.51-2.39 (m, 1H), 2.37-2.30 (m, 2H), 2.23 (t, J = 7.5 Hz, 2H), 2.10-1.85 (m, 1H), 1.44-1.36 (m, 2H), 1.26 (t, J = 7.5 Hz, 3H), 0.76 (t, J = 7.5 Hz, 3H). | Example 149 |
| 161 | 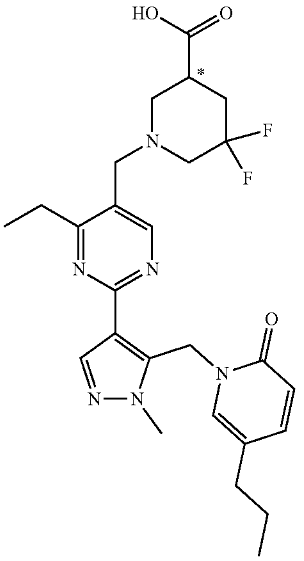 [SMILES: CCCc1ccc(=O)n(Cc2c(-c3ncc(CN4CC(C(=O)O)CC(F)(F)C4)c(CC)n3)cnn2C)c1] enantiomer 2: (R) or (S)-1-((4-ethyl-2-(1-methyl-5-((2-oxo-5-propylpyridin-1(2H)-yl)methyl)-1H-pyrazol-4-yl)pyrimidin-5-yl)methyl)-5,5-difluoropiperidine-3-carboxylic acid | LC/MS (ESI) (m/z): 515 $(M + H)^+$ $^1H$ NMR (400 MHz, $CD_3OD$) δ 8.54 (s, 1H), 8.20 (s, 1H), 7.51 (d, J = 2.5 Hz, 1H), 7.40 (dd, J = 9.2, 2.5 Hz, 1H), 6.55 (d, J = 9.2 Hz, 1H), 5.88 (s, 2H), 3.93 (s, 3H), 3.67 (s, 2H), 3.10-3.03 (m, 1H), 2.99-2.93 (m, 1H), 2.92 (q, J = 7.4 Hz, 2H), 2.80-2.71 (m, 1H), 2.52-2.39 (m, 1H), 2.38-2.30 (m, 1H), 2.23 (t, J = 7.4 Hz, 2H), 2.10-1.86 (m, 1H), 1.45-1.35 (m, 1H), 1.26 (t, J = 7.4 Hz, 3H), 0.76 (t, J = 7.4 Hz, 3H). | Example 149 |

-continued

| Ex# | Structure & name | Analytical data | Method |
| --- | --- | --- | --- |
| 162 | 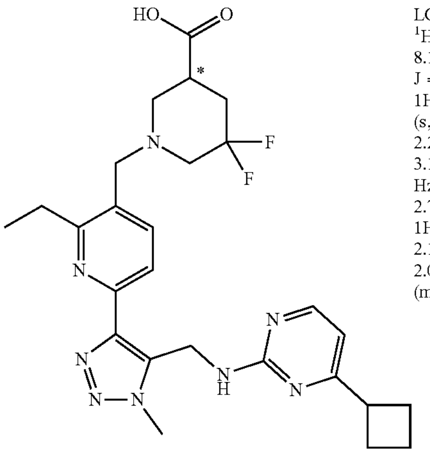 enantiomer P1: (S) or (R)-1-((6-(5-(((4-cyclobutylpyrimidin-2-yl)amino)methyl)-1-methyl-1H-1,2,3-triazol-4-yl)-2-ethylpyridin-3-yl)methyl)-5,5-difluoropiperidine-3-carboxylic acid | LC/MS (ESI) (m/z): 527 $(M + H)^+$. $^1$H NMR (400 MHz, $CD_3OD$) δ 8.15 (d, J = 4.8 Hz, 1H), 7.90 (d, J = 8.0 Hz, 1H), 7.77 (d, J = 8.0 Hz, 1H), 6.54 (d, J = 4.8 Hz, 1H), 5.09 (s, 2H), 4.30 (s, 3H), 3.70 (d, J = 2.2 Hz, 2H), 3.49-3.40 (m, 1H), 3.14-3.10 (m, 1H), 3.05(q, J = 7.5 Hz, 2H), 3.01-2.95 (m, 1H), 2.82-2.73 (m, 1H), 2.48-2.38 (m, 1H), 2.37-2.29 (m, 2H), 2.27-2.19 (m, 4H), 2.07-2.01 (m, 1H), 2.00-1.89 (m, 1H), 1.86-1.78 (m, 1H), 1.38 (t, J = 7.5 Hz, 3H). | Example 151 |
| 163 | 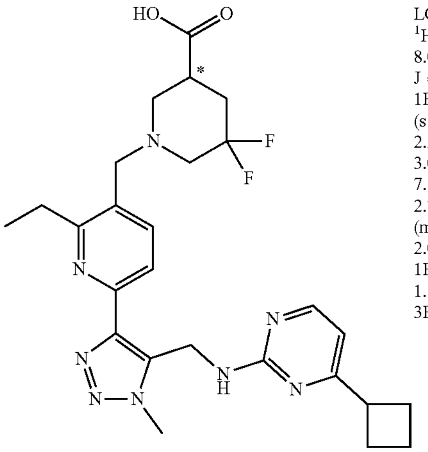 enantiomer P2: (R) or (S)-1-((6-(5-(((4-cyclobutylpyrimidin-2-yl)amino)methyl)-1-methyl-1H-1,2,3-triazol-4-yl)-2-ethylpyridin-3-yl)methyl)-5,5-difluoropiperidine-3-carboxylic acid | LC/MS (ESI) (m/z): 527 $(M + H)^+$. $^1$H NMR (400 MHz, $CD_3OD$) δ 8.05 (d, J = 5.4 Hz, 1H), 7.80 (d, J = 7.9 Hz, 1H), 7.67 (d, J = 7.9 Hz, 1H), 6.44 (d, J = 5.4 Hz, 1H), 4.99 (s, 2H), 4.20 (s, 3H), 3.61 (d, J = 2.2 Hz, 2H), 3.37-3.31 (m, 1H), 3.05-3.01 (m, 1H), 2.95 (q, J = 7.6 Hz, 2H), 2.91-2.80 (m, 1H), 2.74-2.57 (m, 1H), 2.37-2.27 (m, 1H), 2.27-2.18 (m, 2H), 2.17-2.08 (m, 4H), 2.00-1.91 (m, 1H), 1.91-1.79 (m, 1H), 1.76-1.69 (m, 1H), 1.28 (t, J = 7.5 Hz, 3H). | Example 151 |

Example 164 and 165: (S) and (R)-1-((2-ethyl-6-(1-methyl-5-(((methyl(propyl)carbamoyl)oxy)methyl)-1H-1,2,3-triazol-4-yl)pyridin-3-yl)methyl)-5,5-difluoropiperidine-3-carboxylic acid
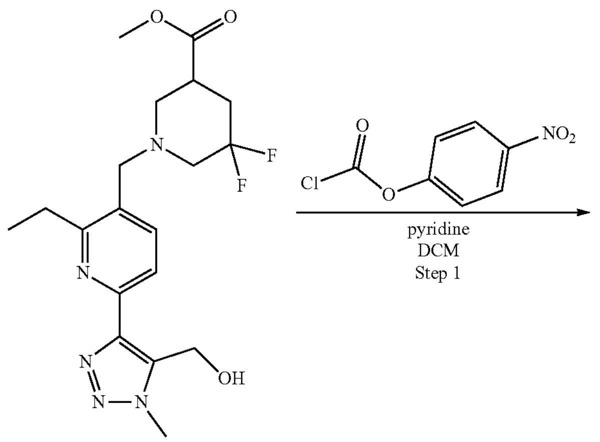
1
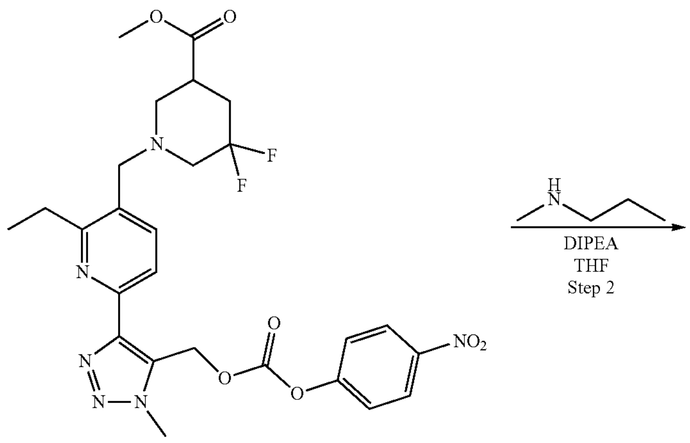
2
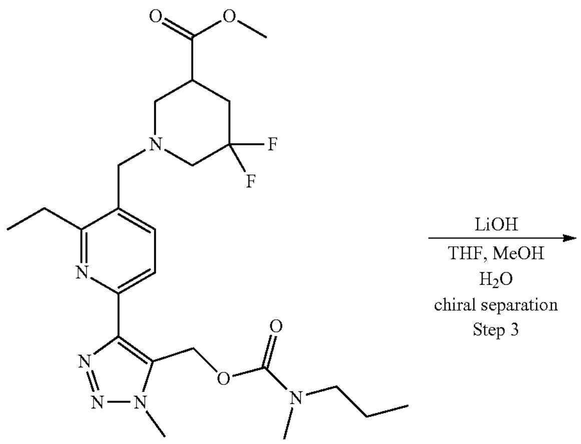
3

-continued

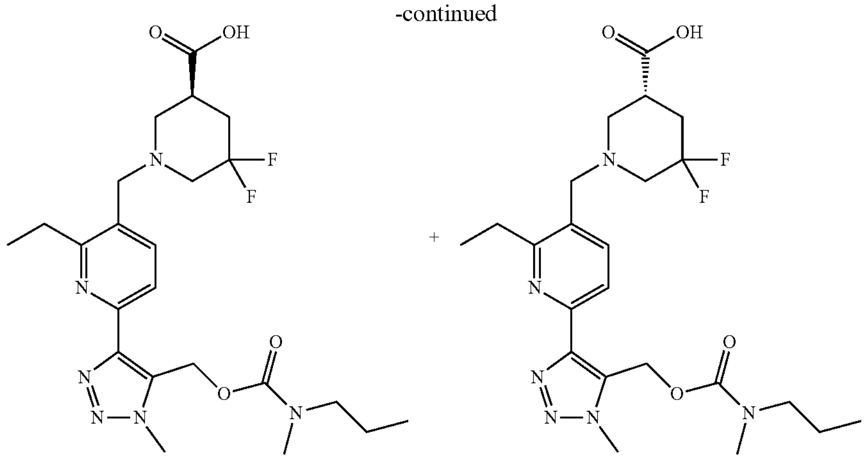

Example 164 and 165
Stereochemisry not assigned

Step 1: Methyl 1-((2-ethyl-6-(1-methyl-5-((((4-nitrophenoxy)carbonyl)oxy)methyl)-1H-1,2,3-triazol-4-yl)pyridin-3-yl)methyl)-5,5-difluoropiperidine-3-carboxylate To a mixture of methyl 1-((2-ethyl-6-(5-(hydroxymethyl)-1-methyl-1H-1,2,3-triazol-4-yl)pyridin-3-yl)methyl)-5,5-difluoropiperidine-3-carboxylate (120 mg, 0.29 mmol) and 4-nitrophenyl chloroformate (177 mg, 0.88 mmol) in DCM (5 mL) was added pyridine (116 mg, 1.47 mmol) and the reaction was stirred at r.t. for 1 hr. The mixture was diluted with DCM (10 mL) and was washed with saturated aq·$NaHCO_3$ solution and brine, dried over $Na_2SO_4$, filtered and concentrated to dryness to give the title compound (170 mg, 100% yield). The crude product was used in the next step without further purification. LC/MS (ESI) (m/z): 575 $(M+H)^+$.

Step 2: Methyl 1-((2-ethyl-6-(1-methyl-5-(((methyl(propyl)carbamoyl)oxy)methyl)-1H-1,2,3-triazol-4-yl)pyridin-3-yl)methyl)-5,5-difluoropiperidine-3-carboxylate To a solution of methyl 1-((2-ethyl-6-(1-methyl-5-((((4-nitrophenoxy)carbonyl)oxy)methyl)-1H-1,2,3-triazol-4-yl)pyridin-3-yl)methyl)-5,5-difluoropiperidine-3-carboxylate (120 mg, 0.21 mmol) in THF (10 mL) was added DIPEA (135 mg, 1.04 mmol) followed by methyl(propyl)amine (76 mg, 1.04 mmol) at 0° C. and the reaction was stirred at r.t. for 2 hrs. The mixture was diluted with EtOAc (10 mL) and was washed with 1M aq·NaOH solution and brine, dried over $Na_2SO_4$, filtered and concentrated to dryness. The residue was purified by perp-TLC (50% EtOAc in PE) to give the title compound (23 mg, 21.7% yield) as yellow solid. LC/MS (ESI) (m/z): 509 $(M+H)^+$.

Step 3: (S) and (R)-1-((2-ethyl-6-(1-methyl-5-(((methyl(propyl)carbamoyl)oxy)methyl)-1H-1,2,3-triazol-4-yl)pyridin-3-yl)methyl)-5,5-difluoropiperidine-3-carboxylic acid The title compound was synthesized according the same procedure as example 147. Example 164: (Peak 1, retention time: 6.385 min) (7.5 mg, 19.2% yield). LC/MS (ESI) (m/z): 495 $(M+H)^+$. $^1$H NMR (400 MHz, $CD_3OD$) δ 7.84 (d, J=8.0 Hz, 1H), 7.74 (d, J=8.0 Hz, 1H), 5.78 (s, 2H), 4.19 (s, 3H), 3.67 (d, J=5.2 Hz, 2H), 3.25-3.17 (m, 1H), 3.13-3.08 (m, 2H), 3.00-2.97 (m, 1H), 2.95 (q, J=7.5 Hz, 2H), 2.82 (d, J=25.1 Hz, 3H), 2.77-2.68 (m, 1H), 2.44-2.36 (m, 1H), 2.30 (t, J=7.5 Hz, 2H), 2.00-1.85 (m, 1H), 1.60-1.50 (m, 1H), 1.38-1.30 (m, 1H), 1.35 (t, 7.5 Hz, 3H), 0.76 (dt, J=81.3, 7.5 Hz, 3H). Example 165: (Peak 2, retention time: 6.663 min) (7 mg, 18.3% yield) as white solid. $^1$H NMR (400 MHz, $CD_3OD$) δ 7.84 (d, J=7.9 Hz, 1H), 7.74 (d, J=7.9 Hz, 1H), 5.78 (s, 2H), 4.19 (s, 3H), 3.67 (d, J=4.5 Hz, 2H), 3.25-3.17 (m, 1H), 3.14-3.07 (m, 2H), 3.00-2.92 (m, 1H), 2.95 (q, J=7.4 Hz, 2H), 2.82 (d, J=25.1 Hz, 3H), 2.76-2.70 (m, 1H), 2.44-2.35 (m, 1H), 2.31 (t, J=7.2 Hz, 2H), 2.01-1.85 (m, 1H), 1.42-1.36 (m, 1H), 1.35 (t, 7.4 Hz, 3H), 0.76 (dt, J=81.6, 7.2 Hz, 3H). SFC condition: Column: ChiralPak IG-H, 250×4.6 mm I.D., 5 μm; Mobile phase: A for $CO_2$ and B for Methanol (0.05% $NH_4OH$); Gradient: B 5%-40%; Flow rate: 50 mL/min; Column temperature: 35° C.

Example 166: 4-((2-methyl-6-(1-methyl-5-(((methyl(propyl)carbamoyl)oxy)methyl)-1H-1,2,3-triazol-4-yl)pyridin-3-yl)methyl)morpholine-2-carboxylic acid

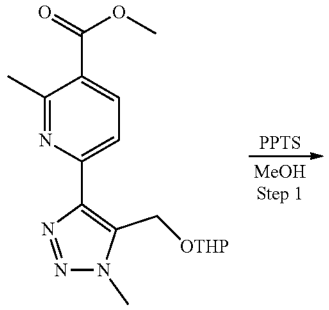

1

-continued

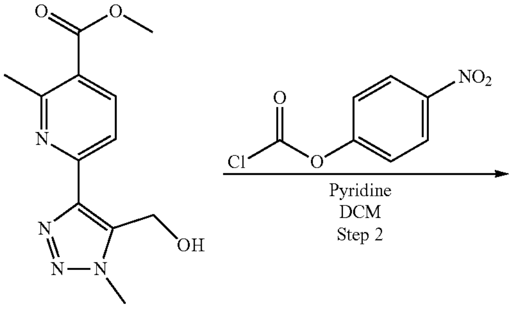

2

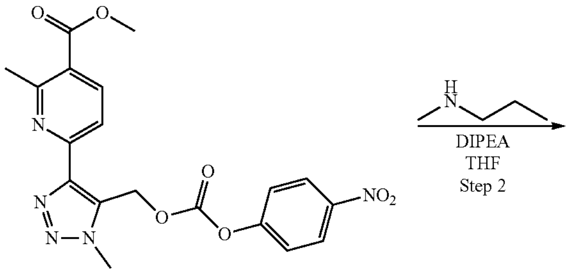

3

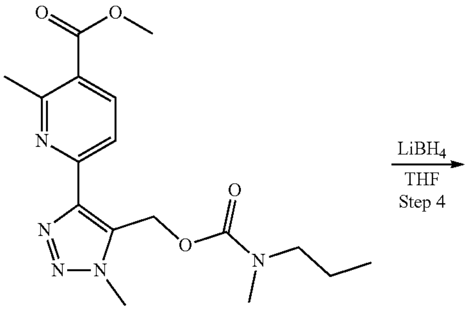

4

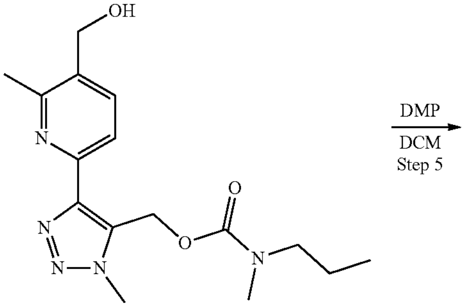

5

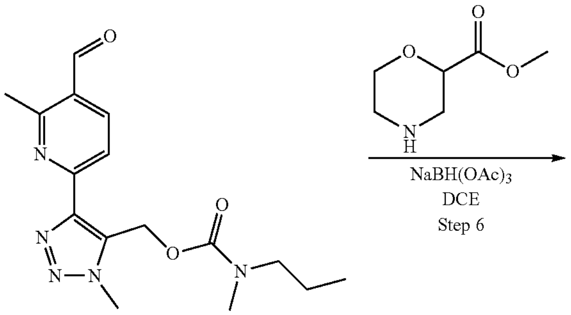

6

-continued

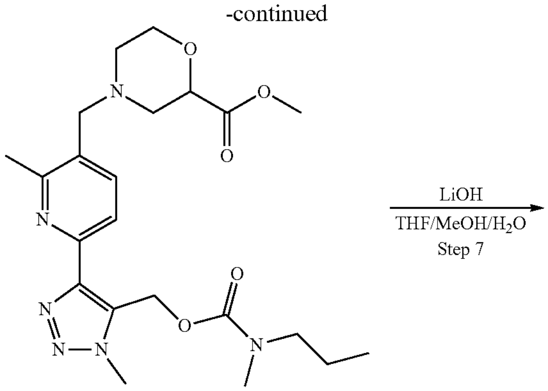

7

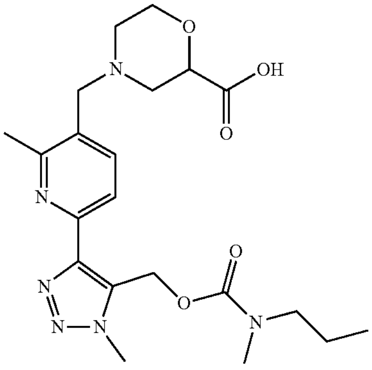

Example 166

Step 1: methyl 6-(5-(hydroxymethyl)-1-methyl-1H-1,2,3-triazol-4-yl)-2-methylnicotinate To a solution of methyl 2-methyl-6-(1-methyl-5-(((tetra-hydro-2H-pyran-2-yl)oxy)methyl)-1H-1,2,3-triazol-4-yl) nicotinate (500 mg, 1.44 mmol) in MeOH (10 mL) was added PPTS (181 mg, 0.72 mmol) and the mixture was stirred at 50° C. for 3 hrs. The mixture was diluted with EtOAc (20 mL), washed with saturated aq·$NaHCO_3$ solution and brine, dried over anhydrous $Na_2SO_4$, filtered and concentrated under reduced pressure to dryness. The residue was purified by flash chromatography (silica gel, 0~50% EtOAc in PE) to give the title compound (290 mg, 76.6% yield) as white solid. LC/MS (ESI) (m/z): 379 $(M+H)^+$.

Step 2: methyl 2-methyl-6-(1-methyl-5-((((4-nitrophenoxy)carbonyl)oxy)methyl)-1H-1,2,3-triazol-4-yl) nicotinate To a solution of methyl 6-(5-(hydroxymethyl)-1-methyl-1H-1,2,3-triazol-4-yl)-2-methylnicotinate (290 mg, 1.1 mmol) in DCM (10 mL) was added pyridine (1.47 g, 5.53 mmol) followed by 4-Nitrophenyl chloroformate (669 mg, 3.32 mmol) at 0° C. and the mixture was stirred at r.t. for 3 hrs. The solvent was removed to give the title compound (450 mg, 95.2% yield) as yellow oil, which was used directly in the next step. LC/MS (ESI) (m/z): 428 $(M+H)^+$.

Step 3: methyl 2-methyl-6-(1-methyl-5-(((methyl (propyl)carbamoyl)oxy)methyl)-1H-1,2,3-triazol-4-yl)nicotinate To a solution of methyl 2-methyl-6-(1-methyl-5-((((4-nitrophenoxy)carbonyl)oxy)methyl)-1H-1,2,3-triazol-4-yl)

nicotinate (450 mg, 1.05 mmol) in THE (10 mL) was added DIPEA (0.52 ml, 3.16 mmol) followed by methyl (propyl) amine (154 mg, 2.10 mmol) and the mixture was stirred at r.t. for 2 hrs. The mixture was diluted with EtOAc (20 mL), washed 1N aq·NaOH solution and brine, dried over anhydrous $Na_2SO_4$, filtered and concentrated under reduced pressure to dryness. The residue was purified by flash chromatography (silica gel, 0~60% EtOAc in PE) to give the title compound (320 mg, 84.1% yield) as yellow oil. LC/MS (ESI) (m/z): 362 $(M+H)^+$.

Step 4: (4-(5-(hydroxymethyl)-6-methylpyridin-2-yl)-1-methyl-1H-1,2,3-triazol-5-yl)methyl methyl (propyl)carbamate To a solution of methyl 2-methyl-6-(1-methyl-5-(((methyl (propyl)carbamoyl)oxy)methyl)-1H-1,2,3-triazol-4-yl)nicotinate (320 mg, 0.89 mmol) in THE (20 mL) was added $LiBH_4$ (1.11 mL, 2.21 mmol, 2M in THF) drop-wisely at 0° C. After addition, the reaction was stirred at 55° C. for 3 hrs. The mixture was poured into saturated aq·$NH_4Cl$ solution and extracted with EtOAc (2×20 mL). The combined organic layers were washed with brine, dried over anhydrous $Na_2SO_4$, filtered and concentrated under reduced pressure to dryness. The residue was purified by flash chromatography (silica gel, 0~50% EtOAc in PE) to give the title compound (250 mg, 84.7% yield) as yellow oil. LC/MS (ESI) (m/z): 334 $(M+H)^+$.

Step 5: (4-(5-formyl-6-methylpyridin-2-yl)-1-methyl-1H-1,2,3-triazol-5-yl)methyl methyl(propyl) carbamate To a solution of (4-(5-(hydroxymethyl)-6-methylpyridin-2-yl)-1-methyl-1H-1,2,3-triazol-5-yl)methyl methyl (propyl)carbamate (250 mg, 0.75 mmol) in DCM (10 mL) was added Dess-Martin periodinane (477 mg, 1.12 mmol) at 0° C. The reaction was stirred at r.t. for 3 hrs. The mixture was washed with saturated aq·$NaHCO_3$ solution and brine, dried over anhydrous $Na_2SO_4$, filtered and concentrated under reduced pressure to dryness. The residue was purified by flash chromatography (silica gel, 0~30% EtOAc in PE) to give the title compound (180 mg, 72.4% yield) as yellow solid. LC/MS (ESI) (m/z): 332 $(M+H)^+$.

Step 6: methyl 4-((2-methyl-6-(1-methyl-5-(((methyl(propyl)carbamoyl)oxy)methyl)-1H-1,2,3-triazol-4-yl)pyridin-3-yl)methyl)morpholine-2-carboxylate To a solution of (4-(5-formyl-6-methylpyridin-2-yl)-1-methyl-1H-1,2,3-triazol-5-yl)methyl methyl(propyl)carbamate (100 mg, 0.30 mmol) in DCE (6 mL) was added methyl morpholine-2-carboxylate (87 mg, 0.60 mmol) followed by $NaBH(OAc)_3$ (191 mg, 0.90 mmol) at 0° C. and the reaction mixture was stirred at r.t. for 16 hrs. The mixture was diluted with DCM (20 mL), washed with brine, dried over anhydrous $Na_2SO_4$, filtered and concentrated under reduced pressure to dryness. The residue was purified by flash chromatography (silica gel, 0~50% EtOAc in PE) to give the title compound (30 mg, 21.6% yield) as yellow solid. LC/MS (ESI) (m/z): 461 $(M+H)^+$.

Step 7: 4-((2-methyl-6-(1-methyl-5-(((methyl (propyl)carbamoyl)oxy)methyl)-1H-1,2,3-triazol-4-yl) pyridin-3-yl)methyl)morpholine-2-carboxylic acid To a solution of methyl 4-((2-methyl-6-(1-methyl-5-(((methyl(propyl)carbamoyl)oxy)methyl)-1H-1,2,3-triazol-4-yl)pyridin-3-yl)methyl)morpholine-2-carboxylate (30 mg, 0.065 mmol) in THE (2 mL)/$H_2O$ (1 mL)/MeOH (41 mL) was added $LiOH·H_2O$ (27 mg, 0.65 mmol) and the reaction was stirred at r.t. for 2 hrs. Volatiles were removed under vacuum and the residue was diluted with $H_2O$ (5 mL). The mixture was adjusted with 1N aq·HCl to pH~4 and extracted with EtOAc (3×5 mL). The combined organic layers were washed with brine, dried over anhydrous $Na_2SO_4$, filtered and concentrated to dryness. The residue was purified by prep-HPLC (C18, 5-95%, MeCN in $H_2O$ with 0.1% HCOOH) to give the title compound (13 mg, 44.7% yield) as white solid. LC/MS (ESI) (m/z): 447 $(M+H)^+$. $^1H$ NMR (400 MHz, $CD_3OD$) δ 7.84 (d, J=7.9 Hz, 1H), 7.76 (d, J=7.9 Hz, 1H), 5.73 (s, 2H), 4.19 (s, 3H), 4.18-4.12 (m, 1H), 4.01-3.95 (m, 1H), 3.76-3.70 (m, 1H), 3.69-3.62 (m, 2H), 3.25-3.19 (m, 1H), 3.17-3.09 (m, 1H), 3.00-2.94 (m, 1H), 2.89-2.80 (m, 3H), 2.70-2.64 (m, 1H), 2.62 (s, 3H), 2.52-2.39 (m, 2H), 1.57-1.36 (m, 2H), 0.93-0.65 (m, 3H).

Example 167&168&169: (R)-2-(1-(6-(5-((4-(cyclopropylmethyl)-2H-1,2,3-triazol-2-yl)methyl)-1-methyl-1H-1,2,3-triazol-4-yl)-2-(difluoromethyl) pyridin-3-yl)piperidin-3-yl)acetic acid & (R)-2-(1-(6-(5-((5-(cyclopropylmethyl)-1H-1,2,3-triazol-1-yl) methyl)-1-methyl-1H-1,2,3-triazol-4-yl)-2-(difluoromethyl)pyridin-3-yl)piperidin-3-yl)acetic acid & (R)-2-(1-(6-(5-((4-(cyclopropylmethyl)-1H-1,2,3-triazol-1-yl)methyl)-1-methyl-11H-1,2,3-triazol-4-yl)-2-(difluoromethyl)pyridin-3-yl)piperidin-3-yl)acetic acid

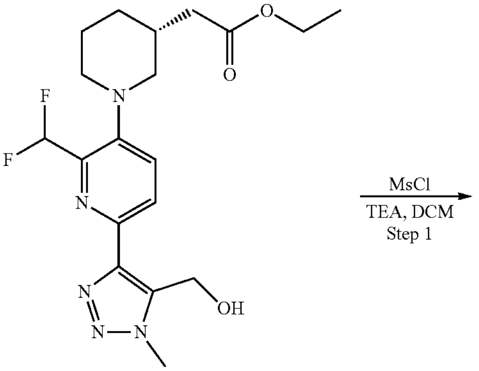

1

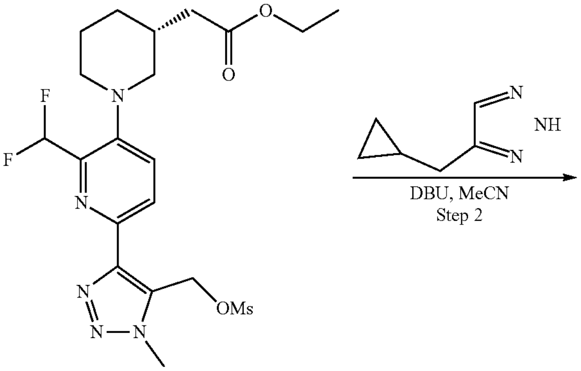

2

-continued

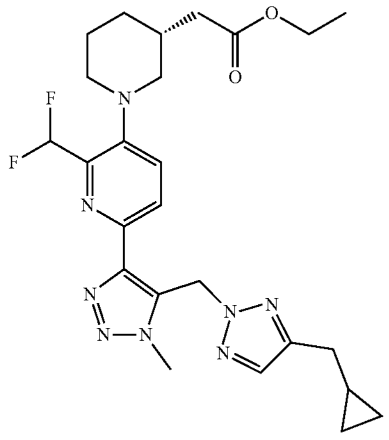

3

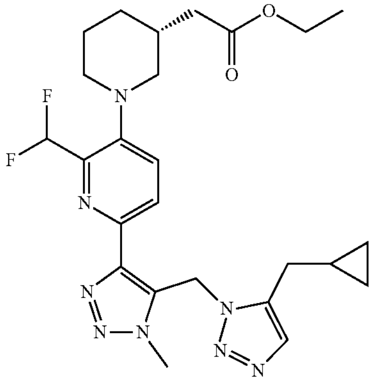

3a

+

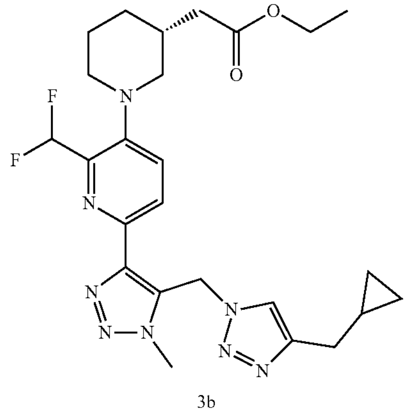

3b

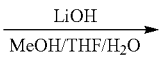

-continued

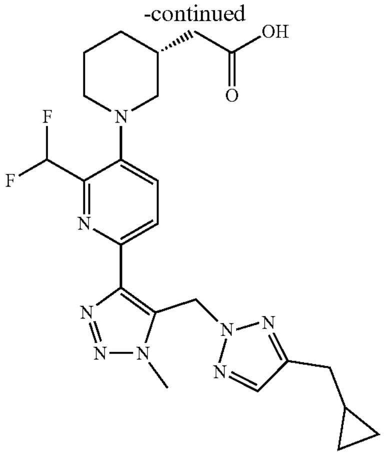

Example 167

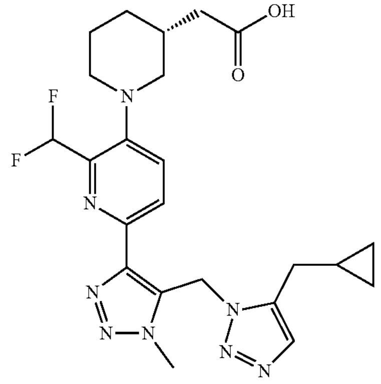

Example 168

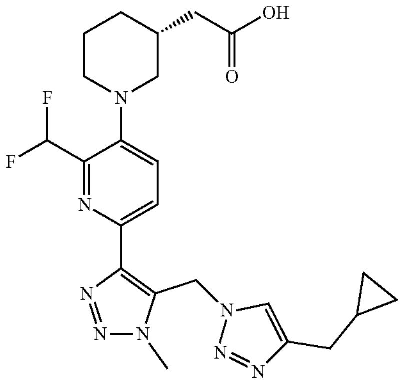

Example 169

Step 1: ethyl (R)-2-(i-(2-(difluoromethyl)-6-(i-methyl-5-(((methylsulfonyl)oxy)methyl)-ill-1,2,3-triazol-4-yl)pyridin-3-yl)piperidin-3-yl)acetate To a mixture of ethyl (R)-2-(1-(2-(difluoromethyl)-6-(5-(hydroxymethyl)-1-methyl-1H-1,2,3-triazol-4-yl)pyridin-3-yl)piperidin-3-yl)acetate (68 mg, 0.17 mmol), TEA (60 mg, 0.6 mmol) in DCM (5 mL) was added drop-wisely MsCl (28 mg, 0.25 mmol) at 0° C. After the addition, the resulting solution was stirred at r.t. for another 2 hrs. The mixture was diluted with DCM (10 mL), washed with brine, dried over anhydrous $Na_2SO_4$, filtered and concentrated to dryness to give the title compound (75 mg, 92.8% yield) as colorless oil, which was directly used in the next reaction without purification. LC-MS (ESI) m/z: 488 $(M+1)^+$.

Step 2: ethyl (R)-2-(1-(6-(5-((4-(cyclopropylmethyl)-2H-1,2,3-triazol-2-yl)methyl)-1-methyl-1H-1,2,3-triazol-4-yl)-2-(difluoromethyl)pyridin-3-yl)piperidin-3-yl)acetate (3) & ethyl (R)-2-(1-(6-(5-((5-(cyclopropylmethyl)-1H-1,2,3-triazol-1-yl)methyl)-1-methyl-11H-1,2,3-triazol-4-yl)-2-(difluoromethyl)pyridin-3-yl)piperidin-3-yl)acetate (3a) & ethyl (R)-2-(1-(6-(5-((4-(cyclopropylmethyl)-1H-1,2,3-triazol-1-yl)methyl)-1-methyl-1H-1,2,3-triazol-4-yl)-2-(difluoromethyl)pyridin-3-yl)piperidin-3-yl)acetate (3b)

To a mixture of ethyl (R)-2-(1-(2-(difluoromethyl)-6-(1-methyl-5-(((methylsulfonyl)oxy)methyl)-1H-1,2,3-triazol-4-yl)pyridin-3-yl)piperidin-3-yl)acetate (75 mg, 0.15 mmol), 4-(cyclopropylmethyl)-2H-1,2,3-triazole (19 mg, 0.15 mmol) in MeCN (2 mL) was added DBU (45.6 mg, 0.3 mmol) and the mixture was stirred in a CEM microwave reactor at 105° C. for 1 hr. The mixture was diluted with DCM (10 mL), washed with brine, dried over anhydrous $Na_2SO_4$, filtered and concentrated to dryness. The residue was purified by flash chromatography (silica gel, 0~40% of EtOAc in PE) to give compound 3 (22 mg, 27.8% yield) and a mixture of compound 3a and 3b (50 mg, 63.1% yield) as colorless oil. LC-MS(ESI) m/z: 515 (M+1)*.

Step 3: (R)-2-(1-(6-(5-((4-(cyclopropylmethyl)-2H-1,2,3-triazol-2-yl)methyl)-1-methyl-1H-1,2,3-triazol-4-yl)-2-(difluoromethyl)pyridin-3-yl)piperidin-3-yl)acetic acid To a solution of ethyl 2-[(3R)-1-[6-(5-{[4-(cyclopropylmethyl)-2H-1,2,3-triazol-2-yl]methyl}-1-methyl-1H-1,2,3-triazol-4-yl)-2-(difluoromethyl)pyridin-3-yl]piperidin-3-yl]acetate (22 mg, 0.04 mmol) in MeOH (1 mL), water (1 mL) and THE (2 mL) was added LiOH (13 mg, 0.4 mmol) and the mixture was stirred at 25° C. for 1 hr. The reaction mixture was acidified with 1M aq·HCl to pH~3 and extracted with DCM (2×3 mL). The combined organic layers were washed with brine, dried over $Na_2SO_4$, filtered and concentrated to dryness. The residue was purified by prep·HPLC to give the title compound (5.2 mg, 30.6% yield) as white solid. LC/MS (ESI) m/z: 487 $(M+1)^+$. $^1H$ NMR (400 MHz, $CD_3OD$) δ 8.00 (d, J=8.6 Hz, 1H), 7.66 (d, J=8.6 Hz, 1H), 7.36 (s, 1H), 6.91 (t, J=54.4 Hz, 1H), 6.25 (s, 2H), 3.90 (s, 3H), 3.06 (d, J=9.7 Hz, 1H), 2.97 (d, J=11.8 Hz, 1H), 2.71-2.61 (m, 1H), 2.47-2.41 (m, 1H), 2.38 (d, J=7.0 Hz, 2H), 2.16 (d, J=6.3 Hz, 2H), 2.13-2.03 (m, 1H), 1.76 (d, J=12.8 Hz, 1H), 1.72-1.58 (m, 2H), 1.13-1.00 (m, 1H), 0.89-0.76 (m, 1H), 0.38-0.30 (m, 2H), 0.06-0.03 (m, 2H).

Example 168: (R)-2-(1-(6-(5-((5-(cyclopropylmethyl)-1H-1,2,3-triazol-1-yl)methyl)-1-methyl-1H-1,2,3-triazol-4-yl)-2-(difluoromethyl)pyridin-3-yl)piperidin-3-yl)acetic acid and example 169: (R)-2-(1-(6-(5-((4-(cyclopropylmethyl)-1H-1,2,3-triazol-1-yl)methyl)-1-methyl-1H-1,2,3-triazol-4-yl)-2-(difluoromethyl)pyridin-3-yl)piperidin-3-yl)acetic acid were prepared as the same manner of example 167, the absolute configuration was confirmed by NOE.

Example 168: LC/MS (ESI) m/z: 487 $(M+1)^+$. $^1H$ NMR (400 MHz, $CD_3OD$) δ 8.22 (d, J=8.6 Hz, 1H), 7.84 (d, J=8.6 Hz, 1H), 7.63 (s, 1H), 7.13 (t, J=54.4 Hz, 1H), 6.35 (s, 2H), 4.14 (s, 3H), 3.21 (d, J=11.3 Hz, 1H), 3.16-3.07 (m, 1H), 2.83 (td, J=11.2, 3.6 Hz, 1H), 2.63-2.55 (m, 3H), 2.31 (d, J=6.5 Hz, 2H), 2.29-2.20 (m, 1H), 1.96-1.88 (m, 1H), 1.88-1.71 (m, 2H), 1.27-1.18 (m, 1H), 0.94-0.85 (m, 1H), 0.54-0.44 (m, 2H), 0.09-0.02 (m, 2H).

Example 169: LC/MS (ESI) m/z: 487 $(M+1)^+$. $^1H$ NMR (400 MHz, $CD_3OD$) δ 8.22 (t, J=4.3 Hz, 2H), 7.86 (d, J=8.6 Hz, 1H), 7.23 (t, J=54.4 Hz, 1H), 6.23 (s, 2H), 4.33 (s, 3H), 3.23 (d, J=11.3 Hz, 1H), 3.17-3.10 (m, 1H), 2.89-2.78 (m, 1H), 2.65-2.58 (m, 1H), 2.55 (d, J=7.0 Hz, 2H), 2.35-2.31 (m, 2H), 2.30-2.22 (m, 1H), 1.97-1.78 (m, 3H), 1.28-1.17 (m, 1H), 1.00-0.90 (m, 1H), 0.54-0.44 (m, 2H), 0.20-0.11 (m, 2H).

Example 170: 2-(4-(2-ethyl-6-(1-methyl-5-(((methyl(propyl)carbamoyl)oxy)methyl)-1H-1,2,3-triazol-4-yl)pyridin-3-yl)morpholin-2-yl)acetic acid

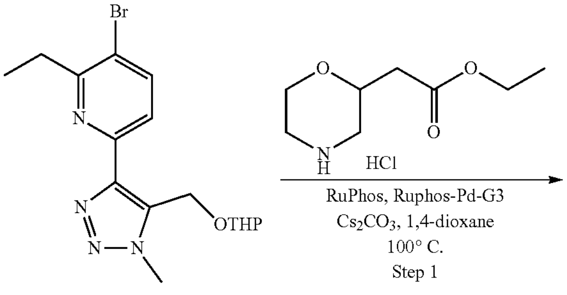

1

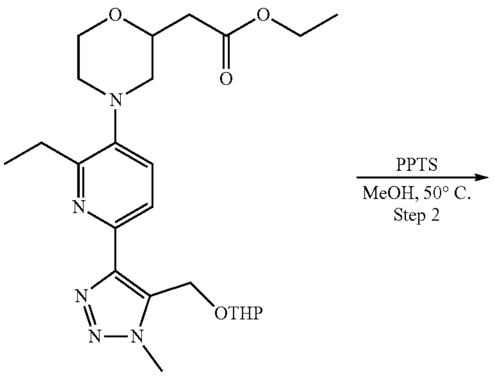

2

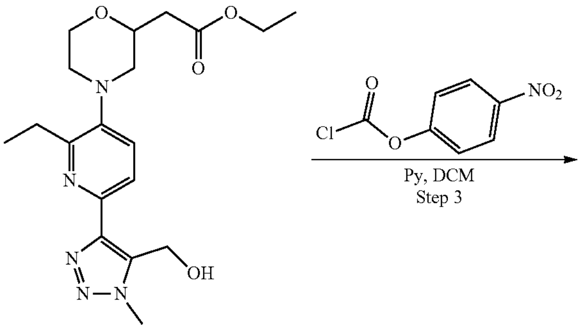

3

-continued

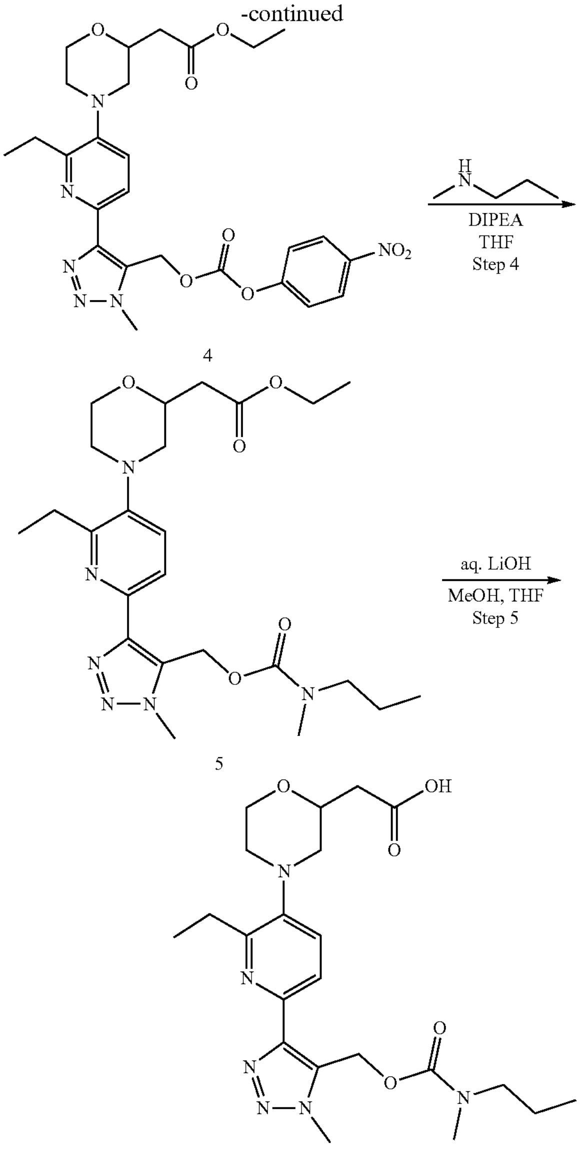

4

5

Example 170

Step 1: ethyl 2-(4-(2-ethyl-6-(1-methyl-5-(((tetrahydro-2H-pyran-2-yl)oxy)methyl)-1H-1,2,3-triazol-4-yl)pyridin-3-yl)morpholin-2-yl)acetate To a mixture of 3-bromo-2-ethyl-6-{1-methyl-5-[(oxan-2-yloxy)methyl]-1H-1,2,3-triazol-4-yl}pyridine (760 mg, 2.0 mmol), ethyl 2-[(3R)-piperidin-3-yl]acetate (210 mg, 2.0 mmol) and $Cs_2CO_3$ (1.9 g, 5.9 mmol) in 1,4-dioxane (20 mL) was added RuPhos (46 mg, 0.1 mmol) and Ruphos-Pd-G3 (80 mg, 0.1 mmol) under $N_2$ atmosphere. The resulting mixture was degassed under $N_2$ atmosphere for three times and stirred at 110° C. for 16 hrs. The reaction mixture was diluted with EtOAc (10 mL), washed with water and brine, dried over anhydrous $Na_2SO_4$, filtered and concentrated to dryness. The residue was purified by flash chromatography (silica gel, 0-30% of EtOAc in PE) to give the title compound (810 mg, 85.8% yield) as colorless oil. LC/MS (ESI) m/z: 474 $(M+H)^+$. $^1H$ NMR (400 MHz, $CDCl_3$) δ 7.99 (d, J=8.3 Hz, 1H), 7.37 (d, J=8.4 Hz, 1H), 5.52-5.31 (m, 2H), 4.76-4.71 (m, 1H), 4.20-4.16 (m, 2H), 4.15 (s, 3H), 4.03-3.96 (m, 1H), 3.92-3.83 (m, 2H), 3.51 (d, J=4.5 Hz, 1H), 3.11-3.02 (m, 1H), 2.95-2.80 (m, 4H), 2.68-2.56 (m, 2H), 2.52-2.43 (m, 1H), 1.82-1.68 (m, 3H), 1.55-1.50 (m, 3H), 1.36 (t, J=7.5 Hz, 3H), 1.28 (t, J=7.1 Hz, 3H), 1.17 (d, J=6.1 Hz, 1H), 1.01 (d, J=6.0 Hz, 1H).

Step 2: ethyl 2-(4-(2-ethyl-6-(5-(hydroxymethyl)-1-methyl-11H-1,2,3-triazol-4-yl)pyridin-3-yl)morpholin-2-yl)acetate To a mixture of ethyl 2-(4-(2-ethyl-6-(1-methyl-5-(((tetrahydro-2H-pyran-2-yl)oxy)methyl)-1H-1,2,3-triazol-4-yl)pyridin-3-yl)morpholin-2-yl)acetate (810 mg, 1.7 mmol) in MeOH (10 mL) was added PPTS (610 mg, 4 mmol) and the mixture was stirred at 60° C. for 16 hrs. The reaction mixture was diluted with DCM (20 mL), washed with saturated aq·$NaHCO_3$ solution and brine, dried over anhydrous $Na_2SO_4$, filtered and concentrated to dryness. The residue was purified by flash chromatography (silica gel, 0~50% of EtOAc in PE) to give the title compound (520 mg, 78.1% yield) as white solid. LC/MS (ESI) m/z: 390 $(M+H)^+$.

Step 3: ethyl 2-(4-(2-ethyl-6-(1-methyl-5-((((4-nitrophenoxy)carbonyl)oxy)methyl)-1H-1,2,3-triazol-4-yl)pyridin-3-yl)morpholin-2-yl)acetate To a mixture of ethyl 2-(4-(2-ethyl-6-(5-(hydroxymethyl)-1-methyl-1H-1,2,3-triazol-4-yl)pyridin-3-yl)morpholin-2-yl)acetate (60 mg, 0.15 mmol) and pyridine (200 mg, 0.75 mmol) in DCM (5 mL) was added a solution of 4-nitrophenyl chloroformate (90 mg, 0.45 mmol) in DCM (1 mL) drop-wisely at 0° C. and the mixture was stirred at r.t. for 3 hrs. The reaction mixture was diluted with DCM (10 mL), washed with water and brine, dried over anhydrous $Na_2SO_4$, filtered and concentrated to dryness to give the title compound (80 mg, 92.3% yield) as yellow solid. LC/MS (ESI) m/z: 555 $(M+H)^+$.

Step 4: ethyl 2-(4-(2-ethyl-6-(1-methyl-5-(((methyl(propyl)carbamoyl)oxy)methyl)-1H-1,2,3-triazol-4-yl)pyridin-3-yl)morpholin-2-yl)acetate To a mixture of ethyl 2-(4-(2-ethyl-6-(1-methyl-5-((((4-nitrophenoxy)carbonyl)oxy)methyl)-1H-1,2,3-triazol-4-yl)pyridin-3-yl)morpholin-2-yl)acetate (80 mg, 0.14 mmol) and DIEA (190 mg, 0.15 mmol) in THE (4 mL) was added methyl(propyl)amine (22 mg, 0.3 mmol) at 0° C. and the reaction mixture was stirred at r.t. for 2 hrs. The mixture was diluted with EtOAc (10 mL), washed with 1N aq·NaOH solution and brine, dried over anhydrous $Na_2SO_4$, filtered and concentrated to dryness to give the title compound (50 mg, 71.0% yield) as white solid. LC/MS (ESI) m/z: 489 $(M+H)^+$.

Step 5: 2-(4-(2-ethyl-6-(1-methyl-5-(((methyl(propyl)carbamoyl)oxy)methyl)-1H-1,2,3-triazol-4-yl)pyridin-3-yl)morpholin-2-yl)acetic acid To a solution of ethyl 2-[(3R)-1-{2-ethyl-6-[1-methyl-5-({[methyl(propyl)carbamoyl]oxy}methyl)-1H-1,2,3-triazol-4-yl]pyridin-3-yl}piperidin-3-yl]acetate (50 mg, 0.11 mmol) in MeOH (1 mL), water (1 mL) and THE (4 mL) was added LiOH (18 mg, 0.5 mmol) and the mixture was stirred at 25° C. for 1 hr. The mixture was concentrated to dryness and the residue was dissolved in $H_2O$ (5 mL). The mixture was washed with EtOAc twice and acidified with 1N aq·HCl to pH=3. The mixture was extracted with EtOAc (3×5 mL) and the combined organic layers were washed with brine, dried over $Na_2SO_4$, filtered and concentrated to dryness. The residue was purified by prep-HPLC to give the title compound (20.1 mg, 42.6% yield) as white solid. LC/MS (ESI) m/z: 461 $(M+H)^+$. $^1H$ NMR (400 MHz, $CD_3OD$) δ 7.84 (d, J=8.3 Hz, 1H), 7.53 (d, J=8.4 Hz, 1H), 5.76 (s, 2H), 4.18 (s, 3H), 4.15-4.08 (m, 1H), 4.00-3.94 (m, 1H), 3.88-3.80 (m, 1H), 3.22 (t, J=7.0 Hz, 1H), 3.12 (dd, J=13.0, 7.3 Hz, 2H), 2.99-2.88 (m, 4H), 2.83 (d, J=17.1 Hz, 3H), 2.66-2.58 (m, 1H), 2.57-2.46 (m, 2H), 1.59-1.49 (m, 1H), 1.42-1.33 (m, 4H), 0.78 (dt, J=74.8, 7.2 Hz, 3H).

Example 171: 2-(4-(6-(5-(((4-cyclobutylpyrimidin-2-yl)oxy)methyl)-1-methyl-1H-1,2,3-triazol-4-yl)-2-ethylpyridin-3-yl)morpholin-2-yl)acetic acid

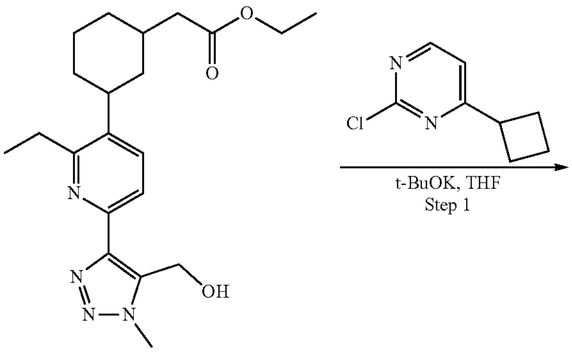

1

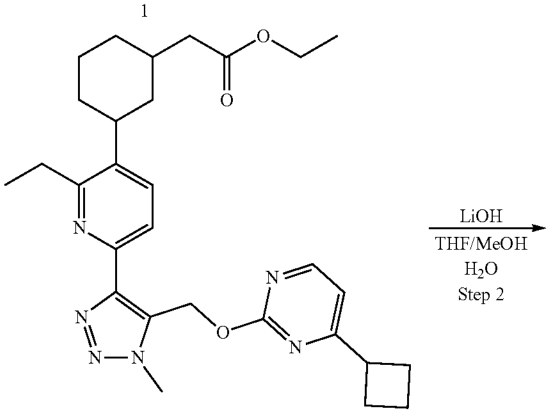

2

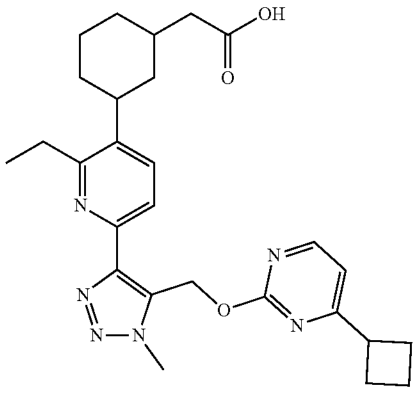

Example 171

Step 1: ethyl 2-(4-(6-(5-(((4-cyclobutylpyrimidin-2-yl)oxy)methyl)-1-methyl-1H-1,2,3-triazol-4-yl)-2-ethylpyridin-3-yl)morpholin-2-yl)acetate To a mixture of ethyl 2-(4-(2-ethyl-6-(5-(hydroxymethyl)-1-methyl-1H-1,2,3-triazol-4-yl)pyridin-3-yl)morpholin-2-yl)acetate (50 mg, 0.13 mmol) and 2-chloro-4-cyclobutylpyrimidine (32.5 mg, 0.19 mmol) in THE (2 mL) was added t-BuOK (0.26 mL, 0.26 mmol, 1M in THF) drop-wisely at 0° C. and the mixture was stirred at r.t. for 2 hrs. The mixture was quenched with ice-water and extracted with EtOAc (2×5 mL). The combined organic layers were washed with brine, dried over anhydrous $Na_2SO_4$, filtered and concentrated to dryness to give the title compound (60 mg, 89.6% yield) as yellow solid, which was used in the next step directly. LC/MS (ESI) m/z: 522 $(M+H)^+$.

Step 2: 2-(4-(6-(5-(((4-cyclobutylpyrimidin-2-yl)oxy)methyl)-1-methyl-1H-1,2,3-triazol-4-yl)-2-ethylpyridin-3-yl)morpholin-2-yl)acetic acid To a solution of ethyl 2-(4-(6-(5-(((4-cyclobutylpyrimidin-2-yl)oxy)methyl)-1-methyl-1H-1,2,3-triazol-4-yl)-2-ethylpyridin-3-yl)morpholin-2-yl)acetate (60 mg, 0.12 mmol) in THE (2 mL), MeOH (0.5 mL) and $H_2O$ (0.5 mL) was added $LiOH{\cdot}H_2O$ (24 mg, 0.6 mmol) and the mixture was stirred at r.t. for 2 hrs. The reaction mixture was concentrated to dryness and the residue was dissolved in water. The mixture was washed with EtOAc twice, acidified with 1N aq·HCl to pH=4 and extracted with EtOAc (3×3 mL). The combined organic layers were washed with brine, dried over anhydrous $Na_2SO_4$, filtered and concentrated to dryness. The residue was purified by prep-HPLC (C18, 10-95%, MeCN in $H_2O$ with 0.1% HCOOH) to give the title compound (11.9 mg, 20% yield) as white solid. LC/MS (ESI) m/z: 494 $(M+H)^+$. $^1H$ NMR (400 MHz, $CD_3OD$) δ 8.41 (d, J=5.1 Hz, 1H), 7.88 (d, J=8.4 Hz, 1H), 7.55 (d, J=8.4 Hz, 1H), 6.99 (d, J=5.1 Hz, 1H), 6.20 (s, 2H), 4.23 (s, 3H), 4.13-4.06 (m, 1H), 3.99-3.93 (m, 1H), 3.87-3.79 (m, 1H), 3.56-3.47 (m, 1H), 3.15-3.09 (m, 1H), 2.95-2.83 (m, 4H), 2.65-2.58 (m, 1H), 2.56-2.46 (m, 2H), 2.28-2.18 (m, 4H), 2.08-1.97 (m, 1H), 1.85-1.76 (m, 1H), 1.24 (t, J=7.5 Hz, 3H).

Example 172: 2-(4-(2-ethyl-6-(1-methyl-5-((2-oxo-5-propylpyridin-1(2H)-yl)methyl)-1H-1,2,3-triazol-4-yl)pyridin-3-yl)morpholin-2-yl)acetic acid

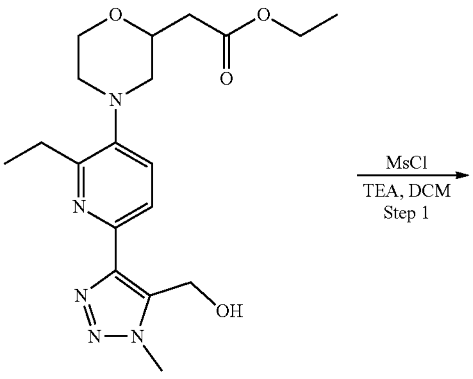

1

-continued

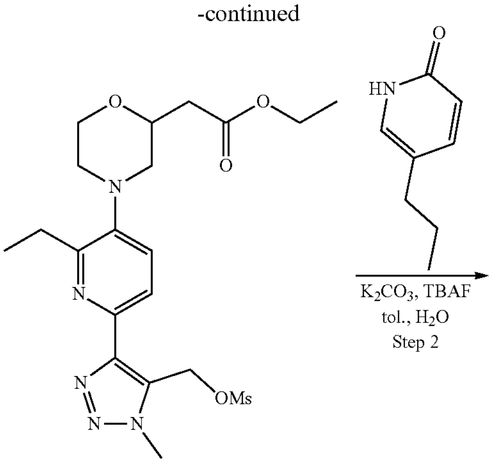

2

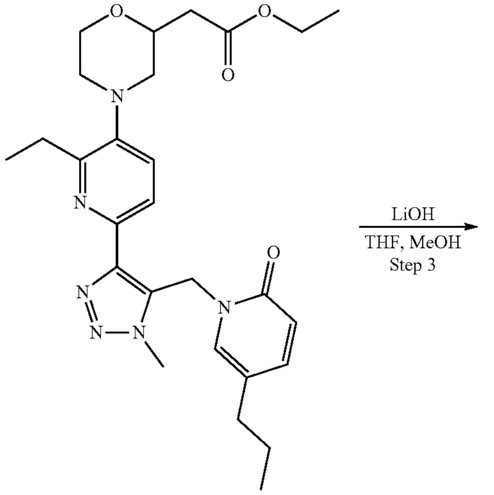

3

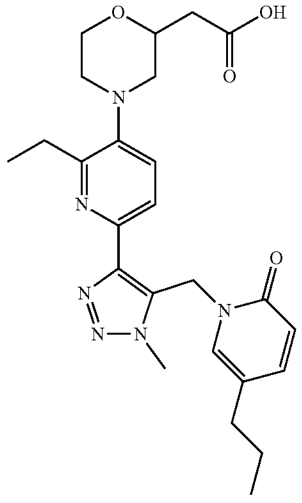

Example 172

Step 1: ethyl 2-(4-(2-ethyl-6-(1-methyl-5-(((methylsulfonyl)oxy)methyl)-1H-1,2,3-triazol-4-yl)pyridin-3-yl)morpholin-2-yl)acetate To a solution of ethyl 2-(4-(2-ethyl-6-(5-(hydroxymethyl)-1-methyl-1H-1,2,3-triazol-4-yl)pyridin-3-yl)morpholin-2-yl)acetate (60 mg, 0.154 mmol) in DCM (2 mL) was added TEA (47 mg, 0.46 mmol) followed by MsCl (35 mg, 0.3 mmol) at 0° C. and the mixture was stirred at r.t. for 2 hrs. The mixture was diluted with DCM (5 mL), washed with saturated aq·$NaHCO_3$ solution and brine, dried over $Na_2SO_4$, filtered and concentrated to dryness to give the title compound (59 mg, 81.9% yield) as yellow solid, which was directly used in the next reaction without purification. LC/MS (ESI) m/z: 468 $(M+H)^+$.

Step 2: ethyl 2-(4-(2-ethyl-6-(1-methyl-5-((2-oxo-5-propylpyridin-1(2H)-yl)methyl)-1H-1,2,3-triazol-4-yl)pyridin-3-yl)morpholin-2-yl)acetate To a solution of ethyl 2-(4-(2-ethyl-6-(1-methyl-5-(((methylsulfonyl)oxy)methyl)-1H-1,2,3-triazol-4-yl)pyridin-3-yl)morpholin-2-yl)acetate (59 mg, 0.13 mmol) in toluene (3 mL) and $H_2O$ (0.5 mL) was added 5-propyl-1,2-dihydropyridin-2-one (35 mg, 0.25 mmol), $K_2CO_3$ (52 mg, 0.38 mmol) and TBAF (5 mg, cat.) and the mixture was stirred at 110° C. for 3 hrs. The mixture was diluted with EtOAc (5 mL), washed with water and brine, dried over $Na_2SO_4$, filtered and concentrated to dryness to give the title compound (55 mg, 85.7% yield) as yellow solid, which was directly used in the next step. LC/MS (ESI) m/z: 509 $(M+H)^+$.

Step 3: 2-[(2R)-4-(2-ethyl-6-{1-methyl-5-[(2-oxo-5-propyl-1,2-dihydropyridin-1-yl)methyl]-1H-1,2,3-triazol-4-yl}pyridin-3-yl)morpholin-2-yl]acetic acid To a solution of ethyl 2-(4-(2-ethyl-6-(1-methyl-5-((2-oxo-5-propylpyridin-1(2H)-yl)methyl)-1H-1,2,3-triazol-4-yl)pyridin-3-yl)morpholin-2-yl)acetate (55 mg, 0.11 mmol) in THF (4 mL) was added MeOH (1 mL), water (1 mL), LiOH (26 mg, 1.08 mmol) and the mixture was stirred at 25° C. for 1 hr. The reaction mixture was concentrated to dryness and the residue was dissolved in $H_2O$ (5 mL). The mixture was acidified with 1N aq·HCl to pH~4 and extracted with EtOAc (3x3 mL). The combined organic layers were washed with brine, dried over anhydrous $Na_2SO_4$, filtered and concentrated to dryness. The residue was purified by pre·HPLC to give the title compound (20 mg, 38.5% yield) as white solid. LC/MS (ESI) m/z: 481 $(M+H)^+$. $^1H$ NMR (400 MHz, $CD_3OD$) δ 7.90 (d, J=8.4 Hz, 1H), 7.69-7.65 (m, 1H), 7.61 (d, J=8.4 Hz, 1H), 7.44-7.37 (m, 1H), 6.54 (d, J=9.2 Hz, 1H), 5.89 (s, 2H), 4.17 (s, 3H), 4.15-4.10 (m, 1H), 4.03-3.97 (m, 1H), 3.91-3.83 (m, 1H), 3.20-3.12 (m, 1H), 3.04-2.93 (m, 4H), 2.69-2.61 (m, 1H), 2.59-2.50 (m, 2H), 2.23 (t, J=7.5 Hz, 2H), 1.41-1.32 (m, 5H), 0.78 (t, J=7.3 Hz, 3H).

Biological Assays

LPA1 Calcium Flux Assays

The effectiveness of compounds of the present invention as LPA1 inhibitors can be determined in an LPA1 functional antagonist assay as follows:

PathHunter® CHO-K1 EDG2 β-Arrestin Cell Line (Eurofins DiscoverX Corporation, Cat #93-0644$C_2$) were plated overnight (11,500 cells/well) in poly-D-lysine coated 384-well microplates (Corning, Cat #356697) in AssayComplete™ Cell Plating 35 Reagent (Eurofins DiscoverX Corporation, Cat #93-0563R35). Following overnight culture, cells were loaded with calcium indicator dye from the HitHunter Calcium No WashPLUS Assay kit (Eurofins DiscoverX Corporation, Cat #93-0091) for 45 minutes at 37° C. Test compounds solubilized in DMSO (Sigma, Cat #276855) on 384-well polypropylene microplates (Greiner bio-one, Cat #781280) were then diluted to intermediate concentration with assay buffer [1×HBSS calcium/magnesium (Corning, Cat #21-023-CM) and 20 mM HEPES (Corning, Cat #25-060-C1)]before addition to cells by Agilent Velocity 11 with a final concentration of 0.4% DMSO. After compound addition, assay plates were equilibrated to room temperature for 30 minutes. Cells were then stimulated by addition of EC80 concentration of LPA (Cat #, 10010093) in assay buffer containing [1×HBSS calcium/magnesium (Corning, Cat #21-023-CM), 20 mM HEPES (Corning, Cat #25-060-C1), and 0.1% BSA (Sigma, Cat #A8806)] using Molecular Devices FLIPR Tetra PLUS©. IC50 values were determined by Chemical and Biological Information System from ChemInnovation Software, Inc.

The compounds of this invention were tested for their activity to inhibit LPA1 as determined in an LPA1 functional antagonist assay as described herein. Results of LPA1 assay are given in Table 1.

TABLE 1

Activity data in LPA1 assay*

| Example No. | LPA1 $IC_{50}$ |
|---|---|
| 1 | C |
| 2 | C |
| 3 | C |
| 4 | B |
| 5 | D |
| 6 | A |
| 7 | C |
| 8 | D |
| 9 | D |
| 10 | B |
| 11 | D |
| 12 | A |
| 13 | A |
| 14 | A |
| 15 | A |
| 16 | A |
| 17 | A |
| 18 | C |
| 19 | D |
| 20 | D |
| 21 | C |
| 22 | B |
| 23 | D |
| 24 | A |
| 25 | B |
| 26 | B |
| 27 | C |
| 28 | C |
| 29 | B |
| 30 | C |
| 31 | D |
| 32 | C |
| 33 | D |
| 34 | C |
| 35 | B |
| 36 | B |
| 37 | D |
| 38 | D |
| 39 | C |
| 40 | C |
| 41 | B |
| 42 | C |
| 43 | D |
| 44 | D |
| 45 | B |
| 46 | D |
| 47 | D |
| 48 | D |
| 49 | D |
| 50 | D |
| 51 | D |
| 52 | C |
| 53 | D |
| 54 | D |
| 55 | D |
| 56 | D |
| 57 | D |
| 58 | A |
| 59 | A |
| 60 | A |
| 61 | C |
| 62 | C |
| 63 | B |
| 64 | C |
| 65 | D |
| 66 | A |
| 67 | B |
| 68 | C |
| 69 | C |
| 70 | D |
| 71 | D |
| 72 | D |
| 73 | D |
| 74 | A |
| 75 | C |
| 76 | A |
| 77 | B |
| 78 | A |
| 79 | A |
| 80 | A |
| 81 | D |
| 82 | A |
| 83 | B |
| 84 | A |
| 85 | A |
| 86 | B |
| 87 | A |
| 88 | B |
| 89 | A |
| 90 | A |
| 91 | D |
| 92 | D |
| 93 | B |
| 94 | C |
| 95 | A |
| 96 | B |
| 97 | B |
| 98 | B |
| 99 | A |
| 100 | B |
| 101 | A |
| 102 | A |
| 103 | A |
| 104 | A |
| 105 | A |
| 106 | D |
| 107 | D |
| 108 | C |
| 109 | C |
| 110 | D |
| 111 | D |
| 112 | C |
| 113 | C |
| 114 | D |
| 115 | D |
| 116 | A |
| 117 | B |
| 118 | D |
| 119 | B |
| 120 | C |
| 121 | C |
| 122 | B |
| 123 | B |
| 124 | A |
| 125 | A |
| 126 | B |
| 127 | B |
| 128 | B |

TABLE 1-continued

| Activity data in LPA1 assay* | |
|---|---|
| Example No. | LPA1 $IC_{50}$ |
| 129 | A |
| 130 | A |
| 131 | B |
| 132 | A |
| 133 | B |
| 134 | B |
| 135 | D |
| 136 | B |
| 137 | B |
| 138 | B |
| 139 | B |
| 140 | B |
| 141 | B |
| 142 | B |
| 143 | A |
| 144 | C |
| 145 | C |
| 146 | D |
| 147 | A |
| 148 | A |
| 149 | B |
| 150 | B |
| 151 | C |
| 152 | A |
| 153 | C |
| 154 | B |
| 155 | C |
| 156 | B |
| 157 | C |
| 158 | D |
| 159 | D |
| 160 | C |
| 161 | C |
| 162 | A |
| 163 | B |
| 164 | D |
| 165 | B |
| 166 | D |
| 167 | A |
| 168 | A |
| 169 | B |
| 170 | C |
| 171 | A |
| 172 | C |

*A: <100 nM; B: 100~500 nM; C: 500~ 000 nM; D: 5000 nM~0 μM

We claim:

1. A compound of formula (I), (I)

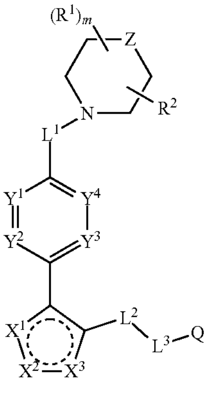

or a pharmaceutically acceptable salt, tautomer or stereoisomer thereof, wherein:

$L^1$ is a covalent bond or $CH_2$ optionally substituted with 1 or 2 methyl groups;

$L^2$ is a covalent bond or $(CR^7R^7)_p$;

$L^3$ is a covalent bond, O or $NR^7$, provided that at least one of $L^2$ and $L^3$ is not a covalent bond;

Q is $C(=O)NR^9R^{10}$, $C(=O)OR^{10}$, or a ring selected from a 5- or 6-membered heteroaryl group or a 5- or 6-membered heterocyclyl group, wherein the ring comprises at least one carbon atom, at least one nitrogen atom, and optionally 1-4 additional heteroatoms selected from nitrogen, oxygen and sulfur wherein oxygen may be a ring member and/or an oxo group attached to a ring member, and wherein the ring is substituted with $(R^3)_n$ and one $R^4$;

$X^1$ is N, O or $CR^{6a}$;

$X^2$ is N or $NR^6$;

$X^3$ is N, $NR^6$ or $CR^6$, wherein the dashed circle denotes bonds forming a five-membered aromatic ring;

$Y^1$, $Y^2$, $Y^3$ and $Y^4$ are each independently N or $CR^5$, provided that at least one but no more than two of $Y^1$, $Y^2$, $Y^3$ and $Y^4$ are N;

Z is $CH_2$ or O;

$R^1$ at each occurrence is independently hydrogen, halogen, $C_{1-6}$alkyl, halo$C_{1-6}$alkyl, OH, $C_{1-6}$alkyl-OH, $C_{1-6}$alkoxy, halo$C_{1-6}$alkoxy, CN, $C_{3-7}$cycloalkyl, $NR^aR^b$, $C_{1-6}$alkyl-$NR^aR^b$, or 4-6-membered heterocylyl, or two $R^1$ groups, together with the carbon atom to which they are attached, form C=O;

$R^2$ is $(CR^7R^7)_q$—$R^8$;

$R^3$ at each occurrence is independently hydrogen, halogen, CN, $C_{1-6}$alkyl, or $C_{3-7}$cycloalkyl;

$R^4$ is independently hydrogen, halogen, $C_{1-6}$alkyl, halo$C_{1-6}$ alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, $(CH_2)_q$-5-6-membered heteroaryl ring substituted with 1-4 $R^{11}$, $(CH_2)_q$-5-7-membered heterocyclyl ring substituted with 1-4 $R^{11}$, in which each phenyl is independently optionally substituted with 1-3 of halogen, $C_{1-6}$alkyl, or $C_{1-6}$alkoxy;

$R^5$ at each occurrence is independently hydrogen, halogen, $C_{1-6}$alkyl, halo$C_{1-6}$alkyl, OH, $C_{1-6}$alkyl-OH, $C_{1-6}$alkoxy, $C_{1-6}$alkyl-$C_{1-6}$alkoxy, halo$C_{1-6}$alkoxy, CN, $C_{3-7}$cycloalkyl, $NR^aR^b$, or $C_{1-6}$alkyl-$NR^aR^b$;

each occurrence of $R^{6a}$ and $R^6$ is independently hydrogen, halogen, CN, methyl, ethyl, propyl, or cyclopropyl;

$R^7$ at each occurrence is independently hydrogen, $C_{1-4}$alkyl, $C_{3-5}$cycloalkyl, or two $R^7$ groups together with the carbon atom to which they are attached, form a 3-5-membered cycloalkyl ring;

$R^8$ is $C(=O)OR^7$, $C(=O)NR^aR^b$, CN, $C(=O)NHC(=O)R^7$, $C(=O)NHS(=O)_2R^7$, $C(=O)NHS(=O)R^7$, $S(=O)_2R^7$, $P(=O)(OH)_2$, or

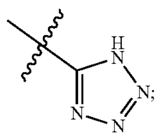

each occurrence of $R^9$ and $R^{10}$ is independently hydrogen, $C_{1-6}$alkyl substituted with 1-4 $R^{11}$, $(CR^{12}R^{12})_q$—$C_{2-6}$ alkenyl substituted with 1-4 $R^{11}$, $(CR^{12}R^{12})_q$—$C_{2-6}$ alkynyl substituted with 1-4 $R^{11}$, $(CR^{12}R^{12})_q$—$C_{3-7}$ cycloalkyl substituted with 1-4 $R^{11}$, $(CR^{12}R^{12})_q$-phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$; or $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur;

$R^{11}$ at each occurrence is independently hydrogen, $C_{1-6}$alkyl, halo$C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy;

$R^{12}$ at each occurrence is independently hydrogen, $C_{1-4}$alkyl, $C_{3-7}$cycloalkyl, or two $R^{12}$ groups, together with the carbon atom to which they are attached, form a 3-6-membered cycloalkyl ring;

each occurrence of $R^a$ and $R^b$ is independently hydrogen or $C_{1-6}$alkyl, or $R^a$ and $R^b$, together with the nitrogen atom to which they are attached, form a saturated or unsaturated heterocyclic ring containing from three to seven ring atoms, which ring may optionally contain additional one or two heteroatoms selected from the group consisting of nitrogen, oxygen and sulfur and may be optionally substituted by from one to three groups which may be the same or different selected from the group consisting of $C_{1-4}$alkyl, phenyl and benzyl;

m is 1, or 2;

n is 0, 1, or 2;

p at each occurrence is independently 1, 2, 3 or 4; and q at each occurrence is independently 0, 1, 2, 3 or 4.

2. The compound of claim 1, wherein Z is $CH_2$.

3. The compound of claim 1, wherein Z is O.

4. The compound of claim 1, wherein $L^1$ is a covalent bond.

5. The compound of claim 1, wherein $L^1$ is $CH_2$ optionally substituted with 1 or 2 methyl groups.

6. The compound of claim 1, wherein $L^1$ is $CH_2$.

7. The compound of claim 1, wherein each occurrence of $R^1$ is independently hydrogen.

8. The compound of claim 1, wherein each occurrence of $R^1$ is independently halogen.

9. The compound of claim 1, wherein m is 2, one $R^1$ is hydrogen, and the other $R^1$ is halogen.

10. The compound of claim 1, wherein m is 2, one $R^1$ is hydrogen, and the other $R^1$ is F.

11. The compound of claim 1, wherein m is 2, each occurrence of $R^1$ is F.

12. The compound of claim 1, wherein $Y^2$ is N, and each of $Y^1$, $Y^3$ and $Y^4$ is independently $CR^5$.

13. The compound of claim 1, wherein $Y^1$ is $CR^5$, $Y^2$ is N, and each of $Y^3$ and $Y^4$ is independently CH.

14. The compound of claim 1, wherein $Y^1$ is $CR^5$, $Y^2$ is N, $Y^3$ is N, and $Y^4$ CH.

15. The compound of claim 1, wherein $R^5$ at each occurrence is independently hydrogen, methyl or ethyl.

16. The compound of claim 1, wherein $R^5$ at each occurrence is independently hydrogen, $CHF_2$ or $CF_3$.

17. The compound of claim 1, wherein $R^5$ at each occurrence is independently hydrogen, or CN.

18. The compound of claim 1, wherein $X^1$ is N, $X^2$ is N, and $X^3$ is $NR^6$.

19. The compound of claim 1, wherein $X^1$ is CH, $X^2$ is N, and $X^3$ is $NR^6$.

20. The compound of claim 1, wherein $X^1$ is 0, $X^2$ is N, and $X^3$ is $CR^6$.

21. The compound of claim 1, wherein $R^6$ is methyl.

22. The compound of claim 1, wherein $L^2$ is a covalent bond.

23. The compound of claim 1, wherein $L^2$ is $(CR^7R^7)_p$.

24. The compound of claim 1, wherein $L^2$ is $CH_2$.

25. The compound of claim 1, wherein $L^3$ is a covalent bond.

26. The compound of claim 1, wherein $L^3$ is O.

27. The compound of claim 1, wherein $L^3$ is $NR^7$.

28. The compound of claim 1, wherein q is 0.

29. The compound of claim 1, wherein q is 1.

30. The compound of claim 1, wherein q is 2.

31. The compound of claim 1, wherein $R^8$ is COOH.

32. The compound of claim 1, wherein $R^9$ is $C_{1-4}$alkyl.

33. The compound of claim 1, wherein $R^{10}$ is $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$ phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$.

34. The compound of claim 1, wherein $R^{10}$ is $C_{1-6}$alkyl.

35. The compound of claim 1, wherein $R^{10}$ is $(CH_2)_p$—$C_{3-7}$cycloalkyl.

36. The compound of claim 1, wherein $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur.

37. The compound of claim 1, wherein Q is C(═O)$NR^9R^{10}$.

38. The compound of claim 1, wherein Q is a ring selected from 5-membered heteroaryl or heterocyclyl and 6-membered heteroaryl or heterocyclyl, wherein the ring comprises at least on carbon atom, at least one nitrogen atom and optionally 1-3 heteroatoms selected from nitrogen, oxygen and sulfur wherein oxygen may be a ring member and/or a carbonyl attached to a ring member, and wherein the ring is substituted with $(R^3)_n$ and $R^4$.

39. The compound of claim 1, wherein Q is:

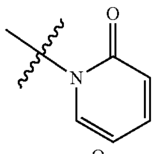,
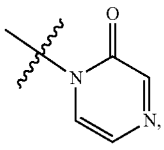,
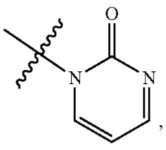,
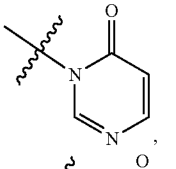,
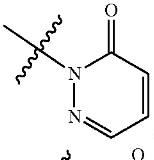,
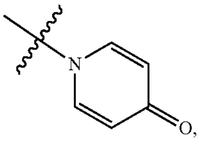,
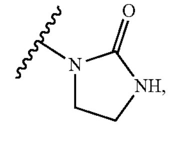,
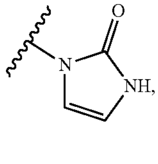,
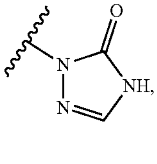, -continued

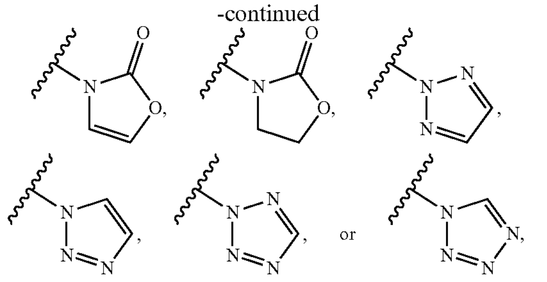

each of which is substituted with $(R^3)_n$ and one $R^4$ at any available carbon or nitrogen position.

40. The compound of claim 38, wherein Q is:

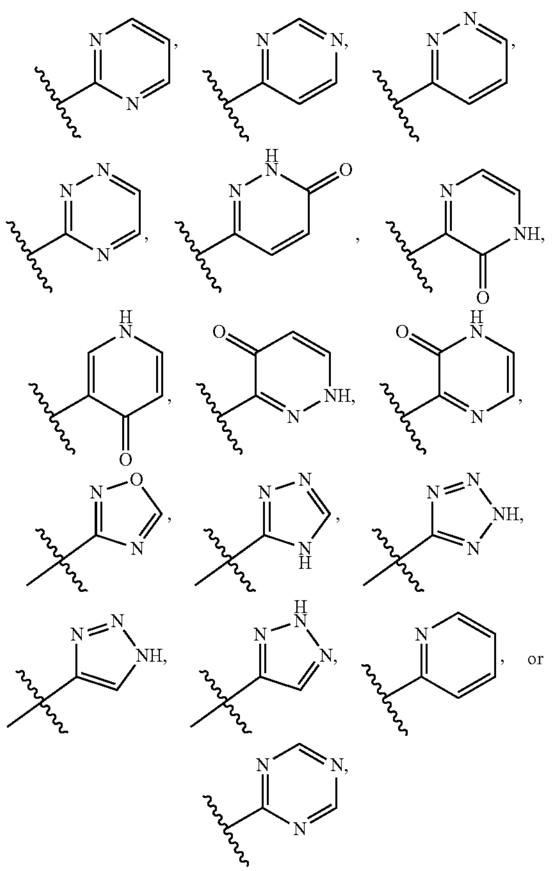

each of which is substituted with $(R^3)_8$ and one $R^4$ at any available carbon or nitrogen position.

41. The compound of claim 1, wherein each occurrence of $R^3$ is independently hydrogen, halogen, or $C_{1-4}$alkyl.

42. The compound of claim 1, wherein each occurrence of $R^3$ is independently $C_{1-4}$alkyl.

43. The compound of claim 1, wherein each occurrence of $R^3$ is independently methyl.

44. The compound of claim 1, wherein $R^4$ is independently hydrogen, $C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy.

45. The compound of claim 1, wherein $R^4$ is independently $(CH_2)_q$-5-6-membered heteroaryl ring substituted with 1-4 $R^{11}$, or $(CH_2)_q$-5-7-membered heterocyclyl ring substituted with 1-4 $R^{11}$.

46. The compound of claim 1, wherein $R^4$ is independently $C_{1-6}$alkyl, $C_{2-6}$alkynyl, $C_{1-6}$alkoxy, $(CH_2)_p$—$C_{1-6}$ alkoxy, $C_{3-7}$cycloalkyl, $(CH_2)_p$—$C_{3-7}$cycloalkyl, or $C_{2-6}$alkenyl-$C_{3-7}$cycloalkyl.

47. The compound of claim 1, having a structure of Formula (II), (II)

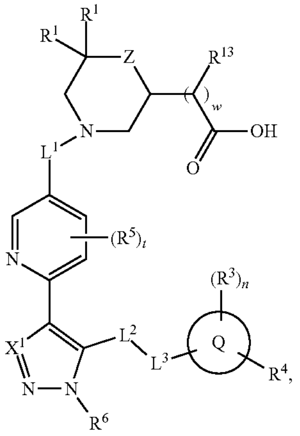

wherein:

Q is a ring selected from the group consisting of 5-membered heteroaryl, 5-membered heterocyclyl, 6-membered heteroaryl, and 6-membered heterocyclyl, wherein the ring comprises at least one carbon atom, at least one nitrogen atom and optionally 1-4 additional heteroatoms selected from the group consisting of nitrogen, oxygen and sulfur wherein oxygen may be a ring member and/or an oxo attached to a ring member, and wherein the ring is substituted with $(R^3)_n$ and one $R^4$;

X1 is N, or CR6a;

$R^{6a}$ is hydrogen, or methyl;

$R^6$ is hydrogen, halogen, CN, methyl, ethyl, propyl, or cyclopropyl;

$R^{13}$ at each occurrence is independently hydrogen, $C_{1-4}$alkyl, or $C_{3-5}$cycloalkyl; and t is 0, 1, 2 or 3; and w is 0 or 1, provided that when $L^1$ is a covalent bond, w is 1; and further provided that when $L_1$ is $CH_2$ optionally substituted with 1 or 2 methyl groups, w is 0.

48. The compound of claim 47, wherein the moiety

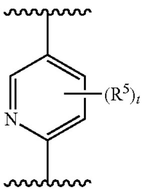

is

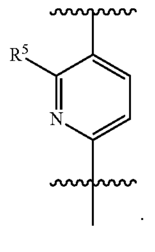

49. The compound of claim 47, wherein each $R^5$ is independently hydrogen, halogen, $C_{1-6}$alkyl or halo$C_{1-6}$alkyl.

50. The compound of claim 47, wherein each $R^5$ is independently $C_{1-6}$alkyl.

51. The compound of claim 47, wherein each $R^5$ is independently methyl or ethyl.

52. The compound of claim 47, wherein each $R^5$ is independently $CHF_2$ or $CF_3$.

53. The compound of claim 47, wherein $X^1$ is N or CH.

54. The compound of claim 47, wherein $R^6$ is methyl.

55. The compound of claim 47, wherein $L^2$ is a $(CR^7R^7)_p$ or $CH_2$.

56. The compound of claim 47, wherein $L^3$ is a covalent bond, O or $NR^7$.

57. The compound of claim 47, wherein Q is:

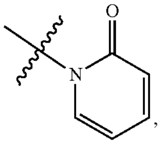, 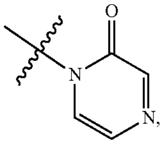, 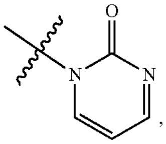, 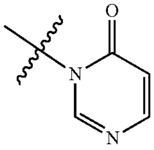, 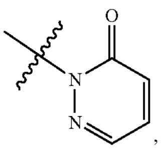, 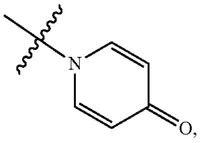, 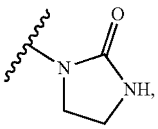, 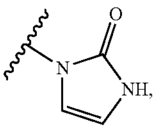, 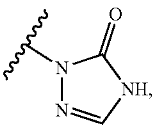, 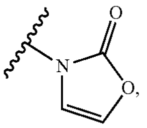, 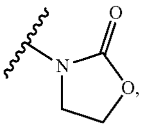, 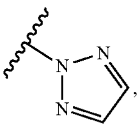, 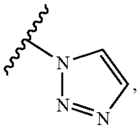, 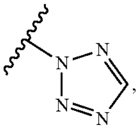, or 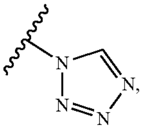, each of which is substituted with $(R^3)_n$ and one $R^4$ at any available carbon or nitrogen position, and n is 0, 1 or 2.

58. The compound of claim 57, wherein Q is

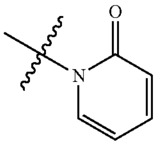 [SMILES: *n1ccccc1=O]

substituted with $(R^3)_n$ and one $R^4$ at any available carbon or nitrogen position, and n is 0, 1 or 2.

59. The compound of claim 57, wherein Q is:

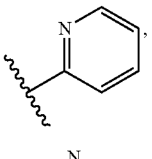, 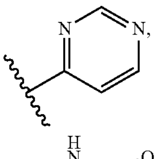, 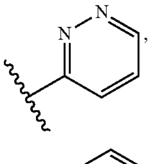, 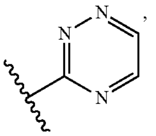, 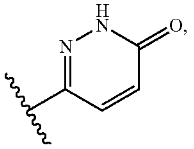, 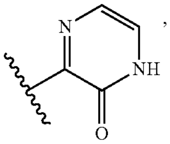, 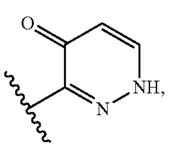, 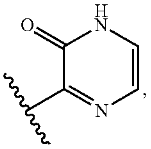, 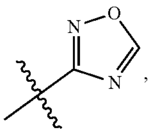, 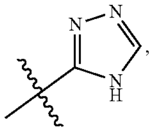, 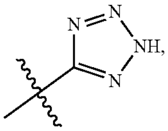, 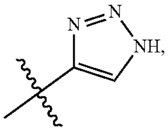, 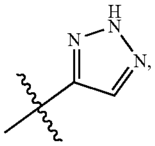, 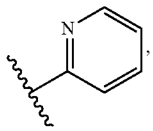, or 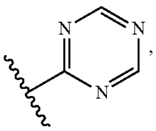, each of which is substituted with $(R^3)_n$ and one $R^4$ at any available carbon or nitrogen position, and n is 0, 1 or 2.

60. The compound of claim 47, wherein each occurrence of $R^3$ is independently hydrogen, halogen, or $C_{1-4}$alkyl.

61. The compound of claim 47, wherein $R^4$ is independently hydrogen, $C_{1-6}$alkyl, $C_{2-6}$alkenyl, $C_{2-6}$alkynyl, $C_{1-6}$alkoxy, $(CH_2)_p$—$C_{1-6}$alkoxy, phenyl, $(CH_2)_p$-phenyl, $O(CH_2)_p$-phenyl, CN, $C_{3-7}$cycloalkyl, $(CH_2)_p$—$C_{3-7}$cycloalkyl, $C_{2-6}$alkenyl-$C_{3-7}$cycloalkyl, $C_{2-6}$alkynyl-$C_{3-7}$cycloalkyl, $O(CH_2)_p$—$C_{3-7}$cycloalkyl, in which each phenyl is independently optionally substituted with 1-3 of halogen, $C_{1-6}$alkyl, or $C_{1-6}$alkoxy.

62. The compound of claim 47, wherein the

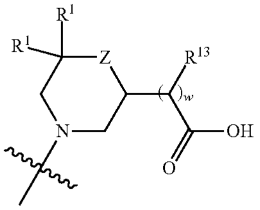

moiety is

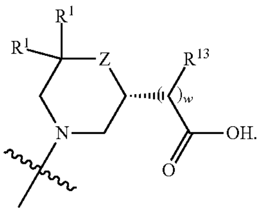

63. The compound of claim 47, wherein $R^{13}$ is hydrogen.

64. The compound of claim 47, wherein $R^{13}$ is methyl.

65. The compound of claim 47, wherein $R^{13}$ is cyclopropyl.

66. The compound of claim 1, having the structure of Formula (III), (III)

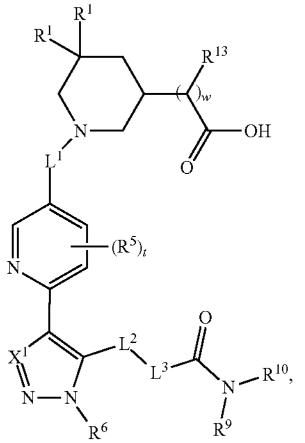

wherein:

$X^1$ is N, or $CR^{6a}$;

$R^{6a}$ is hydrogen, or methyl;

$R^6$ is hydrogen, halogen, CN, methyl, ethyl, propyl, or cyclopropyl;

$R^{13}$ at each occurrence is independently hydrogen, $C_{1-4}$alkyl, or $C_{3-5}$cycloalkyl; and t is 0, 1, 2 or 3; and w is 0 or 1, provided that when $L^1$ is a covalent bond, w is 1, and further provided that when $L^1$ is $CH_2$ optionally substituted with 1 or 2 methyl groups, w is 0.

67. The compound of claim 66, wherein $R^9$ is $C_{1-4}$alkyl.

68. The compound of claim 66, wherein $R^{10}$ is $C_{1-6}$alkyl substituted with 1-4 $R^{11}$, $(CR^{12}R^{12})_q$—$C_{2-6}$alkenyl substituted with 1-4 $R^{11}$, $(CR^{12}R^{12})_q$—$C_{2-6}$alkynyl substituted with 1-4 $R^{11}$, $(CR^{12}R^{12})_q$—$C_{3-7}$cycloalkyl substituted with 1-4 $R^{11}$, $(CR^{12}R^{12})_q$ phenyl substituted with 1-4 $R^{11}$, $(CR^{12}R^{12})_q$-5-6-membered heteroaryl ring substituted with 1-4 $R^{11}$, $(CR^{12}R^{12})_q$-5-7-membered heterocyclyl ring substituted with 1-4 $R^{11}$.

69. The compound of claim 66, wherein $R^{10}$ is $C_{1-6}$alkyl or $(CH_2)_q$—$C_{3-7}$cycloalkyl.

70. The compound of claim 66, wherein $R^9$ and $R^{10}$, together with the nitrogen atom to which they are attached, form a saturated or unsaturated 3-7-membered heterocyclic ring substituted with 1-4 $R^{11}$, which ring may optionally contain additional one or two heteroatoms selected from the group consisting of nitrogen, oxygen and sulfur.

71. The compound of claim 66, wherein the

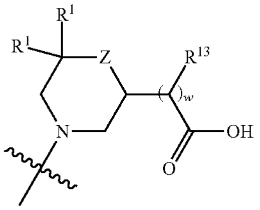

moiety is

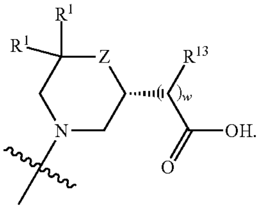

72. The compound of claim 66, wherein $R^{13}$ is hydrogen.

73. The compound of claim 66, wherein $R^{13}$ is methyl.

74. The compound of claim 66, wherein $R^{13}$ is cyclopropyl.

75. The compound of claim 1, selected from:

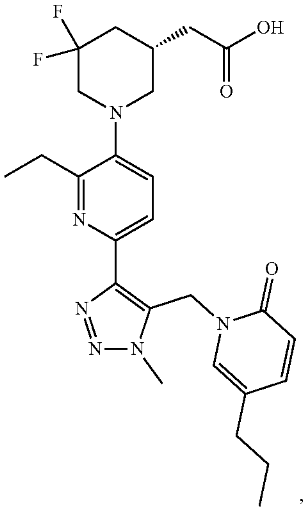

,

-continued
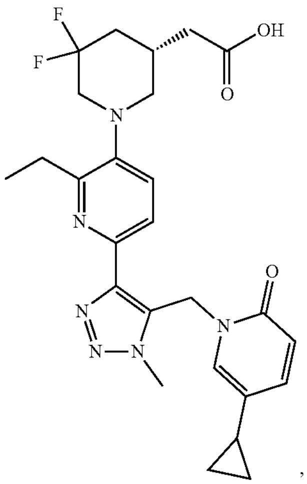
,
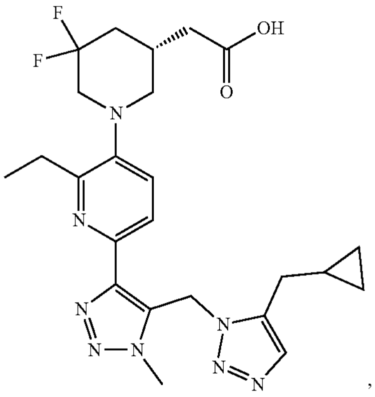
,
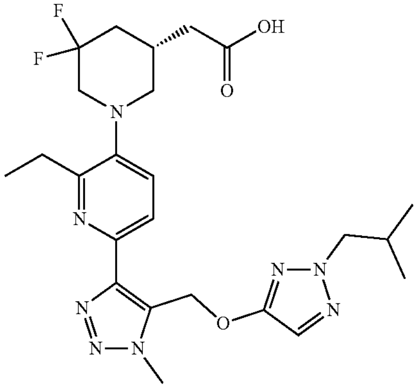
and
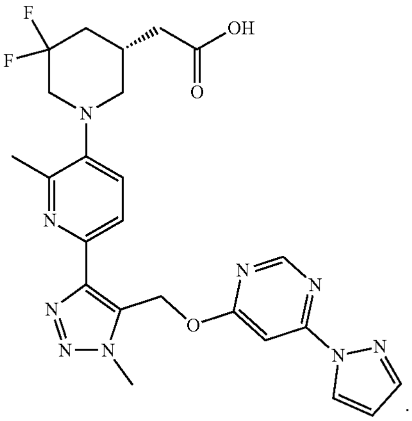
.
76. The compound of claim 1, selected from:
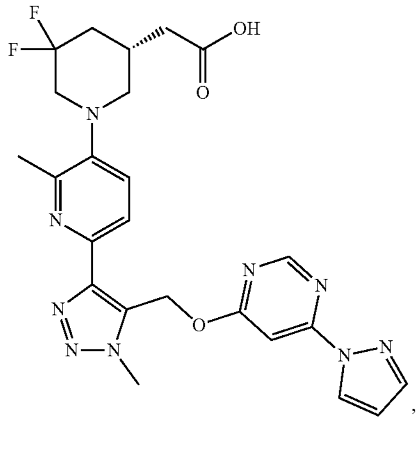
,
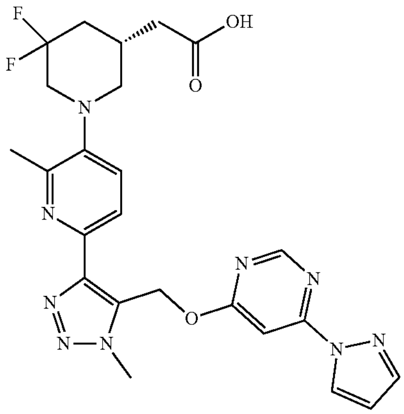
,
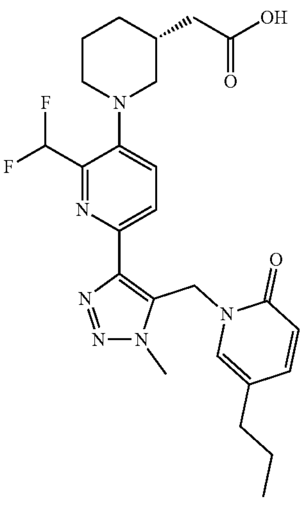
, -continued
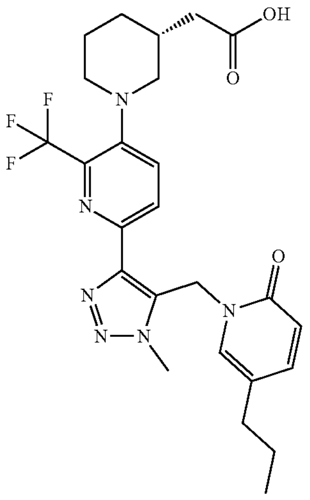
and
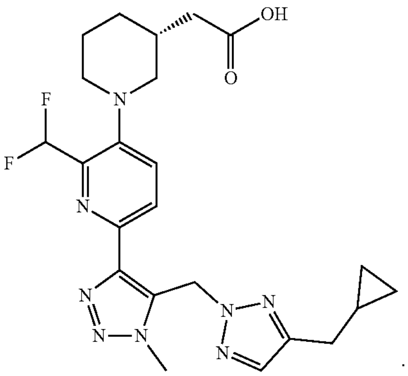
.
77. The compound of claim 1, selected from:
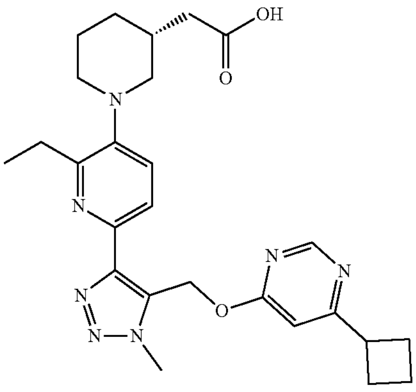
,
-continued
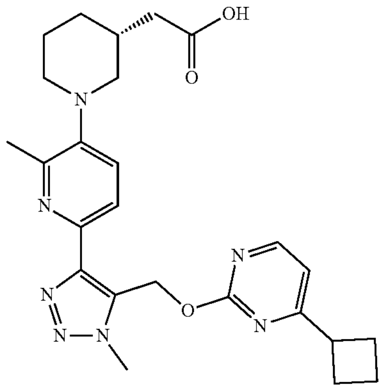
,
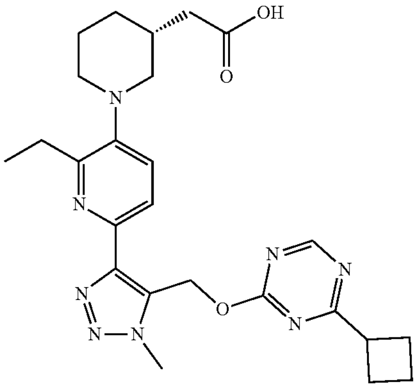
,
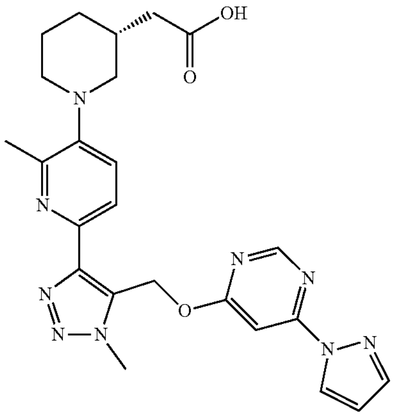
and
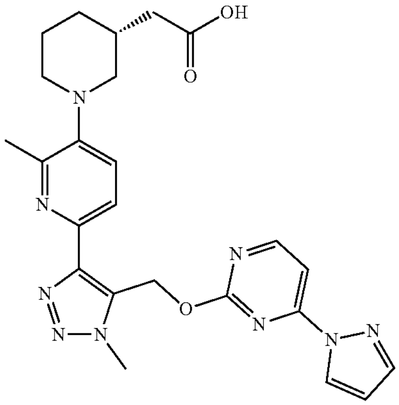
.

78. The compound of claim 1, selected from:

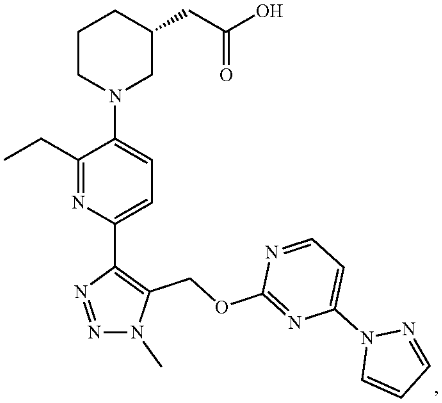

,

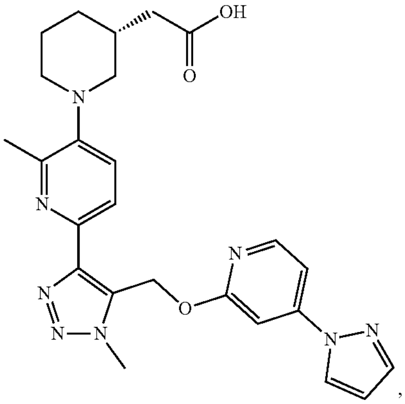

,

-continued

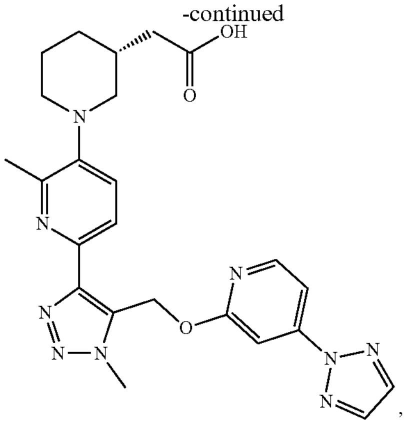

, and

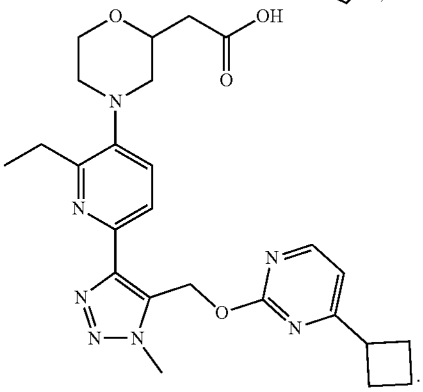

.

79. A pharmaceutical composition comprising the compound of claim 1, and a pharmaceutically acceptable carrier.

80. A method for treating a disease associated with dysregulation of lysophosphatidic acid receptor 1 (LPAi) in a subject in need thereof, comprising administering an effective amount of a compound of claim 1 to the subject.

81. The method of claim 80, wherein the disease is pathological fibrosis, idiopathic pulmonary fibrosis (IPF), non-alcoholic steatohepatitis (NASH), non-alcoholic fatty liver disease (NAFLD), chronic kidney disease, diabetic kidney disease, or systemic sclerosis.

82. The method of claim 81, wherein the pathological fibrosis comprises pulmonary, liver, renal, cardiac, dermal, ocular, or pancreatic fibrosis.

* * * * *